(12) United States Patent
Murata et al.

(10) Patent No.: US 10,005,739 B2
(45) Date of Patent: Jun. 26, 2018

(54) QUINAZOLINONE AND ISOQUINOLINONE DERIVATIVE

(71) Applicant: CHUGAI SEIYAKU KABUSHIKI KAISHA, Tokyo (JP)

(72) Inventors: Takeshi Murata, Shizuoka (JP); Sousuke Hara, Shizuoka (JP); Satoshi Niizuma, Shizuoka (JP); Kihito Hada, Shizuoka (JP); Hatsuo Kawada, Shizuoka (JP); Masahiro Sakaitani, Hokkaido (JP); Hideaki Shimada, Shizuoka (JP); Yoshito Nakanishi, Kanagawa (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days. days.

(21) Appl. No.: 15/030,804

(22) PCT Filed: Oct. 23, 2014

(86) PCT No.: PCT/JP2014/078165
§ 371 (c)(1),
(2) Date: Aug. 12, 2016

(87) PCT Pub. No.: WO2015/060373
PCT Pub. Date: Apr. 30, 2015

(65) Prior Publication Data
US 2016/0272595 A1    Sep. 22, 2016

(30) Foreign Application Priority Data
Oct. 23, 2013  (JP) ................. 2013-219901

(51) Int. Cl.
| | | |
|---|---|---|
| *C07D 217/24* | (2006.01) | |
| *C07D 239/90* | (2006.01) | |
| *C07D 239/91* | (2006.01) | |
| *C07D 401/06* | (2006.01) | |
| *C07D 401/12* | (2006.01) | |
| *C07D 403/06* | (2006.01) | |
| *C07D 403/12* | (2006.01) | |
| *C07D 403/14* | (2006.01) | |
| *C07D 405/04* | (2006.01) | |
| *C07D 405/12* | (2006.01) | |
| *C07D 409/12* | (2006.01) | |
| *C07D 413/06* | (2006.01) | |
| *C07D 471/04* | (2006.01) | |
| *C07D 487/04* | (2006.01) | |
| *C07D 239/92* | (2006.01) | |
| *C07D 239/94* | (2006.01) | |
| *C07D 491/056* | (2006.01) | |

(52) U.S. Cl.
CPC ........ *C07D 239/92* (2013.01); *C07D 217/24* (2013.01); *C07D 239/90* (2013.01); *C07D 239/91* (2013.01); *C07D 239/94* (2013.01); *C07D 401/06* (2013.01); *C07D 401/12* (2013.01); *C07D 403/06* (2013.01); *C07D 403/12* (2013.01); *C07D 403/14* (2013.01); *C07D 405/04* (2013.01); *C07D 405/12* (2013.01); *C07D 409/12* (2013.01); *C07D 413/06* (2013.01); *C07D 471/04* (2013.01); *C07D 487/04* (2013.01); *C07D 491/056* (2013.01)

(58) Field of Classification Search
CPC .. C07D 217/24; C07D 239/90; C07D 239/91; C07D 239/94; C07D 401/06; C07D 401/12; C07D 403/06; C07D 403/12; C07D 403/14; C07D 405/04; C07D 405/12; C07D 409/12; C07D 413/06; C07D 471/04; C07D 487/04
See application file for complete search history.

(56) References Cited

U.S. PATENT DOCUMENTS

| | | |
|---|---|---|
| 4,943,583 A | 7/1990 | Lüthy |
| 4,968,805 A | 11/1990 | Okada et al. |
| 9,090,568 B2 | 7/2015 | Lui et al. |
| 9,102,631 B2 | 8/2015 | Cai et al. |
| 9,290,460 B2 | 3/2016 | Cai et al. |
| 2005/0009894 A1 | 1/2005 | Babin et al. |
| 2006/0106062 A1 | 5/2006 | Kuang et al. |

(Continued)

FOREIGN PATENT DOCUMENTS

| | | |
|---|---|---|
| CA | 2093203 C | 4/1993 |
| CN | 101842368 A | 9/2010 |

(Continued)

OTHER PUBLICATIONS

STN, printed Jun. 24, 2017.*

(Continued)

*Primary Examiner* — Kendra D Carter
(74) *Attorney, Agent, or Firm* — Nixon & Vanderhye P.C.

(57) ABSTRACT

The present invention relates to quinazolinone and isoquinolinone derivatives represented by formula (I) or pharmaceutically acceptable salts thereof.

(I)

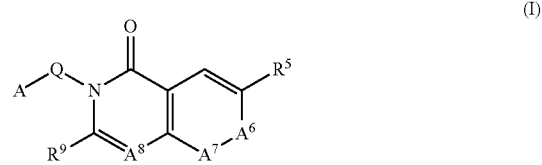

10 Claims, 1 Drawing Sheet

(56) References Cited

U.S. PATENT DOCUMENTS

| | | |
|---|---|---|
| 2008/0280900 A1 | 11/2008 | Pajouhesh et al. |
| 2009/0023746 A1 | 1/2009 | Hallam et al. |
| 2009/0099184 A1 | 4/2009 | Delombaert et al. |
| 2010/0298298 A1 | 11/2010 | Clauss et al. |
| 2011/0124670 A1 | 5/2011 | Buchdunger et al. |
| 2012/0094997 A1 | 4/2012 | England et al. |
| 2013/0137660 A1 | 5/2013 | Burns et al. |
| 2015/0141400 A1 | 5/2015 | Murata et al. |
| 2015/0152047 A1 | 6/2015 | Murata et al. |

FOREIGN PATENT DOCUMENTS

| | | |
|---|---|---|
| CN | 102036990 A | 4/2011 |
| CN | 102099039 A | 6/2011 |
| EP | 0 329 020 A | 8/1989 |
| EP | 0564409 A1 | 10/1993 |
| EP | 1702917 A1 | 9/2006 |
| JP | H05-255268 | 10/1993 |
| JP | H07-133266 A | 5/1995 |
| JP | H10259176 A | 9/1998 |
| JP | 2006504665 A | 2/2006 |
| JP | 2007500129 A | 1/2007 |
| JP | 2009502830 A | 1/2009 |
| JP | 2009-528992 A | 8/2009 |
| JP | 2009541223 A | 11/2009 |
| JP | 2010509375 A | 3/2010 |
| JP | 2010-523674 A | 7/2010 |
| JP | 2010523533 A | 7/2010 |
| JP | 2010-540602 A | 12/2010 |
| JP | 2011-515397 A | 5/2011 |
| JP | 2011-528015 A | 11/2011 |
| JP | 2012-505881 A | 3/2012 |
| JP | 2012513481 A | 6/2012 |
| JP | 6130828 B2 | 5/2017 |
| WO | WO 03/053958 A1 | 7/2003 |
| WO | WO 2004/005281 A1 | 1/2004 |
| WO | WO-2004014866 A1 | 2/2004 |
| WO | WO 2004/085388 A2 | 10/2004 |
| WO | WO-2005012241 A2 | 2/2005 |
| WO | WO-2005014576 A1 | 2/2005 |
| WO | WO 2005/063709 A1 | 7/2005 |
| WO | WO-2007012422 A1 | 2/2007 |
| WO | WO 2007/098352 A2 | 8/2007 |
| WO | WO-2007147217 A1 | 12/2007 |
| WO | WO-2008058341 A1 | 5/2008 |
| WO | WO 2008/127615 A1 | 10/2008 |
| WO | WO-2008122765 A1 | 10/2008 |
| WO | WO 2009/117097 A1 | 9/2009 |
| WO | WO 2010/007034 A1 | 1/2010 |
| WO | WO 2010/056230 A1 | 5/2010 |
| WO | WO 2010/062038 A2 | 6/2010 |
| WO | WO-2010075561 A1 | 7/2010 |
| WO | WO 2011/050120 A1 | 4/2011 |
| WO | WO 2011/062927 A1 | 5/2011 |
| WO | WO 2012/061926 A1 | 5/2012 |
| WO | WO 2013/161851 A1 | 10/2013 |
| WO | WO 2013/161853 A1 | 10/2013 |

OTHER PUBLICATIONS

STN , Registry, Registry No. 1001876-02-3, Feb. 7, 2008.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Avivi-Green, C., et al., "Discoidin Domain Receptor 1-deficient Mice Are Resistant to Bleomycin-induced Lung Fibrosis," *American Journal of Respiratory and Critical Care Medicine* 174:420-427, American Thoracic Society, United States (2006).
Barker, K.T., et al., "Expression patterns of the novel receptor-like tyrosine kinase, DDR, in human breast tumors," *Oncogene* 10:569-575, Stockton Press, United States (1995).
Day, E., et al., "Inhibition of collagen-induced discoidin domain receptor 1 and 2 activation by imatinib, nilotinib and dasatinib," *European Journal of Pharmacology* 599:44-53, Elsevier B.V., Netherlands (2008).
Deng, X., et al., "Discovery of 3,5-Diamino-1,2,4-triazole Ureas as Potent Anaplastic Lymphoma Kinase Inhibitors," *ACS Med Chem. Lett*. 2:379-384, American Chemical Society, United States (2011).
Franco, C., et al., "Discoidin Domain Receptor 1 (Ddr1) Deletion Decreases Atherosclerosis by Accelerating Matrix Accumulation and Reducing Inflammation in Low-Density Lipoprotein Receptor-Deficient Mice," *Circulation Research* 102: 1202-1211, American Heart Association, Inc., United States (2008).
Gao, M., et al., "Discovery and Optimization of 3-(2-(Pyrazolo[1,5-α]pyrimidin-6-yl)-ethynyl)benzamides as Novel Selective and Orally Bioavailable Discoidin Domain Receptor 1 (DDR1) Inhibitors," *Journal of Medicinal Chemistry* 56:3281-3295, American Chemical Society, United States (2013).
Gu, T.-L., et al., "Survey of Tyrosine Kinase Signaling Reveals ROS Kinase Fusions in Human Cholangiocarcinoma," *PLoS One* 6(1):e15640, PLoS, United States, 55 pages (2011).
Guerrot, D., et al., "Discoidin Domain Receptor 1 Is a Major Mediator of Inflammation and Fibrosis in Obstructive Nephropathy," *The American Journal of Pathology* 179(1):83-91, Elsevier Inc., United States (2011).
International Search Report for International Application No. PCT/JP2013/062003, Japanese Patent Office, Japan, dated Jul. 23, 2013 (Not a Corresponding Application).
International Search Report for International Application No. PCT/JP2014/078165, Japanese Patent Office, dated Jan. 13, 2015, 2 pages.
International Search Report for International Application No. PCT/JP2013/062006, Japanese Patent Office, Japan, dated May 28, 2013 (Not a Corresponding Application).
Kamohara, H., et al., "Discoidin domain receptor 1 isoform-a (DDR1a) promotes migration of leukocytes in three-dimensional collagen lattices," *FASEB J*. 14:2724-2726, Federation of the American Societies for Experimental Biology, United States (2001).
Kim, H.-G., et al., "DDR1 Receptor Tyrosine Kinase Promotes Prosurvival Pathway through Notch1 Activation," *Journal of Biological Chemistry* 286(20):17672-17681, The American Society for Biochemistry and Molecular Biology Inc., United States (2011).
Kim, H.-G., et al., "Discovery of a Potent and Selective DDR1 Receptor Tyrosine Kinase Inhibitor," *ACS Chemical Biology* 8:2145-2150, American Chemical Society, United States (2013).
McMahon, G., "VEGF Receptor Signaling in Tumor Angiogenesis," *The Oncologist* 5(suppl 1):3-10, AlphaMed Press, United States (2000).
Pinedo, H.M. and Slamon, D.J., "Translational Research: The Role of VEGF in Tumor Angiogenesis," *The Oncologist* 5 (suppl 1):1-2, AlphaMed Press, United States (2000).
Rikova, K., et al., "Global Survey of Phosphotyrosine Signaling Identifies Oncogenic Kinases in Lung Cancer," *Cell* 131:1190-1203, Elsevier Inc., United States (2007).
Rix, U., et al., "A comprehensive target selectivity survey of the BCR-ABL kinase inhibitor INNO-406 by kinase profiling and chemical proteomics in chronic myeloid leukemia cells," *Leukemia* 24:44-50, Macmillian Publishers Ltd., England (2010).
Rix, U., et al., "Chemical proteomic profiles of the BCR-ABL inhibitors imatinib, nilotinib, and dasatinib reveal novel kinase and nonkinase targets," *Blood* 110:4055-4063, The American Society of Hematology, United States (2007).
Song, S., et al., "Discoidin Domain Receptor 1 Isoform Expression and Potential Functions in Cirrhotic Human Liver," *The American Journal of Pathology* 178(3):1134-1144, Elsevier Inc., United States (2011).
Sun, X., at al., "LCB 03-0110, a Novel Pan-Discoidin Domain Receptor/c-Src Family Tyrosine Kinase Inhibitor, Suppresses Scar Formation by Inhibiting Fibroblast and Macrophage Activation," *The Journal of Pharmacology and Experimental Therapeutics* 340(3):510-519, The American Society for Pharmacology and Experimental Therapeutics, United States (2012).
Unverified English language machine translation of JP H05-255268, Oct. 19, 2015.

(56) References Cited

OTHER PUBLICATIONS

Unveried English language translation of Japanese Patent Publication No. JP H07-133266A, Japanese Patent Office, Japan, Jun. 10, 2016.
Valencia, K., et al., "Inhibition of Collagen Receptor Discoidin Domain Receptor-1 (DDR1) Reduces Cell Survival, Homing, and Colonization in Lung Cancer Bone Metastasis," *Clinical Cancer Research* 18(4):969-980, American Association for Cancer Research, United States (2012).
Valiathan, R. R., et al., "Discoidin domain receptor tyrosine kinases: new players in cancer progression," *Cancer Metastasis Reviews* 31:295-321, Springer Science + Business Media, LLC, United States (2012).
Vogel, W., et al., "Discoidin domain receptors: structural relations and functional implications," *FASEB J.* 13:S77-S82, Federation of the American Societies for Experimental Biology, United States (1999).
Vogel, W., et al., "The Discoidin Domain Receptor Tyrosine Kinases Are Activated by Collagen," *Molecular Cell* 1:13-23, Cell Press, United States (1997).
Yamanaka, R., et al., "Identification of expressed genes characterizing long-term survival in malignant giloma patients," *Oncogene* 25:5994-6002, Nature Publishing Group, England (2006).
Yang, S. H., et al., "Discoidin domain receptor 1 is associated with poor prognosis of non-small cell lung carcinomas," *Oncology Reports* 24:311-319, National Hellenic Research Foundation, Greece (2010).
Zubarev, A.A., et al., "3-Cyanopyridine-2(1H)-thiones and 3-cyano-2-(methylthio)pyridines in the synthesis of substituted 3-(aminomethyl)pyridines," *Russian Chemical Bulletin* 52(4):978-983, Springer, Germany (2003) (Abstract).
Borza, C.M. and Pozzi, A., "Discoidin domain receptors in disease," *Matrix Biology* 34:185-192, Elsevier B.V., Netherlands (2014).
Matsuo, Y. and Maruyama, M., "The chemistry of four-membered aromatics," *Chemical Communications* 48:9334-9342, The Royal Society of Chemistry, England (2012).
Extended European Search Report in European Application No. 14855498.3, dated May 2, 2017, European Patent Office, Germany, 9 pages.

\* cited by examiner

QUINAZOLINONE AND ISOQUINOLINONE DERIVATIVE

TECHNICAL FIELD

The present invention relates to quinazolinone and isoquinolinone derivatives or salts thereof, or solvates thereof. More specifically, the present invention relates to quinazolinone and isoquinolinone derivatives, and provides pharmaceuticals, pharmaceutical compositions, and DDR1 inhibitors comprising the compounds, as well as pharmaceuticals comprising the above-mentioned compounds for treatment of diseases including cancer, cancer metastasis and invasion, fibrosis, and inflammation. The present invention also relates to methods for treating the above-mentioned diseases comprising administering effective doses of the compounds or salts thereof, or solvates thereof, and to use of the quinazolinone and isoquinolinone derivatives for the manufacture of the above-mentioned pharmaceutical compositions.

BACKGROUND ART

Discoidin Domain Receptor 1 (DDR1) is a receptor tyrosine kinase, and it is known that DDR1 is activated by collagen as a ligand to transduce signals into cells, and to promote invasion/metastasis or survival of the cells (Non-Patent Document 1, Non-Patent Document 2, and Non-Patent Document 3). DDR1 is considered to be an important factor that links extracellular matrix with malignant transformation of cancer, because high expression and activation of DDR1 is observed in various types of cancers.

For example, it is known that clinically DDR1 is highly expressed in non-small-cell lung cancer, glioma, breast cancer, and the like (Non-Patent Document 4, Non-Patent Document 5, Non-Patent Document 6, and Non-Patent Document 7), and it is reported that high expression correlates with poor prognosis in non-small-cell lung cancer and glioma. Further, in non-small-cell lung cancer and bile duct cancer, enhancement of DDR1 phosphorylation is observed, and its activation is strongly suggested (Non-Patent Document 8, and Non-Patent Document 9).

Studies using RNA interference reveal that DDR1 plays an important role in bone metastasis of lung cancer cells (Non-Patent Document 5), and contributes to tumorigenicity of colon cancer or breast cancer cells as well as their survival in the presence of DNA-damaging agents (Non-Patent Document 10). Accordingly, compounds having a DDR1 inhibitory effect are extremely useful for cancer treatment.

It is also reported that the DDR1 ligand, collagen, is abundantly present in fibrous tissues, and functions mediated through DDR1 activation are involved in various types of fibrosis. For example, DDR1 expression is enhanced in the liver of hepatic cirrhosis patients (Non-Patent Document 11). It is reported that in DDR1 knockout mice, fibrosis in the kidney induced by unilateral ureteral ligation is suppressed (Non-Patent Document 12), and fibrosis in a pulmonary fibrosis model induced by bleomycin is reduced (Non-Patent Document 13). As it is clear from above, DDR1 inhibition is extremely useful for the prevention and treatment of organ fibrosis. DDR1 also enhances lymphocyte migration, and migration and inflammatory functions of macrophages (Non-Patent Document 14, and Non-Patent Document 15). For example, in DDR1 knockout mice, accumulation of macrophages is suppressed in an arteriosclerosis model (Non-Patent Document 15). It is reported that lymphocytes and macrophages also accumulate and are activated in inflammatory diseases such as rheumatoid arthritis, Crohn's disease, ulcerative colitis, and multiple sclerosis. Accordingly, DDR1 inhibition is also extremely useful for the prevention and treatment of these diseases which originate from inflammation.

Examples of DDR1 inhibitory substances include multi-kinase inhibitors which have DDR1 inhibitory effect as one of their effects. Reported examples include Gleevec which has a 3-pyridylpyrimidine structure and serves as an inhibitor for bcr-abl, c-kit, CSF1R, PDGFRα, and the like (Patent Document 1, Non-Patent Document 16, and Non-Patent Document 17), and Tasigna which has a 3-pyridylpyrimidine structure and serves as an inhibitor for bcr-abl, c-kit, PDGFRα, Lck, Lyn, and the like (Patent Document 2, Non-Patent Document 16, and Non-Patent Document 17). Other reported examples include Sprycel which has a 2-methylpyrimidine structure and serves as an inhibitor for the Src family and the like (Patent Document 3, Non-Patent Document 16, and Non-Patent Document 17), INNO-406 which has a bipyrimidin-2-ylamino structure and serves as an inhibitor for bcr-abl, PDGFRα, Lyn, ZAK, and the like (Patent Document 4, and Non-Patent Document 18), and LCB03-0110 which has a thieno[3,2-b]pyridine structure and serves as an inhibitor for the Src family and the like (Non-Patent Document 19).

However, compounds that selectively inhibit DDR1 are not yet known.

CITATION LIST

Patent Documents

Patent Document 1: European Patent Application Publication No. 0564409
Patent Document 2: International Publication No. WO 2004/005281
Patent Document 3: International Publication No. WO 2004/085388
Patent Document 4: International Publication No. WO 2005/063709

Non-Patent Documents

Non-Patent Document 1: FASEB J, 13, S77-S82, 1999
Non-Patent Document 2: Mol Cell, 1, 13-23, 1997
Non-Patent Document 3: Cancer Metastasis Rev, electronic edition, Feb. 26, 2012
Non-Patent Document 4: Oncol Rep, 24, 311-319, 2010
Non-Patent Document 5: Clin Cancer Res, 18, 969-980, 2012
Non-Patent Document 6: Oncogene, 25, 5994-6002, 2006
Non-Patent Document 7: Oncogene, 10, 569-575, 1995
Non-Patent Document 8: Cell, 131, 1190-1203, 2007
Non-Patent Document 9: PloS One, 6, e15640, 2011
Non-Patent Document 10: J Biol Chem, 286, 17672-17681, 2011
Non-Patent Document 11: Am J Pathol, 178, 1134-44, 2011
Non-Patent Document 12: Am J Pathol, 179, 83-91, 2011
Non-Patent Document 13: Am J Respir Crit Care Med, 174, 420-427, 2006
Non-Patent Document 14: FASEB J, 15, 2724-2726, 2001
Non-Patent Document 15: Circ Res, 102, 1202-1211, 2008
Non-Patent Document 16: Blood, 110, 4055-4063, 2007
Non-Patent Document 17: European Journal of Pharmacology 599, 44-53, 2008
Non-Patent Document 18: Leukemia, 22, 44-50, 2010

Non-Patent Document 19: THE JOURNAL OF PHARMACOLOGY AND EXPERIMENTAL THERAPEUTICS 340, 510-519, 2012

SUMMARY OF INVENTION

Technical Problem

An objective of the present invention is to provide low-molecular-weight compounds that can selectively inhibit Discoidin Domain Receptor 1 (DDR1) and to provide drugs effective for diseases associated with abnormalities of DDR1, such as cancer, cancer metastasis and invasion, fibrosis, and inflammation.

Solution to Problem

Specifically, the present invention includes:

[1] a compound represented by general formula (I) below or a pharmaceutically acceptable salt thereof:

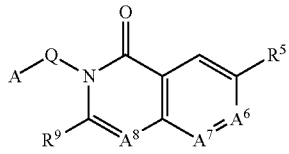

(I)

wherein
A represents formula (1) or (2) below:

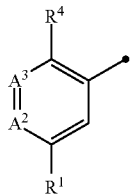

(1)

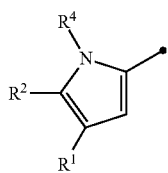

(2)

Q represents $CH_2$ or NH;
$R^1$ represents a hydrogen atom, $C_{1-6}$ alkyl group, $C_{1-6}$ alkoxy group, $C_{2-6}$ alkenyl group, $C_{2-6}$ alkynyl group, halogen atom, cyano group, nitro group or amino group, wherein the $C_{1-6}$ alkyl group, $C_{2-6}$ alkenyl group, $C_{2-6}$ alkynyl group, and $C_{1-6}$ alkoxy group may be substituted with 1 to 5 halogen atoms;
$A^2$ represents $CR^2$ or N;
$R^2$ represents a hydrogen atom, $C_{1-3}$ alkyl group, $C_{1-3}$ alkoxy group, or halogen atom;
$A^3$ represents $CR^3$ or N;
$R^3$ represents a hydrogen atom, $C_{1-3}$ alkyl group, $C_{1-3}$ alkoxy group, or halogen atom;
$R^4$ represents a $C_{3-6}$ alkyl group, $C_{3-8}$ cycloalkyl group, ($C_{3-8}$ cycloalkyl)methyl group, $C_{1-6}$ alkylsulfonyl group, $C_{1-6}$ alkylsulfanyl group, $C_{1-6}$ alkylsulfinyl group, $C_{6-10}$ arylsulfonyl group, $C_{6-10}$ arylsulfanyl group, $C_{6-10}$ arylsulfinyl group, $C_{3-8}$ cycloalkylsulfonyl group, $C_{3-8}$ cycloalkylsulfanyl group or $C_{3-8}$ cycloalkylsulfinyl group, wherein the $C_{3-6}$ alkyl group, $C_{3-8}$ cycloalkyl group, ($C_{3-8}$ cycloalkyl)methyl group, $C_{1-6}$ alkylsulfonyl group, $C_{1-6}$ alkylsulfanyl group, $C_{1-6}$ alkylsulfinyl group, $C_{6-10}$ arylsulfonyl group, $C_{6-10}$ arylsulfanyl group, $C_{6-10}$ arylsulfinyl group, $C_{3-8}$ cycloalkylsulfonyl group, $C_{3-8}$ cycloalkylsulfanyl group, and $C_{3-8}$ cycloalkylsulfinyl group may be substituted with 1 to 5 halogen atoms;
$R^5$ represents a hydrogen atom, halogen atom, $C_{1-6}$ alkyl group, $C_{1-6}$ alkoxy group, $C_{2-6}$ alkenyl group, $C_{2-6}$ alkynyl group, nitro group, amino group, cyano group, $C_{1-6}$ alkylsulfonyl group, $C_{1-6}$ alkylsulfanyl group or $C_{1-6}$ alkylsulfinyl group, wherein the $C_{1-6}$ alkyl group, $C_{2-6}$ alkenyl group, $C_{2-6}$ alkynyl group, and $C_{1-6}$ alkoxy group may be substituted with 1 to 5 halogen atoms;
$A^6$ represents $CR^6$ or N;
$R^6$ represents a hydrogen atom, $C_{1-6}$ alkyl group, $C_{1-6}$ alkoxy group, $C_{3-8}$ cycloalkyl group, $C_{2-6}$ alkenyl group, halogen atom, formyl group, [1,3]dioxolane, or a group represented by formula (i) below, wherein the $C_{1-6}$ alkyl group, $C_{1-6}$ alkoxy group, $C_{3-8}$ cycloalkyl group or $C_{2-6}$ alkenyl group may be substituted with 1 to 5 amino, hydroxyl, and/or $OSO_2CH_3$ groups, $$\bullet\text{-X-Y-Z} \quad (i)$$

wherein in formula (i),
X represents $-(CH_2)_n-$, $-(CH_2)_nNH(CH_2)_l-$, or $-(CH_2)_nO(CH_2)_l-$;
Y represents a $C_{3-8}$ cycloalkyl group, 4- to 10-membered aromatic ring, 3- to 12-membered heterocycle, or 4- to 10-membered aromatic heterocycle, wherein the $C_{3-8}$ cycloalkyl group, 4- to 10-membered aromatic ring, 3- to 12-membered heterocycle, and 4- to 10-membered aromatic heterocycle may be substituted with 1 to 5 halogen atoms, oxo groups and/or $C_{1-3}$ alkyl groups;
Z represents a hydrogen atom, a $C_{1-6}$ alkyl group, a $C_{2-6}$ alkenyl group, a $C_{2-6}$ alkynyl group, a $C_{3-8}$ cycloalkyl group, $-(CH_2)_mNRaRb$, $-NHCO(CH_2)_mRc$, $-(CH_2)_mNHCORc$, $-NH(CH_2)_mCORc$, $-(CH_2)_mN(CH_3)CORc$, $-(CH_2)_mORd$, $-(CH_2)_mCORe$, $-(CH_2)_mCOORe$, $-(CH_2)_mNHSO_2Rf$, $-(CH_2)_mSO_2Rf$, $-(CH_2)_mCONRgRh$, a 4- to 10-membered aromatic ring, 4- to 10-membered aromatic heterocycle, or a 3- to 12-membered heterocycle, wherein the $C_{1-6}$ alkyl group may be substituted with 1 to 5 halogen atoms, hydroxyl groups, $C_{3-8}$ cycloalkyl groups, 4- to 10-membered aromatic rings, 4- to 10-membered aromatic heterocycles, 3- to 12-membered heterocycles, and/or cyano groups; and the 3- to 12-membered heterocycle and 4- to 10-membered aromatic heterocycle may be substituted with 1 to 5 halogen atoms, $C_{1-3}$ alkyl groups and/or oxo groups;
n represents 0, 1, 2, or 3;
l represents 0, 1, 2, or 3;
m represents 0, 1, 2, or 3;
Ra and Rb are identical or different, each representing a hydrogen atom, $C_{1-6}$ alkyl group, $C_{2-6}$ alkenyl group, $C_{2-6}$ alkynyl group, 3- to 12-membered heterocycle, 4- to 10-membered aromatic heterocycle, or $-SO_2CH_3$, wherein the $C_{1-6}$ alkyl group may be substituted with 1 to 5 halogen atoms, amino groups, mono-$C_{1-6}$ alkylamino groups, di-$C_{1-6}$ alkylamino groups, hydroxyl groups, and/or cyano groups;
Rc represents a $C_{1-6}$ alkyl group, $C_{2-6}$ alkenyl group, $C_{2-6}$ alkynyl group, $C_{1-6}$ alkoxy group, $C_{3-8}$ cycloalkyl group, amino group, mono-$C_{1-6}$ alkylamino group, di-$C_{1-6}$ alkylamino group or 3- to 12-membered heterocycle, wherein the C₁ alkyl group may be substituted with 1 to 3 amino groups, mono-$C_{1-6}$ alkylamino groups, di-$C_{1-6}$ alkylamino groups, and/or 3- to 12-membered heterocycles;

Rd represents a hydrogen atom, $C_{1-6}$ alkyl group, $C_{2-6}$ alkenyl group or $C_{2-6}$ alkynyl group, wherein the $C_{1-6}$ alkyl group, $C_{2-6}$ alkenyl group, and $C_{2-6}$ alkynyl group may be substituted with 1 to 5 $C_{1-6}$ alkoxy groups and/or amino groups;

Re represents a hydrogen atom or $C_{1-6}$ alkyl group, wherein the $C_{1-6}$ alkyl group may be substituted with an amino group;

Rf represents a $C_{1-6}$ alkyl group, an amino group, a mono-$C_{1-6}$ alkylamino group, or a di-$C_{1-6}$ alkylamino group, wherein the $C_{1-6}$ alkyl group, mono-$C_{1-6}$ alkylamino group, and di-$C_{1-6}$ alkylamino group may be substituted with 1 to 5 halogen atoms;

Rg and Rh are identical or different, each representing a hydrogen atom, $C_{1-6}$ alkyl group, or 3- to 12-membered heterocycle, wherein the $C_{1-6}$ alkyl group may be substituted with 1 to 3 amino groups, mono-$C_{1-6}$ alkylamino groups, and/or di-$C_{1-6}$ alkylamino groups;

$R^5$ and $R^6$ may be taken together to form a 4- to 10-membered aromatic ring, 3- to 12-membered heterocycle or 4- to 10-membered aromatic heterocycle;

$A^7$ represents $CR^7$ or N; and $R^7$ represents a hydrogen atom, halogen atom, $C_{1-6}$ alkyl group, $C_{2-6}$ alkenyl group, $C_{1-6}$ alkoxy group, cyano group, or a group represented by formula (ii) below, wherein the $C_{1-6}$ alkyl group may be substituted with 1 to 5 halogen atoms:

●-$X^2$—$Y^2$—$Z^2$         (ii)

wherein $X^2$ represents —$(CH_2)_p$—;

$Y^2$ represents a $C_{3-8}$ cycloalkyl group, 4- to 10-membered aromatic ring, 3- to 12-membered heterocycle or 4- to 10-membered aromatic heterocycle;

$Z^2$ represents a hydrogen atom, halogen atom, $C_{1-6}$ alkyl group, $C_{2-6}$ alkenyl group, $C_{1-6}$ alkoxy group, $C_{3-8}$ cycloalkyl group, cyano group, 4- to 10-membered aromatic ring, 4- to 10-membered aromatic heterocycle, 3- to 12-membered heterocycle, or COORi;

p represents 0, 1, or 2;

Ri represents a $C_{1-6}$ alkyl group;

$A^8$ represents CH or N; and $R^9$ represents a hydrogen atom or amino group;

[2] the compound or pharmaceutically acceptable salt thereof according to [1], wherein A is formula (3) below:

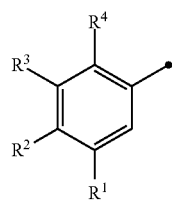

(3)

[3] the compound or pharmaceutically acceptable salt thereof according to [1] or [2], wherein $R^4$ is a $C_{1-6}$ alkylsulfonyl group or $C_{1-6}$ alkylsulfanyl group;

[4] the compound or pharmaceutically acceptable salt thereof according to any one of [1] to [3], wherein $R^5$ represents a halogen atom, $C_{1-3}$ alkyl group, or $C_{1-3}$ alkoxy group, wherein the $C_{1-3}$ alkyl group or $C_{1-3}$ alkoxy group may be substituted with 1 to 5 halogen atoms;

[5] the compound or pharmaceutically acceptable salt thereof according to any one of [1] to [4], wherein $R^6$ represents a hydrogen atom or a group represented by formula (i) below:

●-X—Y—Z         (i)

wherein X represents $CH_2$ or $(CH_2)_2NH(CH_2)_2$;

Y represents piperazine, pyrrolidine, piperidine, morpholine, homomorpholine, 3,3-dimethylpiperazine, (R) or (S)-hexahydro-pyrrolo[1,2-a]pyrazine, 3-oxopiperazine, azetidine or 2-oxo-imidazolidine;

Z represents a hydrogen atom, a $C_{1-3}$ alkyl group, a $C_{4-6}$ cycloalkyl group, —$(CH_2)_m$NRaRb, —NHCO$(CH_2)_m$Rc, —$(CH_2)_m$NHCORc, —NH$(CH_2)_m$CORc, —$(CH_2)_m$N$(CH_3)$CORc, ORd, —CORe, —COORe, —NHSO₂Rf, —SO₂Rf, —$(CH_2)_m$CONRgRh, or azetidine, piperazine, pyrrolidine, piperidine, tetrahydropyran, tetrahydrothiopyran, morpholine, or oxetane, wherein the azetidine, piperazine, pyrrolidine, piperidine, tetrahydropyran, tetrahydrothiopyran, morpholine, or oxetane may be substituted with 1 to 5 halogen atoms, $C_{1-3}$ alkyl groups, and/or oxo groups; m represents 0 or 1;

Ra and Rb are identical or different, each representing a hydrogen atom, a $C_{1-3}$ alkyl group, —SO₂CH₃, prop-2-ynyl, or oxetane, wherein the $C_{1-3}$ alkyl group may be substituted with 1 to 5 halogen atoms or amino groups;

Rc represents a $C_{1-3}$ alkyl group, a $C_{1-4}$ alkoxy group, a $C_{4-6}$ cycloalkyl group, or an amino group, wherein the $C_{1-3}$ alkyl group may be substituted with 1 to 2 amino, mono-$C_{1-2}$ alkylamino, and/or di-$C_{1-2}$ alkylamino groups;

Rd represents a hydrogen atom, $C_{1-2}$ alkyl group, or $C_{2-3}$ alkenyl group, wherein the $C_{1-2}$ alkyl group may be substituted with 1 to 2 $C_{1-2}$ alkoxy groups;

Re represents a hydrogen atom or $C_{1-4}$ alkyl group, wherein the $C_{1-4}$ alkyl group may be substituted with an amino group;

Rf represents a $C_{1-3}$ alkyl group, an amino group, a mono-$C_{1-3}$alkylamino group, or a di-$C_{1-3}$ alkylamino group; and Rg and Rh are identical or different, each representing a hydrogen atom or $C_{1-3}$ alkyl group;

[6] the compound or pharmaceutically acceptable salt thereof according to any one of [1] to [5], wherein $R^7$ represents a hydrogen atom or a halogen atom;

[7] the compound or pharmaceutically acceptable salt thereof according to any one of [1] to [6], wherein $R^9$ represents a hydrogen atom;

[8] a pharmaceutical comprising the compound or pharmaceutically acceptable salt thereof according to any one of [1] to [7] as an active ingredient;

[9] the pharmaceutical according to [8], wherein the pharmaceutical is used for treatment of cancer and/or cancer invasion/metastasis;

[10] the pharmaceutical according to [8], wherein the pharmaceutical is used for treatment of fibrosis and/or inflammation;

[11]

a method for treating cancer and/or cancer invasion/metastasis, comprising administering a pharmaceutically effective amount of a composition comprising the compound or pharmaceutically acceptable salt thereof according to any one of [1] to [7] to a patient in need thereof;

[12]

a method for treating fibrosis and/or inflammation, comprising administering a pharmaceutically effective amount of a composition comprising the compound or pharmaceutically acceptable salt thereof according to any one of [1] to [7] to a patient in need thereof;

[13]

use of the compound or pharmaceutically acceptable salt thereof according to any one of [1] to [7] for the manufacture of an agent for treating cancer and/or cancer invasion/metastasis;

[14]

use of the compound or pharmaceutically acceptable salt thereof according to any one of [1] to [7] for the manufacture of an agent for treating fibrosis and/or inflammation;

[15]

the compound or pharmaceutically acceptable salt thereof according to any one of [1] to [7] for use in treating cancer and/or cancer invasion/metastasis; and

[16]

the compound or pharmaceutically acceptable salt thereof according to any one of [1] to [7] for use in treating fibrosis and/or inflammation.

Advantageous Effects of Invention

The compounds according to the present invention or pharmaceutically acceptable salts thereof, or solvates thereof have an effect of selectively inhibiting Discoidin Domain Receptor 1 (DDR1). The compounds of the present application can have a medicinal effect for diseases associated with abnormalities of DDR1, such as cancer, cancer metastasis and invasion, fibrosis, and inflammation; and can prevent and/or treat diseases for which previous therapeutic agents are not sufficiently effective.

DESCRIPTION OF EMBODIMENTS

Figure 1:
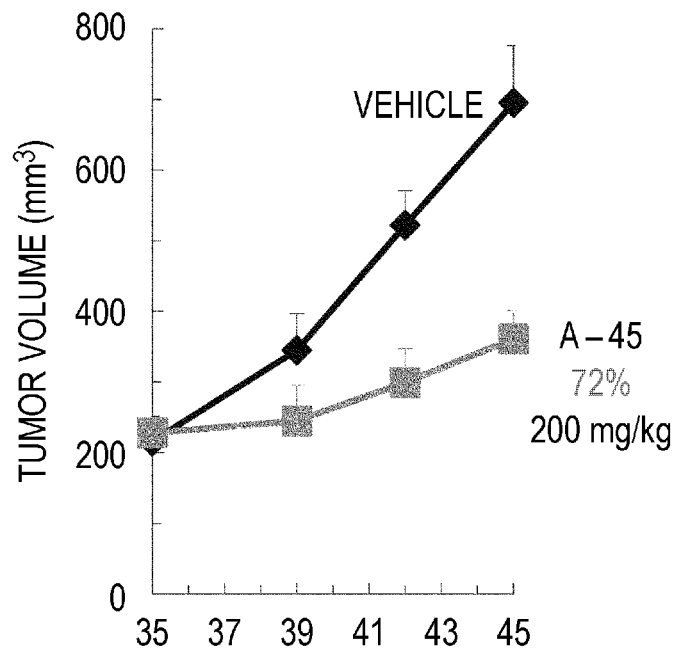
FIG. 1 is a graph showing an antitumor effect of Compound A-45.

The present invention relates to quinazolinone and isoquinolinone derivatives and uses thereof. The present inventors have synthesized compounds represented by formula (I) above or pharmaceutically acceptable salts thereof for the first time, and discovered that the compounds or salts thereof have a DDR1 inhibitory effect.

Herein, "alkyl" refers to a monovalent group derived by removing any one hydrogen atom from an aliphatic hydrocarbon, and covers a subset of hydrocarbyl or hydrocarbon group structures that include hydrogen and carbon atoms, but do not contain a heteroatom or an unsaturated carbon-carbon bond in the backbone. Examples of the alkyl group include those of linear or branched structures. The alkyl group is preferably an alkyl group having 1 to 6 carbon atoms ($C_{1-6}$; "$C_{p-q}$" hereinafter means that the group has p to q carbon atoms), such as a $C_{1-5}$ alkyl group, $C_{1-4}$ alkyl group, or $C_{1-3}$ alkyl group.

Specific examples of the alkyl include a methyl group, an ethyl group, an n-propyl group, an isopropyl group, an n-butyl group, an isobutyl group, an s-butyl group, a t-butyl group, a pentyl group, an isopentyl group, a 2,3-dimethylpropyl group, a 3,3-dimethylbutyl group, and a hexyl group.

Herein, "alkenyl" refers to a monovalent hydrocarbon group having at least one double bond (two adjacent SP2 carbon atoms), and includes linear or branched ones. Depending on the configuration of a double bond and a substituent (if present), the geometry of the double bond can be an entgegen (E) or zuzammen (Z) configuration, or a cis or trans configuration. Preferred examples of the alkenyl group include $C_{2-6}$ alkenyl groups.

Specific examples of the alkenyl include a vinyl group, an allyl group, a 1-propenyl group, a 2-propenyl group, a 1-butenyl group, a 2-butenyl group (including cis and trans), a 3-butenyl group, a pentenyl group, and a hexenyl group.

Herein, "alkynyl" refers to a monovalent hydrocarbon group having at least one triple bond (two adjacent SP carbon atoms), and includes linear or branched ones. Preferred examples include $C_{2-6}$ alkynyl groups.

Specific examples of the alkynyl include an ethynyl group, a 1-propynyl group, a propargyl group, a 3-butynyl group, a pentynyl group, and a hexynyl group.

The alkenyl or alkynyl can have one or more double bonds or triple bonds, respectively.

Herein, "cycloalkyl" refers to a saturated or partially saturated cyclic, monovalent aliphatic hydrocarbon group, and includes single rings, bicyclo rings, and spiro rings. Preferred examples of the cycloalkyl include $C_{3-8}$ cycloalkyl groups, and more preferably, $C_{3-7}$ cycloalkyl groups. Specific examples of the cycloalkyl group include a cyclopropyl group, cyclobutyl group, cyclopentyl group, cyclohexyl group, and cycloheptyl group.

Herein, "aryl" refers to a monovalent aromatic hydrocarbon ring. Preferred examples include $C_{6-10}$ aryl. Specific examples of the aryl include a phenyl group and naphthyl group (e.g., a 1-naphthyl group or 2-naphthyl group).

Herein, "halogen atom" refers to a fluorine atom, a chlorine atom, a bromine atom, or an iodine atom.

Herein, "alkoxy" refers to an oxy group to which the above-defined "alkyl" is bonded. Preferred examples include $C_{1-6}$ alkoxy groups, $C_{1-4}$ alkoxy groups, and $C_{1-3}$ alkoxy groups. Specific examples of the alkoxy include a methoxy group, an ethoxy group, a 1-propoxy group, a 2-propoxy group, an n-butoxy group, an i-butoxy group, a sec-butoxy group, and a tert-butoxy group.

Herein, "aromatic ring" refers to an aromatic monovalent or divalent hydrocarbon ring. The aromatic ring may be a single ring or a fused ring. The number of the ring-forming atoms is preferably 4 to 10 (4- to 10-membered aromatic ring).

Specific examples of the aromatic ring include benzene and naphthalene.

Herein, "heterocycle" refers to a non-aromatic monovalent or divalent heterocycle containing preferably 1 to 5 heteroatoms in the ring-forming atoms. The heterocycle may have a double and/or triple bond in the ring, and a carbon atom in the ring oxidized to form carbonyl; and it may be a single ring, fused ring, or spiro ring. The number of ring-forming atoms is preferably 3 to 12 (3- to 12-membered heterocycle), more preferably 4 to 7 (4- to 7-membered heterocycle), and even more preferably 5 to 6 (5- to 6-membered heterocycle).

Specific examples of the heterocycle include piperazine, pyrrolidine, piperidine, morpholine, homomorpholine, (R)-hexahydropyrrolo[1,2-a]pyrazine, (S)-hexahydropyrrolo[1,2-a]pyrazine, 3-oxopiperazine, 2-oxopyrrolidine, azetidine, 2-oxoimidazolidine, oxetane, dihydrofuran, tetrahydrofuran, dihydropyran, tetrahydropyran, tetrahydropyridine, thiomorpholine, pyrazolidine, imidazoline, oxazolidine, isoxazolidine, thiazolidine, imidazolidine, isothiazolidine, thiadiazolidine, oxazolidone, benzodioxane, benzoxazoline, dioxolane, dioxane, and tetrahydrothiopyran.

Herein, "aromatic heterocycle" refers to an aromatic monovalent or divalent heterocycle containing preferably 1 to 5 heteroatoms in the ring-forming atoms. The aromatic heterocycle may be partially saturated, and may be a single ring, fused ring (such as a bicyclic aromatic heterocycle in which a monocyclic aromatic heterocycle is fused with a benzene ring or another monocyclic aromatic heterocycle), or spiro ring. The number of ring-forming atoms is preferably 4 to 10 (4- to 10-membered aromatic heterocycle).

Specific examples of the aromatic heterocycle include furan, thiophene, pyrrole, imidazole, pyrazole, thiazole, isothiazole, oxazole, isoxazole, oxadiazole, thiadiazole, triazole, tetrazole, pyridine, pyrimidine, pyridazine, pyrazine, triazine, benzofuran, benzothiophene, benzothiadiazole, benzothiazole, benzoxazole, benzoxadiazole, benzimidazole, indole, isoindole, indazole, quinoline, isoquinoline, cinnoline, quinazoline, quinoxaline, indolizine, and imidazopyridine.

Herein, "heteroatom" refers to a nitrogen atom (N), an oxygen atom (O), or a sulfur atom (S).

Herein, "monoalkylamino" refers to an amino group to which one of the above-defined "alkyl" groups is bonded. Preferred examples of the monoalkylamino include mono-$C_{1-6}$ alkylamino.

Herein, "dialkylamino" refers to an amino group to which two of the above-defined "alkyl" groups are bonded, where the alkyl groups may be identical or different. Preferred examples of the dialkylamino include di-$C_{1-6}$ alkylamino.

Herein, "alkylsulfonyl" refers to a sulfonyl group to which the above-defined "alkyl" is bonded (i.e., alkyl-$SO_2$—). Preferred examples of the alkylsulfonyl include $C_{1-6}$ alkylsulfonyl and $C_{1-3}$ alkylsulfonyl, specifically methylsulfonyl, ethylsulfonyl, n-propylsulfonyl, and i-propylsulfonyl.

Herein, "alkylsulfanyl" refers to a sulfanyl group to which the above-defined "alkyl" is bonded (i.e., alkyl-S—). Preferred examples of the alkylsulfanyl include $C_{1-6}$ alkylsulfanyl and $C_{1-3}$ alkylsulfanyl, specifically methylsulfanyl, ethylsulfanyl, n-propylsulfanyl, and i-propylsulfanyl.

Herein, "alkylsulfinyl" refers to a sulfinyl group to which the above-defined "alkyl" is bonded (i.e., alkyl-SO—). Preferred examples of the alkylsulfinyl include $C_{1-6}$ alkylsulfinyl and $C_{1-3}$ alkylsulfinyl, specifically methylsulfinyl, ethylsulfinyl, n-propylsulfinyl, and i-propylsulfinyl.

Herein, "arylsulfonyl" refers to a sulfonyl group to which the above-defined "aryl" is bounded (i.e., aryl-$SO_2$—). Preferred examples of the arylsulfonyl include $C_{6-10}$ arylsulfonyl, specifically, phenylsulfonyl, 1-naphthylsulfonyl, and 2-naphthylsulfonyl.

Herein, "arylsulfanyl" refers to a sulfanyl group to which the above-defined "aryl" is bounded (i.e., aryl-S—). Preferred examples of the arylsulfanyl include $C_{6-10}$ arylsulfanyl, specifically, phenylsulfanyl, 1-naphthylsulfanyl, and 2-naphthylsulfanyl.

Herein, "arylsulfinyl" refers to a sulfinyl group to which the above-defined "aryl" is bounded (i.e., aryl-SO—). Preferred examples of the arylsulfinyl include $C_{6-10}$ arylsulfinyl, specifically, phenylsulfinyl, 1-naphthylsulfinyl, and 2-naphthylsulfinyl.

Herein, "cycloalkylsulfonyl" refers to a sulfonyl group to which the above-defined "cycloalkyl" is bounded (i.e., cycloalkyl-$SO_2$—). Preferred examples of the cycloalkylsulfonyl include $C_{3-8}$ cycloalkylsulfonyl, specifically, cyclopentylsulfonyl, cyclohexylsulfonyl, and cycloheptylsulfonyl.

Herein, "cycloalkylsulfanyl" refers to a sulfanyl group to which the above-defined "cycloalkyl" is bounded (i.e., cycloalkyl-S—). Preferred examples of the cycloalkylsulfanyl include $C_{3-8}$ cycloalkylsulfanyl, specifically, cyclopentylsulfanyl, cyclohexylsulfanyl, and cycloheptylsulfanyl.

Herein, "cycloalkylsulfinyl" refers to a sulfinyl group to which the above-defined "cycloalkyl" is bounded (i.e., cycloalkyl-SO—). Preferred examples of the cycloalkylsulfinyl include $C_{3-8}$ cycloalkylsulfinyl, specifically, cyclopentylsulfinyl, cyclohexylsulfinyl, and cycloheptylsulfinyl.

Herein, "cycloalkylmethyl" refers to a methyl group to which the above-defined "cycloalkyl" is bounded (i.e., cycloalkyl-$CH_2$—). Preferred examples of the cycloalkylmethyl include $C_{3-8}$ cycloalkylmethyl, specifically, cyclopentylmethyl, cyclohexylmethyl, and cycloheptylmethyl.

In this specification, each black circle in the chemical formulae below denotes the point of attachment.

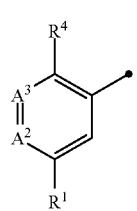

(1)

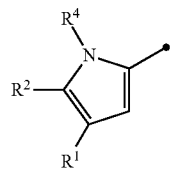

(2)

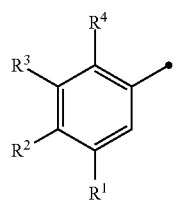

(3)

●—X—Y—Z (i)

●—$X^2$—$Y^2$—$Z^2$ (ii)

The compounds according to the present invention, whether free forms or pharmacologically acceptable salts, are included in the present invention. Examples of such "salts" include inorganic acid salts, organic acid salts, inorganic base salts, organic base salts, and acidic or basic amino acid salts.

Preferred examples of the inorganic acid salts include hydrochlorides, hydrobromides, sulfates, nitrates, and phosphates. Preferred examples of the organic acid salts include acetates, succinates, fumarates, maleates, tartrates, citrates, lactates, malates, stearates, benzoates, methanesulfonates, and p-toluenesulfonates.

Preferred examples of the inorganic base salts include alkali metal salts such as sodium salts and potassium salts, alkaline earth metal salts such as calcium salts and magnesium salts, aluminum salts, and ammonium salts. Preferred examples of the organic base salts include diethylamine salts, diethanolamine salts, meglumine salts, and N,N-dibenzylethylenediamine salts.

Preferred examples of the acidic amino acid salts include aspartates and glutamates. Preferred examples of the basic amino acid salts include arginine salts, lysine salts, and ornithine salts.

The compounds of the present invention may absorb moisture, contain adsorbed water, or form hydrates when left in the air. Such hydrates are also included in the salts of the present invention.

Further, the compounds according to the present invention may absorb certain other solvents to form solvates. Such solvates are also included in the salts of the present invention.

The present invention includes all isomers (such as geometric isomers, optical isomers, stereoisomers, and tautomers) that arise structurally from the compounds of the present invention, as well as mixtures of these isomers.

The compounds according to the present invention may exhibit crystalline polymorphism, and all polymorphs of the compounds are included in the present invention.

The compounds according to the present invention include prodrugs thereof. The prodrugs are derivatives of the compounds of the present invention which have chemically or metabolically decomposable groups, and are converted back to the original compounds after administration in vivo to exhibit their original efficacy; and they include non-covalently bonded complexes and salts.

The compounds according to the present invention include those in which one or more atoms in the molecule are substituted with isotopes. In the present invention, the isotope refers to an atom having the same atomic number (proton number) but a different mass number (sum of the number of protons and neutrons). Examples of atoms contained in the compounds of the present invention to be substituted with isotopes include a hydrogen atom, a carbon atom, a nitrogen atom, an oxygen atom, a phosphorus atom, a sulfur atom, a fluorine atom, and a chlorine atom. Examples of the isotopes include $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$. In particular, radioisotopes that decay by emitting radioactivity such as $^3H$ and $^{14}C$ are useful in tests of body tissue distribution for pharmaceuticals or compounds. Stable isotopes do not decay, and are almost equally abundant. They do not emit radioactivity, and thus can be used safely. Isotopically-substituted forms of the compounds of the present invention can be obtained according to conventional methods by substituting a reagent containing a corresponding isotope for the reagent used for synthesis.

The compounds represented by formula (I) above according to the present invention are preferably as follows.

The above A is preferably formula (3) below.

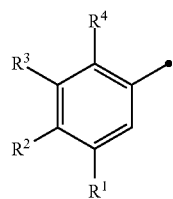

(3)

The above $R^1$ is preferably a chlorine atom, a bromine atom, a fluorine atom, a methyl group, or a cyano group, and more preferably a chlorine atom.

The above $A^2$ is preferably $CR^2$.

The above $R^2$ is preferably a hydrogen atom, a chlorine atom, or $C_{1-3}$ alkyl group, and more preferably a hydrogen atom.

The above $A^3$ is preferably $CR^3$.

The above $R^3$ is preferably a hydrogen atom, $C_{1-3}$ alkyl group, or halogen atom, more preferably a chlorine atom, hydrogen atom, or methyl group, and more preferably a hydrogen atom.

The above $R^4$ is preferably a $C_{2-4}$ alkylsulfonyl group, $C_{2-4}$ alkylsulfanyl group, or $C_{2-4}$ alkylsulfinyl group, more preferably a $C_{2-4}$ alkylsulfonyl group, and still more preferably an ethylsulfonyl group.

Preferably, the above $R^5$ represents a halogen atom, $C_{1-3}$ alkyl group, or $C_{1-3}$ alkoxy group, where the $C_{1-3}$ alkyl group or $C_{1-3}$ alkoxy group may be substituted with 1 to 5 halogen atoms. More preferably, the above $R^5$ represents a halogen atom, $C_{1-2}$ alkyl group, or $C_{1-2}$ alkoxy group, where the $C_{1-2}$ alkyl group or $C_{1-2}$ alkoxy group may be substituted with 1 to 3 halogen atoms. The above $R^5$ is more preferably a trifluoromethyl group, difluoromethyl group, trifluoromethoxy group, methyl group, ethyl group, chlorine atom, or bromine atom, and particularly preferably a trifluoromethyl group.

The above $A^6$ is preferably $CR^6$.

Preferably, the above $R^6$ represents a hydrogen atom or a group represented by formula (i) below.

●-X—Y—Z       (i)

The above X is preferably —(CH$_2$)n-, where n represents 1 or 2, and n is preferably 1.

The above Y preferably represents a 5- to 6-membered heterocycle, where the 5- to 6-membered heterocycle may be substituted with 1 to 5 halogen atoms and/or $C_{1-3}$ alkyl groups. The above Y is more preferably piperazine, pyrrolidine, piperidine, morpholine, homomorpholine, 3,3-dimethylpiperazine, (R) or (S)-hexahydro-pyrrolo[1,2-a]pyrazin-2-yl, 3-oxopiperazin-1-yl, azetidin-3-yl, or 2-oxoimidazolidin-1-yl.

The above Z preferably represents a hydrogen atom, a $C_{1-3}$ alkyl group, a $C_{4-6}$ cycloalkyl group, —(CH$_2$)$_m$—NRaRb, —NHCO(CH$_2$)$_m$Rc, —(CH$_2$)$_m$NHCORc, —NH(CH$_2$)$_m$CORc, —(CH$_2$)$_m$N(CH$_3$)CORc, —ORd, —CORe, —COORe, —NHSO$_2$Rf, —SO$_2$Rf, —(CH$_2$)$_m$CONRgRh, or a 4- to 6-membered heterocycle, where the $C_{1-3}$ alkyl group may be substituted with 1 to 5 halogen atoms, hydroxyl groups, and/or cyano groups; the 4- to 6-membered heterocycle may be substituted with 1 to 5 halogen atoms, $C_{1-3}$ alkyl groups, and/or oxo groups; and m represents 0 or 1. Examples of the heterocycle preferably include azetidine, piperazine, pyrrolidine, piperidine, tetrahydropyran, tetrahydrothiopyran, morpholine, or oxetane. The above Z is more preferably a hydrogen atom, —(CH$_2$)$_m$—NRaRb, —NHCO(CH$_2$)$_m$Rc, —(CH$_2$)$_m$NHCORc, —CORe, —NHSO$_2$Rf, —SO$_2$Rf or a 5- to 6-membered heterocycle, where m represents 0 or 1. Examples of the heterocycle preferably include piperazine, pyrrolidine, piperidine, tetrahydropyran, tetrahydrothiopyran, or morpholine.

Preferably, the above Ra and Rb are identical or different, each representing a hydrogen atom, a $C_{1-3}$ alkyl group, —SO$_2$CH$_3$, a prop-2-ynyl group, or an oxetan-3-yl group, where the $C_{1-3}$ alkyl group may be substituted with 1 to 5 halogen atoms, amino groups, or hydroxyl groups. More preferably, the above Ra and Rb are identical or different, each representing a hydrogen atom, a $C_{1-3}$ alkyl group, or —SO$_2$CH$_3$.

Preferably, the above Rc represents a $C_{1-4}$ alkyl group, a $C_{1-4}$ alkoxy group, a $C_{4-6}$ cycloalkyl group, or an amino group, where the $C_{1-4}$ alkyl group may be substituted with 1 to 3 groups independently selected from amino, mono-$C_{1-4}$ alkylamino, and di-$C_{1-4}$ alkylamino groups. More preferably, the above Rc represents a $C_{1-2}$ alkyl group, a $C_{1-2}$ alkoxy group, or an amino group, where the $C_{1-2}$ alkyl group may be substituted with 1 to 2 groups independently selected from amino, mono-$C_{1-2}$ alkylamino, and di-$C_{1-2}$ alkylamino groups.

The above Rd preferably represents a hydrogen atom, $C_{1-3}$ alkyl group, or $C_{2-3}$ alkenyl group, where the $C_{1-3}$ alkyl group may be substituted with 1 to 2 $C_{1-2}$ alkoxy groups. The above Rd is more preferably a hydrogen atom or methyl group.

Preferably, the above Re represents a hydrogen atom or $C_{1-4}$ alkyl group, where the $C_{1-4}$ alkyl group may be substituted with 1 to 3 amino groups. More preferably, the above Re represents a $C_{1-2}$ alkyl group, where the $C_{1-2}$ alkyl group may be substituted with 1 to 2 amino groups.

The above Rf is preferably a $C_{1-3}$ alkyl group, an amino group, a mono-$C_{1-3}$ alkylamino group, or a di-$C_{1-3}$ alkylamino group, and more preferably a methyl group, an amino group, a monomethylamino group, or a dimethylamino group.

Preferably, the above Rg and Rh are identical or different, and each is preferably a hydrogen atom or $C_{1-3}$ alkyl group, and more preferably, a hydrogen atom.

The above $A^7$ is preferably $CR^7$.

The above $R^7$ is preferably a hydrogen atom, a halogen atom, a cyano group, a methyl group, an ethyl group, or a group represented by formula (ii) below, and more preferably, a hydrogen atom or a halogen atom.

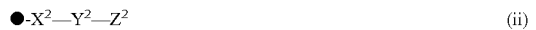  (ii)

For the groups represented by formula (ii) below, it is preferable that:
$X^2$ represents —$(CH_2)_p$—;
$Y^2$ represents piperazine or benzene;
$Z^2$ represents a hydrogen atom, fluorine atom, methyl group, isopropyl group, tetrahydropyran or azetidine; and
p represents 0 or 1.

The above $A^8$ is preferably N.

The $R^9$ is preferably a hydrogen atom.

Such compounds represented by formula (I) or pharmaceutically acceptable salts thereof according to the present invention are useful as compounds having an effect of selectively inhibiting Discoidin Domain Receptor 1 (DDR1), and are useful for prevention and/or treatment of cancer, prevention and/or treatment of cancer invasion and metastasis, and prevention and/or treatment of fibrosis and inflammation.

Examples of the cancer include leukemia (such as acute myeloid leukemia, chronic myeloid leukemia, acute lymphocytic leukemia, and chronic lymphocytic leukemia), malignant lymphoma (such as Hodgkin's lymphoma and non-Hodgkin's lymphoma), brain tumor, neuroblastoma, glioma, thyroid cancer, myelodysplastic syndrome, head and neck cancer, esophageal cancer, gastric cancer, colon cancer, colorectal cancer, breast cancer, ovarian cancer, lung cancer, pancreatic cancer, liver cancer, gallbladder cancer, skin cancer, malignant melanoma, renal cancer, renal pelvic and ureteral cancer, bladder cancer, uterine cancer, testicular cancer, and prostatic cancer. Preferred examples include non-small-cell lung cancer, pancreatic cancer, endometrial cancer, brain tumor, bile duct cancer, colon cancer, breast cancer, ovarian cancer, and prostatic cancer.

Examples of the fibrosis and inflammation include hepatic fibrosis, renal fibrosis, pulmonary fibrosis, scleroderma/systemic sclerosis, myelofibrosis, endomyocardial fibrosis, hepatitis (nonalcoholic steatohepatitis, alcoholic hepatitis, drug-induced hepatitis, autoimmune hepatitis, and primary biliary cirrhosis), diabetic nephropathy, membranoproliferative glomerulonephritis, focal glomerulosclerosis, IgA nephropathy, membranous nephropathy, light chain deposition disease, lupus nephritis, cryoglobulinemic nephritis, HIV-associated nephritis, purpura nephritis, membranoproliferative nephritis, endocapillary proliferative nephritis, mesangial proliferative nephritis, crescentic nephritis, interstitial nephritis, hypertensive nephrosclerosis, anti-GBM nephritis (Goodpasture syndrome), HCV, HBV-associated nephropathy, ANCA nephritis, Alport's syndrome, chronic pancreatitis, rheumatoid arthritis, atherosclerosis, Crohn's disease, ulcerative colitis, and multiple sclerosis.

The compounds or salts thereof according to the present invention can be formulated by conventional methods into tablets, powders, fine granules, granules, coated tablets, capsules, syrups, troches, inhalations, suppositories, injections, ointments, ophthalmic ointments, ophthalmic preparations, nasal preparations, ear preparations, cataplasms, lotions, and the like. Commonly used excipients, binding agents, lubricants, colorants, corrigents; and as necessary, stabilizers, emulsifiers, absorption promoters, surfactants, pH adjusters, preservatives, antioxidants, and the like can be used for formulation. They are blended with ingredients commonly used as raw materials in pharmaceutical preparations, and formulated by conventional methods.

For example, oral preparations are manufactured by adding to the compound or a pharmacologically acceptable salt thereof according to the present invention, an excipient, and as necessary, a binding agent, disintegrant, lubricant, colorant, corrigent, and the like, and then formulating them into powder, fine granules, granules, tablets, coated tablets, capsules, and the like by a conventional method.

Examples of these ingredients include animal and vegetable oils such as soybean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil, and polyoxyethylene-polyoxypropylene block copolymer; water-soluble polymers such as hydroxyethylcellulose, polyacrylic acid, carboxyvinyl polymer, polyethylene glycol, polyvinylpyrrolidone, and methylcellulose; lower alcohols such as ethanol and isopropanol; polyhydric alcohols such as glycerol, propylene glycol, dipropylene glycol, and sorbitol; sugars such as glucose and sucrose; inorganic powders such as silicic anhydride, magnesium aluminum silicate, and aluminum silicate; and purified water.

Examples of the excipients include lactose, corn starch, white soft sugar, glucose, mannitol, sorbitol, microcrystalline cellulose, and silicon dioxide.

Examples of the binding agents include polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, polypropylene glycol-polyoxyethylene block polymer, and meglumine.

Examples of the disintegrants include starch, agar, gelatin powder, microcrystalline cellulose, calcium carbonate, sodium bicarbonate, calcium citrate, dextrin, pectin, and carboxymethylcellulose calcium.

Examples of the lubricants include magnesium stearate, talc, polyethylene glycol, silica, and hydrogenated vegetable oil.

Colorants used are approved for addition into pharmaceuticals. Corrigents used are cocoa powder, peppermint camphor, empasm, mentha oil, borneol, powdered cinnamon bark, and the like.

By all means, these tablets and granules may be sugar-coated or appropriately coated with something else as necessary. Liquid preparations such as syrups and injectable preparations are manufactured by adding a pH adjuster, solubilizer, tonicity adjusting agent, or such, and as necessary, a solubilizing agent, stabilizer, or such to the compound or a pharmacologically acceptable salt thereof according to the present invention, followed by formulation using a conventional method.

The method of manufacturing external preparations is not limited, and they can be manufactured by conventional methods. Specifically, various raw materials commonly used for pharmaceuticals, quasi drugs, cosmetics, and such can be used as base materials for formulation. Specific examples of the base materials used include raw materials such as animal and vegetable oils, mineral oils, ester oils, waxes, higher alcohols, fatty acids, silicone oil, surfactants, phospholipids, alcohols, polyhydric alcohols, water-soluble polymers, clay minerals, and purified water. Further, pH adjusters, antioxidants, chelators, preservatives and fungicides, colorants, flavoring ingredients, and the like may be added as necessary. The base materials for external preparations according to the present invention are not limited to these materials.

Ingredients such as ingredients having a differentiation-inducing effect, blood flow promoters, bactericides, anti-inflammatory agents, cell activators, vitamins, amino acids, humectants, and keratolytic agents may also be blended as necessary. The aforementioned base materials are added in an amount to yield a concentration commonly set for the manufacture of external preparations.

The mode of administering the compounds or salts thereof, or solvates of the compounds or salts according to the present invention is not particularly limited, and they may be orally or parenterally administered by methods commonly used. For example, they can be administered after they are formulated into preparations such as tablets, powders, granules, capsules, syrups, troches, inhalations, suppositories, injections, ointments, ophthalmic ointments, ophthalmic preparations, nasal preparations, ear preparations, cataplasms, or lotions.

The dosage of the medicine according to the present invention can be appropriately selected depending on the symptom severity, age, sex, body weight, mode of administration, type of salt, specific type of the disease, and such.

Although the dosage varies significantly according to the type of the disease, symptom severity, patient's age, sex, and drug sensitivity, and such, the dosage is usually about 0.03 to 1000 mg, preferably 0.1 to 500 mg, and more preferably 0.1 to 100 mg per day for adults, and is administered in one to several doses a day. For injections, the dosage is usually about 1 µg/kg to 3000 µg/kg, preferably about 3 µg/kg to 1000 µg/kg.

In the manufacturing of the compounds according to the present invention, raw material compounds and various reagents may form salts, hydrates, or solvates; and all vary depending on the starting material, solvent used, and such, and there is no particular limitation as long as they do not inhibit the reaction.

The solvent used also varies depending on the starting material, reagent, and such, and is not particularly limited as long as it does not inhibit the reaction and dissolves the starting material to a certain extent.

Various isomers (e.g., geometric isomers, optical isomers based on asymmetric carbons, rotamers, stereoisomers, and tautomers) can be purified and isolated using common separation means, e.g., recrystallization, diastereomeric salt methods, enzymatic resolution methods, and various chromatography methods (e.g., thin-layer chromatography, column chromatography, high performance liquid chromatography, and gas chromatography).

When the compounds of the present invention are obtained as free forms, they can be converted into salts or solvates of the compounds by conventional methods. When the compounds of the present invention are obtained as salts or solvates of the compounds, they can also be converted into free forms of the compounds by conventional methods.

The compounds according to the present invention can be isolated and purified by applying common chemical operations such as extraction, concentration, evaporation, crystallization, filtration, recrystallization, and various chromatographic methods.

All prior art documents cited herein are incorporated by reference.

General production methods for the compounds of the present invention and examples thereof will be shown below.

Compounds of the present invention can be synthesized by various methods, some of which will be described with reference to the following schemes. The schemes are illustrative, and the present invention is not limited to only the chemical reactions and conditions explicitly indicated. Although some substituents may be excluded in the following schemes for the sake of clarity, such exclusion is not intended to limit the disclosure of the schemes. Representative compounds of the present invention can be synthesized using appropriate intermediates, known compounds, and reagents.

Abbreviations generally used in the General production methods and Examples below, and the names of reagents and solvents corresponding to the chemical formulas will be described below.

$Boc_2O$ Di-t-butyl dicarbonate
BPO Benzoyl peroxide
BuPAd2 Butyldi-1-adamantylphosphine
DBU 1,8-Diazabicyclo[5.4.0]-7-undecene
DCM Dichloromethane
DIPEA N,N-Diisopropylethylamine
DMF Dimethylformamide
DMAP N,N-Dimethyl-4-aminopyridine
DMSO Dimethyl sulfoxide
EtOH Ethanol
2-PrOH 2-Propanol
EtOAc Ethyl acetate
HATU O-(7-Azabenzotriazol-1-yl)-N,N,N',N'-tetramethyluronium hexafluorophosphate
HBTU O-(Benzotriazol-1-yl)-N,N,N',N'-tetramethyluronium hexafluorophosphate
HOBT 1-Hydroxybenzotriazole
m-CPBA m-Chloroperbenzoic acid
MeOH Methanol
NMP N-Methylpyrrolidone
NBS N-Bromosuccinimide
NCS N-Chlorosuccinimide
NIS N-iodosuccinimide
MeOH Methanol
PTSA p-Toluenesulfonic acid
RuPhos 2-Dicyclohexylphosphino-2',6'-di-1-propoxy-1,1'-biphenyl
TBME tert-Butyl methyl ether
TEA Triethylamine
TFA Trifluoroacetic acid
THF Tetrahydrofuran
WSCDI 1-Ethyl-3-(3-dimethylaminopropyl)carbodiimide hydrochloride
XantPhos 4,5-Bis(diphenylphosphino)-9,9-dimethylxanthene X-Phos 2',4',6'-Triisopropyl-2-(dicyclohexylphosphino)biphenyl Production Method I The method is a method for forming a backbone of general formula (I), where A represents formula (1); Q represents NH; $R^4$ represents a sulfanyl group or a sulfonyl group; and $A^6$ represents CH (i.e., $R^6$ is H).

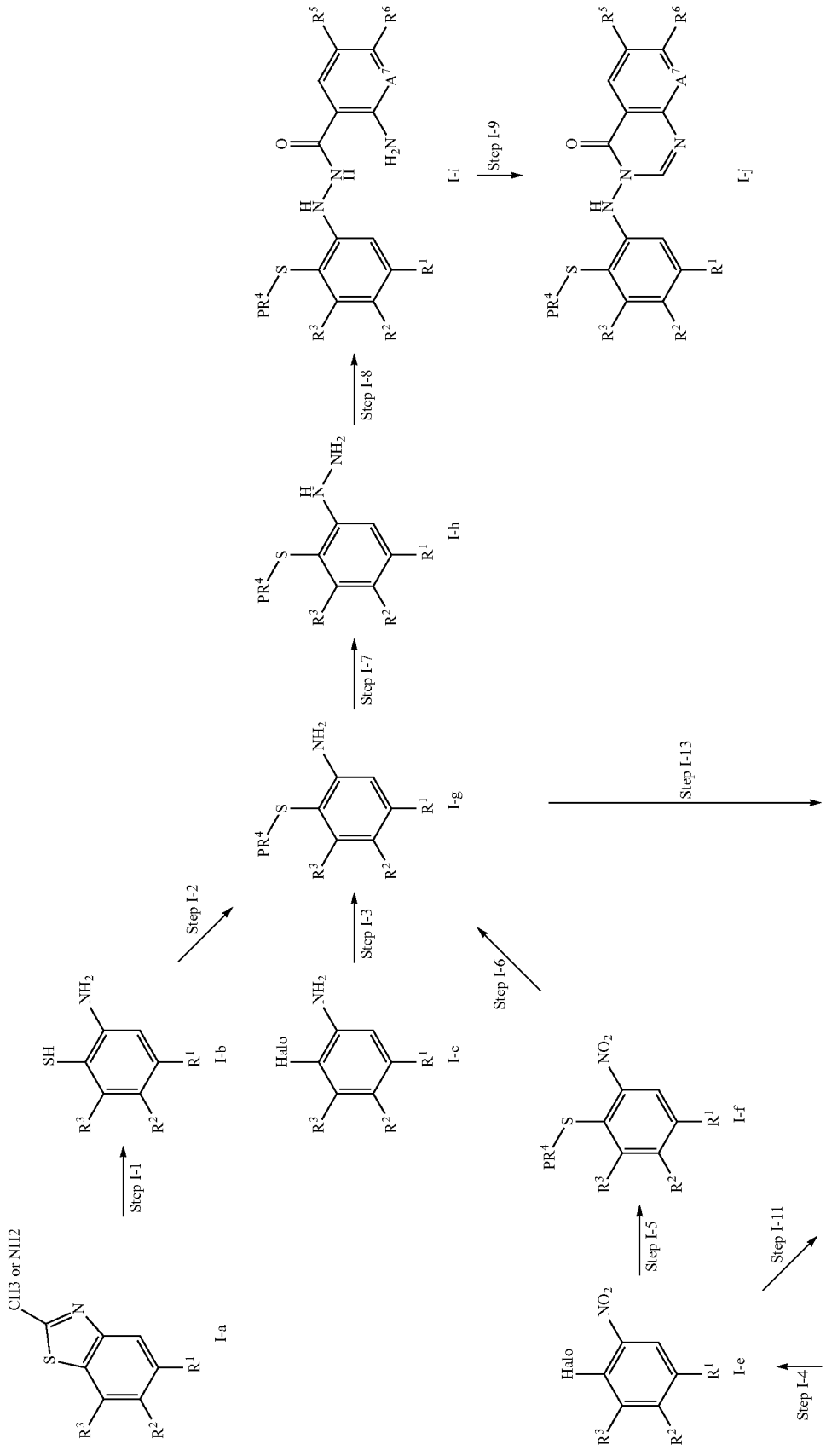

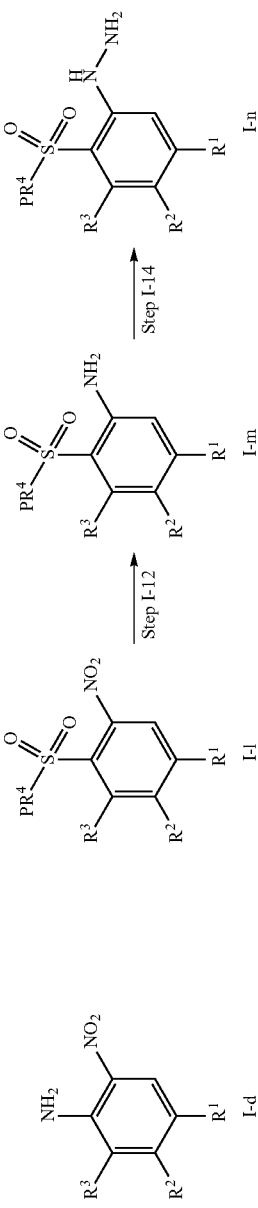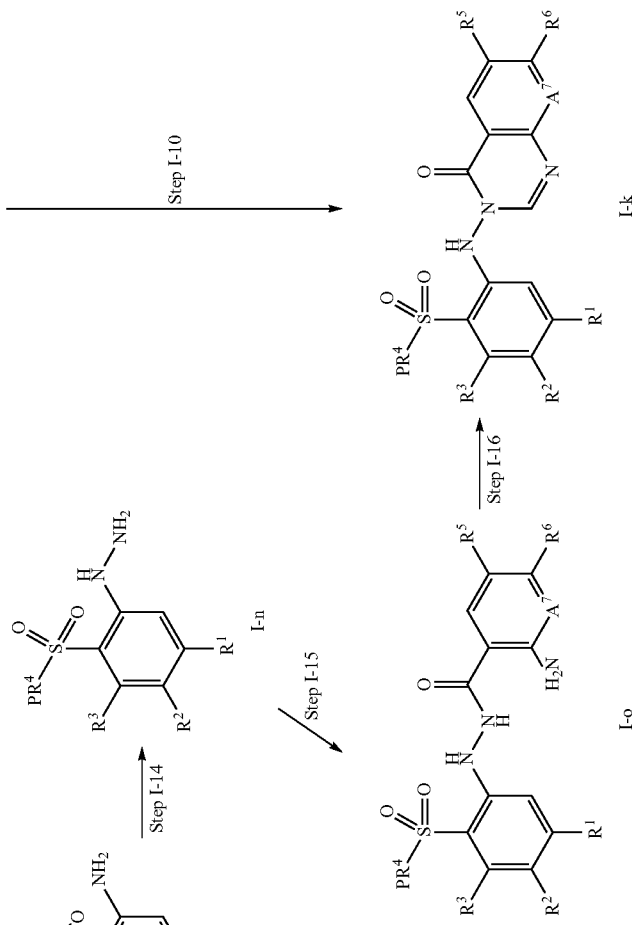

Step I-1

The step is cleavage of the thiazole ring of a benzothiazole derivative I-a by hydrolysis. This step can be performed by hydrolyzing the benzothiazole derivative I-a by reaction with an inorganic base under heating. The step can be performed using, for example, the method of J. Med. Chem. 2002, 45, 2229-2239. Examples of the inorganic base include sodium hydroxide, lithium hydroxide, and potassium hydroxide. Sodium hydroxide is preferred. Examples of the solvent include ethylene glycol, water, dimethoxyethane, and mixed solvents thereof. A mixed solvent of ethylene glycol and water is preferred. The heating is preferably performed at 100° C. or higher.

Step I-2

The step is alkylation of a thiophenol derivative I-b. This step can be performed by reacting the thiophenol derivative I-b with an alkylating agent which corresponds to $PR^4$ in the presence of a base and a phase-transfer catalyst. Examples of the alkylating agent include alkyl iodides, alkyl bromides, alkyl triflates, and alkyl mesylates. Alkyl iodides such as ethyl iodide are preferred. Examples of the base include inorganic bases such as potassium carbonate, sodium carbonate, cesium carbonate, and lithium carbonate; and organic bases such as DBU, t-BuOK, LDA, LiHMDS, and N,N-dimethyl-4-aminopyridine. Cesium carbonate, potassium carbonate, and DBU are preferred. Examples of the phase-transfer catalyst include tetrabutylammonium iodide and tetrabutylammonium bromide. Examples of the solvent include aprotic polar solvents and ether solvents. DMF and THF are preferred.

Step I-3

The step is sulfanylation of a halobenzene derivative I-c. This step can be performed by reacting the halobenzene derivative I-c with a metal alkyl/aryl thiolate which corresponds to $PR^4$ under heating with reference to, for example, the method described in a patent (WO2009131245). Examples of the metal alkyl/aryl thiolate include sodium ethanethiolate, sodium methanethiolate, potassium ethanethiolate, and sodium benzenethiolate. Examples of the solvent include DMF, DMA, DMSO, dichloromethane, THF, acetonitrile, and mixtures thereof. DMF is preferred. The heating is preferably performed at 50° C. to 160° C. It is more effective to use microwave. This step can also be performed by reacting the halobenzene derivative I-c with an alkyl- or arylthiol reagent which corresponds to $PR^4$ under basic conditions.

Step I-4

The step is iodination of a nitroaniline derivative I-d. This step can be performed by converting the nitroaniline derivative I-d to a diazonium salt using a nitrite under acidic conditions (Griess reaction), and then reacting it with a metal iodide without isolation (Sandmeyer reaction). The step can be performed by referring to, for example, the method described in a United States International patent publication (US2007/0129334). The nitrite used for the conversion to a diazonium salt is preferably sodium nitrite. Examples of the acid include sulfuric acid, hydrochloric acid, methanesulfonic acid, and TFA. Hydrochloric acid or sulfuric acid is preferred. Examples of the solvent here include polar solvents such as trifluoroethanol, DMF, acetonitrile, acetic acid, and water. Water is preferred. Examples of the metal iodide include potassium iodide, sodium iodide, and lithium iodide. Potassium iodide is preferred.

Step I-5

The step is sulfanylation of a nitroiodobenzene derivative I-e by producing a carbon-sulfur bond. This step can be performed by reacting the nitroiodobenzene derivative I-e with an alkylthiol or arylthiol reagent which corresponds to $PR^4$ in the presence of a base. Examples of the thiol reagent include acyclic alkylthiols such as methanethiol, ethanethiol, n-propylthiol, and i-propylthiol; cyclic alkylthiols such as cyclopentylthiol; and arylthiols such as phenylthiol. Examples of the base include inorganic bases such as potassium carbonate, sodium carbonate, cesium carbonate, calcium carbonate, and sodium hydride; and organic bases such as triethylamine, t-BuOK, LDA, LiHMDS, N,N-dimethyl-4-aminopyridine, and DBU. Potassium carbonate, sodium carbonate, and triethylamine are preferred. Examples of the solvent include DMF, DMA, DMSO, dichloromethane, THF, acetonitrile, and mixtures thereof. DMF is preferred. This step can also be performed by reacting the nitroiodobenzene derivative I-e with a metal alkyl/aryl thiolate which corresponds to $PR^4$ under heating in a polar solvent such as DMF as in the method described in WO 2009/131245. Further, this step can be performed by an alternative method of reacting the nitroiodobenzene derivative I-e with an acyclic alkylthiol which corresponds to $PR^4$ by heating in a polar solvent such as 1,4-dioxane in the presence of a Pd catalyst, a Pd catalyst ligand, and a base as in the method described in WO 2006/038741. Here, the Pd catalyst is preferably $Pd_2(dba)_3$, the Pd catalyst ligand is preferably Xantphos, the base is preferably N,N-diisobutylethylamine, and the solvent is preferably 1,4-dioxane.

Step I-6

The step is amination (reduction) of a sulfanylnitrobenzene derivative I-f. This step can be performed by reacting the sulfanylnitrobenzene derivative I-f with a metal reducing agent under acidic conditions. The step can be performed by referring to, for example, the method described in a patent (EP 1065204). Examples of the reducing agent include iron powder, zinc powder, and tin reagents. Iron powder and zinc powder are preferred. Examples of the acid to be added include ammonium chloride, acetic acid, and hydrochloric acid. Ammonium chloride and hydrochloric acid are preferred. Examples of the solvent include protic alcohol solvents, water, and mixed solvents thereof. A mixed solvent of an alcohol solvent and water is preferred.

Step I-7

The step is conversion of a sulfanylaniline derivative I-g to a hydrazine. This step can be performed by converting the sulfanylaniline derivative I-g to a diazonium salt using a nitrite under strongly acidic conditions (Griess reaction), and then reacting it with a metal reducing agent without isolation. The nitrite used for the conversion to a diazonium salt is preferably sodium nitrite. The metal reducing agent used for the reduction of a diazonium salt to a phenylhydrazine is preferably tin(II) chloride. Examples of the solvent include protic acidic solvents. An aqueous hydrochloric acid solution is preferred.

Step I-8

The step is amidation of a sulfanylphenylhydrazine derivative I-h. This step can be performed by reacting the sulfanylphenylhydrazine derivative I-h with a corresponding carboxylic acid in the presence of a condensing agent and a base. A condensing additive may be added as necessary. Examples of the condensing agent include WSCDI, HBTU, HATU, BOP, DCC, DPPA, and DMT-MM. WSCDI, HBTU, and HATU are preferred. Examples of the base include tertiary amines. N,N-Diisobutylethylamine is preferred. Examples of the condensing additive under the above conditions include HOBT and HOOBT. HOBT is preferred. Examples of the solvent include aprotic solvents. Dichloromethane, THF, DMF, and such are preferred.

Step I-9

The step is construction of a quinazolinone ring of a sulfanylketohydrazine derivative I-i. This step can be performed by reacting the sulfanylketohydrazine derivative I-i with formic acid and trialkyl orthoformate by heating. The trialkyl orthoformate is preferably trimethyl orthoformate. The heating is preferably performed under reflux and it is more effective to use microwave. The reaction also proceeds by reacting the sulfanylketohydrazine derivative I-i only with the formic acid with heat in the absence of trialkyl orthoformate.

Step I-10

The step is oxidation of a sulfanylquinazolinone derivative I-j to a sulfonyl derivative. This step can be performed by reacting the sulfanylquinazolinone derivative I-j with an oxidizing agent. Examples of the oxidizing agent include peracids such as mCPBA, tBuOOH, $H_2O_2$, oxone, and potassium permanganate. It is preferably two or more equivalents of mCPBA. Examples of the solvent include aprotic solvents. Dichloromethane and ethyl acetate are preferred.

Step I-11

The step is conversion of the nitroiodobenzene derivative I-e to a nitroalkylsulfonylbenzene derivative. This step can be performed by reacting the nitroiodobenzene derivative I-e with the sodium salt of an alkylsulfinic acid by heating. Examples of the solvent include aprotic solvents. DMF and DMSO are preferred. The heating temperature is preferably 60° C. or higher.

Step I-12

The step is amination (reduction) of a nitroalkylsulfonylbenzene derivative I-1. This step can be performed by reacting the nitroalkylsulfonylbenzene derivative I-1 with a metal reducing agent under acidic conditions. The conditions to be selected in this step such as the reaction reagent and solvent are the same as those in Step I-6.

Step I-13

The step is oxidation of the sulfanylaniline derivative I-g to a sulfoxide derivative. This step can be performed by reacting the sulfanylaniline derivative I-g with an oxidizing agent. The conditions to be selected in this step such as the reaction reagent and solvent are the same as those in Step I-10.

Step I-14

The step is conversion of a sulfonylaniline derivative I-m to a hydrazine. This step can be performed by converting the sulfonylaniline derivative I-m to a diazonium salt using a nitrite under strongly acidic conditions (Griess reaction), and then reacting it with a metal reducing agent without isolation. The conditions to be selected in this step such as the reaction reagent and solvent are the same as those in Step I-7.

Step I-15

The step is amidation of a sulfonylphenylhydrazine derivative I-n. This step can be performed by reacting the sulfonylphenylhydrazine derivative I-n with a corresponding carboxylic acid in the presence of a condensing agent and a base. A condensing additive may be added as necessary. The conditions to be selected in this step such as the reaction reagent and solvent are the same as those in Step I-8.

Step I-16

The step is construction of a quinazolinone ring of a sulfonylketohydrazine derivative I-o. This step can be performed by reacting the sulfonylketohydrazine derivative I-o with formic acid and trialkyl orthoformate by heating. The conditions to be selected in this step such as the reaction reagent and solvent are the same as those in Step I-9.

Production Method II

The method is a method for forming a backbone of general formula (I), where A represents formula (1); Q represents NH; $R^4$ represents an alkyl group; and $A^6$ represents CH (i.e., $R^6$ is H).

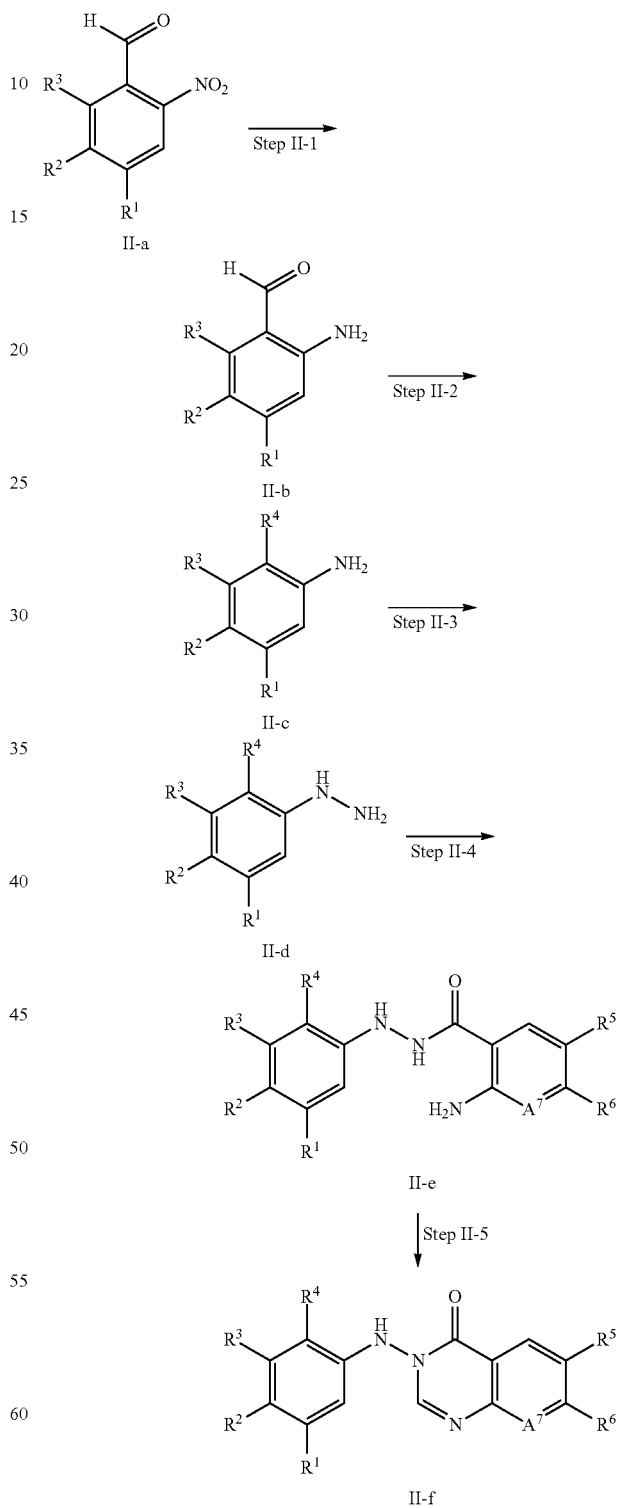

Step II-1

The step is amination (reduction) of a nitrobenzaldehyde derivative II-a. This step can be performed by reacting the nitrobenzaldehyde derivative II-a with a metal reducing agent under acidic conditions. The conditions to be selected in this step such as the reaction reagent and solvent are the same as those in Step I-6.

Step II-2

The step is formation of a carbon-carbon bond from an aminobenzaldehyde derivative II-b. This step can be performed by reacting the aminobenzaldehyde derivative II-b with tosylhydrazine by heating to convert it in situ to a tosylhydrazone derivative, and then carrying out a reductive coupling without isolating the tosylhydrazone derivative under heating conditions using an alkylboronic acid which corresponds to $R^4$ in the presence of a base. The step can be performed by referring to, for example, the method described in Nature Chemistry, 1(6), 494-499, 2009. Examples of the base used for the reductive coupling include inorganic bases such as potassium carbonate, sodium carbonate, tripotassium phosphate, and tetra-n-butylammonium fluoride. Potassium carbonate is preferred. Examples of the solvent include 1,4-dioxane, THF, and toluene. 1,4-dioxane is preferred. The heating temperature is preferably 80° C. or higher.

Step II-3

The step is conversion of an alkylaniline derivative II-c to a hydrazine. This step can be performed by converting the alkylaniline derivative II-c to a diazonium salt using a nitrite under strongly acidic conditions (Griess reaction), and then reacting it with a metal reducing agent without isolation. The conditions to be selected in this step such as the reaction reagent and solvent are the same as those in Step I-7.

Step II-4

The step is amidation of a phenylhydrazine derivative II-d. This step can be performed by reacting the phenylhydrazine derivative II-d with a corresponding carboxylic acid in the presence of a condensing agent and a base. A condensing additive may be added as necessary. The conditions to be selected in this step such as the reaction reagent and solvent are the same as those in Step I-8.

Step II-5

The step is construction of a quinazolinone ring of a phenylketohydrazine derivative II-e.

This step can be performed by reacting the phenylketohydrazine derivative II-e with formic acid and trialkyl orthoformate by heating. The conditions to be selected in this step such as the reaction reagent and solvent are the same as those in Step I-9.

Production Method III

The method is a method for forming a backbone of general formula (I), where A represents formula (1); Q represents $CH_2$; $R^4$ represents a sulfanyl group or a sulfonyl group; and $A^6$ represents CH (i.e., $R^6$ is H).

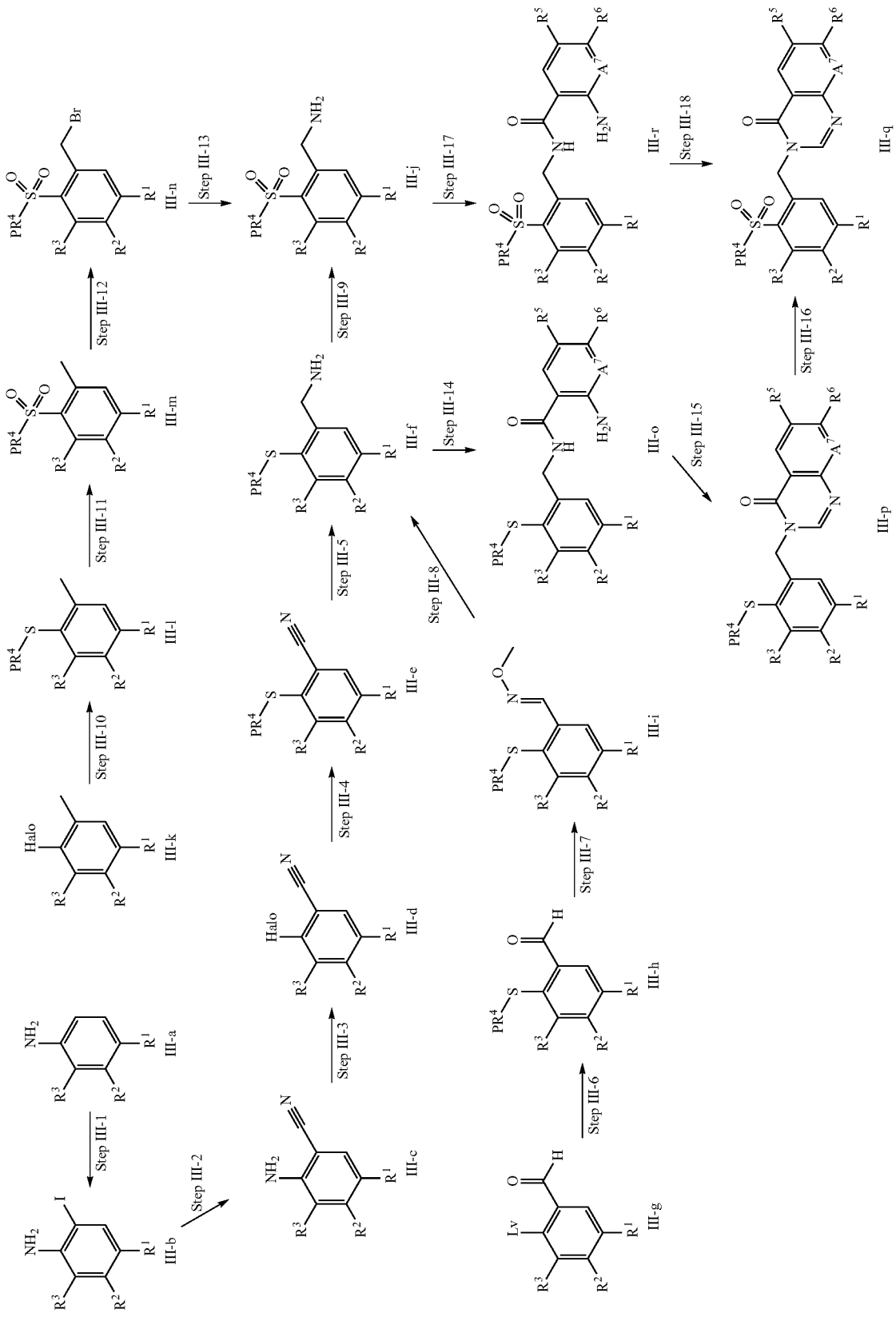

Step III-1

The step is halogenation (iodination) of an aniline derivative III-a by electrophilic substitution reaction. This step can be performed by reacting the aniline derivative III-a with iodine ($I_2$) in the presence of sodium hydrogen carbonate. This step can be performed using, for example, the method of Org. Synth., Coll. Vol. 2, p. 347 (1943); Vol. 11, p. 62 (1931). Examples of the solvent include alcohols, water, and mixed solvents thereof. An aqueous ethanol solution is preferred.

Step III-2

The step is cyanation of an iodoaniline derivative III-b by nucleophilic substitution reaction. This step can be performed by reacting the iodoaniline derivative III-b with a transition-metal cyanide by heating. This step can be performed using, for example, the method of J. Org. Chem., 26, 2522 (1961). The transition-metal cyanide is preferably copper(I) cyanide. Examples of the solvent include aromatic amines such as pyridine and quinoline; and polar aprotic solvents such as DMF, NMP, and HMPA. DMF is preferred. The heating condition is preferably 150° C. or higher or heating under reflux.

Step III-3

The step is iodination of a cyanoaniline derivative III-c. This step can be performed by converting the cyanoaniline derivative III-c to a diazonium salt using a nitrite under acidic conditions (Griess reaction), and then reacting it with a metal iodide without isolation (Sandmeyer reaction). The nitrite used for the conversion to a diazonium salt is preferably sodium nitrite. Examples of the acid include sulfuric acid, hydrochloric acid, mesylic acid, and TFA. TFA or sulfuric acid is preferred. Examples of the solvent here include polar solvents such as trifluoroethanol, DMF, and acetonitrile. Trifluoroethanol is preferred. Examples of the metal iodide include potassium iodide, sodium iodide, and lithium iodide. Potassium iodide is preferred.

Step III-4

The step is sulfanylation of a halobenzonitrile derivative III-d by producing a carbon-sulfur bond. This step can be performed by reacting the halobenzonitrile derivative III-d with an alkylthiol or arylthiol reagent which corresponds to $PR^4$ in the presence of a base. Examples of the thiol reagent include acyclic alkylthiols such as methanethiol, ethanethiol, n-propylthiol, and i-propylthiol; cyclic alkylthiols such as cyclopentylthiol; and arylthiols such as phenylthiol. Examples of the base include inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. Examples of the solvent include DMF, DMA, DMSO, dichloromethane, THF, acetonitrile, and mixtures thereof. DMF is preferred. This step can also be performed by reacting the halobenzonitrile derivative III-d with a metal alkyl/aryl thiolate which corresponds to $PR^4$ under heating in a polar solvent such as DMF as in the method described in a patent (WO2009131245). Further, this step can be performed by an alternative method of reacting the halobenzonitrile derivative III-d with an acyclic alkylthiol which corresponds to $PR^4$ by heating in a polar solvent such as 1,4-dioxane in the presence of a Pd catalyst, a Pd catalyst ligand, and a base as in the method described in a patent (WO2006038741). Here, the Pd catalyst is preferably $Pd_2(dba)_3$, the Pd catalyst ligand is preferably Xantphos, the base is preferably N,N-diisobutylethylamine, and the solvent is preferably 1,4-dioxane.

Step III-5

The step is reduction of an alkylsulfanylbenzonitrile derivative III-e. This step can be performed by reducing the nitrile group of the alkylsulfanylbenzonitrile derivative III-e by reaction with a reducing agent. Examples of the reducing agent include metal reducing agents such as lithium aluminum hydride, diisobutylaluminum hydride, Selectride, Super-Hydride, and sodium borohydride-nickel chloride; and boron reducing agents such as borane-THF complex and borane-dimethyl sulfide complex. Lithium aluminum hydride and borane-THF complex are preferred. Examples of the solvent include THF, dimethyl ether, and dimethoxyethane. THF is preferred.

Step III-6

The step is sulfanylation of an aldehyde III-g by producing a carbon-sulfur bond. This step can be performed by reacting the aldehyde III-g with a metal alkyl/aryl thiolate which corresponds to $PR^4$ under heating by referring to, for example, the method described in a patent (WO2009131245). Examples of the metal alkyl/aryl thiolate include sodium ethanethiolate, sodium methanethiolate, and potassium ethanethiolate. Examples of the solvent include DMF, DMA, DMSO, dichloromethane, THF, acetonitrile, and mixtures thereof. DMF is preferred. The heating is preferably performed at 50° C. to 90° C. This step can also be performed by reacting the aldehyde III-g with an alkyl- or arylthiol reagent which corresponds to $PR^4$ in the presence of a base as in the method described in Step I-5. Further, this step can be performed by an alternative method of reacting the aldehyde III-g with an acyclic alkylthiol which corresponds to $PR^4$ by heating in a polar solvent such as 1,4-dioxane in the presence of a Pd catalyst, a Pd catalyst ligand, and a base as in the method described in a patent (WO2006038741).

Step III-7

The step is oximation of an alkylsulfanylbenzaldehyde derivative III-h. This step can be performed by reacting the alkylsulfanylbenzaldehyde derivative III-h with O-methylhydroxylamine hydrochloride in the presence of a base. Examples of the base include pyridine, triethylamine, N,N-diisobutylethylamine, and N,N-dimethyl-4-aminopyridine. Pyridine is preferred. Examples of the solvent used for the reaction include dichloromethane, THF, acetonitrile, and CPME. The solvent need not be used when pyridine is used as a base.

Step III-8

The step is reduction of an O-methyl oxime derivative III-i. This step can be performed by reducing the O-methyl oxime derivative III-i with a boron reagent under heating and then treating with an acid. Examples of the boron reagent include boron reducing agents such as borane-THF complex, borane-dimethyl sulfide complex, thexylborane, and 9-BBN. Borane-THF complex is preferred. Examples of the acid include hydrochloric acid solutions. An aqueous hydrochloric acid solution is preferred. Examples of the solvent include aprotic solvents. THF is preferred. The heating can be performed at 50° C. to 90° C.

Step III-9

The step is conversion of a sulfanylbenzylamine derivative III-f to a sulfonyl in three steps. This step can be performed by protecting the free primary amine of the sulfanylbenzylamine derivative III-f with a Boc group or the like, converting the derivative to a sulfone by oxidation with a peracid such as mCPBA, tBuOOH, $H_2O_2$, oxone, or potassium permanganate, and deprotecting the Boc or such by treatment with hydrochloric acid, with reference to the method described in a patent (WO2009131245). The protecting group is preferably a Boc group, and the oxidizing agent is preferably two or more equivalents of mCPBA. The resulting sulfonylbenzylamine derivative III-j may be isolated as a hydrochloride.

Step III-10

The step is sulfanylation of a halobenzene derivative III-k by producing a carbon-sulfur bond. This step can be performed by reacting the halobenzene derivative III-k with an alkylthiol or arylthiol reagent which corresponds to $PR^4$ in the presence of a base. The conditions to be selected in this step such as the reaction reagent and solvent are the same as those in Step I-5.

Step III-11

The step is oxidation of a sulfanyltoluene derivative III-l to a sulfonyl. This step can be performed by reacting the sulfanyltoluene derivative III-l with an oxidizing agent. The conditions to be selected in this step such as the reaction reagent and solvent are the same as those in Step I-10.

Step III-12

The step is bromination of a sulfonyltoluene derivative III-m (Wohl-Ziegler reaction).

This step can be performed by reacting the sulfonyltoluene derivative III-m with a brominating agent by heating in the presence of a catalytic amount of a radical initiator. Examples of the brominating agent include NBS and N-bromoimide. NBS is preferred. Examples of the radical initiator include benzoyl peroxide and AIBN. Benzoyl peroxide is preferred. Examples of the solvent include carbon tetrachloride, benzene, cyclohexane, and acetonitrile. Acetonitrile and carbon tetrachloride are preferred. The heating temperature is preferably 70° C. or higher.

Step III-13

The step is amination of a benzyl bromide derivative III-n. This step can be performed by reacting the benzyl bromide derivative III-n with an aminating agent. Examples of the aminating agent include aqueous ammonia, liquid ammonia, and ammonia gas. Aqueous ammonia is preferred. Examples of the solvent include protic alcohol solvents, water, THF, and mixed solvents thereof. Ethanol is preferred. The resulting sulfonylbenzylamine derivative III-j may be isolated as a hydrochloride.

Step III-14

The step is amidation of the sulfanylbenzylamine derivative III-f. This step can be performed by reacting the sulfanylbenzylamine derivative III-f with a corresponding carboxylic acid in the presence of a condensing agent and a base. A condensing additive may be added as necessary. The conditions to be selected in this step such as the reaction reagent and solvent are the same as those in Step I-8.

Step III-15

The step is construction of a quinazolinone ring of a sulfanylamide derivative III-o. This step can be performed by reacting the sulfanylamide derivative III-o with formic acid and trialkyl orthoformate by heating. The conditions to be selected in this step such as the reaction reagent and solvent are the same as those in Step I-9.

Step III-16

The step is oxidation of a sulfanylquinazolinone derivative III-p to a sulfonyl. This step can be performed by reacting the sulfanylquinazolinone derivative III-p with an oxidizing agent. The conditions to be selected in this step such as the reaction reagent and solvent are the same as those in Step I-10.

Step III-17

The step is amidation of the sulfonylbenzylamine derivative III-j. This step can be performed by reacting the sulfonylbenzylamine derivative III-j with a corresponding carboxylic acid in the presence of a condensing agent and a base. A condensing additive may be added as necessary. The conditions to be selected in this step such as the reaction reagent and solvent are the same as those in Step I-8.

Step III-18

The step is construction of a quinazolinone ring of a sulfonylamide derivative III-r. This step can be performed by reacting the sulfonylamide derivative III-r with formic acid and trialkyl orthoformate by heating. The conditions to be selected in this step such as the reaction reagent and solvent are the same as those in Step I-9.

Production Method IV

The method is a method for forming a backbone of general formula (I), where A represents formula (1); Q represents $CH_2$; $R^4$ represents a sulfonyl group; $A^6$ represents $CR^6$; $R^6$ represents $CH_2Y^1Z^1$; and $A^7$ represents CH.

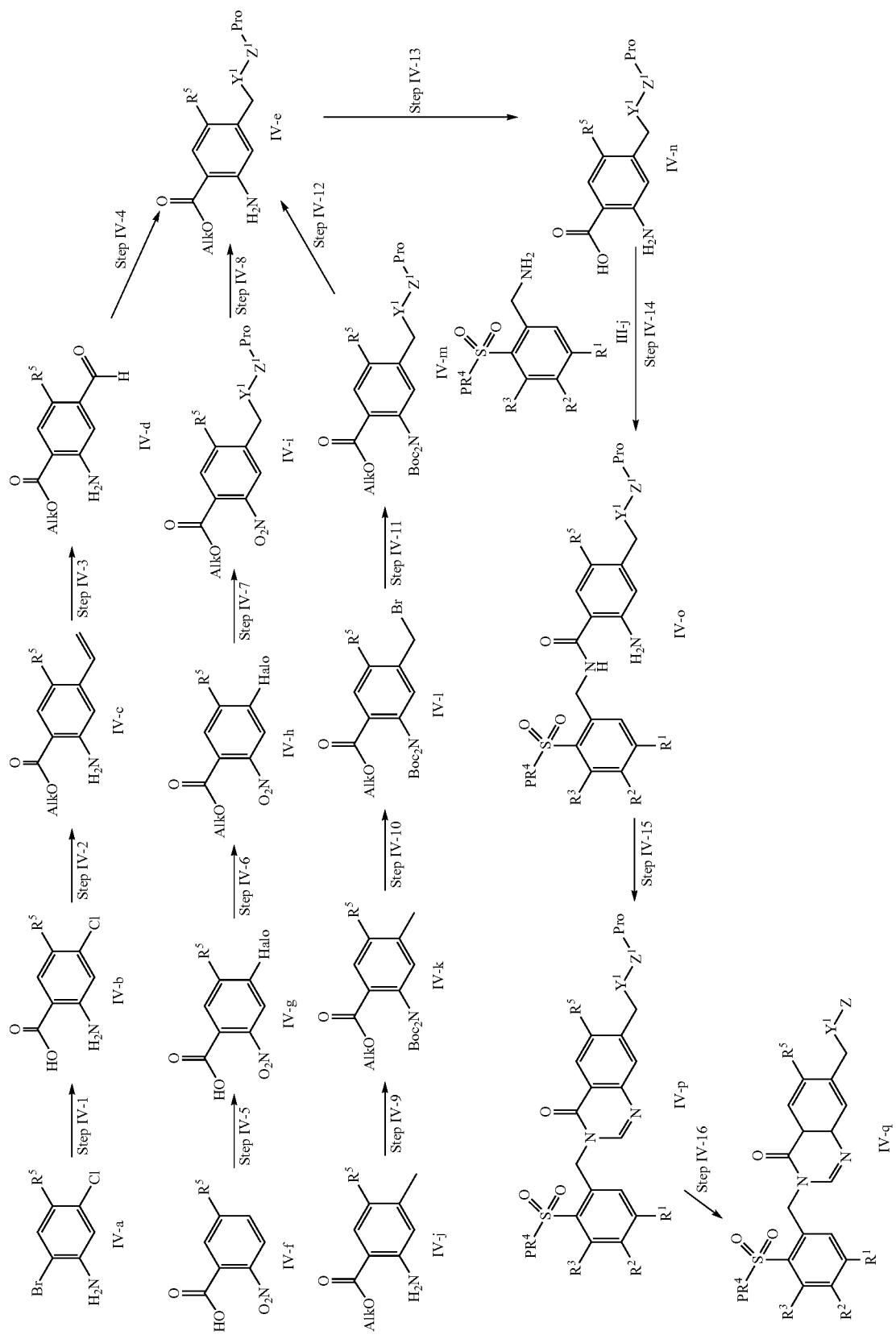

Step IV-1

The step is conversion of a bromoaniline derivative IV-a to a benzoic acid derivative IV-b in three steps. This step can be performed by protecting the amino group of the bromoaniline derivative IV-a with a diBoc group under basic conditions, and isolating and purifying the protected derivative; subsequently transferring the t-butoxycarbonyl group by treatment with n-butyllithium at −78° C.; and further deprotecting both the t-Bu group of the ester and the Boc group of the amine protecting group under acidic conditions. The step is performed by referring to the method of SYNLETT 20 (2005) 3107-3108. Under the diBoc protection conditions, a catalytic amount of 4-dimethylaminopyridine is preferably used, and the solvent can be an aprotic solvent such as a halomethane or ether solvent, and is preferably THF. In the t-butoxycarbonyl transfer, the solvent can be a strongly basic and stable aprotic solvent, and is preferably THF. In the deprotection of the t-Bu and Boc groups, the acid can be hydrochloric acid, sulfuric acid, TFA, or the like, and is preferably TFA; and the solvent is preferably dichloromethane.

Step IV-2

The step is conversion of the benzoic acid derivative IV-b to a vinylbenzoate IV-c in two steps. This step can be performed by carrying out esterification using an alkylating agent under basic conditions, isolation and purification, and subsequent reaction by heating using a Pd catalyst in the presence of a base and a vinylating agent. Examples of the alkylating agent in the esterification include alkyl halides. Alkyl iodides are preferred. Examples of the base include inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. Examples of the solvent include aprotic polar solvents and ether solvents. DMF is preferred. Examples of the Pd catalyst in the vinylation include zerovalent Pd complexes represented by tetrakis(triphenylphosphine) palladium. Palladium acetate using X-Phos or BuPAd2 as a ligand is preferred. Examples of the vinylating agent include potassium vinyltrifluoroborate, vinylboronic acid, and vinylboronates. Potassium vinyltrifluoroborate is preferred. The base is preferably potassium carbonate or cesium carbonate. The solvent is preferably a mixed solvent of toluene and water.

Step IV-3

The step is conversion of the vinylbenzene derivative IV-c to a benzaldehyde derivative IV-d in two steps. This step can be performed by carrying out dihydroxylation of the vinylbenzene derivative IV-c using an osmium reagent, isolation and purification, and subsequent glycol cleavage. The step can be performed by referring to, for example, the method described in a patent (WO2010065760). In the dihydroxylation, the osmium reagent can be osmium tetroxide, AD-mix, or the like, and is preferably AD-mix-α or AD-mix-β. The solvent can be a mixed solvent of a water-soluble solvent and water, and is preferably a mixed solvent of t-BuOH and water. In the glycol cleavage, the oxidizing agent can be sodium metaperiodate, lead tetraacetate, or the like, and is preferably sodium metaperiodate. The solvent can be a mixed solvent of an organic solvent and water, an acetic acid solution, or the like, and is preferably a mixed solvent of TBME and water.

Step IV-4

The step is formation of a C—N bond from the benzaldehyde derivative IV-d by reductive amination. This step can be performed by reacting the benzaldehyde derivative IV-d with a primary or secondary amine which corresponds to $Y^1$—$Z^1$-Pro in the presence of a reducing agent. Examples of the reducing agent include sodium triacetoxyborohydride, sodium cyanoborohydride, and 2-picoline-borane. Sodium triacetoxyborohydride is preferred. Examples of the solvent include halomethane solvents and ether solvents. Chloroform, dichloromethane, and THF are preferred.

Step IV-5

The step is halogenation of a nitrobenzene derivative IV-f. This step can be performed by reacting the nitrobenzene derivative IV-f with a halogenating agent by heating under acidic conditions. Examples of the halogenating agent include N-halosuccinimides, chlorine, bromine, and iodine. Preferably, the reaction is performed using N-halosuccinimide in concentrated sulfuric acid under heating conditions at 60° C. to 90° C.

Step IV-6

The step is esterification of a benzoic acid derivative IV-g. This step can be performed by reacting the benzoic acid derivative IV-g with an alkylating agent in the presence of a base. Examples of the alkylating agent include alkyl halides. Alkyl iodides are preferred. Examples of the base include inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. Examples of the solvent include aprotic polar solvents. DMF is preferred.

Step IV-7

The step is formation of a C—C bond from a halobenzoate derivative IV-h by Suzuki-Molander coupling reaction. This step can be performed by reacting the halobenzoate derivative IV-h with a Moldander reagent (potassium trifluoroborate derivative) which corresponds to $CH_2$—$Y^1$—$Z^1$-Pro by heating in the presence of a palladium reagent and a base. Here, a reagent for palladium ligands is added as necessary. The step can be performed using the method of Acc. Chem. Res. 2007, 40, 275-286, for example. Typical examples of the Pd reagent include palladium acetate, tetrakis(triphenylphosphine) palladium, and a 1,1'-bis(diphenylphosphino)ferrocene-palladium(II) dichloride-dichloromethane complex. Palladium acetate is preferred. Examples of the reagent for palladium ligands include X-Phos, S-Phos, triphenylphosphine, and tricyclohexylphosphine. X-Phos, S-Phos, and $nBuPAd_2$ are preferred. Examples of the base include inorganic bases such as potassium carbonate, sodium carbonate, cesium carbonate, and tripotassium phosphate; and organic amines such as triethylamine, t-butylamine, N,N-diisobutylethylamine, and pyridine. Potassium carbonate and cesium carbonate are preferred. Examples of the solvent include alcohols, toluene, THF, and mixed solvents of these solvents and water. A mixed solvent of THF and water, toluene, and a mixed solvent of toluene and water are preferred.

Step IV-8

The step is amination (reduction) of a nitrobenzene derivative IV-i. This step can be performed by reacting the nitrobenzene derivative IV-i with a metal reducing agent under acidic conditions. The conditions to be selected in this step such as the reaction reagent and solvent are the same as those in Step I-6.

Step IV-9

The step is Boc protection of an amino group of an aniline derivative IV-j with two Boc groups. This step can be performed by reacting the aniline derivative IV-j with a BOC-reagent under basic conditions. Examples of the BOC-reagent include di-tert-butyl dicarbonate, tert-butoxycarbonyl chloride, tert-butoxycarbonyl azide, and 1-tert-butoxycarbonyl triazole. Di-tert-butyl dicarbonate is preferred. Examples of the base include organic amines such as pyridine, triethylamine, and N,N-dimethylaminopyridine and inorganic amines such as potassium carbonate. A mixed base of triethylamine and a catalytic amount of N,N-dimethylaminopyridine is preferred. Various solvents can be exemplified, including dichloromethane, dichloroethane, DMF, THF, acetonitrile, and t-butanol. THF and acetonitrile are preferred.

Step IV-10

The step is bromination of a sulfonyltoluene derivative N-k (Wohl-Ziegler reaction). This step can be performed by reacting the sulfonyltoluene derivative IV-k with a brominating agent by heating in the presence of a catalytic amount of a radical initiator. The conditions to be selected in this step such as the reaction reagent and solvent are the same as those in Step III-12.

Step IV-11

The step is formation of a C—N bond from a benzyl bromide derivative IV-1 by substitution reaction. This step can be performed by reacting the benzyl bromide derivative IV-1 with a primary or secondary amine which corresponds to Y1-Z1-Pro in the presence of a base. Examples of the base include inorganic bases such as potassium carbonate, sodium carbonate, cesium carbonate, calcium carbonate, and sodium hydride; and organic bases such as pyridine, triethylamine, N,N-diisobutylethylamine, N,N-dimethyl-4-aminopyridine, t-BuOK, LDA, LiHMDS, N,N-dimethyl-4-aminopyridine, and DBU. Triethylamine and potassium carbonate are preferred. Examples of the solvent include halomethane solvents, ether solvents, and aprotic polar solvents. Dichloromethane, THF, and DMF are preferred. Heating can be performed at 40° C. to 80° C. when the reaction proceeds slowly.

Step IV-12

The step is deprotection of the Boc groups of a diBoc amine derivative IV-m. This step can be performed by reacting the diBoc amine derivative IV-m under strongly acidic conditions. Examples of the acid include TFA, hydrochloric acid, sulfuric acid, mesylic acid, and Lewis acids. TFA and hydrochloric acid are preferred. Examples of the solvent include dichloromethane, ethyl acetate, 1,4-dioxane, acetonitrile, water, and mixed solvents thereof. Dichloromethane, ethyl acetate, and 1,4-dioxane are preferred.

Step IV-13

The step is saponification (hydrolysis) of a benzoate derivative IV-e. This step can be performed by reacting the benzoate derivative IV-e with an inorganic base. Examples of the inorganic base include sodium hydroxide, lithium hydroxide, potassium hydroxide, calcium hydroxide, and barium hydroxide. Sodium hydroxide and potassium hydroxide are preferred. Examples of the solvent include alcohols, water, and mixed solvents thereof. An aqueous ethanol solution and an aqueous methanol solution are preferred. Heating can be performed at 40° C. to 60° C. when the reaction is slow.

Step IV-14

The step is amidation of an anthranilic acid derivative N-n. This step can be performed by reacting the anthranilic acid derivative IV-n with a corresponding benzylamine III-j in the presence of a condensing agent and a base. A condensing additive may be added as necessary. The conditions to be selected in this step such as the reaction reagent and solvent are the same as those in Step I-8.

Step IV-15

The step is construction of a quinazolinone ring of the sulfonylphenylamide derivative IV-o. This step can be performed by reacting the sulfonylphenylamide derivative IV-o with formic acid and trialkyl orthoformate by heating. The conditions to be selected in this step such as the reaction reagent and solvent are the same as those in Step I-9.

Step IV-16

The step is deprotection of the amine protecting group of a protected amine derivative IV-p. Here, the protecting group mainly refers to a Boc group. This step can be performed by reacting the protected amine derivative IV-p under strongly acidic conditions. Examples of the acid include TFA, hydrochloric acid, sulfuric acid, mesylic acid, and Lewis acids. TFA and hydrochloric acid are preferred. Examples of the solvent include dichloromethane, ethyl acetate, 1,4-dioxane, acetonitrile, water, and mixed solvents thereof. Dichloromethane, ethyl acetate, and 1,4-dioxane are preferred.

Production Method V

The method is a method for forming a backbone of general formula (I), where A represents formula (1); Q represents NH; $R^4$ represents a sulfonyl group; $A^6$ represents $CR^6$; $R^6$ represents $CH_2Y^1Z^1$; and $A^7$ represents CH.

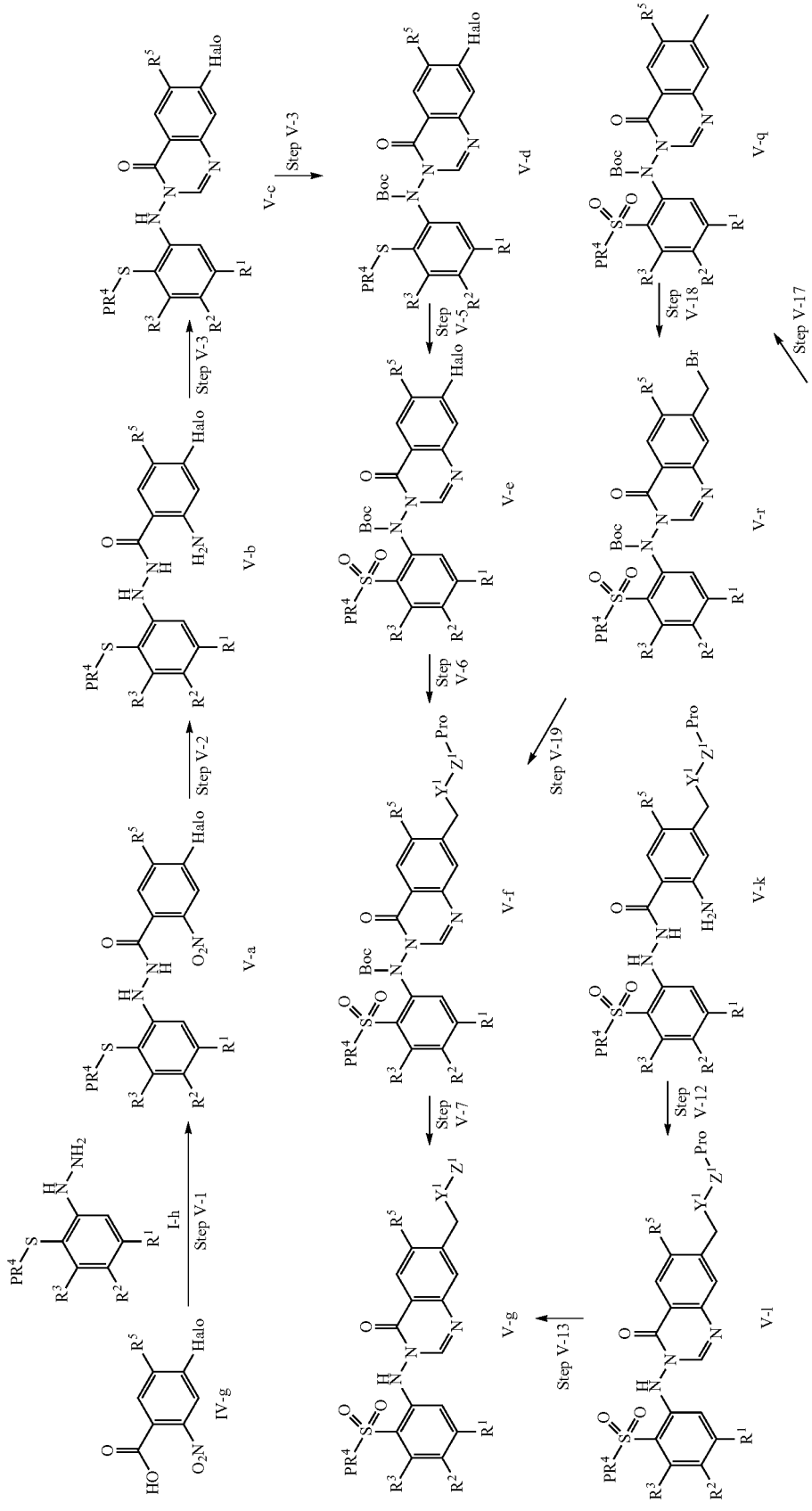

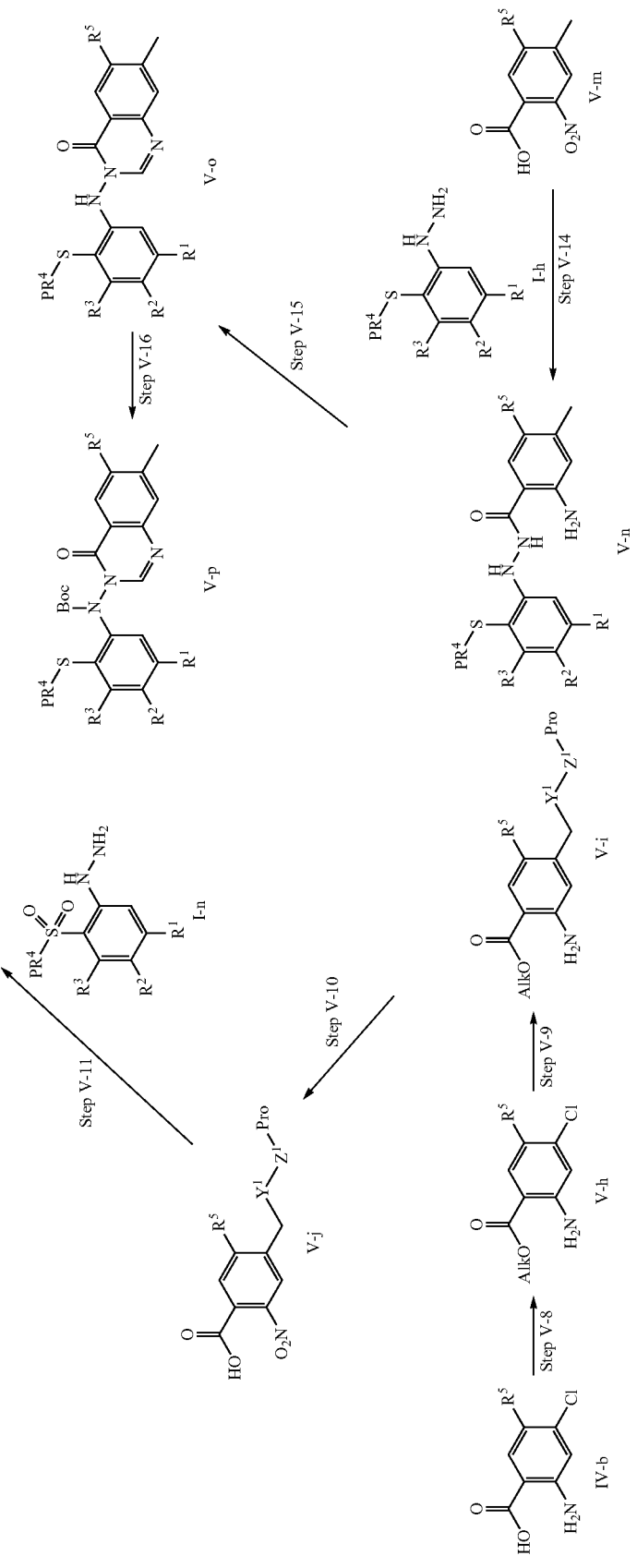

Step V-1
The step is condensation (amidation) of the nitrobenzoic acid derivative IV-g. This step can be performed by reacting the nitrobenzoic acid derivative IV-g with a corresponding hydrazine I-h in the presence of a condensing agent and a base. A condensing additive may be added as necessary. The conditions to be selected in this step such as the reaction reagent and solvent are the same as those in Step I-8.

Step V-2
The step is reduction of a nitro group of a nitrobenzene derivative V-a to an amino group. This step can be performed by reacting the nitrobenzene derivative V-a with a metal reducing agent under acidic conditions. The conditions to be selected in this step such as the reaction reagent and solvent are the same as those in Step I-6.

Step V-3
The step is construction of a quinazolinone ring of a sulfanylphenylketohydrazide derivative V-b. This step can be performed by reacting the sulfanylphenylketohydrazide derivative V-b with formic acid and trialkyl orthoformate by heating. The conditions to be selected in this step such as the reaction reagent and solvent are the same as those in Step I-9.

Step V-4
The step is Boc protection of a secondary amino group of a sulfanylphenylquinazolinone derivative V-c. This step can be performed by reacting the sulfanylphenylquinazolinone derivative V-c with a Boc-reagent under basic conditions. The conditions to be selected in this step such as the reaction reagent and solvent are the same as those in Step IV-9.

Step V-5
The step is oxidation of a sulfanylphenylquinazolinone derivative V-d to a sulfonyl derivative. This step can be performed by reacting the sulfanylphenylquinazolinone derivative V-d with an oxidizing agent. The conditions to be selected in this step such as the reaction reagent and solvent are the same as those in Step I-10.

Step V-6
The step is formation of a C—C bond from a haloquinazolinone derivative V-e by Suzuki-Molander coupling reaction. This step can be performed by reacting the haloquinazolinone derivative V-e with a Moldander reagent (potassium trifluoroborate derivative) which corresponds to $CH_2$—$Y^1$—$Z^1$-Pro by heating in the presence of a palladium reagent and a base. Here, a reagent for palladium ligands is added as necessary. The conditions to be selected in this step such as the reaction reagent and solvent are the same as those in Step IV-7.

Step V-7
The step is deprotection of two Boc groups of a Boc amine derivative V-f. This step can be performed by reacting the diBoc amine derivative V-f under strongly acidic conditions. The conditions to be selected in this step such as the reaction reagent and solvent are the same as those in Step IV-12.

Step V-8
The step is esterification of the anthranilic acid derivative IV-b. This step can be performed by reacting the anthranilic acid derivative IV-b with an alkylating agent in the presence of a base. The conditions to be selected in this step such as the reaction reagent and solvent are the same as those in Step IV-6.

Step V-9
The step is formation of a C—C bond from a halobenzene derivative V-h by Suzuki-Molander coupling reaction. This step can be performed by reacting the halobenzene derivative V-h with a Moldander reagent (potassium trifluoroborate derivative) which corresponds to $CH_2$—$Y^1$—$Z^1$-Pro by heating in the presence of a palladium reagent and a base. Here, a reagent for palladium ligands is added as necessary. The conditions to be selected in this step such as the reaction reagent and solvent are the same as those in Step IV-7.

Step V-10
The step is saponification (hydrolysis) of an anthranilate derivative V-i. This step can be performed by reacting the anthranilate derivative V-i with an inorganic base. The conditions to be selected in this step such as the reaction reagent and solvent are the same as those in Step IV-13.

Step V-11
The step is amidation of an anthranilic acid derivative V-j. This step can be performed by reacting the anthranilic acid derivative V-j with a corresponding hydrazine I-n in the presence of a condensing agent and a base. A condensing additive may be added as necessary. The conditions to be selected in this step such as the reaction reagent and solvent are the same as those in Step I-8.

Step V-12
The step is construction of a quinazolinone ring of a sulfonylphenylketohydrazide derivative V-k. This step can be performed by reacting the sulfonylphenylketohydrazide derivative V-k with formic acid and trialkyl orthoformate by heating. The conditions to be selected in this step such as the reaction reagent and solvent are the same as those in Step I-9.

Step V-13
The step is deprotection of the amine protecting group of a protected amine derivative V-1. Here, the protecting group mainly refers to a Boc group. This step can be performed by reacting the protected amine derivative V-I under strongly acidic conditions. The conditions to be selected in this step such as the reaction reagent and solvent are the same as those in Step IV-16.

Step V-14
The step is condensation (amidation) of an anthranilic acid derivative V-m. This step can be performed by reacting the anthranilic acid derivative V-m with a corresponding hydrazine I-h in the presence of a condensing agent and a base. A condensing additive may be added as necessary. The conditions to be selected in this step such as the reaction reagent and solvent are the same as those in Step I-8.

Step V-15
The step is construction of a quinazolinone ring of a sulfanylphenylketohydrazide derivative V-n. This step can be performed by reacting the sulfanylphenylketohydrazide derivative V-n with formic acid and trialkyl orthoformate by heating. The conditions to be selected in this step such as the reaction reagent and solvent are the same as those in Step I-9.

Step V-16
The step is Boc protection of a secondary amino group of a sulfanylphenylquinazolinone derivative V-o. This step can be performed by reacting the sulfanylphenylquinazolinone derivative V-o with a Boc-reagent under basic conditions. The conditions to be selected in this step such as the reaction reagent and solvent are the same as those in Step IV-9.

Step V-17
The step is oxidation of a sulfanyl derivative V-p to a sulfonyl derivative. This step can be performed by reacting the sulfanyl derivative V-p with an oxidizing agent. The conditions to be selected in this step such as the reaction reagent and solvent are the same as those in Step I-10.

Step V-18
The step is bromination of a toluene derivative V-q (Wohl-Ziegler reaction). This step can be performed by reacting the toluene derivative V-q with a brominating agent by heating in the presence of a catalytic amount of a radical initiator. The conditions to be selected in this step such as the reaction reagent and solvent are the same as those in Step III-12.

Step V-19

The step is formation of a C—N bond from a benzyl bromide derivative V-r by substitution reaction. This step can be performed by reacting the benzyl bromide derivative V-r with a primary or secondary amine which corresponds to Y1-Z1-Pro in the presence of a base. The conditions to be selected in this step such as the reaction reagent and solvent are the same as those in Step IV-11.

Production Method VI

The method is a method for forming a backbone of general formula (I), where A represents formula (1); Q represents $CH_2$; $R^4$ represents a sulfonyl group; $A^6$ represents $CR^6$; $R^6$ represents $CH_2Y^1Z^1$; $A^7$ represents $CR^7$; and $R^7$ represents halogen.

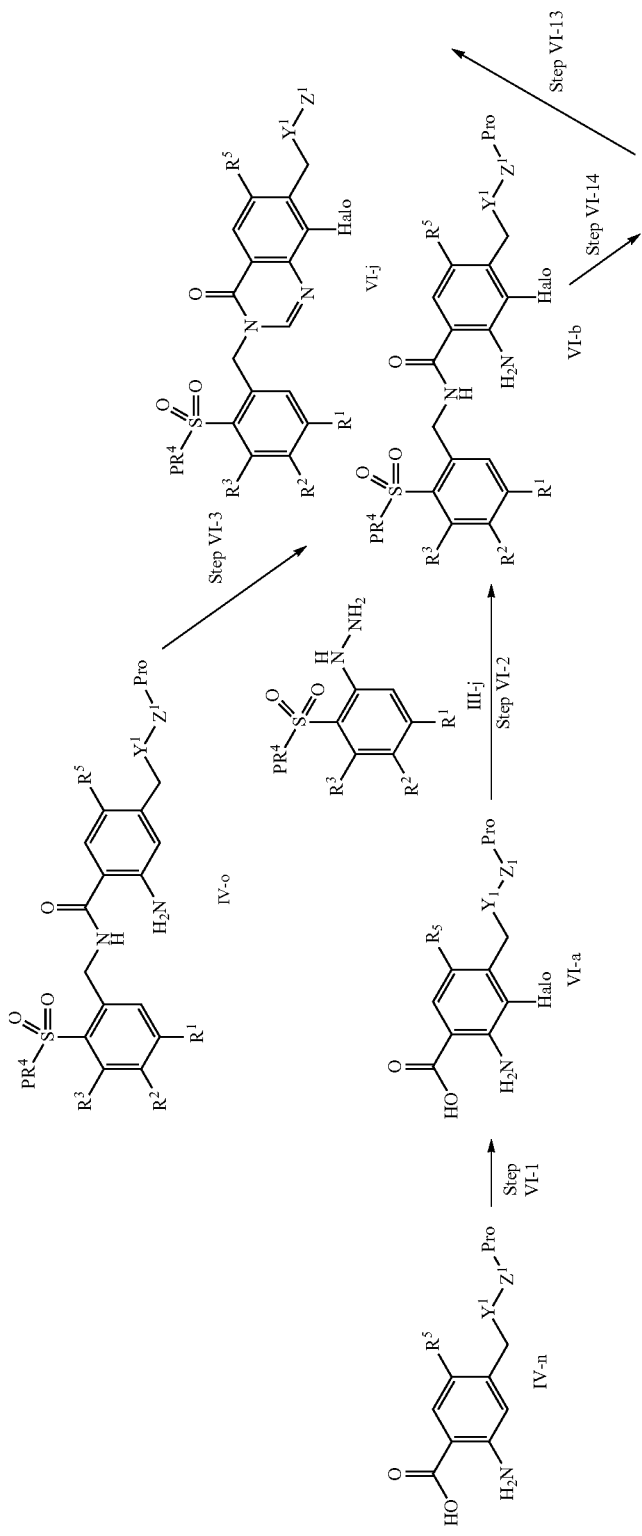

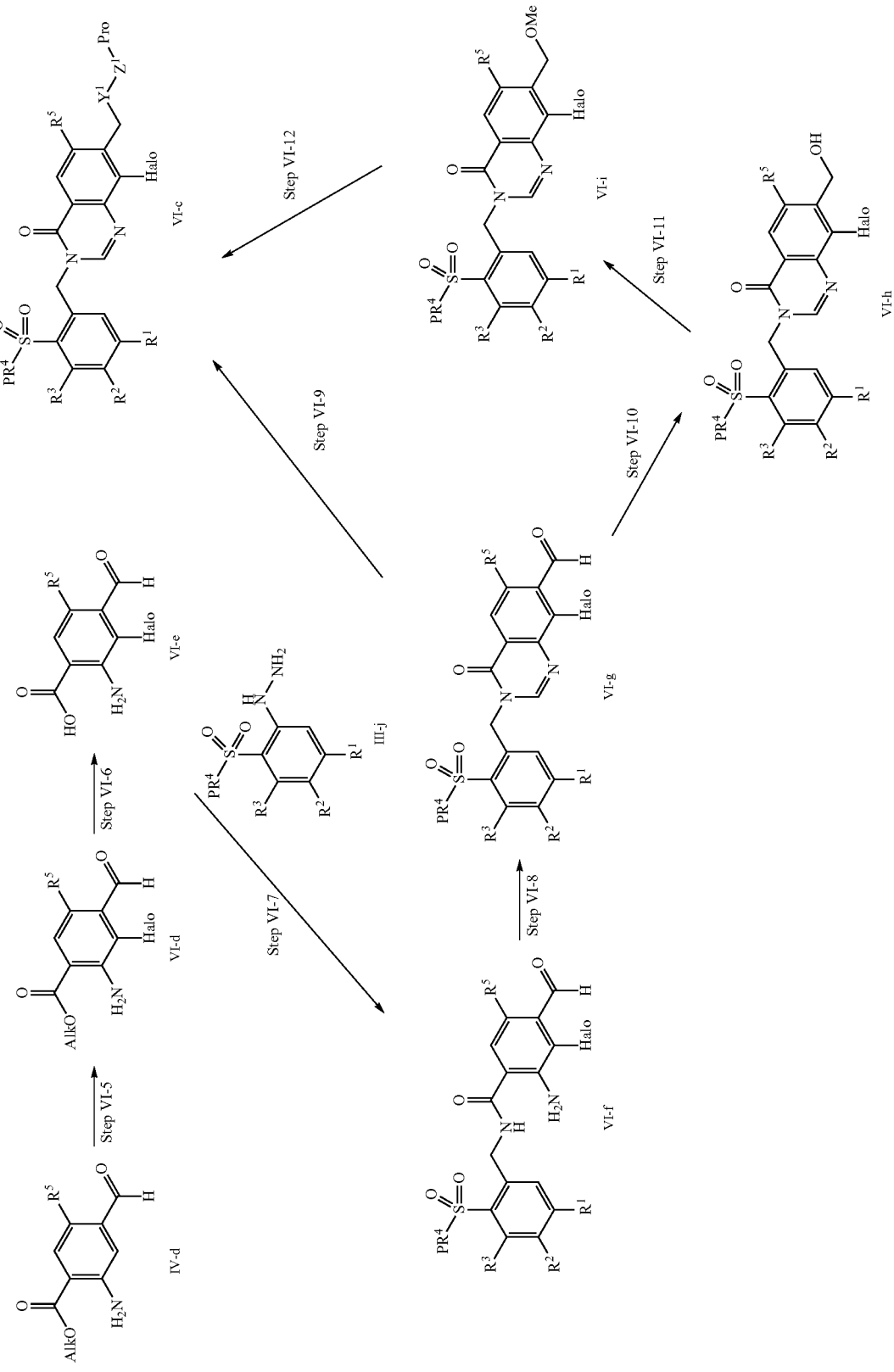

Step VI-1

The step is halogenation of the anthranilic acid derivative IV-n. This step can be performed by reacting the anthranilic acid derivative IV-n with a halogenating agent under heating. An acid or a catalytic amount of a radical initiator can be added when the reaction proceeds slowly. Examples of the halogenating agent include N-halosuccinimides, sulfuryl halides, and chlorine, bromine, and iodine under acidic conditions or in the presence of reduced iron powder. N-Halosuccinimide is preferred. Examples of the solvent include aprotic polar solvents, halomethane solvents, ether solvents, alcohols, and water. DMF is preferred.

Step VI-2

The step is condensation (amidation) of an anthranilic acid derivative VI-a. This step can be performed by reacting the anthranilic acid derivative VI-a with a corresponding benzylamine III-j in the presence of a condensing agent and a base. A condensing additive may be added as necessary. The conditions to be selected in this step such as the reaction reagent and solvent are the same as those in Step I-8.

Step VI-3

The step is halogenation of the sulfonylphenylamide derivative IV-o. This step can be performed by reacting the sulfonylphenylamide derivative IV-o with a halogenating agent under heating. The conditions to be selected in this step such as the reaction reagent and solvent are the same as those in Step VI-1.

Step VI-4

The step is construction of a quinazolinone ring of an amide derivative VI-b. This step can be performed by reacting the amide derivative VI-b with formic acid and trialkyl orthoformate by heating. The conditions to be selected in this step such as the reaction reagent and solvent are the same as those in Step I-9.

Step VI-5

The step is halogenation of the benzaldehyde derivative IV-d. This step can be performed by reacting the benzaldehyde derivative IV-d with a halogenating agent under heating. The conditions to be selected in this step such as the reaction reagent and solvent are the same as those in Step VI-1.

Step VI-6

The step is saponification (hydrolysis) of an anthranilate derivative VI-d. This step can be performed by reacting the anthranilate derivative VI-d with an inorganic base. The conditions to be selected in this step such as the reaction reagent and solvent are the same as those in Step IV-13.

Step VI-7

The step is amidation of an anthranilic acid derivative VI-e. This step can be performed by reacting the anthranilic acid derivative VI-e with a corresponding benzylamine III-j in the presence of a condensing agent and a base. A condensing additive may be added as necessary. The conditions to be selected in this step such as the reaction reagent and solvent are the same as those in Step I-8.

Step VI-8

The step is construction of a quinazolinone ring of an amide derivative VI-f. This step can be performed by reacting the amide derivative VI-f with formic acid and trialkyl orthoformate by heating. The conditions to be selected in this step such as the reaction reagent and solvent are the same as those in Step I-9.

Step VI-9

The step is formation of a C—N bond from a benzaldehyde derivative VI-g by reductive amination. This step can be performed by reacting the benzaldehyde derivative VI-g with a primary or secondary amine which corresponds to $Y^1$—$Z^1$-Pro in the presence of a reducing agent. The conditions to be selected in this step such as the reaction reagent and solvent are the same as those in Step IV-4.

Step VI-10

The step is reduction of the benzaldehyde derivative VI-g to an alcohol. This step can be performed by reacting the benzaldehyde derivative VI-g with a hydride reducing agent. Examples of the hydride reducing agent include sodium borohydride, lithium aluminium hydride, sodium-lithium borohydride, and borane complexes. Sodium borohydride is preferred. Examples of the solvent include alcoholic solvents and ether solvents. Methanol or ethanol is preferred.

Step VI-11

The step is introduction of a leaving group into a benzyl alcohol derivative VI-h (methanesulfonation). This step can be performed by reacting the benzyl alcohol derivative VI-h with a methanesulfonylating agent under basic conditions. Examples of the methanesulfonylating agent include methanesulfonyl halide and methanesulfonic anhydride. Methanesulfonyl chloride is preferred. Examples of the base include tertiary amines and pyridine. Triethylamine is preferred. Examples of the solvent include pyridine used as a base and solvent, alkyl halide, and ether solvents. Dichloromethane is preferred.

Step VI-12

The step is substitution reaction of a methanesulfonyl derivative VI-i. This step can be performed by reacting the methanesulfonyl derivative VI-i with a primary or secondary amine which corresponds to $Y^1$—$Z^1$-Pro. Examples of the solvent include aprotic polar solvents, ether solvents, and halomethane solvents. DMF is preferred. When the reaction is slow, it is preferable that an inorganic salt such as potassium carbonate or sodium carbonate is added or the reaction is heated at 40° C. to 80° C.

Step VI-13

The step is deprotection of the amine protecting group of a protected amine derivative VI-c. Here, the protecting group mainly refers to a Boc group. This step can be performed by reacting the protected amine derivative VI-c under strongly acidic conditions. The conditions to be selected in this step such as the reaction reagent and solvent are the same as those in Step IV-16.

Production Method VII

The method is a method for forming a backbone of general formula (I), where A represents formula (1); Q represents $CH_2$; $R^4$ represents a sulfonyl group; $A^6$ represents CH; $A^7$ represents $CR^7$; and $R^7$ represents $CH_2Y^2Z^2$.

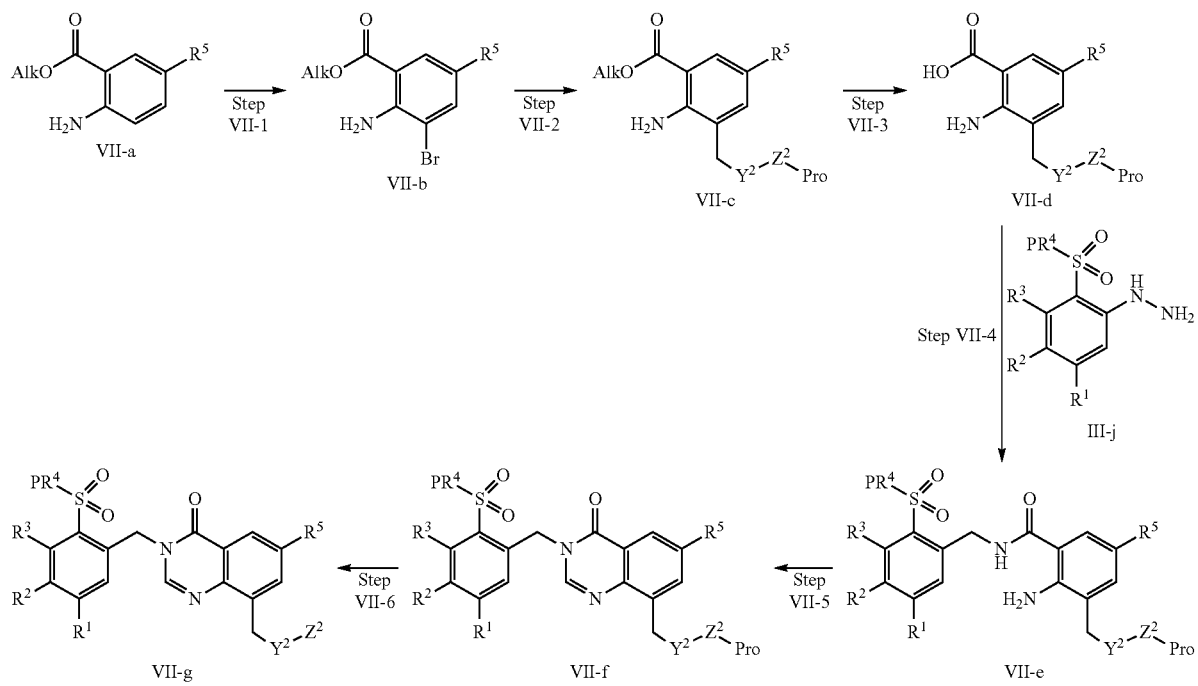

Step VII-1

The step is bromination of an anthranilate derivative VII-a. This step can be performed by reacting the anthranilate derivative VII-a with a brominating agent. Examples of the brominating agent include bromine, N-bromosuccinimide, and dibromoisocyanuric acid. Bromine is preferred. Examples of the solvent include aprotic polar solvents such as DMF and alkylhalide. Dichloromethane is preferred.

Step VII-2

The step is formation of a C—C bond from a haloanthranilate derivative VII-b by Suzuki-Molander coupling reaction. This step can be performed by reacting the haloanthranilate derivative VII-b with a Moldander reagent (potassium trifluoroborate derivative) which corresponds to $CH_2$—$Y^2$—$Z^2$-Pro by heating in the presence of a palladium reagent and a base. The conditions to be selected in this step such as the reaction reagent and solvent are the same as those in Step IV-7.

Step VII-3

The step is saponification (hydrolysis) of an anthranilate derivative VII-c. This step can be performed by reacting the anthranilate derivative VII-c with an inorganic base. The conditions to be selected in this step such as the reaction reagent and solvent are the same as those in Step IV-13.

Step VII-4

The step is amidation of an anthranilic acid derivative VII-d. This step can be performed by reacting the anthranilic acid derivative VII-d with a corresponding benzylamine III-j in the presence of a condensing agent and a base. A condensing additive may be added as necessary. The conditions to be selected in this step such as the reaction reagent and solvent are the same as those in Step I-8.

Step VII-5

The step is construction of a quinazolinone ring of an amide derivative VII-e. This step can be performed by reacting the amide derivative VII-e with formic acid and trialkyl orthoformate by heating. The conditions to be selected in this step such as the reaction reagent and solvent are the same as those in Step I-9.

Step VII-6

The step is deprotection of the amine protecting group of a protected amine derivative VII-f. Here, the protecting group mainly refers to a Boc group. This step can be performed by reacting the protected amine derivative VII-f under strongly acidic conditions. The conditions to be selected in this step such as the reaction reagent and solvent are the same as those in Step IV-16.

EXAMPLES

Herein below, the present invention will be more specifically described with reference to the Examples, but it is not to be construed as being limited thereto.

NMR Analysis

NMR analysis was performed using either ARX 300 (300 MHz) manufactured by Bruker Corporation, AVANCEIII600 (600 MHz) manufactured by Bruker Corporation, JNM-GSX 400 (400 MHz) manufactured by JEOL Corporation, JNM-EX 270 (270 MHz) manufactured by JEOL Corporation, ECA-400 (400 MHz) manufactured by JEOL Corporation or 400 MR (400 MHz) manufactured by Varian Corporation. NMR data are shown in ppm (parts per million) (5) and refers to the deuterium lock signal from the sample solvent.

Data from Mass Spectrometry with High Performance Liquid Chromatography (LC-MS)

The data were obtained using a Micromass (SQD) equipped with an Acquity gradient ultra high performance liquid chromatography system (manufactured by Waters Corporation), SQD2 Mass Spectrometer paired with Acquity Gradient Ultra High Performance Liquid Chromatography (manufactured by Waters Corporation), a Micromass (ZQ) equipped with a 2525 gradient high performance liquid chromatography system (manufactured by Waters Corporation), a Micromass (SQD) equipped with a 2524 gradient high performance liquid chromatography system (manufactured by Waters Corporation), or a Micromass equipped with an Nexera 2020 gradient ultra high performance liquid chromatography system (manufactured by Shimadzu Corporation).

Any one of the conditions shown in Table 1 below was used for high performance liquid chromatography.

TABLE 1

| Analysis condition | Equipment | Column used | Column temperature | Mobile phase, gradient | Flow rate (mL/min) | Detection wavelength (PDA total) |
|---|---|---|---|---|---|---|
| A | ZQ | Sunfire C18 (Waters) 4.6 mm I.D. × 50 mm, 5 um | Room Temp. | A) 0.05% TFA, CH3CN, B) 0.05% TFA, H2O, A/B = 30/70→98/2 (3.5 min)→ 30/70 (1 min)→30/70 (0.5 min) | 4 | 210-400 nm |
| B | SQD | Sunfire C18 (Waters) 4.5 mm I.D × 50 mm, 5 um | Room Temp. | A) 0.05% TFA, CH3CN, B) 0.05% TFA, H2O, A/B = 10/90→95/5 (3.5 min)→ 10/90 (1 min)→95/5 (0.5 min) | 4 | 210-370 nm |
| C | ZQ | Sunfire C18 (Waters) 4.6 mm I.D. × 50 mm, 5 um | Room Temp. | A) 0.05% TFA, CH3CN, B) 0.05% TFA, H2O, A/B = 10/90→95/5 (3.5 min)→ 10/90 (1 min)→10/90 (0.5 min) | 4 | 210-400 nm |
| D | Acquity SQD | Ascentis Express C18 HPLC column, 5 cm × 2.1 mm, 2.7 μm | 35° C. | A) 0.1% FA, CH3CN, B) 0.1% FA, H2O, A/B = 5/95 to 100/0 (1 min)→100/0 (0.4 min) | 1 | 210-400 nm |
| E | ZQ | Wakosil-II 3C18 AR, 4.6 mm * 30 mm | Room Temp. | A) 0.05% TFA, CH3CN, B) 0.05% TFA, H2O, A/B = 10/90→10/90 (0.2 min)→ 95/5 (3.1 min)→95/5 (1.4 min) | 2 | 210-400 nm |
| F | Acquity SQD | Ascentis Express C18 HPLC column, 5 cm × 2.1 mm, 2.7 μm | Room Temp. | A) 0.1% FA, CH3CN B) 0.1% FA, H2O, A/B = 10/90→98/2 (1 min) →98/2 (0.4 min) | 1 | 210-400 nm |
| G | Acquity SQD | Ascentis Express C18 HPLC column, 5 cm × 2.1 mm, 2.7 μm | Room Temp. | A) 0.05% TFA, CH3CN, B) 0.05% TFA, H2O, A/B = 10/90→98/2 (1 min) →98/2 (0.4 min) | 1 | 210-400 nm |
| H | Acquity I-Class SQD2 | Ascentis Express C18 HPLC column, 5 cm × 2.1 mm, 2.7 μm | 35° C. | A) 0.1% FA, CH3CN, B) 0.1% FA, H2O, A/B = 5/95 to 100/0 (1 min)→100/0 (0.4 min) | 1 | 210-400 nm |
| I | Acquity I-Class SQD | Ascentis Express C18 HPLC column, 5 cm × 2.1 mm, 2.7 μm | 35° C. | A) 0.1% FA, CH3CN, B) 0.1% FA, H2O, A/B = 5/95 to 100/0 (1 min)→100/0 (0.4 min) | 0.9 | 210-400 nm |
| J | Nexera/2020 | Kinetex 1.7u C18, 5 cm × 2.1 mm, 1.7 μm | 35° C. | A) 0.05% TFA, CH3CN, B) 0.05% TFA, H2O, A/B = 5/95 to 100/0 (1.5 min)→100/0 (0.5 min) | 1 | 210-400 nm |

Microwave Reaction

It was performed using a snap cap vial with Biotage Initiator. The cooling of the reaction vessel with air for preventing temperature increase due to microwave was considered to determine the maximum power.

Commercially available reagents were used without further purification. "Room temperature" refers to a temperature within the range of about 20-25° C.

All nonaqueous reactions were performed in anhydrous solvents. Concentration under reduced pressure or solvent evaporation was performed using a rotary evaporator. For the HPLC fractionation, the products of interest were isolated, then neutralized as necessary, and obtained as free forms.

When an undesirable side reaction could occur in the preparation of a compound, a functional group was protected by a protecting group as necessary, and the protecting group was removed after preparing the target molecule. Selection and detachment of the protecting group was performed, for example, by a method described in Greene and Wuts, "Protective Groups in Organic Synthesis" (Fourth edition, John Wiley & Sons 2007).

Example 1

Compound 1

5-Chloro-2-ethylsulfanylbenzonitrile

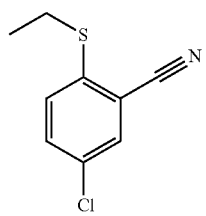

A solution of 5-chloro-2-fluoro-benzonitrile (3.60 g, 23.1 mmol) in DMF (46 ml) was cooled to 0° C. Potassium carbonate (9.60 g, 69.4 mmol) was added thereto under nitrogen atmosphere, and the mixture was stirred at room temperature for five minutes. Ethanethiol (2.05 ml, 27.8 mmol) was added thereto, and the mixture was stirred at room temperature for three hours. Ethyl acetate was added to the reaction mixture. After washing with brine, the organic layer was dried over anhydrous magnesium sulfate. After the drying agent was removed by filtration, concentration was performed under reduced pressure. The resulting residue was purified by silica gel column chromatography (ethyl acetate/hexane) to give the title compound (4.57 g, quant.) as a colorless solid.

HPLC retention time: 2.47 min (analysis condition C)

$^1$H-NMR (400 MHz, DMSO-d$_6$) δ: 8.01 (1H, d, J=2.2 Hz), 7.73 (1H, dd, J=2.2, 8.8 Hz), 7.58 (1H, d, J=8.8 Hz), 3.14 (2H, q, J=7.7 Hz), 1.27 (3H, t, J=7.7 Hz).

Example 2

Compound 2

(5-Chloro-2-ethylsulfanylphenyl)methanamine

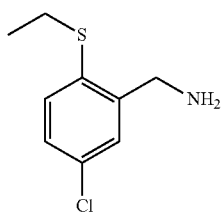

Lithium aluminum hydride (2.63 g, 69.4 mmol) was added to a solution of 5-chloro-2-ethylsulfanylbenzonitrile (Compound 1, 4.57 g, 23.1 mmol) in THF (40 ml) under cooling at 0° C. The mixture was stirred at 0° C. for 30 minutes and then at room temperature for one hour. Under cooling at 0° C., water was added to the reaction mixture, and this was filtered through celite. The filtrate was dried over anhydrous magnesium sulfate. After the drying agent was removed by filtration, concentration was performed under reduced pressure. The resulting residue was purified by silica gel column chromatography (ethyl acetate/hexane) to give the title compound (4.00 g, 85%) as a yellow oily substance.

LCMS: m/z 202 [M+H]$^+$

HPLC retention time: 0.97 min (analysis condition C)

Example 3

Compound 3

(5-Chloro-2-ethylsulfonylphenyl)methanamine hydrochloride

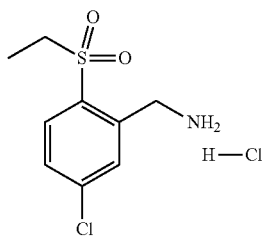

The title compound was synthesized from (5-chloro-2-ethylsulfanylphenyl)methanamine (Compound 2) according to the method described in a patent (WO 2009131245).

LCMS: m/z 234 [M+H−HCl]$^+$

HPLC retention time: 0.57 min (analysis condition C)

Example 4

Compound 4

(2-Ethylsulfonylphenyl)methanamine hydrochloride

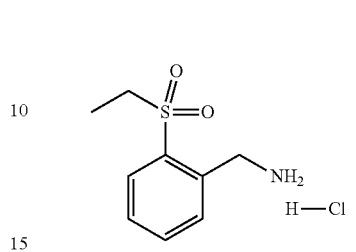

10% Pd/C was added to a solution of (5-chloro-2-ethylsulfonylphenyl)methanamine hydrochloride (Compound 3, 100 mg, 0.37 mmol) in methanol (1.8 mL), and the mixture was stirred under hydrogen atmosphere for three hours. Pd/C was removed by filtration, and the solution was then washed with methanol. The filtrate and the washings were combined and the solvent was evaporated under reduced pressure to give the title compound (89.3 mg, quant.) as a colorless solid.

LCMS: m/z 200 [M+H−HCl]$^+$

HPLC retention time: 0.27 min (analysis condition D)

Example 5

Compound 5

(5-Chloro-2-propan-2-ylsulfanylphenyl)methanamine

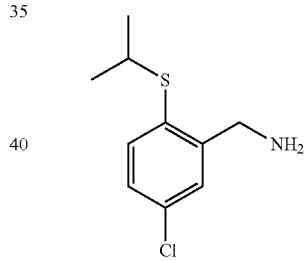

The title compound was synthesized from 5-chloro-2-fluorobenzonitrile under the same conditions as for Compounds 1 and 2. However, propane-2-thiol was used in place of ethanethiol under the conditions for Compound 1.

Example 6

Compound 6

5-Bromo-2-ethylsulfanyl-benzaldehyde

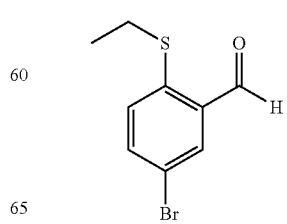

Sodium ethanethiolate (362 mg, 4.3 mmol) was added to a solution of 5-bromo-2-fluorobenzaldehyde (546 mg, 2.7 mmol) in DMF (1.08 ml), and the mixture was stirred at 80° C. After one hour, sodium ethanethiolate (123 mg, 1.5 mmol) was added thereto. After 15 minutes, the reaction solution was returned to room temperature, and a 1 N aqueous hydrochloric acid solution was added thereto, and extraction was performed with ethyl acetate. The organic layer was sequentially washed with a saturated aqueous sodium bicarbonate solution and brine, and dried over anhydrous sodium sulfate. After the drying agent was removed by filtration, concentration was performed under reduced pressure. The resulting residue was purified by silica gel column chromatography (ethyl acetate/hexane) to give the title compound (163 mg, 24%) as a yellow oily substance.

HPLC retention time: 0.91 min (analysis condition D)
$^1$H-NMR (400 MHz, CDCl$_3$) δ: 10.33 (1H, s), 7.95 (1H, d, J=2.2 Hz), 7.62 (1H, dd, J=2.2, 8.4 Hz), 7.30 (1H, d, J=8.4 Hz), 2.97 (2H, q, J=7.5 Hz), 1.36 (3H, t, J=7.5 Hz).

Example 7

Compound 7

5-Bromo-2-ethylsulfanyl-benzaldehyde O-methyl-oxime

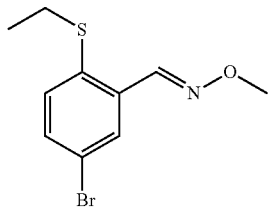

Hydroxylamine methyl ether hydrochloride (61 mg, 0.73 mmol) was added to a solution of 5-bromo-2-ethylsulfanyl-benzaldehyde (Compound 6, 163 mg, 0.66 mmol) in pyridine (0.42 ml), and the mixture was stirred at room temperature for two hours. Water was added to the reaction mixture, and extraction was performed with ethyl acetate. The organic layer was washed with a 1 N aqueous hydrochloric acid solution twice and then with brine, and then dried over anhydrous sodium sulfate. After the drying agent was removed by filtration, concentration was performed under reduced pressure to give a crude product of the title compound.

LCMS: m/z 274 [M+H]$^+$
HPLC retention time: 1.10 min (analysis condition D)

Example 8

Compound 8

(5-Bromo-2-ethylsulfanylphenyl)methanamine

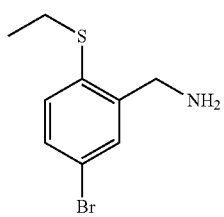

A 1 mol/l solution of tetrahydrofuran-borane in THF (1.66 ml, 1.7 mmol) was added to a solution of the crude product of 5-bromo-2-ethylsulfanyl-benzaldehyde O-methyl-oxime (Compound 7, 182 mg, 0.66 mmol) in THF, and the mixture was stirred at 80° C. for 2.5 hours. The reaction mixture was cooled to 0° C., and crushed ice and a 1 N aqueous hydrochloric acid solution (3 ml) were added thereto, and this was stirred at 90° C. for one hour. The reaction solution was cooled to room temperature, and separated by adding water and ethyl acetate. The aqueous layer was made basic with a 5 N aqueous sodium hydroxide solution, and extraction was performed with dichloromethane three times. The organic layers were combined and dried over anhydrous sodium sulfate. After the drying agent was removed by filtration, concentration was performed under reduced pressure to give a crude product of the title compound.

HPLC retention time: 0.48 min (analysis condition D)
$^1$H-NMR (400 MHz, CDCl$_3$) δ: 7.48 (1H, d, J=2.2 Hz), 7.33 (1H, dd, J=2.2, 8.4 Hz), 7.17 (1H, d, J=8.4 Hz), 3.89 (2H, s), 2.93 (2H, q, J=7.5 Hz), 1.32 (3H, t, J=7.5 Hz).

Example 9

Compound 9

(5-Bromo-2-ethylsulfonylphenyl)methanamine hydrochloride

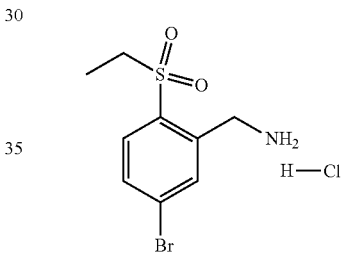

Boc$_2$O was added to a solution of the crude product of 5-bromo-2-ethylsulfanyl-benzylamine (Compound 8) in THF (2 ml), and the mixture was stirred at room temperature for one hour. Water was added to the reaction mixture, and extraction was performed with ethyl acetate. The organic layer was washed with brine and then dried over anhydrous sodium sulfate. After the drying agent was removed by filtration, concentration was performed under reduced pressure. The resulting residue was purified by silica gel column chromatography (ethyl acetate/hexane) to give (5-bromo-2-ethylsulfanyl-benzyl)-carbamic acid tert-butyl ester (168 mg, total yield from Compound 6 in three steps: 73%) as a yellow oily substance.

HPLC retention time: 1.01 min (analysis condition D)
$^1$H-NMR (400 MHz, CDCl$_3$) δ: 7.46 (1H, d, J=2.2 Hz), 7.35 (1H, dd, J=2.2, 8.4 Hz), 7.18 (1H, d, J=8.4 Hz), 4.97 (1H, brs), 4.38 (2H, brd, J=5.7 Hz), 2.91 (2H, q, J=7.5 Hz), 1.46 (9H, s), 1.30 (3H, t, J=7.5 Hz).

m-CPBA (234 mg, 1.02 mmol) was added to a solution of (5-bromo-2-ethylsulfanyl-benzyl)-carbamic acid tert-butyl ester (168 mg, 0.49 mmol) in dichloromethane (2.4 ml) under cooling at 0° C. The mixture was then returned to room temperature and stirred for four hours. A saturated aqueous sodium bicarbonate solution was added to the reaction mixture, and extraction was performed with ethyl acetate. The organic layer was washed with brine and then dried over anhydrous sodium sulfate. After the drying agent was removed by filtration, concentration was performed under reduced pressure. The resulting residue was purified by silica gel column chromatography (ethyl acetate/hexane) to give (5-bromo-2-ethanesulfonyl-benzyl)-carbamic acid tert-butyl ester (180 mg, yield: 98%) as a yellow oily substance.

LCMS: m/z 322 [M−(2-methylpropene)+H]$^+$

HPLC retention time: 0.84 min (analysis condition D)

A 4 N solution of hydrochloric acid in ethyl acetate (2.4 ml) was added to (5-bromo-2-ethanesulfonyl-benzyl)-carbamic acid tert-butyl ester (180 mg, 0.48 mmol), and the mixture was stirred at room temperature for 1.5 hours. The reaction solution was concentrated under reduced pressure to give the title compound (130 mg, yield: 87%) as a colorless solid.

LCMS: m/z 278 [M+H−HCl]$^+$

HPLC retention time: 0.38 min (analysis condition D)

Example 10

Compound 10

(2-Ethylsulfanyl-5-fluorophenyl)methanamine

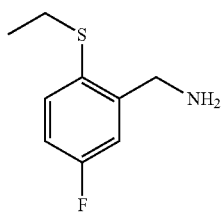

The title compound was synthesized from 2,5-difluorobenzonitrile under the same conditions as for Compounds 1 and 2.

Example 11

Compound 11

5-Fluoro-2-methylsulfanylbenzonitrile

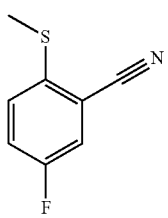

The title compound was synthesized from 2,5-difluorobenzonitrile under the same conditions as for Compound 6. However, sodium methanethiolate was used in place of sodium ethanethiolate and the reaction was performed at 90° C.

Example 12

Compound 12

(5-Fluoro-2-methylsulfanylphenyl)methanamine

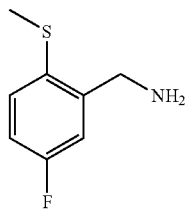

The title compound was synthesized from 5-fluoro-2-methylsulfanylbenzonitrile (Compound 11) under the same conditions as for Compound 2.

Example 13

Compound 13

4-Ethylsulfanyl-3-methylbenzonitrile

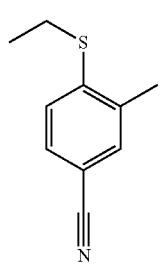

The title compound was synthesized from 4-fluoro-3-methylbenzonitrile under the same conditions as for Compound 1.

Example 14

Compound 14

4-Ethylsulfonyl-3-methylbenzonitrile

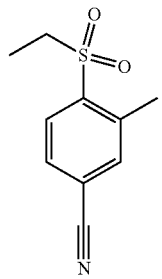

m-CPBA (15.0 g, 67.0 mmol) was added to a solution of 4-ethylsulfanyl-3-methylbenzonitrile (Compound 13, 3.96 g, 22.3 mmol) in DCM (100 ml), and the mixture was stirred at room temperature overnight. The reaction mixture was concentrated under reduced pressure, and the resulting residue was dissolved in ethyl acetate, and this was washed with water. The organic layer was filtered using amino silica gel, and the filtrate was concentrated under reduced pressure. The resulting residue was purified by amino silica gel column chromatography (ethyl acetate/hexane) to give the title compound (4.51 g, yield: 97%).

HPLC retention time: 1.58 min (analysis condition C)
$^{1}$H-NMR (270 MHz, CDCl$_{3}$) δ: 8.13 (1H, d, J=8.1 Hz), 7.69 (1H, dd, J=0.8, 8.1 Hz), 7.66 (1H, d, J=0.8 Hz), 3.19 (2H, q, J=7.6 Hz), 2.75 (3H, s), 1.29 (3H, t, J=7.6 Hz).

Example 15

Compound 15

3-Bromomethyl-4-ethylsulfonylbenzonitrile

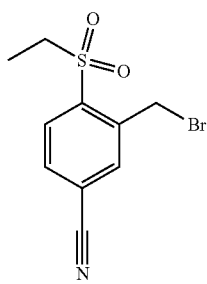

70% benzoyl peroxide (746 mg, 2.2 mmol) was added to a solution of 4-ethanesulfonyl-3-methyl-benzonitrile (Compound 14, 4.51 g, 21.6 mmol) and NBS (4.22 g, 23.7 mmol) in carbon tetrachloride (100 ml), and the mixture was stirred at 80° C. for four hours. The reaction mixture was concentrated under reduced pressure, and the resulting residue was dissolved in DCM. The solution was filtered using silica gel and amino silica gel. The filtrate was concentrated under reduced pressure, and the resulting solid was suspended in and washed with a mixed solvent of diisopropyl ether and DCM to give the title compound (4.14 g, 64%) as a colorless solid.

HPLC retention time: 1.87 min (analysis condition C)
$^{1}$H-NMR (270 MHz, CDCl$_{3}$) δ: 8.15 (1H, d, J=8.1 Hz), 7.91 (1H, d, J=1.4 Hz), 7.80 (1H, dd, J=1.4, 8.1 Hz), 5.04 (2H, s), 3.41 (2H, q, J=7.3 Hz), 1.33 (3H, t, J=7.3 Hz).

Example 16

Compound 16

3-Aminomethyl-4-ethylsulfonylbenzonitrile

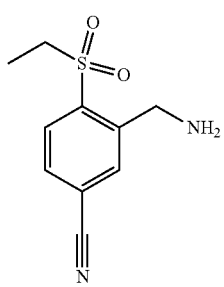

A 25% aqueous ammonia solution (2.5 ml) was added to a solution of 3-bromomethyl-4-ethanesulfonyl-benzonitrile (Compound 15, 250 mg, 0.87 mmol) in EtOH (12.5 ml), and the mixture was stirred at room temperature for 2.5 hours. The reaction mixture was concentrated under reduced pressure, and the resulting residue was purified by silica gel column chromatography (MeOH/DCM) to give the title compound (102 mg, 46%) as a colorless solid.

LCMS: m/z 225 [M+H]$^{+}$
HPLC retention time: 0.25 min (analysis condition D)

Example 17

Compound 17

(2-Ethylsulfanyl-5-methoxyphenyl)methanamine

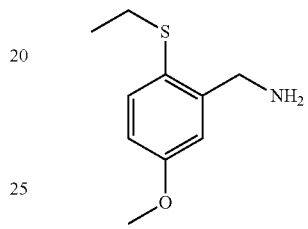

The title compound was synthesized from 2-fluoro-5-methoxybenzonitrile under the same conditions as for Compounds 1 and 2. However, the reaction was performed at 80° C. under the conditions for Compound 1.

Example 18

Compound 18

(2-Ethylsulfanyl-4-methylphenyl)methanamine

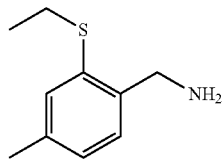

The title compound was synthesized from 2-bromo-4-methylbenzonitrile under the same conditions as for Compounds 1 and 2. However, the reaction was performed at 90° C. under the conditions for Compound 1.

Example 19

Compound 19

1-Ethylsulfonylpyrrole-2-carbonitrile

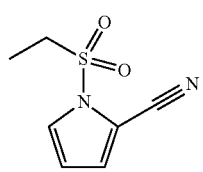

Ethanesulfonyl chloride (0.98 g, 7.60 mmol) was added to a mixed solution of 1H-pyrrole-2-carbonitrile (500 mg, 5.43 mmol) and TEA (1.51 ml, 10.9 mmol) in THF (5 ml) and DCM (5 ml), and this was stirred for three hours. A saturated aqueous sodium chloride solution was added to the reaction mixture, and extraction was performed with DCM. The organic layer was then dried over anhydrous sodium sulfate. After the drying agent was removed by filtration, concentration was performed under reduced pressure. The resulting residue was purified by silica gel column chromatography (ethyl acetate/hexane) to give the title compound (694 mg, 69%) as a colorless oily substance.

LCMS: m/z 185 [M+H]$^+$
HPLC retention time: 0.55 min (analysis condition D)

Example 20

Compound 20 tert-Butyl N-[(1-ethylsulfonylpyrrol-2-yl)methyl]carbamate

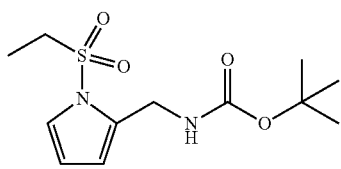 [SMILES: CCS(=O)(=O)n1cccc1CNC(=O)OC(C)(C)C]

Sodium borohydride (1.13 g, 29.8 mmol) was added in five portions at five-minute intervals to a solution of 1-ethylsulfonylpyrrole-2-carbonitrile (Compound 19, 686 mg, 3.72 mmol), Boc$_2$O (1.71 ml, 7.44 mmol) and nickel(II) chloride hexahydrate (221 mg, 0.93 mmol) in methanol (15 ml) under cooling at 0° C., and the mixture was stirred at 0° C. for one hour. A saturated aqueous sodium bicarbonate solution was added to the reaction mixture, and extraction was performed with ethyl acetate. The organic layer was then dried over anhydrous sodium sulfate. After the drying agent was removed by filtration, concentration was performed under reduced pressure. The resulting residue was purified by silica gel column chromatography (ethyl acetate/hexane) to give the title compound (629 mg, 59%) as a colorless solid.

LCMS: m/z 172 [M-Boc-NH$_2$]$^+$
HPLC retention time: 0.72 min (analysis condition D)

Example 21

Compound 21

(1-Ethylsulfonylpyrrol-2-yl)methanamine hydrochloride

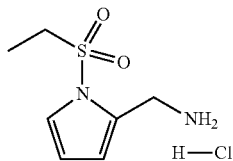

A 4 N solution of hydrochloric acid in ethyl acetate (1.5 ml) was added to a solution of tert-butyl N-[(1-ethylsulfonylpyrrol-2-yl)methyl]carbamate (Compound 20, 232 mg, 0.805 mmol) in ethyl acetate (3.0 ml) at room temperature, and the mixture was stirred at room temperature for 15 hours. The resulting precipitate was separated by filtration to give the title compound (164 mg, 91%) as a white solid.

$^1$H-NMR (400 MHz, DMSO-d$_6$) δ: 8.43 (2H, brs), 7.26 (1H, dd, J=1.6, 3.3 Hz), 6.55-6.58 (1H, m), 6.39 (1H, dd, J=3.3, 3.3 Hz), 4.20 (2H, s), 3.68 (2H, q, J=7.1 Hz), 1.11 (3H, t, J=7.1 Hz).

Example 22

Compound 22

1-Ethylsulfanyl-2-methyl-4-nitrobenzene

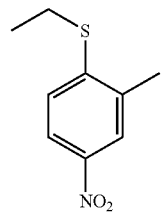

The title compound was synthesized from 1-fluoro-2-methyl-4-nitrobenzene under the same conditions as for Compound 1.

Example 23

Compound 23

2-(Bromomethyl)-1-ethylsulfonyl-4-nitrobenzene

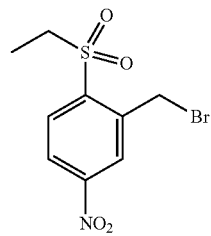 [SMILES: CCS(=O)(=O)c1ccc([N+](=O)[O-])cc1CBr]

The title compound was synthesized from 1-ethylsulfanyl-2-methyl-4-nitrobenzene (Compound 22) under the same conditions as for Compounds 14 and 15.

Example 24

Compound 24

4-Ethylsulfanyl-3-methylaniline

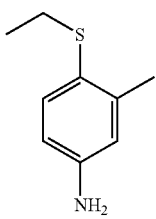

Ammonium chloride (5.7 g, 107 mmol) and zinc (21.9 g, 335 mmol) were added to a solution of 1-ethylsulfanyl-2-methyl-4-nitro-benzene (Compound 22, 6.6 g, 33.5 mmol) in MeOH (297 ml)/water (33 ml), and the mixture was stirred at room temperature for three hours. The reaction mixture was filtered through celite, and ethyl acetate was added to the filtrate. After washing with water, the organic layer was dried over anhydrous magnesium sulfate. After the drying agent was removed by filtration, concentration was performed under reduced pressure. The resulting residue was purified by silica gel column chromatography (ethyl acetate/hexane) to give the title compound (5.4 g, 97%) as a brown oily substance.

$^1$H-NMR (300 MHz, CDCl$_3$) δ: 7.22 (1H, d, J=7.8 Hz), 6.58 (1H, d, J=2.7 Hz), 6.50 (1H, dd, J=2.7, 7.8 Hz), 3.24 (2H, brs), 2.74 (2H, q, J=7.2 Hz), 2.37 (3H, s), 1.22 (3H, t, J=7.2 Hz).

Example 25

Compound 25

4-Chloro-1-ethylsulfanyl-2-methylbenzene

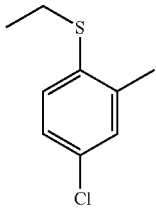

A solution of (4-ethylsulfanyl-3-methylaniline (Compound 24, 1.0 g, 5.98 mmol) in acetonitrile (20 ml) was added to a solution of nitrous acid tert-butyl (1.07 ml, 8.97 mmol) and copper(II) chloride (965 mg, 7.17 mmol) in acetonitrile (40 ml), and the mixture was stirred at 65° C. for ten minutes. The reaction mixture was cooled to room temperature, diluted with a 20% aqueous hydrochloric acid solution, and extracted with diethyl ether. The organic layer was dried over anhydrous magnesium sulfate. After the drying agent was removed by filtration, concentration was performed under reduced pressure. The resulting residue was purified by silica gel column chromatography (ethyl acetate/hexane) to give the title compound (0.84 g, 75%) as a yellow oily substance.

$^1$H-NMR (300 MHz, CDCl$_3$) δ: 7.11-7.20 (3H, m), 2.89 (2H, q, J=7.2 Hz), 2.33 (3H, s), 1.32 (3H, t, J=7.2 Hz).

Example 26

Compound 26

2-(Bromomethyl)-4-chloro-1-ethylsulfonylbenzene

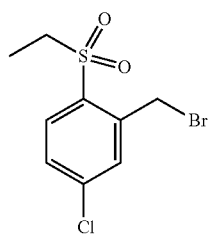

The title compound was synthesized from 4-chloro-1-ethylsulfanyl-2-methylbenzene (Compound 25) under the same conditions as for Compounds 14 and 15.

Example 27

Compound 27

2-Ethylsulfanyl-5-fluoroaniline

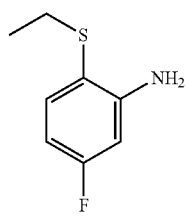

Ethyl iodide (0.66 ml, 8.3 mmol) was added to a suspension of 2-amino-4-fluoro-benzenethiol (1.13 g, 7.9 mmol), cesium carbonate (3.09 g, 9.5 mmol), and tetra-n-butylammonium iodide (3.21 g, 8.7 mmol) in DMF (10 ml) under nitrogen atmosphere, and this was stirred for 2.5 hours. Ethyl acetate was added to the reaction mixture. After washing with a saturated aqueous sodium chloride solution, the organic layer was dried over anhydrous sodium sulfate. After the drying agent was removed by filtration, concentration was performed under reduced pressure. The resulting residue was purified by silica gel column chromatography (ethyl acetate/hexane) to give the title compound (1.19 g, 88%) as a colorless oily substance.

LCMS: m/z 172 [M+H]$^+$

HPLC retention time: 2.35 min (analysis condition C)

Example 28

Compound 28

(2-Ethylsulfanyl-5-fluorophenyl)hydrazine

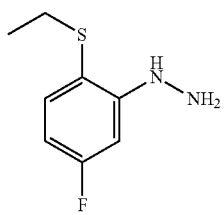

Concentrated hydrochloric acid (1.8 ml) and sodium nitrite (145 mg, 2.1 mmol) were added to an aqueous suspension (1.8 ml) of 2-ethylsulfanyl-5-fluoroaniline (Compound 27, 300 mg, 1.8 mmol), and the mixture was stirred for two hours under ice-cooling. A solution of stannic chloride dihydrate (9.9 mg, 4.0 mmol) in concentrated hydrochloric acid (1.8 ml) was added, and the mixture was stirred for one hour under ice-cooling. A 5 N aqueous sodium hydroxide solution (9 ml) was added thereto, and extraction was performed with DCM. The extract was dried over anhydrous sodium sulfate. After the drying agent was removed by filtration, concentration was performed under reduced pressure to give the title compound (299 mg, 91%) as a pink oily substance.

HPLC retention time: 0.51 min (analysis condition D)

$^1$H-NMR (400 MHz, CDCl$_3$) δ: 7.33 (1H, dd, J=8.2, 6.6 Hz), 6.79 (1H, dd, J=11.0, 2.7 Hz), 6.48 (1H, s), 6.40 (1H, td, J=8.2, 2.7 Hz), 3.58 (2H, br s), 2.65 (2H, q, J=7.3 Hz), 1.17 (3H, t, J=7.3 Hz).

Example 29

Compound 29

[2-Ethylsulfanyl-5-(trifluoromethyl)phenyl]hydrazine

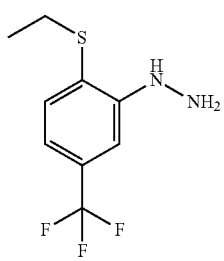

The title compound was synthesized from 2-amino-4-(trifluoromethyl)benzenethiol under the same conditions as for Compounds 27 and 28.

Example 30

Compound 30

(5-Chloro-2-ethylsulfanylphenyl)hydrazine

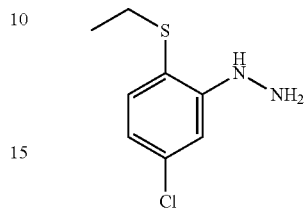

The title compound was synthesized from 2-amino-4-chlorobenzenethiol under the same conditions as for Compounds 27 and 28.

Example 31

Compound 31

(5-Chloro-2-ethylsulfonylphenyl)hydrazine

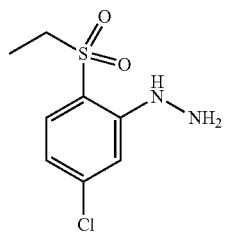

The title compound was synthesized from (5-chloro-2-ethylsulfanylphenyl)hydrazine (Compound 30) under the same conditions as for Compound 14.

Example 32

Compound 32

(5-Chloro-2-methylsulfanylphenyl)hydrazine

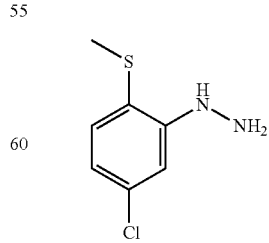

The title compound was synthesized from 2-amino-4-chlorobenzenethiol under the same conditions as for Compounds 27 and 28. However, methyl iodide was used in place of ethyl iodide under the conditions for Compound 27.

Example 33

Compound 33

(5-Chloro-2-propylsulfanylphenyl)hydrazine

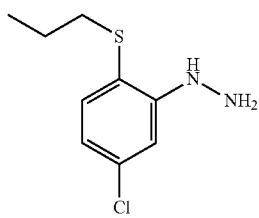

The title compound was synthesized from 2-amino-4-chlorobenzenethiol under the same conditions as for Compounds 27 and 28. However, 1-iodopropane was used in place of ethyl iodide under the conditions for Compound 27.

Example 34

Compound 34

5-Chloro-2-propan-2-ylsulfanylaniline

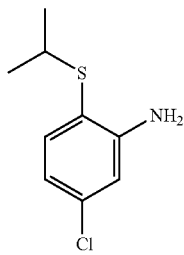

The title compound was synthesized from 2-amino-4-chlorobenzenethiol under the same conditions as for Compound 27. However, the reaction was performed without tetra-n-butylammonium iodide using 2-iodopropane in place of ethyl iodide.

Example 35

Compound 35

5-Chloro-2-propan-2-ylsulfonylaniline

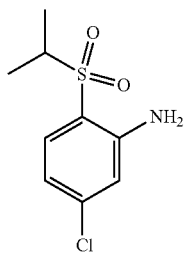

The title compound was synthesized from 5-chloro-2-propan-2-ylsulfanylaniline (Compound 34) under the same conditions as for Compound 14.

Example 36

Compound 36

(5-Chloro-2-propan-2-ylsulfonylphenyl)hydrazine

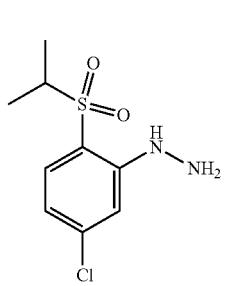

The title compound was synthesized from 5-chloro-2-propan-2-ylsulfonylaniline (Compound 35) under the same conditions as for Compound 28.

Example 37

Compound 37

(5-Chloro-2-cyclopentylsulfonylphenyl)hydrazine

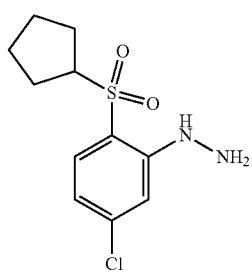 [SMILES: NNc1cc(Cl)ccc1S(=O)(=O)C1CCCC1]

The title compound was synthesized from 2-amino-4-chlorobenzenethiol under the same conditions as for Compounds 34, 35, and 36. However, bromocyclopentane was used in place of 2-iodopropane under the conditions for Compound 34.

Example 38

Compound 38

4-Chloro-1-cyclopropylsulfonyl-2-nitrobenzene

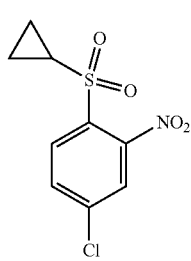 [SMILES: O=[N+]([O-])c1cc(Cl)ccc1S(=O)(=O)C1CC1]

Cyclopropanesulfinic acid sodium salt (890 mg, 6.95 mmol) was added to a solution of 4-chloro-1-fluoro-2-nitrobenzene (1.02 g, 5.78 mmol) in DMF (5 ml), and the mixture was stirred at 70° C. for 2.5 hours. Water was added to the reaction mixture, and the precipitate generated was collected by filtration. The resulting solid was washed with water and diethyl ether, and then dried to give the title compound (1.26 g, 83%) as a colorless solid.

LCMS: m/z 262 [M+H]$^+$
HPLC retention time: 0.72 min (analysis condition D)

Example 39

Compound 39

5-Chloro-2-cyclopropylsulfonylaniline

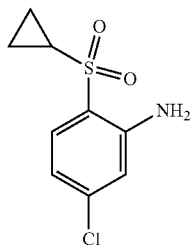 [SMILES: Nc1cc(Cl)ccc1S(=O)(=O)C1CC1]

Iron powder (779 mg, 13.3 mmol) and a 37% aqueous hydrochloric acid solution (0.191 mL, 2.33 mmol) were added to a solution of 4-chloro-1-cyclopropylsulfonyl-2-nitrobenzene (Compound 38, 1.26 g, 4.65 mmol) in EtOH (19 ml) and water (5 ml), and the mixture was stirred at 85° C. for 1.5 hours. The reaction mixture was filtered through celite, and washed with EtOH. The filtrate was concentrated under reduced pressure. After water was added to the resulting residue and extraction was performed with ethyl acetate, the organic layer was washed with brine and dried over anhydrous sodium sulfate. After the drying agent was removed by filtration, concentration was performed under reduced pressure. The resulting residue was purified by silica gel column chromatography (ethyl acetate/hexane) to give the title compound (817 mg, 73%) as a colorless solid.

LCMS: m/z 232 [M+H]$^+$
HPLC retention time: 0.68 min (analysis condition D)

Example 40

Compound 40

(5-Chloro-2-cyclopropylsulfonylphenyl)hydrazine

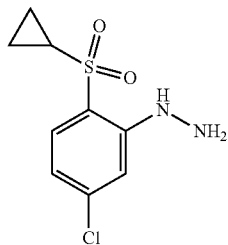 [SMILES: NNc1cc(Cl)ccc1S(=O)(=O)C1CC1]

The title compound was synthesized from 5-chloro-2-cyclopropylsulfonylaniline (Compound 39) under the same conditions as for Compound 28.

Example 41

Compound 41

4-Chloro-2-nitro-1-phenylsulfanylbenzene

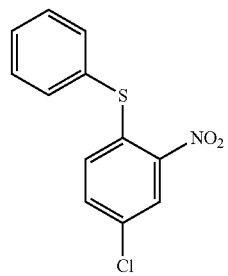 [SMILES: O=[N+]([O-])c1cc(Cl)ccc1Sc1ccccc1]

A solution of 1,4-dichloro-2-nitrobenzene (190 mg, 0.990 mmol), benzenethiol (0.101 ml, 0.988 mmol), and sodium hydroxide (40 mg, 1.00 mmol) in EtOH (0.8 ml) was stirred under reflux for one hour. The reaction mixture was cooled to room temperature, concentrated by removing EtOH under reduced pressure, and then extracted twice with ethyl acetate. The organic layer was dried over anhydrous magnesium sulfate. After the drying agent was removed by filtration, concentration was performed under reduced pressure and hexane was added to the resulting residue. The mixture was stirred at 0° C. overnight. The precipitated yellow solid was purified by preparative TLC (ethyl acetate/hexane) to give the title compound (160 mg, 61%).

$^1$H-NMR (300 MHz, CDCl$_3$) δ:8.14 (1H, d, J=2.3 Hz), 7.51-7.55 (2H, m), 7.44-7.47 (3H, m), 7.22-7.26 (1H, m), 6.74 (1H, d, J=8.7 Hz)

Example 42

Compound 42

5-Chloro-2-phenylsulfanylaniline

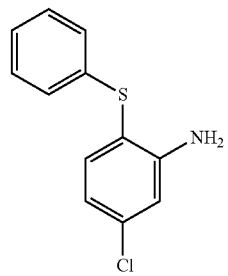 [SMILES: Nc1cc(Cl)ccc1Sc1ccccc1]

The title compound was synthesized from 4-chloro-2-nitro-1-phenylsulfanylbenzene (Compound 41) under the same conditions as for Compound 24.

Example 43

Compound 43

(5-Chloro-2-phenylsulfanylphenyl)hydrazine

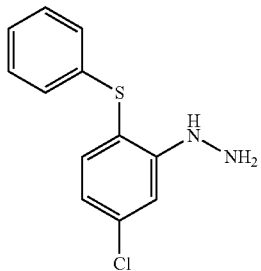 [SMILES: NNc1cc(Cl)ccc1Sc1ccccc1]

The title compound was synthesized from 5-chloro-2-phenylsulfanylaniline (Compound 42) under the same conditions as for Compound 28.

Example 44

Compound 44

3-Amino-4-phenylsulfanylbenzonitrile

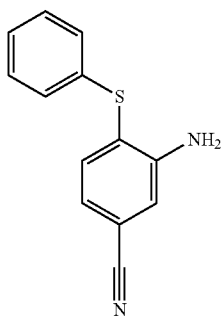 [SMILES: N#Cc1ccc(Sc2ccccc2)c(N)c1]

A solution of 3-amino-4-chlorobenzonitrile (562 mg, 3.69 mmol) and sodiothiobenzene (731 mg, 5.53 mmol) in DMF (3.7 ml) was stirred at 150° C. for 50 minutes using a microwave reaction system. A saturated aqueous ammonium chloride solution was added to the reaction mixture, and extraction was performed with ethyl acetate. The organic layer was then washed with water and brine, and dried over anhydrous magnesium sulfate. After the drying agent was removed by filtration, concentration was performed under reduced pressure. The resulting residue was purified by silica gel column chromatography (ethyl acetate/hexane) to give the title compound (637 mg, 76%) as a colorless solid.

LCMS: m/z 227 [M+H]$^+$

HPLC retention time: 2.40 min (analysis condition C)

Example 45

Compound 45

3-Hydrazinyl-4-phenylsulfanylbenzonitrile

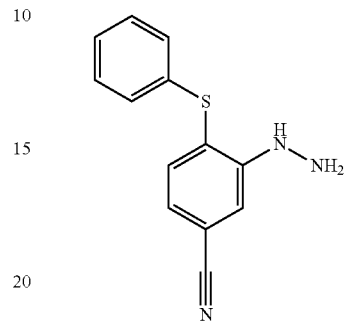

The title compound was synthesized from 3-amino-4-phenylsulfanylbenzonitrile (Compound 44) under the same conditions as for Compound 28.

Example 46

Compound 46

3-Amino-4-ethylsulfanylbenzonitrile

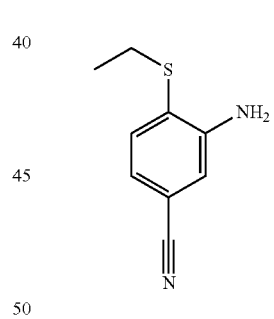

Sodium ethanethiolate (1.62 g, 19.27 mmol) was added to a solution of 3-amino-4-chlorobenzonitrile (1.96 g, 12.85 mmol) in DMF (12 ml), and the mixture was stirred at 80° C. for 50 minutes using a microwave reaction system. The reaction solution was cooled to room temperature and diluted with EtOAc (250 ml). The resulting solution was washed with half-saturated brine (100 ml, three times), and the organic layer was dried over anhydrous sodium sulfate. After the drying agent was removed by filtration, the solution was concentrated under reduced pressure. The resulting residue was purified by amino silica gel column chromatography (EtOAc/n-hexane) to give the title compound (2.13 g, 93%) as a pale yellow solid.

LCMS: m/z 179 [M+H]$^+$

HPLC retention time: 2.00 min (analysis condition C)

Example 47

Compound 47

4-Ethylsulfanyl-3-hydrazinylbenzonitrile

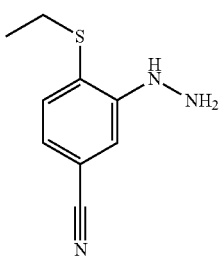

The title compound was synthesized from 3-amino-4-ethylsulfanylbenzonitrile (Compound 46) under the same conditions as for Compound 28.

Example 48

Compound 48

5-Ethoxy-2-methyl-1,3-benzothiazole

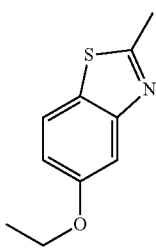

The title compound was synthesized from 2-methyl-1,3-benzothiazol-5-ol under the same conditions as for Compound 27.

Example 49

Compound 49

2-Amino-4-ethoxybenzenethiol

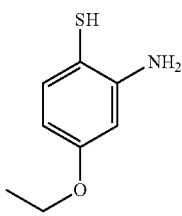

A 30% by weight sodium hydroxide solution (13 ml) and ethylene glycol (13 ml) were added to 5-ethoxy-2-methyl-1,3-benzothiazole (Compound 48, 858 mg, 4.44 mmol) under nitrogen atmosphere at room temperature. The suspension mixture was stirred under reflux for 5.5 hours. After cooling to room temperature, the mixture was washed three times with diethyl ether (20 ml×3). The aqueous layer was cooled to 0° C., adjusted to pH 2-3 with a 36% aqueous hydrochloric acid solution, and extracted with diethyl ether. The combined organic layers were sequentially washed with brine and water. The organic layer was dried over anhydrous sodium sulfate. After the drying agent was removed by filtration, concentration was performed under reduced pressure to give the title compound as a crude product.

$^1$H-NMR (400 MHz, DMSO-$d_6$) δ: 7.28 (1H, d, J=7.9 Hz), 6.24-6.29 (2H, m), 4.29 (2H, brs), 3.97 (2H, q, J=6.9 Hz), 2.76 (1H, s), 1.38 (3H, t, J=6.9 Hz).

Example 50

Compound 50

5-Ethoxy-2-ethylsulfanylaniline

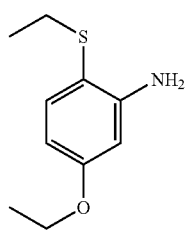

The title compound was synthesized from 2-amino-4-ethoxybenzenethiol (Compound 49) under the same conditions as for Compound 27.

Example 51

Compound 51

(5-Ethoxy-2-ethylsulfanylphenyl)hydrazine

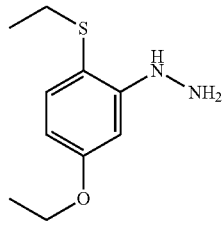

The title compound was synthesized from 5-ethoxy-2-ethylsulfanylaniline (Compound 50) under the same conditions as for Compound 28.

Example 52

Compound 52

(2-Ethylsulfanyl-5-methoxyphenyl)hydrazine

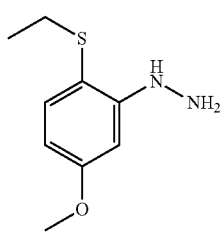

The title compound was synthesized from 5-methoxy-2-methyl-1,3-benzothiazole under the same conditions as for Compounds 49, 50, and 51.

Example 53

Compound 53

5-Bromo-2-ethylsulfanylaniline

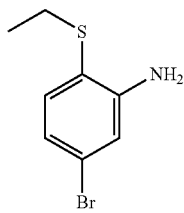

The title compound was synthesized from 5-bromo-2-methyl-1,3-benzothiazole under the same conditions as for Compounds 49 and 50.

Example 54

Compound 54

(5-Bromo-2-ethylsulfanylphenyl)hydrazine

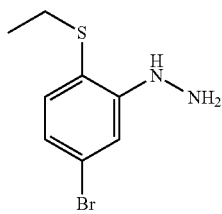

The title compound was synthesized from 5-bromo-2-ethylsulfanylaniline (Compound 53) under the same conditions as for Compound 28.

Example 55

Compound 55

2-Ethylsulfanyl-5-(2-trimethylsilylethynyl)aniline

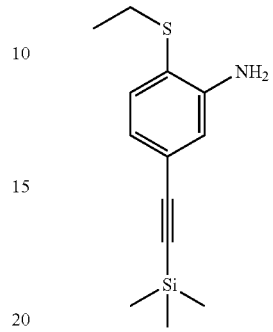

Trimethylsilylacetylene (0.19 ml, 1.35 mmol), palladium (II) acetate (15.2 mg, 0.068 mmol), triphenylphosphine (35.5 mg, 0.14 mmol), and potassium carbonate (125 mg, 0.90 mmol) were added to a solution of 5-bromo-2-ethylsulfanylaniline (Compound 53, 105 mg, 0.45 mmol) in DMF (2 ml) under nitrogen atmosphere, and the mixture was stirred at 80° C. for five hours. After the reaction mixture was cooled to room temperature, ethyl acetate was added thereto. The organic layer was washed with brine and then dried over anhydrous sodium sulfate. After the drying agent was removed by filtration, concentration was performed under reduced pressure. The resulting residue was purified by silica gel chromatography (ethyl acetate/hexane) to give the title compound (79.5 mg, 71%) as a pale yellow oily substance.

LCMS: m/z 250 [M+H]$^+$
HPLC retention time: 3.16 min (analysis condition C)

Example 56

Compound 56

2-Ethylsulfanyl-5-ethynylaniline

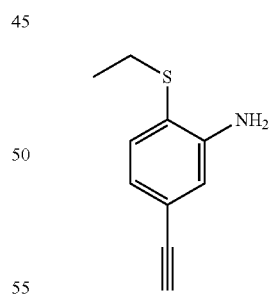

A solution of tetrabutylammonium fluoride in 1M-THF (0.63 ml, 0.63 mmol) was added to a solution of 2-ethylsulfanyl-5-(2-trimethylsilylethynyl)aniline (Compound 55, 79.5 mg, 0.32 mmol) in THF (2.0 ml), and the mixture was stirred at room temperature for four hours. The reaction mixture was concentrated under reduced pressure, and the resulting residue was purified by silica gel column chromatography (ethyl acetate/hexane) to give the title compound (31.6 mg, 42%) as a pale yellow oily substance.

LCMS: m/z 178 [M+H]$^+$
HPLC retention time: 2.17 min (analysis condition C)

Example 57

Compound 57

(2-Ethylsulfanyl-5-ethynylphenyl)hydrazine

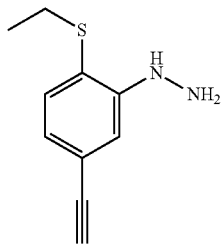

The title compound was synthesized from 2-ethylsulfanyl-5-ethynylaniline (Compound 56) under the same conditions as for Compound 28.

Example 58

Compound 58

1-Iodo-2-nitro-4-(trifluoromethoxy)benzene

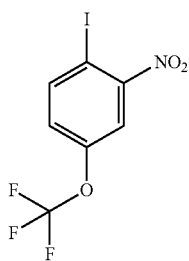 [SMILES: O=[N+]([O-])c1cc(OC(F)(F)F)ccc1I]

Ice (8 g) and sodium nitrite (378 mg, 5.48 mmol) were added to a mixture of 2-nitro-4-(trifluoromethoxy)aniline (1.11 g, 4.98 mmol), a 35% aqueous hydrochloric acid solution (7.2 ml), and water (7.2 ml) under ice-cooling, and the mixture was stirred for 20 minutes. Subsequently, acetic acid (5 ml) was added, and the mixture was stirred at room temperature for 20 minutes. Under ice-cooling, sodium nitrite (80.7 mg, 1.17 mmol) was added and the mixture was stirred for 20 minutes. Subsequently, potassium iodide (1.22 g, 7.38 mmol) dissolved in water (1.5 ml) was added, and the mixture was stirred for 30 minutes. Followed by addition of water to the reaction mixture and extraction with ethyl acetate, the organic layer was then washed with a saturated aqueous sodium thiosulfate solution and dried over anhydrous magnesium sulfate. After the drying agent was removed by filtration, concentration was performed under reduced pressure. The resulting residue was purified by silica gel column chromatography (ethyl acetate/n-hexane) to give the title compound (1.07 g, 65%) as an orange oily substance.

LCMS: m/z 334[M+H]$^+$

HPLC retention time: 0.90 min (analysis condition H)

Example 59

Compound 59

1-Ethylsulfanyl-2-nitro-4-(trifluoromethoxy)benzene

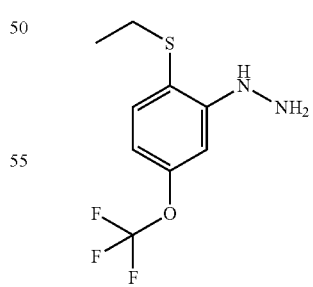

Tris(dibenzylideneacetone)dipalladium(0) (17.3 mg, 0.019 mmol), (5-diphenylphosphanyl-9,9-dimethylxanthen-4-yl)-diphenylphosphane (23.5 mg, 0.041 mmol), DIPEA (0.098 ml, 0.574 mmol), and ethanethiol (0.028 ml, 0.383 mmol) were added to a solution of 1-iodo-2-nitro-4-(trifluoromethoxy)benzene (63.7 mg, 0.191 mmol) in 1,4-dioxane (1 ml), and the mixture was stirred at 80° C. for 30 minutes. The reaction solution was cooled to room temperature, followed by addition of water and extraction with ethyl acetate. The organic layer was dried over anhydrous sodium thiosulfate. After the drying agent was removed by filtration, concentration was performed under reduced pressure. The resulting residue was purified by silica gel column chromatography (ethyl acetate/hexane) to give the title compound (41.1 mg, 80%) as a yellow solid.

$^1$H-NMR (600 MHz, CDCl$_3$) δ: 8.10 (1H, s), 7.44 (2H, s), 3.01 (2H, q, J=7.2 Hz), 1.42 (3H, t, J=7.2 Hz).

Example 60

Compound 60

[2-Ethylsulfanyl-5-(trifluoromethoxy)phenyl]hydrazine

The title compound was synthesized from 1-ethylsulfanyl-2-nitro-4-(trifluoromethoxy)benzene (Compound 59) under the same conditions as for Compounds 42 and 43. However, acetic acid was used in place of the saturated aqueous ammonium chloride solution under the conditions for Compound 42.

Example 61

Compound 61

1,2-Dichloro-4-ethylsulfanyl-5-nitrobenzene

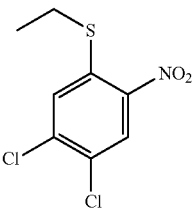

The title compound was synthesized from 1,2-dichloro-4-fluoro-5-nitrobenzene under the same conditions as for Compound 1. However, TEA was used in place of potassium carbonate.

Example 62

Compound 62

4,5-Dichloro-2-ethylsulfanylaniline

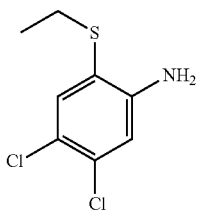

The title compound was synthesized from 1,2-dichloro-4-ethylsulfanyl-5-nitrobenzene (Compound 61) under the same conditions as for Compound 39. However, a saturated aqueous ammonium chloride solution was used in place of the 37% aqueous hydrochloric acid solution.

Example 63

Compound 63

(4,5-Dichloro-2-ethylsulfanylphenyl)hydrazine

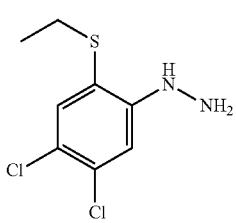

The title compound was synthesized from 4,5-dichloro-2-ethylsulfanylaniline (Compound 62) under the same conditions as for Compound 28.

Example 64

Compound 64

5,7-Dichloro-1,3-benzothiazol-2-amine

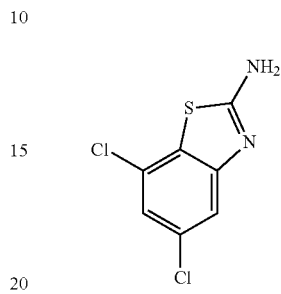

A bromine-1,4-dioxane complex (561 mg, 2.26 mol) was added to a solution of (3,5-dichlorophenyl)thiourea (500 mg, 2.26 mmol) in chloroform (4.0 ml) under nitrogen atmosphere at 0° C. The mixture was stirred at 0° C. for 1.0 hour, and at 80° C. for 22 hours. The reaction mixture was cooled and then concentrated under reduced pressure. The resulting residue was washed with water and recrystallized with ethanol. The powders thus obtained were separated by filtration. The filtrate was concentrated under reduced pressure, the resulting residue was washed with ethanol, and the powders were collected by filtration. These two powders were combined to give the title compound (209 mg, 42%).

LCMS: m/z 219 [M+H]$^+$

HPLC retention time: 1.89 min (analysis condition C)

Example 65

Compound 65

(3,5-Dichloro-2-ethylsulfanylphenyl)hydrazine

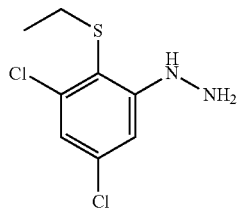

The title compound was synthesized from 5,7-dichloro-1,3-benzothiazol-2-amine (Compound 64) under the same conditions as for Compounds 49, 50, and 51.

Example 66

Compound 66

2-Chloro-4-fluoro-5-nitrobenzonitrile

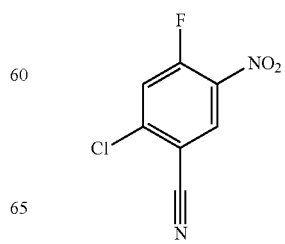

Fuming nitric acid (3.0 ml) was added to a solution of 2-chloro-4-fluorobenzonitrile (500 mg, 3.21 mmol) in sulfuric acid (3.0 ml) at room temperature, and the mixture was stirred for two hours. The reaction mixture was diluted with water, neutralized with a saturated sodium carbonate solution, and extracted with dichloromethane. The organic layer was washed with a saturated aqueous sodium chloride solution, and then dried over anhydrous sodium sulfate. After the drying agent was removed by filtration, concentration was performed under reduced pressure to give a crude product of the title compound (605 mg).

$^1$H-NMR (270 MHz, CDCl$_3$) δ: 8.47 (1H, d, J=7.3 Hz), 7.56 (1H, d, J=9.9 Hz).

Example 67

Compound 67

2-Chloro-4-ethylsulfanyl-5-nitrobenzonitrile

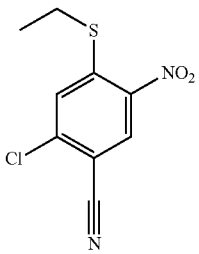

The title compound was synthesized from 2-chloro-4-fluoro-5-nitrobenzonitrile (Compound 66) under the same conditions as for Compound 1.

Example 68

Compound 68

5-Amino-2-chloro-4-ethylsulfanylbenzonitrile

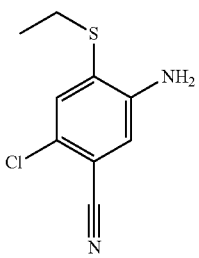

The title compound was synthesized from 2-chloro-4-ethylsulfanyl-5-nitrobenzonitrile (Compound 67) under the same conditions as for Compound 39. However, the reaction was performed with the addition of acetic acid.

Example 69

Compound 69

2-Chloro-4-ethylsulfanyl-5-hydrazinylbenzonitrile

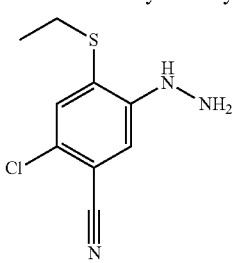

The title compound was synthesized from 5-amino-2-chloro-4-ethylsulfanylbenzonitrile (Compound 68) under the same conditions as for Compound 28.

Example 70

Compound 70

2-Amino-4-chlorobenzaldehyde

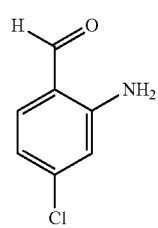

The title compound was synthesized from 4-chloro-2-nitrobenzaldehyde under the same conditions as for Compound 39.

Example 71

Compound 71

5-Chloro-2-propylaniline

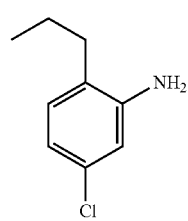

A solution of 2-amino-4-chlorobenzaldehyde (Compound 70, 83.5 mg, 0.52 mmol) and 4-methylbenzenesulfonohydrazide (97.6 mg, 0.52 mmol) in 1,4-dioxane (2 ml) was stirred at 80° C. for one hour. To this reaction mixture, potassium carbonate (110.0 mg, 0.80 mmol) and ethylboronic acid (58.1 mg, 0.79 mmol) were added, and the mixture was stirred at 110° C. for 3.5 hours. DCM (20 ml) was added to the reaction mixture. The organic layer was washed with a saturated aqueous sodium bicarbonate solution (10 ml) and brine (10 ml), and then dried over anhydrous sodium sulfate. After the drying agent was removed by filtration, concentration was performed under reduced pressure. The resulting residue was purified by silica gel column chromatography (ethyl acetate/hexane) to give the title compound (56.2 mg, 64%) as an orange oily substance.

LCMS: m/z 170[M+H]$^+$

HPLC retention time: 0.84 min (analysis condition D)

Example 72

Compound 72

(5-Chloro-2-propylphenyl)hydrazine

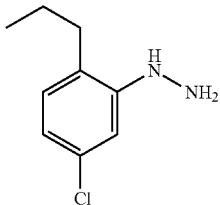

The title compound was synthesized from 5-chloro-2-propylaniline (Compound 71) under the same conditions as for Compound 28.

Examples 73 to 76

The following compounds of Table 2 were synthesized from 2-amino-4-chlorobenzaldehyde (Compound 70) under the same conditions as for Compounds 71 and 72. However, boronic acids that correspond to the respective compounds were used under the conditions for Compound 71.

TABLE 2

| Example | Compound number | Structure | Compound name |
|---|---|---|---|
| 73 | 73 | 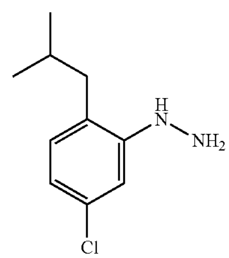 | [5-Chloro-2-(2-methylpropyl)phenyl]hydrazine |
| 74 | 74 | 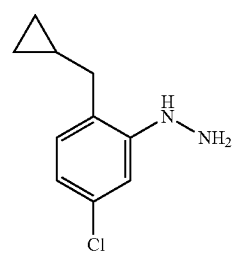 [SMILES: NNc1cc(Cl)ccc1CC1CC1] | [[5-Chloro-2-(cyclopropymethyl)phenyl]hydrazine |
| 75 | 75 | 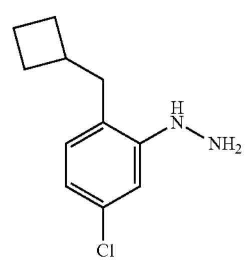 [SMILES: NNc1cc(Cl)ccc1CC1CCC1] | [5-Chloro-2-(cyclopropymethyl)phenyl]hydrazine |
| 76 | 76 | 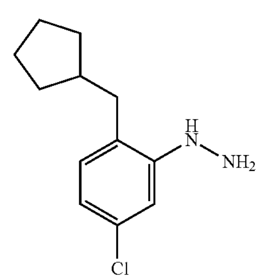 [SMILES: NNc1cc(Cl)ccc1CC1CCCC1] | [5-Chloro-2-(cyclopropymethyl)phenyl]hydrazine |

Example 77

Compound 77

5-Chloro-2-ethylsulfanyl-3-nitropyridine

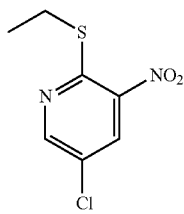

A catalytic amount of copper(II) oxide and ethanethiol (0.038 ml, 0.52 mmol) were added to a mixture of 2,5-dichloro-3-nitro-pyridine (100 mg, 0.52 mmol) and potassium hydroxide (38 mg, 0.67 mmol) in DMSO (2.5 ml), and the mixture was stirred in a sealed tube at 80° C. for three hours. The reaction mixture was cooled to room temperature, diluted with water, and extracted with ethyl acetate. The organic layer was dried with anhydrous magnesium sulfate. After the drying agent was removed by filtration, concentration was performed under reduced pressure. The resulting residue was purified by silica gel column chromatography (ethyl acetate/hexane) to give the title compound (60 mg, purity 70%) as a yellow oily substance.

LCMS: m/z 219 [M+H]$^+$
HPLC retention time: 3.70 min (analysis condition B)

Example 78

Compound 78

(5-Chloro-2-ethylsulfanylpyridin-3-yl)hydrazine

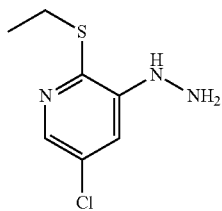

The title compound was synthesized from 5-chloro-2-ethylsulfanyl-3-nitropyridine (Compound 77) under the same conditions as for Compounds 42 and 43.

Example 79

Compound 79

2-Chloro-5-ethylsulfanylpyridin

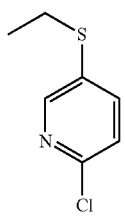

Under nitrogen atmosphere, ethanethiol (172 ul, 2.32 mmol) was added to a mixed solution of 2-chloro-5-iodo-pyridine (0.50 g, 2.1 mmol), palladium(II) acetate (52 mg, 0.23 mmol), XantPhos (135 mg, 0.23 mmol), and sodium tert-butoxide (112 mg, 1.2 mmol) in toluene (10 ml), and the mixture was stirred in a sealed tube at 80° C. for 24 hours. The reaction mixture was cooled to room temperature, and the insoluble matter was then removed by filtration through celite. The filtrate was concentrated under reduced pressure, and the resulting residue was purified by silica gel column chromatography (ethyl acetate/hexane) to give the title compound (0.32 g, 88%).

$^1$H-NMR (300 MHz, CDCl$_3$) δ: 8.32 (1H, d, J=2.7 Hz), 7.60 (1H, dd, J=2.7, 8.4 Hz), 7.25-7.27 (1H, m), 2.94 (2H, q, J=7.2 Hz), 1.29 (3H, t, J=7.2 Hz).

Example 80

Compound 80

2-Chloro-5-ethylsulfanyl-4-iodopyridine

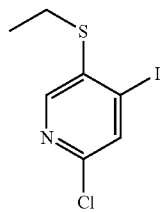

A 1.7 M solution of tert-butyllithium in hexane (262 ul, 0.45 mmol) was added to a solution of 2-chloro-5-ethylsulfanylpyridine (Compound 79, 70.8 mg, 0.41 mmol) in diethyl ether (1.0 ml) and the mixture was stirred for 20 minutes, under nitrogen atmosphere at −78° C. Subsequently, a solution of iodine (123 mg, 0.49 mmol) in diethyl ether (1.0 ml) was added and the mixture was stirred at −78° C. for one hour. The reaction mixture was warmed to room temperature, diluted with water, and extracted with diethyl ether. The organic layer was dried over anhydrous magnesium sulfate. After the drying agent was removed by filtration, concentration was performed under reduced pressure. The resulting residue was purified by preparative TLC (ethyl acetate/hexane) to give a mixture (20.0 mg) of the title compound and the unreacted starting material (Compound 79) in approximately 1:1 ratio.

Example 81

Compound 81

(2-Chloro-5-ethylsulfanylpyridin-4-yl)hydrazine

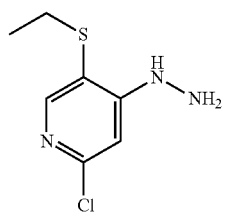

Hydrazine monohydrate (0.052 ul, 1.07 mmol) was added to a solution of a mixture of 2-chloro-5-ethylsulfanyl-4-iodopyridine (Compound 80) and 2-chloro-5-ethylsulfanylpyridine (Compound 79) in approximately 1:1 ratio (20.0 mg), which was obtained in Example 80, in 1,4-dioxane (2 ml), and the mixture was stirred at 110° C. for seven hours. The reaction mixture was cooled to room temperature, diluted with water, and extracted with dichloromethane. The organic layer was dried over anhydrous magnesium sulfate. After the drying agent was removed by filtration, concentration was performed under reduced pressure to give a crude product of the title compound.

Example 82

Compound 82

4-Bromo-5-methyl-2-nitrobenzoic Acid

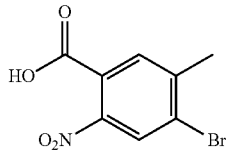

A solution of 5-methyl-2-nitrobenzoic acid (1.02 g, 5.64 mmol) and concentrated sulfuric acid (3 ml) was warmed to 60-80° C., to which NBS (1.01 g, 5.69 mmol) was gradually added. The mixture was stirred at 60-80° C. for four hours. NBS (508 mg, 2.85 mmol) was gradually added to this reaction mixture, which was stirred at 60° C. for 30 minutes. Water was added to the reaction mixture, and the precipitate generated was collected by filtration. The resulting solid was washed with water and hexane and then dried to give the title compound (1.24 g, 85%) as a colorless solid.

$^1$H-NMR (DMSO-$d_6$) δ: 14.02 (1H, br s), 8.28 (1H, s), 7.86 (1H, s), 2.46 (3H, s).

Example 83

Compound 83

4-Bromo-2-nitro-5-(trifluoromethoxy)benzoic Acid

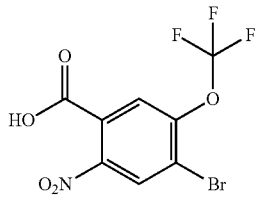

The title compound was synthesized from 2-nitro-5-(trifluoromethoxy)benzoic acid under the same conditions as for Compound 82.

Example 84

Compound 84

Ethyl 2-amino-3-bromo-5-(trifluoromethyl)benzoate

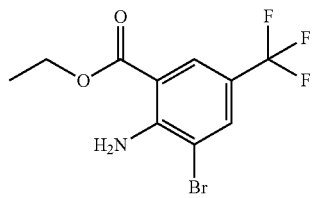 [SMILES: CCOC(=O)c1cc(C(F)(F)F)cc(Br)c1N]

Bromine (3.43 ml, 130 mmol) was added to a solution of ethyl 2-amino-5-(trifluoromethyl)benzoate (5.34 g, 23 mmol) in DCM (26.5 ml) at room temperature, and the mixture was stirred for 30 minutes. A saturated aqueous sodium thiosulfate solution (30 ml) was added thereto under ice-cooling, and extraction was performed with ethyl acetate. The extract was washed with brine and then dried over anhydrous sodium sulfate. After the drying agent was removed by filtration, concentration was performed under reduced pressure. The resulting residue was purified by silica gel column chromatography (ethyl acetate/hexane) to give the title compound (6.97 g, 97%) as a pale yellow oily substance.

LCMS: m/z 312 [M+H]$^+$

HPLC retention time: 1.02 min (analysis condition D)

Example 85

Compound 85

2-Amino-3-bromo-5-(trifluoromethyl)benzoic Acid

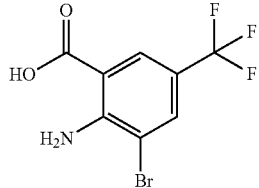 [SMILES: Nc1c(Br)cc(C(F)(F)F)cc1C(=O)O]

A 1 N aqueous sodium hydroxide solution (37 ml) was added to a solution of ethyl 2-amino-3-bromo-5-(trifluoromethyl)benzoate (Compound 84, 7.00 g, 22.3 mmol) in ethanol (37 ml), and the mixture was stirred at 50° C. for one hour. The reaction mixture was cooled to room temperature, to which a 1N hydrochloric acid (37 ml) was added. The solid produced was collected by filtration, washed with water, and dried under reduced pressure to give the title compound (6.08 g, 96%) as a colorless solid.

LCMS: m/z 284 [M+H]$^+$

HPLC retention time: 0.77 min (analysis condition D)

Example 86

Compound 86

2-Amino-3-chloro-5-(trifluoromethyl)benzoic Acid

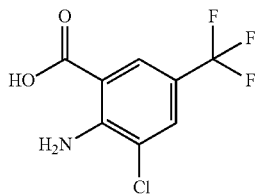

The title compound was synthesized from 2-amino-5-(trifluoromethyl)benzoic acid under the same conditions as for Compound 84. However, NCS was used in place of bromine.

Example 87

Compound 87

2-Amino-5-iodo-4-methylbenzoic Acid

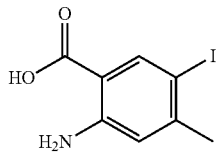

Iodine (252 mg, 0.99 mmol) and a 31% hydrogen peroxide solution (109 μl) were added to a solution of 2-amino-4-methylbenzoic acid (300 mg, 1.98 mmol) in n-butanol (1.8 ml) at room temperature, and the mixture was stirred at 50° C. for 1.0 hour. After cooling to room temperature, the solid was separated by filtration. The resulting solid was washed with water (10 ml) and methanol (2 ml) to give a crude product of the title compound.

LCMS: m/z 278 [M+H]$^+$

HPLC retention time: 1.92 min (analysis condition C)

Example 88

Compound 88 tert-Butyl N-(4-ethoxyphenyl)carbamate

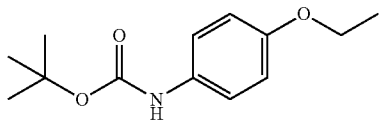 [SMILES: CCOc1ccc(NC(=O)OC(C)(C)C)cc1]

The title compound was synthesized from 4-ethoxyaniline according to the method described in the literature (J. Med. Chem. 1995, 38, 1679-1688).

LCMS: m/z 238 [M+H]$^+$

HPLC retention time: 2.38 min (analysis condition C)

Example 89

Compound 89

2-Amino-5-ethoxybenzoic Acid

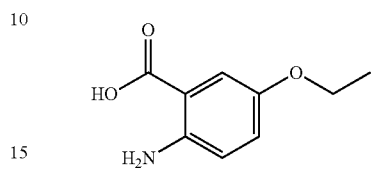

The title compound was synthesized from tert-butyl N-(4-ethoxyphenyl)carbamate (Compound 88) according to the method described in the literature (J. Med. Chem. 1995, 38, 1679-1688).

LCMS: m/z 182 [M+H]$^+$

HPLC retention time: 0.70 min (analysis condition C)

Example 90

Compound 90

Methyl 2-[(4-methoxyphenyl)methylamino]-5-(trifluoromethyl)pyridine-3-carboxylate

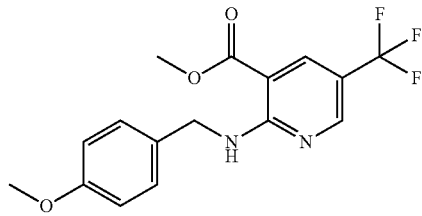 [SMILES: COC(=O)c1cc(C(F)(F)F)cnc1NCc1ccc(OC)cc1]

Triethylamine (0.70 ml, 5.0 mmol) and 4-methoxybenzylamine (0.14 ml, 1.10 mmol) were added to a solution of 2-chloro-5-(trifluoromethyl)-3-pyridine carboxylic acid (166 mg, 0.74 mmol) in acetonitrile (5 ml), and the mixture was stirred at 80° C. for two hours. The reaction mixture was cooled to room temperature and then concentrated under reduced pressure. The resulting residue was suspended in dichloromethane (6 ml), to which a 0.6 M solution of trimethylsilyldiazomethane in hexane (1.50 ml, 0.88 mmol) was added. The mixture was stirred at room temperature for one hour. The insoluble matter of the reaction mixture was separated by filtration, and the filtrate was concentrated under reduced pressure. The resulting residue was purified by silica gel column chromatography (ethyl acetate/hexane) to give the title compound (44.4 mg, 18%) as a white solid.

LCMS: m/z 341 [M+H]$^+$

HPLC retention time: 3.02 min (analysis condition C)

Example 91

Compound 91

Methyl 2-amino-5-(trifluoromethyl)pyridine-3-carboxylate

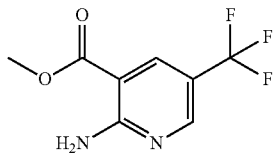

Anisole (25.2 ul, 0.23 mmol) and trifluoroacetic acid (1.0 ml) were added to a solution of methyl 2-[(4-methoxyphenyl)methylamino]-5-(trifluoromethyl)pyridine-3-carboxylate (Compound 90, 39.3 mg, 0.12 mmol) in dichloromethane (1 ml), and the mixture was stirred at 40° C. for 24 hours. The reaction mixture was cooled to room temperature and then concentrated under reduced pressure. The resulting residue was purified by silica gel column chromatography (ethyl acetate/hexane) to give the title compound (24.1 mg, 95%) as a white solid.

LCMS: m/z 221 [M+H]$^+$

HPLC retention time: 1.82 min (analysis condition C)

Example 92

Compound 92

2-Amino-5-(trifluoromethyl)pyridine-3-carboxylic Acid

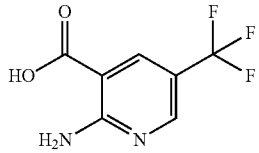

The title compound was synthesized from methyl 2-amino-5-(trifluoromethyl)pyridine-3-carboxylate (Compound 91) under the same conditions as for Compound 85. However, methanol was used in place of ethanol as a solvent and the reaction was performed at room temperature.

Example 93

Compound 93

2-Amino-5-methylsulfanylbenzoic Acid

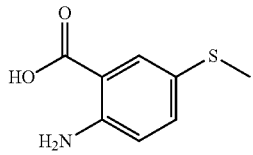

The title compound was synthesized from 5-chloro-2-nitrobenzoic acid according to the method described in the literature (J. Med. Chem. 1983, 26, 420-425).

LCMS: m/z 184 [M+H]$^+$

HPLC retention time: 1.35 min (analysis condition C)

Example 94

Compound 94

2-Amino-3-chloro-5-(trifluoromethoxy)benzoic Acid

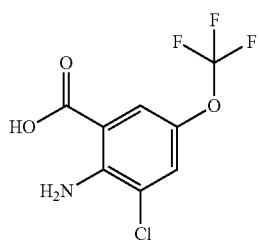 [SMILES: Nc1c(Cl)cc(OC(F)(F)F)cc1C(=O)O]

The title compound was synthesized from methyl 2-amino-3-chloro-5-(trifluoromethoxy)benzoate under the same conditions as for Compound 85. However, methanol was used in place of ethanol as a solvent and the reaction was performed at room temperature.

Example 95

Compound 95

6-(Trifluoromethyl)-3H-quinazolin-4-one

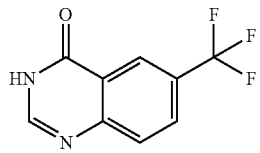 [SMILES: O=c1[nH]cnc2ccc(C(F)(F)F)cc12]

Formamide acetate (129 mg, 1.24 mmol) was added to a solution of 2-amino-5-(trifluoromethyl)benzoic acid (50.8 mg, 0.25 mmol) in ethanol (1.0 ml), and the mixture was stirred under microwave irradiation at 140° C. for 80 minutes. The reaction mixture was cooled and then concentrated under reduced pressure. The resulting residue was purified by silica gel column chromatography (ethyl acetate/hexane) to give the title compound (34.4 mg, 65%) as a white solid.

LCMS: m/z 215 [M+H]$^+$

HPLC retention time: 1.35 min (analysis condition C)

Example 96

Compound 96

(E)-3-[4-(Trifluoromethoxy)phenyl]prop-2-enoyl azide

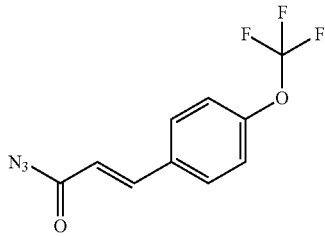 [SMILES: [N-]=[N+]=NC(=O)/C=C/c1ccc(OC(F)(F)F)cc1]

Oxalyl chloride (0.82 ml, 8.61 mmol) was added to a solution of (E)-3-[4-(trifluoromethoxy)phenyl]prop-2-enoic acid (1.0 g, 4.31 mmol) in dichloromethane (20 ml), and the mixture was stirred at room temperature for five hours. The reaction mixture was concentrated under reduced pressure, and the resulting residue was dissolved in acetone (10 ml), to which a solution of sodium azide (840 mg, 12.9 mmol) in acetone (10 ml) was added at 0° C. After the solution was stirred at 0° C. for two hours, the insoluble matter was separated by filtration, and the filtrate was concentrated under reduced pressure to give a crude product of the title compound (1.1 g) as a white solid.

$^1$H-NMR (DMSO-$d_6$) δ: 7.93 (2H, d, J=8.4 Hz), 7.80 (1H, d, J=15.9 Hz), 7.43 (2H, d, J=8.4 Hz), 6.74 (1H, d, J=15.9 Hz).

Example 97

Compound 97

7-(Trifluoromethoxy)-2H-isoquinolin-1-one

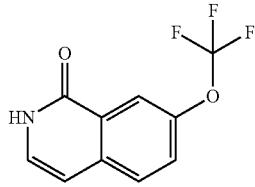 [SMILES: O=c1[nH]ccc2ccc(OC(F)(F)F)cc12]

Mercury(II) acetate (136 mg, 0.43 mmol) was added to a solution of a crude product of (E)-3-[4-(trifluoromethoxy)phenyl]prop-2-enoyl azide (Compound 96, 1.1 g) in o-dichlorobenzene (43 ml), and the mixture was stirred at 195° C. for 20 hours. The reaction mixture was cooled to room temperature, and then purified by silica gel column chromatography (methanol/dichloromethane). The fraction containing the target substance was concentrated. The resulting residue was suspended in a solution of dichloromethane-hexane, and the resulting solid was collected by filtration to give the title compound (0.24 g, yield in two steps: 25%) as a white solid.

$^1$H-NMR (DMSO-$d_6$) δ: 11.51 (1H, br), 8.00 (1H, s), 7.84 (1H, d, J=8.7 Hz), 7.72 (1H, dd, J=2.4, 8.7 Hz), 7.25 (1H, d, J=7.2 Hz), 6.63 (1H, d, J=7.2 Hz).

Example 98

Compound 98

7-(Trifluoromethyl)-2H-isoquinolin-1-one

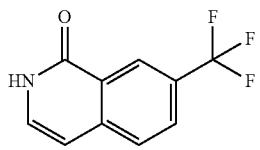 [SMILES: O=c1[nH]ccc2ccc(C(F)(F)F)cc12]

The title compound was synthesized from (E)-3-[4-(trifluoromethyl)phenyl]prop-2-enoic acid under the same conditions as for Compounds 96 and 97. However, the reaction was performed at 45° C. under the conditions for Compound 96.

Example 99

Compound 99

7-Methoxy-2H-isoquinolin-1-one

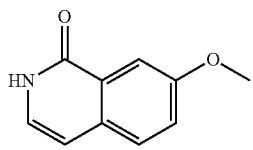

The title compound was synthesized from (E)-3-(4-methoxyphenyl)prop-2-enoic acid under the same conditions as for Compounds 96 and 97.

Example 100

Compound 100

(E)-3-[2-Chloro-4-(trifluoromethyl)phenyl]prop-2-enoic Acid

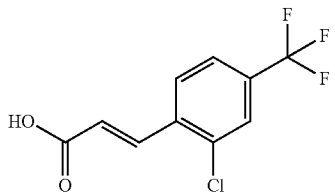 [SMILES: O=C(O)/C=C/c1ccc(C(F)(F)F)cc1Cl]

Triethylamine (0.11 ml, 0.82 mmol) was added to a solution of 2-chloro-1-iodo-4-(trifluoromethyl)benzene (100 mg, 0.33 mmol), acrylic acid (0.029 ml, 0.42 mmol), and palladium(II) acetate (3.7 mg, 0.016 mmol) in acetonitrile (1.0 ml), and the mixture was stirred under microwave irradiation at 110° C. for 30 minutes. The reaction mixture was cooled to room temperature, and the insoluble matter was then separated by filtration through celite. The filtrate was diluted with a 1 N aqueous hydrochloric acid solution, and extraction was performed with ethyl acetate. Subsequently, the organic layer was dried over anhydrous magnesium sulfate. After the drying agent was removed by filtration, concentration was performed under reduced pressure. The resulting residue was purified by silica gel column chromatography (methanol/dichloromethane) to give the title compound (75 mg, 92%).

$^1$H-NMR (DMSO-$d_6$) δ: 12.90 (1H, brs), 8.15 (1H, d, J=8.1 Hz), 7.98 (1H, s), 7.85 (1H, d, J=15.9 Hz), 7.74-7.78 (1H, m), 6.74 (1H, d, J=15.9 Hz).

Example 101

Compound 101

5-Chloro-7-(trifluoromethyl)-2H-isoquinolin-1-one

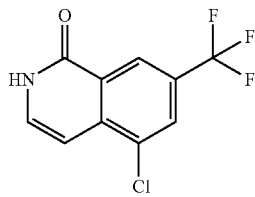

The title compound was synthesized from (E)-3-[2-chloro-4-(trifluoromethyl)phenyl]prop-2-enoic acid (Compound 100) under the same conditions as for Compounds 96 and 97.

Example 102

Compound 102

(E)-3-[2-Bromo-4-(trifluoromethyl)phenyl]prop-2-enoic Acid

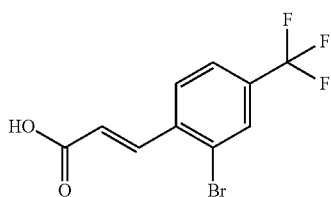

The title compound was synthesized from 2-bromo-1-iodo-4-(trifluoromethyl)benzene under the same conditions as for Compound 100. However, the reaction was performed without microwave irradiation at 65° C.

Example 103

Compound 103

5-Bromo-7-(trifluoromethyl)-2H-isoquinolin-1-one

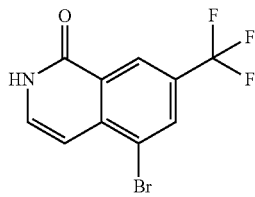 [SMILES: O=c1[nH]ccc2c(Br)cc(C(F)(F)F)cc12]

The title compound was synthesized from (E)-3-[2-bromo-4-(trifluoromethyl)phenyl]prop-2-enoic acid (Compound 102) under the same conditions as for Compounds 96 and 97.

Example 104

Compound 104 tert-Butyl N-[2-bromo-5-chloro-4-(trifluoromethyl)phenyl]-N-[(2-methylpropan-2-yl)oxycarbonyl]carbamate

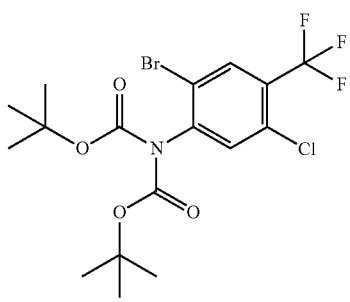 [SMILES: CC(C)(C)OC(=O)N(C(=O)OC(C)(C)C)c1cc(Cl)c(C(F)(F)F)cc1Br]

Boc$_2$O (35.2 ml, 153 mmol) was added to a suspension of 2-bromo-5-chloro-4-trifluoromethyl-phenylamine (14.0 g, 51.0 mmol), DMAP (3.12 g, 25.5 mmol), and triethylamine (35.9 ml, 255 mmol) in THF (255 ml), and the mixture was stirred at room temperature for 1.5 hours. The reaction solution was concentrated under reduced pressure, and the resulting residue was purified by silica gel column chromatography (ethyl acetate/hexane) to give the title compound (20.6 g, 85%) as a colorless solid.

HPLC retention time: 1.12 min (analysis condition D)
$^1$H-NMR (400 MHz, CDCl$_3$) δ: 7.92 (1H, s), 7.40 (1H, s), 1.43 (18H, s).

Example 105

Compound 105 tert-Butyl 4-chloro-2-[(2-methylpropan-2-yl)oxycarbonylamino]-5-(trifluoromethyl)benzoate

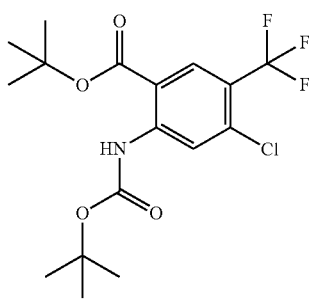 [SMILES: CC(C)(C)OC(=O)Nc1cc(Cl)c(C(F)(F)F)cc1C(=O)OC(C)(C)C]

A 1.57 M solution of n-BuLi in hexane (33 ml, 52 mmol) was added to a solution of tert-butyl N-[2-bromo-5-chloro-4-(trifluoromethyl)phenyl]-N-[(2-methylpropan-2-yl)oxycarbonyl]carbamate (Compound 104, 20.5 g, 43 mmol) in THF (430 ml) at −78° C. over 10 minutes, and this solution was stirred for one hour. A saturated aqueous ammonium chloride solution (200 ml) was added thereto, and the mixture was then warmed to room temperature. Ethyl acetate (400 ml) was added thereto, and this was washed with a saturated aqueous sodium chloride solution. The organic layer was dried over anhydrous sodium sulfate. After the drying agent was removed by filtration, concentration was performed under reduced pressure. The resulting residue was purified by silica gel column chromatography (ethyl acetate/hexane) to give the title compound (13.9 g, 82%) as a colorless solid.

HPLC retention time: 1.29 min (analysis condition D)
$^1$H-NMR (400 MHz, CDCl$_3$) δ: 10.55 (1H, s), 8.72 (1H, s), 8.22 (1H, s), 1.62 (9H, s), 1.55 (9H, s).

Example 106

Compound 106

2-Amino-4-chloro-5-(trifluoromethyl)benzoic Acid

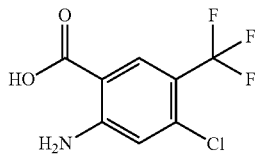

Trifluoroacetic acid (88 ml) was added to a solution of tert-butyl 4-chloro-2-[(2-methylpropan-2-yl)oxycarbonylamino]-5-(trifluoromethyl)benzoate (Compound 105, 13.9 g, 35 mmol) in DCM (350 ml), and the mixture was stirred at room temperature for 15 hours. The reaction solution was concentrated under reduced pressure to give a crude product of the title compound.

LCMS: m/z 240 [M+H]$^+$
HPLC retention time: 0.71 min (analysis condition D)

Example 107

Compound 107

Ethyl 2-amino-4-chloro-5-(trifluoromethyl)benzoate

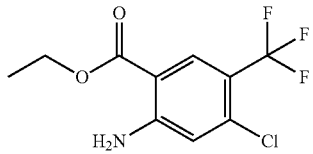 [SMILES: CCOC(=O)c1cc(C(F)(F)F)c(Cl)cc1N]

Potassium carbonate (19.4 g, 141 mmol) and ethyl iodide (4.22 ml, 53 mmol) were added to a solution of the crude product of 2-amino-4-chloro-5-(trifluoromethyl)benzoic acid (Compound 106) in DMF (176 ml), and the mixture was stirred at room temperature for two hours. Water (170 ml) was added to the reaction solution, and extraction was performed with ethyl acetate. The extract was washed with a saturated aqueous sodium chloride solution and dried over anhydrous sodium sulfate. After the drying agent was removed by filtration, concentration was performed under reduced pressure. The resulting residue was purified by silica gel column chromatography (ethyl acetate/hexane) to give the title compound (5.89 g, yield in two steps: 63%) as a yellow solid.

LCMS: m/z 268 [M+H]$^+$
HPLC retention time: 0.93 min (analysis condition D)

Example 108

Compound 108

Ethyl 2-amino-4-ethenyl-5-(trifluoromethyl)benzoate

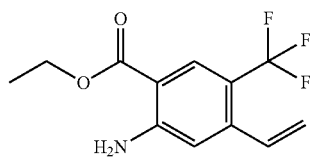 [SMILES: C=Cc1cc(N)c(C(=O)OCC)cc1C(F)(F)F]

Distilled water (112 ml) was added to a suspension of ethyl 2-amino-4-chloro-5-(trifluoromethyl)benzoate (Compound 107, 9.00 g, 34 mmol), potassium vinyltrifluoroborate (6.31 g, 47 mmol), BuPAd$_2$ (1.21 g, 3.4 mmol), palladium acetate (378 mg, 1.7 mmol), and potassium carbonate (13.9 g, 100 mmol) in toluene (336 ml), and the mixture was stirred at 90° C. under argon atmosphere for 18 hours. The reaction solution was cooled to room temperature, and ethyl acetate was then added thereto, and this was washed with water. The organic layer was dried over anhydrous sodium sulfate. After the drying agent was removed by filtration, concentration was performed under reduced pressure. The resulting residue was purified by silica gel column chromatography (ethyl acetate/hexane) to give the title compound (7.93 g, 91%) as a yellow solid.

LCMS: m/z 260 [M+H]$^+$
HPLC retention time: 0.94 min (analysis condition D)

Example 109

Compound 109

Ethyl 2-amino-4-(1,2-dihydroxyethyl)-5-(trifluoromethyl)benzoate

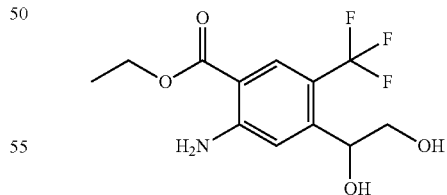

Water (140 ml) was added to a solution of AD-mixα (manufactured by Aldrich) (61.3 g) in t-butyl alcohol (140 ml), and the mixture was stirred at room temperature for 0.5 hours. A solution of ethyl 2-amino-4-ethenyl-5-(trifluoromethyl)benzoate (Compound 108, 14.4 g, 56 mmol) in t-butyl alcohol (140 ml) and water (140 ml) were added to this reaction solution, and the mixture was stirred at room temperature for 3.5 hours. Sodium sulfite (35.1 g) was added to the reaction mixture, and the mixture was stirred at room temperature for one hour. Ethyl acetate was added to the reaction mixture. After washing with a saturated aqueous sodium chloride solution, the organic layer was dried over anhydrous sodium sulfate. After the drying agent was removed by filtration, concentration was performed under reduced pressure. The resulting solid was washed with DCM to give the title compound (12.9 g, 79%) as a colorless solid.

LCMS: m/z 294 [M+H]+

HPLC retention time: 0.63 min (analysis condition D)

Example 110

Compound 110

Ethyl 2-amino-4-formyl-5-(trifluoromethyl)benzoate

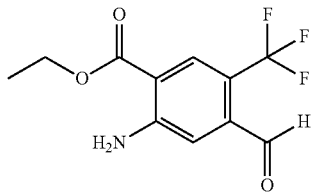 [SMILES: CCOC(=O)c1cc(C(F)(F)F)c(C=O)cc1N]

Water (273 ml) and sodium periodate (16.4 g, 76 mmol) were added to a solution of ethyl 2-amino-4-(1,2-dihydroxyethyl)-5-(trifluoromethyl)benzoate (Compound 109, 16.0 g, 54 mmol) in TBME (546 ml), and the mixture was stirred at room temperature for seven hours. TBME was added to the reaction mixture. After washing with a saturated aqueous sodium chloride solution, the organic layer was dried over anhydrous sodium sulfate. After the drying agent was removed by filtration, concentration was performed under reduced pressure to give the title compound (14.1 g, 99%) as a yellow solid.

LCMS: m/z 262[M+H]+

HPLC retention time: 0.87 min (analysis condition D)

Example 111

Compound 111

Ethyl 2-amino-3-chloro-4-formyl-5-(trifluoromethyl)benzoate

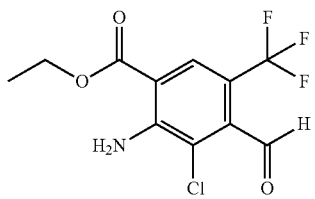 [SMILES: CCOC(=O)c1cc(C(F)(F)F)c(C=O)c(Cl)c1N]

NCS (3.71 g, 14 mmol) was added to a solution of ethyl 2-amino-4-formyl-5-(trifluoromethyl)benzoate (Compound 110, 3.63 g, 14 mmol) in DMF (42 mL), and the mixture was stirred at 70° C. for 0.5 hours. Water (40 mL) was added thereto, and extraction was performed with TBME. The extract was dried over anhydrous sodium sulfate. After the drying agent was removed by filtration, concentration was performed under reduced pressure. The resulting residue was purified by silica gel column chromatography (ethyl acetate/hexane) to give the title compound (3.47 g, 85%) as a yellow solid.

LCMS: m/z 296 [M+H]+

HPLC retention time: 0.89 min (analysis condition D)

Example 112

Compound 112

2-Amino-3-chloro-4-formyl-5-(trifluoromethyl)benzoic Acid

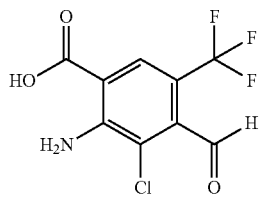 [SMILES: Nc1c(C(=O)O)cc(C(F)(F)F)c(C=O)c1Cl]

The title compound was synthesized from ethyl 2-amino-3-chloro-4-formyl-5-(trifluoromethyl)benzoate (Compound 111) under the same conditions as for Compound 85.

Example 113

Compound 113

2-Amino-3-chloro-N-[(5-chloro-2-ethylsulfonylphenyl)methyl]-4-formyl-5-(trifluoromethyl)benzamide

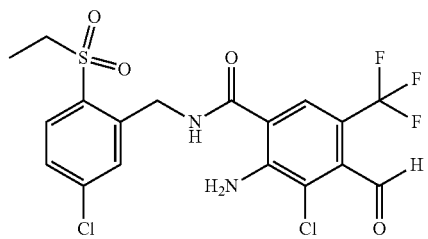 [SMILES: CCS(=O)(=O)c1ccc(Cl)cc1CNC(=O)c1cc(C(F)(F)F)c(C=O)c(Cl)c1N]

WSCDI (2.48 g, 12.9 mmol) was added to a suspension of the crude product of 2-amino-3-chloro-4-formyl-5-(trifluoromethyl)benzoic acid (Compound 112, 11.7 mmol) and HOBT (1.98 g, 12.9 mmol) in DCM (58.7 ml), and the mixture was stirred for 0.5 hours at room temperature. (5-chloro-2-ethylsulfonylphenyl)methanamine hydrochloride (Compound 3, 3.17 g, 11.7 mmol) and DIPEA (2.25 ml, 12.9 mmol) were added to this reaction solution, and the mixture was stirred for 11 hours at room temperature. A 1 N aqueous hydrochloric acid solution (5.9 ml) was added to the reaction solution, and the mixture was stirred for 20 minutes at room temperature. Then, a 1 N aqueous sodium hydroxide solution (5.4 ml) was added thereto. The reaction solution was extracted with DCM, and the extract was washed with a saturated aqueous sodium chloride solution and then dried over anhydrous sodium sulfate. After the drying agent was removed by filtration, concentration was performed under reduced pressure. The resulting residue was purified by silica gel column chromatography (ethyl acetate/hexane) to give the title compound (4.84 g, 85%) as a pale yellow foamy substance.

LCMS: m/z 483 [M+H]+

HPLC retention time: 0.87 min (analysis condition D)

Example 114

Compound 114

4-Bromo-2-nitro-5-(trifluoromethoxy)benzoic Acid

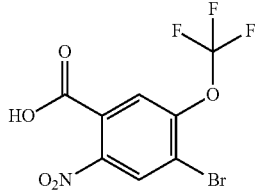 [SMILES: O=C(O)c1cc(OC(F)(F)F)c(Br)cc1[N+](=O)[O-]]

The title compound was synthesized from 2-nitro-5-(trifluoromethoxy)benzoic acid under the same conditions as for Compound 82.

Example 115

Compound 115

Ethyl 4-bromo-2-nitro-5-(trifluoromethoxy)benzoate

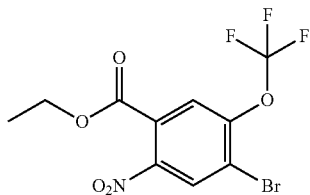 [SMILES: CCOC(=O)c1cc(OC(F)(F)F)c(Br)cc1[N+](=O)[O-]]

The title compound was synthesized from 4-bromo-2-nitro-5-(trifluoromethoxy)benzoic acid (Compound 114) under the same conditions as for Compound 107.

Example 116

Compound 116

Ethyl 4-ethenyl-2-nitro-5-(trifluoromethoxy)benzoate

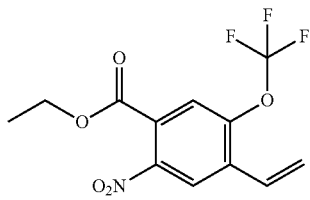

The title compound was synthesized from ethyl 4-bromo-2-nitro-5-(trifluoromethoxy)benzoate (Compound 115) under the same conditions as for Compound 108.

Example 117

Compound 117

Ethyl 2-amino-4-ethenyl-5-(trifluoromethoxy)benzoate

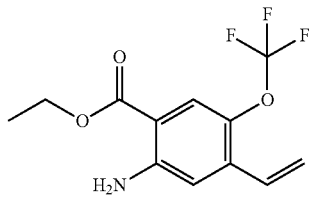

The title compound was synthesized from ethyl 4-ethenyl-2-nitro-5-(trifluoromethoxy)benzoate (Compound 116) under the same conditions as for Compound 24. However, 2-PrOH was used in place of MeOH as a solvent and the reaction was performed at 60° C.

Example 118

Compound 118

Ethyl 2-amino-3-chloro-4-formyl-5-(trifluoromethoxy)benzoate

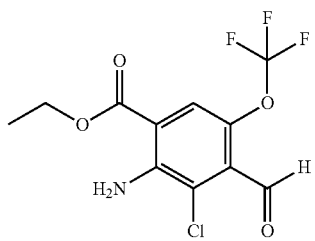 [SMILES: CCOC(=O)c1cc(OC(F)(F)F)c(C=O)c(Cl)c1N]

The title compound was synthesized from ethyl 2-amino-4-ethenyl-5-(trifluoromethoxy)benzoate (Compound 117) under the same conditions as for Compounds 109, 110, and 111.

Example 119

Compound 119

Ethyl 2-amino-3-chloro-4-(1,3-dioxolan-2-yl)-5-(trifluoromethoxy)benzoate

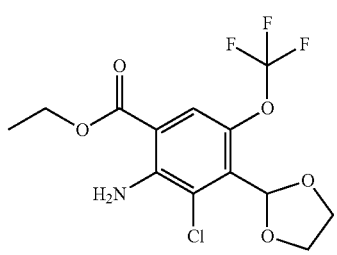 [SMILES: CCOC(=O)c1cc(OC(F)(F)F)c(C2OCCO2)c(Cl)c1N]

Ethylene glycol (387 ul, 6.9 mmol) and PTSA/H$_2$O (132 mg, 0.69 mmol) were added to a solution of ethyl 2-amino-3-chloro-4-formyl-5-(trifluoromethoxy)benzoate (Compound 118, 1.08 g, 3.5 mmol) in toluene (20 ml), and the mixture was stirred at 90° C. for one hour. A saturated aqueous sodium bicarbonate solution was added to the reaction mixture, and extraction was performed with ethyl acetate. The organic layer was then washed with brine and dried over anhydrous sodium sulfate. After the drying agent was removed by filtration, concentration was performed under reduced pressure. The resulting residue was purified by silica gel column chromatography (ethyl acetate/hexane) to give the title compound (1.13 g, 92%) as an orange solid.

LCMS: m/z 356 [M+H]$^+$

HPLC retention time: 0.92 min (analysis condition D)

Example 120

Compound 120

2-Amino-3-chloro-4-(1,3-dioxolan-2-yl)-5-(trifluoromethoxy)benzoic Acid

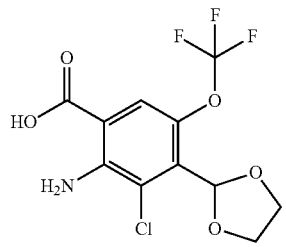 [SMILES: Nc1c(C(=O)O)cc(OC(F)(F)F)c(C2OCCO2)c1Cl]

The title compound was synthesized from ethyl 2-amino-3-chloro-4-(1,3-dioxolan-2-yl)-5-(trifluoromethoxy)benzoate (Compound 119) under the same conditions as for Compound 85.

Example 121

Compound 121

2-Amino-3-chloro-N-[(5-chloro-2-ethylsulfonylphenyl)methyl]-4-(1,3-dioxolan-2-yl)-5-(trifluoromethoxy)benzamide

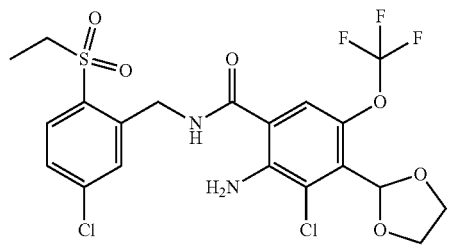 [SMILES: CCS(=O)(=O)c1ccc(Cl)cc1CNC(=O)c1cc(OC(F)(F)F)c(C2OCCO2)c(Cl)c1N]

The title compound was synthesized from (5-chloro-2-ethylsulfonylphenyl)methanamine hydrochloride (Compound 3) under the same conditions as for Compound 113. However, 2-amino-3-chloro-4-(1,3-dioxolan-2-yl)-5-(trifluoromethoxy)benzoic acid (Compound 120) was used in place of 2-amino-3-chloro-4-formyl-5-(trifluoromethyl)benzoic acid (Compound 112) as a carboxylic acid.

Example 122

Compound 122

Ethyl 4-methyl-2-nitrobenzoate

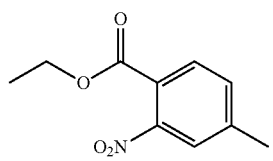

The title compound was synthesized from 4-methyl-2-nitrobenzoic acid under the same conditions as for Compound 107.

Example 123

Compound 123

Ethyl 2-amino-4-methylbenzoate

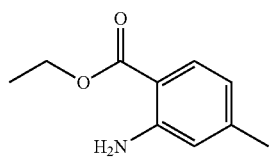

10% palladium carbon (638 mg) was added to a solution of ethyl 4-methyl-2-nitrobenzoate (Compound 122, 6.38 g, 30.5 mmol) in MeOH (64 ml), and the mixture was stirred at room temperature under hydrogen atmosphere for 17 hours. DCM was added to the reaction mixture, and the mixture was filtrated through celite. The filtrate was concentrated under reduced pressure to give a crude product of the title compound.

HPLC retention time: 0.78 min (analysis condition F)

$^1$H-NMR (400 MHz, CDCl$_3$) δ: 7.76 (1H, d, J=8.4 Hz), 6.44-6.49 (2H, m), 5.65 (2H, s), 4.31 (2H, q, J=7.1 Hz), 2.25 (3H, s), 1.37 (3H, t, J=7.1 Hz).

Example 124

Compound 124

Ethyl 2-amino-5-chloro-4-methylbenzoate

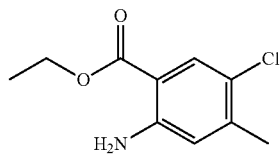

The title compound was synthesized from ethyl 2-amino-4-methylbenzoate (Compound 123) under the same conditions as for Compound 111.

Example 125

Compound 125

Ethyl 2-[bis[(2-methylpropan-2-yl)oxycarbonyl]amino]-5-chloro-4-methylbenzoate

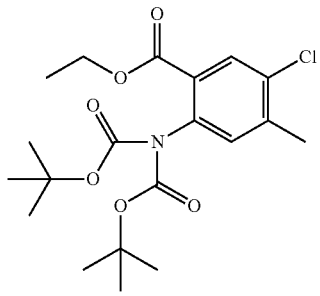 [SMILES: CCOC(=O)c1cc(Cl)c(C)cc1N(C(=O)OC(C)(C)C)C(=O)OC(C)(C)C]

The title compound was synthesized from ethyl 2-amino-5-chloro-4-methylbenzoate (Compound 124) under the same conditions as for Compound 104. However, acetonitrile was used in place of THF as a solvent.

Example 126

Compound 126

Ethyl 2-[bis[(2-methylpropan-2-yl)oxycarbonyl]amino]-4-(bromomethyl)-5-chlorobenzoate

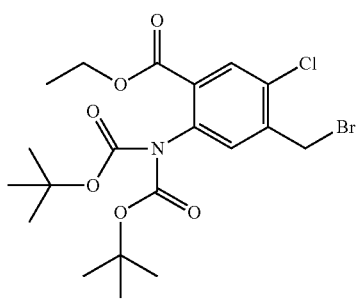 [SMILES: CCOC(=O)c1cc(Cl)c(CBr)cc1N(C(=O)OC(C)(C)C)C(=O)OC(C)(C)C]

The title compound was synthesized from ethyl 2-[bis[(2-methylpropan-2-yl)oxycarbonyl]amino]-5-chloro-4-methylbenzoate (Compound 125) under the same conditions as for Compound 15.

Example 127

Compound 127 tert-Butyl 4-[[5-[bis[(2-methylpropan-2-yl)oxycarbonyl]amino]-2-chloro-4-ethoxycarbonylphenyl]methyl]piperazine-1-carboxylate

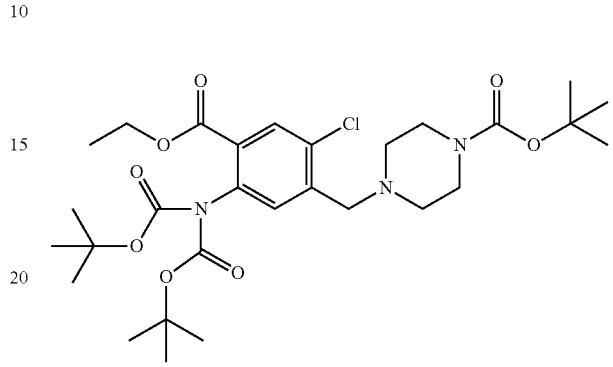

1-(tert-Butoxycarbonyl)piperazine (493 mg, 2.7 mmol) was added to a solution of ethyl 2-[bis[(2-methylpropan-2-yl)oxycarbonyl]amino]-4-(bromomethyl)-5-chlorobenzoate (Compound 126, 604 mg, 0.88 mol) in THF (6.1 ml), and the mixture was stirred at 50-75° C. for 6.5 hours. Water was added to the reaction mixture, and extraction was performed with ethyl acetate. The organic layer was washed with brine and then dried over anhydrous sodium sulfate. After the drying agent was removed by filtration, concentration was performed under reduced pressure. The resulting residue was purified by silica gel column chromatography (ethyl acetate/hexane) to give the title compound (498 mg, yield: 94%) as a colorless amorphous.

LCMS: m/z 598 [M+H]$^+$

HPLC retention time: 0.97 min (analysis condition F)

Example 128

Compound 128

Ethyl 2-amino-5-chloro-4-(piperazin-1-ylmethyl)benzoate

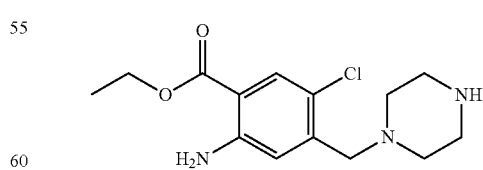

The title compound was synthesized from tert-butyl 4-[[5-[bis[(2-methylpropan-2-yl)oxycarbonyl]amino]-2-chloro-4-ethoxycarbonylphenyl]methyl]piperazine-1-carboxylate (Compound 127) under the same conditions as for Compound 21.

Example 129

Compound 129 tert-Butyl 4-[(5-amino-2-chloro-4-ethoxycarbonyl-phenyl)methyl]piperazine-1-carboxylate

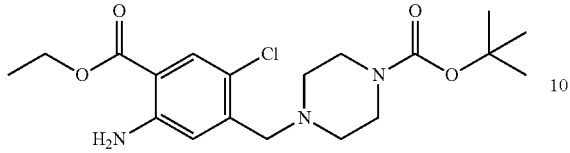

A solution of ethyl 2-amino-5-chloro-4-(piperazin-1-yl-methyl)benzoate (Compound 128, 241 mg, 0.83 mmol) and triethylamine (0.350 ml, 2.5 mmol) in DCM (8 ml) was cooled to 0° C., and Boc$_2$O (0.230 ml, 1.0 mmol) was added thereto. Then the solution was stirred for 30 minutes while gradually warming it from 0° C. to room temperature. Water was added to the reaction mixture, and extraction was performed with ethyl acetate. The organic layer was washed with brine and then dried over anhydrous sodium sulfate. After the drying agent was removed by filtration, concentration was performed under reduced pressure. The resulting residue was purified by silica gel column chromatography (ethyl acetate/hexane) to give the title compound (287 mg, yield: 86%) as a yellow solid.
LCMS: m/z 398 [M+H]$^+$
HPLC retention time: 0.57 min (analysis condition F)

Example 130

Compound 130

Ethyl 2-amino-5-bromo-4-methylbenzoate

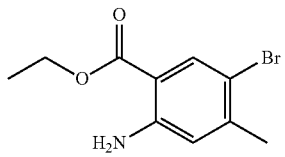

The title compound was synthesized from ethyl 2-amino-4-methylbenzoate (Compound 123) under the same conditions as for Compound 111. However, NBS was used in place of NCS.

Example 131

Compound 131

Ethyl 2-[bis[(2-methylpropan-2-yl)oxycarbonyl]amino]-5-bromo-4-(bromomethyl)benzoate

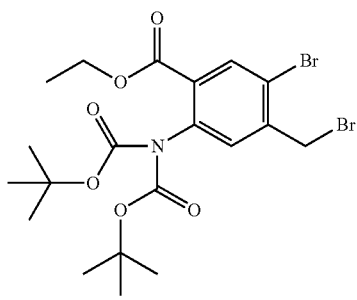

The title compound was synthesized from ethyl 2-amino-5-bromo-4-methylbenzoate (Compound 130) under the same conditions as for Compounds 125 and 126.

Example 132

Compound 132

Ethyl 2-amino-3,5-dibromo-4-methylbenzoate

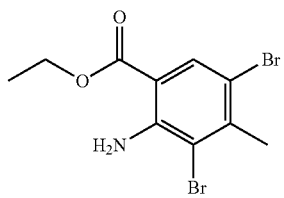

The title compound was synthesized from ethyl 2-amino-5-bromo-4-methylbenzoate (Compound 130) under the same conditions as for Compound 15.

Example 133

Compound 133

2-Amino-3,5-dibromo-4-methylbenzoic Acid

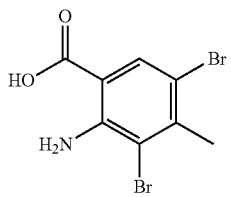

The title compound was synthesized from ethyl 2-amino-3,5-dibromo-4-methylbenzoate (Compound 132) under the same conditions as for Compound 85.

Example 134

Compound 134

2-Amino-3-iodo-5-(trifluoromethyl)benzoic Acid

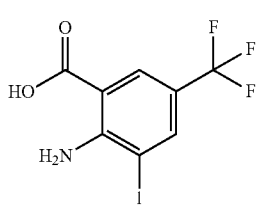

The title compound was synthesized from 2-amino-5-(trifluoromethyl)benzoic acid under the same conditions as for Compound 111. However, NIS was used in place of NCS.

Example 135

Compound a1

4-Bromo-N'-(5-chloro-2-ethylsulfanylphenyl)-5-methyl-2-nitrobenzhydrazide

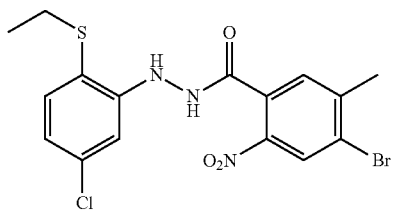 [SMILES: CCSc1ccc(Cl)cc1NNC(=O)c1cc(C)c(Br)cc1[N+](=O)[O-]]

WSCDI (279.6 mg, 1.46 mmol) was added to a solution of (5-chloro-2-ethylsulfanylphenyl)hydrazine (Compound 30, 284 mg, 1.40 mmol) and 4-bromo-5-methyl-2-nitrobenzoic acid (Compound 82, 433 mg, 1.43 mmol, purity: 86%) in DCM (5.6 ml), and the mixture was stirred at room temperature for one hour. This reaction mixture was concentrated under reduced pressure and the resulting residue was purified by silica gel column chromatography (ethyl acetate/hexane) to give the title compound (292.6 mg, 47%) as a colorless solid.

LCMS: m/z 444 [M+H]$^+$
HPLC retention time: 2.75 min (analysis condition C)

Example 136

Compound a2

2-Amino-3-bromo-N'-(5-chloro-2-ethylsulfanylphenyl)-5-methylbenzohydrazide

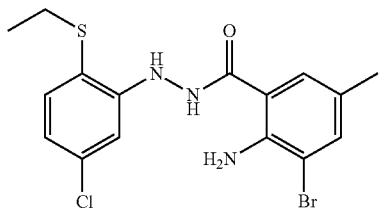 [SMILES: CCSc1ccc(Cl)cc1NNC(=O)c1cc(C)cc(Br)c1N]

The title compound was synthesized from (5-chloro-2-ethylsulfanylphenyl)hydrazine (Compound 30) and 2-amino-3-bromo-5-methylbenzoic acid under the same conditions as for Compound a1.

Example 137

Compound A-1

8-Bromo-3-(5-chloro-2-ethylsulfanylanilino)-6-methylquinazolin-4-one

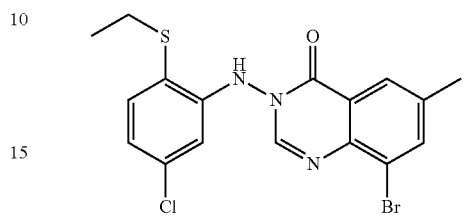

A solution of 2-amino-3-bromo-N'-(5-chloro-2-ethylsulfanylphenyl)-5-methylbenzohydrazide (Compound a2, 2.44 g, 5.9 mmol) in formic acid (10 mL) was heated at 100-110° C. Water (10 mL) was added to the reaction mixture, and the mixture was then neutralized to pH 7-8 by adding a 6 N aqueous sodium hydroxide solution. The reaction solution was extracted with DCM, and the extract was washed with brine and then dried over anhydrous magnesium sulfate. After the drying agent was removed by filtration, concentration was performed under reduced pressure. The resulting residue was purified by silica gel column chromatography (ethyl acetate/hexane) to give the title compound (1.28 g, 51%) as a solid.

LCMS: m/z 424 [M+H]$^+$
HPLC retention time: 3.00 min (analysis condition C)

Example 138

Compound a3 tert-Butyl N-(8-bromo-6-methyl-4-oxoquinazolin-3-yl)-N-(5-chloro-2-ethylsulfanylphenyl)carbamate

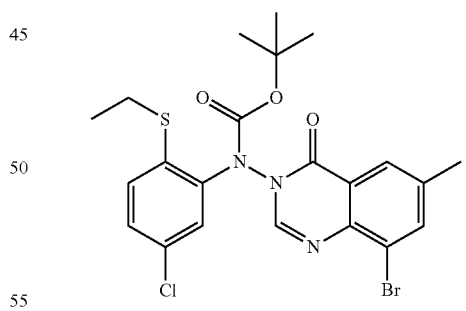

Sodium hydride (>61% oil, 21 mg, 0.53 mmol) was added to a solution of 8-bromo-3-(5-chloro-2-ethylsulfanylanilino)-6-methylquinazolin-4-one (Compound A-1, 150 mg, 0.35 mmol) in DMF (3 ml), and the mixture was stirred at room temperature for 30 minutes. Boc$_2$O (120 mg, 0.53 mmol) was added to the reaction mixture. The mixture was stirred for additional three hours, followed by addition of water and extraction with DCM. The organic layer was washed with a saturated aqueous sodium chloride solution and then dried over anhydrous magnesium sulfate. After the drying agent was removed by filtration, concentration was performed under reduced pressure. The resulting residue was purified by silica gel chromatography (ethyl acetate/DCM/hexane) to give the title compound (160 mg, 85%) as a pale yellow solid.

¹H-NMR (300 MHz, CDCl₃) δ: 8.73 (1H, d, J=17.7 Hz), 8.13 (1H, s), 7.89 (2H, s), 7.26-7.29 (2H, m), 2.99 (2H, q, J=7.2 Hz), 2.49 (3H, s), 1.44-1.46 (9H, m), 1.37 (3H, t, J=7.2 Hz).

Example 139

Compound a4 tert-Butyl N-(8-bromo-6-methyl-4-oxoquinazolin-3-yl)-N-(5-chloro-2-ethylsulfonylphenyl)carbamate

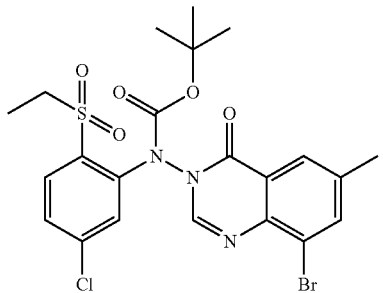 [SMILES: CCS(=O)(=O)c1ccc(Cl)cc1N(C(=O)OC(C)(C)C)n1cnc2c(Br)cc(C)cc2c1=O]

The title compound was synthesized from tert-butyl N-(8-bromo-6-methyl-4-oxoquinazolin-3-yl)-N-(5-chloro-2-ethylsulfanylphenyl)carbamate (Compound a3) under the same conditions as for Compound 14.

Example 140

Compound A-2

8-Bromo-3-(5-chloro-2-ethylsulfonylanilino)-6-methylquinazolin-4-one

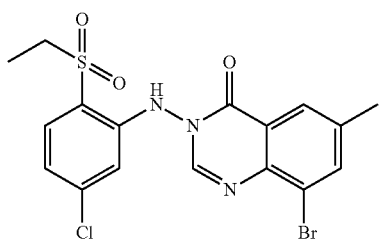 [SMILES: CCS(=O)(=O)c1ccc(Cl)cc1Nn1cnc2c(Br)cc(C)cc2c1=O]

A solution of tert-butyl N-(8-bromo-6-methyl-4-oxoquinazolin-3-yl)-N-(5-chloro-2-ethylsulfonylphenyl)carbamate (Compound a4, 90 mg, 0.16 mmol) in DCM (3 ml)/TFA (1.5 ml) was stirred at room temperature for two hours. The reaction solution was concentrated under reduced pressure and the resulting residue was purified by silica gel chromatography (ethyl acetate/DCM/hexane) to give the title compound (45 mg, 62%).

LCMS: m/z 456 [M+H]⁺

HPLC retention time: 2.53 min (analysis condition C)

Example 141

Compound A-3

3-(5-Chloro-2-ethylsulfanylanilino)-8-(4-fluorophenyl)-6-methylquinazolin-4-one

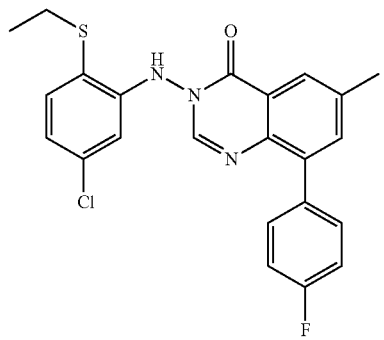 [SMILES: CCSc1ccc(Cl)cc1Nn1cnc2c(-c3ccc(F)cc3)cc(C)cc2c1=O]

A mixture of tert-butyl N-(8-bromo-6-methyl-4-oxoquinazolin-3-yl)-N-(5-chloro-2-ethylsulfanylphenyl)carbamate (Compound a3, 25 mg, 0.0476 mmol), (4-fluorophenyl)boronic acid (7 mg, 0.0476 mmol), tetrakis(triphenylphosphine)palladium (0) (3 mg, 0.00238 mmol), potassium carbonate (15 mg, 0.105 mmol), and DME (2.5 ml)/water (0.5 ml) was stirred under microwave irradiation at 130° C. for one hour. After the reaction mixture was cooled to room temperature, brine was added thereto and extraction was performed with ethyl acetate. The organic layer was then dried over anhydrous magnesium sulfate. After the drying agent was removed by filtration, concentration was performed under reduced pressure. The resulting residue was purified by silica gel chromatography (ethyl acetate/hexane) and then preparative HPLC (water/acetonitrile, 0.05% TFA) to give the title compound (8 mg, 31%).

LCMS: m/z 440 [M+H]⁺

HPLC retention time: 3.55 min (analysis condition B)

Example 142

Compound A-4

3-(5-Chloro-2-ethylsulfonylanilino)-8-(4-fluorophenyl)-6-methylquinazolin-4-one

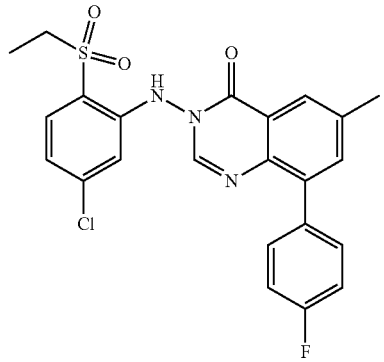 [SMILES: CCS(=O)(=O)c1ccc(Cl)cc1Nn1cnc2c(-c3ccc(F)cc3)cc(C)cc2c1=O]

The title compound was synthesized from 3-(5-chloro-2-ethylsulfanylanilino)-8-(4-fluorophenyl)-6-methylquinazolin-4-one (Compound A-3) under the same conditions as for Compound 14.

LCMS: m/z 472 [M+H]+

HPLC retention time: 3.52 min (analysis condition B)

Example 143

Compound a5

2-Amino-4-bromo-N'-(5-chloro-2-ethylsulfanylphenyl)-5-methylbenzohydrazide

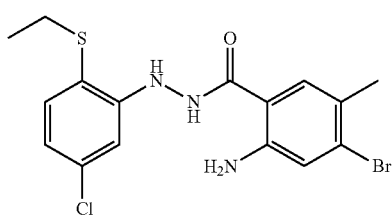

Tin(II) chloride (633 mg, 3.34 mmol) was added to a solution of 4-bromo-N'-(5-chloro-2-ethylsulfanylphenyl)-5-methyl-2-nitrobenzohydrazide (Compound a1, 293 mg, 0.66 mmol) in water (0.2 ml) and EtOAc (2.2 ml), and the mixture was stirred at 60° C. for 10 minutes. A 1 N aqueous sodium hydroxide solution (8 ml) and ethyl acetate (20 ml) were added to the reaction mixture. The organic layer was separated, washed with water and brine, and then dried over anhydrous magnesium sulfate. After the drying agent was removed by filtration, concentration was performed under reduced pressure. The resulting residue was purified by silica gel column chromatography (ethyl acetate/hexane) to give the title compound (212 mg, 78%) as a colorless solid.

LCMS: m/z 414 [M+H]+

HPLC retention time: 4.17 min (analysis condition C)

Example 144

Compound A-5

7-Bromo-3-(5-chloro-2-ethylsulfanylanilino)-6-methylquinazolin-4-one

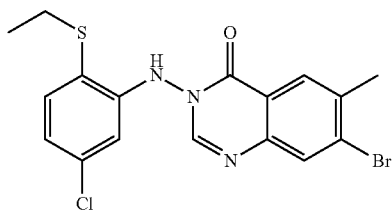 [SMILES: CCSc1ccc(Cl)cc1Nn1cnc2cc(Br)c(C)cc2c1=O]

A mixture of 2-amino-4-bromo-N'-(5-chloro-2-ethylsulfanylphenyl)-5-methylbenzohydrazide (Compound a5, 164 mg, 0.40 mmol), trimethyl orthoformate (2.0 ml), and formic acid (0.2 ml) was stirred under microwave irradiation at 100° C. for 20 minutes. The reaction mixture was concentrated under reduced pressure and the resulting residue was purified by silica gel column chromatography (ethyl acetate/hexane) to give the title compound (167 mg, 99%).

LCMS: m/z 424 [M+H]+

HPLC retention time: 3.87 min (analysis condition A)

Example 145

Compound a6 tert-Butyl N-(7-bromo-6-methyl-4-oxoquinazolin-3-yl)-N-(5-chloro-2-ethylsulfanylphenyl)carbamate

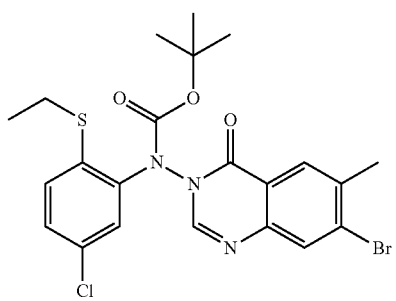 [SMILES: CCSc1ccc(Cl)cc1N(C(=O)OC(C)(C)C)n1cnc2cc(Br)c(C)cc2c1=O]

DMAP (6.1 mg, 0.05 mmol) and Boc$_2$O (102 mg, 0.47 mmol) were added to a solution of 7-bromo-3-(5-chloro-2-ethylsulfanylanilino)-6-methylquinazolin-4-one (Compound A-5, 167 mg, 0.39 mmol) in THF (3.9 ml), and the mixture was stirred at 70° C. for 40 minutes. The reaction mixture was cooled to room temperature and then concentrated under reduced pressure. The resulting residue was purified by silica gel column chromatography (ethyl acetate/hexane) to give the title compound (170 mg, 82%) as a colorless foamy substance.

LCMS: m/z 524 [M+H]+

HPLC retention time: 3.67 min (analysis condition C)

Example 146

Compound a7 tert-Butyl N-(7-bromo-6-methyl-4-oxoquinazolin-3-yl)-N-(5-chloro-2-ethylsulfonylphenyl)carbamate

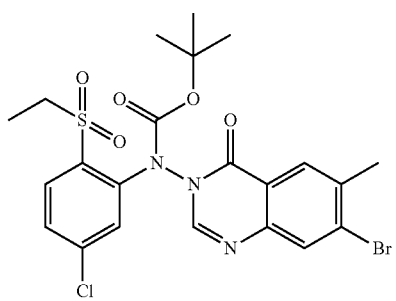 [SMILES: CCS(=O)(=O)c1ccc(Cl)cc1N(C(=O)OC(C)(C)C)n1cnc2cc(Br)c(C)cc2c1=O]

The title compound was synthesized from tert-butyl N-(7-bromo-6-methyl-4-oxoquinazolin-3-yl)-N-(5-chloro-2-ethylsulfanylphenyl)carbamate (Compound a6) under the same conditions as for Compound 14.

Example 147

Compound a8 tert-Butyl N-[7-bromo-6-(dibromomethyl)-4-oxoquinazolin-3-yl]-N-(5-chloro-2-ethylsulfonylphenyl)carbamate

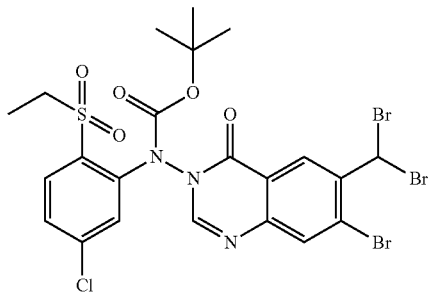 [SMILES: CCS(=O)(=O)c1ccc(Cl)cc1N(C(=O)OC(C)(C)C)n1cnc2cc(Br)c(C(Br)Br)cc2c1=O]

A solution of tert-butyl N-(7-bromo-6-methyl-4-oxoquinazolin-3-yl)-N-(5-chloro-2-ethylsulfonylphenyl)carbamate (Compound a7, 550 mg, 0.99 mmol), NBS (531 mg, 2.98 mmol), and BPO (35.2 mg, 0.10 mmol) in carbon tetrachloride (10 ml) was stirred under argon atmosphere at 80° C. for 18.5 hours. The reaction mixture was cooled to room temperature and the insoluble matter was then filtered out. The filtrate was concentrated under reduced pressure and the resulting residue was purified by silica gel column chromatography (ethyl acetate/hexane) to give the title compound (338 mg, 48%) as a colorless solid.
LCMS: m/z 712 [M+H]$^+$
HPLC retention time: 3.55 min (analysis condition C)

Example 148

Compound a9 tert-Butyl N-(7-bromo-6-formyl-4-oxoquinazolin-3-yl)-N-(5-chloro-2-ethylsulfonylphenyl)carbamate

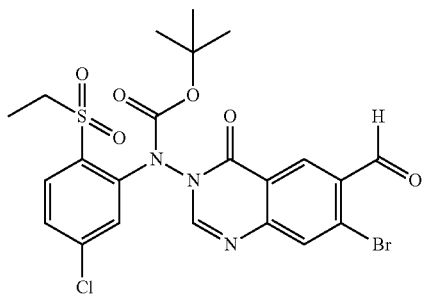 [SMILES: CCS(=O)(=O)c1ccc(Cl)cc1N(C(=O)OC(C)(C)C)n1cnc2cc(Br)c(C=O)cc2c1=O]

A mixed solution of tert-butyl N-[7-bromo-6-(dibromomethyl)-4-oxoquinazolin-3-yl]-N-(5-chloro-2-ethylsulfonylphenyl)carbamate (Compound a8, 338 mg, 0.47 mmol), and silver nitrate (194 mg, 1.14 mmol) in water (0.8 ml) and acetone (4.7 ml) was stirred at 60° C. for 50 minutes. The reaction mixture was cooled to room temperature and the insoluble matter was then filtered out. The resulting filtrate was concentrated under reduced pressure to give the title compound (104 mg, 38%) as a colorless solid.
LCMS: m/z 570 [M+H]$^+$
HPLC retention time: 3.03 min (analysis condition C)

Example 149

Compound a10 tert-Butyl N-[7-bromo-6-(difluoromethyl)-4-oxoquinazolin-3-yl]-N-(5-chloro-2-ethylsulfonylphenyl)carbamate

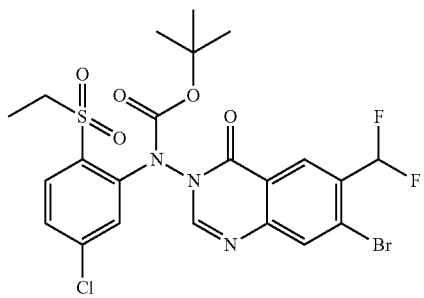 [SMILES: CCS(=O)(=O)c1ccc(Cl)cc1N(C(=O)OC(C)(C)C)n1cnc2cc(Br)c(C(F)F)cc2c1=O]

Deoxo-Fluor™ (0.057 ml, 0.31 mmol) was added to a solution of tert-butyl N-(7-bromo-6-formyl-4-oxoquinazolin-3-yl)-N-(5-chloro-2-ethylsulfonylphenyl)carbamate (Compound a9, 104 mg, 0.18 mmol) in DCM (1 ml), and the mixture was stirred at room temperature for 50 minutes. Additional Deoxo-Fluor™ (0.134 ml, 0.73 mmol) was gradually and slowly added to the reaction mixture, and the mixture was stirred at room temperature for 4.5 hours. A saturated aqueous sodium bicarbonate solution was added to the reaction mixture. The organic layer was then washed with brine, and dried over anhydrous magnesium sulfate. After the drying agent was removed by filtration, concentration was performed under reduced pressure. The resulting residue was purified by silica gel column chromatography (ethyl acetate/hexane) to give the title compound (93 mg, 86%) as a colorless solid.
LCMS: m/z 592 [M+H]$^+$
HPLC retention time: 3.20 min (analysis condition C)

Example 150

Compound A-6

7-Bromo-3-(5-chloro-2-ethylsulfonylanilino)-6-(difluoromethyl)quinazolin-4-one

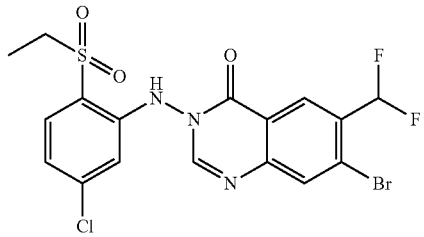 [SMILES: CCS(=O)(=O)c1ccc(Cl)cc1Nn1cnc2cc(Br)c(C(F)F)cc2c1=O]

The title compound was synthesized from tert-butyl N-[7-bromo-6-(difluoromethyl)-4-oxoquinazolin-3-yl]-N-(5-chloro-2-ethylsulfonylphenyl)carbamate (Compound a10) under the same conditions as for Compound A-2.

LCMS: m/z 492 [M+H]$^+$

HPLC retention time: 2.57 min (analysis condition C)

$^1$H-NMR (400 MHz, CD$_3$OD) δ: 8.47 (1H, s), 8.45 (1H, s), 8.13 (1H, s), 7.80 (1H, d, J=8.2 Hz), 7.14 (1H, dd, J=8.2, 1.8 Hz), 7.10 (1H, t, J=54.3 Hz), 6.83 (1H, d, J=1.8 Hz), 3.49 (2H, q, J=7.3 Hz), 1.31 (3H, t, J=7.3 Hz).

Example 151

Compound a11

2-Amino-5-bromo-N'-(5-chloro-2-ethylsulfanylphenyl)-4-methylbenzohydrazide

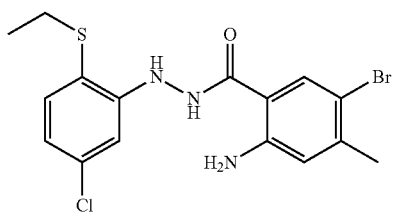 [SMILES: CCSc1ccc(Cl)cc1NNC(=O)c1cc(Br)c(C)cc1N]

The title compound was synthesized from (5-chloro-2-ethylsulfanylphenyl)hydrazine (Compound 30) and 2-amino-5-bromo-4-methylbenzoic acid under the same conditions as for Compound a1.

Example 152

Compound A-7

6-Bromo-3-(5-chloro-2-ethylsulfanylanilino)-7-methylquinazolin-4-one

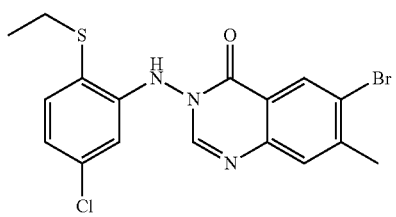 [SMILES: CCSc1ccc(Cl)cc1Nn1cnc2cc(C)c(Br)cc2c1=O]

The title compound was synthesized from 2-amino-5-bromo-N'-(5-chloro-2-ethylsulfanylphenyl)-4-methylbenzohydrazide (Compound a11) under the same conditions as for Compound A-5.

LCMS: m/z 424 [M+H]$^+$

HPLC retention time: 3.22 min (analysis condition C)

Example 153

Compound a12 tert-Butyl N-(6-bromo-7-methyl-4-oxoquinazolin-3-yl)-N-(5-chloro-2-ethylsulfonylphenyl)carbamate

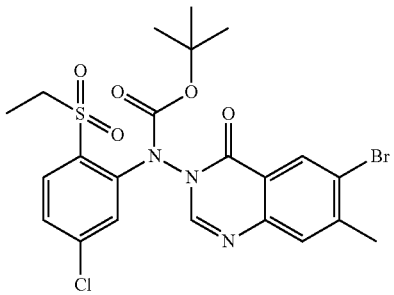 [SMILES: CCS(=O)(=O)c1ccc(Cl)cc1N(C(=O)OC(C)(C)C)n1cnc2cc(C)c(Br)cc2c1=O]

The title compound was synthesized from 6-bromo-3-(5-chloro-2-ethylsulfanylanilino)-7-methylquinazolin-4-one (Compound A-7) under the same conditions as for Compounds a6 and a7.

Example 154

Compound A-8

6-Bromo-3-(5-chloro-2-ethylsulfonylanilino)-7-methylquinazolin-4-one

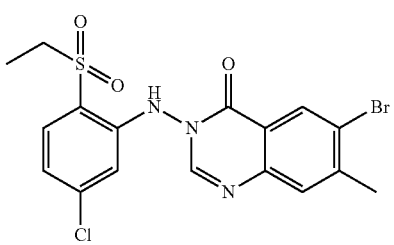 [SMILES: CCS(=O)(=O)c1ccc(Cl)cc1Nn1cnc2cc(C)c(Br)cc2c1=O]

The title compound was synthesized from tert-butyl N-(6-bromo-7-methyl-4-oxoquinazolin-3-yl)-N-(5-chloro-2-ethylsulfonylphenyl)carbamate (Compound a12) under the same conditions as for Compound A-2.

LCMS: m/z 456 [M+H]$^+$

HPLC retention time: 2.57 min (analysis condition C)

Examples 155 to 162

The following compounds of Table 3 were synthesized from (5-chloro-2-ethylsulfanylphenyl)hydrazine (Compound 30) under the same conditions as for Compounds a11 and A-7. However, corresponding carboxylic acids were used under the conditions for Compound a11. For Compound A-25, the reaction was performed with the addition of HOBt and DIPEA using DMF in place of dichloromethane as a solvent under the conditions for Compound a11.

TABLE 3

| Example | Compound number | Structure | Compound name | HPLC condition | Retention time (min) | m/z [M + H]+ |
|---|---|---|---|---|---|---|
| 155 | A-9 | 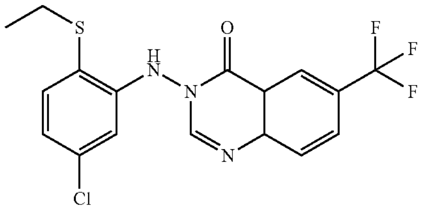 [SMILES: CCSc1ccc(Cl)cc1NN1C=NC2C=CC(C(F)(F)F)=CC2C1=O] | 3-(5-Chloro-2-ethylsulfanylanilino)-6-(trifluoromethyl)quinazolin-4-one | C | 2.93 | 400 |
| 156 | A-11 | 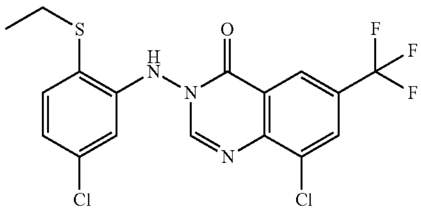 [SMILES: CCSc1ccc(Cl)cc1Nn1cnc2c(Cl)cc(C(F)(F)F)cc2c1=O] | 8-Chloro-3-(5-chloro-2-ethylsulfanylanilino)-6-(trifluoromethyl)quinazolin-4-one | C | 3.15 | 434 |
| 157 | A-14 | 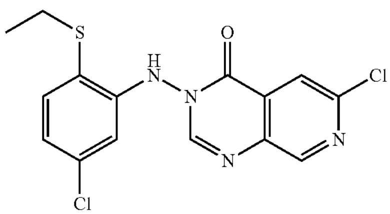 [SMILES: CCSc1ccc(Cl)cc1Nn1cnc2cnc(Cl)cc2c1=O] | 6-Chloro-3-(5-chloro-2-ethylsulfanylanilino)pyrido[3,4-d]pyrimidin-4-one | C | 2.58 | 367 |
| 158 | A-16 | 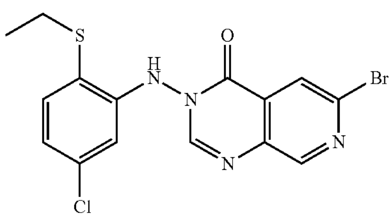 [SMILES: CCSc1ccc(Cl)cc1Nn1cnc2cnc(Br)cc2c1=O] | 6-Bromo-3-(5-chloro-2-ethylsulfanylanilino)pyrido[2,3-d]pyrimidin-4-one | C | 2.40 | 411 |
| 159 | A-19 | 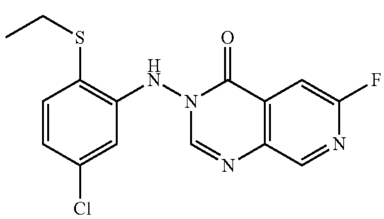 [SMILES: CCSc1ccc(Cl)cc1Nn1cnc2cnc(F)cc2c1=O] | 3-(5-Chloro-2-ethylsulfanylanilino)-6-fluoropyrido[3,4-d]pyrimidin-4-one | C | 2.53 | 351 |
| 160 | A-21 | 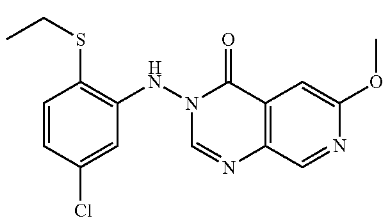 [SMILES: CCSc1ccc(Cl)cc1Nn1cnc2cnc(OC)cc2c1=O] | 3-(5-Chloro-2-ethylsulfanylanilino)-6-methoxypyrido[3,4-d]pyrimidin-4-one | C | 2.57 | 363 |
| 161 | A-23 | 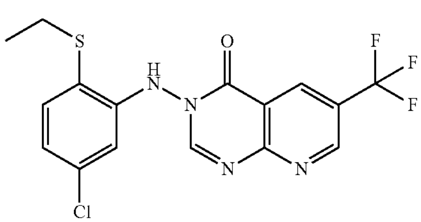 [SMILES: CCSc1ccc(Cl)cc1Nn1cnc2ncc(C(F)(F)F)cc2c1=O] | 3-(5-Chloro-2-ethylsulfanylanilino)-6-(trifluoromethyl)pyrido[2,3-d]pyrimidin-4-one | C | 2.60 | 401 |

TABLE 3-continued

| Example | Compound number | Structure | Compound name | HPLC condition | Retention time (min) | m/z [M + H]+ |
|---|---|---|---|---|---|---|
| 162 | A-25 | 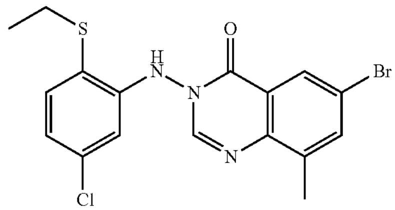 [SMILES: CCSc1ccc(Cl)cc1Nn1cnc2c(C)cc(Br)cc2c1=O] | 6-Bromo-3-(5-chloro-2-ethylsulfanylanilino)-8-methylquinazolin-4-one | C | 1.11 | 424 |

Examples 163 to 170

The following compounds of Table 4 were synthesized using the corresponding compounds in Table 3 under the same conditions as for Compound 14.

TABLE 4

| Example | Compound number | Structure | Compound name | HPLC condition | Retention time (min) | m/z [M + H]+ |
|---|---|---|---|---|---|---|
| 163 | A-10 | 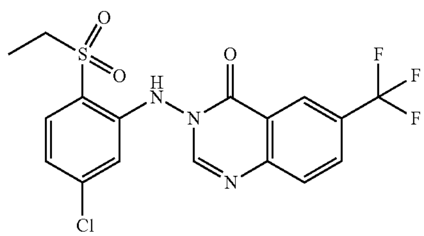 [SMILES: CCS(=O)(=O)c1ccc(Cl)cc1Nn1cnc2ccc(C(F)(F)F)cc2c1=O] | 3-(5-Chloro-2-ethylsulfonylanilino)-6-(trifluoromethyl)quinazolin-4-one | C | 2.50 | 432 |
| 164 | A-12 | 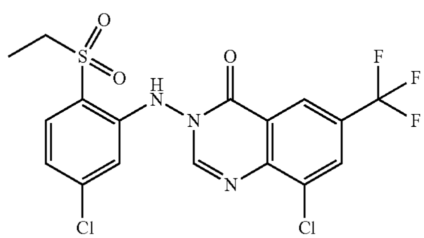 [SMILES: CCS(=O)(=O)c1ccc(Cl)cc1Nn1cnc2c(Cl)cc(C(F)(F)F)cc2c1=O] | 8-Chloro-3-(5-chloro-2-ethylsulfonylanilino)-6-(trifluoromethyl)quinazolin-4-one | C | 2.73 | 466 |
| 165 | A-15 | 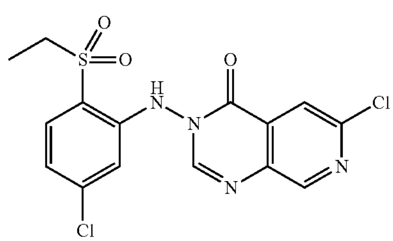 [SMILES: CCS(=O)(=O)c1ccc(Cl)cc1Nn1cnc2cnc(Cl)cc2c1=O] | 6-Chloro-3-(5-chloro-2-ethylsulfonylanilino)pyrido[3,4-d]pyrimidin-4-one | C | 2.12 | 399 |
| 166 | A-17 | 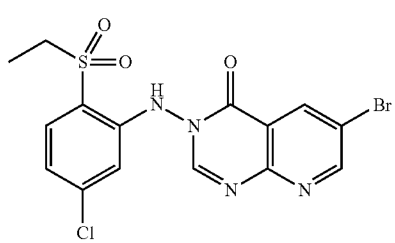 [SMILES: CCS(=O)(=O)c1ccc(Cl)cc1Nn1cnc2ncc(Br)cc2c1=O] | 6-Bromo-3-(5-chloro-2-ethylsulfonylanilino)pyrido[2,3-d]pyrimidin-4-one | C | 1.97 | 443 |

TABLE 4-continued

| Example | Compound number | Structure | Compound name | HPLC condition | Retention time (min) | m/z [M + H]+ |
|---|---|---|---|---|---|---|
| 167 | A-20 | 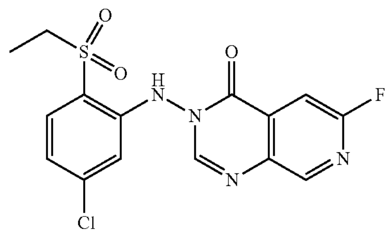 [SMILES: CCS(=O)(=O)c1ccc(Cl)cc1Nn1cnc2cnc(F)cc2c1=O] | 3-(5-Chloro-2-ethylsulfonylanilino)-6-fluoropyrido[3,4-d]pyrimidin-4-one | C | 2.05 | 383 |
| 168 | A-22 | 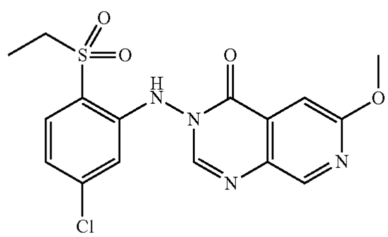 [SMILES: CCS(=O)(=O)c1ccc(Cl)cc1Nn1cnc2cnc(OC)cc2c1=O] | 3-(5-Chloro-2-ethylsulfonylanilino)-6-methoxypyrido[3,4-d]pyrimidin-4-one | C | 2.08 | 395 |
| 169 | A-24 | 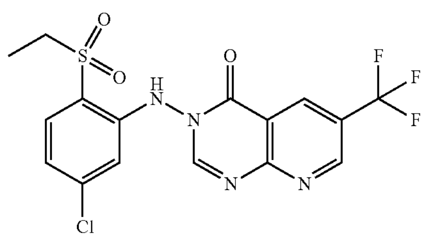 [SMILES: CCS(=O)(=O)c1ccc(Cl)cc1Nn1cnc2ncc(C(F)(F)F)cc2c1=O] | 3-(5-Chloro-2-ethylsulfonylanilino)-6-(trifluoromethyl)pyrido[2,3-d]pyrimidin-4-one | C | 2.18 | 433 |
| 170 | A-26 | 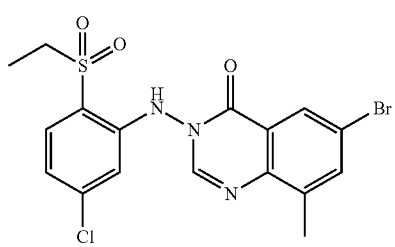 [SMILES: CCS(=O)(=O)c1ccc(Cl)cc1Nn1cnc2c(C)cc(Br)cc2c1=O] | 6-Bromo-3-(5-chloro-2-ethylsulfonylanilino)-8-methylquinazolin-4-one | D | 0.95 | 456 |

Example 171

Compound A-18

3-(5-Chloro-2-ethylsulfonylanilino)-4-oxopyrido[2,3-d]pyrimidine-6-carbonitrile

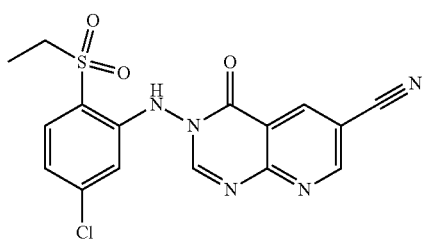 [SMILES: CCS(=O)(=O)c1ccc(Cl)cc1Nn1cnc2ncc(C#N)cc2c1=O]

A solution of 6-bromo-3-(5-chloro-2-ethylsulfonylanilino)pyrido[2,3-d]pyrimidin-4-one (Compound A-17, 36.8 mg, 0.083 mmol), zinc(II) cyanide (31.1 mg, 0.16 mmol), and tetrakis(triphenylphosphine)palladium (0) (5.5 mg, 0.0048 mmol) in DMF (0.83 ml) was stirred under microwave irradiation at 180° C. for 15 minutes. The reaction mixture was cooled to room temperature and the insoluble matter was then filtered out. Ethyl acetate was added. It was washed with water and a saturated aqueous sodium chloride solution and dried over anhydrous magnesium sulfate. After the drying agent was removed by filtration, concentration was performed under reduced pressure. The resulting residue was purified by silica gel column chromatography (ethyl acetate/hexane). The resulting solid was further washed with a mixed solution of hexane and ethyl acetate in 1:1 ratio to give the title compound (17.5 mg, 54%) as a colorless solid.

LCMS: m/z 390 [M+H]+

HPLC retention time: 1.80 min (analysis condition C)

Example 172

Compound a13

3-(5-Chloro-2-ethylsulfanylanilino)-8-iodo-6-(trifluoromethyl)quinazolin-4-one

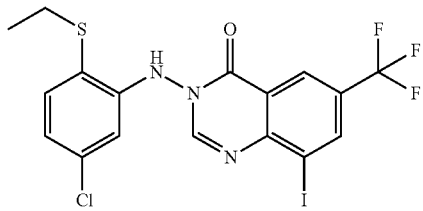

The title compound was synthesized from (5-chloro-2-ethylsulfanylphenyl)hydrazine (Compound 30) under the same conditions as for Compounds a11 and A-7. However, 2-amino-3-iodo-5-(trifluoromethyl)benzoic acid (Compound 134) was used as a carboxylic acid under the conditions for Compound a11.

Example 173

Compound A-13

3-(5-Chloro-2-ethylsulfonylanilino)-8-iodo-6-(trifluromethyl)quinazolin-4-one

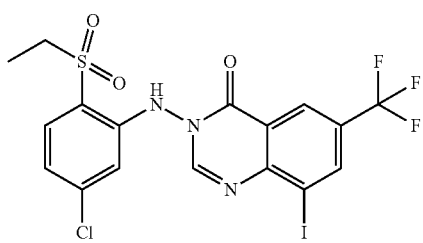 [SMILES: CCS(=O)(=O)c1ccc(Cl)cc1Nn1cnc2c(I)cc(C(F)(F)F)cc2c1=O]

The title compound was synthesized from 3-(5-chloro-2-ethylsulfanylanilino)-8-iodo-6-(trifluoromethyl)quinazolin-4-one (Compound a13) under the same conditions as for Compound 14.

LCMS: m/z 558 [M+H]$^+$
HPLC retention time: 2.90 min (analysis condition C)

Example 174

Compound a14

8-Chloro-3-(5-chloro-2-ethylsulfanylanilino)-6-(trifluoromethoxy)quinazolin-4-one

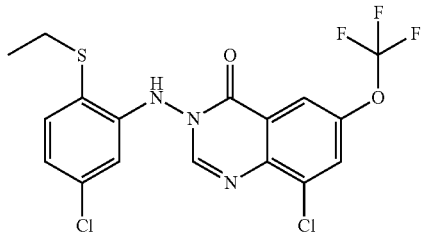 [SMILES: CCSc1ccc(Cl)cc1Nn1cnc2c(Cl)cc(OC(F)(F)F)cc2c1=O]

The title compound was synthesized from (5-chloro-2-ethylsulfanylphenyl)hydrazine (Compound 30) under the same conditions as for Compounds a11 and A-7. However, 2-amino-3-chloro-5-(trifluoromethoxy)benzoic acid (Compound 94) was used as a carboxylic acid, DMF was used in place of dichloromethane as a solvent, and HOBT was added under the conditions for Compound a11.

Example 175

Compound A-27

8-Chloro-3-(5-chloro-2-ethylsulfonylanilino)-6-(trifluoromethoxy)quinazolin-4-one

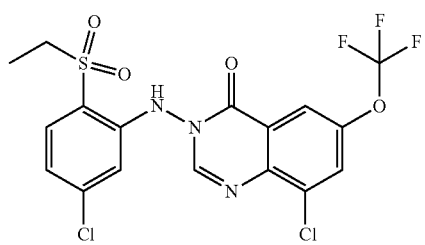 [SMILES: CCS(=O)(=O)c1ccc(Cl)cc1Nn1cnc2c(Cl)cc(OC(F)(F)F)cc2c1=O]

The title compound was synthesized from 8-chloro-3-(5-chloro-2-ethylsulfanylanilino)-6-(trifluoromethoxy)quinazolin-4-one (Compound a14) under the same conditions as for Compound 14.

LCMS: m/z 482 [M+H]$^+$
HPLC retention time: 2.93 min (analysis condition E)

Example 176

Compound a15

2-Amino-N'-(5-chloro-2-ethylsulfanylphenyl)-5-fluorobenzohydrazide

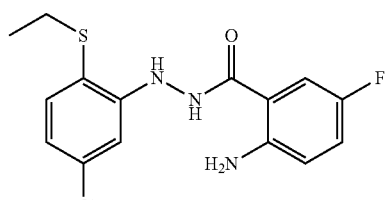

The title compound was synthesized from (5-chloro-2-ethylsulfanylphenyl)hydrazine (Compound 30) and 2-amino-5-fluorobenzoic acid under the same conditions as for Compound a1.

Example 177

Compound A-28

3-(5-Chloro-2-ethylsulfanylanilino)-6-fluoroquinazolin-4-one

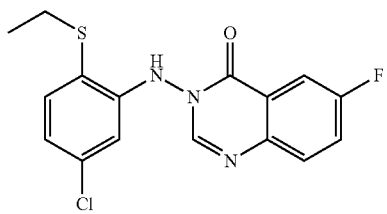 [SMILES: CCSc1ccc(Cl)cc1Nn1cnc2ccc(F)cc2c1=O]

Trimethyl orthoformate (3.2 mL) and formic acid (0.32 mL) were added to 2-amino-N'-(5-chloro-2-ethylsulfanylphenyl)-5-fluorobenzohydrazide (Compound a15, 108.2 mg, 0.32 mmol), and the mixture was stirred at 100° C. for one hour. After the reaction solution was cooled to room temperature, it was concentrated and the resulting residue was purified by silica gel column chromatography (ethyl acetate/hexane) to give the title compound (92.3 mg, 83%) as a colorless solid.

LCMS: m/z 350 [M+H]$^+$
HPLC retention time: 2.63 min (analysis condition C)

Example 178

Compound A-29

3-(5-Chloro-2-ethylsulfonylanilino)-6-fluoroquinazolin-4-one

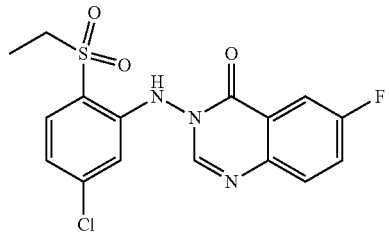 [SMILES: CCS(=O)(=O)c1ccc(Cl)cc1Nn1cnc2ccc(F)cc2c1=O]

The title compound was synthesized from 3-(5-chloro-2-ethylsulfanylanilino)-6-fluoroquinazolin-4-one (Compound A-28) under the same conditions as for Compound 14.

LCMS: m/z 382 [M+H]$^+$
HPLC retention time: 2.17 min (analysis condition C)

Examples 179 to 192

The following compounds of Table 5 were synthesized from (5-chloro-2-ethylsulfanylphenyl)hydrazine (Compound 30) under the same conditions as for Compounds a15 and A-28. However, corresponding carboxylic acids were used under the conditions for Compound a15.

TABLE 5

| Example | Compound number | Structure | Compound name | HPLC condition | Retention time (min) | m/z [M + H]$^+$ |
|---|---|---|---|---|---|---|
| 179 | A-30 | 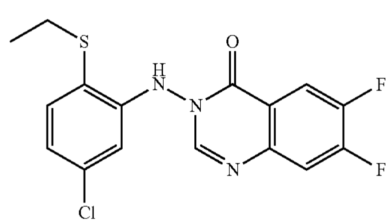 [SMILES: CCSc1ccc(Cl)cc1Nn1cnc2cc(F)c(F)cc2c1=O] | 3-(5-Chloro-2-ethylsulfanylanilino)-6,7-difluoroquinazolin-4-one | C | 2.77 | 368 |
| 180 | A-32 | 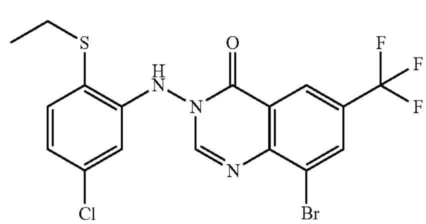 | 8-Bromo-3-(5-chloro-2-ethylsulfanylanilino)-6-(trifluoromethyl)quinazolin-4-one | C | 3.20 | 478 |
| 181 | A-34 | 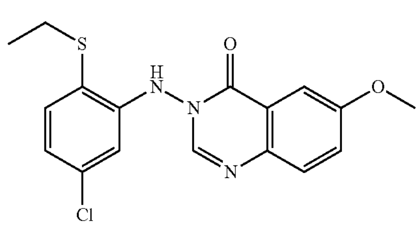 [SMILES: CCSc1ccc(Cl)cc1Nn1cnc2ccc(OC)cc2c1=O] | 3-(5-Chloro-2-ethylsulfanylanilino)-6-methoxyquinazolin-4-one | C | 2.60 | 362 |

TABLE 5-continued

| Example | Compound number | Structure | Compound name | HPLC condition | Retention time (min) | m/z [M + H]+ |
|---|---|---|---|---|---|---|
| 182 | A-36 | 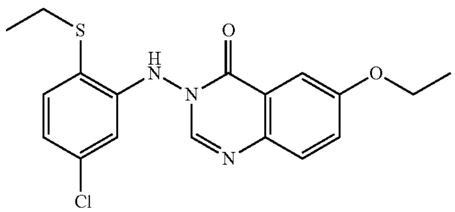 [SMILES: CCOc1ccc2ncn(Nc3cc(Cl)ccc3SCC)c(=O)c2c1] | 3-(5-Chloro-2-ethylsulfanylanilino)-6-ethoxyquinazolin-4-one | C | 2.80 | 376 |
| 183 | A-38 | 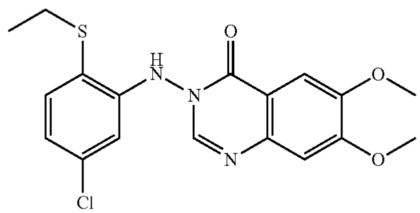 [SMILES: CCSc1ccc(Cl)cc1Nn1cnc2cc(OC)c(OC)cc2c1=O] | 3-(5-Chloro-2-ethylsulfanylanilino)-6,7-dimethoxyquinazolin-4-one | C | 2.43 | 392 |
| 184 | A-40 | 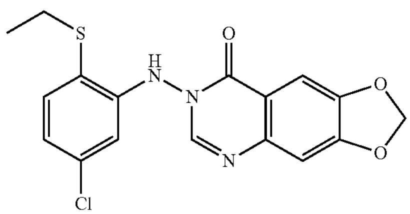 [SMILES: CCSc1ccc(Cl)cc1Nn1cnc2cc3c(cc2c1=O)OCO3] | 7-(5-Chloro-2-ethylsulfanylanilino)-[1,3]dioxolo[4,5-g]quinazolin-8-one | C | 2.52 | 376 |
| 185 | A-42 | 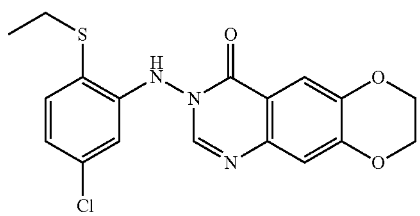 [SMILES: CCSc1ccc(Cl)cc1Nn1cnc2cc3c(cc2c1=O)OCCO3] | 3-(5-Chloro-2-ethylsulfanylanilino)-7,8-dihydro-[1,4]dioxino[2,3-g]quinazolin-4-one | C | 2.65 | 390 |
| 186 | A-44 | 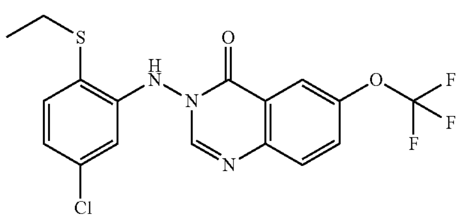 [SMILES: CCSc1ccc(Cl)cc1Nn1cnc2ccc(OC(F)(F)F)cc2c1=O] | 3-(5-Chloro-2-ethylsulfanylanilino)-6-(trifluoromethoxy)quinazolin-4-one | C | 2.98 | 416 |
| 187 | A-46 | 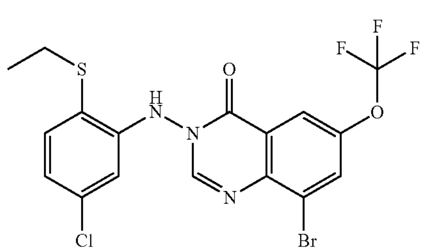 [SMILES: CCSc1ccc(Cl)cc1Nn1cnc2c(Br)cc(OC(F)(F)F)cc2c1=O] | 8-Bromo-3-(5-chloro-2-ethylsulfanylanilino)-6-(trifluoromethoxy)quinazolin-4-one | B | 3.68 | 494 |
| 188 | A-48 | 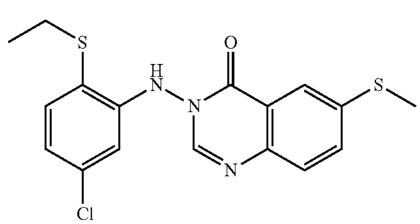 [SMILES: CCSc1ccc(Cl)cc1Nn1cnc2ccc(SC)cc2c1=O] | 3-(5-Chloro-2-ethylsulfanylanilino)-6-methylsulfanylquinazolin-4-one | C | 2.80 | 378 |

TABLE 5-continued

| Example | Compound number | Structure | Compound name | HPLC condition | Retention time (min) | m/z [M + H]+ |
|---|---|---|---|---|---|---|
| 189 | A-50 | 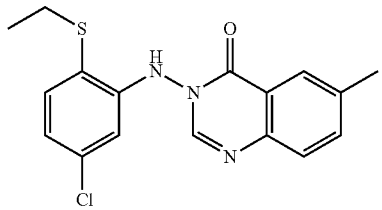 [SMILES: CCSc1ccc(Cl)cc1Nn1cnc2ccc(C)cc2c1=O] | 3-(5-Chloro-2-ethylsulfanylanilino)-6-methylquinazolin-4-one | C | 2.73 | 346 |
| 190 | A-52 | 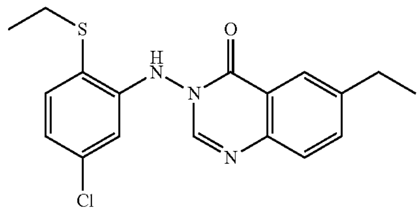 [SMILES: CCSc1ccc(Cl)cc1Nn1cnc2ccc(CC)cc2c1=O] | 3-(5-Chloro-2-ethylsulfanylanilino)-6-ethylquinazolin-4-one | C | 2.92 | 360 |
| 191 | A-54 | 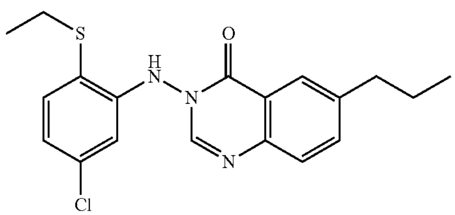 [SMILES: CCCc1ccc2ncn(Nc3cc(Cl)ccc3SCC)c(=O)c2c1] | 3-(5-Chloro-2-ethylsulfanylanilino)-6-propylquinazolin-4-one | C | 3.12 | 374 |
| 192 | A-56 | 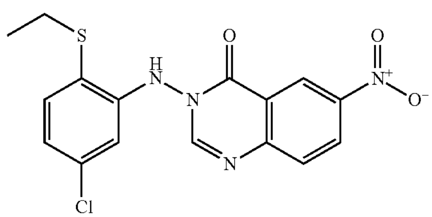 [SMILES: CCSc1ccc(Cl)cc1Nn1cnc2ccc([N+](=O)[O-])cc2c1=O] | 3-(5-Chloro-2-ethylsulfanylanilino)-6-nitroquinazolin-4-one | C | 2.65 | 377 |

Examples 193 to 206

The following compounds of Table 6 were synthesized using the corresponding compounds in Table 5 under the same conditions as for Compound 14.

TABLE 6

| Example | Compound number | Structure | Compound name | HPLC condition | Retention time (min) | m/z [M + H]+ |
|---|---|---|---|---|---|---|
| 193 | A-31 | 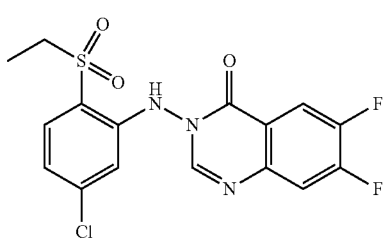 [SMILES: CCS(=O)(=O)c1ccc(Cl)cc1Nn1cnc2cc(F)c(F)cc2c1=O] | 3-(5-Chloro-2-ethylsulfonylanilino)-6,7-difluoroquinazolin-4-one | C | 2.30 | 400 |

TABLE 6-continued

| Example | Compound number | Structure | Compound name | HPLC condition | Retention time (min) | m/z [M + H]+ |
|---|---|---|---|---|---|---|
| 194 | A-33 | 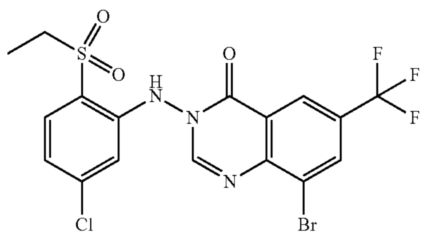 [SMILES: CCS(=O)(=O)c1ccc(Cl)cc1Nn1cnc2c(Br)cc(C(F)(F)F)cc2c1=O] | 8-Bromo-3-(5-chloro-2-ethylsulfonylanilino)-6-(trifluoromethyl)quinazolin-4-one | C | 2.78 | 510 |
| 195 | A-35 | 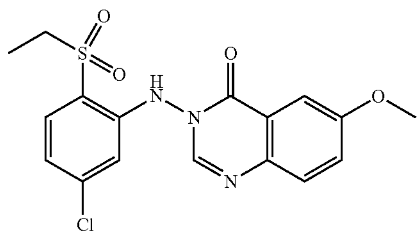 [SMILES: CCS(=O)(=O)c1ccc(Cl)cc1Nn1cnc2ccc(OC)cc2c1=O] | 3-(5-Chloro-2-ethylsulfonylanilino)-6-methoxyquinazolin-4-one | C | 2.12 | 394 |
| 196 | A-37 | 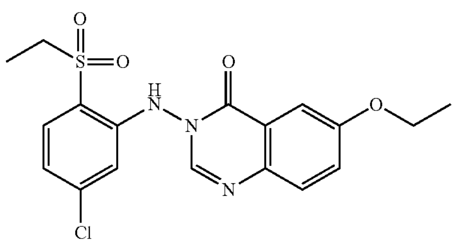 [SMILES: CCOc1ccc2ncn(Nc3cc(Cl)ccc3S(=O)(=O)CC)c(=O)c2c1] | 3-(5-Chloro-2-ethylsulfonylanilino)-6-ethoxyquinazolin-4-one | C | 2.33 | 408 |
| 197 | A-39 | 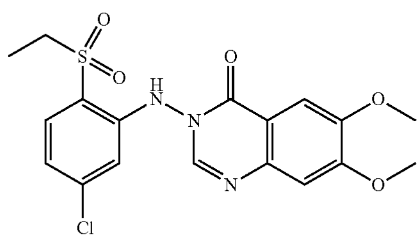 | 3-(5-Chloro-2-ethylsulfonylanilino)-6-dimethoxyquinazolin-4-one | C | 1.97 | 424 |
| 198 | A-41 | 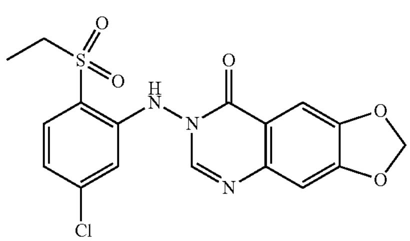 [SMILES: CCS(=O)(=O)c1ccc(Cl)cc1Nn1cnc2cc3c(cc2c1=O)OCO3] | 7-(5-Chloro-2-ethylsulfonylanilino)-[1,3]dioxolo[4,5-g]quinazolin-8-one | C | 2.02 | 408 |
| 199 | A-43 | 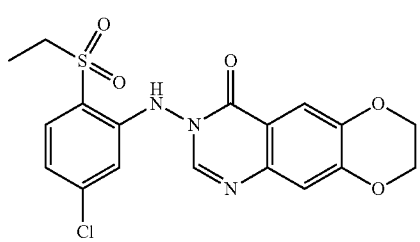 [SMILES: CCS(=O)(=O)c1ccc(Cl)cc1Nn1cnc2cc3c(cc2c1=O)OCCO3] | 3-(5-Chloro-2-ethylsulfonylanilino)-7,8-dihydro-[1,4]dioxino[2,3-g]quinazolin-4-one | C | 2.22 | 422 |

TABLE 6-continued

| Example | Compound number | Structure | Compound name | HPLC condition | Retention time (min) | m/z [M + H]+ |
|---|---|---|---|---|---|---|
| 200 | A-45 | 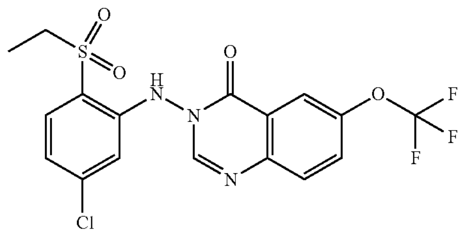 [SMILES: CCS(=O)(=O)c1ccc(Cl)cc1Nn1cnc2ccc(OC(F)(F)F)cc2c1=O] | 3-(5-Chloro-2-ethylsulfonylanilino)-6-(trifluoromethoxy)quinazolin-4-one | C | 2.53 | 448 |
| 201 | A-47 | 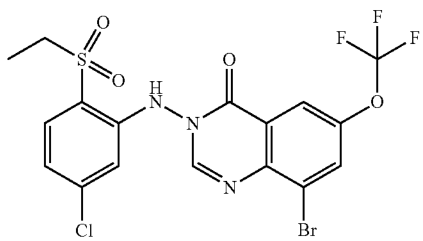 [SMILES: CCS(=O)(=O)c1ccc(Cl)cc1Nn1cnc2c(Br)cc(OC(F)(F)F)cc2c1=O] | 8-Bromo-3-(5-chloro-2-ethylsulfonylanilino)-6-(trifluoromethoxy)quinazolin-4-one | D | 0.91 | 526 |
| 202 | A-49 | 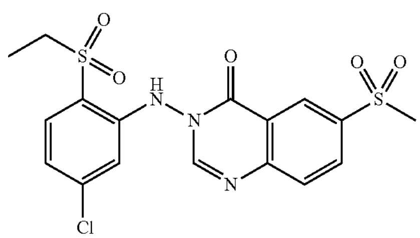 [SMILES: CCS(=O)(=O)c1ccc(Cl)cc1Nn1cnc2ccc(S(C)(=O)=O)cc2c1=O] | 3-(5-Chloro-2-ethylsulfonylanilino)-6-methylsulfonylquinazolin-4-one | C | 1.85 | 442 |
| 203 | A-51 | 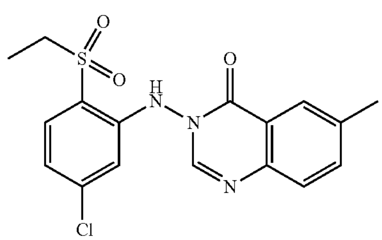 [SMILES: CCS(=O)(=O)c1ccc(Cl)cc1Nn1cnc2ccc(C)cc2c1=O] | 3-(5-Chloro-2-ethylsulfonylanilino)-6-methylquinazolin-4-one | C | 2.23 | 378 |
| 204 | A-53 | 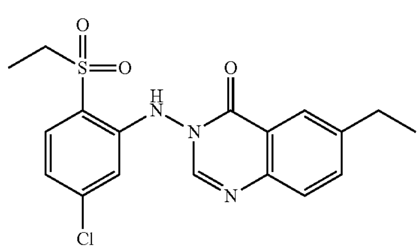 [SMILES: CCc1ccc2ncn(Nc3cc(Cl)ccc3S(=O)(=O)CC)c(=O)c2c1] | 3-(5-Chloro-2-ethylsulfonylanilino)-6-ethylquinazolin-4-one | C | 2.43 | 392 |
| 205 | A-55 | 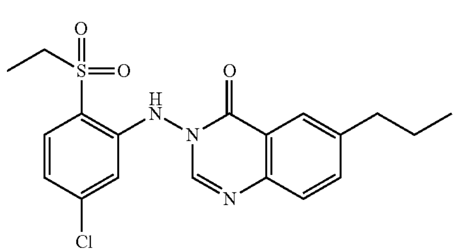 [SMILES: CCCc1ccc2ncn(Nc3cc(Cl)ccc3S(=O)(=O)CC)c(=O)c2c1] | 3-(5-Chloro-2-ethylsulfonylanilino)-6-propylquinazolin-4-one | C | 2.63 | 406 |

TABLE 6-continued

| Example | Compound number | Structure | Compound name | HPLC condition | Retention time (min) | m/z [M + H]+ |
|---|---|---|---|---|---|---|
| 206 | A-57 | 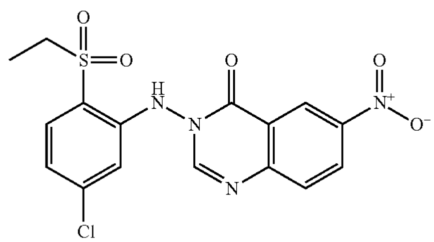 [SMILES: CCS(=O)(=O)c1ccc(Cl)cc1Nn1cnc2ccc([N+](=O)[O-])cc2c1=O] | 3-(5-Chloro-2-ethylsulfonylanilino)-6-nitroquinazolin-4-one | C | 2.22 | 409 |

Example 207

Compound A-58

6-Amino-3-(5-chloro-2-ethylsulfonylanilino)quinazolin-4-one

Sodium dithionite (30.5 mg, 0.175 mmol) was added to a mixture of 3-(5-chloro-2-ethylsulfonylanilino)-6-nitroquinazolin-4-one (Compound A-57, 10.2 mg, 0.025 mmol) in THF/water, and the mixture was stirred at room temperature overnight. Water was added to the reaction mixture, and extraction was performed with ethyl acetate. The organic layer was dried over anhydrous sodium sulfate. After the drying agent was removed by filtration, concentration was performed under reduced pressure. The resulting residue was purified by silica gel column chromatography (ethyl acetate/hexane) to give the title compound (3.9 mg, 41%) as a colorless solid.

LCMS: m/z 379 [M+H]+
HPLC retention time: 1.55 min (analysis condition C)

Example 208

Compound A-59

6-Amino-3-(5-chloro-2-ethylsulfanylanilino)quinazolin-4-one

The title compound was synthesized from 3-(5-chloro-2-ethylsulfanylanilino)-6-nitroquinazolin-4-one (Compound A-56) under the same conditions as for Compound A-58.

LCMS: m/z 347 [M+H]+
HPLC retention time: 1.97 min (analysis condition C)

Example 209

Compound A-60

3-(5-Chloro-2-ethylsulfanylanilino)-6-iodoquinazolin-4-one

The title compound was synthesized from (5-chloro-2-ethylsulfanylphenyl)hydrazine (Compound 30) under the same conditions as for Compounds a15 and A-28. However, 2-amino-5-iodobenzoic acid was used as a carboxylic acid under the conditions for Compound a15.

LCMS: m/z 458 [M+H]+
HPLC retention time: 2.98 min (analysis condition C)

Example 210

Compound A-61

3-(5-Chloro-2-ethylsulfonylanilino)-6-iodoquinazolin-4-one

The title compound was synthesized from 3-(5-chloro-2-ethylsulfanylanilino)-6-iodoquinazolin-4-one (Compound A-60) under the same conditions as for Compound 14.
LCMS: m/z 490 [M+H]⁺
HPLC retention time: 2.48 min (analysis condition C)

Example 211

Compound A-62

3-(5-Chloro-2-ethylsulfonylanilino)-6-prop-1-en-2-ylquinazolin-4-one

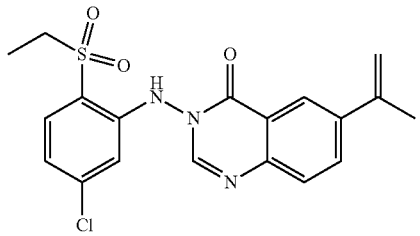 [SMILES: C=C(C)c1ccc2ncn(Nc3cc(Cl)ccc3S(=O)(=O)CC)c(=O)c2c1]

A mixture of 3-(5-chloro-2-ethylsulfonylanilino)-6-iodoquinazolin-4-one (Compound A-61, 49.0 mg, 0.10 mmol), 4,4,5,5-tetramethyl-2-prop-1-en-2-yl-1,3,2-dioxaborolane (20.7 µl, 0.11 mmol), 1,1'-bis(diphenylphosphino)ferrocene-palladium(II) dichloride (1.5 mg, 0.002 mmol), potassium carbonate (41.5 mg, 0.30 mmol), and THF (1.8 mL)/water (0.2 mL) was stirred under microwave irradiation at 100° C. for 1.5 hours. The reaction mixture was cooled to room temperature, followed by addition of water and extraction with ethyl acetate. The organic layer was dried over anhydrous sodium sulfate. After the drying agent was removed by filtration, concentration was performed under reduced pressure. The resulting residue was purified by silica gel column chromatography (ethyl acetate/hexane) to give the title compound (34.9 mg, 86%) as a colorless solid.
LCMS: m/z 404 [M+H]⁺
HPLC retention time: 2.53 min (analysis condition C)

Example 212

Compound A-63

3-(5-Chloro-2-ethylsulfonylanilino)-6-propan-2-ylquinazolin-4-one

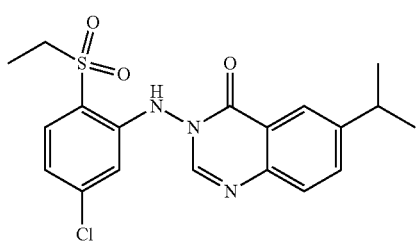 [SMILES: CCS(=O)(=O)c1ccc(Cl)cc1Nn1cnc2ccc(C(C)C)cc2c1=O]

3-(5-Chloro-2-ethylsulfonylanilino)-6-prop-1-en-2-ylquinazolin-4-one (Compound A-62, 17.3 mg, 0.043 mmol) was dissolved in a mixed solution of ethyl acetate (0.5 mL)/methanol (1 mL), and 10% Pd/C was added thereto. The mixture was stirred under hydrogen atmosphere for two hours. Pd/C was removed by filtration, and the solution was then washed with methanol. The filtrate and the washings were combined and concentrated. The resulting residue was purified by silica gel column chromatography (ethyl acetate/hexane) and preparative HPLC (water/acetonitrile, 0.05% TFA) to give the title compound (11.4 mg, 66%) as a colorless foamy substance.
LCMS: m/z 406 [M+H]⁺
HPLC retention time: 2.60 min (analysis condition C)

Example 213

Compound A-64

3-(5-Chloro-2-ethylsulfonylanilino)-6-ethenylquinazolin-4-one

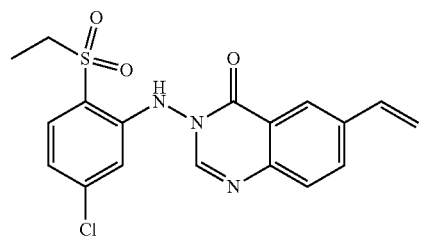 [SMILES: C=Cc1ccc2ncn(Nc3cc(Cl)ccc3S(=O)(=O)CC)c(=O)c2c1]

The title compound was synthesized from 3-(5-chloro-2-ethylsulfonylanilino)-6-iodoquinazolin-4-one (Compound A-61) under the same conditions as for Compound A-62. However, potassium vinyltrifluoroborate was used in place of 4,4,5,5-tetramethyl-2-prop-1-en-2-yl-1,3,2-dioxaborolane as a boronic acid.
LCMS: m/z 390[M+H]⁺
HPLC retention time: 2.35 min (analysis condition C)

Example 214

Compound A-65

3-(5-Chloro-2-ethylsulfonylanilino)-6-prop-1-ynylquinazolin-4-one

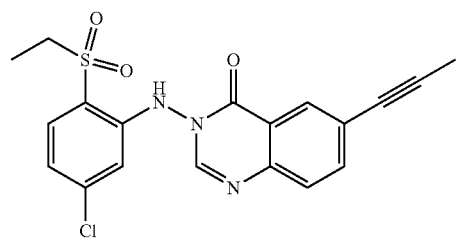 [SMILES: CC#Cc1ccc2ncn(Nc3cc(Cl)ccc3S(=O)(=O)CC)c(=O)c2c1]

Tetrakis(triphenylphosphine)palladium (0) (5.8 mg, 0.005 mmol) was added to a solution of 3-(5-chloro-2-ethylsulfonylanilino)-6-iodoquinazolin-4-one (Compound A-61, 49.0 mg, 0.10 mmol), tributyl(1-propynyl)tin (60.8 µl) in THF. The mixture was stirred under microwave irradiation at 80° C. for one hour. The reaction mixture was cooled to room temperature, followed by addition of water and extraction with ethyl acetate. The organic layer was dried over anhy-

Example 215

Compound a16

2-Amino-N'-(5-chloro-2-ethylsulfonylphenyl)-5-methylsulfonylbenzohydrazide

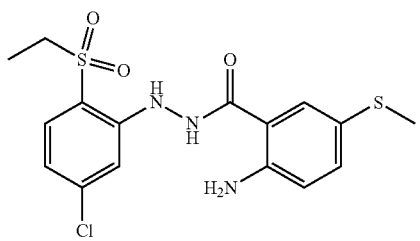 [SMILES: CCS(=O)(=O)c1ccc(Cl)cc1NNC(=O)c1cc(SC)ccc1N]

The title compound was synthesized from (5-chloro-2-ethylsulfonylphenyl)hydrazine (Compound 31) and 2-amino-5-methylsulfanylbenzoic acid (Compound 93) under the same conditions as for Compound a1. However, HOBT was added and DMF was used in place of dichloromethane as a solvent.

Example 216

Compound A-66

3-(5-Chloro-2-ethylsulfonylanilino)-6-methylsulfanylquinazolin-4-one

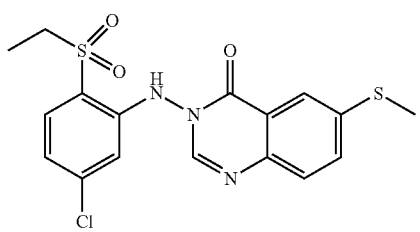 [SMILES: CCS(=O)(=O)c1ccc(Cl)cc1Nn1cnc2ccc(SC)cc2c1=O]

The title compound was synthesized from 2-amino-N'-(5-chloro-2-ethylsulfonylphenyl)-5-methylsulfanylbenzohydrazide (Compound a16) under the same conditions as for Compound A-28.

LCMS: m/z 410 [M+H]$^+$

HPLC retention time: 2.33 min (analysis condition C)

Example 217

Compound b1

2-Amino-3-bromo-N'-(5-chloro-2-methylsulfanylphenyl)-5-methylbenzohydrazide

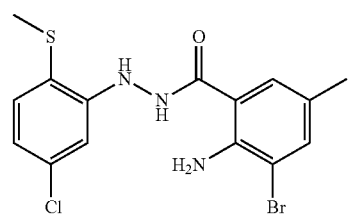 [SMILES: CSc1ccc(Cl)cc1NNC(=O)c1cc(C)cc(Br)c1N]

The title compound was synthesized from (5-chloro-2-methylsulfanylphenyl)hydrazine (Compound 32) and 2-amino-3-bromo-5-methylbenzoic acid under the same conditions as for Compound a1.

Example 218

Compound B-1

8-Bromo-3-(5-chloro-2-methylsulfanylanilino)-6-methylquinazolin-4-one

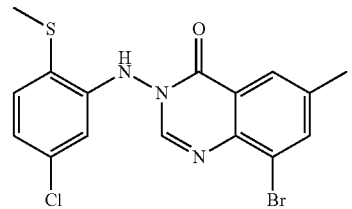 [SMILES: CSc1ccc(Cl)cc1Nn1cnc2c(Br)cc(C)cc2c1=O]

The title compound was synthesized from 2-amino-3-bromo-N'-(5-chloro-2-methylsulfanylphenyl)-5-methylbenzohydrazide (Compound b1) under the same conditions as for Compound A-1.

LCMS: m/z 410 [M+H]$^+$

HPLC retention time: 2.82 min (analysis condition C)

Example 219

Compound b2 tert-Butyl N-(8-bromo-6-methyl-4-oxo-quinazolin-3-yl)-N-(5-chloro-2-methylsulfanyl-phenyl)carbamate

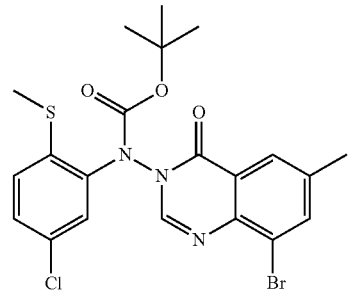 [SMILES: CSc1ccc(Cl)cc1N(C(=O)OC(C)(C)C)n1cnc2c(Br)cc(C)cc2c1=O]

---

(continued from previous page)

drous sodium sulfate. After the drying agent was removed by filtration, concentration was performed under reduced pressure. The resulting residue was purified by silica gel column chromatography (ethyl acetate/hexane) to give the title compound (30.2 mg, 75%) as a colorless solid.

LCMS: m/z 402 [M+H]$^+$

HPLC retention time: 2.43 min (analysis condition C)

The title compound was synthesized from 8-bromo-3-(5-chloro-2-methylsulfanylanilino)-6-methylquinazolin-4-one (Compound B-1) under the same conditions as for Compound a3.

Example 220

Compound b3 tert-Butyl N-(8-bromo-6-methyl-4-oxoquinazolin-3-yl)-N-(5-chloro-2-methylsulfinylphenyl)carbamate

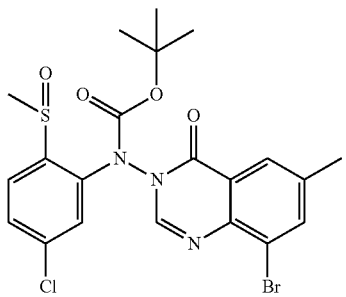 [SMILES: Cc1cc(Br)c2ncn(N(C(=O)OC(C)(C)C)c3cc(Cl)ccc3S(C)=O)c(=O)c2c1]

Tetrabutylammonium hydrogen sulfate (40 mg, 0.12 mmol), and oxone (761 mg, 1.24 mmol) dissolved in water (1.2 ml) were added to a solution of tert-butyl N-(8-bromo-6-methyl-4-oxoquinazolin-3-yl)-N-(5-chloro-2-methylsulfanylphenyl)carbamate (Compound b2, 241 mg, 0.47 mmol) in DCM (1.2 ml), and the mixture was stirred at room temperature for 48 hours. Water was added to the reaction mixture, and extraction was performed twice with DCM. The organic layer was then washed with an aqueous sodium thiosulfate solution and dried over anhydrous magnesium sulfate. After the drying agent was removed by filtration, concentration was performed under reduced pressure to give a crude product of the title compound (271 mg).

LCMS: m/z 526 [M+H]$^+$

HPLC retention time: 3.77 min (analysis condition B)

Example 221

Compound b4 tert-Butyl N-(8-bromo-6-methyl-4-oxo-quinazolin-3-yl)-N-(5-chloro-2-methylsulfonyl-phenyl)carbamate

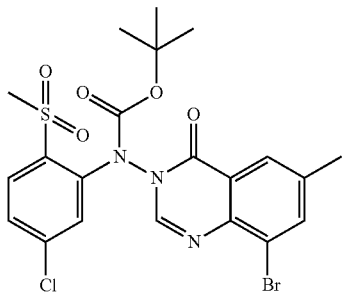 [SMILES: Cc1cc(Br)c2ncn(N(C(=O)OC(C)(C)C)c3cc(Cl)ccc3S(C)(=O)=O)c(=O)c2c1]

The title compound was synthesized from tert-butyl N-(8-bromo-6-methyl-4-oxoquinazolin-3-yl)-N-(5-chloro-2-methylsulfinylphenyl)carbamate (Compound b3) under the same conditions as for Compound 14.

Example 222

Compound B-2

8-Bromo-3-(5-chloro-2-methylsulfonylanilino)-6-methylquinazolin-4-one

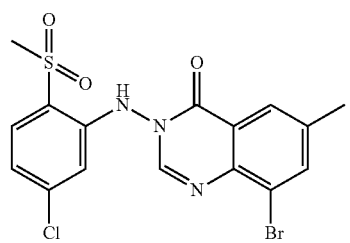 [SMILES: Cc1cc(Br)c2ncn(Nc3cc(Cl)ccc3S(C)(=O)=O)c(=O)c2c1]

The title compound was synthesized from tert-butyl N-(8-bromo-6-methyl-4-oxo-quinazolin-3-yl)-N-(5-chloro-2-methylsulfonyl-phenyl)carbamate (Compound b4) under the same conditions as for Compound A-2.

LCMS: m/z 442 [M+H]$^+$

HPLC retention time: 0.81 min (analysis condition D)

$^1$H-NMR (300 MHz, DMSO-d$_6$) δ:9.18 (1H, s), 8.52 (1H, s), 8.09 (1H, d, J=1.8 Hz), 7.97 (1H, d, J=1.8 Hz), 7.79 (1H, d, J=8.5 Hz), 7.17 (1H, dd, J=1.8, 8.5 Hz), 7.04 (1H, J=1.8 Hz), 3.40 (3H, s), 2.47 (3H, s).

Example 223

Compound b5

2-Amino-3-bromo-N'-(5-chloro-2-propylsulfanyl-phenyl)-5-methyl-benzohydrazide

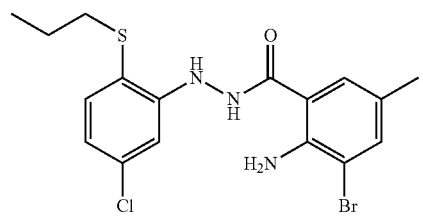 [SMILES: CCCSc1ccc(Cl)cc1NNC(=O)c1cc(C)cc(Br)c1N]

The title compound was synthesized from (5-chloro-2-propylsulfanylphenyl)hydrazine (Compound 33) and 2-amino-3-bromo-5-methylbenzoic acid under the same conditions as for Compound a1.

Example 224

Compound B-3

8-Bromo-3-(5-chloro-2-propylsulfanylanilino)-6-methylquinazolin-4-one

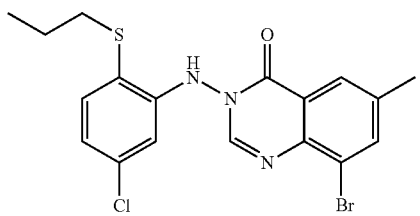 [SMILES: CCCSc1ccc(Cl)cc1Nn1cnc2c(Br)cc(C)cc2c1=O]

The title compound was synthesized from 2-amino-3-bromo-N'-(5-chloro-2-propylsulfanyl-phenyl)-5-methyl-benzohydrazide (Compound b5) under the same conditions as for Compound A-1.

LCMS: m/z 438 [M+H]$^+$

HPLC retention time: 3.73 min (analysis condition B)

Example 225

Compound b6 tert-Butyl N-(8-bromo-6-methyl-4-oxo-quinazolin-3-yl)-N-(5-chloro-2-propylsulfanyl-phenyl)carbamate

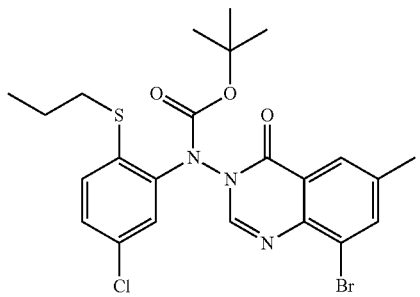 [SMILES: CCCSc1ccc(Cl)cc1N(C(=O)OC(C)(C)C)n1cnc2c(Br)cc(C)cc2c1=O]

The title compound was synthesized from 8-bromo-3-(5-chloro-2-propylsulfanylanilino)-6-methylquinazolin-4-one (Compound B-3) under the same conditions as for Compound a3.

Example 226

Compound b7 tert-Butyl N-(8-bromo-6-methyl-4-oxo-quinazolin-3-yl)-N-(5-chloro-2-propylsulfonyl-phenyl)carbamate

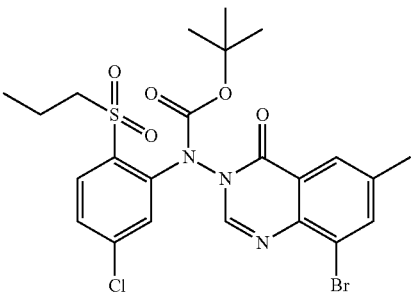 [SMILES: CCCS(=O)(=O)c1ccc(Cl)cc1N(C(=O)OC(C)(C)C)n1cnc2c(Br)cc(C)cc2c1=O]

The title compound was synthesized from tert-butyl N-(8-bromo-6-methyl-4-oxo-quinazolin-3-yl)-N-(5-chloro-2-propylsulfanyl-phenyl)carbamate (Compound b6) under the same conditions as for Compound 14.

Example 227

Compound B-4

8-Bromo-3-(5-chloro-2-propylsulfonylanilino)-6-methylquinazolin-4-one

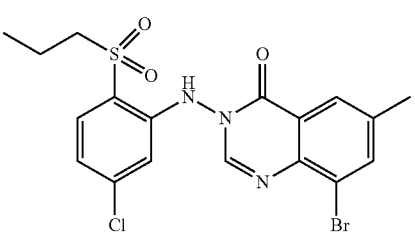 [SMILES: CCCS(=O)(=O)c1ccc(Cl)cc1Nn1cnc2c(Br)cc(C)cc2c1=O]

The title compound was synthesized from tert-butyl N-(8-bromo-6-methyl-4-oxo-quinazolin-3-yl)-N-(5-chloro-2-propylsulfonyl-phenyl)carbamate (Compound b7) under the same conditions as for Compound A-2.

LCMS: m/z 470 [M+H]$^+$

HPLC retention time: 3.35 min (analysis condition B)

Example 228

Compound b8

2-Amino-N'-(5-chloro-2-isopropylsulfonyl-phenyl)-5-(trifluoromethoxy)benzohydrazide

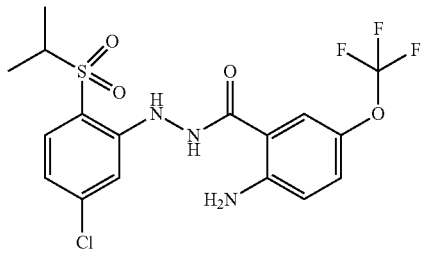 [SMILES: CC(C)S(=O)(=O)c1ccc(Cl)cc1NNC(=O)c1cc(OC(F)(F)F)ccc1N]

The title compound was synthesized from (5-chloro-2-isopropylsulfonyl-phenyl)hydrazine (Compound 36) and 2-amino-5-(trifluoromethoxy)benzoic acid under the same conditions as for Compound a1.

Example 229

Compound B-5

3-(5-Chloro-2-propan-2-ylsulfonylanilino)-6-(trifluoromethoxy)quinazolin-4-one

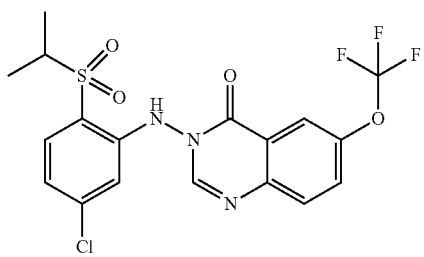 [SMILES: CC(C)S(=O)(=O)c1ccc(Cl)cc1Nn1cnc2ccc(OC(F)(F)F)cc2c1=O]

The title compound was synthesized from 2-amino-N'-(5-chloro-2-isopropylsulfonyl-phenyl)-5-(trifluoromethoxy)benzohydrazide (Compound b8) under the same conditions as for Compound A-5.
LCMS: m/z 462 [M+H]$^+$
HPLC retention time: 0.91 min (analysis condition D)

Example 230

Compound b9

2-Amino-3-bromo-N'-(5-chloro-2-isopropylsulfonyl-phenyl)-5-(trifluoromethyl)benzohydrazide

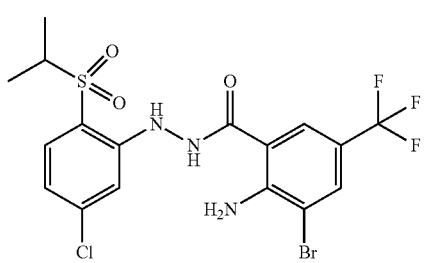

The title compound was synthesized from (5-chloro-2-isopropylsulfonyl-phenyl)hydrazine (Compound 36) and 2-amino-3-bromo-5-(trifluoromethyl)benzoic acid (Compound 85) under the same conditions as for Compound a1.

Example 231

Compound B-6

8-Bromo-3-(5-chloro-2-propan-2-ylsulfonylanilino)-6-(trifluoromethyl)quinazolin-4-one

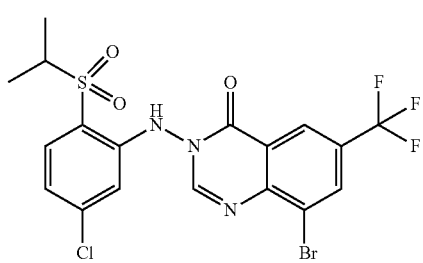 [SMILES: CC(C)S(=O)(=O)c1ccc(Cl)cc1Nn1cnc2c(Br)cc(C(F)(F)F)cc2c1=O]

The title compound was synthesized from 2-amino-3-bromo-N'-(5-chloro-2-isopropylsulfonyl-phenyl)-5-(trifluoromethyl)benzohydrazide (Compound b9) under the same conditions as for Compound A-5.
LCMS: m/z 524 [M+H]$^+$
HPLC retention time: 0.97 min (analysis condition D)

Example 232

Compound b10

2-Amino-3-chloro-N'-(5-chloro-2-isopropylsulfonyl-phenyl)-5-(trifluoromethyl)benzohydrazide

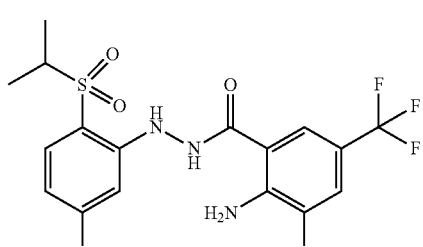

The title compound was synthesized from (5-chloro-2-isopropylsulfonyl-phenyl)hydrazine (Compound 36) and 2-amino-3-chloro-5-(trifluoromethyl)benzoic acid (Compound 86) under the same conditions as for Compound a1.

Example 233

Compound B-7

8-Chloro-3-(5-chloro-2-propan-2-ylsulfonylanilino)-6-(trifluoromethyl)quinazolin-4-one

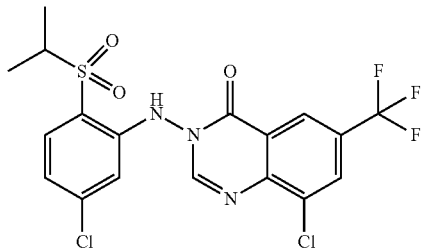 [SMILES: CC(C)S(=O)(=O)c1ccc(Cl)cc1Nn1cnc2c(Cl)cc(C(F)(F)F)cc2c1=O]

The title compound was synthesized from 2-amino-3-chloro-N'-(5-chloro-2-isopropylsulfonyl-phenyl)-5-(trifluoromethyl)benzohydrazide (Compound b10) under the same conditions as for Compound A-5.

LCMS: m/z 480 [M+H]$^+$

HPLC retention time: 0.96 min (analysis condition D)

Example 234

Compound b11

2-Amino-N'-(5-chloro-2-cyclopentylsulfonyl-phenyl)-5-(trifluoromethoxy)benzohydrazide

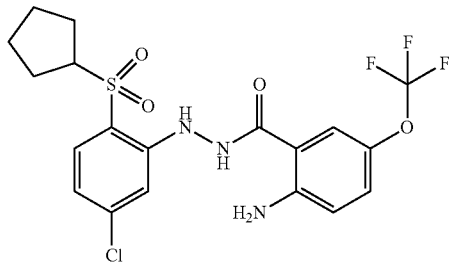 [SMILES: Nc1ccc(OC(F)(F)F)cc1C(=O)NNc1cc(Cl)ccc1S(=O)(=O)C1CCCC1]

The title compound was synthesized from (5-chloro-2-cyclopentylsulfonyl-phenyl)hydrazine (Compound 37) and 2-amino-5-(trifluoromethoxy)benzoic acid under the same conditions as for Compound a1.

Example 235

Compound B-8

3-(5-Chloro-2-cyclopentylsulfonylanilino)-6-(trifluoromethoxy)quinazolin-4-one

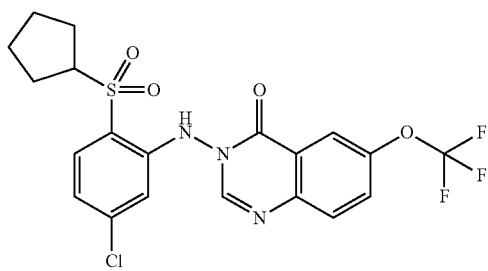 [SMILES: O=c1c2cc(OC(F)(F)F)ccc2ncn1Nc1cc(Cl)ccc1S(=O)(=O)C1CCCC1]

The title compound was synthesized from 2-amino-N'-(5-chloro-2-cyclopentylsulfonyl-phenyl)-5-(trifluoromethoxy)benzohydrazide (Compound b11) under the same conditions as for Compound A-5.

LCMS: m/z 488 [M+H]$^+$

HPLC retention time: 0.97 min (analysis condition D)

Example 236

Compound b12

2-Amino-N'-(5-chloro-2-cyclopropylsulfonyl-phenyl)-5-(trifluoromethoxy)benzohydrazide

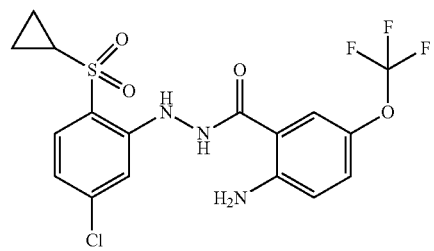 [SMILES: Nc1ccc(OC(F)(F)F)cc1C(=O)NNc1cc(Cl)ccc1S(=O)(=O)C1CC1]

The title compound was synthesized from (5-chloro-2-cyclopropylsulfonyl-phenyl)hydrazine (Compound 40) and 2-amino-5-(trifluoromethoxy)benzoic acid under the same conditions as for Compound a1.

Example 237

Compound B-9

3-(5-Chloro-2-cyclopropylsulfonylanilino)-6-(trifluoromethoxy)quinazolin-4-one

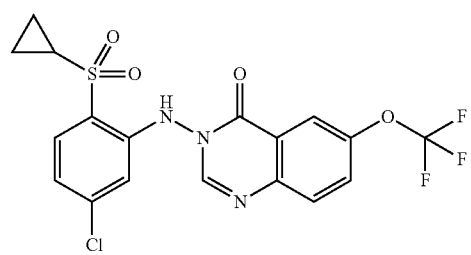 [SMILES: O=c1c2cc(OC(F)(F)F)ccc2ncn1Nc1cc(Cl)ccc1S(=O)(=O)C1CC1]

The title compound was synthesized from 2-amino-N'-(5-chloro-2-cyclopropylsulfonyl-phenyl)-5-(trifluoromethoxy)benzohydrazide (Compound b12) under the same conditions as for Compound A-5.

LCMS: m/z 460 [M+H]$^+$

HPLC retention time: 0.89 min (analysis condition D)

Example 238

Compound B-10

8-Chloro-3-(5-chloro-2-cyclopropylsulfonylanilino)-6-(trifluoromethyl)quinazolin-4-one

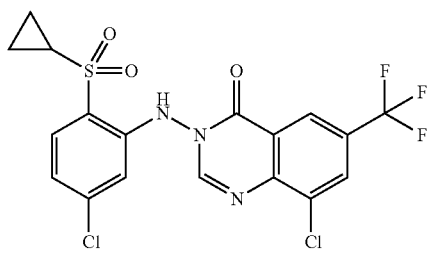 [SMILES: O=c1c2cc(C(F)(F)F)cc(Cl)c2ncn1Nc1cc(Cl)ccc1S(=O)(=O)C1CC1]

The title compound was synthesized from (5-chloro-2-cyclopropylsulfonyl-phenyl)hydrazine (Compound 40) under the same conditions as for Compounds b12 and B-9. However, the reaction was performed using 2-amino-3-chloro-5-(trifluoromethyl)benzoic acid (Compound 86) in place of 2-amino-5-(trifluoromethoxy)benzoic acid under the conditions for Compound b12.

LCMS: m/z 478 [M+H]$^+$

HPLC retention time: 0.94 min (analysis condition D)

Example 239

Compound B-11

8-Bromo-3-(5-chloro-2-cyclopropylsulfonylanilino)-6-(trifluoromethyl)quinazolin-4-one

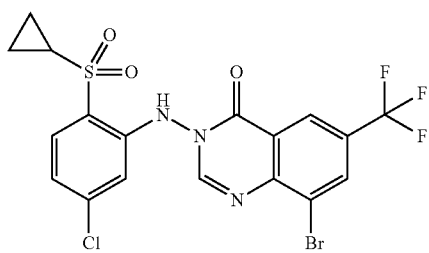 [SMILES: O=c1c2cc(C(F)(F)F)cc(Br)c2ncn1Nc1cc(Cl)ccc1S(=O)(=O)C1CC1]

The title compound was synthesized from (5-chloro-2-cyclopropylsulfonyl-phenyl)hydrazine (Compound 40) under the same conditions as for Compounds b12 and B-9. However, the reaction was performed using 2-amino-3-bromo-5-(trifluoromethyl)benzoic acid (Compound 85) in place of 2-amino-5-(trifluoromethoxy)benzoic acid under the conditions for Compound b12.

LCMS: m/z 522 [M+H]$^+$

HPLC retention time: 0.95 min (analysis condition D)

Example 240

Compound b13

2-Amino-3-bromo-N'-(5-chloro-2-phenylsulfanyl-phenyl)-5-methyl-benzohydrazide

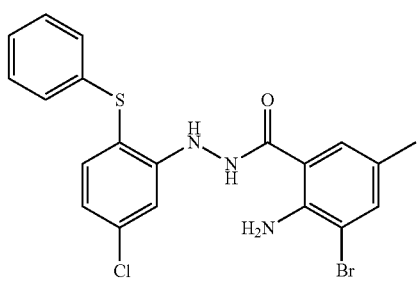 [SMILES: Cc1cc(Br)c(N)c(C(=O)NNc2cc(Cl)ccc2Sc2ccccc2)c1]

The title compound was synthesized from (5-chloro-2-phenylsulfanyl-phenyl)hydrazine (Compound 43) and 2-amino-3-bromo-5-methylbenzoic acid under the same conditions as for Compound a1.

Example 241

Compound B-12

8-Bromo-3-(5-chloro-2-phenylsulfanylanilino)-6-methylquinazolin-4-one

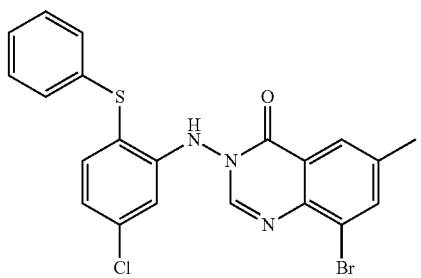 [SMILES: Cc1cc(Br)c2ncn(Nc3cc(Cl)ccc3Sc3ccccc3)c(=O)c2c1]

The title compound was synthesized from 2-amino-3-bromo-N'-(5-chloro-2-phenylsulfanyl-phenyl)-5-methyl-benzohydrazide (Compound b13) under the same conditions as for Compound A-1.

LCMS: m/z 472 [M+H]$^+$

HPLC retention time: 4.05 min (analysis condition C)

Example 242

Compound b14 tert-Butyl N-(8-bromo-6-methyl-4-oxo-quinazolin-3-yl)-N-(5-chloro-2-phenylsulfanyl-phenyl)carbamate

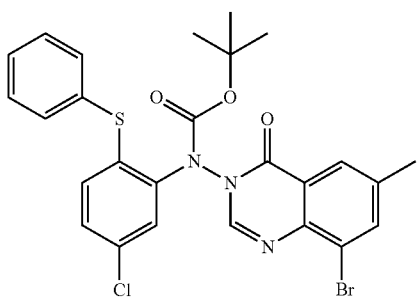 [SMILES: Cc1cc(Br)c2ncn(N(C(=O)OC(C)(C)C)c3cc(Cl)ccc3Sc3ccccc3)c(=O)c2c1]

The title compound was synthesized from 8-bromo-3-(5-chloro-2-phenylsulfanylanilino)-6-methylquinazolin-4-one (Compound B-12) under the same conditions as for Compound a3.

Example 243

Compound b15 tert-Butyl N-[2-(benzenesulfinyl)-5-chloro-phenyl]-N-(8-bromo-6-methyl-4-oxo-quinazolin-3-yl)carbamate

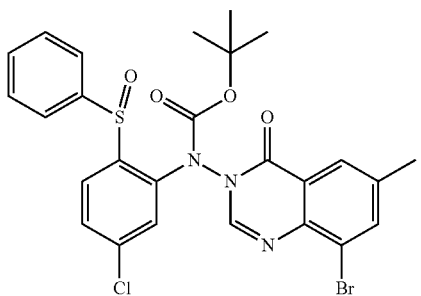 [SMILES: Cc1cc(Br)c2ncn(N(C(=O)OC(C)(C)C)c3cc(Cl)ccc3S(=O)c3ccccc3)c(=O)c2c1]

The title compound was synthesized from tert-butyl N-(8-bromo-6-methyl-4-oxo-quinazolin-3-yl)-N-(5-chloro-2-phenylsulfanyl-phenyl)carbamate (Compound b14) under the same conditions as for Compound b3.

Example 244

Compound B-13

3-[2-(Benzenesulfinyl)-5-chloroanilino]-8-bromo-6-methylquinazolin-4-one

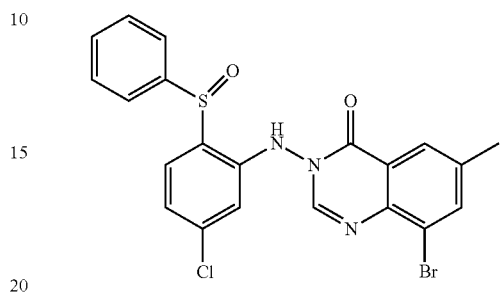

The title compound was synthesized from tert-butyl N-[2-(benzenesulfinyl)-5-chloro-phenyl]-N-(8-bromo-6-methyl-4-oxo-quinazolin-3-yl)carbamate (Compound b15) under the same conditions as for Compound A-2.

LCMS: m/z 488 [M+H]$^+$

HPLC retention time: 2.58 min (analysis condition C)

Example 245

Compound b16 tert-Butyl N-[2-(benzenesulfonyl)-5-chlorophenyl]-N-(8-bromo-6-methyl-4-oxoquinazolin-3-yl)carbamate

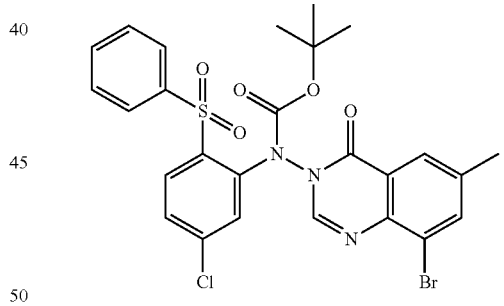

Tetrabutylammonium hydrogen sulfate (55 mg, 0.162 mmol), and oxone (3.13 g, 5.09 mmol) dissolved in water (4 ml) were added to a solution of tert-butyl N-(8-bromo-6-methyl-4-oxoquinazolin-3-yl)-N-(5-chloro-2-phenylsulfanylphenyl)carbamate (Compound b14, 220 mg, 0.384 mmol) in DCM (4 ml). The mixture was stirred at room temperature for one day, and at 50° C. for additional one day. The reaction solution was cooled to room temperature, followed by addition of water and extraction with DCM. The resulting organic layer was washed with a saturated aqueous sodium thiosulfate solution and dried over anhydrous magnesium sulfate. After the drying agent was removed by filtration, concentration was performed under reduced pressure to give a crude product of the title compound.

LCMS: m/z 604 [M+H]$^+$

HPLC retention time: 4.30 min (analysis condition B)

Example 246

Compound B-14

3-[2-(Benzenesulfonyl)-5-chloroanilino]-8-bromo-6-methylquinazolin-4-one

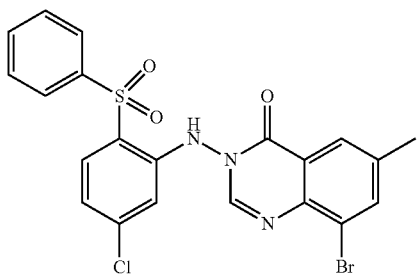 [SMILES: Cc1cc(Br)c2ncn(Nc3cc(Cl)ccc3S(=O)(=O)c3ccccc3)c(=O)c2c1]

The title compound was synthesized from tert-butyl N-[2-(benzenesulfonyl)-5-chlorophenyl]-N-(8-bromo-6-methyl-4-oxoquinazolin-3-yl)carbamate (Compound b16) under the same conditions as for Compound A-2.

LCMS: m/z 504 [M+H]$^+$

HPLC retention time: 3.73 min (analysis condition B)

Example 247

Compound b17

2-Amino-N'-(5-cyano-2-phenylsulfanyl-phenyl)-5-(trifluoromethyl)benzohydrazide

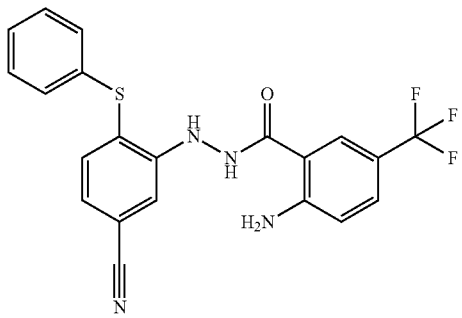 [SMILES: N#Cc1ccc(Sc2ccccc2)c(NNC(=O)c2cc(C(F)(F)F)ccc2N)c1]

The title compound was synthesized from 3-hydrazino-4-phenylsulfanyl-benzonitrile (Compound 45) and 2-amino-5-(trifluoromethyl)benzoic acid under the same conditions as for Compound a1.

Example 248

Compound B-15

3-[[4-Oxo-6-(trifluoromethyl)quinazolin-3-yl]amino]-4-phenylsulfanylbenzonitrile

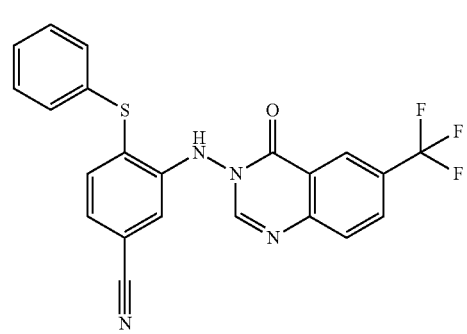 [SMILES: N#Cc1ccc(Sc2ccccc2)c(Nn2cnc3ccc(C(F)(F)F)cc3c2=O)c1]

The title compound was synthesized from 2-amino-N'-(5-cyano-2-phenylsulfanyl-phenyl)-5-(trifluoromethyl)benzo-hydrazide (Compound b17) under the same conditions as for Compound A-5.

LCMS: m/z 439 [M+H]$^+$

HPLC retention time: 2.75 min (analysis condition C)

Example 249

Compound B-16

4-(Benzenesulfonyl)-3-[[4-oxo-6-(trifluoromethyl)quinazolin-3-yl]amino]benzonitrile

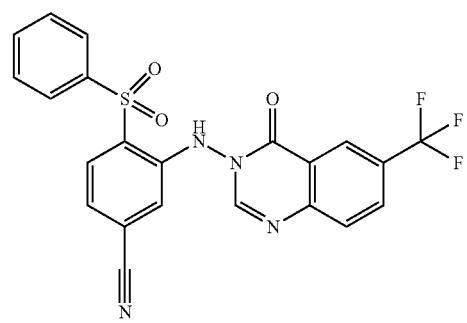 [SMILES: N#Cc1ccc(S(=O)(=O)c2ccccc2)c(Nn2cnc3ccc(C(F)(F)F)cc3c2=O)c1]

The title compound was synthesized from 3-[[4-oxo-6-(trifluoromethyl)quinazolin-3-yl]amino]-4-phenylsulfanyl-benzonitrile (Compound B-15) under the same conditions as for Compound 14.

LCMS: m/z 471 [M+H]$^+$

HPLC retention time: 2.50 min (analysis condition C)

Example 250

Compound B-17

3-(5-Chloro-2-propylanilino)-6-(trifluoromethoxy)quinazolin-4-one

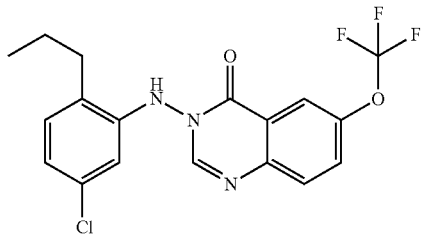 [SMILES: CCCc1ccc(Cl)cc1Nn1cnc2ccc(OC(F)(F)F)cc2c1=O]

The title compound was synthesized from ((5-chloro-2-propyl-phenyl)hydrazine (Compound 72) under the same conditions as for Compounds b8 and B-5.
LCMS: m/z 398 [M+H]$^+$
HPLC retention time: 1.01 min (analysis condition D)

Example 251

Compound B-18

8-Chloro-3-(5-chloro-2-propylanilino)-6-(trifluoromethyl)quinazolin-4-one

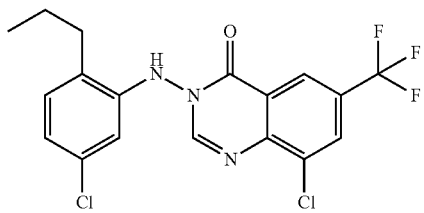 [SMILES: CCCc1ccc(Cl)cc1Nn1cnc2c(Cl)cc(C(F)(F)F)cc2c1=O]

The title compound was synthesized from ((5-chloro-2-propyl-phenyl)hydrazine (Compound 72) under the same conditions as for Compounds b10 and B-7.
LCMS: m/z 416 [M+H]$^+$
HPLC retention time: 3.18 min (analysis condition C)

Example 252

Compound B-19

3-[5-Chloro-2-(2-methylpropyl)anilino]-6-(trifluoromethoxy)quinazolin-4-one

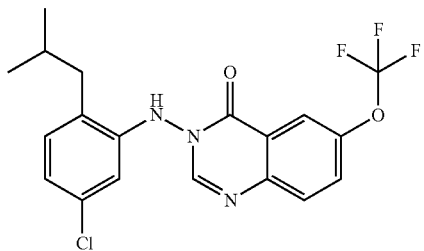 [SMILES: CC(C)Cc1ccc(Cl)cc1Nn1cnc2ccc(OC(F)(F)F)cc2c1=O]

The title compound was synthesized from [5-chloro-2-(2-methylpropyl)phenyl]hydrazine (Compound 73) under the same conditions as for Compounds b8 and B-5.
LCMS: m/z 412 [M+H]$^+$
HPLC retention time: 1.06 min (analysis condition D)

Example 253

Compound B-20

3-[5-Chloro-2-(cyclopropylmethyl)anilino]-6-(trifluoromethoxy)quinazolin-4-one

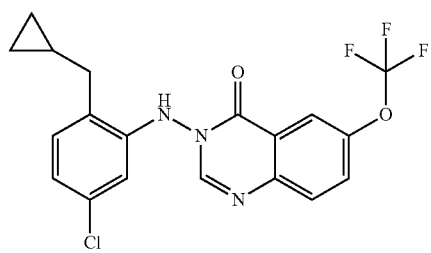 [SMILES: O=c1c2cc(OC(F)(F)F)ccc2ncn1Nc1cc(Cl)ccc1CC1CC1]

The title compound was synthesized from [[5-chloro-2-(cyclopropylmethyl)phenyl]hydrazine (Compound 74) under the same conditions as for Compounds b8 and B-5.
LCMS: m/z 410 [M+H]$^+$
HPLC retention time: 1.01 min (analysis condition D)

Example 254

Compound B-21

3-[5-Chloro-2-(cyclobutylmethyl)anilino]-6-(trifluoromethoxy)quinazolin-4-one

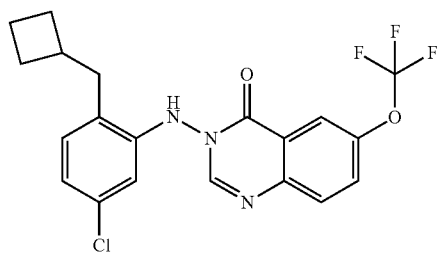 [SMILES: O=c1c2cc(OC(F)(F)F)ccc2ncn1Nc1cc(Cl)ccc1CC1CCC1]

The title compound was synthesized from [5-chloro-2-(cyclobutylmethyl)phenyl]hydrazine (Compound 75) under the same conditions as for Compounds b8 and B-5.
LCMS: m/z 424 [M+H]$^+$
HPLC retention time: 1.07 min (analysis condition D)

Example 255

Compound B-22

8-Chloro-3-[5-chloro-2-(cyclobutylmethyl)anilino]-6-(trifluoromethyl)quinazolin-4-one

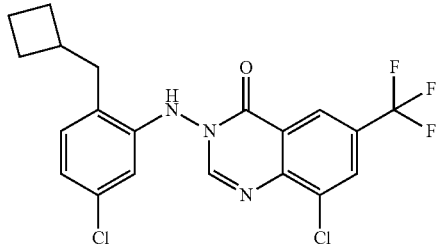 [SMILES: O=c1c2cc(C(F)(F)F)cc(Cl)c2ncn1Nc1cc(Cl)ccc1CC1CCC1]

The title compound was synthesized from [5-chloro-2-(cyclobutylmethyl)phenyl]hydrazine (Compound 75) under the same conditions as for Compounds b10 and B-7.
LCMS: m/z 442 [M+H]$^+$
HPLC retention time: 1.11 min (analysis condition D)

Example 256

Compound B-23

3-[5-Chloro-2-(cyclopentylmethyl)anilino]-6-(trifluoromethoxy)quinazolin-4-one

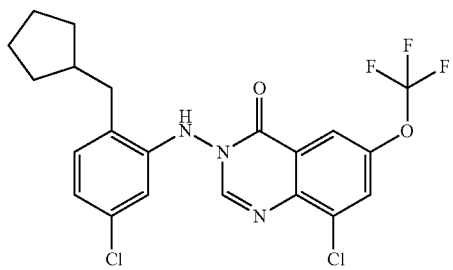 [SMILES: O=c1c2cc(OC(F)(F)F)cc(Cl)c2ncn1Nc1cc(Cl)ccc1CC1CCCC1]

The title compound was synthesized from [[5-chloro-2-(cyclopentylmethyl)phenyl]hydrazine (Compound 76) under the same conditions as for Compounds b8 and B-5.
LCMS: m/z 438 [M+H]$^+$
HPLC retention time: 1.11 min (analysis condition D)

Example 257

Compound B-24

8-Chloro-3-[5-chloro-2-(cyclopentylmethyl)anilino]-6-(trifluoromethyl)quinazolin-4-one

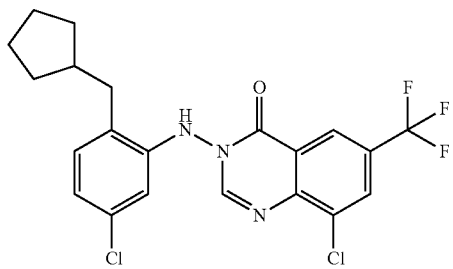 [SMILES: O=c1c2cc(C(F)(F)F)cc(Cl)c2ncn1Nc1cc(Cl)ccc1CC1CCCC1]

The title compound was synthesized from [[5-chloro-2-(cyclopentylmethyl)phenyl]hydrazine (Compound 76) under the same conditions as for Compounds b10 and B-7.
LCMS: m/z 456 [M+H]$^+$
HPLC retention time: 1.14 min (analysis condition D)

Example 258

Compound c1

2-Amino-3-bromo-N'-(5-cyano-2-ethylsulfanylphenyl)-5-methylbenzohydrazide

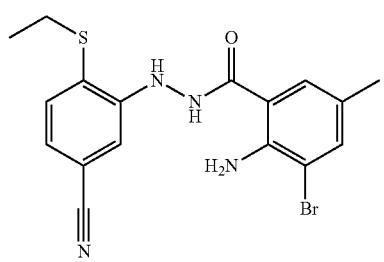 [SMILES: CCSc1ccc(C#N)cc1NNC(=O)c1cc(C)cc(Br)c1N]

The title compound was synthesized from 4-ethylsulfanyl-3-hydrazinylbenzonitrile (Compound 47) and 2-amino-3-bromo-5-methylbenzoic acid under the same conditions as for Compound 113. However, DMF was used in place of dichloromethane as a solvent.

Example 259

Compound C-1

3-[(8-Bromo-6-methyl-4-oxoquinazolin-3-yl)amino]-4-ethylsulfanylbenzonitrile

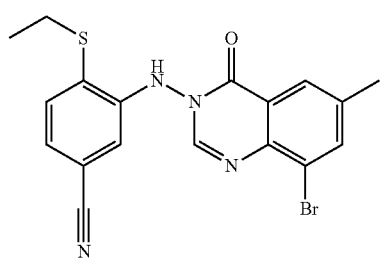 [SMILES: CCSc1ccc(C#N)cc1Nn1cnc2c(Br)cc(C)cc2c1=O]

The title compound was synthesized from 2-amino-3-bromo-N'-(5-cyano-2-ethylsulfanylphenyl)-5-methylbenzohydrazide (Compound c1) under the same conditions as for Compound A-5.
LCMS: m/z 415 [M+H]$^+$
HPLC retention time: 3.00 min (analysis condition B)

Example 260

Compound C-2

3-[(8-Bromo-6-methyl-4-oxoquinazolin-3-yl)amino]-4-ethylsulfonylbenzonitrile

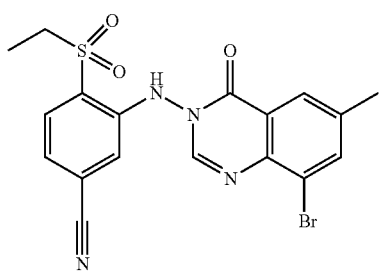 [SMILES: CCS(=O)(=O)c1ccc(C#N)cc1Nn1cnc2c(Br)cc(C)cc2c1=O]

The title compound was synthesized from 3-[(8-bromo-6-methyl-4-oxoquinazolin-3-yl)amino]-4-ethylsulfanylbenzonitrile (Compound C-1) under the same conditions as for Compound 14.

LCMS: m/z 447 [M+H]$^+$

HPLC retention time: 2.95 min (analysis condition B)

Example 261

Compound c2

2-Amino-3-chloro-N'-(5-cyano-2-ethylsulfanylphenyl)-5-(trifluoromethoxy)benzohydrazide

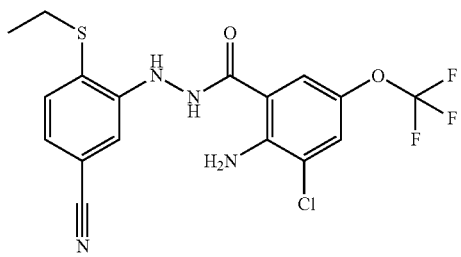 [SMILES: CCSc1ccc(C#N)cc1NNC(=O)c1cc(OC(F)(F)F)cc(Cl)c1N]

The title compound was synthesized from 4-ethylsulfanyl-3-hydrazinylbenzonitrile (Compound 47) and 2-amino-3-chloro-5-(trifluoromethoxy)benzoic acid (Compound 94) under the same conditions as for Compound a1. However, HOBt was added and DMF was used in place of dichloromethane as a solvent.

Example 262

Compound c3

3-[[8-Chloro-4-oxo-6-(trifluoromethoxy)quinazolin-3-yl]amino]-4-ethylsulfanylbenzonitrile

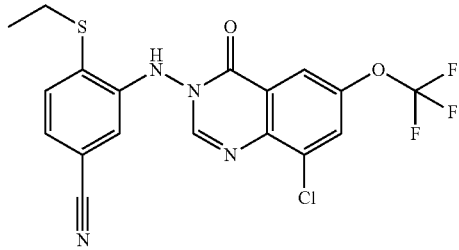 [SMILES: CCSc1ccc(C#N)cc1Nn1cnc2c(Cl)cc(OC(F)(F)F)cc2c1=O]

The title compound was synthesized from 2-amino-3-chloro-N'-(5-cyano-2-ethylsulfanylphenyl)-5-(trifluoromethoxy)benzohydrazide (Compound c2) under the same conditions as for Compound A-5.

Example 263

Compound C-3

3-[[8-Chloro-4-oxo-6-(trifluoromethoxy)quinazolin-3-yl]amino]-4-ethylsulfonylbenzonitrile

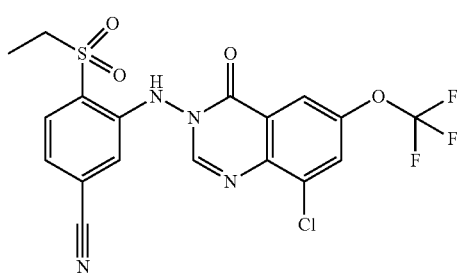 [SMILES: CCS(=O)(=O)c1ccc(C#N)cc1Nn1cnc2c(Cl)cc(OC(F)(F)F)cc2c1=O]

The title compound was synthesized from 3-[[8-chloro-4-oxo-6-(trifluoromethoxy)quinazolin-3-yl]amino]-4-ethylsulfanylbenzonitrile (Compound c3) under the same conditions as for Compound 14.

LCMS: m/z 473 [M+H]$^+$

HPLC retention time: 2.72 min (analysis condition E)

Example 264

Compound C-4

3-[[8-Chloro-4-oxo-6-(trifluoromethyl)quinazolin-3-yl]amino]-4-ethylsulfonylbenzonitrile

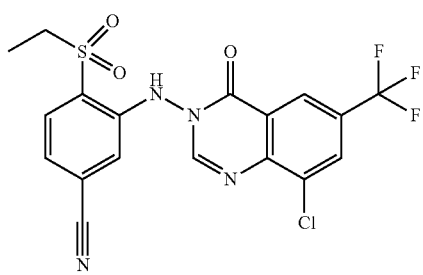 [SMILES: CCS(=O)(=O)c1ccc(C#N)cc1Nn1cnc2c(Cl)cc(C(F)(F)F)cc2c1=O]

The title compound was synthesized from 4-ethylsulfanyl-3-hydrazinylbenzonitrile (Compound 47) under the same conditions as for Compounds c2, c3, and C-3. However, 2-amino-3-chloro-5-(trifluoromethyl)benzoic acid (Compound 86) was used in place of 2-amino-3-chloro-5-(trifluoromethoxy)benzoic acid (Compound 94) in the reaction conditions for c2.

LCMS: m/z 457 [M+H]$^+$

HPLC retention time: 2.67 min (analysis condition E)

Example 265

Compound c4

2-Amino-5-bromo-N'-(5-cyano-2-ethylsulfanylphenyl)-4-methylbenzohydrazide

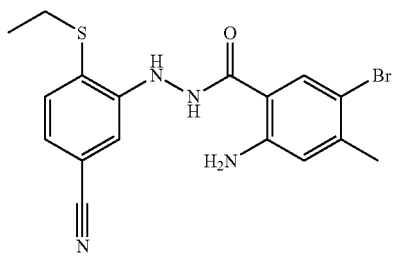 [SMILES: CCSc1ccc(C#N)cc1NNC(=O)c1cc(Br)c(C)cc1N]

The title compound was synthesized from 4-ethylsulfanyl-3-hydrazinylbenzonitrile (Compound 47) and 2-amino-5-bromo-4-methylbenzoic acid under the same conditions as for Compound 113. However, DMF was used in place of dichloromethane as a solvent.

Example 266

Compound C-5

3-[(6-Bromo-7-methyl-4-oxoquinazolin-3-yl)amino]-4-ethylsulfanylbenzonitrile

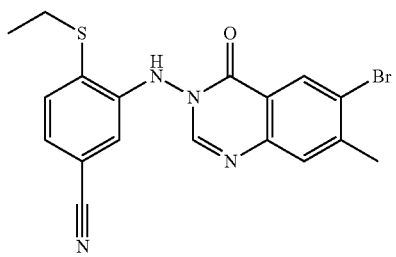 [SMILES: CCSc1ccc(C#N)cc1Nn1cnc2cc(C)c(Br)cc2c1=O]

The title compound was synthesized from 2-amino-5-bromo-N'-(5-cyano-2-ethylsulfanylphenyl)-4-methylbenzohydrazide (Compound c4) under the same conditions as for Compound A-28.

LCMS: m/z 415 [M+H]$^+$

HPLC retention time: 0.90 min (analysis condition D)

Example 267

Compound C-6

3-[(6-Bromo-7-methyl-4-oxoquinazolin-3-yl)amino]-4-ethylsulfonylbenzonitrile

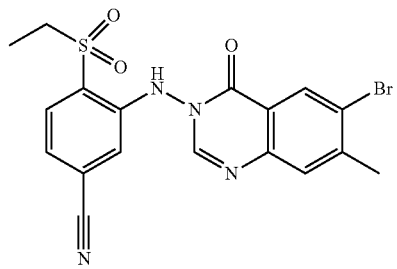 [SMILES: CCS(=O)(=O)c1ccc(C#N)cc1Nn1cnc2cc(C)c(Br)cc2c1=O]

The title compound was synthesized from 3-[(6-bromo-7-methyl-4-oxoquinazolin-3-yl)amino]-4-ethylsulfanylbenzonitrile (Compound C-5) under the same conditions as for Compound 14.

LCMS: m/z 447 [M+H]$^+$

HPLC retention time: 0.80 min (analysis condition D)

Example 268

Compound c5

2-Amino-5-bromo-N'-(5-cyano-2-ethylsulfanylphenyl)pyridine-3-carbohydrazide

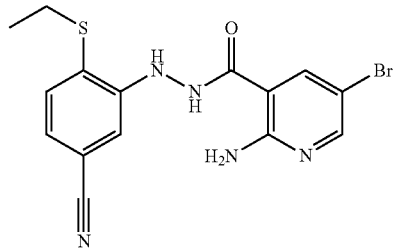 [SMILES: CCSc1ccc(C#N)cc1NNC(=O)c1cc(Br)cnc1N]

The title compound was synthesized from 4-ethylsulfanyl-3-hydrazinylbenzonitrile (Compound 47) and 2-amino-5-bromopyridine-3-carboxylic acid under the same conditions as for Compound a1.

Example 269

Compound C-7

3-[(6-Bromo-4-oxopyrido[2,3-d]pyrimidin-3-yl)amino]-4-ethylsulfanylbenzonitrile

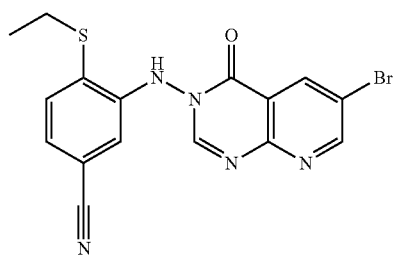 [SMILES: CCSc1ccc(C#N)cc1Nn1cnc2ncc(Br)cc2c1=O]

The title compound was synthesized from 2-amino-5-bromo-N'-(5-cyano-2-ethylsulfanylphenyl)pyridine-3-carbohydrazide (Compound c5) under the same conditions as for Compound A-5.

LCMS: m/z 402 [M+H]$^+$

HPLC retention time: 2.05 min (analysis condition C)

Example 270

Compound C-8

3-[(6-Bromo-4-oxopyrido[2,3-d]pyrimidin-3-yl)amino]-4-ethylsulfonylbenzonitrile

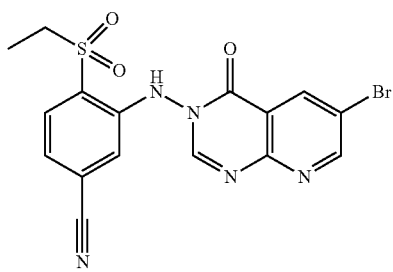 [SMILES: CCS(=O)(=O)c1ccc(C#N)cc1Nn1cnc2ncc(Br)cc2c1=O]

The title compound was synthesized from 3-[(6-bromo-4-oxopyrido[2,3-d]pyrimidin-3-yl)amino]-4-ethylsulfanylbenzonitrile (Compound C-7) under the same conditions as for Compound 14.

LCMS: m/z 434 [M+H]$^+$

HPLC retention time: 1.80 min (analysis condition C)

Example 271

Compound C-9

4-Ethylsulfanyl-3-[[4-oxo-6-(trifluoromethyl)quinazolin-3-yl]amino]benzonitrile

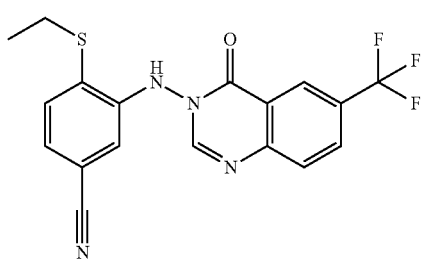 [SMILES: CCSc1ccc(C#N)cc1Nn1cnc2ccc(C(F)(F)F)cc2c1=O]

The title compound was synthesized from 4-ethylsulfanyl-3-hydrazinylbenzonitrile (Compound 47) and 2-amino-5-(trifluoromethyl)benzoic acid under the same conditions as for Compounds c5 and C-7.

LCMS: m/z 391 [M+H]$^+$

HPLC retention time: 2.50 min (analysis condition C)

Example 272

Compound C-10

4-Ethylsulfonyl-3-[[4-oxo-6-(trifluoromethyl)quinazolin-3-yl]amino]benzonitrile

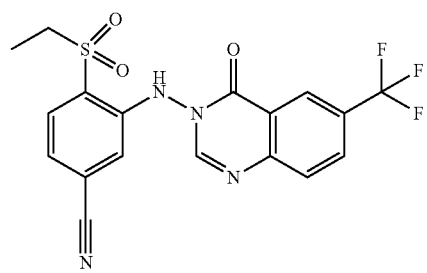 [SMILES: CCS(=O)(=O)c1ccc(C#N)cc1Nn1cnc2ccc(C(F)(F)F)cc2c1=O]

The title compound was synthesized from 4-ethylsulfanyl-3-[[4-oxo-6-(trifluoromethyl)quinazolin-3-yl]amino]benzonitrile (Compound C-9) under the same conditions as for Compound 14.

LCMS: m/z 423 [M+H]$^+$

HPLC retention time: 2.25 min (analysis condition C)

Example 273

Compound C-11

3-[[8-Bromo-4-oxo-6-(trifluoromethyl)quinazolin-3-yl]amino]-4-ethylsulfanylbenzonitrile

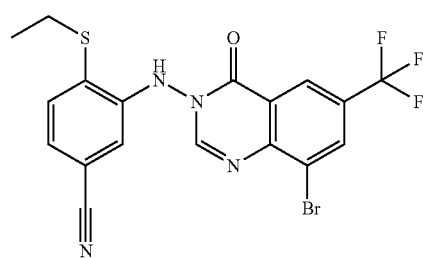 [SMILES: CCSc1ccc(C#N)cc1Nn1cnc2c(Br)cc(C(F)(F)F)cc2c1=O]

The title compound was synthesized from 4-ethylsulfanyl-3-hydrazinylbenzonitrile (Compound 47) and 2-amino-3-bromo-5-(trifluoromethyl)benzoic acid (Compound 85) under the same conditions as for Compounds c5 and C-7.

LCMS: m/z 469 [M+H]$^+$

HPLC retention time: 2.73 min (analysis condition C)

Example 274

Compound C-12

3-[[8-Bromo-4-oxo-6-(trifluoromethyl)quinazolin-3-yl]amino]-4-ethylsulfonylbenzonitrile

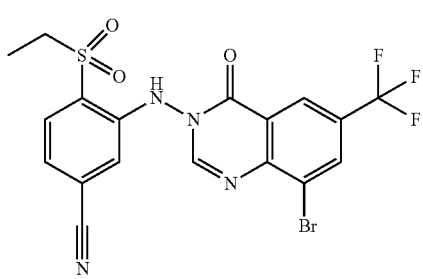 [SMILES: CCS(=O)(=O)c1ccc(C#N)cc1Nn1cnc2c(Br)cc(C(F)(F)F)cc2c1=O]

The title compound was synthesized from 3-[[8-bromo-4-oxo-6-(trifluoromethyl)quinazolin-3-yl]amino]-4-ethylsulfanylbenzonitrile (Compound C-11) under the same conditions as for Compound 14.

LCMS: m/z 501 [M+H]+

HPLC retention time: 2.47 min (analysis condition C)

Example 275

Compound C-13

3-[[8-Bromo-4-oxo-6-(trifluormethyl)quinazolin-3-yl]amino]-4-ethylsulfanylbenzonitrile

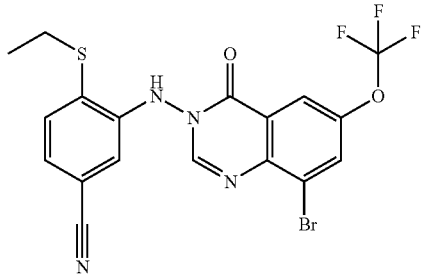 [SMILES: CCSc1ccc(C#N)cc1Nn1cnc2c(Br)cc(OC(F)(F)F)cc2c1=O]

The title compound was synthesized from 4-ethylsulfanyl-3-hydrazinylbenzonitrile (Compound 47) and 2-amino-3-bromo-5-(trifluoromethoxy)benzoic acid under the same conditions as for Compounds c5 and C-7.

LCMS: m/z 485 [M+H]+

HPLC retention time: 2.83 min (analysis condition C)

Example 276

Compound C-14

3-[[8-Bromo-4-oxo-6-(trifluoromethoxy)quinazolin-3-yl]amino]-4-ethylsulfonylbenzonitrile

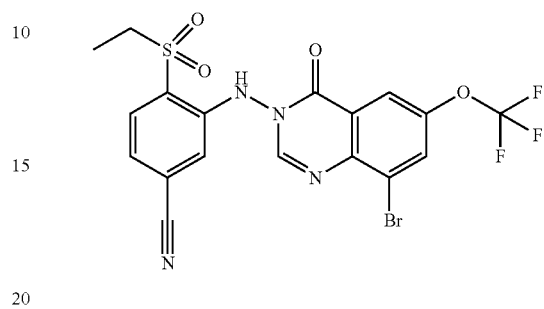

The title compound was synthesized from 3-[[8-bromo-4-oxo-6-(trifluoromethoxy)quinazolin-3-yl]amino]-4-ethylsulfanylbenzonitrile (Compound C-13) under the same conditions as for Compound 14.

LCMS: m/z 517 [M+H]+

HPLC retention time: 2.57 min (analysis condition C)

Example 277

Compound c6

2-Amino-N'-(5-cyano-2-ethylsulfanylphenyl)-5-(trifluoromethoxy)benzohydrazide

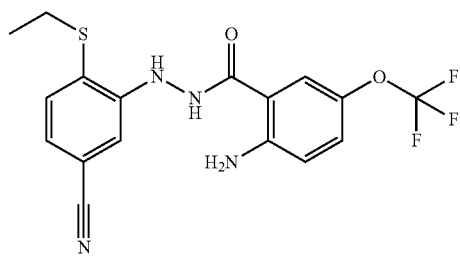 [SMILES: CCSc1ccc(C#N)cc1NNC(=O)c1cc(OC(F)(F)F)ccc1N]

The title compound was synthesized from 4-ethylsulfanyl-3-hydrazinylbenzonitrile (Compound 47) and 2-amino-5-(trifluoromethoxy)benzoic acid under the same conditions as for Compound a1.

Example 278

Compound C-15

4-Ethylsulfanyl-3-[[4-oxo-6-(trifluoromethoxy)quinazolin-3-yl]amino]benzonitrile

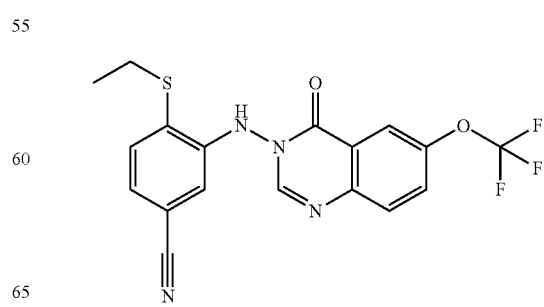

The title compound was synthesized from 2-amino-N'-(5-cyano-2-ethylsulfanylphenyl)-5-(trifluoromethoxy)benzohydrazide (Compound c6) under the same conditions as for Compound A-28.

LCMS: m/z 407 [M+H]$^+$

HPLC retention time: 2.57 min (analysis condition C)

Example 279

Compound C-16

4-Ethylsulfonyl-3-[[4-oxo-6-(trifluoromethoxy)quinazolin-3-yl]amino]benzonitrile

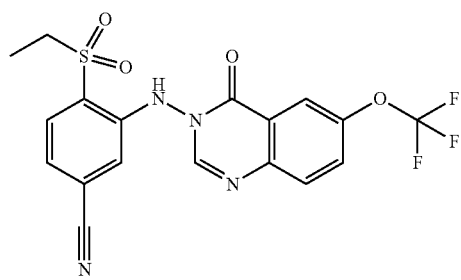 [SMILES: CCS(=O)(=O)c1ccc(C#N)cc1Nn1cnc2ccc(OC(F)(F)F)cc2c1=O]

The title compound was synthesized from 4-ethylsulfanyl-3-[[4-oxo-6-(trifluoromethoxy)quinazolin-3-yl]amino]benzonitrile (Compound C-15) under the same conditions as for Compound 14.

LCMS: m/z 439 [M+H]$^+$

HPLC retention time: 2.28 min (analysis condition C)

Example 280

Compound c7

4-Bromo-N'-(5-cyano-2-ethylsulfanylphenyl)-2-nitro-5-(trifluoromethoxy)benzohydrazide

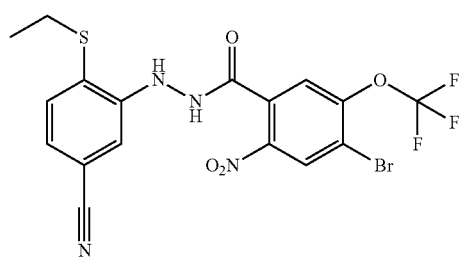 [SMILES: CCSc1ccc(C#N)cc1NNC(=O)c1cc(OC(F)(F)F)c(Br)cc1[N+](=O)[O-]]

The title compound was synthesized from 4-ethylsulfanyl-3-hydrazinylbenzonitrile (Compound 47) and 4-bromo-2-nitro-5-(trifluoromethoxy)benzoic acid (Compound 114) under the same conditions as for Compound 113. However, DMF was used in place of dichloromethane as a solvent.

Example 281

Compound c8

2-Amino-4-bromo-N'-(5-cyano-2-ethylsulfanylphenyl)-5-(trifluoromethoxy)benzohydrazide

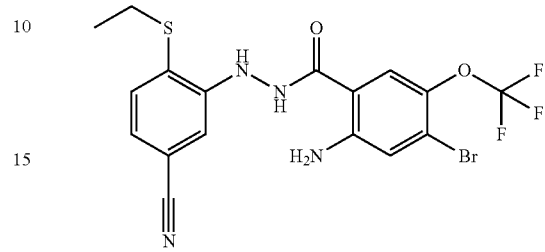

The title compound was synthesized from 4-bromo-N'-(5-cyano-2-ethylsulfanylphenyl)-2-nitro-5-(trifluoromethoxy)benzohydrazide (Compound c7) under the same conditions as for Compound a5.

Example 282

Compound C-17

3-[[7-Bromo-4-oxo-6-(trifluoromethoxy)quinazolin-3-yl]amino]-4-ethylsulfanylbenzonitrile

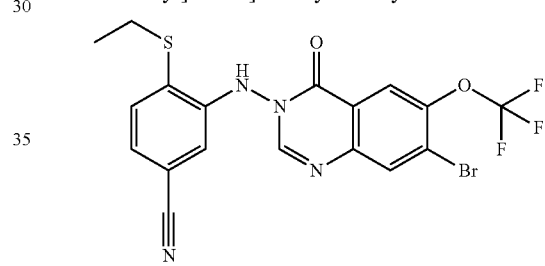

The title compound was synthesized from 2-amino-4-bromo-N'-(5-cyano-2-ethylsulfanylphenyl)-5-(trifluoromethoxy)benzohydrazide (Compound c8) under the same conditions as for Compound A-5.

LCMS: m/z 485 [M+H]$^+$

HPLC retention time: 0.95 min (analysis condition D)

Example 283

Compound C-18

3-[[7-Bromo-4-oxo-6-(trifluoromethoxy)quinazolin-3-yl]amino]-4-ethylsulfonylbenzonitrile

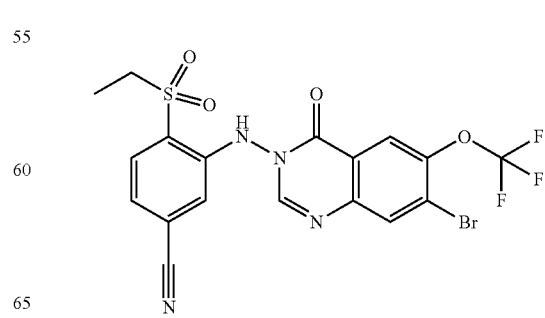

The title compound was synthesized from 3-[[7-bromo-4-oxo-6-(trifluoromethoxy)quinazolin-3-yl]amino]-4-ethyl-sulfanylbenzonitrile (Compound C-17) under the same conditions as for Compound 14.
LCMS: m/z 517 [M+H]$^+$
HPLC retention time: 0.87 min (analysis condition D)

Example 284

Compound C-19

8-Bromo-3-(2-ethylsulfanyl-5-fluoroanilino)-6-(trifluoromethoxy)quinazolin-4-one

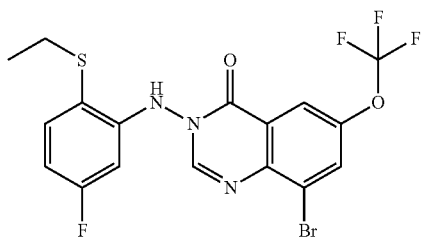 [SMILES: CCSc1ccc(F)cc1Nn1cnc2c(Br)cc(OC(F)(F)F)cc2c1=O]

The title compound was synthesized from (2-ethylsulfanyl-5-fluorophenyl)hydrazine (Compound 28) and 2-amino-3-bromo-5-(trifluoromethoxy)benzoic acid under the same conditions as for Compounds c5 and C-7.
LCMS: m/z 478 [M+H]$^+$
HPLC retention time: 0.99 min (analysis condition D)

Example 285

Compound C-20

8-Bromo-3-(2-ethylsulfonyl-5-fluoroanilino)-6-(trifluoromethoxy)quinazolin-4-one

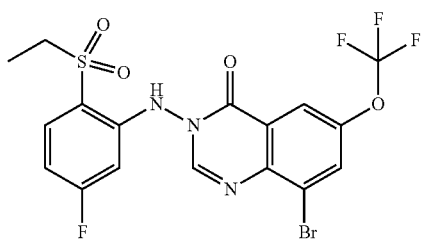 [SMILES: CCS(=O)(=O)c1ccc(F)cc1Nn1cnc2c(Br)cc(OC(F)(F)F)cc2c1=O]

The title compound was synthesized from 8-bromo-3-(2-ethylsulfanyl-5-fluoroanilino)-6-(trifluoromethoxy)quinazolin-4-one (Compound C-19) under the same conditions as for Compound 14.
LCMS: m/z 510 [M+H]$^+$
HPLC retention time: 0.87 min (analysis condition D)

Example 286

Compound C-21

8-Bromo-3-(2-ethylsulfanyl-5-fluoroanilino)-6-(trifluromethyl)quinazolin-4-one

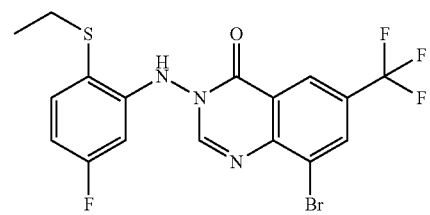

The title compound was synthesized from (2-ethylsulfanyl-5-fluorophenyl)hydrazine (Compound 28) and 2-amino-3-bromo-5-(trifluoromethyl)benzoic acid (Compound 85) under the same conditions as for Compounds c5 and C-7.
LCMS: m/z 462 [M+H]$^+$
HPLC retention time: 3.00 min (analysis condition C)

Example 287

Compound C-22

8-Bromo-3-(2-ethylsulfonyl-5-fluoroanilino)-6-(trifluoromethyl)quinazolin-4-one

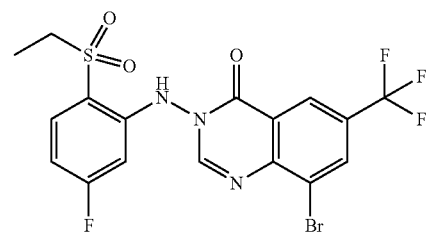 [SMILES: CCS(=O)(=O)c1ccc(F)cc1Nn1cnc2c(Br)cc(C(F)(F)F)cc2c1=O]

The title compound was synthesized from 8-bromo-3-(2-ethylsulfanyl-5-fluoroanilino)-6-(trifluoromethyl)quinazolin-4-one (Compound C-21) under the same conditions as for Compound 14.
LCMS: m/z 494 [M+H]$^+$
HPLC retention time: 2.58 min (analysis condition C)

Example 288

Compound C-23

8-Bromo-3-(5-bromo-2-ethylsulfanylanilino)-6-(trifluoromethoxy)quinazolin-4-one

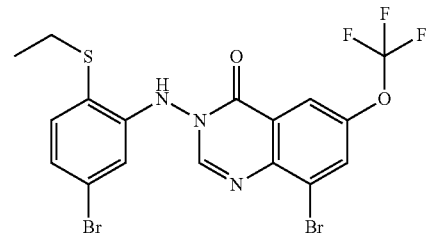

The title compound was synthesized from (5-bromo-2-ethylsulfanylphenyl)hydrazine (Compound 54) and 2-amino-3-bromo-5-(trifluoromethoxy)benzoic acid under the same conditions as for Compounds c5 and C-7.

LCMS: m/z 538 [M+H]$^+$

HPLC retention time: 1.04 min (analysis condition D)

Example 289

Compound C-24

8-Bromo-3-(5-bromo-2-ethylsulfonylanilino)-6-(trifluoromethoxy)quinazolin-4-one

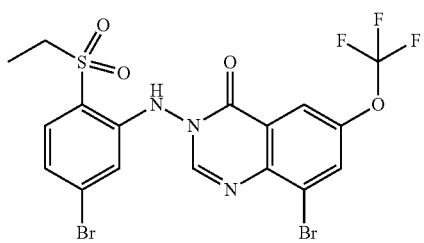 [SMILES: CCS(=O)(=O)c1ccc(Br)cc1Nn1cnc2c(Br)cc(OC(F)(F)F)cc2c1=O]

The title compound was synthesized from 8-bromo-3-(5-bromo-2-ethylsulfanylanilino)-6-(trifluoromethoxy)quinazolin-4-one (Compound C-23) under the same conditions as for Compound 14.

LCMS: m/z 570 [M+H]$^+$

HPLC retention time: 0.92 min (analysis condition D)

Example 290

Compound C-25

8-Bromo-3-(5-bromo-2-ethylsulfanylanilino)-6-(trifluoromethyl)quinazolin-4-one

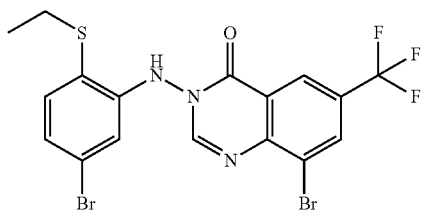

The title compound was synthesized from (5-bromo-2-ethylsulfanylphenyl)hydrazine (Compound 54) and 2-amino-3-bromo-5-(trifluoromethyl)benzoic acid (Compound 85) under the same conditions as for Compounds c6 and C-15.

LCMS: m/z 522 [M+H]$^+$

HPLC retention time: 3.32 min (analysis condition C)

Example 291

Compound C-26

8-Bromo-3-(5-bromo-2-ethylsulfonylanilino)-6-(trifluoromethyl)quinazolin-4-one

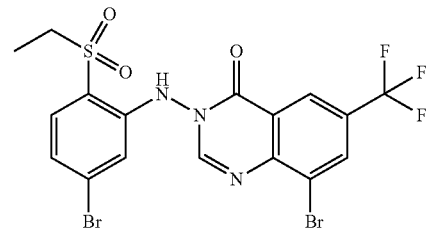

The title compound was synthesized from 8-bromo-3-(5-bromo-2-ethylsulfanylanilino)-6-(trifluoromethyl)quinazolin-4-one (Compound C-25) under the same conditions as for Compound 14.

LCMS: m/z 554 [M+H]$^+$

HPLC retention time: 2.98 min (analysis condition C)

Example 292

Compound C-27

3-(2-Ethylsulfanyl-5-methoxyanilino)-6-(trifluoromethoxy)quinazolin-4-one

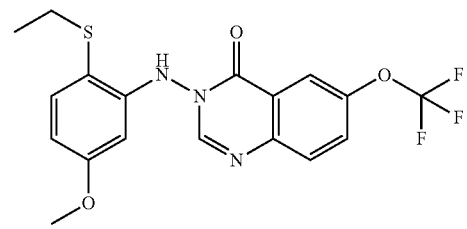 [SMILES: CCSc1ccc(OC)cc1Nn1cnc2ccc(OC(F)(F)F)cc2c1=O]

The title compound was synthesized from (2-ethylsulfanyl-5-methoxyphenyl)hydrazine (Compound 52) and 2-amino-5-(trifluoromethoxy)benzoic acid under the same conditions as for Compounds c6 and C-15.

LCMS: m/z 412 [M+H]$^+$

HPLC retention time: 0.96 min (analysis condition D)

Example 293

Compound C-28

3-(2-Ethylsulfonyl-5-methoxyanilino)-6-(trifluoromethoxy)quinazolin-4-one

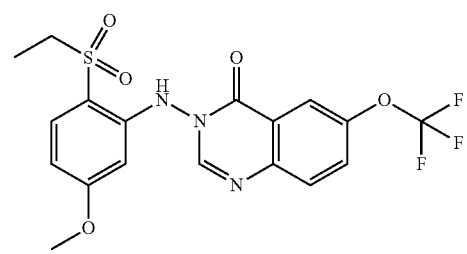 [SMILES: CCS(=O)(=O)c1ccc(OC)cc1Nn1cnc2ccc(OC(F)(F)F)cc2c1=O]

The title compound was synthesized from 3-(2-ethylsulfanyl-5-methoxyanilino)-6-(trifluoromethoxy)quinazolin-4-one (Compound C-27) under the same conditions as for Compound 14.

LCMS: m/z 444 [M+H]$^+$

HPLC retention time: 0.82 min (analysis condition D)

Example 294

Compound C-29

8-Bromo-3-(2-ethylsulfanyl-5-methoxyanilino)-6-(trifluoromethyl)quinazolin-4-one

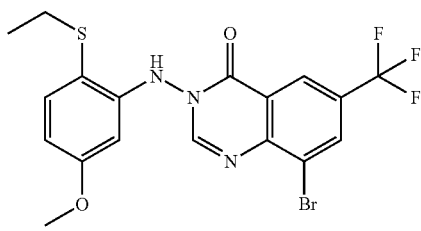 [SMILES: CCSc1ccc(OC)cc1Nn1cnc2c(Br)cc(C(F)(F)F)cc2c1=O]

The title compound was synthesized from (2-ethylsulfanyl-5-methoxyphenyl)hydrazine (Compound 52) and 2-amino-3-bromo-5-(trifluoromethyl)benzoic acid (Compound 85) under the same conditions as for Compounds c5 and C-7.

LCMS: m/z 474 [M+H]$^+$

HPLC retention time: 3.18 min (analysis condition C)

Example 295

Compound C-30

8-Bromo-3-(2-ethylsulfonyl-5-methoxyanilino)-6-(trifluoromethyl)quinazolin-4-one

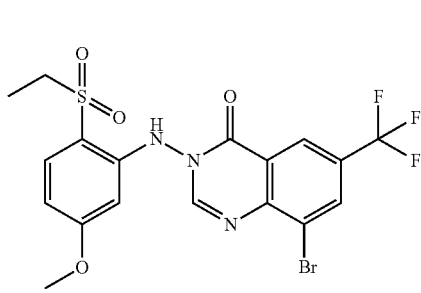 [SMILES: CCS(=O)(=O)c1ccc(OC)cc1Nn1cnc2c(Br)cc(C(F)(F)F)cc2c1=O]

The title compound was synthesized from 8-bromo-3-(2-ethylsulfanyl-5-methoxyanilino)-6-(trifluoromethyl)quinazolin-4-one (Compound C-29) under the same conditions as for Compound 14.

LCMS: m/z 506 [M+H]$^+$

HPLC retention time: 2.72 min (analysis condition C)

Example 296

Compound C-31

8-Bromo-3-(5-ethoxy-2-ethylsulfanylanilino)-6-(trifluoromethyl)quinazolin-4-one

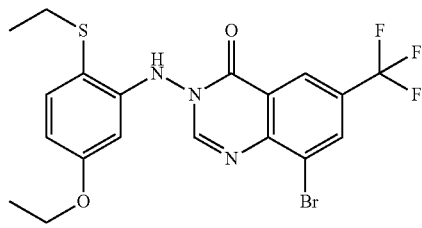 [SMILES: CCOc1ccc(SCC)c(Nn2cnc3c(Br)cc(C(F)(F)F)cc3c2=O)c1]

The title compound was synthesized from (5-ethoxy-2-ethylsulfanylphenyl)hydrazine (Compound 51) and 2-amino-3-bromo-5-(trifluoromethyl)benzoic acid (Compound 85) under the same conditions as for Compounds c5 and C-7.

LCMS: m/z 488 [M+H]$^+$

HPLC retention time: 3.15 min (analysis condition C)

Example 297

Compound C-32

8-Bromo-3-(5-ethoxy-2-ethylsulfonylanilino)-6-(trifluoromethyl)quinazolin-4-one

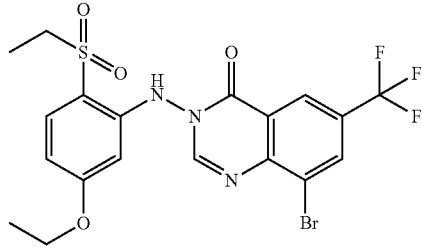 [SMILES: CCOc1ccc(S(=O)(=O)CC)c(Nn2cnc3c(Br)cc(C(F)(F)F)cc3c2=O)c1]

The title compound was synthesized from 8-bromo-3-(5-ethoxy-2-ethylsulfanylanilino)-6-(trifluoromethyl)quinazolin-4-one (Compound C-31) under the same conditions as for Compound 14.

LCMS: m/z 520 [M+H]$^+$

HPLC retention time: 2.73 min (analysis condition C)

Example 298

Compound C-33

8-Bromo-3-[2-ethylsulfanyl-5-(trifluoromethoxy)anilino]-6-(trifluoromethyl)quinazolin-4-one

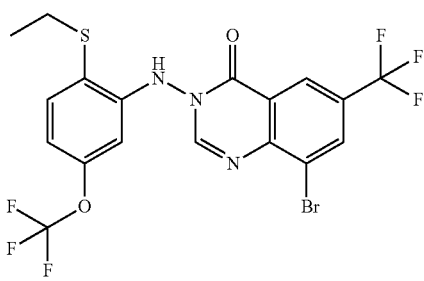 [SMILES: CCSc1ccc(OC(F)(F)F)cc1Nn1cnc2c(Br)cc(C(F)(F)F)cc2c1=O]

The title compound was synthesized from [2-ethylsulfanyl-5-(trifluoromethoxy)phenyl]hydrazine (Compound 60) and 2-amino-3-bromo-5-(trifluoromethyl)benzoic acid (Compound 85) under the same conditions as for Compounds c1 and C-1.

LCMS: m/z 528 [M+H]$^+$

HPLC retention time: 1.08 min (analysis condition D)

Example 299

Compound C-34

8-Bromo-3-[2-ethylsulfanyl-5-(trifluoromethyl)anilino]-6-(trifluoromethyl)quinazolin-4-one

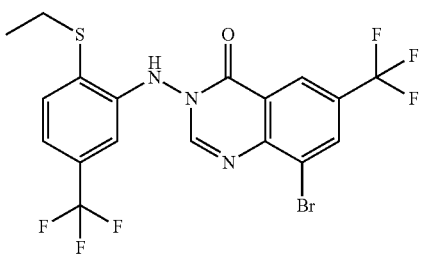 [SMILES: CCSc1ccc(C(F)(F)F)cc1Nn1cnc2c(Br)cc(C(F)(F)F)cc2c1=O]

The title compound was synthesized from [2-ethylsulfanyl-5-(trifluoromethyl)phenyl]hydrazine (Compound 29) and 2-amino-3-bromo-5-(trifluoromethyl)benzoic acid (Compound 85) under the same conditions as for Compounds c5 and C-7.

LCMS: m/z 512 [M+H]$^+$

HPLC retention time: 3.32 min (analysis condition C)

Example 300

Compound C-35

8-Bromo-3-[2-ethylsulfonyl-5-(trifluoromethyl)anilino]-6-(trifluoromethyl)quinazolin-4-one

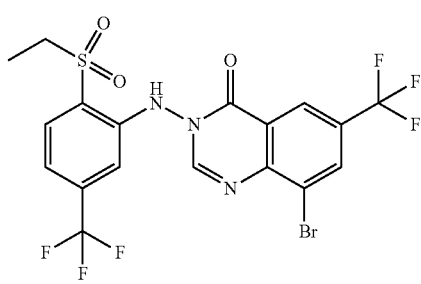 [SMILES: CCS(=O)(=O)c1ccc(C(F)(F)F)cc1Nn1cnc2c(Br)cc(C(F)(F)F)cc2c1=O]

The title compound was synthesized from 8-bromo-3-[2-ethylsulfanyl-5-(trifluoromethyl)anilino]-6-(trifluoromethyl)quinazolin-4-one (Compound C-34) under the same conditions as for Compound 14.

LCMS: m/z 544 [M+H]$^+$

HPLC retention time: 2.98 min (analysis condition C)

Example 301

Compound C-36

8-Bromo-3-(2-ethylsulfanyl-5-ethynylanilino)-6-(trifluoromethyl)quinazolin-4-one

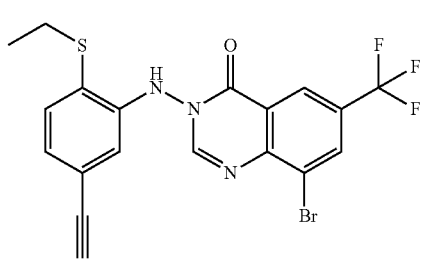 [SMILES: C#Cc1ccc(SCC)c(Nn2cnc3c(Br)cc(C(F)(F)F)cc3c2=O)c1]

The title compound was synthesized from (2-ethylsulfanyl-5-ethynylphenyl)hydrazine (Compound 57) and 2-amino-3-bromo-5-(trifluoromethyl)benzoic acid (Compound 85) under the same conditions as for Compounds c5 and C-7.

LCMS: m/z 468 [M+H]$^+$

HPLC retention time: 3.02 min (analysis condition C)

Example 302

Compound C-37

8-Bromo-3-(2-ethylsulfonyl-5-ethynylanilino)-6-(trifluoromethyl)quinazolin-4-one

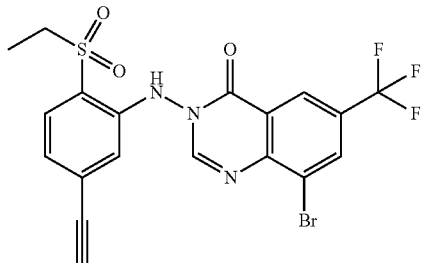 [SMILES: C#Cc1ccc(S(=O)(=O)CC)c(Nn2cnc3c(Br)cc(C(F)(F)F)cc3c2=O)c1]

The title compound was synthesized from 8-bromo-3-(2-ethylsulfanyl-5-ethynylanilino)-6-(trifluoromethyl)quinazolin-4-one (Compound C-36) under the same conditions as for Compound 14.
LCMS: m/z 500 [M+H]$^+$
HPLC retention time: 2.63 min (analysis condition C)

Example 303

Compound C-38

3-(3,5-Dichloro-2-ethylsulfanylanilino)-6-(trifluoromethyl)quinazolin-4-one

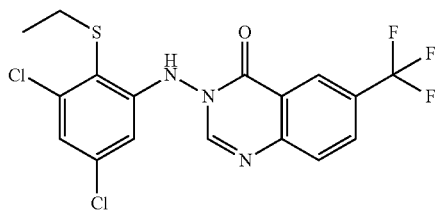 [SMILES: CCSc1c(Cl)cc(Cl)cc1Nn1cnc2ccc(C(F)(F)F)cc2c1=O]

The title compound was synthesized from (3,5-dichloro-2-ethylsulfanylphenyl)hydrazine (Compound 65) and 2-amino-5-(trifluoromethyl)benzoic acid under the same conditions as for Compounds c5 and C-7.
LCMS: m/z 434 [M+H]$^+$
HPLC retention time: 3.23 min (analysis condition C)

Example 304

Compound C-39

3-(3,5-Dichloro-2-ethylsulfonylanilino)-6-(trifluoromethyl)quinazolin-4-one

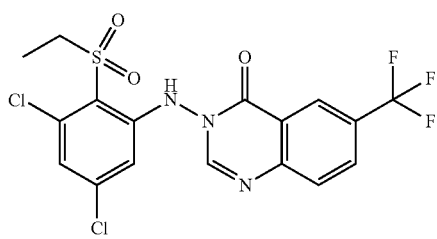 [SMILES: CCS(=O)(=O)c1c(Cl)cc(Cl)cc1Nn1cnc2ccc(C(F)(F)F)cc2c1=O]

The title compound was synthesized from 3-(3,5-dichloro-2-ethylsulfanylanilino)-6-(trifluoromethyl)quinazolin-4-one (Compound C-38) under the same conditions as for Compound 14.
LCMS: m/z 466 [M+H]$^+$
HPLC retention time: 2.68 min (analysis condition C)

Example 305

Compound C-40

3-(4,5-Dichloro-2-ethylsulfanylanilino)-6-(trifluoromethyl)quinazolin-4-one

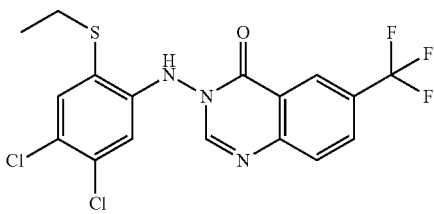 [SMILES: CCSc1cc(Cl)c(Cl)cc1Nn1cnc2ccc(C(F)(F)F)cc2c1=O]

The title compound was synthesized from (4,5-dichloro-2-ethylsulfanylphenyl)hydrazine (Compound 63) and 2-amino-5-(trifluoromethyl)benzoic acid under the same conditions as for Compounds c5 and C-7.
LCMS: m/z 434 [M+H]$^+$
HPLC retention time: 3.13 min (analysis condition C)

Example 306

Compound C-41

3-(4,5-Dichloro-2-ethylsulfonylanilino)-6-(trifluoromethyl)quinazolin-4-one

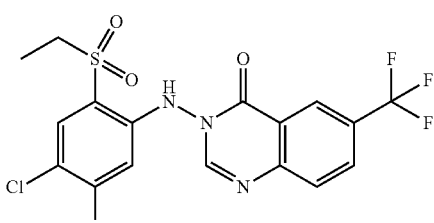

The title compound was synthesized from 3-(4,5-dichloro-2-ethylsulfanylanilino)-6-(trifluoromethyl)quinazolin-4-one (Compound C-40) under the same conditions as for Compound 14.
LCMS: m/z 466 [M+H]$^+$
HPLC retention time: 2.73 min (analysis condition C)

Example 307

Compound C-42

2-Chloro-4-ethylsulfanyl-5-[[4-oxo-6-(trifluoromethyl)quinazolin-3-yl]amino]benzonitrile

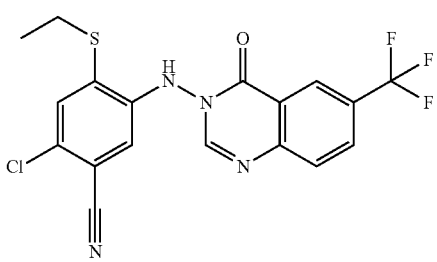 [SMILES: CCSc1cc(Cl)c(C#N)cc1Nn1cnc2ccc(C(F)(F)F)cc2c1=O]

The title compound was synthesized from 2-chloro-4-ethylsulfanyl-5-hydrazinylbenzonitrile (Compound 69) and 2-amino-5-(trifluoromethyl)benzoic acid under the same conditions as for Compounds c5 and C-7.

LCMS: m/z 425 [M+H]$^+$

HPLC retention time: 2.70 min (analysis condition C)

Example 308

Compound C-43

2-Chloro-4-ethylsulfonyl-5-[[4-oxo-6-(trifluoromethyl)quinazolin-3-yl]amino]benzonitrile

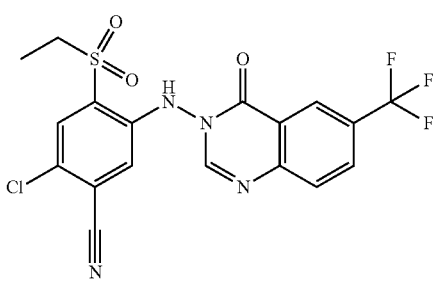 [SMILES: CCS(=O)(=O)c1cc(Cl)c(C#N)cc1Nn1cnc2ccc(C(F)(F)F)cc2c1=O]

The title compound was synthesized from 2-chloro-4-ethylsulfanyl-5-[[4-oxo-6-(trifluoromethyl)quinazolin-3-yl]amino]benzonitrile (Compound C-42) under the same conditions as for Compound 14.

LCMS: m/z 457 [M+H]$^+$

HPLC retention time: 2.48 min (analysis condition C)

Example 309

Compound d1

2-Amino-3-bromo-N'-(5-chloro-2-ethylsulfanylpyridin-3-yl)benzohydrazide

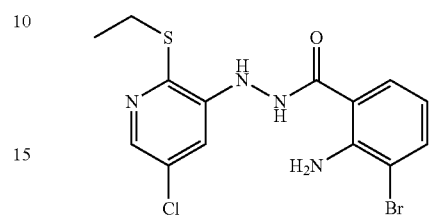

The title compound was synthesized from (5-chloro-2-ethylsulfanylpyridin-3-yl)hydrazine (Compound 78) and 2-amino-3-bromobenzoic acid under the same conditions as for Compound a1.

Example 310

Compound D-1

8-Bromo-3-[(5-chloro-3-ethylsulfanylpyridin-3-yl)amino]quinazolin-4-one

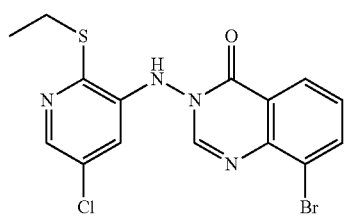 [SMILES: CCSc1ncc(Cl)cc1Nn1cnc2c(Br)cccc2c1=O]

The title compound was synthesized from 2-amino-3-bromo-N'-(5-chloro-2-ethylsulfanylpyridin-3-yl)benzohydrazide (Compound d1) under the same conditions as for Compound A-5.

LCMS: m/z 411 [M+H]$^+$

HPLC retention time: 3.28 min (analysis condition B)

Example 311

Compound D-2

3-[(5-Chloro-2-ethylsulfanylpyridin-3-yl)amino]-6-(trifluoromethyl)quinazolin-4-one

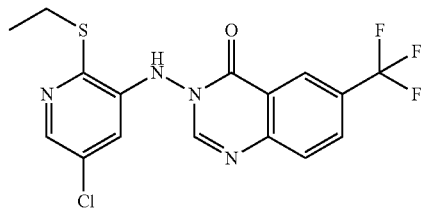 [SMILES: CCSc1ncc(Cl)cc1Nn1cnc2ccc(C(F)(F)F)cc2c1=O]

The title compound was synthesized from (5-chloro-2-ethylsulfanylpyridin-3-yl)hydrazine (Compound 78) and 2-amino-5-(trifluoromethyl)benzoic acid under the same conditions as for Compounds d1 and D-1.

LCMS: m/z 401 [M+H]$^+$

HPLC retention time: 3.78 min (analysis condition B)

Example 312

Compound D-3

3-[(5-Chloro-2-ethylsulfonylpyridin-3-yl)amino]-6-(trifluoromethyl)quinazolin-4-one

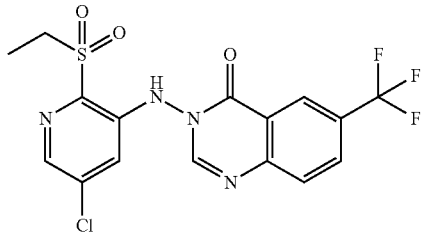 [SMILES: CCS(=O)(=O)c1ncc(Cl)cc1Nn1cnc2ccc(C(F)(F)F)cc2c1=O]

The title compound was synthesized from 3-[(5-chloro-2-ethylsulfanylpyridin-3-yl)amino]-6-(trifluoromethyl)quinazolin-4-one (Compound D-2) under the same conditions as for Compound 14.

LCMS: m/z 433 [M+H]$^+$

HPLC retention time: 3.42 min (analysis condition B)

Example 313

Compound d2

2-Amino-3-bromo-N'-(5-chloro-2-ethylsulfanylpyridin-3-yl)-5-methylbenzohydrazide

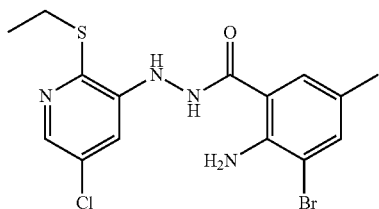 [SMILES: CCSc1ncc(Cl)cc1NNC(=O)c1cc(C)cc(Br)c1N]

The title compound was synthesized from (5-chloro-2-ethylsulfanylpyridin-3-yl)hydrazine (Compound 78) and 2-amino-3-bromo-5-methylbenzoic acid under the same conditions as for Compound 113. However, DMF was used in place of dichloromethane as a solvent.

Example 314

Compound D-4

8-Bromo-3-[(5-chloro-2-ethylsulfanylpyridin-3-yl)amino]-6-methylquinazolin-4-one

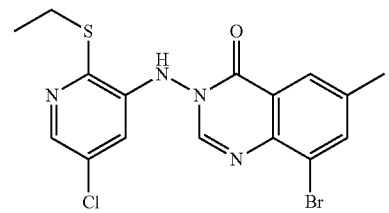 [SMILES: CCSc1ncc(Cl)cc1Nn1cnc2c(Br)cc(C)cc2c1=O]

The title compound was synthesized from 2-amino-3-bromo-N'-(5-chloro-2-ethylsulfanylpyridin-3-yl)-5-methylbenzohydrazide (Compound d2) under the same conditions as for Compound A-5.

LCMS: m/z 425 [M+H]$^+$

HPLC retention time: 3.57 min (analysis condition B)

Example 315

Compound D-5

8-Bromo-3-[(5-chloro-2-ethylsulfonylpyridin-3-yl)amino]-6-methylquinazolin-4-one

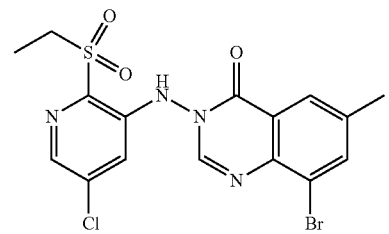 [SMILES: CCS(=O)(=O)c1ncc(Cl)cc1Nn1cnc2c(Br)cc(C)cc2c1=O]

The title compound was synthesized from 8-bromo-3-[(5-chloro-2-ethylsulfanylpyridin-3-yl)amino]-6-methylquinazolin-4-one (Compound D-4) under the same conditions as for Compound 14.

LCMS: m/z 457 [M+H]$^+$

HPLC retention time: 3.12 min (analysis condition B)

Example 316

Compound D-6

3-[(2-Chloro-5-ethylsulfanylpyridin-4-yl)amino]-6-(trifluoromethyl)quinazolin-4-one

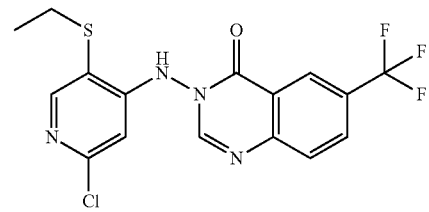 [SMILES: CCSc1cnc(Cl)cc1Nn1cnc2ccc(C(F)(F)F)cc2c1=O]

The title compound was synthesized from (2-chloro-5-ethylsulfanylpyridin-4-yl)hydrazine (Compound 81) and 2-amino-5-(trifluoromethyl)benzoic acid under the same conditions as for Compounds d2 and D-4.

LCMS: m/z 401 [M+H]$^+$

HPLC retention time: 3.37 min (analysis condition B)

Example 317

Compound D-7

3-[(2-Chloro-5-ethylsulfonylpyridin-4-yl)amino]-6-(trifluoromethyl)quinazolin-4-one

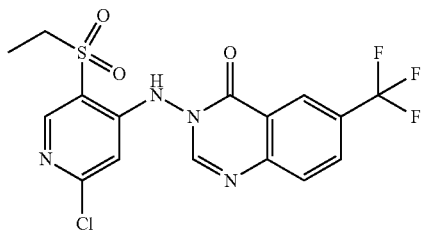

The title compound was synthesized from 3-[(2-chloro-5-ethylsulfanylpyridin-4-yl)amino]-6-(trifluoromethyl)quinazolin-4-one (Compound D-6) under the same conditions as for Compound 14.

LCMS: m/z 433 [M+H]$^+$

HPLC retention time: 3.50 min (analysis condition B)

Example 318

Compound e1

2-Amino-3-bromo-N-[(5-chloro-2-ethylsulfanylphenyl)methyl]-5-methylbenzamide

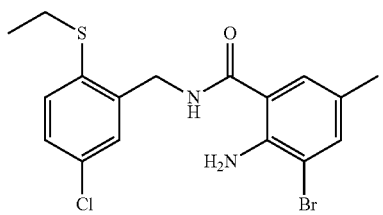 [SMILES: CCSc1ccc(Cl)cc1CNC(=O)c1cc(C)cc(Br)c1N]

The title compound was synthesized from (5-chloro-2-ethylsulfanylphenyl)methanamine (Compound 2) and 2-amino-3-bromo-5-methylbenzoic acid under the same conditions as for Compound a1. However, the reaction was performed with the addition of triethylamine.

Example 319

Compound E-1

8-Bromo-3-[(5-chloro-2-ethylsulfanylphenyl)methyl]-6-methylquinazolin-4-one

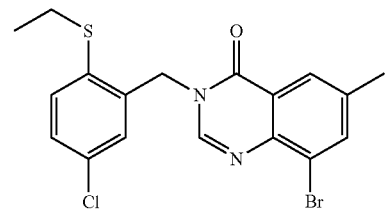 [SMILES: CCSc1ccc(Cl)cc1Cn1cnc2c(Br)cc(C)cc2c1=O]

The title compound was synthesized from 2-amino-3-bromo-N-[(5-chloro-2-ethylsulfanylphenyl)methyl]-5-methylbenzamide (Compound e1) under the same conditions as for Compound A-1.

LCMS: m/z 423 [M+H]$^+$

HPLC retention time: 3.87 min (analysis condition B)

Example 320

Compound e2

2-Amino-N-[(5-chloro-2-ethylsulfanylphenyl)methyl]-5-(trifluoromethoxy)benzamide

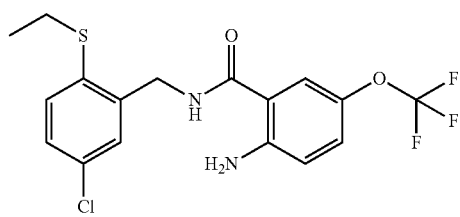 [SMILES: CCSc1ccc(Cl)cc1CNC(=O)c1cc(OC(F)(F)F)ccc1N]

The title compound was synthesized from (5-chloro-2-ethylsulfanylphenyl)methanamine (Compound 2) and 2-amino-5-(trifluoromethoxy)benzoic acid under the same conditions as for Compound a1.

Example 321

Compound E-3

3-[(5-Chloro-2-ethylsulfanylphenyl)methyl]-6-(trifluoromethoxy)quinazolin-4-one

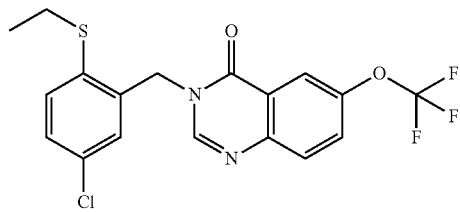 [SMILES: CCSc1ccc(Cl)cc1Cn1cnc2ccc(OC(F)(F)F)cc2c1=O]

The title compound was synthesized from 2-amino-N-[(5-chloro-2-ethylsulfanylphenyl)methyl]-5-(trifluoromethoxy)benzamide (Compound e2) under the same conditions as for Compound A-5.

LCMS: m/z 415 [M+H]$^+$

HPLC retention time: 3.02 min (analysis condition C)

Example 322

Compound E-5

6-Bromo-3-[(5-chloro-2-ethylsulfanylphenyl)methyl]-7-methylquinazolin-4-one

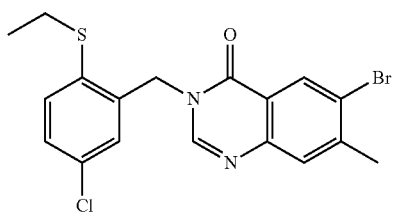 [SMILES: CCSc1ccc(Cl)cc1Cn1cnc2cc(C)c(Br)cc2c1=O]

The title compound was synthesized from (5-chloro-2-ethylsulfanylphenyl)methanamine (Compound 2) under the same conditions as for Compounds e2 and E-3. However, 2-amino-5-bromo-4-methylbenzoic acid was used in place of 2-amino-5-(trifluoromethoxy)benzoic acid as a carboxylic acid under the conditions for Compound e2.

LCMS: m/z 423 [M+H]$^+$

HPLC retention time: 3.10 min (analysis condition C)

Example 323

Compound E-7

3-[(5-Chloro-2-ethylsulfanylphenyl)methyl]-6-iodo-7-methylquinazolin-4-one

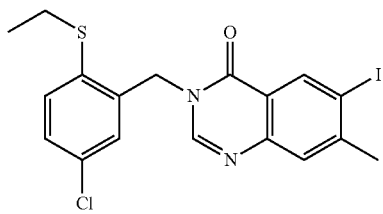 [SMILES: CCSc1ccc(Cl)cc1Cn1cnc2cc(C)c(I)cc2c1=O]

The title compound was synthesized from (5-chloro-2-ethylsulfanylphenyl)methanamine (Compound 2) under the same conditions as for Compounds e2 and E-3. However, 2-amino-5-iodo-4-methylbenzoic acid (Compound 87) was used in place of 2-amino-5-(trifluoromethoxy)benzoic acid as a carboxylic acid under the conditions for Compound e2.

LCMS: m/z 471 [M+H]$^+$

HPLC retention time: 3.17 min (analysis condition C)

Example 324

Compound e3

2-Amino-3-bromo-N-[(5-chloro-2-ethylsulfanylphenyl)methyl]-5-(trifluoromethyl)benzamide

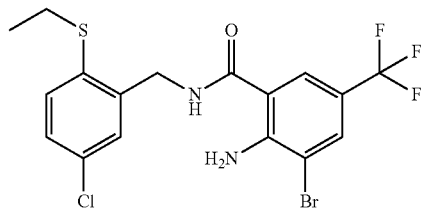 [SMILES: CCSc1ccc(Cl)cc1CNC(=O)c1cc(C(F)(F)F)cc(Br)c1N]

The title compound was synthesized from (5-chloro-2-ethylsulfanylphenyl)methanamine (Compound 2) and 2-amino-3-bromo-5-(trifluoromethyl)benzoic acid (Compound 85) under the same conditions as for Compound a1.

Example 325

Compound E-9

8-Bromo-3-[(5-chloro-2-ethylsulfanylphenyl)methyl]-6-(trifluoromethyl)quinazolin-4-one

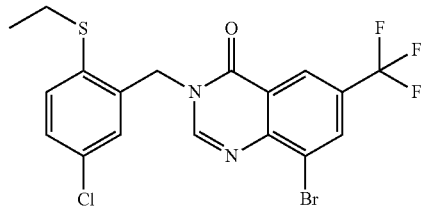 [SMILES: CCSc1ccc(Cl)cc1Cn1cnc2c(Br)cc(C(F)(F)F)cc2c1=O]

The title compound was synthesized from 2-amino-3-bromo-N-[(5-chloro-2-ethylsulfanylphenyl)methyl]-5-(trifluoromethyl)benzamide (Compound e3) under the same conditions as for Compound A-28.

LCMS: m/z 477 [M+H]$^+$

HPLC retention time: 3.23 min (analysis condition C)

Example 326

Compound E-11

8-Bromo-3-[(5-chloro-2-ethylsulfanylphenyl)methyl]-6-(trifluoromethoxy)quinazolin-4-one

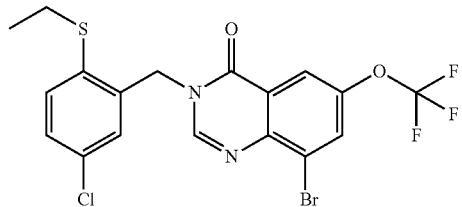 [SMILES: CCSc1ccc(Cl)cc1Cn1cnc2c(Br)cc(OC(F)(F)F)cc2c1=O]

The title compound was synthesized from (5-chloro-2-ethylsulfanylphenyl)methanamine (Compound 2) under the same conditions as for Compounds e3 and E-9. However, 2-amino-3-bromo-5-(trifluoromethoxy)benzoic acid was used in place of 2-amino-3-bromo-5-(trifluoromethyl)benzoic acid (Compound 85) as a carboxylic acid under the conditions for Compound e3.

LCMS: m/z 493 [M+H]$^+$

HPLC retention time: 1.06 min (analysis condition D)

Example 327

Compound e4

8-Chloro-3-[(5-chloro-2-ethylsulfanylphenyl)methyl]-6-(trifluoromethyl)quinazolin-4-one

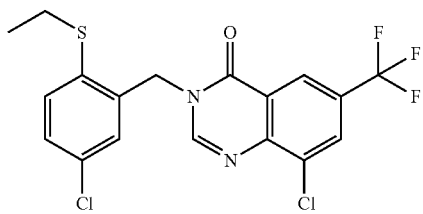 [SMILES: CCSc1ccc(Cl)cc1Cn1cnc2c(Cl)cc(C(F)(F)F)cc2c1=O]

The title compound was synthesized from (5-chloro-2-ethylsulfanylphenyl)methanamine (Compound 2) under the same conditions as for Compounds e2 and E-3. However, 2-amino-3-chloro-5-(trifluoromethyl)benzoic acid (Compound 86) was used in place of 2-amino-5-(trifluoromethoxy)benzoic acid as a carboxylic acid, DMF was used in place of dichloromethane as a solvent, and HOBT was added under the conditions for Compound e2.

Example 328

Compound e5

8-Chloro-3-[(5-chloro-2-ethylsulfanylphenyl)methyl]-6-(trifluoromethoxy)quinazolin-4-one

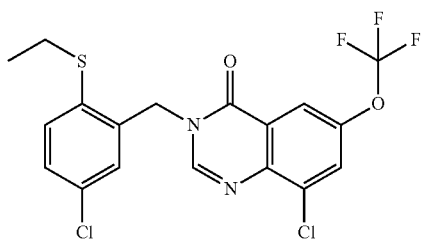 [SMILES: CCSc1ccc(Cl)cc1Cn1cnc2c(Cl)cc(OC(F)(F)F)cc2c1=O]

The title compound was synthesized from (5-chloro-2-ethylsulfanylphenyl)methanamine (Compound 2) under the same conditions as for Compounds e2 and E-3. However, 2-amino-3-chloro-5-(trifluoromethoxy)benzoic acid (Compound 94) was used in place of 2-amino-5-(trifluoromethoxy)benzoic acid as a carboxylic acid, DMF was used in place of dichloromethane as a solvent, and HOBT was added under the conditions for Compound e2.

Example 329

Compound e6

2-Amino-N-[(5-chloro-2-ethylsulfanylphenyl)methyl]-5-(trifluoromethyl)benzamide

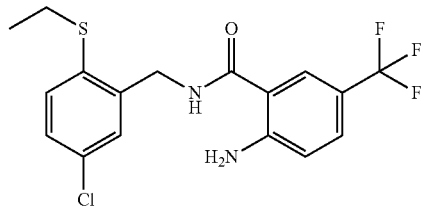 [SMILES: CCSc1ccc(Cl)cc1CNC(=O)c1cc(C(F)(F)F)ccc1N]

The title compound was synthesized from (5-chloro-2-ethylsulfanylphenyl)methanamine (Compound 2) and 2-amino-5-(trifluoromethyl)benzoic acid under the same conditions as for Compound 113. However, DMF was used in place of DCM as a solvent.

Example 330

Compound E-15

3-[(5-Chloro-2-ethylsulfanylphenyl)methyl]-6-(trifluoromethyl)quinazolin-4-one

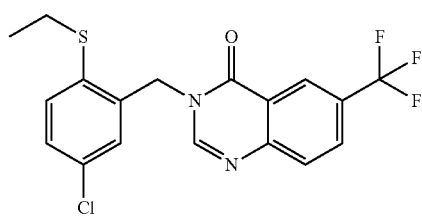 [SMILES: CCSc1ccc(Cl)cc1Cn1cnc2ccc(C(F)(F)F)cc2c1=O]

The title compound was synthesized from 2-amino-N-[(5-chloro-2-ethylsulfanylphenyl)methyl]-5-(trifluoromethyl)benzamide (Compound e6) under the same conditions as for Compound A-5. However, the reaction was performed without the addition of methyl orthoformate.

LCMS: m/z 399 [M+H]$^+$

HPLC retention time: 3.80 min (analysis condition B)

Example 331

Compound e7

2-Amino-3,5-dibromo-N-[(5-chloro-2-ethylsulfonylphenyl)methyl]-4-methylbenzamide

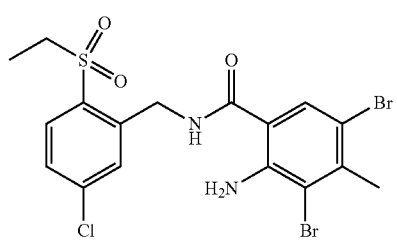 [SMILES: CCS(=O)(=O)c1ccc(Cl)cc1CNC(=O)c1cc(Br)c(C)c(Br)c1N]

The title compound was synthesized from (5-chloro-2-ethylsulfonylphenyl)methanamine hydrochloride (Compound 3) and 2-amino-3,5-dibromo-4-methylbenzoic acid (Compound 133) under the same conditions as for Compound 113. However, DMF was used in place of DCM as a solvent.

Example 332

Compound E-17

6,8-Dibromo-3-[(5-chloro-2-ethylsulfonylphenyl)methyl]-7-methylquinazolin-4-one

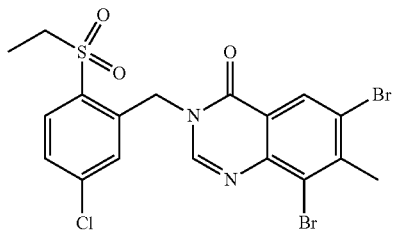 [SMILES: CCS(=O)(=O)c1ccc(Cl)cc1Cn1cnc2c(Br)c(C)c(Br)cc2c1=O]

The title compound was synthesized from 2-amino-3,5-dibromo-N-[(5-chloro-2-ethylsulfonylphenyl)methyl]-4-methylbenzamide (Compound e7) under the same conditions as for Compound A-5.

LCMS: m/z 533 [M+H]$^+$

HPLC retention time: 1.02 min (analysis condition D)

Example 333

Compound E-18

8-Chloro-3-[(5-chloro-2-propan-2-ylsulfanylphenyl)methyl]-6-(trifluoromethyl)quinazolin-4-one

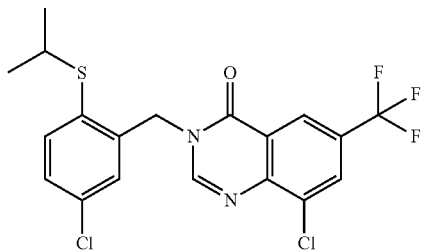 [SMILES: CC(C)Sc1ccc(Cl)cc1Cn1cnc2c(Cl)cc(C(F)(F)F)cc2c1=O]

The title compound was synthesized from (5-chloro-2-propan-2-ylsulfanylphenyl)methanamine (Compound 5) under the same conditions as for Compounds e2 and E-3. However, 2-amino-3-chloro-5-(trifluoromethyl)benzoic acid (Compound 86) was used in place of 2-amino-5-(trifluoromethoxy)benzoic acid as a carboxylic acid under the conditions for Compound e2.

LCMS: m/z 447 [M+H]$^+$

HPLC retention time: 1.10 min (analysis condition D)

Example 334

Compound e8

2-Amino-N-[(5-bromo-2-ethylsulfonylphenyl)methyl]-5-(trifluoromethyl)benzamide

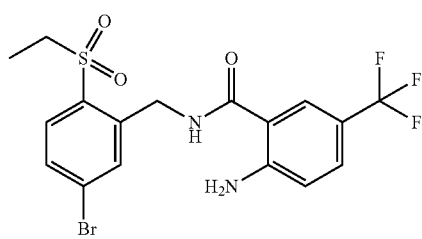 [SMILES: CCS(=O)(=O)c1ccc(Br)cc1CNC(=O)c1cc(C(F)(F)F)ccc1N]

A solution of (5-bromo-2-ethylsulfonylphenyl)methanamine hydrochloride (Compound 9, 60.0 mg, 0.191 mmol), 2-amino-5-(trifluoromethyl)benzoic acid (43.0 mg, 0.210 mmol), and HBTU (80.0 mg, 0.210 mmol) in DCM (1 ml) was cooled to 0° C., and DIPEA (0.100 ml, 0.572 mmol) was added thereto. The mixture was stirred at room temperature for 4.5 hours. Water was added to the reaction mixture, and extraction was performed with ethyl acetate. The organic layer was washed with a saturated aqueous sodium chloride solution and then dried over anhydrous sodium sulfate. After the drying agent was removed by filtration, concentration was performed under reduced pressure. The resulting residue was purified by silica gel column chromatography (ethyl acetate/hexane) to give the title compound (74.0 mg, 83%) as a white solid.

LCMS: m/z 465[M+H]$^+$

HPLC retention time: 0.86 min (analysis condition D)

Example 335

Compound E-20

3-[(5-Bromo-2-ethylsulfonylphenyl)methyl]-6-(trifluoromethyl)quinazolin-4-one

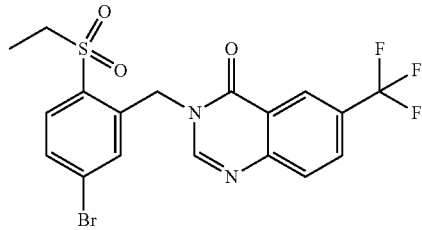 [SMILES: CCS(=O)(=O)c1ccc(Br)cc1Cn1cnc2ccc(C(F)(F)F)cc2c1=O]

The title compound was synthesized from 2-amino-N-[(5-bromo-2-ethylsulfonylphenyl)methyl]-5-(trifluoromethyl)benzamide (Compound e8) under the same conditions as for Compound A-28.

LCMS: m/z 475 [M+H]$^+$

HPLC retention time: 0.88 min (analysis condition D)

Example 336

Compound E-21

3-[(5-Bromo-2-ethylsulfonylphenyl)methyl]-8-chloro-6-(trifluoromethyl)quinazolin-4-one

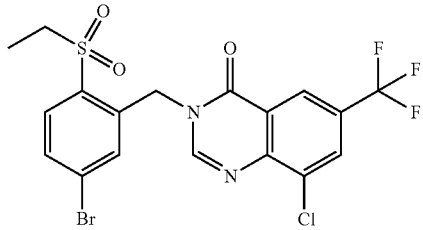

The title compound was synthesized from (5-bromo-2-ethylsulfonylphenyl)methanamine hydrochloride (Compound 9) and 2-amino-3-chloro-5-(trifluoromethyl)benzoic acid (Compound 86) under the same conditions as for Compounds e8 and E-20.

LCMS: m/z 509 [M+H]$^+$

HPLC retention time: 0.96 min (analysis condition D)

Example 337

Compound E-22

3-[(5-Bromo-2-ethylsulfonylphenyl)methyl]-6-(trifluoromethoxy)quinazolin-4-one

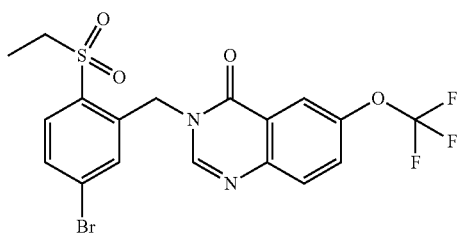 [SMILES: CCS(=O)(=O)c1ccc(Br)cc1Cn1cnc2ccc(OC(F)(F)F)cc2c1=O]

The title compound was synthesized from (5-bromo-2-ethylsulfonylphenyl)methanamine hydrochloride (Compound 9) and 2-amino-5-(trifluoromethoxy)benzoic acid under the same conditions as for Compounds e8 and E-20.

LCMS: m/z 491 [M+H]$^+$

HPLC retention time: 0.90 min (analysis condition D)

Example 338

Compound E-23

3-[(5-Bromo-2-ethylsulfonylphenyl)methyl]-8-chloro-6-(trifluoromethoxy)quinazolin-4-one

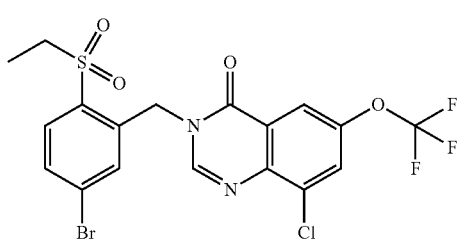 [SMILES: CCS(=O)(=O)c1ccc(Br)cc1Cn1cnc2c(Cl)cc(OC(F)(F)F)cc2c1=O]

The title compound was synthesized from (5-bromo-2-ethylsulfonylphenyl)methanamine hydrochloride (Compound 9) and 2-amino-3-chloro-5-(trifluoromethoxy)benzoic acid (Compound 94) under the same conditions as for Compounds e8 and E-20.

LCMS: m/z 525 [M+H]$^+$

HPLC retention time: 0.98 min (analysis condition D)

Example 339

Compound E-24

3-[(2-Ethylsulfanyl-5-fluorophenyl)methyl]-6-(trifluoromethyl)quinazolin-4-one

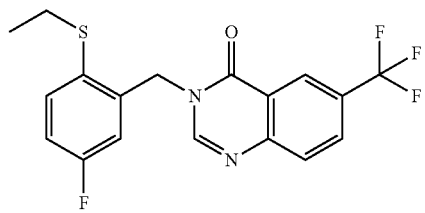 [SMILES: CCSc1ccc(F)cc1Cn1cnc2ccc(C(F)(F)F)cc2c1=O]

The title compound was synthesized from (2-ethylsulfanyl-5-fluorophenyl)methanamine (Compound 10) and 2-amino-5-(trifluoromethyl)benzoic acid under the same conditions as for Compounds e3 and E-9. However, the reaction was performed with the addition of HOBt under the conditions for Compound e3.

LCMS: m/z 383[M+H]$^+$

HPLC retention time: 1.00 min (analysis condition D)

Example 340

Compound e9

3-[(5-Fluoro-2-methylsulfanylphenyl)methyl]-6-(trifluoromethyl)quinazolin-4-one

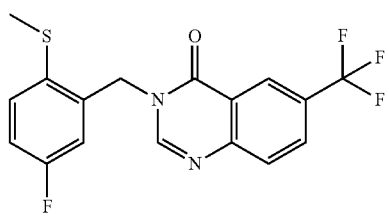 [SMILES: CSc1ccc(F)cc1Cn1cnc2ccc(C(F)(F)F)cc2c1=O]

The title compound was synthesized from (5-fluoro-2-methylsulfanylphenyl)methanamine (Compound 12) and 2-amino-5-(trifluoromethyl)benzoic acid under the same conditions as for Compounds e3 and E-9. However, the reaction was performed with the addition of HOBt under the conditions for Compound e3.

Example 341

Compound E-27

3-[[8-Bromo-4-oxo-6-(trifluoromethyl)quinazolin-3-yl]methyl]-4-ethylsulfonylbenzonitrile

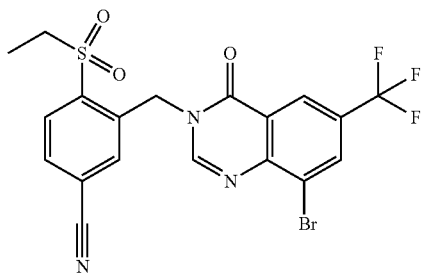 [SMILES: CCS(=O)(=O)c1ccc(C#N)cc1Cn1cnc2c(Br)cc(C(F)(F)F)cc2c1=O]

The title compound was synthesized from 3-(aminomethyl)-4-ethylsulfonylbenzonitrile (Compound 16) and 2-amino-3-bromo-5-(trifluoromethyl)benzoic acid (Compound 85) under the same conditions as for Compounds e2 and E-3. However, the reaction was performed without the addition of methyl orthoformate under the conditions for Compound E-3.
LCMS: m/z 500[M+H]$^+$
HPLC retention time: 0.86 min (analysis condition D)

Example 342

Compound E-28

4-Ethylsulfonyl-3-[[4-oxo-6-(trifluoromethyl)quinazolin-3-yl]methyl]benzonitrile

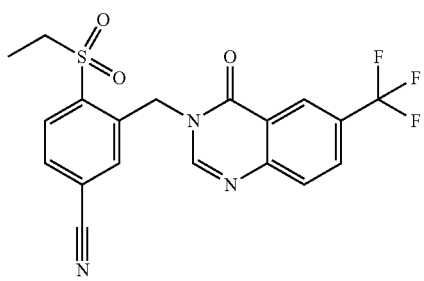 [SMILES: CCS(=O)(=O)c1ccc(C#N)cc1Cn1cnc2ccc(C(F)(F)F)cc2c1=O]

6-(Trifluoromethyl)-3H-quinazolin-4-one (Compound 95, 32.4 mg, 0.15 mmol) and cesium carbonate (49.4 mg, 0.15 mmol) were added to a solution of 3-(bromomethyl)-4-ethylsulfonylbenzonitrile (Compound 15, 29.1 mg, 0.10 mmol) in DMF (1.5 ml), and the mixture was stirred at room temperature for 2.5 hours. Ethyl acetate was added to the reaction mixture. After washing with water, the organic layer was dried over anhydrous sodium sulfate. After the drying agent was removed by filtration, concentration was performed under reduced pressure. The resulting residue was purified by silica gel column chromatography (ethyl acetate/hexane) to give the title compound (23.1 mg, 54%) as a white solid.
LCMS: m/z 422 [M+H]$^+$
HPLC retention time: 2.23 min (analysis condition C)

Example 343

Compound E-29

8-Bromo-3-[(2-ethylsulfanyl-5-methoxyphenyl)methyl]-6-(trifluoromethyl)quinazolin-4-one

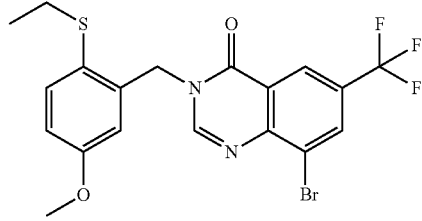 [SMILES: CCSc1ccc(OC)cc1Cn1cnc2c(Br)cc(C(F)(F)F)cc2c1=O]

The title compound was synthesized from (2-ethylsulfanyl-5-methoxyphenyl)methanamine (Compound 17) and 2-amino-3-bromo-5-(trifluoromethyl)benzoic acid (Compound 85) under the same conditions as for Compounds e2 and E-3.
LCMS: m/z 473 [M+H]$^+$
HPLC retention time: 1.05 min (analysis condition D)

Example 344

Compound e10

2-Amino-N-[(2-ethylsulfonylphenyl)methyl]-5-(trifluoromethyl)benzamide

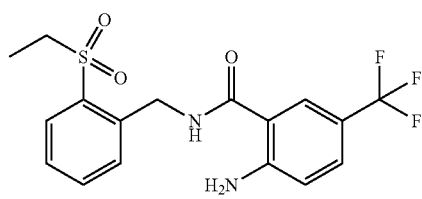 [SMILES: CCS(=O)(=O)c1ccccc1CNC(=O)c1cc(C(F)(F)F)ccc1N]

The title compound was synthesized from ((2-ethylsulfonylphenyl)methanamine (Compound 4) and 2-amino-5-(trifluoromethyl)benzoic acid under the same conditions as for Compound 113.

Example 345

Compound E-31

3-[(2-Ethylsulfonylphenyl)methyl]-6-(trifluoromethyl)quinazolin-4-one

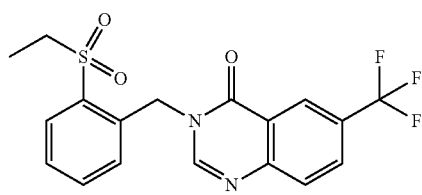 [SMILES: CCS(=O)(=O)c1ccccc1Cn1cnc2ccc(C(F)(F)F)cc2c1=O]

The title compound was synthesized from 2-amino-N-[(2-ethylsulfonylphenyl)methyl]-5-(trifluoromethyl)benzamide (Compound e10) under the same conditions as for Compound A-28.

LCMS: m/z 397 [M+H]$^+$
HPLC retention time: 0.80 min (analysis condition D)

Example 346

Compound e11

3-[(2-Ethylsulfanyl-4-methylphenyl)methyl]-6-(trifluoromethyl)quinazolin-4-one

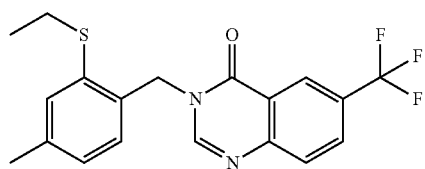 [SMILES: CCSc1cc(C)ccc1Cn1cnc2ccc(C(F)(F)F)cc2c1=O]

The title compound was synthesized from ((2-ethylsulfanyl-4-methylphenyl)methanamine (Compound 18) and 2-amino-5-(trifluoromethyl)benzoic acid under the same conditions as for Compounds e3 and E-9. However, the reaction was performed with the addition of HOBt under the conditions for Compound e3.

Example 347

Compound E-33

3-[(1-Ethylsulfonylpyrrol-2-yl)methyl]-6-(trifluoromethyl)quinazolin-4-one

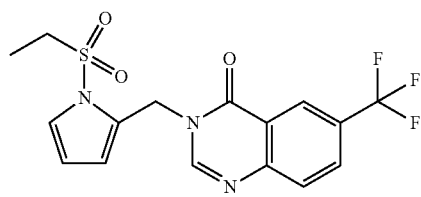 [SMILES: CCS(=O)(=O)n1cccc1Cn1cnc2ccc(C(F)(F)F)cc2c1=O]

The title compound was synthesized from (1-ethylsulfonylpyrrol-2-yl)methanamine hydrochloride (Compound 21) and 2-amino-5-(trifluoromethyl)benzoic acid under the same conditions as for Compounds e10 and E-31.

LCMS: m/z 386 [M+H]$^+$
HPLC retention time: 0.84 min (analysis condition D)

Example 348

Compound E-2

8-Bromo-3-[(5-chloro-2-ethylsulfonylphenyl)methyl]-6-methylquinazolin-4-one

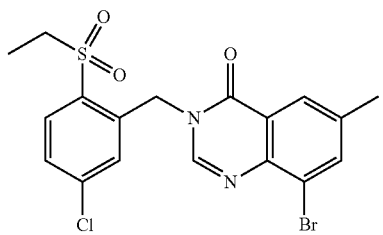 [SMILES: CCS(=O)(=O)c1ccc(Cl)cc1Cn1cnc2c(Br)cc(C)cc2c1=O]

The title compound was synthesized from 8-bromo-3-[(5-chloro-2-ethylsulfanylphenyl)methyl]-6-methylquinazolin-4-one (Compound E-1) under the same conditions as for Compound 14.

LCMS: m/z 455 [M+H]$^+$
HPLC retention time: 3.47 min (analysis condition B)

Examples 349 to 361

The following compounds of Table 7 were synthesized using corresponding sulfides under the same conditions as for Compound 14.

TABLE 7

| Example | Compound number | Structure | Compound name | HPLC condition | Retention time (min) | m/z [M + H]$^+$ |
|---|---|---|---|---|---|---|
| 349 | E-4 | 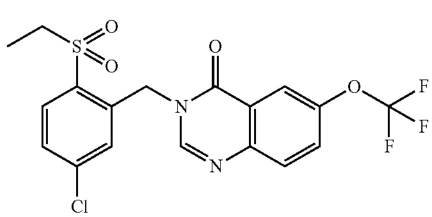 [SMILES: CCS(=O)(=O)c1ccc(Cl)cc1Cn1cnc2ccc(OC(F)(F)F)cc2c1=O] | 3-[(5-Chloro-2-ethylsulfonylphenyl)methyl]-6-(trifluoromethoxy)quinazolin-4-one | C | 2.52 | 447 |

TABLE 7-continued

| Example | Compound number | Structure | Compound name | HPLC condition | Retention time (min) | m/z [M + H]+ |
|---|---|---|---|---|---|---|
| 350 | E-6 | 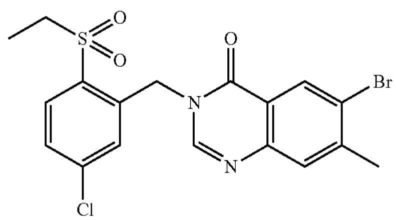 [SMILES: CCS(=O)(=O)c1ccc(Cl)cc1Cn1cnc2cc(C)c(Br)cc2c1=O] | 6-Bromo-3-[(5-chloro-2-ethylsulfonylphenyl)methyl]--7-methylquinazolin-4-one | C | 2.57 | 455 |
| 351 | E-8 | 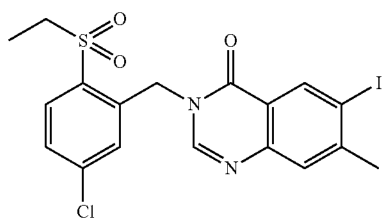 [SMILES: CCS(=O)(=O)c1ccc(Cl)cc1Cn1cnc2cc(C)c(I)cc2c1=O] | 3-[(5-Chloro-2-ethylsulfonylphenyl)methyl]-6-iodo-7-methylquinazolin-4-one | C | 2.65 | 503 |
| 352 | E-10 | 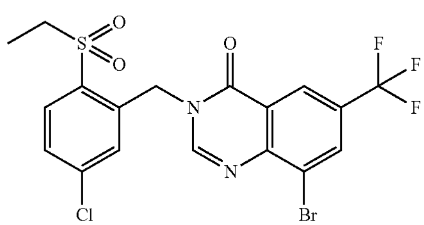 [SMILES: CCS(=O)(=O)c1ccc(Cl)cc1Cn1cnc2c(Br)cc(C(F)(F)F)cc2c1=O] | 8-Bromo-3-[(5-chloro-2-ethylsulfonylphenyl)methyl]-6-(trifluoromethyl)quinazolin-4-one | C | 2.75 | 509 |
| 353 | E-12 | 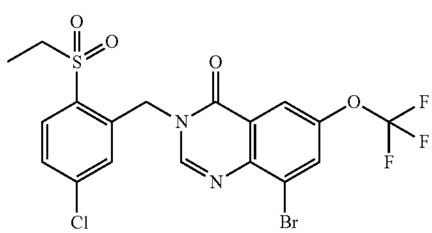 [SMILES: CCS(=O)(=O)c1ccc(Cl)cc1Cn1cnc2c(Br)cc(OC(F)(F)F)cc2c1=O] | 8-Bromo-3-[(5-chloro-2-ethylsulfonylphenyl)methyl]-6-(trifluoromethoxy)quinazolin-4-one | D | 0.92 | 525 |
| 354 | E-13 | 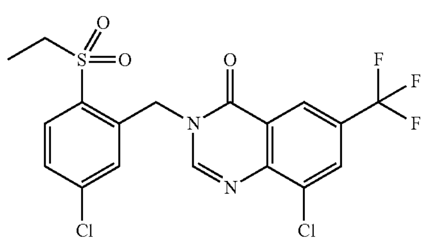 [SMILES: CCS(=O)(=O)c1ccc(Cl)cc1Cn1cnc2c(Cl)cc(C(F)(F)F)cc2c1=O] | 8-Chloro-3-[(5-chloro-2-ethylsulfonylphenyl)methyl]-6-(trifluoromethyl)quinazolin-4-one | E | 2.88 | 465 |
| 355 | E-14 | 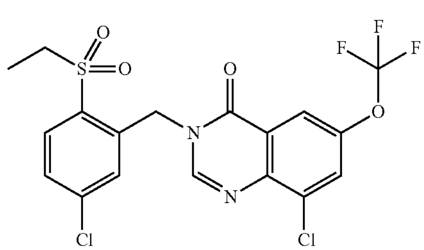 [SMILES: CCS(=O)(=O)c1ccc(Cl)cc1Cn1cnc2c(Cl)cc(OC(F)(F)F)cc2c1=O] | 8-Chloro-3-[(5-chloro-2-ethylsulfonylphenyl)methyl]-6-(trifluoromethoxy)quinazolin-4-one | E | 2.93 | 481 |

TABLE 7-continued

| Example | Compound number | Structure | Compound name | HPLC condition | Retention time (min) | m/z [M + H]+ |
|---|---|---|---|---|---|---|
| 356 | E-16 | 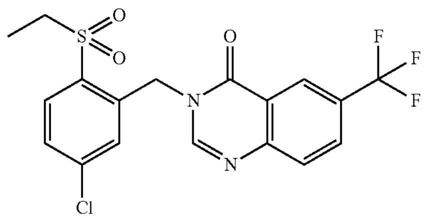 [SMILES: CCS(=O)(=O)c1ccc(Cl)cc1Cn1cnc2ccc(C(F)(F)F)cc2c1=O] | 3-[(5-Chloro-2-ethylsulfonylphenyl)methyl]-6-(trifluoromethyl)quinazolin-4-one | B | 3.42 | 431 |
| 357 | E-19 | 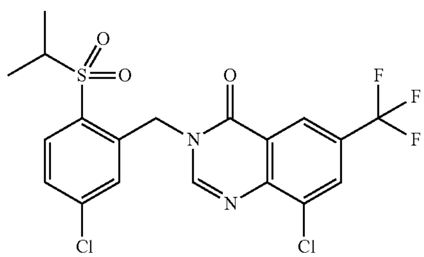 [SMILES: CC(C)S(=O)(=O)c1ccc(Cl)cc1Cn1cnc2c(Cl)cc(C(F)(F)F)cc2c1=O] | 8-Chloro-3-[(5-chloro-2-propan-2-ylsulfonylphenyl)methyl]-6-(trifluoromethyl)quinazolin-4-one | D | 0.95 | 479 |
| 358 | E-25 | 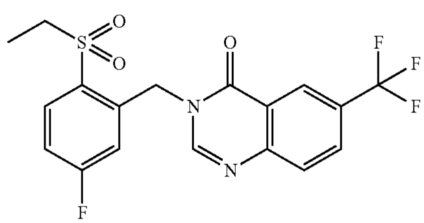 [SMILES: CCS(=O)(=O)c1ccc(F)cc1Cn1cnc2ccc(C(F)(F)F)cc2c1=O] | 3-[(2-ethylsulfonyl-5-fluorophenyl)methyl]-6-(trifluoromethyl)quinazolin-4-one | D | 0.85 | 415 |
| 359 | E-26 | 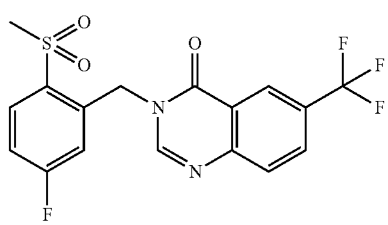 [SMILES: CS(=O)(=O)c1ccc(F)cc1Cn1cnc2ccc(C(F)(F)F)cc2c1=O] | 3-[(5-fluoro-2-methylsulfonylphenyl)methyl]-6-(trifluoromethyl)quinazolin-4-one | D | 0.83 | 401 |
| 360 | E-30 | 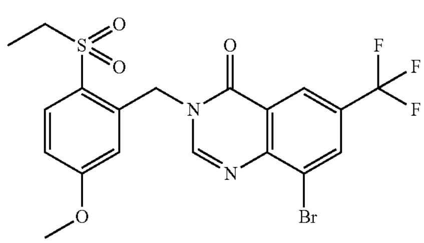 [SMILES: CCS(=O)(=O)c1ccc(OC)cc1Cn1cnc2c(Br)cc(C(F)(F)F)cc2c1=O] | 8-Bromo-3-[(2-ethylsulfonyl-5-methoxyphenyl)methyl]-6-(trifluoromethyl)quinazolin-4-one | D | 0.89 | 505 |
| 361 | E-32 | 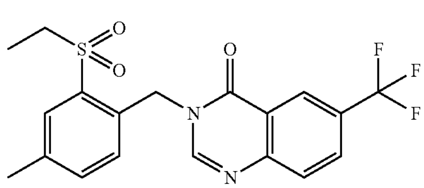 [SMILES: CCS(=O)(=O)c1cc(C)ccc1Cn1cnc2ccc(C(F)(F)F)cc2c1=O] | 3-[(2-ethylsulfonyl-4-methylphenyl)methyl]-6-(trifluoromethyl)quinazolin-4-one | D | 0.90 | 411 |

Example 362

Compound F-1

2-[(5-Chloro-2-ethylsulfonylphenyl)methyl]-7-(trifluoromethyl)isoquinolin-1-one

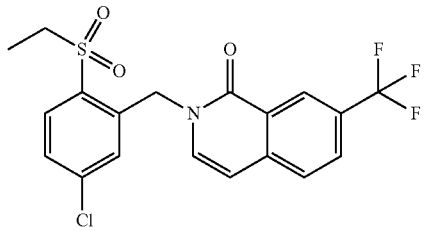 [SMILES: CCS(=O)(=O)c1ccc(Cl)cc1Cn1ccc2ccc(C(F)(F)F)cc2c1=O]

Sodium hydride (60% oil, 7.5 mg, 0.19 mmol) was added to a solution of 7-(trifluoromethyl)-2H-isoquinolin-1-one (Compound 98, 20.0 mg, 0.094 mmol) in DMF (1.8 ml), and the mixture was stirred at room temperature for 30 minutes. A solution of 2-(bromomethyl)-4-chloro-1-ethylsulfonylbenzene (Compound 26, 149 mg, 0.38 mmol) in DMF (1 ml) was added thereto, and the mixture was stirred at room temperature overnight. The reaction mixture was diluted with water, and extracted twice with ethyl acetate. The combined organic layers were washed with brine. The resulting organic layer was dried over anhydrous magnesium sulfate, and the drying agent was removed by filtration. Concentration was performed under reduced pressure and the resulting residue was purified by silica gel column chromatography (ethyl acetate/hexane) and preparative TLC (ethyl acetate/hexane) to give the title compound (29.0 mg, 73%) as a white solid.

LCMS: m/z 430 [M+H]$^+$
HPLC retention time: 0.92 min (analysis condition D)

Example 363

Compound F-2

2-[(5-Chloro-2-ethylsulfonylphenyl)methyl]-7-(trifluoromethoxy)isoquinolin-1-one

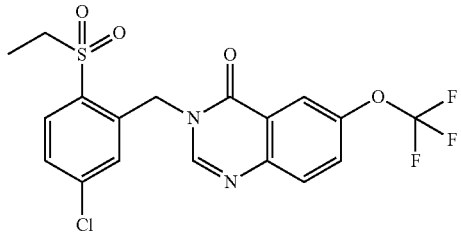 [SMILES: CCS(=O)(=O)c1ccc(Cl)cc1Cn1cnc2ccc(OC(F)(F)F)cc2c1=O]

The title compound was synthesized from 2-(bromomethyl)-4-chloro-1-ethylsulfonylbenzene (Compound 26) and 7-(trifluoromethoxy)-2H-isoquinolin-1-one (Compound 97) under the same conditions as for Compound F-1.

LCMS: m/z 446 [M+H]$^+$
HPLC retention time: 0.93 min (analysis condition D)

Example 364

Compound F-3

2-[(5-Chloro-2-ethylsulfonylphenyl)methyl]-7-methoxyisoquinolin-1-one

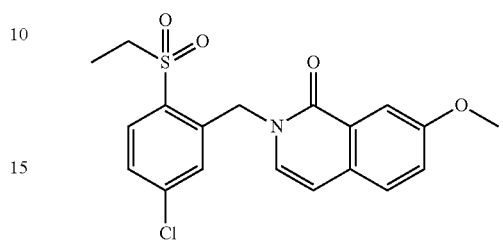

The title compound was synthesized from 2-(bromomethyl)-4-chloro-1-ethylsulfonylbenzene (Compound 26) and 7-methoxy-2H-isoquinolin-1-one (Compound 99) under the same conditions as for Compound F-1.

LCMS: m/z 392 [M+H]$^+$
HPLC retention time: 0.81 min (analysis condition D)

Example 365

Compound F-4

5-Chloro-2-[(5-chloro-2-ethylsulfonylphenyl)methyl]-7-(trifluoromethyl)isoquinolin-1-one

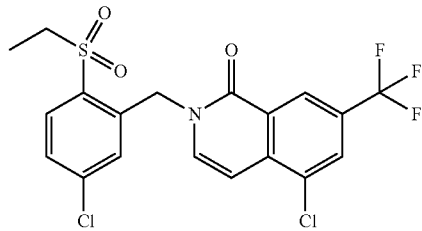 [SMILES: CCS(=O)(=O)c1ccc(Cl)cc1Cn1ccc2c(Cl)cc(C(F)(F)F)cc2c1=O]

The title compound was synthesized from 2-(bromomethyl)-4-chloro-1-ethylsulfonylbenzene (Compound 26) and 5-chloro-7-(trifluoromethyl)-2H-isoquinolin-1-one (Compound 101) under the same conditions as for Compound F-1.

LCMS: m/z 464 [M+H]$^+$
HPLC retention time: 1.03 min (analysis condition D)

Example 366

Compound F-5

5-Bromo-2-[(5-chloro-2-ethylsulfonylphenyl)methyl]-7-(trifluoromethyl)isoquinolin-1-one

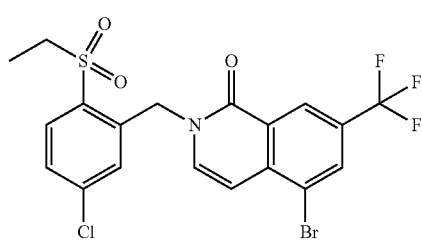 [SMILES: CCS(=O)(=O)c1ccc(Cl)cc1Cn1ccc2c(Br)cc(C(F)(F)F)cc2c1=O]

The title compound was synthesized from 2-(bromomethyl)-4-chloro-1-ethylsulfonylbenzene (Compound 26) and 5-bromo-7-(trifluoromethyl)-2H-isoquinolin-1-one (Compound 103) under the same conditions as for Compound F-1.

LCMS: m/z 508 [M+H]$^+$

HPLC retention time: 1.04 min (analysis condition D)

Example 367

Compound F-6

2-[(2-Ethylsulfonyl-5-nitrophenyl)methyl]-7-(trifluoromethyl)isoquinolin-1-one

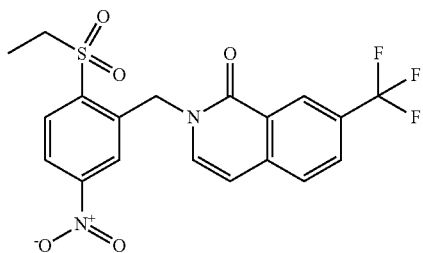

The title compound was synthesized from 2-(bromomethyl)-1-ethylsulfonyl-4-nitrobenzene (Compound 23) and 7-(trifluoromethyl)-2H-isoquinolin-1-one (Compound 98) under the same conditions as for Compound F-1.

LCMS: m/z 441 [M+H]$^+$

HPLC retention time: 0.86 min (analysis condition D)

Example 368

Compound F-7

2-[(5-Amino-2-ethylsulfonylphenyl)methyl]-7-(trifluoromethyl)isoquinolin-1-one

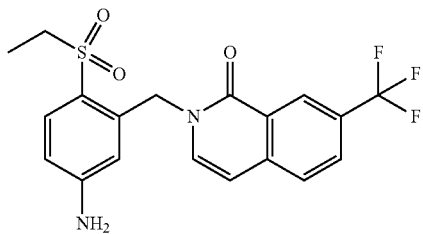 [SMILES: CCS(=O)(=O)c1ccc(N)cc1Cn1ccc2ccc(C(F)(F)F)cc2c1=O]

The title compound was synthesized from 2-[(2-ethylsulfonyl-5-nitrophenyl)methyl]-7-(trifluoromethyl)isoquinolin-1-one (Compound F-6) under the same conditions as for Compound 123.

LCMS: m/z 411 [M+H]$^+$

HPLC retention time: 0.74 min (analysis condition D)

Example 369

Compound F-8

4-Ethylsulfonyl-3-[[1-oxo-7-(trifluoromethyl)isoquinolin-2-yl]methyl]benzonitrile

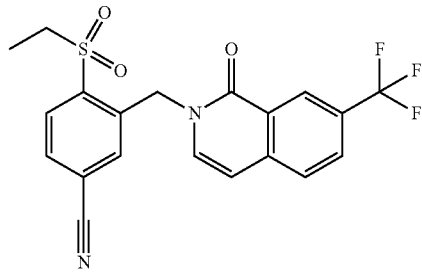 [SMILES: CCS(=O)(=O)c1ccc(C#N)cc1Cn1ccc2ccc(C(F)(F)F)cc2c1=O]

The title compound was synthesized from 3-(bromomethyl)-4-ethylsulfonylbenzonitrile (Compound 15) and 7-(trifluoromethyl)-2H-isoquinolin-1-one (Compound 98) under the same conditions as for Compound F-1.

LCMS: m/z 421 [M+H]$^+$

HPLC retention time: 0.83 min (analysis condition D)

Example 370

Compound F-9

2-[(2-Ethylsulfonyl-5-nitrophenyl)methyl]-7-(trifluoromethoxy)isoquinolin-1-one

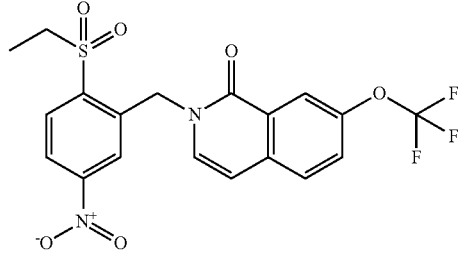

The title compound was synthesized from 2-(bromomethyl)-1-ethylsulfonyl-4-nitrobenzene (Compound 23) and 7-(trifluoromethoxy)-2H-isoquinolin-1-one (Compound 97) under the same conditions as for Compound F-1.

LCMS: m/z 457 [M+H]$^+$

HPLC retention time: 0.87 min (analysis condition D)

Example 371

Compound F-10

2-[(5-Amino-2-ethylsulfonylphenyl)methyl]-7-(trifluoromethoxy)isoquinolin-1-one

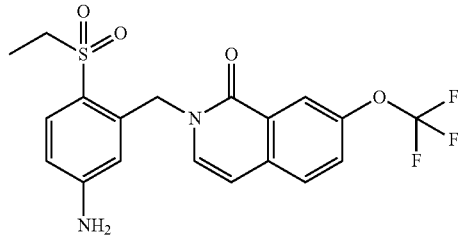 [SMILES: CCS(=O)(=O)c1ccc(N)cc1Cn1ccc2ccc(OC(F)(F)F)cc2c1=O]

The title compound was synthesized from 2-[(2-ethylsulfonyl-5-nitrophenyl)methyl]-7-(trifluoromethoxy)isoquinolin-1-one (Compound F-9) under the same conditions as for Compound 123.

LCMS: m/z 427 [M+H]$^+$
HPLC retention time: 0.76 min (analysis condition D)

Example 372

Compound F-11

4-Ethylsulfonyl-3-[[1-oxo-7-(trifluoromethoxy)isoquinolin-2-yl]methyl]benzonitrile

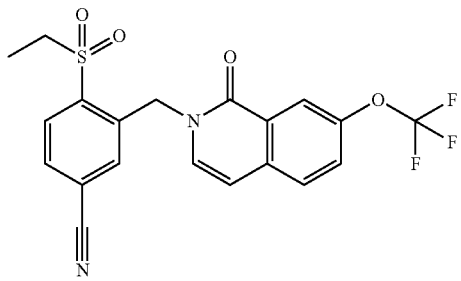 [SMILES: CCS(=O)(=O)c1ccc(C#N)cc1Cn1ccc2ccc(OC(F)(F)F)cc2c1=O]

The title compound was synthesized from 3-(bromomethyl)-4-ethylsulfonylbenzonitrile (Compound 15) and 7-(trifluoromethoxy)-2H-isoquinolin-1-one (Compound 97) under the same conditions as for Compound F-1.

LCMS: m/z 437 [M+H]$^+$
HPLC retention time: 0.84 min (analysis condition D)

Example 373

Compound g1 tert-Butyl 4-[[5-amino-4-ethoxycarbonyl-2-(trifluoromethyl)phenyl]methyl]piperazine-1-carboxylate

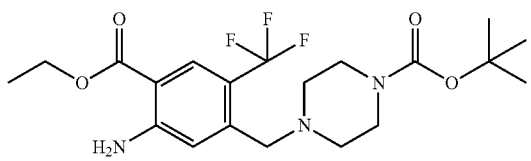 [SMILES: CCOC(=O)c1cc(C(F)(F)F)c(CN2CCN(C(=O)OC(C)(C)C)CC2)cc1N]

A mixture of ethyl 2-amino-4-chloro-5-(trifluoromethyl)benzoate (Compound 107, 1.07 g, 4.0 mmol), potassium (4-tert-butoxycarbonylpiperazin-1-yl)methyltrifluoroborate (1.71 g, 5.6 mmol), palladium acetate (44.9 mg, 0.2 mmol), X-Phos (191 mg, 0.4 mmol), and cesium carbonate (3.91 g, 12 mmol) in THF (40 mL) and water (20 mL) was stirred at 90° C. for three hours. The reaction solution was cooled to room temperature, diluted with water, and then extracted with ethyl acetate. The extract was dried over anhydrous sodium sulfate. After the drying agent was removed by filtration, concentration was performed under reduced pressure. The resulting residue was purified by silica gel column chromatography (ethyl acetate/hexane) to give the title compound (1.49 g, 86%) as a pale yellow solid.

LCMS: m/z 432 [M+H]$^+$
HPLC retention time: 0.75 min (analysis condition D)

Example 374

Compound g2

2-Amino-4-[[4-[(2-methylpropan-2-yl)oxycarbonyl]piperazin-1-yl]methyl]-5-(trifluoromethyl)benzoic Acid

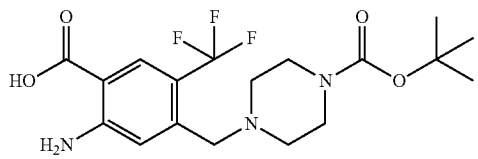 [SMILES: CC(C)(C)OC(=O)N1CCN(Cc2cc(N)c(C(=O)O)cc2C(F)(F)F)CC1]

The title compound was synthesized from tert-butyl 4-[[5-amino-4-ethoxycarbonyl-2-(trifluoromethyl)phenyl]methyl]piperazine-1-carboxylate (Compound g1) under the same conditions as for Compound 85.

Example 375

Compound g3 tert-Butyl 4-[[5-amino-4-[(5-chloro-2-ethylanilino)carbamoyl]-2-(trifluoromethyl)phenyl]methyl]piperazine-1-carboxylate

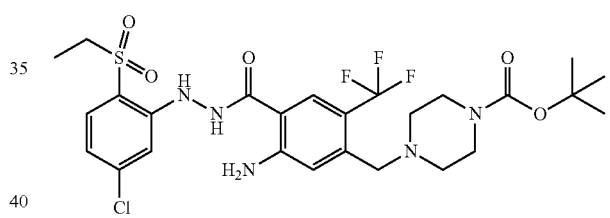

The title compound was synthesized from (5-chloro-2-ethylsulfonylphenyl)hydrazine (Compound 31) and 2-amino-4-[[4-[(2-methylpropan-2-yl)oxycarbonyl]piperazin-1-yl]methyl]-5-(trifluoromethyl)benzoic acid (Compound g2) under the same conditions as for Compound a1.

Example 376

Compound g4 tert-Butyl 4-[[3-(5-chloro-2-ethylsulfonylanilino)-4-oxo-6-(trifluoromethyl)quinazolin-7-yl]methyl]piperazine-1-carboxylate

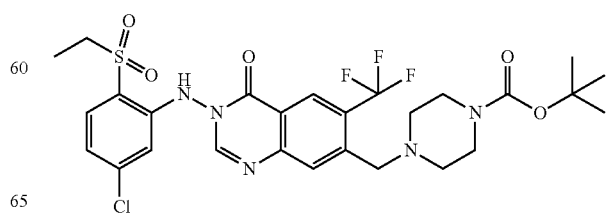

The title compound was synthesized from tert-butyl 4-[[5-amino-4-[(5-chloro-2-ethylsulfonylanilino)carbamoyl]-2-(trifluoromethyl)phenyl]methyl]piperazine-1-carboxylate (Compound g3) under the same conditions as for Compound A-28.

LCMS: m/z 544 [M+H]$^+$
HPLC retention time: 0.56 min (analysis condition D)

Example 377

Compound G-1

3-(5-Chloro-2-ethylsulfonylanilino)-7-(piperazin-1-ylmethyl)-6-(trifluoromethyl)quinazolin-4-one Example 379

Compound G-3

3-(5-Chloro-2-ethylsulfonylanilino)-7-[(4-propan-2-ylpiperazin-1-yl)methyl]-6-(trifluoromethyl)quinazolin-4-one

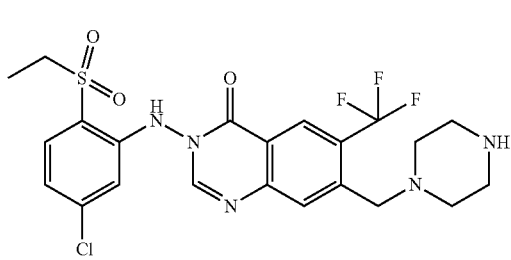 [SMILES: CCS(=O)(=O)c1ccc(Cl)cc1Nn1cnc2cc(CN3CCNCC3)c(C(F)(F)F)cc2c1=O]

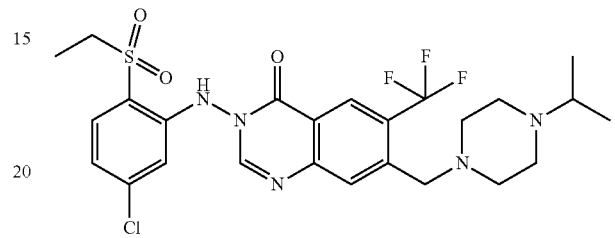

The title compound was synthesized from tert-butyl 4-[[3-(5-chloro-2-ethylsulfonylanilino)-4-oxo-6-(trifluoromethyl)quinazolin-7-yl]methyl]piperazine-1-carboxylate (Compound g4) under the same conditions as for Compound 21.
LCMS: m/z 530 [M+H]$^+$
HPLC retention time: 0.57 min (analysis condition D)

Sodium triacetoxyborohydride (31.8 mg, 0.15 mmol) was added to a solution of 3-(5-chloro-2-ethylsulfonylanilino)-7-(piperazin-1-ylmethyl)-6-(trifluoromethyl)quinazolin-4-one (Compound G-1, 26.5 mg, 0.05 mmol) and acetone (14.7 ul, 0.20 mmol) in THF, and the mixture was stirred at 50° C. for one hour. After the reaction mixture was cooled to room temperature, a saturated aqueous sodium bicarbonate solution was added thereto and extraction was performed with ethyl acetate. The organic layer was dried over anhydrous sodium sulfate. After the drying agent was removed by filtration, concentration was performed under reduced pressure. The resulting residue was purified by silica gel column chromatography (methanol/DCM) to give the title compound (22.0 mg, 77%) as a colorless foamy substance.
LCMS: m/z 572 [M+H]$^+$
HPLC retention time: 0.59 min (analysis condition: D)

Example 378

Compound G-2

3-(5-Chloro-2-ethylsulfonylanilino)-7-[(4-methylpiperazin-1-yl)methyl]-6-(trifluoromethyl)quinazolin-4-one Example 380

Compound G-4

3-(5-Chloro-2-ethylsulfonylanilino)-7-[[4-(oxan-4-yl)piperazin-1-yl]methyl]-6-(trifluoromethyl)quinazolin-4-one

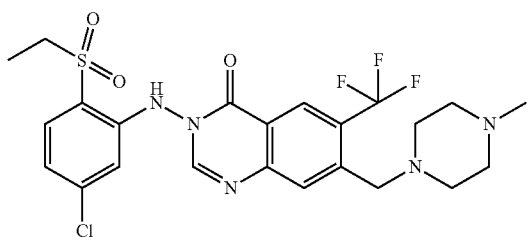 [SMILES: CCS(=O)(=O)c1ccc(Cl)cc1Nn1cnc2cc(CN3CCN(C)CC3)c(C(F)(F)F)cc2c1=O]

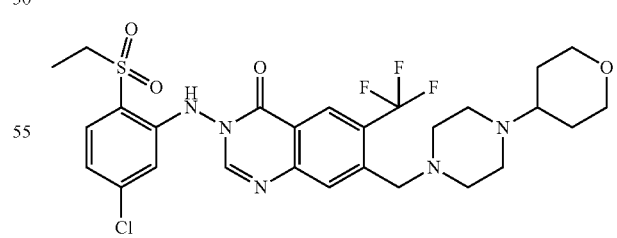

A solution of 3-(5-chloro-2-ethylsulfonylanilino)-7-(piperazin-1-ylmethyl)-6-(trifluoromethyl)quinazolin-4-one (Compound G-1, 47.7 mg, 0.09 mmol) and paraformaldehyde (10.8 mg, 0.3 mmol) in formic acid (477 μL) was stirred at 80° C. for one hour. The reaction solution was cooled to room temperature and then concentrated under reduced pressure. Ethyl acetate was added to the resulting residue, and was washed with a saturated aqueous sodium bicarbonate solution. The organic layer was dried over anhydrous sodium sulfate. After the drying agent was removed by filtration, concentration was performed under reduced pressure. The resulting residue was purified by silica gel column chromatography (methanol/DCM) to give the title compound (43.3 mg, 88%) as a colorless foamy substance.

The title compound was synthesized from 3-(5-chloro-2-ethylsulfonylanilino)-7-(piperazin-1-ylmethyl)-6-(trifluoromethyl)quinazolin-4-one (Compound G-1) under the same conditions as for Compound G-3. However, tetrahydro-4H-pyran-4-one was used in place of acetone.
LCMS: m/z 614 [M+H]$^+$
HPLC retention time: 0.57 min (analysis condition D)

Example 381

Compound g5 tert-Butyl 4-[[3-amino-2-chloro-4-ethoxycarbonyl-6-(trifluoromethyl)phenyl]methyl]piperazine-1-carboxylate

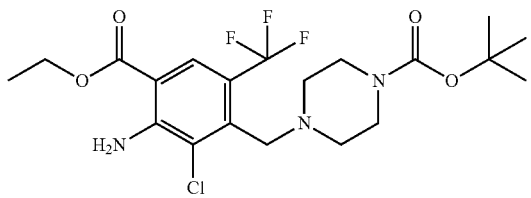 [SMILES: CCOC(=O)c1cc(C(F)(F)F)c(CN2CCN(C(=O)OC(C)(C)C)CC2)c(Cl)c1N]

The title compound was synthesized from tert-butyl 4-[[5-amino-4-ethoxycarbonyl-2-(trifluoromethyl)phenyl]methyl]piperazine-1-carboxylate (Compound g1) under the same conditions as for Compound 111.

Example 382

Compound g6

2-Amino-3-chloro-4-[[4-[(2-methylpropan-2-yl)oxycarbonyl]piperazin-1-yl]methyl]-5-(trifluoromethyl)benzoic Acid

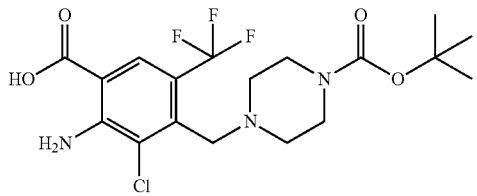 [SMILES: CC(C)(C)OC(=O)N1CCN(Cc2c(C(F)(F)F)cc(C(=O)O)c(N)c2Cl)CC1]

The title compound was synthesized from tert-butyl 4-[[3-amino-2-chloro-4-ethoxycarbonyl-6-(trifluoromethyl)phenyl]methyl]piperazine-1-carboxylate (Compound g5) under the same conditions as for Compound 85.

Example 383

Compound g7 tert-Butyl 4-[[8-chloro-2,4-dioxo-6-(trifluoromethyl)-1H-3,1-benzoxazin-7-yl]methyl]piperazine-1-carboxylate

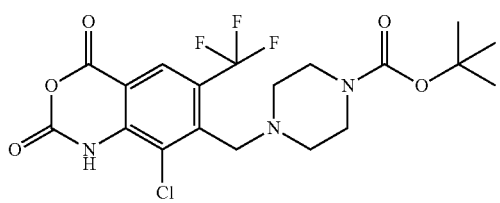 [SMILES: CC(C)(C)OC(=O)N1CCN(Cc2c(C(F)(F)F)cc3c(=O)oc(=O)[nH]c3c2Cl)CC1]

DBU (171 ul, 1.1 mmol) was added to a solution of 2-amino-3-chloro-4-[[4-[(2-methylpropan-2-yl)oxycarbonyl]piperazin-1-yl]methyl]-5-(trifluoromethyl)benzoic acid (Compound g6, 127 mg, 0.23 mmol) in THF (4 ml), and a solution of triphosgene (102 mg, 0.34 mmol) in THF (0.5 ml) was slowly added while cooling it in an ice water bath. The mixture was stirred at 0° C. for 1.5 hours. After the reaction mixture was warmed to room temperature, a saturated aqueous sodium bicarbonate solution was added to the reaction mixture, followed by extraction with ethyl acetate. The organic layer was washed with brine and dried over anhydrous sodium sulfate. After the drying agent was removed by filtration, concentration was performed under reduced pressure to give a crude product of the title compound.

LCMS: m/z 464 [M+H]$^+$

HPLC retention time: 0.86 min (analysis condition D)

Example 384

Compound g8 tert-Butyl 4-[[3-amino-2-chloro-4-[(5-chloro-2-ethylsulfonylanilino)carbamoyl]-6-(trifluoromethyl)phenyl]methyl]piperazine-1-carboxylate

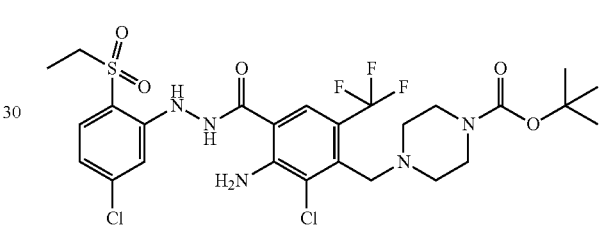

A solution of tert-butyl 4-[[8-chloro-2,4-dioxo-6-(trifluoromethyl)-1H-3,1-benzoxazin-7-yl]methyl]piperazine-1-carboxylate (Compound g7, 70.0 mg, 0.15 mmol) and (5-chloro-2-ethylsulfonylphenyl)hydrazine (Compound 31, 42.5 mg, 0.18 mmol) in THF (1 ml) was stirred in a sealed tube at 100° C. for 22 hours. The reaction mixture was cooled to room temperature, and concentrated under reduced pressure. The resulting residue was purified by silica gel column chromatography (ethyl acetate/hexane) to give the title compound (24.2 mg, 25%).

LCMS: m/z 654 [M+H]$^+$

HPLC retention time: 0.93 min (analysis condition D)

Example 385

Compound g9 tert-Butyl 4-[[8-chloro-3-(5-chloro-2-ethylsulfonylanilino)-4-oxo-6-(trifluoromethyl)quinazolin-7-yl]methyl]piperazine-1-carboxylate

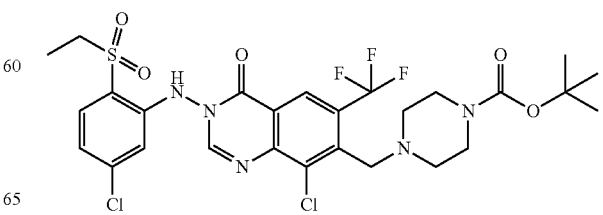

The title compound was synthesized from tert-butyl 4-[[3-amino-2-chloro-4-[(5-chloro-2-ethylsulfonylanilino)carbamoyl]-6-(trifluoromethyl)phenyl]methyl]piperazine-1-carboxylate (Compound g8) under the same conditions as for Compound A-28. However, the reaction was performed at 60° C.

Example 386

Compound G-5

8-Chloro-3-(5-chloro-2-ethylsulfonylanilino)-7-(piperazin-1-ylmethyl)-6-(trifluoromethyl)quinazolin-4-one

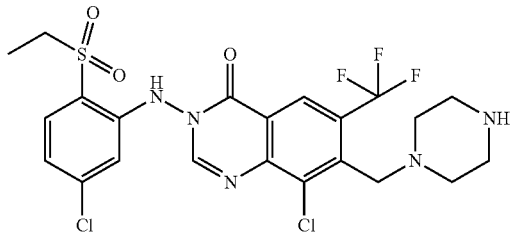 [SMILES: CCS(=O)(=O)c1ccc(Cl)cc1Nn1cnc2c(Cl)c(CN3CCNCC3)c(C(F)(F)F)cc2c1=O]

The title compound was synthesized from tert-butyl 4-[[8-chloro-3-(5-chloro-2-ethylsulfonylanilino)-4-oxo-6-(trifluoromethyl)quinazolin-7-yl]methyl]piperazine-1-carboxylate (Compound g9) under the same conditions as for Compound 21.

LCMS: m/z 564 [M+H]$^+$

HPLC retention time: 0.56 min (analysis condition D)

Example 387

Compound G-6

8-Chloro-3-(5-chloro-2-ethylsulfonylanilino)-7-[(4-methylpiperazin-1-yl)methyl]-6-(trifluoromethyl)quinazolin-4-one

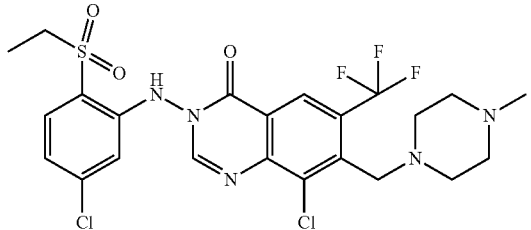 [SMILES: CCS(=O)(=O)c1ccc(Cl)cc1Nn1cnc2c(Cl)c(CN3CCN(C)CC3)c(C(F)(F)F)cc2c1=O]

The title compound was synthesized from 8-chloro-3-(5-chloro-2-ethylsulfonylanilino)-7-(piperazin-1-ylmethyl)-6-(trifluoromethyl)quinazolin-4-one (Compound G-5) under the same conditions as for Compound G-2.

LCMS: m/z 578 [M+H]$^+$

HPLC retention time: 0.59 min (analysis condition D)

Example 388

Compound g10 tert-Butyl N-[7-bromo-4-oxo-6-(trifluoromethoxy)quinazolin-3-yl]-N-(5-cyano-2-ethylsulfonylphenyl)carbamate

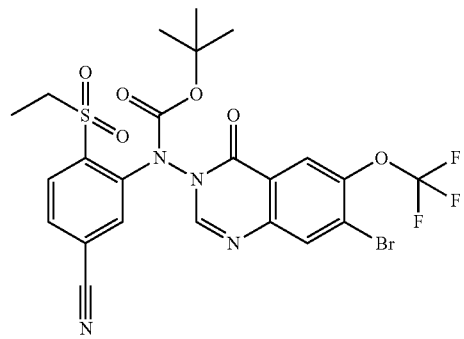 [SMILES: CCS(=O)(=O)c1ccc(C#N)cc1N(C(=O)OC(C)(C)C)n1cnc2cc(Br)c(OC(F)(F)F)cc2c1=O]

The title compound was synthesized from 3-[[7-bromo-4-oxo-6-(trifluoromethoxy)quinazolin-3-yl]amino]-4-ethylsulfonylbenzonitrile (Compound C-18) under the same conditions as for Compound a6.

Example 389

Compound g11 tert-Butyl 4-[[3-[5-cyano-2-ethylsulfonyl-N-[(2-methylpropan-2-yl)oxycarbonyl]anilino]-4-oxo-6-(trifluoromethoxy)quinazolin-7-yl]methyl]piperazine-1-carboxylate

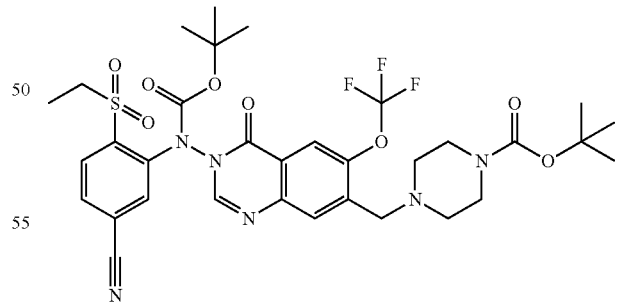

The title compound was synthesized from tert-butyl N-[7-bromo-4-oxo-6-(trifluoromethoxy)quinazolin-3-yl]-N-(5-cyano-2-ethylsulfonylphenyl)carbamate (Compound g10) under the same conditions as for Compound g1. However, the reaction was performed under microwave irradiation at 120° C.

Example 390

Compound G-7

4-Ethylsulfonyl-3-[[4-oxo-7-(piperazin-1-ylmethyl)-6-(trifluoromethoxy)quinazolin-3-yl]amino]benzonitrile

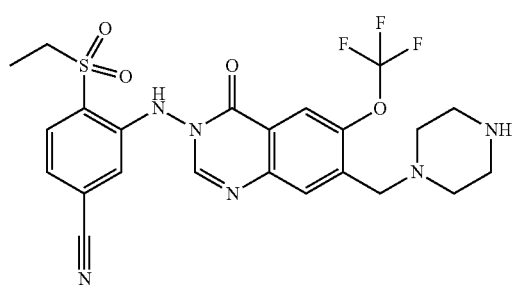 [SMILES: CCS(=O)(=O)c1ccc(C#N)cc1Nn1cnc2cc(CN3CCNCC3)c(OC(F)(F)F)cc2c1=O]

The title compound was synthesized from tert-butyl 4-[[3-[5-cyano-2-ethylsulfonyl-N-[(2-methylpropan-2-yl)oxycarbonyl]anilino]-4-oxo-6-(trifluoromethoxy)quinazolin-7-yl]methyl]piperazine-1-carboxylate (Compound g11) under the same conditions as for Compound A-2.

LCMS: m/z 537 [M+H]$^+$

HPLC retention time: 0.49 min (analysis condition D)

Example 391

Compound G-8

4-Ethylsulfonyl-3-[[7-(morpholin-4-ylmethyl)-4-oxo-6-(trifluoromethoxy)quinazolin-3-yl]amino]benzonitrile

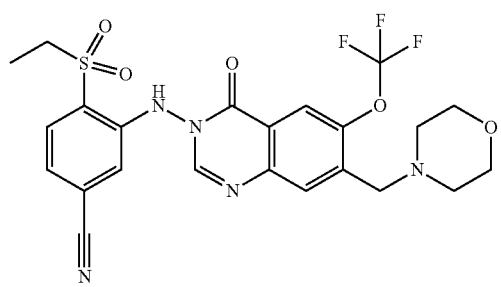 [SMILES: CCS(=O)(=O)c1ccc(C#N)cc1Nn1cnc2cc(CN3CCOCC3)c(OC(F)(F)F)cc2c1=O]

The title compound was synthesized from tert-butyl N-[7-bromo-4-oxo-6-(trifluoromethoxy)quinazolin-3-yl]-N-(5-cyano-2-ethylsulfonylphenyl)carbamate (Compound g10) under the same conditions as for Compounds g11 and G-7. However, potassium (morpholin-4-yl)methyltrifluoroborate was used in place of potassium (4-tert-butoxycarbonylpiperazin-1-yl)methyltrifluoroborate under the conditions for Compound g11.

LCMS: m/z 538 [M+H]$^+$

HPLC retention time: 0.53 min (analysis condition D)

Example 392

Compound g12

3-Amino-4-ethylsulfonyl-benzonitrile

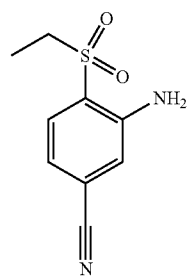

The title compound was synthesized from 3-amino-4-ethylsulfanyl-benzonitrile (Compound 46) under the same conditions as for Compound 14.

Example 393

Compound g13

4-Ethylsulfonyl-3-hydrazino-benzonitrile

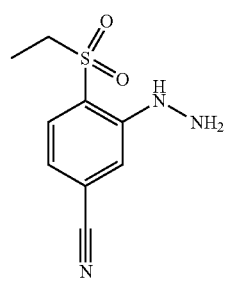

The title compound was synthesized from 3-amino-4-ethylsulfonyl-benzonitrile (Compound g12) under the same conditions as for Compound 28.

Example 394

Compound g14 tert-Butyl 4-[[3-amino-2-chloro-4-[(5-cyano-2-ethylsulfonylanilino)carbamoyl]-6-(trifluoromethyl)phenyl]methyl]piperazine-1-carboxylate

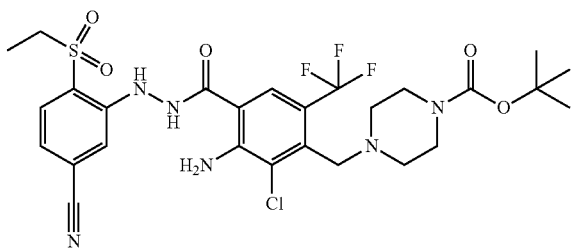 [SMILES: CCS(=O)(=O)c1ccc(C#N)cc1NNC(=O)c1cc(C(F)(F)F)c(CN2CCN(C(=O)OC(C)(C)C)CC2)c(Cl)c1N]

The title compound was synthesized from 4-ethylsulfonyl-3-hydrazino-benzonitrile (Compound g13) and 2-amino-3-chloro-4-[[4-[(2-methylpropan-2-yl)oxycarbonyl]piperazin-1-yl]methyl]-5-(trifluoromethyl)benzoic acid (Compound g6) under the same conditions as for Compound a1.

Example 395

Compound g15 tert-Butyl 4-[[8-chloro-3-(5-cyano-2-ethylsulfonylanilino)-4-oxo-6-(trifluoromethyl)quinazolin-7-yl]methyl]piperazine-1-carboxylate

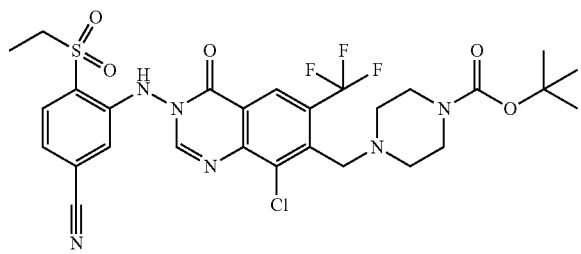 [SMILES: CCS(=O)(=O)c1ccc(C#N)cc1Nn1cnc2c(Cl)c(CN3CCN(C(=O)OC(C)(C)C)CC3)c(C(F)(F)F)cc2c1=O]

The title compound was synthesized from tert-butyl 4-[[3-amino-2-chloro-4-[(5-cyano-2-ethylsulfonylanilino)carbamoyl]-6-(trifluoromethyl)phenyl]methyl]piperazine-1-carboxylate (Compound g14) under the same conditions as for Compound A-28. However, the reaction was performed at 60° C.

Example 396

Compound G-9

3-[[8-Chloro-4-oxo-7-(piperazin-1-ylmethyl)-6-(trifluoromethyl)quinazolin-3-yl]amino]-4-ethylsulfonylbenzonitrile

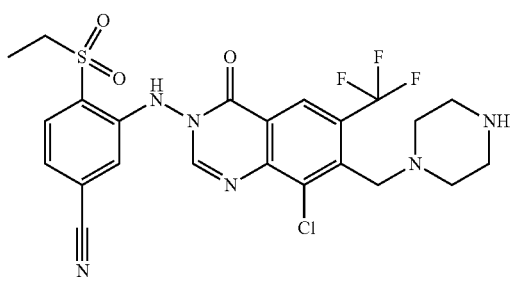 [SMILES: CCS(=O)(=O)c1ccc(C#N)cc1Nn1cnc2c(Cl)c(CN3CCNCC3)c(C(F)(F)F)cc2c1=O]

The title compound was synthesized from tert-butyl 4-[[8-chloro-3-(5-cyano-2-ethylsulfonylanilino)-4-oxo-6-(trifluoromethyl)quinazolin-7-yl]methyl]piperazine-1-carboxylate (Compound g15) under the same conditions as for Compound A-2.

LCMS: m/z 555 [M+H]$^+$

HPLC retention time: 0.52 min (analysis condition D)

Example 397

Compound h1 tert-Butyl N-[6-bromo-7-(bromomethyl)-4-oxoquinazolin-3-yl]-N-(5-chloro-2-ethylsulfonylphenyl)carbamate

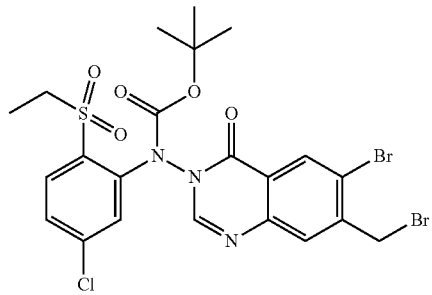 [SMILES: CCS(=O)(=O)c1ccc(Cl)cc1N(C(=O)OC(C)(C)C)n1cnc2cc(CBr)c(Br)cc2c1=O]

The title compound was synthesized from tert-butyl N-(6-bromo-7-methyl-4-oxoquinazolin-3-yl)-N-(5-chloro-2-ethylsulfonylphenyl)carbamate (Compound a12) under the same conditions as for Compound 15.

Example 398

Compound h2 tert-Butyl 4-[[6-bromo-3-[5-chloro-2-ethylsulfonyl-N-[(2-methylpropan-2-yl)oxycarbonyl]anilino]-4-oxoquinazolin-7-yl]methyl]piperazine-1-carboxylate

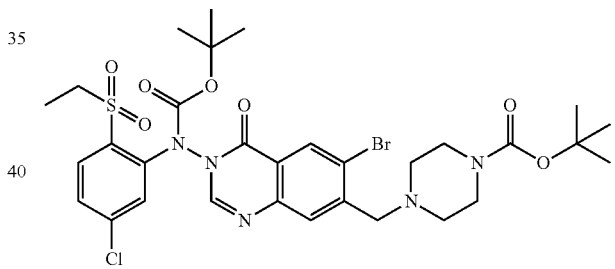

The title compound was synthesized from tert-butyl N-[6-bromo-7-(bromomethyl)-4-oxoquinazolin-3-yl]-N-(5-chloro-2-ethylsulfonylphenyl)carbamate (Compound h1) under the same conditions as for Compound 127.

Example 399

Compound H-1

6-Bromo-3-(5-chloro-2-ethylsulfonylanilino)-7-(piperazin-1-ylmethyl)quinazolin-4-one

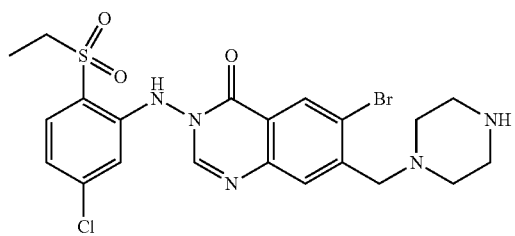

The title compound was synthesized from tert-butyl 4-[[6-bromo-3-[5-chloro-2-ethylsulfonyl-N-[(2-methylpropan-2-yl)oxycarbonyl]anilino]-4-oxoquinazolin-7-yl]methyl]piperazine-1-carboxylate (Compound h2) under the same conditions as for Compound A-2.

LCMS: m/z 540 [M+H]$^+$

HPLC retention time: 1.38 min (analysis condition C)

Example 400

Compound H-2

6-Bromo-3-(5-chloro-2-ethylsulfonylanilino)-7-[(4-methylpiperazin-1-yl)methyl]quinazolin-4-one

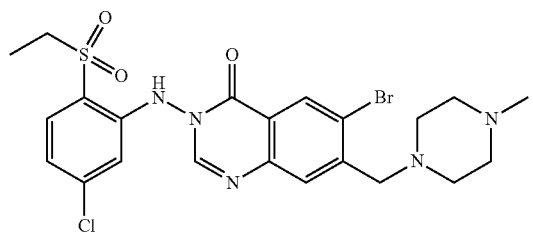 [SMILES: CCS(=O)(=O)c1ccc(Cl)cc1Nn1cnc2cc(CN3CCN(C)CC3)c(Br)cc2c1=O]

The title compound was synthesized from 6-bromo-3-(5-chloro-2-ethylsulfonylanilino)-7-(piperazin-1-ylmethyl)quinazolin-4-one (Compound H-1) under the same conditions as for Compound G-2.

LCMS: m/z 554 [M+H]$^+$

HPLC retention time: 1.93 min (analysis condition E)

Example 401

Compound H-3

6-Bromo-3-(5-chloro-2-ethylsulfonylanilino)-7-[(4-propan-2-ylpiperazin-1-yl)methyl]quinazolin-4-one

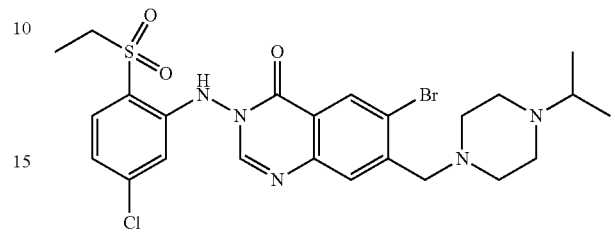

The title compound was synthesized from 6-bromo-3-(5-chloro-2-ethylsulfonylanilino)-7-(piperazin-1-ylmethyl)quinazolin-4-one (Compound H-1) under the same conditions as for Compound G-3. However, 1,2-dichloroethane was used in place of THF as a solvent and the reaction was performed at room temperature.

LCMS: m/z 582 [M+H]$^+$

HPLC retention time: 2.00 min (analysis condition E)

Examples 402 to 411

The following compounds of Table 8 were synthesized by reductive amination using 6-bromo-3-(5-chloro-2-ethylsulfonylanilino)-7-(piperazin-1-ylmethyl)quinazolin-4-one (Compound H-1) and ketones or aldehydes that correspond to respective compounds, under the same conditions as for Compound G-3. However, ethyl acetate was used in place of THF as a solvent.

TABLE 8

| Example | Compound number | Structure | Compound name | HPLC condition | Retention time (min) | m/z [M + H]$^+$ |
|---|---|---|---|---|---|---|
| 402 | H-4 | 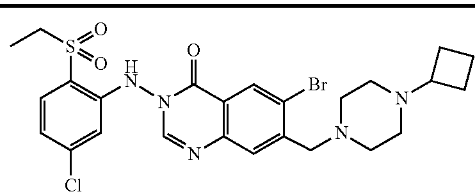 | 6-Bromo-3-(5-chloro-2-ethylsulfonylanilino)-7-[(4-cyclobutylpiperazin-1-yl)methyl]quinazolin-4-one | E | 2.05 | 594 |
| 403 | H-5 | 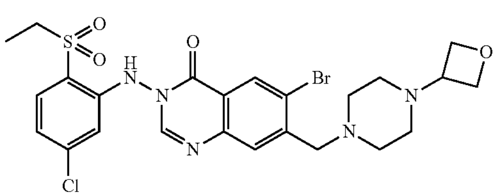 [SMILES: CCS(=O)(=O)c1ccc(Cl)cc1Nn1cnc2cc(CN3CCN(C4COC4)CC3)c(Br)cc2c1=O] | 6-Bromo-3-(5-chloro-2-ethylsulfonylanilino)-7-[[4-(oxetan-3-yl)piperazin-1-yl]methyl]quinazolin-4-one | E | 1.87 | 596 |
| 404 | H-6 | 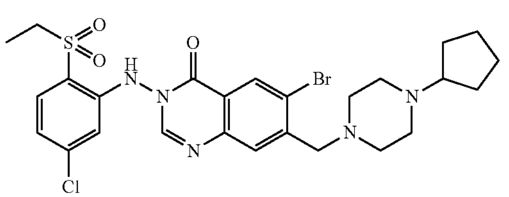 [SMILES: CCS(=O)(=O)c1ccc(Cl)cc1Nn1cnc2cc(CN3CCN(C4CCCC4)CC3)c(Br)cc2c1=O] | 6-Bromo-3-(5-chloro-2-ethylsulfonylanilino)-7-[(4-cyclopentylpiperazin-1-yl)methyl]quinazolin-4-one | E | 2.10 | 608 |

TABLE 8-continued

| Example | Compound number | Structure | Compound name | HPLC condition | Retention time (min) | m/z [M + H]+ |
|---|---|---|---|---|---|---|
| 405 | H-7 | 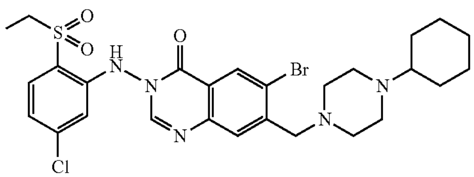 [SMILES: CCS(=O)(=O)c1ccc(Cl)cc1Nn1cnc2cc(CN3CCN(C4CCCCC4)CC3)c(Br)cc2c1=O] | 6-Bromo-3-(5-chloro-2-ethylsulfonylanilino)-7-[(4-cyclohexylpiperazin-1-yl)methyl]quinazolin-4-one | E | 2.18 | 622 |
| 406 | H-8 | 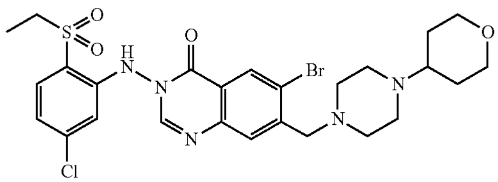 [SMILES: CCS(=O)(=O)c1ccc(Cl)cc1Nn1cnc2cc(CN3CCN(C4CCOCC4)CC3)c(Br)cc2c1=O] | 6-Bromo-3-(5-chloro-2-ethylsulfonylanilino)-7-[[4-(oxan-4-yl)piperazin-1-yl]methyl]quinazolin-4-one | E | 1.97 | 624 |
| 407 | H-9 | 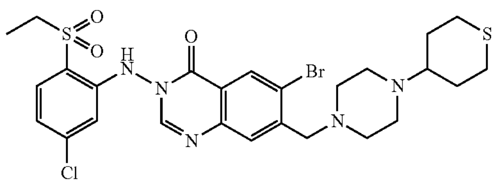 [SMILES: CCS(=O)(=O)c1ccc(Cl)cc1Nn1cnc2cc(CN3CCN(C4CCSCC4)CC3)c(Br)cc2c1=O] | 6-Bromo-3-(5-chloro-2-ethylsulfonylanilino)-7-[[4-(thian-4-yl)piperazin-1-yl]methyl]quinazolin-4-one | E | 2.13 | 640 |
| 408 | H-10 | 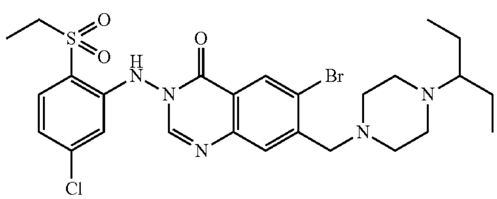 [SMILES: CCC(CC)N1CCN(Cc2cc3ncn(Nc4cc(Cl)ccc4S(=O)(=O)CC)c(=O)c3cc2Br)CC1] | 6-Bromo-3-(5-chloro-2-ethylsulfonylanilino)-7-[(4-pentan-3-ylpiperazin-1-yl)methyl]quinazolin-4-one | E | 2.13 | 610 |
| 409 | H-11 | 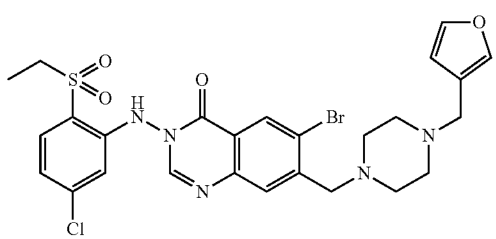 [SMILES: CCS(=O)(=O)c1ccc(Cl)cc1Nn1cnc2cc(CN3CCN(Cc4ccoc4)CC3)c(Br)cc2c1=O] | 6-Bromo-3-(5-chloro-2-ethylsulfonylanilino)-7-[[4-(furan-3-ylmethyl)piperazin-1-yl]methyl]quinazolin-4-one | E | 2.10 | 620 |
| 410 | H-12 | 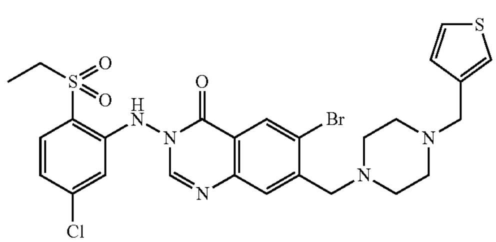 | 6-Bromo-3-(5-chloro-2-ethylsulfonylanilino)-7-[[4-(thiophen-3-ylmethyl)piperazin-1-yl]methyl]quinazolin-4-one | E | 2.17 | 636 |
| 411 | H-13 | 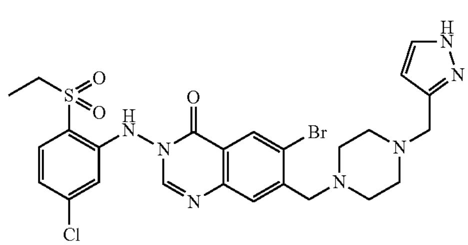 [SMILES: CCS(=O)(=O)c1ccc(Cl)cc1Nn1cnc2cc(CN3CCN(Cc4cc[nH]n4)CC3)c(Br)cc2c1=O] | 6-Bromo-3-(5-chloro-2-ethylsulfonylanilino)-7-[[4-(1H-pyrazol-3-ylmethyl)piperazin-1-yl]methyl]quinazolin-4-one | E | 1.93 | 620 |

Example 412

Compound h3

6-Bromo-3-(5-chloro-2-ethylsulfonylanilino)-7-[[4-(2,2-dimethyl-1,3-dioxan-5-yl)piperazin-1-yl]methyl]quinazolin-4-one

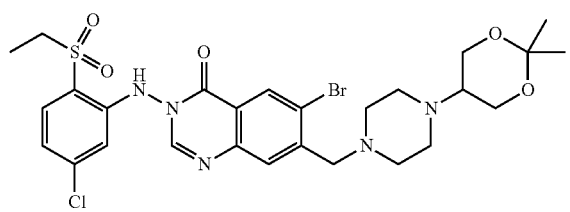 [SMILES: CCS(=O)(=O)c1ccc(Cl)cc1Nn1cnc2cc(CN3CCN(C4COC(C)(C)OC4)CC3)c(Br)cc2c1=O]

The title compound was synthesized from 6-bromo-3-(5-chloro-2-ethylsulfonylanilino)-7-(piperazin-1-ylmethyl)quinazolin-4-one (Compound H-1) under the same conditions as for Compound G-3. However, the reaction was performed using 2,2-dimethyl-1,3-dioxan-5-one in place of acetone, and ethyl acetate in place of THF as a solvent.

Example 413

Compound H-14

6-Bromo-3-(5-chloro-2-ethylsulfonylanilino)-7-[[4-(1,3-dihydroxypropan-2-yl)piperazin-1-yl]methyl]quinazolin-4-one

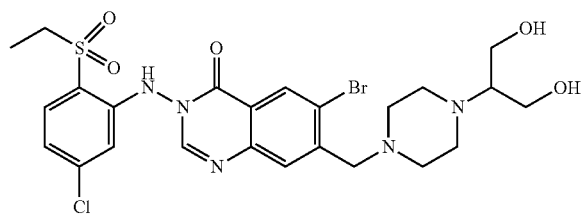 [SMILES: CCS(=O)(=O)c1ccc(Cl)cc1Nn1cnc2cc(CN3CCN(C(CO)CO)CC3)c(Br)cc2c1=O]

A 1 N aqueous hydrochloric acid solution (0.20 ml) was added to a solution of 6-bromo-3-(5-chloro-2-ethylsulfonylanilino)-7-[[4-(2,2-dimethyl-1,3-dioxan-5-yl)piperazin-1-yl]methyl]quinazolin-4-one (Compound h3, 21.5 mg, 32.8 μmol) in methanol (1 ml), and the mixture was stirred at room temperature for 45 minutes, warmed to 50° C. and stirred for one hour. The reaction solution was cooled to room temperature and diluted with DMSO, followed by purification by preparative HPLC (water/acetonitrile, 0.05% TFA) to give the title compound (17.0 mg, 84%) as a white solid.

LCMS: m/z 614 [M+H]$^+$

HPLC retention time: 1.85 min (analysis condition E)

Example 414

Compound h4 tert-Butyl 3-[4-[[6-bromo-3-(5-chloro-2-ethylsulfonylanilino)-4-oxoquinazolin-7-yl]methyl]piperazin-1-yl]azetidine-1-carboxylate

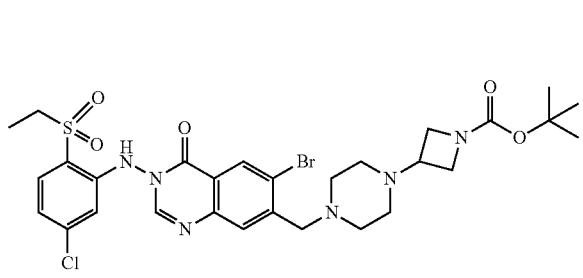 [SMILES: CCS(=O)(=O)c1ccc(Cl)cc1Nn1cnc2cc(CN3CCN(C4CN(C(=O)OC(C)(C)C)C4)CC3)c(Br)cc2c1=O]

The title compound was synthesized from 6-bromo-3-(5-chloro-2-ethylsulfonylanilino)-7-(piperazin-1-ylmethyl)quinazolin-4-one (Compound H-1) under the same conditions as for Compound G-3. However, the reaction was performed using 1-Boc-3-azetidinone in place of acetone.

Example 415

Compound H-15

7-[[4-(Azetidin-3-yl)piperazin-1-yl]methyl]-6-bromo-3-(5-chloro-2-ethylsulfonylanilino)quinazolin-4-one

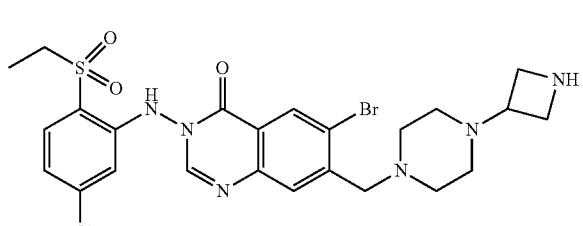

The title compound was synthesized from tert-butyl 3-[4-[[6-bromo-3-(5-chloro-2-ethylsulfonylanilino)-4-oxoquinazolin-7-yl]methyl]piperazin-1-yl]azetidine-1-carboxylate (Compound h4) under the same conditions as for Compound 21.

LCMS: m/z 595 [M+H]$^+$

HPLC retention time: 1.60 min (analysis condition E)

Example 416

Compound H-16

6-Bromo-3-(5-chloro-2-ethylsulfonylanilino)-7-[[4-(2-methoxyethyl)piperazin-1-yl]methyl]quinazolin-4-one

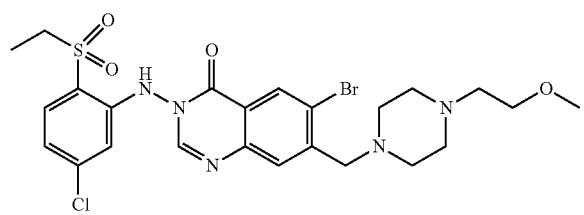 [SMILES: CCS(=O)(=O)c1ccc(Cl)cc1Nn1cnc2cc(CN3CCN(CCOC)CC3)c(Br)cc2c1=O]

A solution of 6-bromo-3-(5-chloro-2-ethylsulfonylanilino)-7-(piperazin-1-ylmethyl)quinazolin-4-one (Compound H-1, 29.8 mg, 55.0 μmol) in DMF (1 ml) was cooled to 0° C., sodium hydride (>61% oil, 4.0 mg, 102 μmol) was added, and the mixture was stirred at 0° C. After 5 minutes, 1-bromo-2-methoxyethane (9.2 μl, 96.7 μmol) was added, and the mixture was stirred at 50° C. for 15 hours. After the reaction mixture was cooled to room temperature, a saturated aqueous sodium chloride solution was added thereto, and extraction was performed with ethyl acetate. The organic layer was washed with a saturated aqueous sodium chloride solution and then dried over anhydrous magnesium sulfate. After the drying agent was removed by filtration, concentration was performed under reduced pressure. The resulting residue was purified by preparative HPLC (water/acetonitrile, 0.05% TFA) to give the title compound (9.2 mg, 28%) as a yellow solid.

LCMS: m/z 598 [M+H]$^+$

HPLC retention time: 1.98 min (analysis condition E)

Example 417

Compound H-17

6-Bromo-3-(5-chloro-2-ethylsulfonylanilino)-7-[(4-methylsulfonylpiperazin-1-yl)methyl]quinazolin-4-one

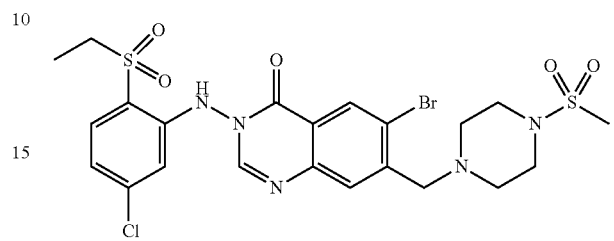

A solution of 6-bromo-3-(5-chloro-2-ethylsulfonylanilino)-7-(piperazin-1-ylmethyl)quinazolin-4-one (Compound H-1, 28.8 mg, 53.2 μmol) in pyridine (1 ml) was cooled to 0° C., methanesulfonyl chloride (4.5 μl, 58.1 μmol) was added, and the mixture was stirred at 0° C. for two hours. A saturated aqueous ammonium chloride solution was added to the reaction mixture, and extraction was performed with ethyl acetate. The organic layer was washed with a saturated aqueous sodium chloride solution and then dried over anhydrous sodium sulfate. After the drying agent was removed by filtration, concentration was performed under reduced pressure. The resulting residue was purified by preparative HPLC (water/acetonitrile, 0.05% TFA) to give the title compound (17.0 mg, 52%) as a brown solid.

LCMS: m/z 618 [M+H]$^+$

HPLC retention time: 1.95 min (analysis condition E)

Examples 418 to 420

The following compounds of Table 9 were synthesized using 6-bromo-3-(5-chloro-2-ethylsulfonylanilino)-7-(piperazin-1-ylmethyl)quinazolin-4-one (Compound H-1) and sulfonic acid chlorides that correspond to respective compounds under the same conditions as for Compound H-17. However, the reaction was performed at room temperature.

TABLE 9

| Example | Compound number | Structure | Compound name | HPLC condition | Retention time (min) | m/z [M + H]$^+$ |
|---|---|---|---|---|---|---|
| 418 | H-18 | 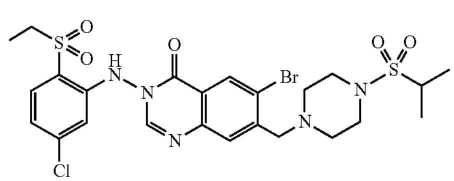 [SMILES: CCS(=O)(=O)c1ccc(Cl)cc1Nn1cnc2cc(CN3CCN(S(=O)(=O)C(C)C)CC3)c(Br)cc2c1=O] | 6-Bromo-3-(5-chloro-2-ethylsulfonylanilino)-7-[(4-propan-2-ylsulfonylpiperazin-1-yl)methyl]quinazolin-4-one | E | 2.10 | 646 |
| 419 | H-19 | 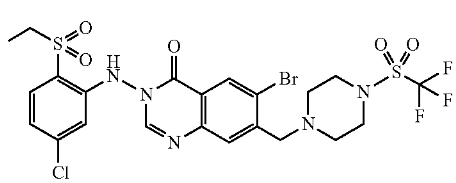 [SMILES: CCS(=O)(=O)c1ccc(Cl)cc1Nn1cnc2cc(CN3CCN(S(=O)(=O)C(F)(F)F)CC3)c(Br)cc2c1=O] | 6-Bromo-3-(5-chloro-2-ethylsulfonylanilino)-7-[[4-(trifluoromethylsulfonyl)piperazin-1-yl]methyl]quinazolin-4-one | E | 2.75 | 672 |

TABLE 9-continued

| Example | Compound number | Structure | Compound name | HPLC condition | Retention time (min) | m/z [M + H]+ |
|---|---|---|---|---|---|---|
| 420 | H-20 | 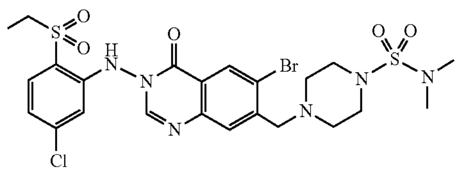 [SMILES: CCS(=O)(=O)c1ccc(Cl)cc1Nn1cnc2cc(CN3CCN(S(=O)(=O)N(C)C)CC3)c(Br)cc2c1=O] | 4-[[6-Bromo-3-(5-chloro-2-ethylsulfonylanilino)-4-oxoquinazolin-7-yl]methyl]-N,N-dimethylpiperazine-1-sulfonamide | E | 2.05 | 647 |

Examples 421 to 433

The following compounds of Table 10 were synthesized from tert-butyl N-[6-bromo-7-(bromomethyl)-4-oxoquinazolin-3-yl]-N-(5-chloro-2-ethylsulfonylphenyl)carbamate (Compound h1) under the same conditions as for Compounds h2 and H-1. However, amines that correspond to respective compounds were used in place of tert-butyl piperazine-1-carboxylate under the conditions of the substitution reaction for Compound h2.

TABLE 10

| Example | Compound number | Structure | Compound name | HPLC condition | Retention time (min) | m/z [M + H]+ |
|---|---|---|---|---|---|---|
| 421 | H-21 | 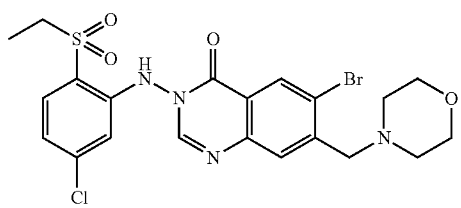 [SMILES: CCS(=O)(=O)c1ccc(Cl)cc1Nn1cnc2cc(CN3CCOCC3)c(Br)cc2c1=O] | 6-Bromo-3-(5-chloro-2-ethylsulfonylanilino)-7-(morpholin-4-ylmethyl)quinazolin-4-one | C | 1.37 | 541 |
| 422 | H-22 | 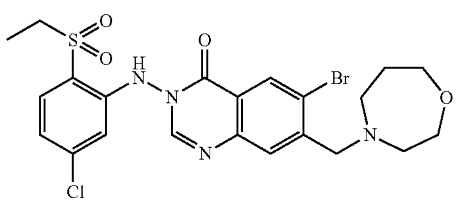 [SMILES: CCS(=O)(=O)c1ccc(Cl)cc1Nn1cnc2cc(CN3CCCOCC3)c(Br)cc2c1=O] | 6-Bromo-3-(5-chloro-2-ethylsulfonylanilino)-7-(1,4-oxazepan-4-ylmethyl)quinazolin-4-one | C | 1.30 | 555 |
| 423 | H-23 | 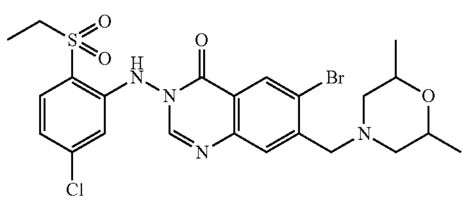 [SMILES: CCS(=O)(=O)c1ccc(Cl)cc1Nn1cnc2cc(CN3CC(C)OC(C)C3)c(Br)cc2c1=O] | 6-Bromo-3-(5-chloro-2-ethylsulfonylanilino)-7-[(2,6-dimethylmorpholin-4-yl)methyl]quinazolin-4-one | C | 1.43 | 569 |
| 424 | H-29 | 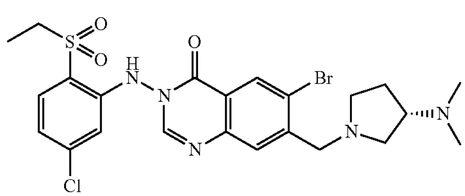 [SMILES: CCS(=O)(=O)c1ccc(Cl)cc1Nn1cnc2cc(CN3CC[C@H](N(C)C)C3)c(Br)cc2c1=O] | 6-Bromo-3-(5-chloro-2-ethylsulfonylanilino)-7-[[(3S)-3-(dimethylamino)pyrrolidin-1-yl]methyl]quinazolin-4-one | G | 0.50 | 568 |
| 425 | H-30 | 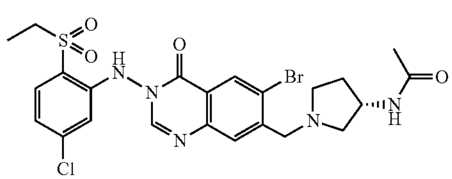 [SMILES: CCS(=O)(=O)c1ccc(Cl)cc1Nn1cnc2cc(CN3CC[C@H](NC(C)=O)C3)c(Br)cc2c1=O] | N-[(3S)-1-[[6-Bromo-3-(5-chloro-2-ethylsulfonylanilino)-4-oxoquinazolin-7-yl]methyl]pyrrolidin-3-yl]acetamide | G | 0.50 | 582 |

TABLE 10-continued

| Example | Compound number | Structure | Compound name | HPLC condition | Retention time (min) | m/z [M + H]+ |
|---|---|---|---|---|---|---|
| 426 | H-31 | 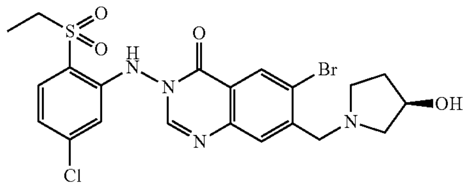 [SMILES: CCS(=O)(=O)c1ccc(Cl)cc1Nn1cnc2cc(CN3CC[C@@H](O)C3)c(Br)cc2c1=O] | 6-Bromo-3-(5-chloro-2-ethylsulfonylanilino)-7-[[(3S)-3-hydroxypyrrolidin-1-yl]methyl]quinazolin-4-one | G | 0.50 | 541 |
| 427 | H-32 | 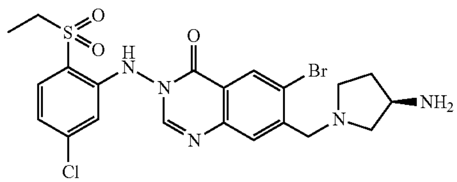 [SMILES: CCS(=O)(=O)c1ccc(Cl)cc1Nn1cnc2cc(CN3CC[C@@H](N)C3)c(Br)cc2c1=O] | 7-[[(3R)-3-Aminopyrrolidin-1-yl]methyl]-6-bromo-3-(5-chloro-2-ethylsulfonylanilino)quinazolin-4-one | G | 0.44 | 540 |
| 428 | H-33 | 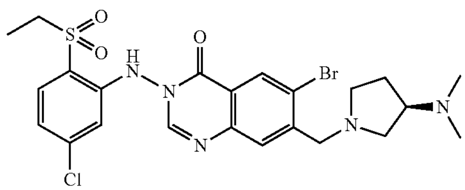 [SMILES: CCS(=O)(=O)c1ccc(Cl)cc1Nn1cnc2cc(CN3CC[C@@H](N(C)C)C3)c(Br)cc2c1=O] | 6-Bromo-3-(5-chloro-2-ethylsulfonylanilino)-7-[[(3R)-3-(dimethylamino)pyrrolidin-1-yl]methyl]quinazolin-4-one | G | 0.48 | 568 |
| 429 | H-34 | 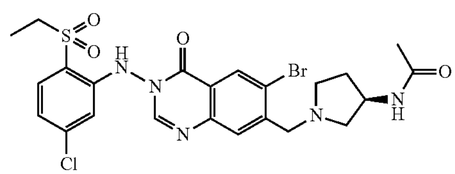 [SMILES: CCS(=O)(=O)c1ccc(Cl)cc1Nn1cnc2cc(CN3CC[C@@H](NC(C)=O)C3)c(Br)cc2c1=O] | N-[(3R)-1-[[6-Bromo-3-(5-chloro-2-ethylsulfonylanilino)-4-oxoquinazolin-7-yl]methyl]pyrrolidin-3-yl]acetamide | G | 0.50 | 582 |
| 430 | H-35 | 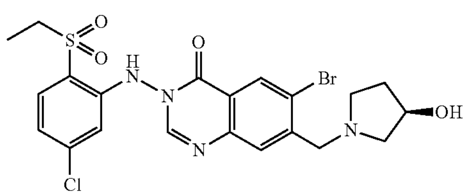 [SMILES: CCS(=O)(=O)c1ccc(Cl)cc1Nn1cnc2cc(CN3CC[C@@H](O)C3)c(Br)cc2c1=O] | 6-Bromo-3-(5-chloro-2-ethylsulfonylanilino)-7-[[(3R)-3-hydroxypyrrolidin-1-yl]methyl]quinazolin-4-one | F | 0.50 | 541 |
| 431 | H-36 | 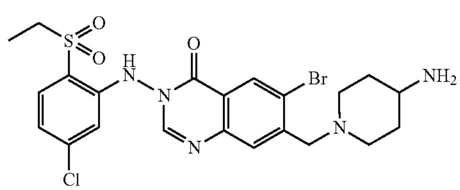 [SMILES: CCS(=O)(=O)c1ccc(Cl)cc1Nn1cnc2cc(CN3CCC(N)CC3)c(Br)cc2c1=O] | 7-[(4-Aminopiperidin-1-yl)methyl]-6-bromo-3-(5-chloro-2-ethylsulfonylanilino)quinazolin-4-one | G | 0.44 | 554 |
| 432 | H-37 | 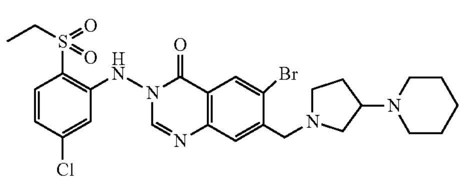 [SMILES: CCS(=O)(=O)c1ccc(Cl)cc1Nn1cnc2cc(CN3CCC(N4CCCCC4)C3)c(Br)cc2c1=O] | 6-Bromo-3-(5-chloro-2-ethylsulfonylanilino)-7-[(3-piperidin-1-ylpyrrolidin-1-yl)methyl]quinazolin-4-one | G | 0.51 | 608 |
| 433 | H-38 | 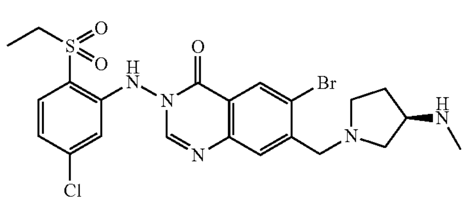 [SMILES: CCS(=O)(=O)c1ccc(Cl)cc1Nn1cnc2cc(CN3CC[C@@H](NC)C3)c(Br)cc2c1=O] | 6-Bromo-3-(5-chloro-2-ethylsulfonylanilino)-7-[[(3R)-3-(methylamino)pyrrolidin-1-yl]methyl]quinazolin-4-one | F | 0.45 | 554 |

Example 434

Compound h5 tert-Butyl N-[6-bromo-7-[[(3S)-3-[(2-methylpropan-2-yl)oxycarbonylamino]pyrrolidin-1-yl]methyl]-4-oxoquinazolin-3-yl]-N-(5-chloro-2-ethylsulfonylphenyl)carbamate

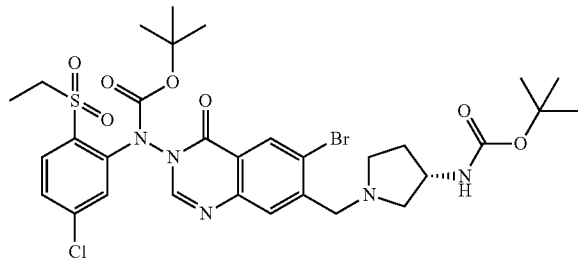 [SMILES: CCS(=O)(=O)c1ccc(Cl)cc1N(C(=O)OC(C)(C)C)n1cnc2cc(CN3CC[C@H](NC(=O)OC(C)(C)C)C3)c(Br)cc2c1=O]

The title compound was synthesized from tert-butyl N-[6-bromo-7-(bromomethyl)-4-oxoquinazolin-3-yl]-N-(5-chloro-2-ethylsulfonylphenyl)carbamate (Compound h1) under the same conditions as for Compound 127. However, tert-butyl N-[(3S)-pyrrolidin-3-yl]carbamate was used in place of tert-butyl piperazine-1-carboxylate amine.

Example 435

Compound H-24

7-[[(3S)-3-aminopyrrolidin-1-yl]methyl]-6-bromo-3-(5-chloro-2-ethylsulfonylanilino)quinazolin-4-one

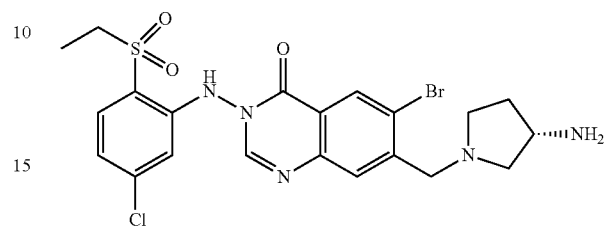

The title compound was synthesized from tert-butyl N-[6-bromo-7-[[(3S)-3-[(2-methylpropan-2-yl)oxycarbonylamino]pyrrolidin-1-yl]methyl]-4-oxoquinazolin-3-yl]-N-(5-chloro-2-ethylsulfonylphenyl)carbamate (Compound h5) under the same conditions as for Compound 21.

LCMS: m/z 540 [M+H]$^+$

HPLC retention time: 0.40 min (analysis condition F)

Examples 436 to 439

The following compounds of Table 11 were synthesized from tert-butyl N-[6-bromo-7-(bromomethyl)-4-oxoquinazolin-3-yl]-N-(5-chloro-2-ethylsulfonylphenyl)carbamate (Compound h1) under the same conditions as for Compounds h5 and H-24. However, amines that correspond to respective compounds were used in place of tert-butyl N-[(3S)-pyrrolidin-3-yl]carbamate under the conditions of the substitution reaction for Compound h5.

TABLE 11

| Example | Compound number | Structure | Compound name | HPLC condition | Retention time (min) | m/z [M + H]$^+$ |
|---|---|---|---|---|---|---|
| 436 | H-25 | 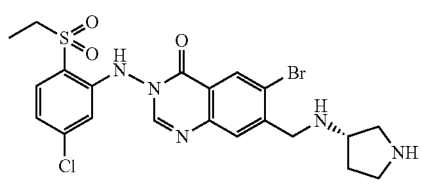 [SMILES: CCS(=O)(=O)c1ccc(Cl)cc1Nn1cnc2cc(CN[C@H]3CCNC3)c(Br)cc2c1=O] | 6-Bromo-3-(5-chloro-2-ethylsulfonylanilino)-7-[[[(3S)-pyrrolidin-3-yl]amino]methyl]quinazolin-4-one | F | 0.38 | 540 |
| 437 | H-26 | 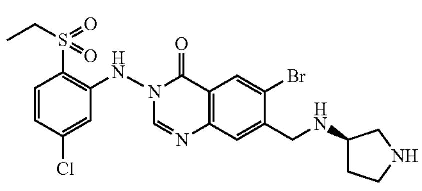 [SMILES: CCS(=O)(=O)c1ccc(Cl)cc1Nn1cnc2cc(CN[C@@H]3CCNC3)c(Br)cc2c1=O] | 6-Bromo-3-(5-chloro-2-ethylsulfonylanilino)-7-[[[(3R)-pyrrolidin-3-yl]amino]methyl]quinazolin-4-one | F | 0.39 | 540 |
| 438 | H-27 | 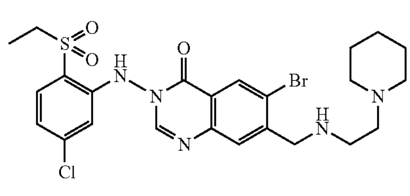 [SMILES: CCS(=O)(=O)c1ccc(Cl)cc1Nn1cnc2cc(CNCCN3CCCCC3)c(Br)cc2c1=O] | 6-Bromo-3-(5-chloro-2-ethylsulfonylanilino)-7-[(2-piperidin-1-ylethylamino)methyl]quinazolin-4-one | F | 0.41 | 582 |

TABLE 11-continued

| Example | Compound number | Structure | Compound name | HPLC condition | Retention time (min) | m/z [M + H]+ |
|---|---|---|---|---|---|---|
| 439 | H-28 | 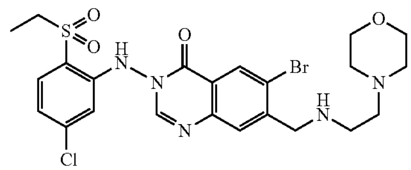 [SMILES: CCS(=O)(=O)c1ccc(Cl)cc1Nn1cnc2cc(CNCCN3CCOCC3)c(Br)cc2c1=O] | 6-Bromo-3-(5-chloro-2-ethylsulfonylanilino)-7-[(2-morpholin-4-ylethylamino)methyl]quinazolin-4-one | F | 0.42 | 584 |

Example 440

Compound H-39

N-[(3R)-1-[[6-bromo-3-(5-chloro-2-ethylsulfonylanilino)-4-oxoquinazolin-7-yl]methyl]pyrrolidin-3-yl]-N-methylacetamide Acetic anhydride (5.3 μl, 56.1 μmol) was added to a solution of 6-bromo-3-(5-chloro-2-ethylsulfonylanilino)-7-[[(3R)-3-(methylamino)pyrrolidin-1-yl]methyl]quinazolin-4-one (Compound H-38, 20.9 mg, 37.7 μmol) and triethylamine (15.8 μl, 0.113 μmol) in DMF (1 ml), and the mixture was stirred at room temperature for one hour. The reaction mixture was diluted with DMSO and water and purified by preparative HPLC (water/acetonitrile, 0.05% TFA) to give the title compound (18.0 mg, 80%) as a white solid.

LCMS: m/z 596 [M+H]+

HPLC retention time: 0.48 min (analysis condition F)

Example 441

Compound H-40

7-[(4-Acetylpiperazin-1-yl)methyl]-6-bromo-3-(5-chloro-2-ethylsulfonylanilino)quinazolin-4-one The title compound was synthesized from 6-bromo-3-(5-chloro-2-ethylsulfonylanilino)-7-(piperazin-1-ylmethyl)quinazolin-4-one (Compound H-1) under the same conditions as for Compound H-39.

LCMS: m/z 582 [M+H]+

HPLC retention time: 1.75 min (analysis condition E)

Example 442

Compound h6 tert-Butyl N-(6-bromo-7-methyl-4-oxoquinazolin-3-yl)-N-(5-cyano-2-ethylsulfanylphenyl)carbamate The title compound was synthesized from 3-[(6-bromo-7-methyl-4-oxoquinazolin-3-yl)amino]-4-ethylsulfanylbenzonitrile (Compound C-5) under the same conditions as for Compound a6.

Example 443

Compound h7 tert-Butyl N-(6-bromo-7-methyl-4-oxoquinazolin-3-yl)-N-(5-cyano-2-ethylsulfonylphenyl)carbamate The title compound was synthesized from tert-butyl N-(6-bromo-7-methyl-4-oxoquinazolin-3-yl)-N-(5-cyano-2-ethylsulfanylphenyl)carbamate (Compound h6) under the same conditions as for Compound 14.

Example 444

Compound H-41

3-[[6-Bromo-4-oxo-7-(piperazin-1-ylmethyl)quinazolin-3-yl]amino]-4-ethylsulfonylbenzonitrile

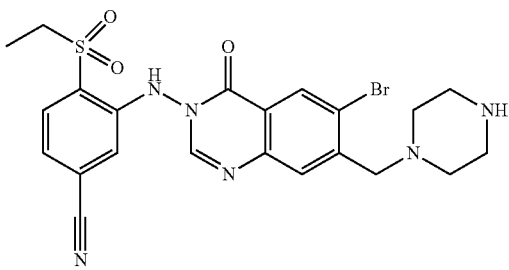 [SMILES: CCS(=O)(=O)c1ccc(C#N)cc1Nn1cnc2cc(CN3CCNCC3)c(Br)cc2c1=O]

The title compound was synthesized from tert-butyl N-(6-bromo-7-methyl-4-oxoquinazolin-3-yl)-N-(5-cyano-2-ethylsulfonylphenyl)carbamate (Compound h7) under the same conditions as for Compounds h1, h2, and H-1.

LCMS: m/z 531 [M+H]$^+$

HPLC retention time: 0.47 min (analysis condition D)

Example 445

Compound h8

2-Amino-3,5-dibromo-4-methylbenzoic Acid

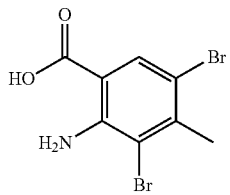

The title compound was synthesized from ethyl 2-amino-3,5-dibromo-4-methylbenzoate (Compound 132) under the same conditions as for Compound 85. However, potassium hydroxide was used in place of sodium hydroxide.

Example 446

Compound h9

2-Amino-3,5-dibromo-N'-(5-chloro-2-ethylsulfanylphenyl)-4-methylbenzohydrazide

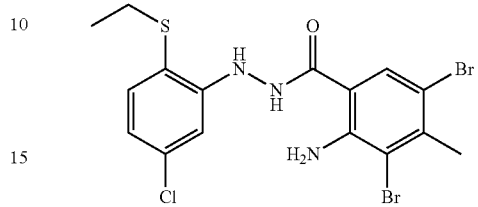

The title compound was synthesized from (5-chloro-2-ethylsulfanylphenyl)hydrazine (Compound 30) and 2-amino-3,5-dibromo-4-methylbenzoic acid (Compound h8) under the same conditions as for Compound e8. However, WSCDI was used in place of HBTU, and DMF was used in place of dichloromethane as a solvent.

Example 447

Compound h10

6,8-Dibromo-3-(5-chloro-2-ethylsulfanylanilino)-7-methylquinazolin-4-one

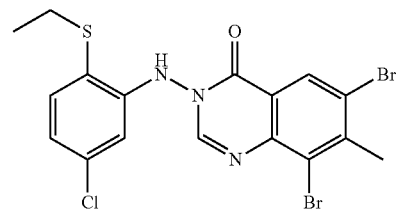 [SMILES: CCSc1ccc(Cl)cc1Nn1cnc2c(Br)c(C)c(Br)cc2c1=O]

The title compound was synthesized from 2-amino-3,5-dibromo-N'-(5-chloro-2-ethylsulfanylphenyl)-4-methylbenzohydrazide (Compound h9) under the same conditions as for Compound A-28.

Example 448

Compound h11

6,8-Dibromo-3-(5-chloro-2-ethylsulfonylanilino)-7-methylquinazolin-4-one

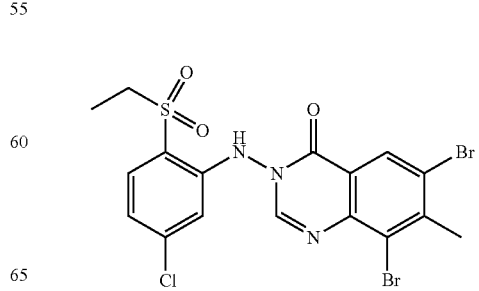

The title compound was synthesized from 6,8-dibromo-3-(5-chloro-2-ethylsulfanylanilino)-7-methylquinazolin-4-one (Compound h10) under the same conditions as for Compound 14.

Example 449

Compound h12 tert-Butyl N-(5-chloro-2-ethylsulfonylphenyl)-N-(6,8-dibromo-7-methyl-4-oxoquinazolin-3-yl)carbamate

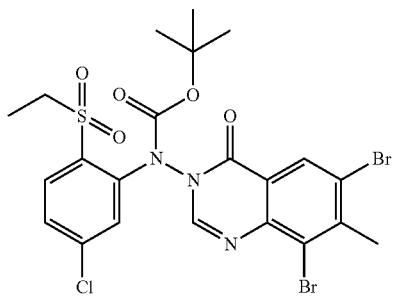 [SMILES: CCS(=O)(=O)c1ccc(Cl)cc1N(C(=O)OC(C)(C)C)n1cnc2c(Br)c(C)c(Br)cc2c1=O]

The title compound was synthesized from 6,8-dibromo-3-(5-chloro-2-ethylsulfonylanilino)-7-methylquinazolin-4-one (Compound h11) under the same conditions as for Compound a6.

Example 450

Compound H-42

6,8-Dibromo-3-(5-chloro-2-ethylsulfonylanilino)-7-(piperazin-1-ylmethyl)quinazolin-4-one

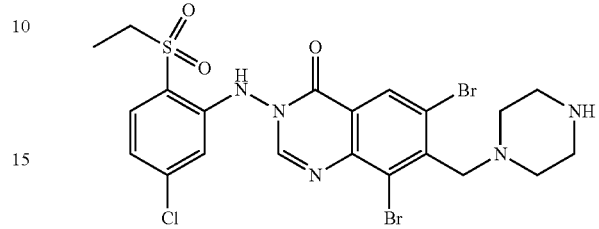

The title compound was synthesized from tert-butyl N-(5-chloro-2-ethylsulfonylphenyl)-N-(6,8-dibromo-7-methyl-4-oxoquinazolin-3-yl)carbamate (Compound h12) under the same conditions as for Compounds h1, h2, and H-1.
LCMS: m/z 618 [M+H]$^+$
HPLC retention time: 0.54 min (analysis condition D)

Examples 451 to 454

The following compounds of Table 12 were synthesized using 6,8-dibromo-3-(5-chloro-2-ethylsulfonylanilino)-7-(piperazin-1-ylmethyl)quinazolin-4-one (Compound H-42) and ketones or aldehydes that correspond to respective compounds, under the same conditions as for Compound G-3. However, 1,4-dioxane was used in place of THF as a solvent, and the reaction was performed under microwave irradiation at 90° C.

TABLE 12

| Example | Compound number | Structure | Compound name | HPLC condition | Retention time (min) | m/z [M + H]$^+$ |
|---|---|---|---|---|---|---|
| 451 | H-43 | 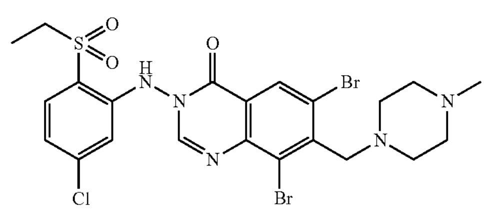 [SMILES: CCS(=O)(=O)c1ccc(Cl)cc1Nn1cnc2c(Br)c(CN3CCN(C)CC3)c(Br)cc2c1=O] | 6,8-Dibromo-3-(5-chloro-2-ethylsulfonylanilino)-7-[(4-methylpiperazin-1-yl)methyl]quinazolin-4-one | E | 2.02 | 632 |
| 452 | H-44 | 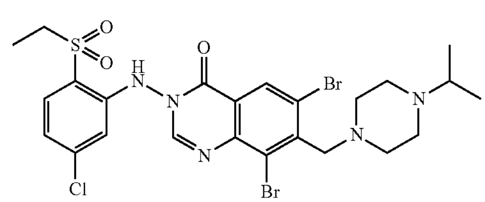 [SMILES: CCS(=O)(=O)c1ccc(Cl)cc1Nn1cnc2c(Br)c(CN3CCN(C(C)C)CC3)c(Br)cc2c1=O] | 6,8-Dibromo-3-(5-chloro-2-ethylsulfonylanilino)-7-[(4-propan-2-ylpiperazin-1-yl)methyl]quinazolin-4-one | D | 0.58 | 660 |
| 453 | H-45 | 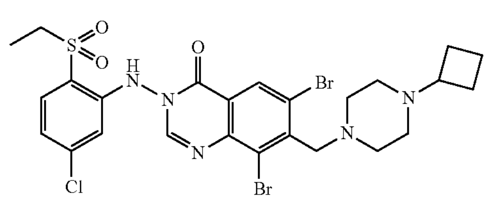 [SMILES: CCS(=O)(=O)c1ccc(Cl)cc1Nn1cnc2c(Br)c(CN3CCN(C4CCC4)CC3)c(Br)cc2c1=O] | 6,8-Dibromo-3-(5-chloro-2-ethylsulfonylanilino)-7-[(4-cyclobutylpiperazin-1-yl)methyl]quinazolin-4-one | D | 0.58 | 672 |

TABLE 12-continued

| Example | Compound number | Structure | Compound name | HPLC condition | Retention time (min) | m/z [M + H]+ |
|---|---|---|---|---|---|---|
| 454 | H-46 | 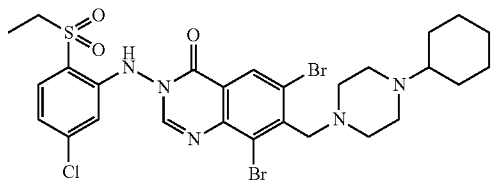 [SMILES: CCS(=O)(=O)c1ccc(Cl)cc1Nn1cnc2c(Br)c(CN3CCN(C4CCCCC4)CC3)c(Br)cc2c1=O] | 6,8-Dibromo-3-(5-chloro-2-ethylsulfonylanilino)-7-[(4-cyclohexylpiperazin-1-yl)methyl]quinazolin-4-one | D | 0.63 | 700 |

Example 455

Compound h13

Ethyl 2-amino-5-bromo-3-chloro-4-methylbenzoate

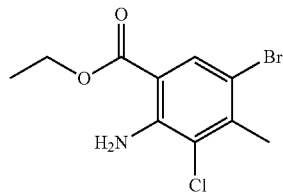

The title compound was synthesized from ethyl 2-amino-5-bromo-4-methylbenzoate (Compound 130) under the same conditions as for Compound 111. However, the reaction was performed at room temperature.

Example 456

Compound h14 tert-Butyl N-(6-bromo-8-chloro-7-methyl-4-oxoquinazolin-3-yl)-N-(5-chloro-2-ethylsulfonylphenyl)carbamate

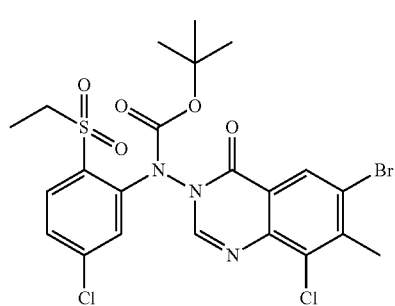 [SMILES: CCS(=O)(=O)c1ccc(Cl)cc1N(C(=O)OC(C)(C)C)n1cnc2c(Cl)c(C)c(Br)cc2c1=O]

The title compound was synthesized from ethyl 2-amino-5-bromo-3-chloro-4-methylbenzoate (Compound h13) under the same conditions as for Compounds h8, h9, h10, h11, and h12.

Example 457

Compound H-47

6-Bromo-8-chloro-3-(5-chloro-2-ethylsulfonylanilino)-7-(piperazin-1-ylmethyl)quinazolin-4-one The title compound was synthesized from tert-butyl N-(6-bromo-8-chloro-7-methyl-4-oxoquinazolin-3-yl)-N-(5-chloro-2-ethylsulfonylphenyl)carbamate (Compound h14) under the same conditions as for Compounds h1, h2, and H-1.

LCMS: m/z 574 [M+H]+

HPLC retention time: 0.54 min (analysis condition D)

Examples 458 to 460

The following compounds of Table 13 were synthesized using 6-bromo-8-chloro-3-(5-chloro-2-ethylsulfonylanilino)-7-(piperazin-1-ylmethyl)quinazolin-4-one (Compound H-47) and ketones or aldehydes that correspond to respective compounds, under the same conditions as for Compound G-3. However, 1,2-dichloroethane was used in place of THF as a solvent, and the reaction was performed under microwave irradiation at 85° C.

TABLE 13

| Example | Compound number | Structure | Compound name | HPLC condition | Retention time (min) | m/z [M + H]+ |
|---|---|---|---|---|---|---|
| 458 | H-48 | 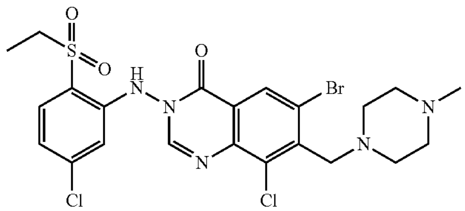 [SMILES: CCS(=O)(=O)c1ccc(Cl)cc1Nn1cnc2c(Cl)c(CN3CCN(C)CC3)c(Br)cc2c1=O] | 6-Bromo-8-chloro-3-(5-chloro-2-ethylsulfonylanilino)-7-[(4-methylpiperazin-1-yl)methyl]quinazolin-4-one | D | 0.55 | 588 |
| 459 | H-49 | 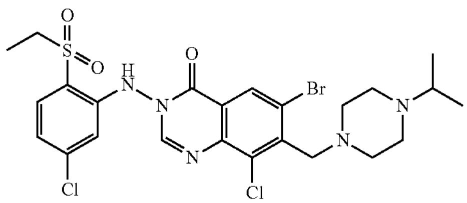 [SMILES: CCS(=O)(=O)c1ccc(Cl)cc1Nn1cnc2c(Cl)c(CN3CCN(C(C)C)CC3)c(Br)cc2c1=O] | 6-Bromo-8-chloro-3-(5-chloro-2-ethylsulfonylanilino)-7-[(4-propan-2-ylpiperazin-1-yl)methyl]quinazolin-4-one | D | 0.57 | 616 |
| 460 | H-50 | 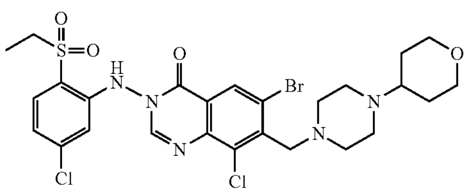 [SMILES: CCS(=O)(=O)c1ccc(Cl)cc1Nn1cnc2c(Cl)c(CN3CCN(C4CCOCC4)CC3)c(Br)cc2c1=O] | 6-Bromo-8-chloro-3-(5-chloro-2-ethylsulfonylanilino)-7-[[4-(oxan-4-yl)piperazin-1-yl]methyl]quinazolin-4-one | D | 0.56 | 658 |

Example 461

Compound i1 tert-Butyl 4-[[5-amino-4-[(5-chloro-2-ethylsulfonylphenyl)methylcarbamoyl]-2-(trifluoromethyl)phenyl]methyl]piperazine-1-carboxylate

Example 462

Compound i2 tert-Butyl 4-[[3-[(5-chloro-2-ethylsulfonylphenyl)methyl]-4-oxo-6-(trifluoromethyl)quinazolin-7-yl]methyl]piperazine-1-carboxylate

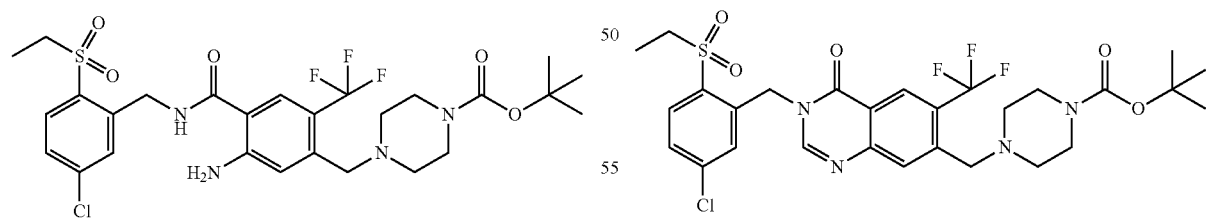

The title compound was synthesized from (5-chloro-2-ethylsulfonylphenyl)methanamine (a free form of Compound 3) and 2-amino-4-[[4-[(2-methylpropan-2-yl)oxycarbonyl]piperazin-1-yl]methyl]-5-(trifluoromethyl)benzoic acid (Compound g2) under the same conditions as for Compound a1.

The title compound was synthesized from tert-butyl 4-[[5-amino-4-[(5-chloro-2-ethylsulfonylphenyl)methylcarbamoyl]-2-(trifluoromethyl)phenyl]methyl]piperazine-1-carboxylate (Compound i1) under the same conditions as for Compound A-28.

Example 463

Compound I-1

3-[(5-Chloro-2-ethylsulfonylphenyl)methyl]-7-(piperazin-1-ylmethyl)-6-(trifluoromethyl)quinazolin-4-one

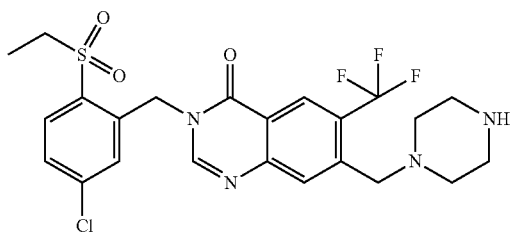 [SMILES: CCS(=O)(=O)c1ccc(Cl)cc1Cn1cnc2cc(CN3CCNCC3)c(C(F)(F)F)cc2c1=O]

The title compound was synthesized from tert-butyl 4-[[3-[(5-chloro-2-ethylsulfonylphenyl)methyl]-4-oxo-6-(trifluoromethyl)quinazolin-7-yl]methyl]piperazine-1-carboxylate (Compound i2) under the same conditions as for Compound A-2.

LCMS: m/z 529 [M+H]$^+$

HPLC retention time: 0.53 min (analysis condition D)

Example 464

Compound I-2

3-[(5-Chloro-2-ethylsulfonylphenyl)methyl]-7-[(4-methylpiperazin-1-yl)methyl]-6-(trifluoromethyl)quinazolin-4-one

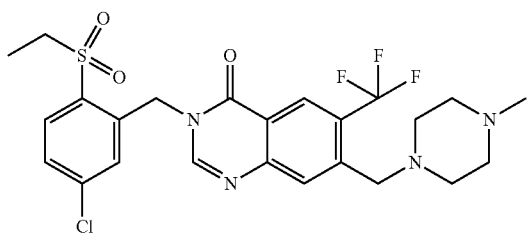 [SMILES: CCS(=O)(=O)c1ccc(Cl)cc1Cn1cnc2cc(CN3CCN(C)CC3)c(C(F)(F)F)cc2c1=O]

The title compound was synthesized from 3-[(5-chloro-2-ethylsulfonylphenyl)methyl]-7-(piperazin-1-ylmethyl)-6-(trifluoromethyl)quinazolin-4-one (Compound I-1) under the same conditions as for Compound G-3. However, paraformaldehyde was used in place of acetone.

LCMS: m/z 543 [M+H]$^+$

HPLC retention time: 0.51 min (analysis condition D)

Example 465

Compound I-3

3-[(5-Chloro-2-ethylsulfonylphenyl)methyl]-7-[(4-propan-2-ylpiperazin-1-yl)methyl]-6-(trifluoromethyl)quinazolin-4-one

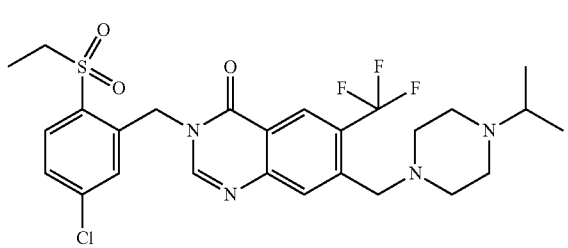 [SMILES: CCS(=O)(=O)c1ccc(Cl)cc1Cn1cnc2cc(CN3CCN(C(C)C)CC3)c(C(F)(F)F)cc2c1=O]

The title compound was synthesized from 3-[(5-chloro-2-ethylsulfonylphenyl)methyl]-7-(piperazin-1-ylmethyl)-6-(trifluoromethyl)quinazolin-4-one (Compound I-1) under the same conditions as for Compound G-3.

LCMS: m/z 571 [M+H]$^+$

HPLC retention time: 0.54 min (analysis condition D)

Example 466

Compound I-4

3-[(5-Chloro-2-ethylsulfonylphenyl)methyl]-7-[[4-(oxan-4-yl)piperazin-1-yl]methyl]-6-(trifluoromethyl)quinazolin-4-one

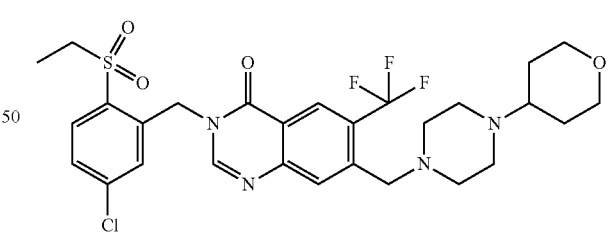

The title compound was synthesized from 3-[(5-chloro-2-ethylsulfonylphenyl)methyl]-7-(piperazin-1-ylmethyl)-6-(trifluoromethyl)quinazolin-4-one (Compound I-1) under the same conditions as for Compound G-3. However, tetrahydro-4H-pyran-4-one was used in place of acetone.

LCMS: m/z 613 [M+H]$^+$

HPLC retention time: 0.55 min (analysis condition D)

Example 467

Compound i3

Ethyl 4-[[(3S)-3-acetamidepyrrolidin-1-yl]methyl]-2-amino-5-(trifluoromethyl)benzoate

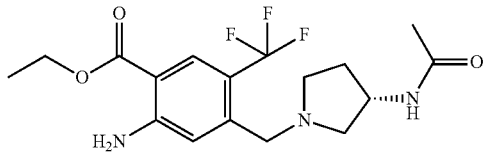 [SMILES: CCOC(=O)c1cc(C(F)(F)F)c(CN2CC[C@H](NC(C)=O)C2)cc1N]

Sodium triacetoxyborohydride (231.4 mg, 1.09 mmol) was added to a solution of ethyl 2-amino-4-formyl-5-(trifluoromethyl)benzoate (Compound 110, 95.0 mg, 0.364 mmol), N-[(3S)-pyrrolidin-3-yl]acetamide (140.0 mg, 1.09 mmol) in THF (1.8 mL), and the mixture was stirred at room temperature for one hour. A saturated aqueous sodium bicarbonate solution was added to the reaction solution, followed by extraction with ethyl acetate. The organic layer was dried over anhydrous sodium sulfate. After the drying agent was removed by filtration, concentration was performed under reduced pressure. The resulting residue was purified by silica gel column chromatography (methanol/DCM) to give the title compound (130.5 mg, 92%) as a colorless solid.

LCMS: m/z 374 [M+H]$^+$

HPLC retention time: 0.49 min (analysis condition: D)

Example 468

Compound i4

4-[[(3S)-3-Acetamidepyrrolidin-1-yl]methyl]-2-amino-5-(trifluoromethyl)benzoic Acid

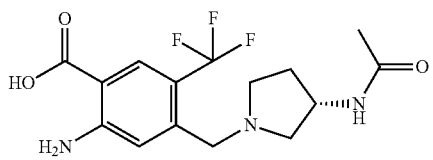

The title compound was synthesized from ethyl 4-[[(3S)-3-acetamidepyrrolidin-1-yl]methyl]-2-amino-5-(trifluoromethyl)benzoate (Compound i3) under the same conditions as for Compound 85.

Example 469

Compound i5

4-[[(3S)-3-Acetamidepyrrolidin-1-yl]methyl]-2-amino-N-[(5-chloro-2-ethylsulfonylphenyl)methyl]-5-(trifluoromethyl)benzamide

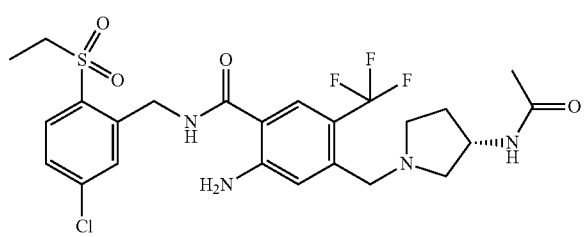 [SMILES: CCS(=O)(=O)c1ccc(Cl)cc1CNC(=O)c1cc(C(F)(F)F)c(CN2CC[C@H](NC(C)=O)C2)cc1N]

The title compound was synthesized from (5-chloro-2-ethylsulfonylphenyl)methanamine (a free form of Compound 3) and 4-[[(3S)-3-acetamidepyrrolidin-1-yl]methyl]-2-amino-5-(trifluoromethyl)benzoic acid (Compound i4) under the same conditions as for Compound a1.

Example 470

Compound I-5

N-[(3S)-1-[[3-[(5-Chloro-2-ethylsulfonylphenyl)methyl]-4-oxo-6-(trifluoromethyl)quinazolin-7-yl]methyl]pyrrolidin-3-yl]acetamide

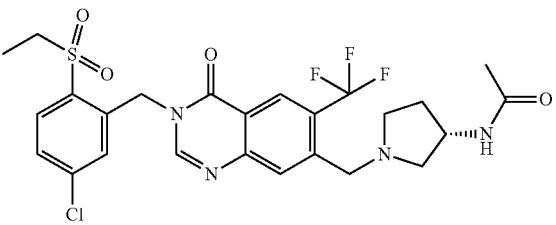 [SMILES: CCS(=O)(=O)c1ccc(Cl)cc1Cn1cnc2cc(CN3CC[C@H](NC(C)=O)C3)c(C(F)(F)F)cc2c1=O]

The title compound was synthesized from 4-[[(3S)-3-acetamidepyrrolidin-1-yl]methyl]-2-amino-N-[(5-chloro-2-ethylsulfonylphenyl)methyl]-5-(trifluoromethyl)benzamide (Compound i5) under the same conditions as for Compound A-28.

LCMS: m/z 571 [M+H]$^+$

HPLC retention time: 0.51 min (analysis condition: D)

Example 471

Compound I-6

N-[(3R)-1-[[3-[(5-Chloro-2-ethylsulfonylphenyl)methyl]-4-oxo-6-(trifluoromethyl)quinazolin-7-yl]methyl]pyrrolidin-3-yl]acetamide

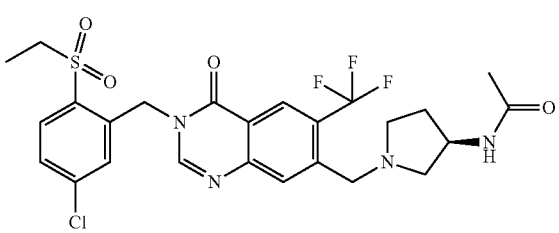

The title compound was synthesized from ethyl 2-amino-4-formyl-5-(trifluoromethyl)benzoate (Compound 110) under the same conditions as for Compounds i3, i4, i5, and I-5. However, N-[(3R)-pyrrolidin-3-yl]acetamide was used in place of N-[(3S)-pyrrolidin-3-yl]acetamide as an amine under the conditions for Compound i3.

LCMS: m/z 571 [M+H]$^+$

HPLC retention time: 0.50 min (analysis condition: D)

Example 472

Compound i6

Ethyl 2-amino-4-(hydroxymethyl)-5-(trifluoromethyl)benzoate

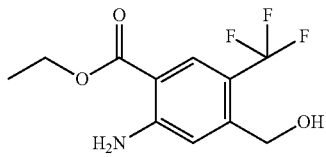 [SMILES: CCOC(=O)c1cc(C(F)(F)F)c(CO)cc1N]

Sodium borohydride (7.2 mg, 0.192 mmol) was added to a suspension of ethyl 2-amino-4-formyl-5-(trifluoromethyl)benzoate (Compound 110, 100 mg, 0.383 mmol) in ethanol (1 mL) under ice-cooling, and the mixture was stirred for 30 minutes. A saturated aqueous sodium bicarbonate solution was added to the reaction mixture, and extraction was performed with ethyl acetate. The organic layer was dried over anhydrous sodium sulfate. After the drying agent was removed by filtration, concentration was performed under reduced pressure to give a crude product of the title compound (101 mg) as a colorless solid.
LCMS: m/z 264 [M+H]$^+$
HPLC retention time: 0.73 min (analysis condition: D)

Example 473

Compound i7

2-Amino-4-(hydroxymethyl)-5-(trifluoromethyl)benzoic Acid

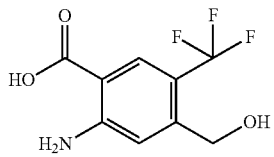

The title compound was synthesized from ethyl 2-amino-4-(hydroxymethyl)-5-(trifluoromethyl)benzoate (Compound i6) under the same conditions as for Compound 85.

Example 474

Compound i8

2-Amino-N-[(5-chloro-2-ethylsulfonylphenyl)methyl]-4-(hydroxymethyl)-5-(trifluoromethyl)benzamide

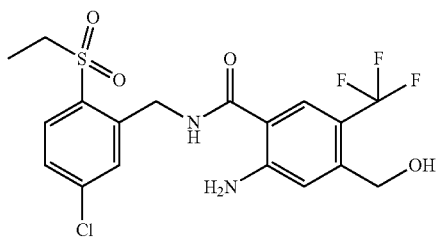 [SMILES: CCS(=O)(=O)c1ccc(Cl)cc1CNC(=O)c1cc(C(F)(F)F)c(CO)cc1N]

The title compound was synthesized from (5-chloro-2-ethylsulfonylphenyl)methanamine hydrochloride (Compound 3) and 2-amino-4-(hydroxymethyl)-5-(trifluoromethyl)benzoic acid (Compound i7) under the same conditions as for Compound e8. However, WSCDI was used in place of HBTU.

Example 475

Compound i9

3-[(5-Chlor-2-ethylsulfonylphenyl)methyl]-7-(hydroxymethyl)-6-(trifluormethyl)quinazolin-4-one

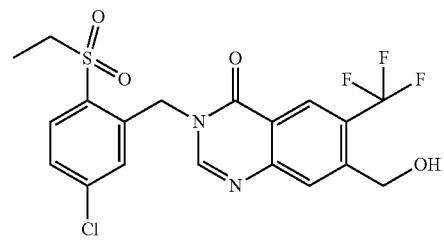 [SMILES: CCS(=O)(=O)c1ccc(Cl)cc1Cn1cnc2cc(CO)c(C(F)(F)F)cc2c1=O]

Formic acid (0.26 mL) was added to a solution of 2-amino-N-[(5-chloro-2-ethylsulfonylphenyl)methyl]-4-(hydroxymethyl)-5-(trifluoromethyl)benzamide (Compound i8, 120 mg, 0.266 mmol) in methyl orthoformate (2.6 mL), and the mixture was stirred at 90° C. for 17 hours. Additional formic acid (1 mL) was added and the mixture was stirred for 4 hours. Methyl orthoformate (1 mL) was added and the mixture was stirred for 0.5 hours. After the reaction solution was cooled to room temperature, it was concentrated under reduced pressure. Methanol (2.6 mL) and 1 N aqueous hydrochloric acid solution (2.6 mL) were added to the resulting residue, and the mixture was stirred at room temperature for 30 minutes. The solvent was removed under reduced pressure. A saturated aqueous sodium bicarbonate solution was added to the resulting residue, and extraction was performed with ethyl acetate. The organic layer was washed with brine and dried over anhydrous sodium sulfate. After the drying agent was removed by filtration, concentration was performed under reduced pressure. The resulting residue was purified by silica gel column chromatography (ethyl acetate/hexane) to give the title compound (81.4 mg, 66%) as a colorless solid.
LCMS: m/z 461 [M+H]$^+$
HPLC retention time: 0.74 min (analysis condition: D)

Example 476

Compound i10

[3-[(5-Chloro-2-ethylsulfonylphenyl)methyl]-4-oxo-6-(trifluoromethyl)quinazolin-7-yl]methyl methanesulfonate

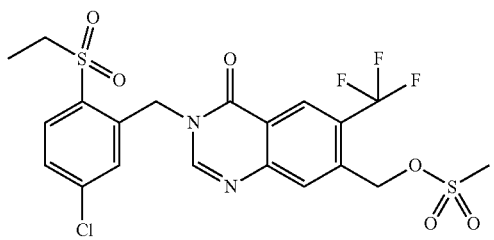 [SMILES: CCS(=O)(=O)c1ccc(Cl)cc1Cn1cnc2cc(COS(C)(=O)=O)c(C(F)(F)F)cc2c1=O]

Methanesulfonyl chloride (27.1 μL, 0.348 mmol) was added to a solution of 3-[(5-chloro-2-ethylsulfonylphenyl)methyl]-7-(hydroxymethyl)-6-(trifluoromethyl)quinazolin-4-one (Compound i9, 80 mg, 0.174 mmol) and triethylamine (48.9 μL, 0.348 mmol) in DCM (1.7 mL) under ice-cooling, and the mixture was stirred for 30 minutes still under ice-cooling. Water was added to the reaction mixture, and extraction was performed with DCM. The organic layer was dried over anhydrous sodium sulfate. After the drying agent was removed by filtration, concentration was performed under reduced pressure to give a partially purified product of the title compound (100.6 mg) as a colorless foamy substance.

LCMS: m/z 539 [M+H]$^+$
HPLC retention time: 0.80 min (analysis condition: D)

Example 477

Compound i11 tert-Butyl N-[(3R)-1-[[3-[(5-Chloro-2-ethylsulfonylphenyl)methyl]-4-oxo-6-(trifluoromethyl)quinazolin-7-yl]methyl]pyrrolidin-3-yl]carbamate

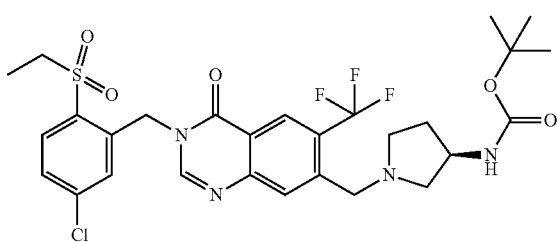 [SMILES: CCS(=O)(=O)c1ccc(Cl)cc1Cn1cnc2cc(CN3CC[C@@H](NC(=O)OC(C)(C)C)C3)c(C(F)(F)F)cc2c1=O]

Triethylamine (26.1 μl, 0.186 mmol) and tert-butyl N-[(3R)-pyrrolidin-3-yl]carbamate (25.9 mg, 0.139 mmol) were added to a solution of [3-[(5-chloro-2-ethylsulfonylphenyl)methyl]-4-oxo-6-(trifluoromethyl)quinazolin-7-yl]methyl methanesulfonate (Compound i10, 50 mg, 0.093 mmol) in DCM (0.5 mL), and the mixture was stirred at room temperature for 1.5 hours. Additional triethylamine (26.1 &d, 0.186 mmol) and tert-butyl N-[(3R)-pyrrolidin-3-yl]carbamate (25.9 mg, 0.139 mmol) were added, and the mixture was stirred at room temperature for 13 hours. Water was added to the reaction mixture, and extraction was performed with methylene chloride. The organic layer was dried over anhydrous sodium sulfate. After the drying agent was removed by filtration, concentration was performed under reduced pressure. The resulting residue was purified by silica gel column chromatography (ethyl acetate/hexane) to give the title compound (46.1 mg, 79%) as a colorless foamy substance.

LCMS: m/z 629[M+H]$^+$
HPLC retention time: 0.61 min (analysis condition: D)

Example 478

Compound I-7

7-[[(3R)-3-Aminopyrrolidin-1-yl]methyl]-3-[(5-chloro-2-ethylsulfonylphenyl)methyl]-6-(trifluoromethyl)quinazolin-4-one

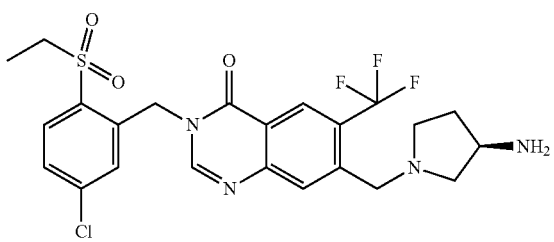 [SMILES: CCS(=O)(=O)c1ccc(Cl)cc1Cn1cnc2cc(CN3CC[C@@H](N)C3)c(C(F)(F)F)cc2c1=O]

The title compound was synthesized from tert-butyl N-[(3R)-1-[[3-[(5-chloro-2-ethylsulfonylphenyl)methyl]-4-oxo-6-(trifluoromethyl)quinazolin-7-yl]methyl]pyrrolidin-3-yl]carbamate (Compound i11) under the same conditions as for Compound 21.

LCMS: m/z 529 [M+H]$^+$
HPLC retention time: 0.51 min (analysis condition: D)

Example 479

Compound I-8

3-[(5-Chloro-2-ethylsulfonylphenyl)methyl]-7-[[(3R)-3-(dimethylamino)pyrrolidin-1-yl]methyl]-6-(trifluoromethyl)quinazolin-4-one

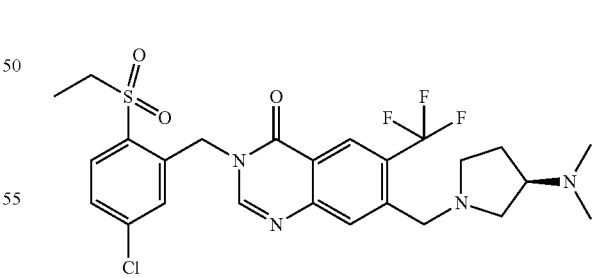

The title compound was synthesized from [3-[(5-chloro-2-ethylsulfonylphenyl)methyl]-4-oxo-6-(trifluoromethyl)quinazolin-7-yl]methyl methanesulfonate (Compound i10) under the same conditions as for Compound i11. However, (3R)—N,N-dimethylpyrrolidin-3-amine was used in place of tert-butyl N-[(3R)-pyrrolidin-3-yl]carbamate.

LCMS: m/z 557 [M+H]$^+$
HPLC retention time: 0.56 min (analysis condition: D)

Example 480

Compound i12 tert-Butyl 4-[[5-amino-4-[(5-cyano-2-ethylsulfonyl-phenyl)methylcarbamoyl]-2-(trifluoromethyl)phenyl]methyl]piperazine-1-carboxylate

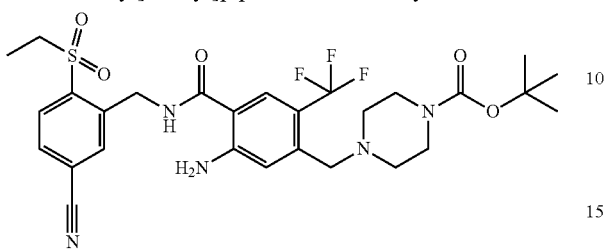

The title compound was synthesized from 3-(aminomethyl)-4-ethylsulfonylbenzonitrile (Compound 16) and 2-amino-4-[[4-[(2-methylpropan-2-yl)oxycarbonyl]piperazin-1-yl]methyl]-5-(trifluoromethyl)benzoic acid (Compound g2) under the same conditions as for Compound e8. However, WSCDI was used in place of HBTU.

Example 481

Compound i13 tert-Butyl 4-[[3-[(5-cyano-2-ethylsulfonylphenyl)methyl]-4-oxo-6-(trifluoromethyl)quinazolin-7-yl]methyl]piperazine-1-carboxylate

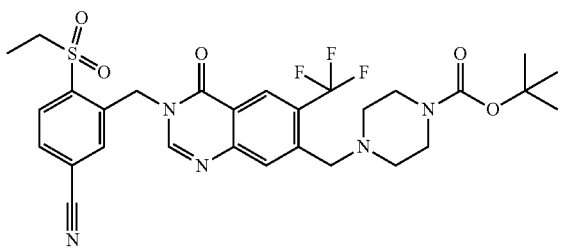 [SMILES: CCS(=O)(=O)c1ccc(C#N)cc1Cn1cnc2cc(CN3CCN(C(=O)OC(C)(C)C)CC3)c(C(F)(F)F)cc2c1=O]

The title compound was synthesized from tert-butyl 4-[[5-amino-4-[(5-cyano-2-ethylsulfonylphenyl)methylcarbamoyl]-2-(trifluoromethyl)phenyl]methyl]piperazine-1-carboxylate (Compound i12) under the same conditions as for Compound A-28.

Example 482

Compound I-9

4-Ethylsulfonyl-3-[[4-oxo-7-(piperazin-1-ylmethyl)-6-(trifluoromethyl)quinazolin-3-yl]methyl]benzonitrile

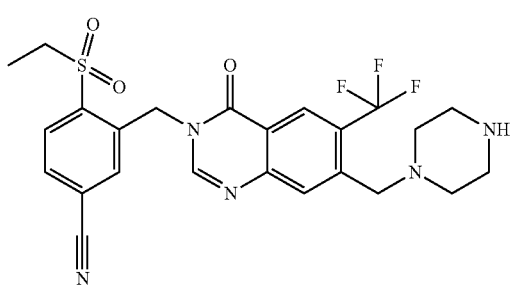

The title compound was synthesized from tert-butyl 4-[[3-[(5-cyano-2-ethylsulfonylphenyl)methyl]-4-oxo-6-(trifluoromethyl)quinazolin-7-yl]methyl]piperazine-1-carboxylate (Compound i13) under the same conditions as for Compound A-2.

LCMS: m/z 520 [M+H]$^+$

HPLC retention time: 0.52 min (analysis condition: D)

Example 483

Compound i14 tert-Butyl 4-[[2-amino-3-ethoxycarbonyl-5-(trifluoromethyl)phenyl]methyl]piperazine-1-carboxylate

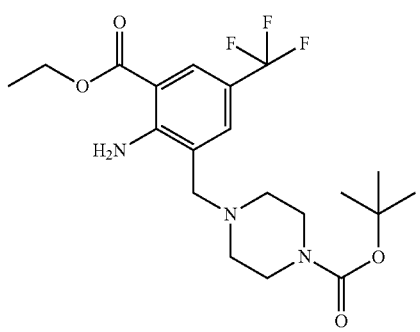 [SMILES: CCOC(=O)c1cc(C(F)(F)F)cc(CN2CCN(C(=O)OC(C)(C)C)CC2)c1N]

The title compound was synthesized from ethyl 2-amino-3-bromo-5-(trifluoromethyl)benzoate (Compound 84) under the same conditions as for Compound g1.

Example 484

Compound i15

2-Amino-3-[[4-[(2-methylpropan-2-yl)oxycarbonyl]piperazin-1-yl]methyl]-5-(trifluoromethyl)benzoic Acid

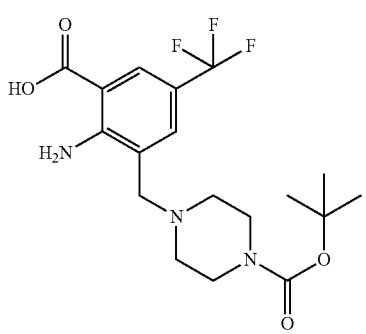 [SMILES: CC(C)(C)OC(=O)N1CCN(Cc2cc(C(F)(F)F)cc(C(=O)O)c2N)CC1]

The title compound was synthesized from tert-butyl 4-[[2-amino-3-ethoxycarbonyl-5-(trifluoromethyl)phenyl]methyl]piperazine-1-carboxylate (Compound i14) under the same conditions as for Compound 85.

Example 485

Compound i16 tert-Butyl 4-[[2-amino-3-[(5-chloro-2-ethylsulfonyl-phenyl)methylcarbamoyl]-5-(trifluoromethyl)phenyl]methyl]piperazine-1-carboxylate

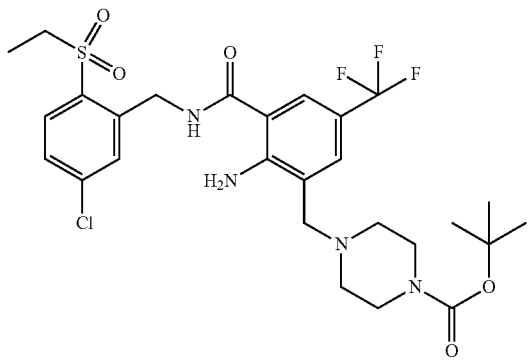 [SMILES: CCS(=O)(=O)c1ccc(Cl)cc1CNC(=O)c1cc(C(F)(F)F)cc(CN2CCN(C(=O)OC(C)(C)C)CC2)c1N]

The title compound was synthesized from (5-chloro-2-ethylsulfonylphenyl)methanamine (a free form of Compound 3) and 2-amino-3-[[4-[(2-methylpropan-2-yl)oxycarbonyl]piperazin-1-yl]methyl]-5-(trifluoromethyl)benzoic acid (Compound i15) under the same conditions as for Compound a1.

Example 486

Compound I-10

3-[(5-Chloro-2-ethylsulfonylphenyl)methyl]-8-(piperazin-1-ylmethyl)-6-(trifluoromethyl)quinazolin-4-one

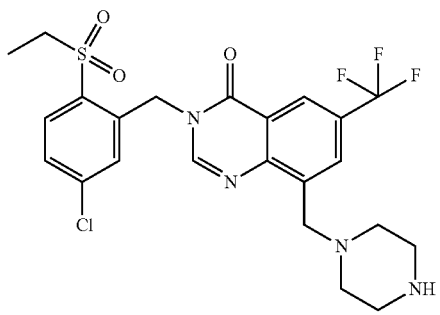 [SMILES: CCS(=O)(=O)c1ccc(Cl)cc1Cn1cnc2c(CN3CCNCC3)cc(C(F)(F)F)cc2c1=O]

The title compound was synthesized from tert-butyl 4-[[2-amino-3-[(5-chloro-2-ethylsulfonylphenyl)methylcarbamoyl]-5-(trifluoromethyl)phenyl]methyl]piperazine-1-carboxylate (Compound i16) under the same conditions as for Compounds i13 and I-9.

LCMS: m/z 529 [M+H]$^+$

HPLC retention time: 0.53 min (analysis condition: D)

Example 487

Compound I-11

3-[(5-Chloro-2-ethylsulfonylphenyl)methyl]-8-[(4-methylpiperazin-1-yl)methyl]-6-(trifluoromethyl)quinazolin-4-one

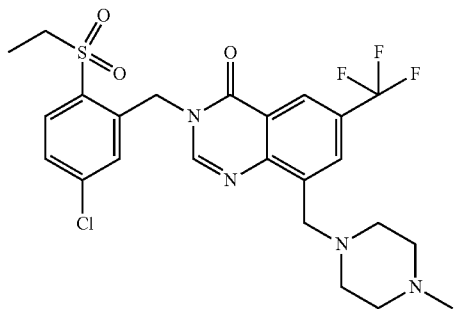 [SMILES: CCS(=O)(=O)c1ccc(Cl)cc1Cn1cnc2c(CN3CCN(C)CC3)cc(C(F)(F)F)cc2c1=O]

The title compound was synthesized from 3-[(5-chloro-2-ethylsulfonylphenyl)methyl]-8-(piperazin-1-ylmethyl)-6-(trifluoromethyl)quinazolin-4-one (Compound I-10) under the same conditions as for Compound G-3. However, paraformaldehyde was used in place of acetone.

LCMS: m/z 543 [M+H]$^+$

HPLC retention time: 1.90 min (analysis condition: E)

Example 488

Compound I-12

3-[(5-Chloro-2-ethylsulfonylphenyl)methyl]-8-[(4-propan-2-ylpiperazin-1-yl)methyl]-6-(trifluoromethyl)quinazolin-4-one

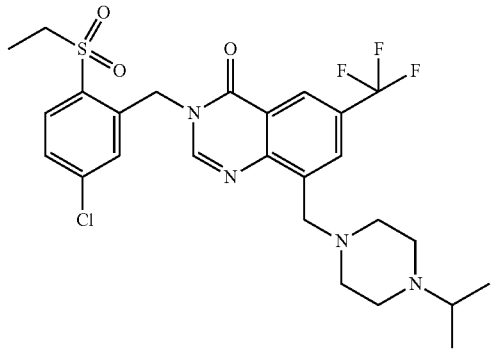 [SMILES: CCS(=O)(=O)c1ccc(Cl)cc1Cn1cnc2c(CN3CCN(C(C)C)CC3)cc(C(F)(F)F)cc2c1=O]

The title compound was synthesized from 3-[(5-chloro-2-ethylsulfonylphenyl)methyl]-8-(piperazin-1-ylmethyl)-6-(trifluoromethyl)quinazolin-4-one (Compound I-10) under the same conditions as for Compound G-3.

LCMS: m/z 571 [M+H]$^+$

HPLC retention time: 1.97 min (analysis condition: E)

Example 489

Compound I-13

3-[(5-Chloro-2-ethylsulfonylphenyl)methyl]-8-[[4-(oxan-4-yl)piperazin-1-yl]methyl]-6-(trifluoromethyl)quinazolin-4-one

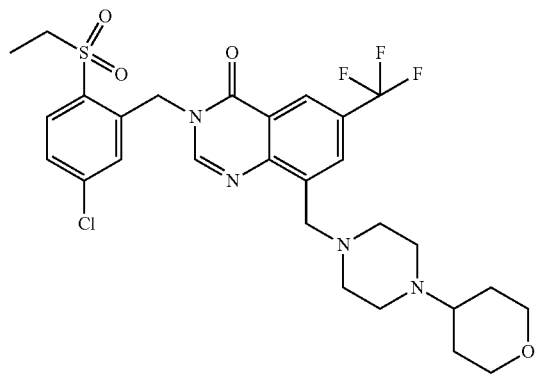 [SMILES: CCS(=O)(=O)c1ccc(Cl)cc1Cn1cnc2c(CN3CCN(C4CCOCC4)CC3)cc(C(F)(F)F)cc2c1=O]

The title compound was synthesized from 3-[(5-chloro-2-ethylsulfonylphenyl)methyl]-8-(piperazin-1-ylmethyl)-6-(trifluoromethyl)quinazolin-4-one (Compound I-10) under the same conditions as for Compound G-3. However, tetrahydro-4H-pyran-4-one was used in place of acetone.

LCMS: m/z 613 [M+H]$^+$

HPLC retention time: 1.97 min (analysis condition: E)

Example 490

Compound i17 tert-Butyl 3-[4-[[3-[(5-chloro-2-ethylsulfonylphenyl)methyl]-4-oxo-6-(trifluoromethyl)quinazolin-8-yl]methyl]piperazin-1-yl]azetidine-1-carboxylate

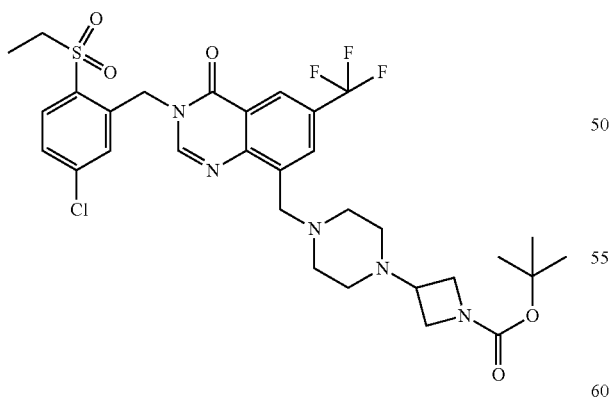

The title compound was synthesized from 3-[(5-chloro-2-ethylsulfonylphenyl)methyl]-8-(piperazin-1-ylmethyl)-6-(trifluoromethyl)quinazolin-4-one (Compound I-10) under the same conditions as for Compound G-3. However, tert-butyl 3-oxoazetidine-1-carboxylate was used in place of acetone.

Example 491

Compound I-14

8-[[4-(Azetidin-3-yl)piperazin-1-yl]methyl]-3-[(5-chloro-2-ethylsulfonylphenyl)methyl]-6-(trifluoromethyl)quinazolin-4-one

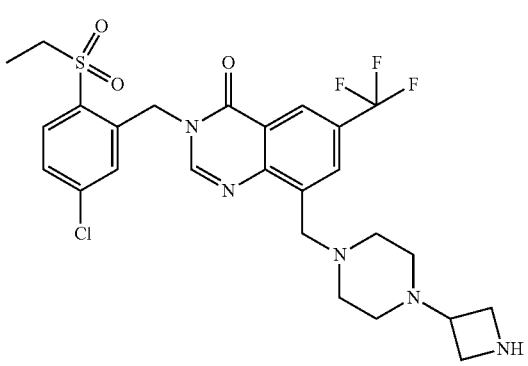 [SMILES: CCS(=O)(=O)c1ccc(Cl)cc1Cn1cnc2c(CN3CCN(C4CNC4)CC3)cc(C(F)(F)F)cc2c1=O]

The title compound was synthesized from tert-butyl 3-[4-[[3-[(5-chloro-2-ethylsulfonylphenyl)methyl]-4-oxo-6-(trifluoromethyl)quinazolin-8-yl]methyl]piperazin-1-yl]azetidine-1-carboxylate (Compound i17) under the same conditions as for Compound 21.

LCMS: m/z 584 [M+H]$^+$

HPLC retention time: 1.75 min (analysis condition: E)

Example 492

Compound i18 tert-Butyl 4-[[4-ethoxycarbonyl-5-nitro-2-(trifluoromethoxy)phenyl]methyl]piperazine-1-carboxylate

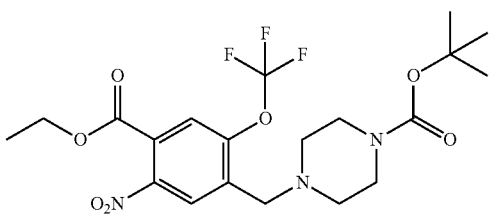 [SMILES: CCOC(=O)c1cc(OC(F)(F)F)c(CN2CCN(C(=O)OC(C)(C)C)CC2)cc1[N+](=O)[O-]]

The title compound was synthesized from ethyl 4-bromo-2-nitro-5-(trifluoromethoxy)benzoate (Compound 115) under the same conditions as for Compound g1.

Example 493

Compound i19 tert-Butyl 4-[[5-amino-4-ethoxycarbonyl-2-(trifluoromethoxy)phenyl]methyl]piperazine-1-carboxylate

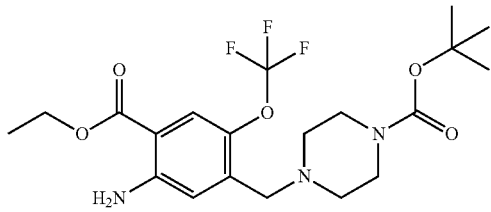

The title compound was synthesized from tert-butyl 4-[[4-ethoxycarbonyl-5-nitro-2-(trifluoromethoxy)phenyl]methyl]piperazine-1-carboxylate (Compound i18) under the same conditions as for Compound 39. However, 2-propanol and a saturated aqueous ammonium chloride solution were used in place of ethanol and a 37% aqueous hydrochloric acid solution, and the reaction was performed at 100° C.

Example 494

Compound i20

2-Amino-4-[[4-[(2-methylpropan-2-yl)oxycarbonyl]piperazin-1-yl]methyl]-5-(trifluoromethoxy)benzoic Acid

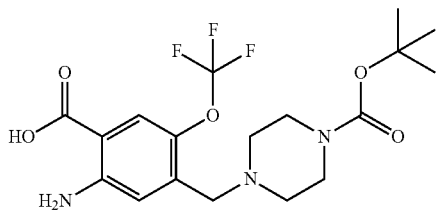 [SMILES: CC(C)(C)OC(=O)N1CCN(Cc2cc(N)c(C(=O)O)cc2OC(F)(F)F)CC1]

The title compound was synthesized from tert-butyl 4-[[5-amino-4-ethoxycarbonyl-2-(trifluoromethoxy)phenyl]methyl]piperazine-1-carboxylate (Compound i19) under the same conditions as for Compound 85.

Example 495

Compound i21 tert-Butyl 4-[[5-amino-4-[(5-chloro-2-ethylsulfonylphenyl)methylcarbamoyl]-2-(trifluoromethoxy)phenyl]methyl]piperazine-1-carboxylate

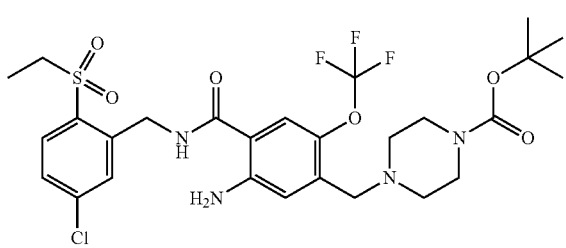 [SMILES: CCS(=O)(=O)c1ccc(Cl)cc1CNC(=O)c1cc(OC(F)(F)F)c(CN2CCN(C(=O)OC(C)(C)C)CC2)cc1N]

The title compound was synthesized from (5-chloro-2-ethylsulfonylphenyl)methanamine (a free form of Compound 3) and 2-amino-4-[[4-[(2-methylpropan-2-yl)oxycarbonyl]piperazin-1-yl]methyl]-5-(trifluoromethoxy)benzoic acid (Compound i20) under the same conditions as for Compound a1.

Example 496

Compound I-15

3-[(5-Chloro-2-ethylsulfonylphenyl)methyl]-7-(piperazin-1-ylmethyl)-6-(trifluoromethoxy)quinazolin-4-one

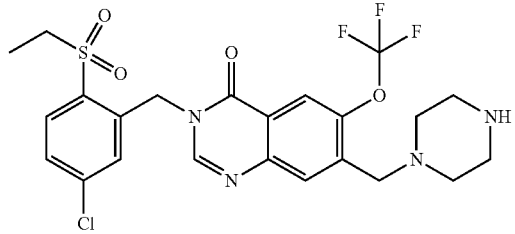 [SMILES: CCS(=O)(=O)c1ccc(Cl)cc1Cn1cnc2cc(CN3CCNCC3)c(OC(F)(F)F)cc2c1=O]

The title compound was synthesized from tert-butyl 4-[[5-amino-4-[(5-chloro-2-ethylsulfonylphenyl)methylcarbamoyl]-2-(trifluoromethoxy)phenyl]methyl]piperazine-1-carboxylate (Compound i21) under the same conditions as for Compounds i13 and 1-9.

LCMS: m/z 545 [M+H]$^+$

HPLC retention time: 0.52 min (analysis condition: D)

Example 497

Compound i22

Ethyl 2-amino-4-(1,2-dihydroxyethyl)-5-(trifluoromethoxy)benzoate

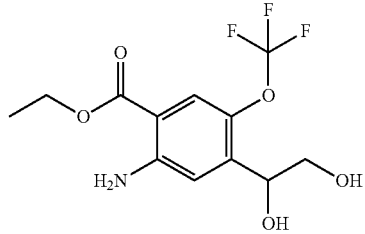 [SMILES: CCOC(=O)c1cc(OC(F)(F)F)c(C(O)CO)cc1N]

The title compound was synthesized from ethyl 2-amino-4-ethenyl-5-(trifluoromethoxy)benzoate (Compound 117) under the same conditions as for Compound 109.

Example 498

Compound i23

Ethyl 2-amino-4-formyl-5-(trifluoromethoxy)benzoate

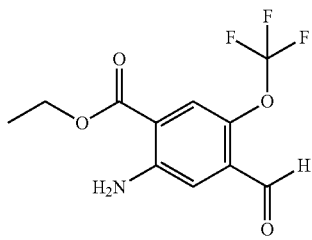 [SMILES: CCOC(=O)c1cc(OC(F)(F)F)c(C=O)cc1N]

The title compound was synthesized from ethyl 2-amino-4-(1,2-dihydroxyethyl)-5-(trifluoromethoxy)benzoate (Compound i22) under the same conditions as for Compound 110.

Example 499

Compound i24

Ethyl 4-[[(3S)-3-acetamidepyrrolidin-1-yl]methyl]-2-amino-5-(trifluoromethoxy)benzoate

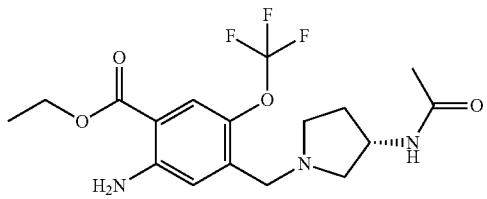 [SMILES: CCOC(=O)c1cc(OC(F)(F)F)c(CN2CC[C@H](NC(C)=O)C2)cc1N]

The title compound was synthesized from ethyl 2-amino-4-formyl-5-(trifluoromethoxy)benzoate (Compound i23) under the same conditions as for Compound i3.

Example 500

Compound i25

4-[[(3S)-3-Acetamidepyrrolidin-1-yl]methyl]-2-amino-5-(trifluoromethoxy)benzoic Acid

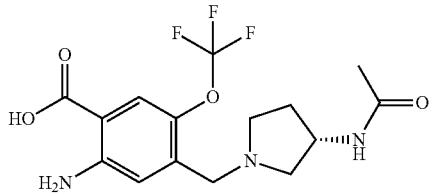 [SMILES: CC(=O)N[C@H]1CCN(Cc2cc(N)c(C(=O)O)cc2OC(F)(F)F)C1]

The title compound was synthesized from ethyl 4-[[(3S)-3-acetamidepyrrolidin-1-yl]methyl]-2-amino-5-(trifluoromethoxy)benzoate (Compound i24) under the same conditions as for Compound 85. However, the reaction was performed at 90° C.

Example 501

Compound i26

4-[[(3S)-3-Acetamidepyrrolidin-1-yl]methyl]-2-amino-N-[(5-chloro-2-ethylsulfonylphenyl)methyl]-5-(trifluoromethoxy)benzamide

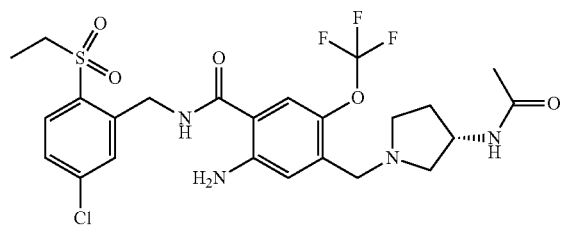 [SMILES: CCS(=O)(=O)c1ccc(Cl)cc1CNC(=O)c1cc(OC(F)(F)F)c(CN2CC[C@H](NC(C)=O)C2)cc1N]

The title compound was synthesized from (5-chloro-2-ethylsulfonylphenyl)methanamine hydrochloride (Compound 3) and 4-[[(3S)-3-acetamidepyrrolidin-1-yl]methyl]-2-amino-5-(trifluoromethoxy)benzoic acid (Compound i25) under the same conditions as for Compound e8. However, WSCDI was used in place of HBTU.

Example 502

Compound I-16

N-[(3S)-1-[[3-[(5-Chloro-2-ethylsulfonylphenyl)methyl]-4-oxo-6-(trifluoromethoxy)quinazolin-7-yl]methyl]pyrrolidin-3-yl]acetamide

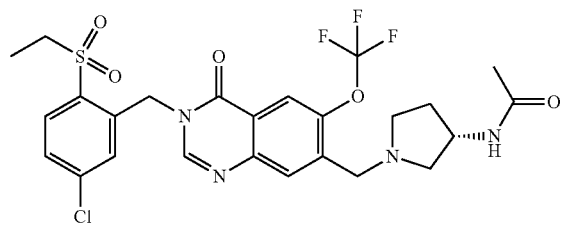 [SMILES: CCS(=O)(=O)c1ccc(Cl)cc1Cn1cnc2cc(CN3CC[C@H](NC(C)=O)C3)c(OC(F)(F)F)cc2c1=O]

The title compound was synthesized from 4-[[(3S)-3-acetamidepyrrolidin-1-yl]methyl]-2-amino-N-[(5-chloro-2-ethylsulfonylphenyl)methyl]-5-(trifluoromethoxy)benzamide (Compound i26) under the same conditions as for Compound A-28.

LCMS: m/z 587 [M+H]$^+$

HPLC retention time: 0.51 min (analysis condition: D)

Example 503

Compound i27

Ethyl 4-[[(3R)-3-[(2-methylpropan-2-yl)oxycarbonylamino]pyrrolidin-1-yl]methyl]-2-nitro-5-(trifluoromethoxy)benzoate

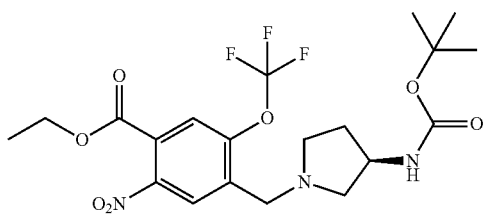 [SMILES: CCOC(=O)c1cc(OC(F)(F)F)c(CN2CC[C@@H](NC(=O)OC(C)(C)C)C2)cc1N]

A mixture of ethyl 4-bromo-2-nitro-5-(trifluoromethoxy)benzoate (Compound 115, 750 mg, 2.1 mmol), potassium (R)-({3-[(tert-butoxycarbonyl)amino]pyrrolidin-1-yl}methyl)trifluoroborate (898 mg, 2.9 mmol), palladium acetate (23.5 mg, 0.10 mmol), Ru-Phos (97.7 mg, 0.21 mmol), and potassium carbonate (869 mg, 6.3 mmol) in toluene (7.0 mL) and water (3.5 mL) was refluxed for five hours. The reaction solution was cooled to room temperature, followed by addition of water and extraction with ethyl acetate. The extract was dried over anhydrous sodium sulfate. After the drying agent was removed by filtration, concentration was performed under reduced pressure. The resulting residue was purified by silica gel column chromatography (ethyl acetate/hexane) to give the title compound (847 mg, 85%) as a pale yellow solid.

LCMS: m/z 478 [M+H]$^+$

HPLC retention time: 0.60 min (analysis condition D)

Example 504

Compound i28

Ethyl 2-amino-4-[[(3R)-3-[(2-methylpropan-2-yl)oxycarbonylamino]pyrrolidin-1-yl]methyl]-5-(trifluoromethoxy)benzoate

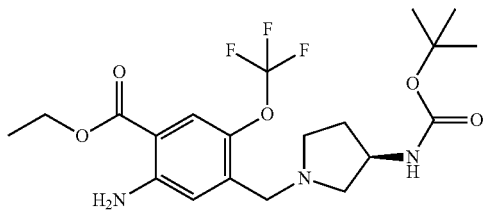

The title compound was synthesized from ethyl 4-[[(3R)-3-[(2-methylpropan-2-yl)oxycarbonylamino]pyrrolidin-1-yl]methyl]-2-nitro-5-(trifluoromethoxy)benzoate (Compound i27) under the same conditions as for Compound 24. However, 2-propanol was used in place of methanol as a solvent and the reaction was performed at 80° C.

Example 505

Compound i29

2-Amino-4-[[(3R)-3-[(2-methylpropan-2-yl)oxycarbonylamino]pyrrolidin-1-yl]methyl]-5-(trifluoromethoxy)benzoic Acid

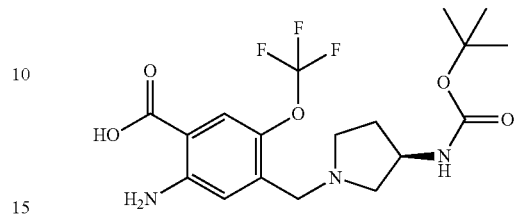

The title compound was synthesized from ethyl 2-amino-4-[[(3R)-3-[(2-methylpropan-2-yl)oxycarbonylamino]pyrrolidin-1-yl]methyl]-5-(trifluoromethoxy)benzoate (Compound i28) under the same conditions as for Compound 85.

Example 506

Compound i30 tert-Butyl N-[(3R)-1-[[5-amino-4-[(5-chloro-2-ethylsulfonylphenyl)methylcarbamoyl]-2-(trifluoromethoxy)phenyl]methyl]pyrrolidin-3-yl]carbamate

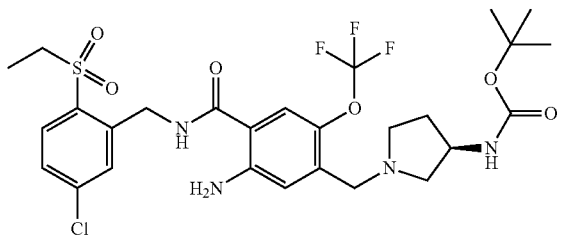 [SMILES: CCS(=O)(=O)c1ccc(Cl)cc1CNC(=O)c1cc(OC(F)(F)F)c(CN2CC[C@@H](NC(=O)OC(C)(C)C)C2)cc1N]

The title compound was synthesized from (5-chloro-2-ethylsulfonylphenyl)methanamine hydrochloride (Compound 3) and 2-amino-4-[[(3R)-3-[(2-methylpropan-2-yl)oxycarbonylamino]pyrrolidin-1-yl]methyl]-5-(trifluoromethoxy)benzoic acid (Compound i29) under the same conditions as for Compound e8. However, WSCDI was used in place of HBTU.

Example 507

Compound i31 tert-Butyl N-[(3R)-1-[[3-[(5-chloro-2-ethylsulfonylphenyl)methyl]-4-oxo-6-(trifluoromethoxy)quinazolin-7-yl]methyl]pyrrolidin-3-yl]carbamate

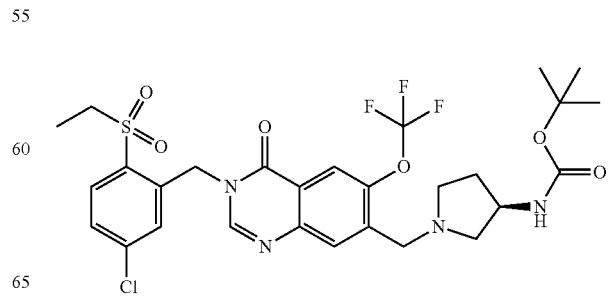

The title compound was synthesized from tert-butyl N-[(3R)-1-[[5-amino-4-[(5-chloro-2-ethylsulfonylphenyl)methylcarbamoyl]-2-(trifluoromethoxy)phenyl]methyl]pyrrolidin-3-yl]carbamate (Compound i30) under the same conditions as for Compound A-28. However, PTSA/H₂O and toluene were used in place of formic acid and trimethyl orthoformate.

Example 508

Compound I-17

7-[[(3R)-3-Aminopyrrolidin-1-yl]methyl]-3-[(5-chloro-2-ethyl)methyl]-6-(trifluoromethoxy)quinazolin-4-one

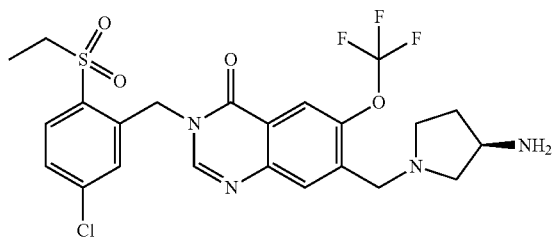 [SMILES: CCS(=O)(=O)c1ccc(Cl)cc1Cn1cnc2cc(CN3CC[C@@H](N)C3)c(OC(F)(F)F)cc2c1=O]

The title compound was synthesized from tert-butyl N-[(3R)-1-[[3-[(5-chloro-2-ethylsulfonylphenyl)methyl]-4-oxo-6-(trifluoromethoxy)quinazolin-7-yl]methyl]pyrrolidin-3-yl]carbamate (Compound i31) under the same conditions as for Compound 21.

LCMS: m/z 545 [M+H]⁺

HPLC retention time: 0.48 min (analysis condition D)

Example 509

Compound I-18

3-[(5-Chloro-2-ethylsulfonylphenyl)methyl]-7-[[(3R)-3-(dimethylamino)pyrrolidin-1-yl]methyl]-6-(trifluoromethoxy)quinazolin-4-one

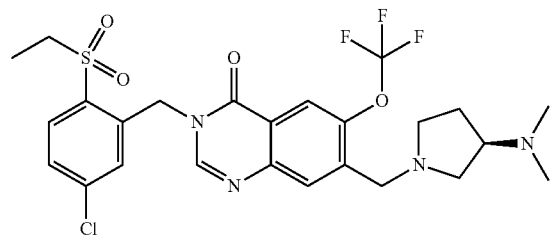 [SMILES: CCS(=O)(=O)c1ccc(Cl)cc1Cn1cnc2cc(CN3CC[C@@H](N(C)C)C3)c(OC(F)(F)F)cc2c1=O]

The title compound was synthesized from 7-[[(3R)-3-aminopyrrolidin-1-yl]methyl]-3-[(5-chloro-2-ethylsulfonylphenyl)methyl]-6-(trifluoromethoxy)quinazolin-4-one (Compound I-17) under the same conditions as for Compound G-2.

LCMS: m/z 573 [M+H]⁺

HPLC retention time: 0.53 min (analysis condition D)

Example 510

Compound I-19

N-[(3R)-1-[[3-[(5-chloro-2-ethylsulfonylphenyl)methyl]-4-oxo-6-(trifluoromethoxy)quinazolin-7-yl]methyl]pyrrolidin-3-yl]acetamide

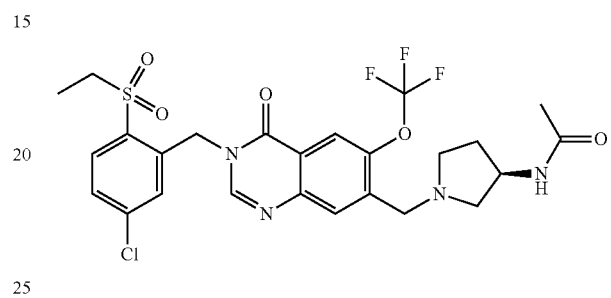

Pyridine (17.8 ul, 0.22 mmol) was added to a solution of 7-[[(3R)-3-aminopyrrolidin-1-yl]methyl]-3-[(5-chloro-2-ethylsulfonylphenyl)methyl]-6-(trifluoromethoxy)quinazolin-4-one (Compound I-17, 40 mg, 0.073 mmol) in DCM (0.5 ml). Acetyl chloride (7.9 ul, 0.11 mmol) was added thereto under ice-cooling, and the mixture was stirred at 0° C. for 6 hours. Acetyl chloride (2.6 ul, 0.037 mmol) was added thereto, and the mixture was stirred at 0° C. for 30 minutes. The reaction mixture was warmed to room temperature, followed by addition of a saturated aqueous ammonium chloride and extraction with ethyl acetate. The organic layer was dried over anhydrous sodium sulfate. After the drying agent was removed by filtration, concentration was performed under reduced pressure. The resulting residue was purified by amino silica gel column chromatography (ethyl acetate/hexane) to give the title compound (32 mg, 74%) as a yellow solid.

LCMS: m/z 587 [M+H]⁺

HPLC retention time: 0.50 min (analysis condition D)

Example 511

Compound i32

Ethyl 2-nitro-4-[(4-pyrrolidin-1-ylpiperidin-1-yl)methyl]-5-(trifluoromethoxy)benzoate

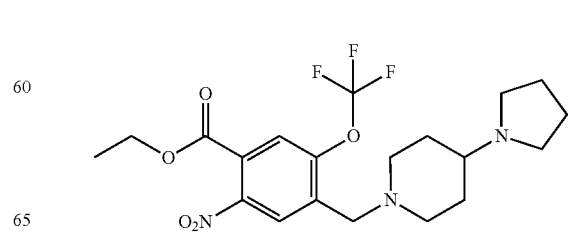

The title compound was synthesized from ethyl 4-bromo-2-nitro-5-(trifluoromethoxy)benzoate (Compound 115) under the same conditions as for Compound g1. However, potassium [(4-pyrrolidin-1-ylpiperidin-1-yl)methyl]trifluoroborate was used in place of potassium (4-tert-butoxycarbonylpiperazin-1-yl)methyltrifluoroborate.

Example 512

Compound i33

Ethyl 2-amino-4-[(4-pyrrolidin-1-ylpiperidin-1-yl)methyl]-5-(trifluoromethoxy)benzoate

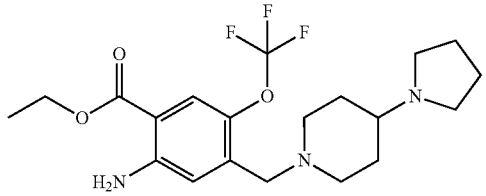 [SMILES: CCOC(=O)c1cc(OC(F)(F)F)c(CN2CCC(N3CCCC3)CC2)cc1[N+](=O)[O-]]

The title compound was synthesized from ethyl 2-nitro-4-[(4-pyrrolidin-1-ylpiperidin-1-yl)methyl]-5-(trifluoromethoxy)benzoate (Compound i32) under the same conditions as for Compound 39. However, 2-propanol and a saturated aqueous ammonium chloride solution were used in place of ethanol and a 37% aqueous hydrochloric acid solution, and the reaction was performed at 100° C.

Example 513

Compound i34

2-Amino-4-[(4-pyrrolidin-1-ylpiperidin-1-yl)methyl]-5-(trifluoromethoxy)benzoic Acid

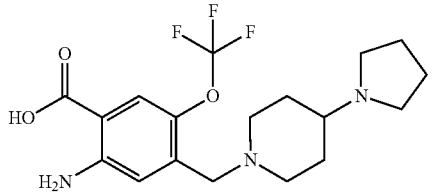 [SMILES: Nc1cc(CN2CCC(N3CCCC3)CC2)c(OC(F)(F)F)cc1C(=O)O]

The title compound was synthesized from ethyl 2-amino-4-[(4-pyrrolidin-1-ylpiperidin-1-yl)methyl]-5-(trifluoromethoxy)benzoate (Compound i33) under the same conditions as for Compound 85.

Example 514

Compound i35

2-Amino-N-[(5-chloro-2-ethylsulfonylphenyl)methyl]-4-[(4-pyrrolidin-1-ylpiperidin-1-yl)methyl]-5-(trifluoromethoxy)benzamide

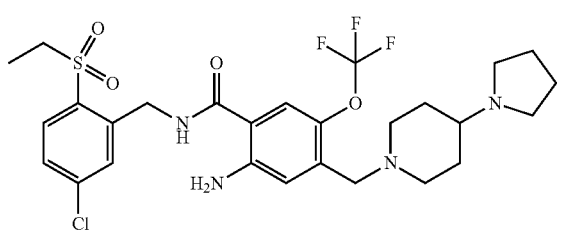 [SMILES: CCS(=O)(=O)c1ccc(Cl)cc1CNC(=O)c1cc(OC(F)(F)F)c(CN2CCC(N3CCCC3)CC2)cc1N]

The title compound was synthesized from (5-chloro-2-ethylsulfonylphenyl)methanamine hydrochloride (Compound 3) and 2-amino-4-[(4-pyrrolidin-1-ylpiperidin-1-yl)methyl]-5-(trifluoromethoxy)benzoic acid (Compound i34) under the same conditions as for Compound e8. However, WSCDI was used in place of HBTU.

Example 515

Compound I-20

3-[(5-Chloro-2-ethylsulfonylphenyl)methyl]-7-[(4-pyrrolidin-1-ylpiperidin-1-yl)methyl]-6-(trifluoromethoxy)quinazolin-4-one

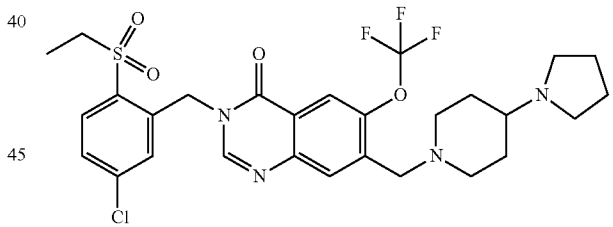

The title compound was synthesized from 2-amino-N-[(5-chloro-2-ethylsulfonylphenyl)methyl]-4-[(4-pyrrolidin-1-ylpiperidin-1-yl)methyl]-5-(trifluoromethoxy)benzamide (Compound i35) under the same conditions as for Compound A-5.

LCMS: m/z 613 [M+H]$^+$

HPLC retention time: 1.72 min (analysis condition E)

Examples 516 to 518

The following compounds of Table 14 were synthesized from ethyl 4-bromo-2-nitro-5-(trifluoromethoxy)benzoate (Compound 115) under the same conditions as for Compounds i32, i33, i34, i35, and I-20. In place of potassium [(4-pyrrolidin-1-ylpiperidin-1-yl)methyl]trifluoroborate, however, corresponding potassium trifluoroborate was used under the conditions for Compound i32.

TABLE 14

| Example | Compound number | Structure | Compound name | HPLC condition | Retention time (min) | m/z [M + H]+ |
|---|---|---|---|---|---|---|
| 516 | I-21 | 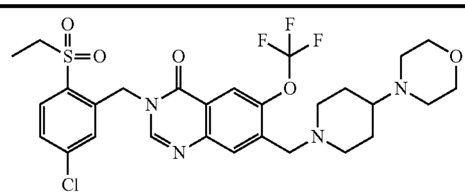 | 3-[(5-Chloro-2-ethylsulfonylphenyl)methyl]-7-[(4-morpholin-4-ylpiperidin-1-yl)methyl]-6-(trifluoromethoxy)quinazolin-4-one | E | 1.68 | 629 |
| 517 | I-22 | 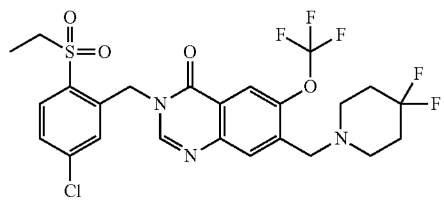 [SMILES: CCS(=O)(=O)c1ccc(Cl)cc1Cn1cnc2cc(CN3CCC(F)(F)CC3)c(OC(F)(F)F)cc2c1=O] | 3-[(5-Chloro-2-ethylsulfonylphenyl)methyl]-7-[(4,4-difluoropiperidin-1-yl)methyl]-6-(trifluoromethoxy)quinazolin-4-one | E | 2.20 | 580 |
| 518 | I-23 | 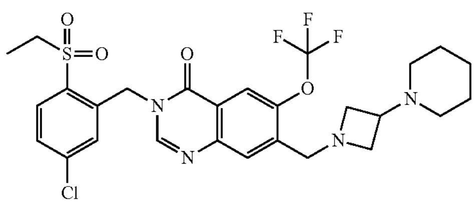 [SMILES: CCS(=O)(=O)c1ccc(Cl)cc1Cn1cnc2cc(CN3CC(N4CCCCC4)C3)c(OC(F)(F)F)cc2c1=O] | 3-[(5-Chloro-2-ethylsulfonylphenyl)methyl]-7-[(3-piperidin-1-ylazetidin-1-yl)methyl]-6-(trifluoromethoxy)quinazolin-4-one | E | 1.82 | 599 |

Example 519

Compound i36 tert-Butyl 4-[[3-[(5-chloro-2-ethylsulfanylphenyl)methyl]-4-oxo-6-(trifluoromethoxy)quinazolin-8-yl]methyl]piperazine-1-carboxylate

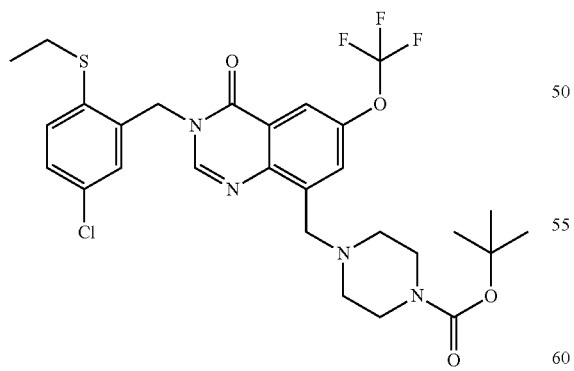

The title compound was synthesized from 8-bromo-3-[(5-chloro-2-ethylsulfanylphenyl)methyl]-6-(trifluoromethoxy)quinazolin-4-one (Compound E-11) under the same conditions as for Compound g1.

Example 520

Compound I-24

3-[(5-Chloro-2-ethylsulfanylphenyl)methyl]-8-(piperazin-1-ylmethyl)-6-(trifluoromethoxy)quinazolin-4-one

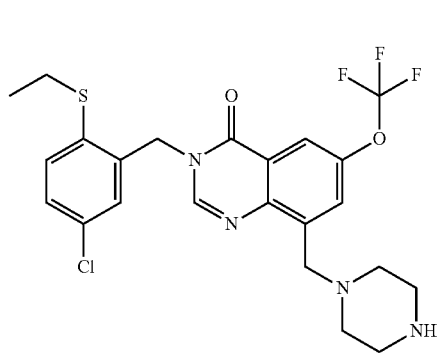 [SMILES: CCSc1ccc(Cl)cc1Cn1cnc2c(CN3CCNCC3)cc(OC(F)(F)F)cc2c1=O]

The title compound was synthesized from tert-butyl 4-[[3-[(5-chloro-2-ethylsulfanylphenyl)methyl]-4-oxo-6-(trifluoromethoxy)quinazolin-8-yl]methyl]piperazine-1-carboxylate (Compound i36) under the same conditions as for Compound A-2.

LCMS: m/z 513 [M+H]+

HPLC retention time: 0.61 min (analysis condition D)

Example 521

Compound i37

Ethyl 2-amino-3-bromo-5-(trifluoromethoxy)benzoate

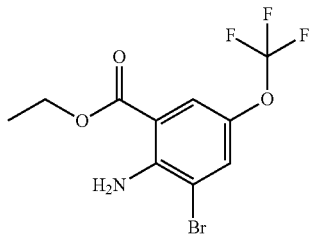 [SMILES: CCOC(=O)c1cc(OC(F)(F)F)cc(Br)c1N]

Concentrated sulfuric acid (0.6 ml) was added to a solution of 2-amino-3-bromo-5-(trifluoromethoxy)benzoic acid (900 mg, 3.0 mmol) in EtOH (2.7 ml), and the mixture was stirred under reflux for 11 hours. EtOH (2.7 mL) and concentrated sulfuric acid (0.6 mL) were added, and the mixture was stirred under reflux for further eight hours. The reaction solution was ice-cooled, and a 5 N aqueous sodium hydroxide solution (9 mL) was added, followed by extraction with ethyl acetate. The extract was washed with brine and dried over anhydrous sodium sulfate. After the drying agent was removed by filtration, concentration was performed under reduced pressure. The resulting residue was purified by silica gel column chromatography (ethyl acetate/hexane) to give the title compound (753 mg, 77%) as a pale brown oily substance.

LCMS: m/z 328 [M+H]$^+$

HPLC retention time: 1.05 min (analysis condition D)

Example 522

Compound i38 tert-Butyl 4-[[2-amino-3-ethoxycarbonyl-5-(trifluoromethoxy)phenyl]methyl]piperazine-1-carboxylate

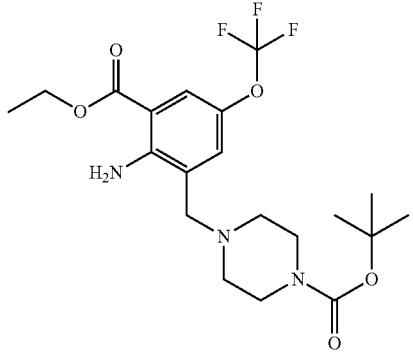 [SMILES: CCOC(=O)c1cc(OC(F)(F)F)cc(CN2CCN(C(=O)OC(C)(C)C)CC2)c1N]

The title compound was synthesized from ethyl 2-amino-3-bromo-5-(trifluoromethoxy)benzoate (Compound i37) under the same conditions as for Compound g1.

Example 523

Compound i39

2-Amino-3-[[4-[(2-methylpropan-2-yl)oxycarbonyl]piperazin-1-yl]methyl]-5-(trifluoromethoxy)benzoic Acid

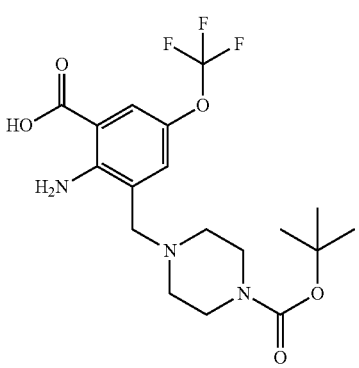 [SMILES: CC(C)(C)OC(=O)N1CCN(Cc2cc(OC(F)(F)F)cc(C(=O)O)c2N)CC1]

The title compound was synthesized from tert-butyl 4-[[2-amino-3-ethoxycarbonyl-5-(trifluoromethoxy)phenyl]methyl]piperazine-1-carboxylate (Compound i38) under the same conditions as for Compound 85.

Example 524

Compound i40 tert-Butyl 4-[[2-amino-3-[(5-chloro-2-ethylsulfonylphenyl)methylcarbamoyl]-5-(trifluoromethoxy)phenyl]methyl]piperazine-1-carboxylate

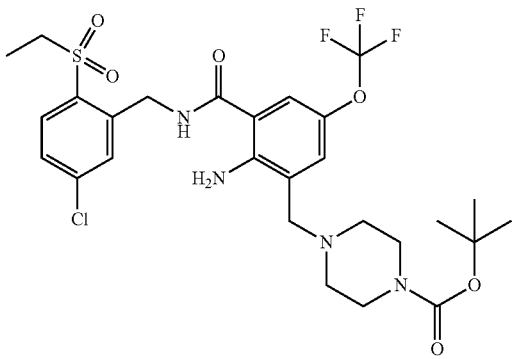 [SMILES: CCS(=O)(=O)c1ccc(Cl)cc1CNC(=O)c1cc(OC(F)(F)F)cc(CN2CCN(C(=O)OC(C)(C)C)CC2)c1N]

The title compound was synthesized from (5-chloro-2-ethylsulfonylphenyl)methanamine (a free form of Compound 3) and 2-amino-3-[[4-[(2-methylpropan-2-yl)oxycarbonyl]piperazin-1-yl]methyl]-5-(trifluoromethoxy)benzoic acid (Compound i39) under the same conditions as for Compound a1.

Example 525

Compound i41 tert-Butyl 4-[[3-[(5-chloro-2-ethylsulfonylphenyl)methyl]-4-oxo-6-(trifluoromethoxy)quinazolin-8-yl]methyl]piperazine-1-carboxylate

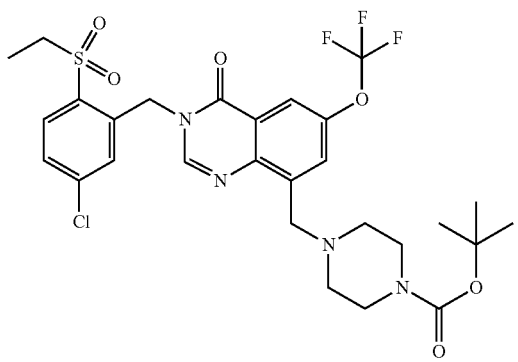 [SMILES: CCS(=O)(=O)c1ccc(Cl)cc1Cn1cnc2c(CN3CCN(C(=O)OC(C)(C)C)CC3)cc(OC(F)(F)F)cc2c1=O]

The title compound was synthesized from tert-butyl 4-[[2-amino-3-[(5-chloro-2-ethylsulfonylphenyl)methylcarbamoyl]-5-(trifluoromethoxy)phenyl]methyl]piperazine-1-carboxylate (Compound i40) under the same conditions as for Compound A-28.

Example 526

Compound I-25

3-[(5-Chloro-2-ethylsulfonylphenyl)methyl]-8-(piperazin-1-ylmethyl)-6-(trifluoromethoxy)quinazolin-4-one

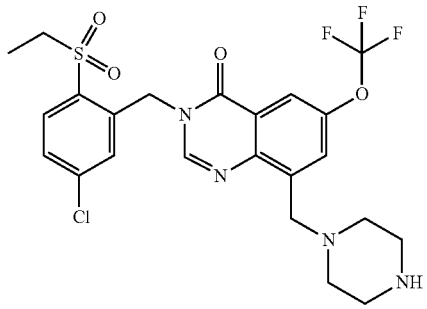 [SMILES: CCS(=O)(=O)c1ccc(Cl)cc1Cn1cnc2c(CN3CCNCC3)cc(OC(F)(F)F)cc2c1=O]

The title compound was synthesized from tert-butyl 4-[[3-[(5-chloro-2-ethylsulfonylphenyl)methyl]-4-oxo-6-(trifluoromethoxy)quinazolin-8-yl]methyl]piperazine-1-carboxylate (Compound i41) under the same conditions as for Compound A-2.

LCMS: m/z 545 [M+H]$^+$

HPLC retention time: 0.53 min (analysis condition D)

Example 527

Compound I-26

3-[(5-Chloro-2-ethylsulfonylphenyl)methyl]-8-[(4-methylpiperazin-1-yl)methyl]-6-(trifluoromethoxy)quinazolin-4-one

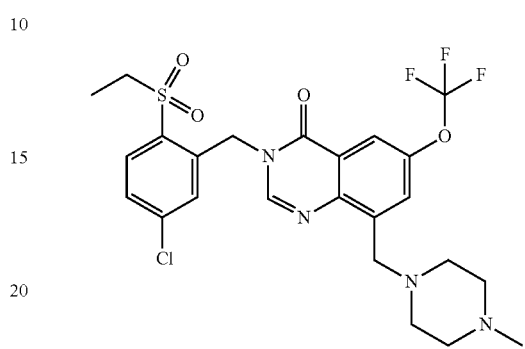

The title compound was synthesized from 3-[(5-chloro-2-ethylsulfonylphenyl)methyl]-8-(piperazin-1-ylmethyl)-6-(trifluoromethoxy)quinazolin-4-one (Compound I-25) under the same conditions as for Compound G-3. However, paraformaldehyde was used in place of acetone.

LCMS: m/z 559 [M+H]$^+$

HPLC retention time: 1.97 min (analysis condition E)

Example 528

Compound i42

2-Amino-8-bromo-6-(trifluoromethoxy)-3H-quinazolin-4-one

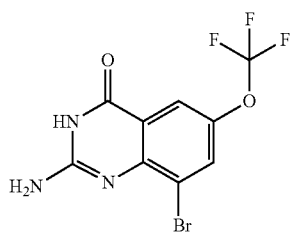 [SMILES: Nc1nc2c(Br)cc(OC(F)(F)F)cc2c(=O)[nH]1]

1,2,4-Triazole-1-carboximidamide (885 mg, 6.00 mmol) was added to a solution of 2-amino-3-bromo-5-(trifluoromethoxy)benzoic acid (600 mg, 2.00 mmol) and DIPEA (1.37 ml, 7.86 mmol) in NMP (10 ml), and the mixture was stirred under microwave irradiation at 200° C. for four hours. Subsequently, DIPEA (1.37 ml, 7.86 mmol) and 1,2,4-triazole-1-carboximidamide (885 mg, 6.00 mmol) were further added, and the mixture was stirred under microwave irradiation at 200° C. for one hour. After the reaction mixture was cooled to room temperature and water was added thereto, the precipitated solid was collected by filtration. The solid was suspended in methanol and subjected to ultrasonic irradiation. The solid was again collected by filtration and dried under reduced pressure to give the title compound (200 mg, 31%) as a brown solid.

LCMS: m/z 324 [M+H]$^+$

HPLC retention time: 0.61 min (analysis condition D)

Example 529

Compound i43 tert-Butyl 4-[[2-amino-4-oxo-6-(trifluoromethoxy)-3H-quinazolin-8-yl]methyl]piperazine-1-carboxylate

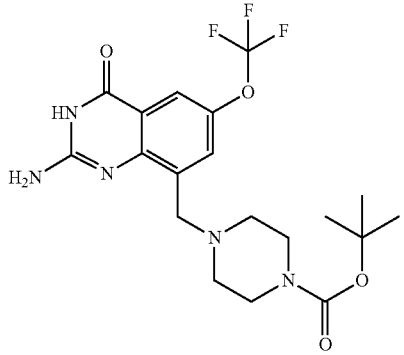 [SMILES: CC(C)(C)OC(=O)N1CCN(Cc2cc(OC(F)(F)F)cc3c(=O)[nH]c(N)nc23)CC1]

The title compound was synthesized from 2-amino-8-bromo-6-(trifluoromethoxy)-3H-quinazolin-4-one (Compound i42) under the same conditions as for Compound g1. However, the reaction was performed under microwave irradiation at 140° C.

Example 530

Compound i44 tert-Butyl 4-[[2-amino-3-[(5-chloro-2-ethylsulfonylphenyl)methyl]-4-oxo-6-(trifluoromethoxy)quinazolin-8-yl]methyl]piperazine-1-carboxylate

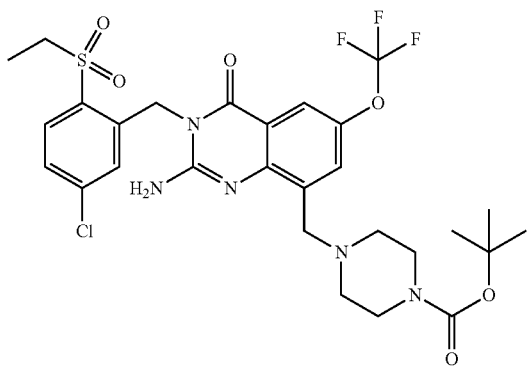 [SMILES: CCS(=O)(=O)c1ccc(Cl)cc1Cn1c(N)nc2c(CN3CCN(C(=O)OC(C)(C)C)CC3)cc(OC(F)(F)F)cc2c1=O]

The title compound was synthesized from 2-(bromomethyl)-4-chloro-1-ethylsulfonylbenzene (Compound 26) and tert-butyl 4-[[2-amino-4-oxo-6-(trifluoromethoxy)-3H-quinazolin-8-yl]methyl]piperazine-1-carboxylate (Compound i43) under the same conditions as for Compound F-1.

Example 531

Compound I-27

2-Amino-3-[(5-chloro-2-ethylsulfonylphenyl)methyl]-8-(piperazin-1-ylmethyl)-6-(trifluoromethoxy)quinazolin-4-one

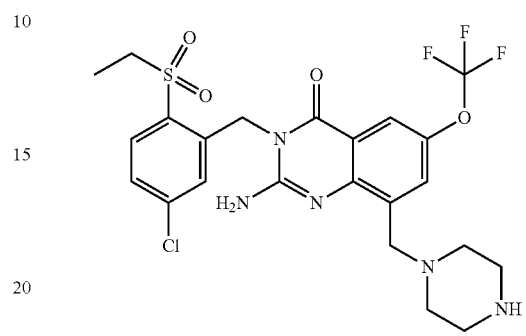

The title compound was synthesized from tert-butyl 4-[[2-amino-3-[(5-chloro-2-ethylsulfonylphenyl)methyl]-4-oxo-6-(trifluoromethoxy)quinazolin-8-yl]methyl]piperazine-1-carboxylate (Compound i44) under the same conditions as for Compound A-2.

LCMS: m/z 560 [M+H]$^+$
HPLC retention time: 1.87 min (analysis condition C)

Example 532

Compound j1

Ethyl 2-amino-5-bromo-4-(bromomethyl)benzoate

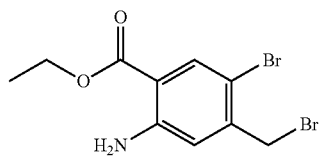

The title compound was synthesized from ethyl 2-[bis[(2-methylpropan-2-yl)oxycarbonyl]amino]-5-bromo-4-(bromomethyl)benzoate (Compound 131) under the same conditions as for Compound A-2.

Example 533

Compound j2 tert-Butyl 4-[(5-amino-2-bromo-4-ethoxycarbonylphenyl)methyl]piperazine-1-carboxylate

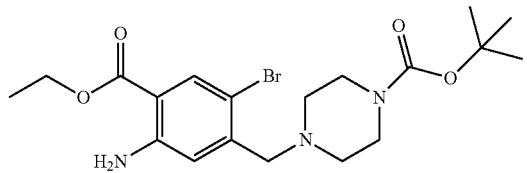 [SMILES: CCOC(=O)c1cc(Br)c(CN2CCN(C(=O)OC(C)(C)C)CC2)cc1N]

The title compound was synthesized from ethyl 2-amino-5-bromo-4-(bromomethyl)benzoate (Compound j1) under the same conditions as for Compound i11. However, tert-butyl piperazine-1-carboxylate was used in place of tert-butyl N-[(3R)-pyrrolidin-3-yl]carbamate as an amine.

Example 534

Compound j3

2-Amino-5-bromo-4-[[4-[(2-methylpropan-2-yl)oxycarbonyl]piperazin-1-yl]methyl]benzoic Acid

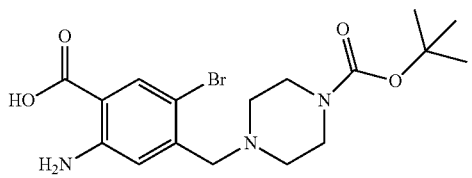 [SMILES: CC(C)(C)OC(=O)N1CCN(Cc2cc(N)c(C(=O)O)cc2Br)CC1]

The title compound was synthesized from tert-butyl 4-[(5-amino-2-bromo-4-ethoxycarbonylphenyl)methyl]piperazine-1-carboxylate (Compound j2) under the same conditions as for Compound 85. However, potassium hydroxide was used in place of sodium hydroxide as a base.

Example 535

Compound j4 tert-Butyl 4-[[5-amino-2-bromo-4-[(5-chloro-2-ethylsulfonylphenyl)methylcarbamoyl]phenyl]methyl]piperazine-1-carboxylate

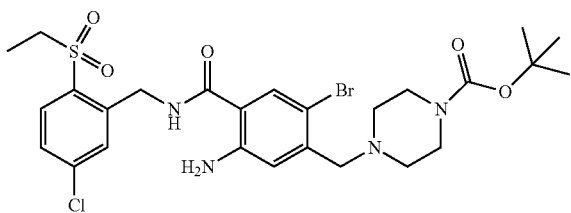

The title compound was synthesized from 2-amino-5-bromo-4-[[4-[(2-methylpropan-2-yl)oxycarbonyl]piperazin-1-yl]methyl]benzoic acid (Compound j3) and (5-chloro-2-ethylsulfonylphenyl)methanamine hydrochloride (Compound 3) under the same conditions as for Compound 113. However, DMF was used in place of dichloromethane as a solvent.

Example 536

Compound j5 tert-Butyl 4-[[6-bromo-3-[(5-chloro-2-ethylsulfonylphenyl)methyl]-4-oxoquinazolin-7-yl]methyl]piperazine-1-carboxylate

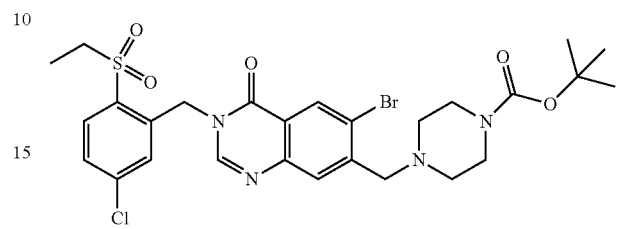

The title compound was synthesized from tert-butyl 4-[[5-amino-2-bromo-4-[(5-chloro-2-ethylsulfonylphenyl)methylcarbamoyl]phenyl]methyl]piperazine-1-carboxylate (Compound j4) under the same conditions as for Compound A-5.

Example 537

Compound J-1

6-Bromo-3-[(5-chloro-2-ethylsulfonylphenyl)methyl]-7-(piperazin-1-ylmethyl)quinazolin-4-one

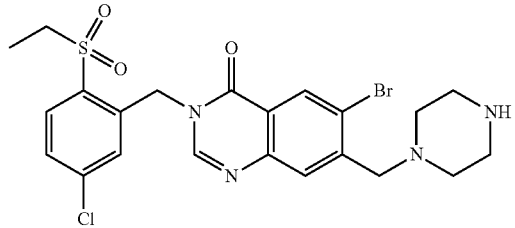

The title compound was synthesized from tert-butyl 4-[[6-bromo-3-[(5-chloro-2-ethylsulfonylphenyl)methyl]-4-oxoquinazolin-7-yl]methyl]piperazine-1-carboxylate (Compound j5) under the same conditions as for Compound A-2.
LCMS: m/z 539 [M+H]$^+$
HPLC retention time: 0.51 min (analysis condition D)

Example 538

Compound J-2

6-Bromo-3-[(5-chloro-2-ethylsulfonylphenyl)methyl]-7-[(4-propan-2-ylpiperazin-1-yl)methyl]quinazolin-4-one

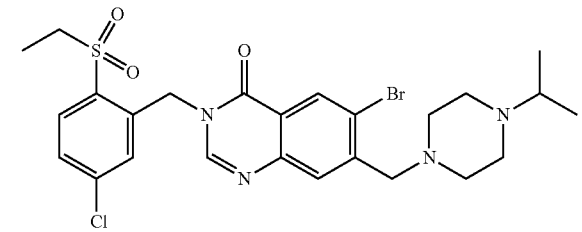 [SMILES: CCS(=O)(=O)c1ccc(Cl)cc1Cn1cnc2cc(CN3CCN(C(C)C)CC3)c(Br)cc2c1=O]

The title compound was synthesized from 6-bromo-3-[(5-chloro-2-ethylsulfonylphenyl)methyl]-7-(piperazin-1-ylmethyl)quinazolin-4-one (Compound J-1) under the same conditions as for Compound G-3. However, ethyl acetate was used in place of THF as a solvent.
LCMS: m/z 581 [M+H]+
HPLC retention time: 1.92 min (analysis condition E)

Example 539

Compound J-3

6-Bromo-3-[(5-chloro-2-ethylsulfonylphenyl)methyl]-7-[(4-cyclobutylpiperazin-1-yl)methyl]quinazolin-4-one

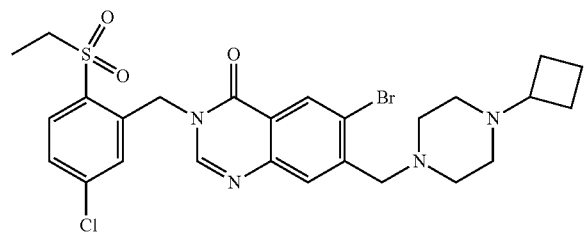 [SMILES: CCS(=O)(=O)c1ccc(Cl)cc1Cn1cnc2cc(CN3CCN(C4CCC4)CC3)c(Br)cc2c1=O]

The title compound was synthesized from 6-bromo-3-[(5-chloro-2-ethylsulfonylphenyl)methyl]-7-(piperazin-1-ylmethyl)quinazolin-4-one (Compound J-1) under the same conditions as for Compound G-3. However, cyclobutanone was used in place of acetone, and ethyl acetate was used in place of THF as a solvent.
LCMS: m/z 593 [M+H]+
HPLC retention time: 1.95 min (analysis condition E)

Example 540

Compound J-4

6-Bromo-3-[(5-chloro-2-ethylsulfonylphenyl)methyl]-7-[[4-(2,2,2-trifluoroethyl)piperazin-1-yl]methyl]quinazolin-4-one

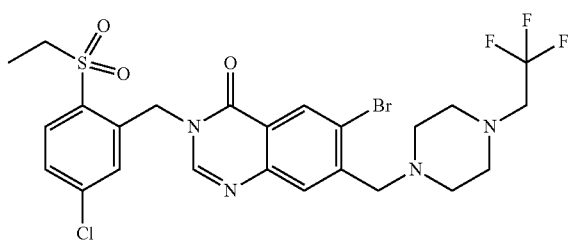 [SMILES: CCS(=O)(=O)c1ccc(Cl)cc1Cn1cnc2cc(CN3CCN(CC(F)(F)F)CC3)c(Br)cc2c1=O]

2,2,2-Trifluoroethyl trifluoromethanesulfonate (16.0 ul, 0.111 mmol) was added to a solution of 6-bromo-3-[(5-chloro-2-ethylsulfonylphenyl)methyl]-7-(piperazin-1-ylmethyl)quinazolin-4-one (Compound J-1, 20.0 mg, 37.0 umol) and DIPEA (19.3 ul, 0.111 mmol) in THF (1 ml), and the mixture was stirred at 80° C. for two hours. After the reaction mixture was cooled to room temperature, water was added to the mixture, which was diluted with DMSO, followed by purification by preparative HPLC (water/acetonitrile, 0.05% TFA) to give the title compound (12.4 mg, 54%) as a white solid.

LCMS: m/z 621 [M+H]+
HPLC retention time: 2.10 min (analysis condition E)

Example 541

Compound J-5

6-Bromo-3-[(5-chloro-2-ethylsulfonylphenyl)methyl]-7-[(4-prop-2-ynylpiperazin-1-yl)methyl]quinazolin-4-one

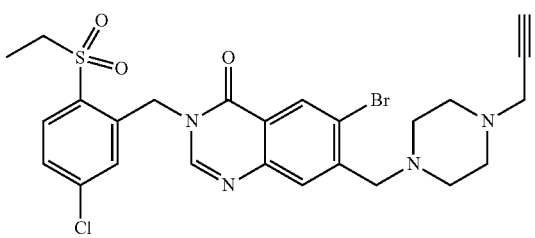 [SMILES: C#CCN1CCN(Cc2cc3ncn(Cc4cc(Cl)ccc4S(=O)(=O)CC)c(=O)c3cc2Br)CC1]

3-Bromoprop-1-yne (3.1 ul, 41.2 umol) was added to a solution of 6-bromo-3-[(5-chloro-2-ethylsulfonylphenyl)methyl]-7-(piperazin-1-ylmethyl)quinazolin-4-one (Compound J-1, 20.0 mg, 37.0 umol) and DIPEA (8.4 ul, 48.2 umol) in chloroform (1 ml), and the mixture was stirred at room temperature for 20 hours. Water was added to the reaction mixture, which was diluted with DMSO, followed by purification by preparative HPLC (water/acetonitrile, 0.05% TFA) to give the title compound (8.6 mg, 40%) as a white solid.
LCMS: m/z 577 [M+H]+
HPLC retention time: 1.98 min (analysis condition E)

Example 542

Compound J-6

6-Bromo-3-[(5-chloro-2-ethylsulfonylphenyl)methyl]-7-[[4-(1-methylpiperidin-4-yl)piperazin-1-yl]methyl]quinazolin-4-one

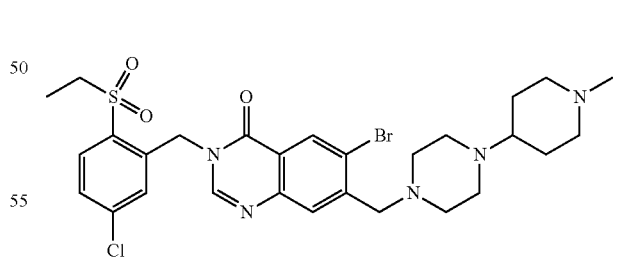

The title compound was synthesized from 6-bromo-3-[(5-chloro-2-ethylsulfonylphenyl)methyl]-7-(piperazin-1-ylmethyl)quinazolin-4-one (Compound J-1) under the same conditions as for Compound G-3. However, 1-methyl-4-piperidone was used in place of acetone and ethyl acetate was used in place of THF as a solvent.
LCMS: m/z 636 [M+H]+
HPLC retention time: 1.67 min (analysis condition E)

Example 543

Compound j6

Ethyl 2-[bis[(2-methylpropan-2-yl)oxycarbonyl]amino]-5-bromo-4-[[(3R)-3-[(2-methylpropan-2-yl)oxycarbonylamino]pyrrolidin-1-yl]methyl]benzoate

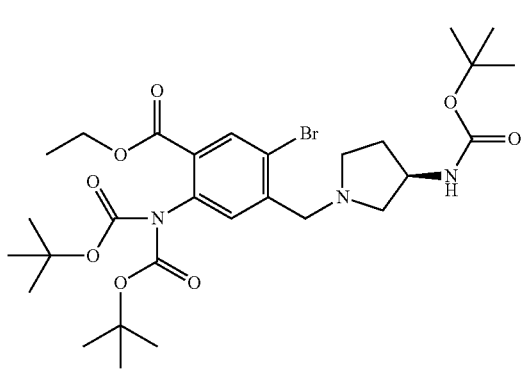 [SMILES: CCOC(=O)c1cc(Br)c(CN2CC[C@@H](NC(=O)OC(C)(C)C)C2)cc1N(C(=O)OC(C)(C)C)C(=O)OC(C)(C)C]

tert-Butyl N-[(3R)-pyrrolidin-3-yl]carbamate (393 mg, 2.11 mmol) was added to a solution of ethyl 2-[bis[(2-methylpropan-2-yl)oxycarbonyl]amino]-5-bromo-4-(bromomethyl)benzoate (Compound 131, 1.08 g, 1.41 mmol) and potassium carbonate (583 mg, 4.22 mmol) in DMF (10 ml), and the mixture was stirred at 50-75° C. for three hours. After the reaction mixture was cooled to room temperature, water was added thereto and extraction was performed with a mixed solution of ethyl acetate and hexane. The organic layer was washed with a saturated aqueous sodium chloride solution and then dried over anhydrous sodium sulfate. After the drying agent was removed by filtration, concentration was performed under reduced pressure. The resulting residue was purified by silica gel column chromatography (ethyl acetate/hexane) to give the title compound (872 mg, 99%) as a yellow solid.

LCMS: m/z 642 [M+H]$^+$

HPLC retention time: 0.73 min (analysis condition G)

Example 544

Compound j7

Ethyl 2-amino-4-[[(3R)-3-aminopyrrolidin-1-yl]methyl]-5-bromobenzoate

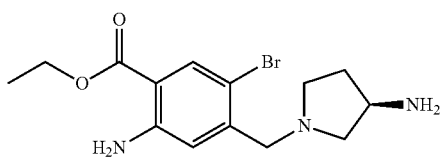 [SMILES: CCOC(=O)c1cc(Br)c(CN2CC[C@@H](N)C2)cc1N]

The title compound was synthesized from ethyl 2-[bis[(2-methylpropan-2-yl)oxycarbonyl]amino]-5-bromo-4-[[(3R)-3-[(2-methylpropan-2-yl)oxycarbonylamino]pyrrolidin-1-yl]methyl]benzoate (Compound j6) under the same conditions as for Compound A-2.

Example 545

Compound j8

Ethyl 2-amino-5-bromo-4-[[(3R)-3-[(2-methylpropan-2-yl)oxycarbonylamino]pyrrolidin-1-yl]methyl]benzoate

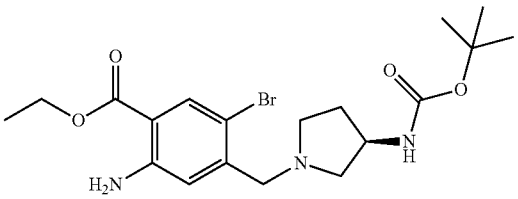 [SMILES: CCOC(=O)c1cc(Br)c(CN2CC[C@@H](NC(=O)OC(C)(C)C)C2)cc1N]

The title compound was synthesized from ethyl 2-amino-4-[[(3R)-3-aminopyrrolidin-1-yl]methyl]-5-bromobenzoate (Compound j7) under the same conditions as for Compound 129.

Example 546

Compound j9

2-Amino-5-bromo-4-[[(3R)-3-[(2-methylpropan-2-yl)oxycarbonylamino]pyrrolidin-1-yl]methyl]benzoic Acid

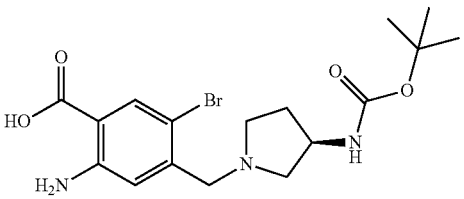 [SMILES: CC(C)(C)OC(=O)N[C@@H]1CCN(Cc2cc(N)c(C(=O)O)cc2Br)C1]

The title compound was synthesized from ethyl 2-amino-5-bromo-4-[[(3R)-3-[(2-methylpropan-2-yl)oxycarbonylamino]pyrrolidin-1-yl]methyl]benzoate (Compound j8) under the same conditions as for Compound 85.

Example 547

Compound j10 tert-Butyl N-[(3R)-1-[[5-amino-2-bromo-4-[(5-chloro-2-ethylsulfonylphenyl)methylcarbamoyl]phenyl]methyl]pyrrolidin-3-yl]carbamate

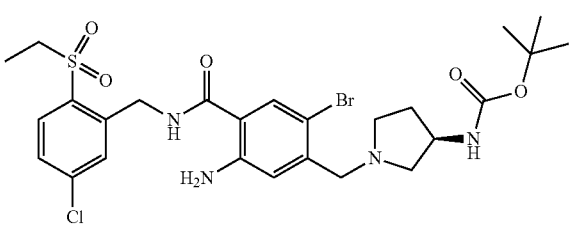 [SMILES: CCS(=O)(=O)c1ccc(Cl)cc1CNC(=O)c1cc(Br)c(CN2CC[C@@H](NC(=O)OC(C)(C)C)C2)cc1N]

The title compound was synthesized from 2-amino-5-bromo-4-[[(3R)-3-[(2-methylpropan-2-yl)oxycarbonylamino]pyrrolidin-1-yl]methyl]benzoic acid (Compound j9) and (5-chloro-2-ethylsulfonylphenyl)methanamine hydrochloride (Compound 3) under the same conditions as for Compound 113.

Example 548

Compound j11 tert-Butyl N-[(3R)-1-[[6-bromo-3-[(5-chloro-2-ethylsulfonylphenyl)methyl]-4-oxoquinazolin-7-yl]methyl]pyrrolidin-3-yl]carbamate

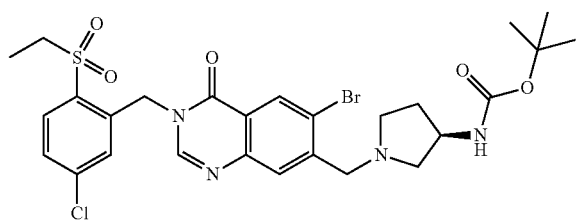 [SMILES: CCS(=O)(=O)c1ccc(Cl)cc1Cn1cnc2cc(CN3CC[C@@H](NC(=O)OC(C)(C)C)C3)c(Br)cc2c1=O]

The title compound was synthesized from tert-butyl N-[(3R)-1-[[5-amino-2-bromo-4-[(5-chloro-2-ethylsulfonylphenyl)methylcarbamoyl]phenyl]methyl]pyrrolidin-3-yl]carbamate (Compound j10) under the same conditions as for Compound A-28.

Example 549

Compound J-7

7-[[(3R)-3-aminopyrrolidin-1-yl]methyl]-6-bromo-3-[(5-chloro-2-ethylsulfonylphenyl)methyl]quinazolin-4-one

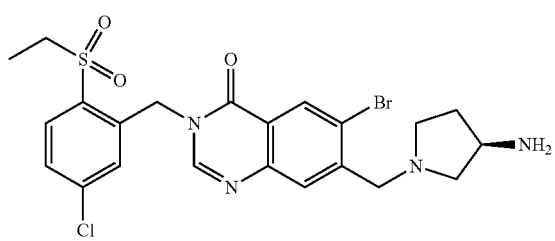 [SMILES: CCS(=O)(=O)c1ccc(Cl)cc1Cn1cnc2cc(CN3CC[C@@H](N)C3)c(Br)cc2c1=O]

The title compound was synthesized from tert-butyl N-[(3R)-1-[[6-bromo-3-[(5-chloro-2-ethylsulfonylphenyl)methyl]-4-oxoquinazolin-7-yl]methyl]pyrrolidin-3-yl]carbamate (Compound j11) under the same conditions as for Compound A-2.

LCMS: m/z 539 [M+H]+

HPLC retention time: 0.43 min (analysis condition G)

Example 550

Compound J-8

7-[[(3S)-3-Aminopyrrolidin-1-yl]methyl]-6-bromo-3-[(5-chloro-2-ethylsulfonylphenyl)methyl]quinazolin-4-one

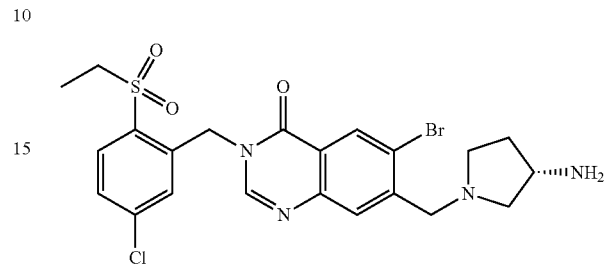

The title compound was synthesized from ethyl 2-[bis[(2-methylpropan-2-yl)oxycarbonyl]amino]-5-bromo-4-(bromomethyl)benzoate (Compound 131) under the same conditions as for Compounds j6, j7, j8, j9, j10, j11, and J-7. However, tert-butyl N-[(3S)-pyrrolidin-3-yl]carbamate was used in place of tert-butyl N-[(3R)-pyrrolidin-3-yl]carbamate under the conditions for Compound j6.

LCMS: m/z 539 [M+H]+

HPLC retention time: 0.41 min (analysis condition F)

Example 551

Compound J-9

6-Bromo-3-[(5-chloro-2-ethylsulfonylphenyl)methyl]-7-[(3-piperidin-1-ylpyrrolidin-1-yl)methyl]quinazolin-4-one

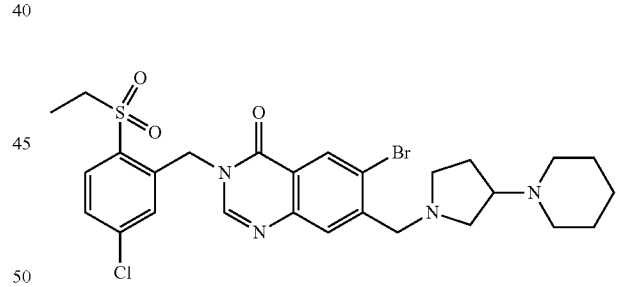

Ethyl 2-amino-5-bromo-4-[(3-piperidin-1-ylpyrrolidin-1-yl)methyl]benzoate was synthesized from ethyl 2-[bis[(2-methylpropan-2-yl)oxycarbonyl]amino]-5-bromo-4-(bromomethyl)benzoate (Compound 131) under the same conditions as for Compounds j6 and j7. However, 1-pyrrolidin-3-ylpiperidine was used in place of tert-butyl N-[(3R)-pyrrolidin-3-yl]carbamate under the conditions for Compound j6

The title compound was synthesized from ethyl 2-amino-5-bromo-4-[(3-piperidin-1-ylpyrrolidin-1-yl)methyl]benzoate under the same conditions as for Compound j9, j10, and j11. However, the reaction was performed at 100° C. using microwave under the conditions for Compound j11.

LCMS: m/z 607[M+H]+

HPLC retention time: 0.50 min (analysis condition F)

Example 552

Compound j12

2-Amino-5-chloro-4-[[4-[(2-methylpropan-2-yl)oxycarbonyl]piperazin-1-yl]methyl]benzoic Acid

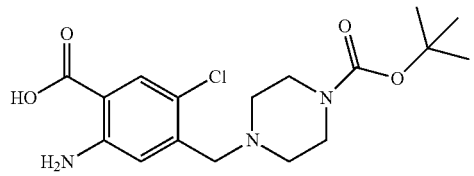 [SMILES: CC(C)(C)OC(=O)N1CCN(Cc2cc(N)c(C(=O)O)cc2Cl)CC1]

The title compound was synthesized from tert-butyl 4-[(5-amino-2-chloro-4-ethoxycarbonylphenyl)methyl]piperazine-1-carboxylate (Compound 129) under the same conditions as for Compound 85.

Example 553

Compound j13 tert-Butyl 4-[[5-amino-2-chloro-4-[(5-chloro-2-ethylsulfonylphenyl)methylcarbamoyl]phenyl]methyl]piperazine-1-carboxylate

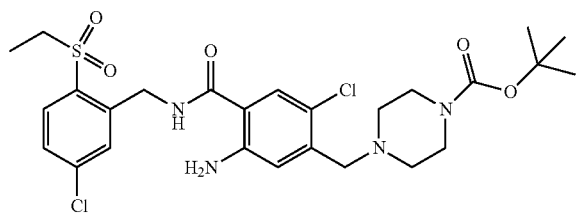 [SMILES: CCS(=O)(=O)c1ccc(Cl)cc1CNC(=O)c1cc(Cl)c(CN2CCN(C(=O)OC(C)(C)C)CC2)cc1N]

The title compound was synthesized from 2-amino-5-chloro-4-[[4-[(2-methylpropan-2-yl)oxycarbonyl]piperazin-1-yl]methyl]benzoic acid (Compound j12) and (5-chloro-2-ethylsulfonylphenyl)methanamine hydrochloride (Compound 3) under the same conditions as for Compound e8. However, WSCDI was used in place of HBTU.

Example 554

Compound j14 tert-Butyl 4-[[6-chloro-3-[(5-chloro-2-ethylsulfonylphenyl)methyl]-4-oxoquinazolin-7-yl]methyl]piperazine-1-carboxylate

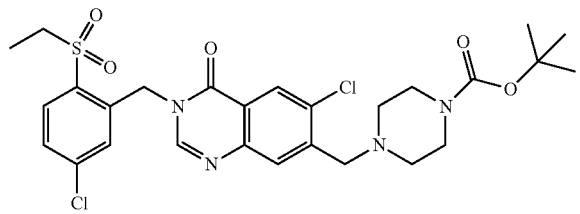 [SMILES: CCS(=O)(=O)c1ccc(Cl)cc1Cn1cnc2cc(CN3CCN(C(=O)OC(C)(C)C)CC3)c(Cl)cc2c1=O]

The title compound was synthesized from tert-butyl 4-[[5-amino-2-chloro-4-[(5-chloro-2-ethylsulfonylphenyl)methylcarbamoyl]phenyl]methyl]piperazine-1-carboxylate (Compound j13) under the same conditions as for Compound A-28.

Example 555

Compound J-10

6-Chloro-3-[(5-chloro-2-ethylsulfonylphenyl)methyl]-7-(piperazin-1-ylmethyl)quinazolin-4-one

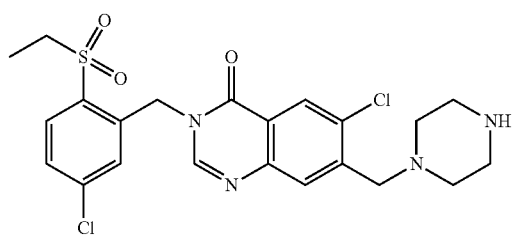 [SMILES: CCS(=O)(=O)c1ccc(Cl)cc1Cn1cnc2cc(CN3CCNCC3)c(Cl)cc2c1=O]

The title compound was synthesized from tert-butyl 4-[[6-chloro-3-[(5-chloro-2-ethylsulfonylphenyl)methyl]-4-oxoquinazolin-7-yl]methyl]piperazine-1-carboxylate (Compound j14) under the same conditions as for Compound A-2.

LCMS: m/z 495 [M+H]$^+$

HPLC retention time: 0.50 min (analysis condition G)

Example 556

Compound J-11

6-Chloro-3-[(5-chloro-2-ethylsulfonylphenyl)methyl]-7-[4-methylpiperazin-1-yl)methyl]quinazolin-4-one

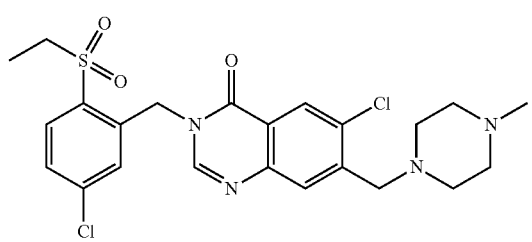 [SMILES: CCS(=O)(=O)c1ccc(Cl)cc1Cn1cnc2cc(CN3CCN(C)CC3)c(Cl)cc2c1=O]

The title compound was synthesized from 6-chloro-3-[(5-chloro-2-ethylsulfonylphenyl)methyl]-7-(piperazin-1-ylmethyl)quinazolin-4-one (Compound J-10) under the same conditions as for Compound G-2.

LCMS: m/z 509 [M+H]$^+$

HPLC retention time: 0.52 min (analysis condition G)

Example 557

Compound k1 tert-Butyl 4-[[3-amino-2-chloro-4-ethoxycarbonyl-6-(trifluoromethyl)phenyl]methyl]piperazine-1-carboxylate

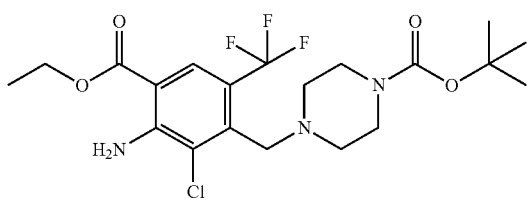 [SMILES: CCOC(=O)c1cc(C(F)(F)F)c(CN2CCN(C(=O)OC(C)(C)C)CC2)c(Cl)c1N]

The title compound was synthesized from tert-butyl 4-[[5-amino-4-ethoxycarbonyl-2-(trifluoromethyl)phenyl]methyl]piperazine-1-carboxylate (Compound g1) under the same conditions as for Compound 111.

Example 558

Compound k2

2-Amino-3-chloro-4-[[4-[(2-methylpropan-2-yl)oxycarbonyl]piperazin-1-yl]methyl]-5-(trifluoromethyl) benzoic Acid

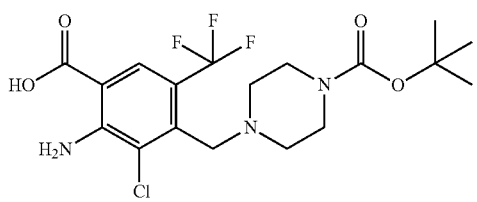 [SMILES: CC(C)(C)OC(=O)N1CCN(Cc2c(C(F)(F)F)cc(C(=O)O)c(N)c2Cl)CC1]

The title compound was synthesized from tert-butyl 4-[[3-amino-2-chloro-4-ethoxycarbonyl-6-(trifluoromethyl)phenyl]methyl]piperazine-1-carboxylate (Compound k1) under the same conditions as for Compound 85.

Example 559

Compound k3 tert-Butyl 4-[[3-amino-2-chloro-4-[(5-chloro-2-ethylsulfonylphenyl)methylcarbamoyl]-6-(trifluoromethyl)phenyl]methyl]piperazine-1-carboxylate

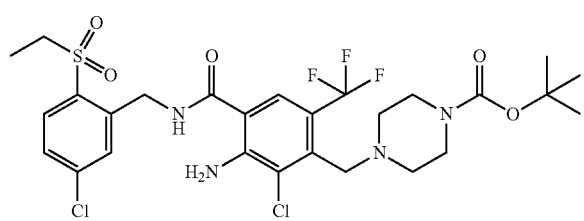 [SMILES: CCS(=O)(=O)c1ccc(Cl)cc1CNC(=O)c1cc(C(F)(F)F)c(CN2CCN(C(=O)OC(C)(C)C)CC2)c(Cl)c1N]

The title compound was synthesized from 2-amino-3-chloro-4-[[4-[(2-methylpropan-2-yl)oxycarbonyl]piperazin-1-yl]methyl]-5-(trifluoromethyl)benzoic acid (Compound k2) and (5-chloro-2-ethylsulfonylphenyl)methanamine hydrochloride (Compound 3) under the same conditions as for Compound e8. However, WSCDI was used in place of HBTU.

Example 560

Compound k4 tert-Butyl 4-[[8-chloro-3-[(5-chloro-2-ethylsulfonylphenyl)methyl]-4-oxo-6-(trifluoromethyl)quinazolin-7-yl]methyl]piperazine-1-carboxylate

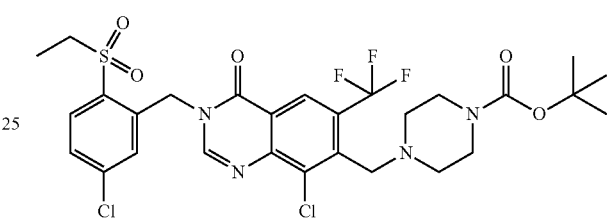

The title compound was synthesized from tert-butyl 4-[[3-amino-2-chloro-4-[(5-chloro-2-ethylsulfonylphenyl)methylcarbamoyl]-6-(trifluoromethyl)phenyl]methyl]piperazine-1-carboxylate (Compound k3) under the same conditions as for Compound A-28.

Example 561

Compound K-1

8-Chloro-3-[(5-chloro-2-ethyl)methyl]-7-(piperazin-1-ylmethyl)-6-(trifluoromethyl)quinazolin-4-one

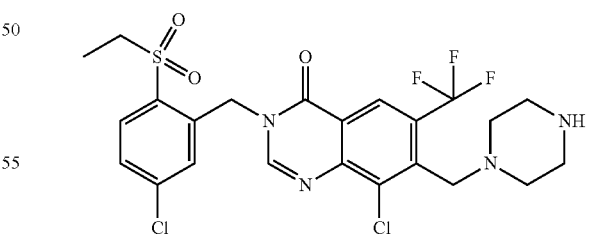

The title compound was synthesized from tert-butyl 4-[[8-chloro-3-[(5-chloro-2-ethylsulfonylphenyl)methyl]-4-oxo-6-(trifluoromethyl)quinazolin-7-yl]methyl]piperazine-1-carboxylate (Compound k4) under the same conditions as for Compound 21.

LCMS: m/z 563 [M+H]$^+$

HPLC retention time: 0.56 min (analysis condition D)

Example 562

Compound K-2

8-Chloro-3-[(5-chloro-2-ethylsulfonylphenyl)methyl]-7-[(4-methylpiperazin-1-yl)methyl]-6-(trifluoromethyl)quinazolin-4-one

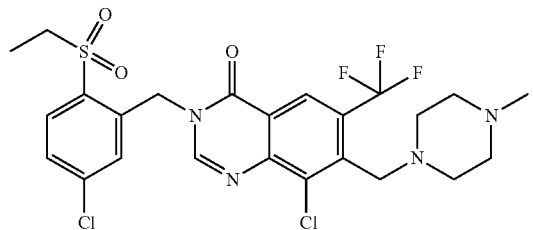 [SMILES: CCS(=O)(=O)c1ccc(Cl)cc1Cn1cnc2c(Cl)c(CN3CCN(C)CC3)c(C(F)(F)F)cc2c1=O]

The title compound was synthesized from 8-chloro-3-[(5-chloro-2-ethylsulfonylphenyl)methyl]-7-(piperazin-1-ylmethyl)-6-(trifluoromethyl)quinazolin-4-one (Compound K-1) under the same conditions as for Compound G-2.
LCMS: m/z 577 [M+H]$^+$
HPLC retention time: 0.57 min (analysis condition D)

Example 563

Compound K-3

8-Chloro-3-[(5-chloro-2-ethylsulfonylphenyl)methyl]-7-[(4-propan-2-ylpiperazin-1-yl)methyl]-6-(trifluoromethyl)quinazolin-4-one

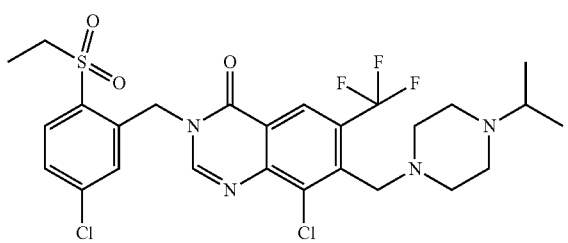 [SMILES: CCS(=O)(=O)c1ccc(Cl)cc1Cn1cnc2c(Cl)c(CN3CCN(C(C)C)CC3)c(C(F)(F)F)cc2c1=O]

The title compound was synthesized from 8-chloro-3-[(5-chloro-2-ethylsulfonylphenyl)methyl]-7-(piperazin-1-ylmethyl)-6-(trifluoromethyl)quinazolin-4-one (Compound K-1) under the same conditions as for Compound G-3.
LCMS: m/z 605 [M+H]$^+$
HPLC retention time: 0.59 min (analysis condition D)

Example 564

Compound k5 tert-Butyl 4-[[5-amino-4-[(5-cyano-2-ethylsulfonylphenyl)methylcarbamoyl]-2-(trifluoromethyl)phenyl]methyl]piperazine-1-carboxylate

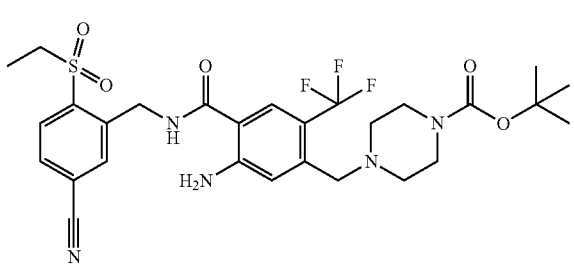 [SMILES: CCS(=O)(=O)c1ccc(C#N)cc1CNC(=O)c1cc(C(F)(F)F)c(CN2CCN(C(=O)OC(C)(C)C)CC2)cc1N]

The title compound was synthesized from 3-aminomethyl-4-ethylsulfonylbenzonitrile (Compound 16) and 2-amino-4-[[4-[(2-methylpropan-2-yl)oxycarbonyl]piperazin-1-yl]methyl]-5-(trifluoromethyl)benzoic acid (Compound g2) under the same conditions as for Compound e8. However, WSCDI was used in place of HBTU.

Example 565

Compound k6 tert-Butyl 4-[[3-amino-2-chloro-4-[(5-cyano-2-ethylsulfonylphenyl)methylcarbamoyl]-6-(trifluoromethyl)phenyl]methyl]piperazine-1-carboxylate

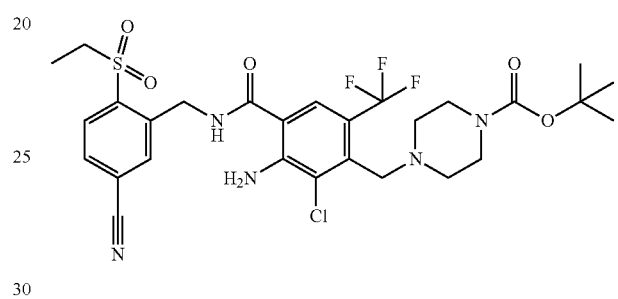

The title compound was synthesized from tert-butyl 4-[[5-amino-4-[(5-cyano-2-ethylsulfonylphenyl)methylcarbamoyl]-2-(trifluoromethyl)phenyl]methyl]piperazine-1-carboxylate (Compound k5) under the same conditions as for Compound 111.

Example 566

Compound k7 tert-Butyl 4-[[8-chloro-3-[(5-cyano-2-ethylsulfonylphenyl)methyl]-4-oxo-6-(trifluoromethyl)quinazolin-7-yl]methyl]piperazine-1-carboxylate

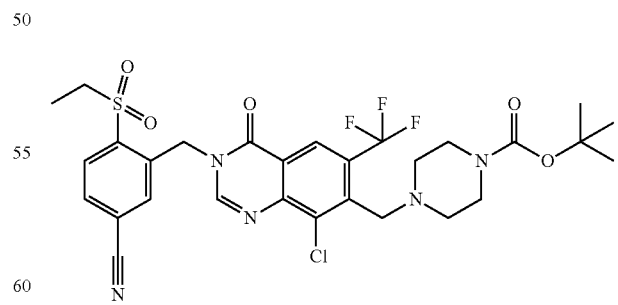

The title compound was synthesized from tert-butyl 4-[[3-amino-2-chloro-4-[(5-cyano-2-ethylsulfonylphenyl)methylcarbamoyl]-6-(trifluoromethyl)phenyl]methyl]piperazine-1-carboxylate (Compound k6) under the same conditions as for Compound A-28.

Example 567

Compound K-4

3-[[8-Chloro-4-oxo-7-(piperazin-1-ylmethyl)-6-(trifluoromethyl)quinazolin-3-yl]methyl]-4-ethylsulfonylbenzonitrile

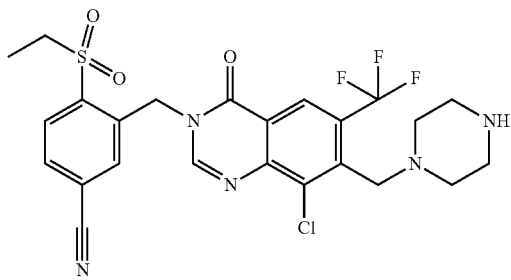 [SMILES: CCS(=O)(=O)c1ccc(C#N)cc1Cn1cnc2c(Cl)c(CN3CCNCC3)c(C(F)(F)F)cc2c1=O]

The title compound was synthesized from tert-butyl 4-[[8-chloro-3-[(5-cyano-2-ethylsulfonylphenyl)methyl]-4-oxo-6-(trifluoromethyl)quinazolin-7-yl]methyl]piperazine-1-carboxylate (Compound k7) under the same conditions as for Compound A-2.

LCMS: m/z 554 [M+H]$^+$
HPLC retention time: 0.51 min (analysis condition D)

Example 568

Compound k8

Ethyl 2-amino-4-[[(3R)-3-[(2-methylpropan-2-yl)oxycarbonylamino]pyrrolidin-1-yl]methyl]-5-(trifluoromethyl)benzoate

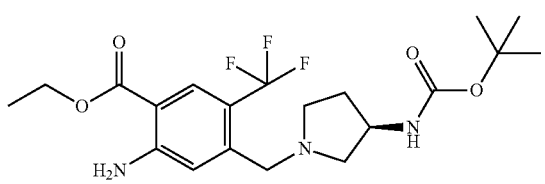 [SMILES: CCOC(=O)c1cc(C(F)(F)F)c(CN2CC[C@@H](NC(=O)OC(C)(C)C)C2)cc1N]

The title compound was synthesized from ethyl 2-amino-4-formyl-5-(trifluoromethyl)benzoate (Compound 110) under the same conditions as for Compound i3. However, tert-butyl N-[(3R)-pyrrolidin-3-yl]carbamate was used in place of N-[(3S)-pyrrolidin-3-yl]acetamide as an amine.

Example 569

Compound k9

2-Amino-4-[[(3R)-3-[(2-methylpropan-2-yl)oxycarbonylamino]pyrrolidin-1-yl]methyl]-5-(trifluoromethyl)benzoic Acid

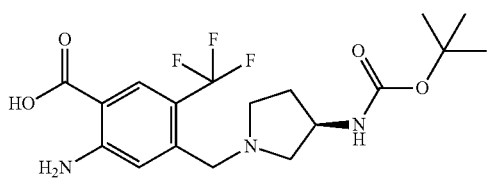 [SMILES: CC(C)(C)OC(=O)N[C@@H]1CCN(Cc2cc(N)c(C(=O)O)cc2C(F)(F)F)C1]

The title compound was synthesized from ethyl 2-amino-4-[[(3R)-3-[(2-methylpropan-2-yl)oxycarbonylamino]pyrrolidin-1-yl]methyl]-5-(trifluoromethyl)benzoate (Compound k8) under the same conditions as for Compound 85.

Example 570

Compound k10 tert-Butyl N-[(3R)-1-[[5-amino-4-[(5-chloro-2-ethylsulfonylphenyl)methylcarbamoyl]-2-(trifluoromethyl)phenyl]methyl]pyrrolidin-3-yl]carbamate

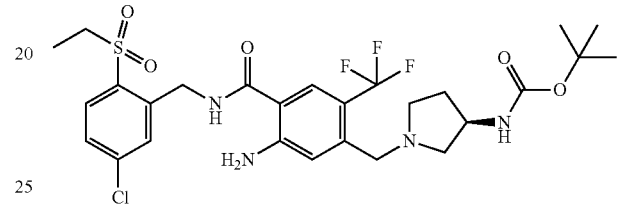

The title compound was synthesized from 2-amino-4-[[(3R)-3-[(2-methylpropan-2-yl)oxycarbonylamino]pyrrolidin-1-yl]methyl]-5-(trifluoromethyl)benzoic acid (Compound k9) and (5-chloro-2-ethylsulfonylphenyl)methanamine (a free form of Compound 3) under the same conditions as for Compound a1.

Example 571

Compound k11 tert-Butyl N-[(3R)-1-[[8-chloro-3-[(5-chloro-2-ethylsulfonylphenyl)methyl]-4-oxo-6-(trifluoromethyl)quinazolin-7-yl]methyl]pyrrolidin-3-yl]carbamate

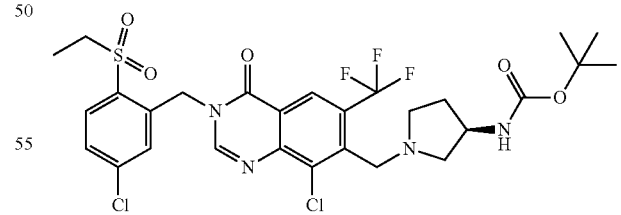

The title compound was synthesized from tert-butyl N-[(3R)-1-[[5-amino-4-[(5-chloro-2-ethylsulfonylphenyl)methylcarbamoyl]-2-(trifluoromethyl)phenyl]methyl]pyrrolidin-3-yl]carbamate (Compound k10) under the same conditions as for Compounds k6 and k7.

Example 572

Compound K-5

7-[[(3R)-3-Aminopyrrolidin-1-yl]methyl]-8-chloro-3-[(5-chloro-2-ethylsulfonylphenyl)methyl]-6-(trifluoromethyl)quinazolin-4-one

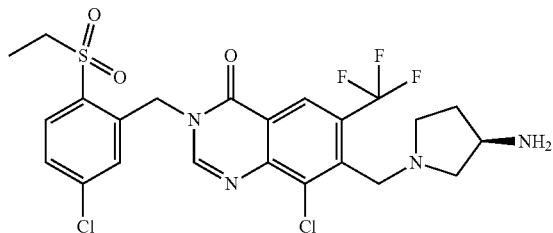 [SMILES: CCS(=O)(=O)c1ccc(Cl)cc1Cn1cnc2c(Cl)c(CN3CC[C@@H](N)C3)c(C(F)(F)F)cc2c1=O]

The title compound was synthesized from tert-butyl N-[(3R)-1-[[8-chloro-3-[(5-chloro-2-ethylsulfonylphenyl)methyl]-4-oxo-6-(trifluoromethyl)quinazolin-7-yl]methyl]pyrrolidin-3-yl]carbamate (Compound k11) under the same conditions as for Compound 21.

LCMS: m/z 563 [M+H]$^+$

HPLC retention time: 0.52 min (analysis condition D)

Example 573

Compound K-6

8-Chloro-3-[(5-chloro-2-ethylsulfonylphenyl)methyl]-7-[[(3R)-3-(dimethylamino)pyrrolidin-1-yl]methyl]-6-(trifluoromethyl)quinazolin-4-one

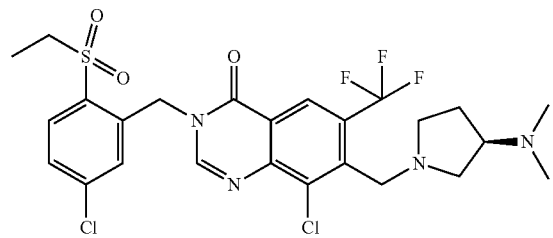

The title compound was synthesized from 7-[[(3R)-3-aminopyrrolidin-1-yl]methyl]-8-chloro-3-[(5-chloro-2-ethylsulfonylphenyl)methyl]-6-(trifluoromethyl)quinazolin-4-one (Compound K-5) under the same conditions as for Compound G-2.

LCMS: m/z 591 [M+H]$^+$

HPLC retention time: 0.57 min (analysis condition D)

Example 574

Compound K-7

N-[(3R)-1-[[8-Chloro-3-[(5-chloro-2-ethylsulfonylphenyl)methyl]-4-oxo-6-(trifluoromethyl)quinazolin-7-yl]methyl]pyrrolidin-3-yl]acetamide

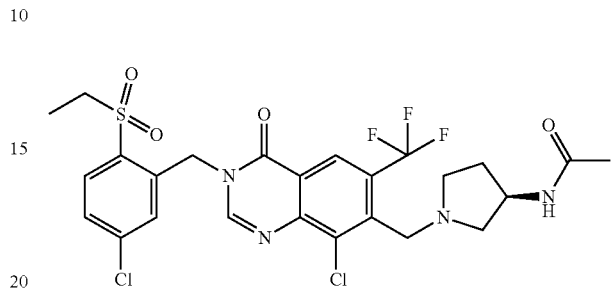

The title compound was synthesized from 7-[[(3R)-3-aminopyrrolidin-1-yl]methyl]-8-chloro-3-[(5-chloro-2-ethylsulfonylphenyl)methyl]-6-(trifluoromethyl)quinazolin-4-one (Compound K-5) under the same conditions as for Compound H-39.

LCMS: m/z 605 [M+H]$^+$

HPLC retention time: 0.52 min (analysis condition D)

Example 575

Compound K-8

N-[(3R)-1-[[8-Chloro-3-[(5-chloro-2-ethylsulfonylphenyl)methyl]-4-oxo-6-(trifluoromethyl)quinazolin-7-yl]methyl]pyrrolidin-3-yl]methanesulfonamide

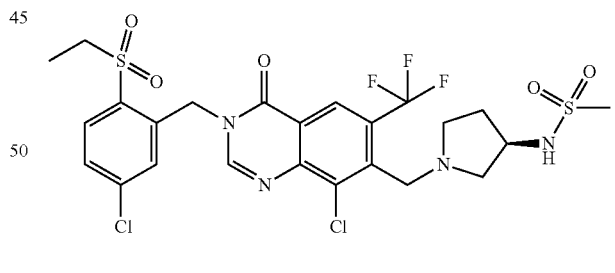

The title compound was synthesized from 7-[[(3R)-3-aminopyrrolidin-1-yl]methyl]-8-chloro-3-[(5-chloro-2-ethylsulfonylphenyl)methyl]-6-(trifluoromethyl)quinazolin-4-one (Compound K-5) under the same conditions as for Compound H-17. However, dichloromethane was used in place of pyridine as a solvent, and triethylamine was added as a base.

LCMS: m/z 641 [M+H]$^+$

HPLC retention time: 0.56 min (analysis condition D)

Example 576

Compound k12

Ethyl 2-amino-3-chloro-4-(1,3-dioxolan-2-yl)-5-(trifluoromethyl)benzoate

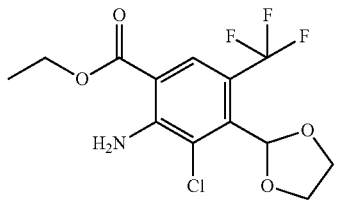 [SMILES: CCOC(=O)c1cc(C(F)(F)F)c(C2OCCO2)c(Cl)c1N]

PTSA/H₂O (147 mg, 0.738 mmol) was added to a solution of ethyl 2-amino-3-chloro-4-formyl-5-(trifluoromethyl)benzoate (Compound 111, 1.09 g, 3.69 mmol) and ethylene glycol (0.618 ml, 11.1 mmol) in toluene (15 ml), and the mixture was stirred at 100° C. for four hours. The reaction mixture was cooled to room temperature, followed by addition of water and extraction with ethyl acetate. The organic layer was dried over anhydrous sodium sulfate. After the drying agent was removed by filtration, concentration was performed under reduced pressure. The resulting residue was purified by amino silica gel column chromatography (ethyl acetate/hexane) to give the title compound (1.21 g, 96%) as a white solid.

LCMS: m/z 340 [M+H]⁺

HPLC retention time: 0.91 min (analysis condition H)

Example 577

Compound k13

2-Amino-3-chloro-4-(1,3-dioxolan-2-yl)-5-(trifluoromethyl)benzoic Acid

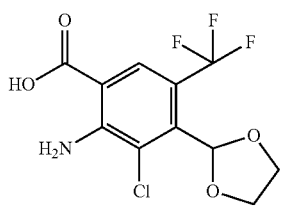 [SMILES: Nc1c(C(=O)O)cc(C(F)(F)F)c(C2OCCO2)c1Cl]

The title compound was synthesized from ethyl 2-amino-3-chloro-4-(1,3-dioxolan-2-yl)-5-(trifluoromethyl)benzoate (Compound k12) under the same conditions as for Compound 85.

Example 578

Compound k14

2-Amino-3-chloro-N-[(5-chloro-2-ethylsulfonylphenyl)methyl]-4-(1,3-dioxolan-2-yl)-5-(trifluoromethyl)benzamide

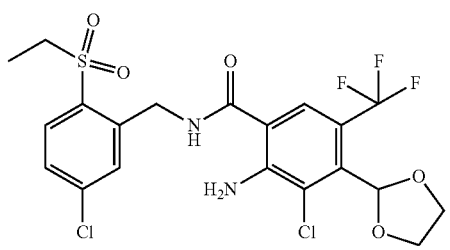 [SMILES: CCS(=O)(=O)c1ccc(Cl)cc1CNC(=O)c1cc(C(F)(F)F)c(C2OCCO2)c(Cl)c1N]

The title compound was synthesized from 2-amino-3-chloro-4-(1,3-dioxolan-2-yl)-5-(trifluoromethyl)benzoic acid (Compound k13) and (5-chloro-2-ethylsulfonylphenyl)methanamine hydrochloride (Compound 3) under the same conditions as for Compound 113.

Example 579

Compound K-9

8-Chloro-3-[(5-chloro-2-ethylsulfonylphenyl)methyl]-7-(1,3-dioxolan-2-yl)-6-(trifluoromethyl)quinazolin-4-one

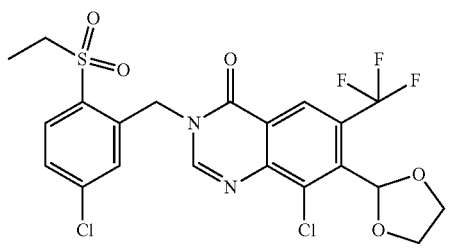 [SMILES: CCS(=O)(=O)c1ccc(Cl)cc1Cn1cnc2c(Cl)c(C3OCCO3)c(C(F)(F)F)cc2c1=O]

The title compound was synthesized from 2-amino-3-chloro-N-[(5-chloro-2-ethylsulfonylphenyl)methyl]-4-(1,3-dioxolan-2-yl)-5-(trifluoromethyl)benzamide (Compound k14) under the same conditions as for Compound A-28. However, toluene was used as a solvent, and p-toluenesulfonic acid monohydrate was added in place of formic acid as an acid.

LCMS: m/z 537 [M+H]⁺

HPLC retention time: 0.88 min (analysis condition F)

Example 580

Compound k15

Ethyl 2-amino-3-chloro-4-[[(3S)-3-[[methyl-[(2-methylpropan-2-yl)oxycarbonyl]amino]methyl]pyrrolidin-1-yl]methyl]-5-(trifluoromethyl)benzoate

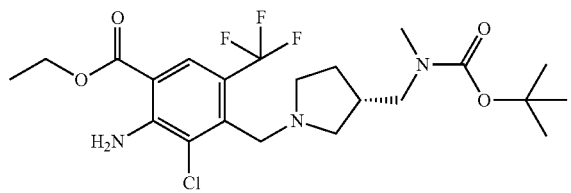 [SMILES: CCOC(=O)c1cc(C(F)(F)F)c(CN2CC[C@H](CN(C)C(=O)OC(C)(C)C)C2)c(Cl)c1N]

The title compound was synthesized from ethyl 2-amino-3-chloro-4-formyl-5-(trifluoromethyl)benzoate (Compound 111) under the same conditions as for Compound i3. However, tert-butyl N-methyl-N-[[(3S)-pyrrolidin-3-yl]methyl] carbamate was used in place of N-[(3S)-pyrrolidin-3-yl] acetamide as an amine.

Example 581

Compound k16

2-Amino-4-[[(3S)-3-[[tert-butoxycarbonyl(methyl) amino]methyl]pyrrolidin-1-yl]methyl]-3-chloro-5-(trifluoromethyl)benzoic Acid

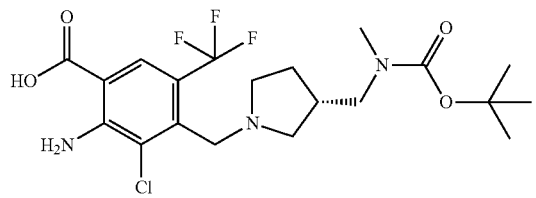 [SMILES: CN(C[C@H]1CCN(Cc2c(C(F)(F)F)cc(C(=O)O)c(N)c2Cl)C1)C(=O)OC(C)(C)C]

The title compound was synthesized from ethyl 2-amino-3-chloro-4-[[(3S)-3-[[methyl-[(2-methylpropan-2-yl)oxycarbonyl]amino]methyl]pyrrolidin-1-yl]methyl]-5-(trifluoromethyl)benzoate (Compound k15) under the same conditions as for Compound 85.

Example 582

Compound k17 tert-Butyl N-[[(3S)-1-[[3-amino-2-chloro-4-[(5-chloro-2-ethylsulfonylphenyl)methylcarbamoyl]-6-(trifluoromethyl)phenyl]methyl]pyrrolidin-3-yl]methyl]-N-methylcarbamate

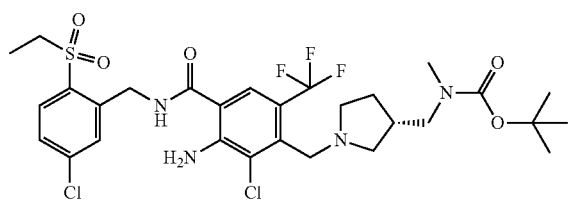 [SMILES: CCS(=O)(=O)c1ccc(Cl)cc1CNC(=O)c1cc(C(F)(F)F)c(CN2CC[C@H](CN(C)C(=O)OC(C)(C)C)C2)c(Cl)c1N]

The title compound was synthesized from 2-amino-4-[[(3S)-3-[[tert-butoxycarbonyl(methyl)amino]methyl]pyrrolidin-1-yl]methyl]-3-chloro-5-(trifluoromethyl)benzoic acid (Compound k16) and 5-chloro-2-ethylsulfonylphenyl) methanamine hydrochloride (Compound 3) under the same conditions as for Compound 113.

Example 583

Compound k18 tert-Butyl N-[[(3S)-1-[[8-chloro-3-[(5-chloro-2-ethylsulfonylphenyl)methyl]-4-oxo-6-(trifluoromethyl) quinazolin-7-yl]methyl]pyrrolidin-3-yl]methyl]-N-methylcarbamate

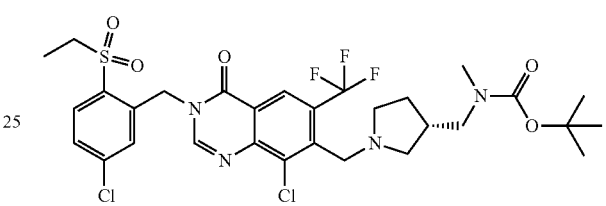

The title compound was synthesized from tert-butyl N-[[(3S)-1-[[3-amino-2-chloro-4-[(5-chloro-2-ethylsulfonylphenyl)methylcarbamoyl]-6-(trifluoromethyl)phenyl] methyl]pyrrolidin-3-yl]methyl]-N-methylcarbamate (Compound k17) under the same conditions as for Compound A-28.

Example 584

Compound K-10

8-Chloro-3-[(5-chloro-2-ethylsulfonylphenyl) methyl]-7-[[(3R)-3-(methylaminomethyl)pyrrolidin-1-yl]methyl]-6-(trifluoromethyl)quinazolin-4-one

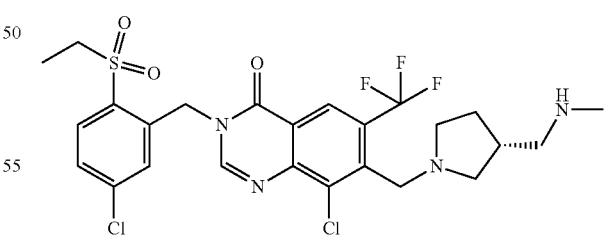

The title compound was synthesized from tert-butyl N-[[(3S)-1-[[8-chloro-3-[(5-chloro-2-ethylsulfonylphenyl) methyl]-4-oxo-6-(trifluoromethyl)quinazolin-7-yl]methyl] pyrrolidin-3-yl]methyl]-N-methylcarbamate (Compound k18) under the same conditions as for Compound 21.

LCMS: m/z 591 [M+H]$^+$

HPLC retention time: 0.43 min (analysis condition D)

Example 585

Compound K-11

8-Chloro-3-[(5-chloro-2-ethylsulfonylphenyl)methyl]-7-[[(3S)-3-(methylaminomethyl)pyrrolidin-1-yl]methyl]-6-(trifluoromethyl)quinazolin-4-one

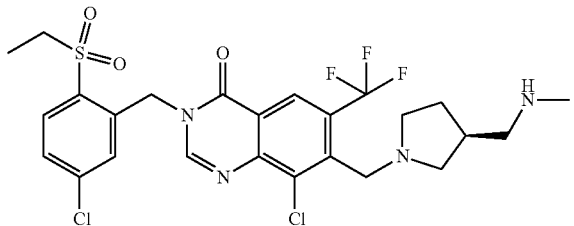 [SMILES: CCS(=O)(=O)c1ccc(Cl)cc1Cn1cnc2c(Cl)c(CN3CC[C@@H](CNC)C3)c(C(F)(F)F)cc2c1=O]

The title compound was synthesized from ethyl 2-amino-3-chloro-4-formyl-5-(trifluoromethyl)benzoate (Compound 111) under the same conditions as for Compounds k15, k16, k17, k18, and K-10. However, tert-butyl N-methyl-N-[[(3R)-pyrrolidin-3-yl]methyl]carbamate was used in place of tert-butyl N-methyl-N-[[(3S)-pyrrolidin-3-yl]methyl]carbamate as an amine under the conditions for Compound k15.

LCMS: m/z 591 [M+H]$^+$

HPLC retention time: 0.43 min (analysis condition D)

Example 586

Compound K-12

7-[[(3S)-3-(Aminomethyl)pyrrolidin-1-yl]methyl]-8-chloro-3-[(5-chloro-2-ethylsulfonylphenyl)methyl]-6-(trifluoromethyl)quinazolin-4-one

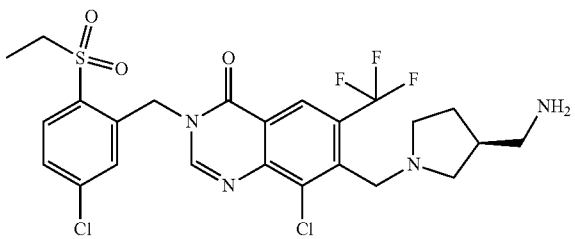 [SMILES: CCS(=O)(=O)c1ccc(Cl)cc1Cn1cnc2c(Cl)c(CN3CC[C@@H](CN)C3)c(C(F)(F)F)cc2c1=O]

The title compound was synthesized from ethyl 2-amino-3-chloro-4-formyl-5-(trifluoromethyl)benzoate (Compound 111) under the same conditions as for Compounds k15, k16, k17, k18, and K-10. However, tert-butyl N-[[(3R)-pyrrolidin-3-yl]methyl]carbamate was used in place of tert-butyl N-methyl-N-[[(3S)-pyrrolidin-3-yl]methyl]carbamate under the conditions for Compound k15.

LCMS: m/z 577 [M+H]$^+$

HPLC retention time: 0.41 min (analysis condition D)

Example 587

Compound K-13

8-Chloro-3-[(5-chloro-2-ethylsulfonylphenyl)methyl]-7-[[(3S)-3-[(dimethylamino)methyl]pyrrolidin-1-yl]methyl]-6-(trifluoromethyl)quinazolin-4-one

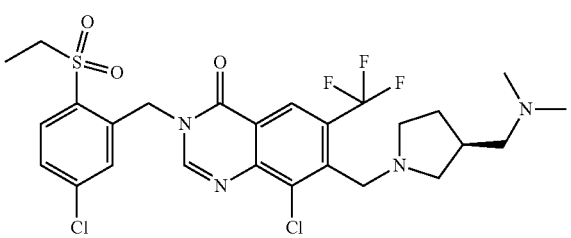 [SMILES: CCS(=O)(=O)c1ccc(Cl)cc1Cn1cnc2c(Cl)c(CN3CC[C@@H](CN(C)C)C3)c(C(F)(F)F)cc2c1=O]

The title compound was synthesized from 7-[[(3S)-3-(aminomethyl)pyrrolidin-1-yl]methyl]-8-chloro-3-[(5-chloro-2-ethylsulfonylphenyl)methyl]-6-(trifluoromethyl)quinazolin-4-one (Compound K-12) under the same conditions as for Compound G-2.

LCMS: m/z 605 [M+H]$^+$

HPLC retention time: 0.43 min (analysis condition D)

Example 588

Compound k19 tert-Butyl N-[(3R)-1-[[8-chloro-3-[(5-chloro-2-ethylsulfonyl-phenyl)methyl]-4-oxo-6-(trifluoromethyl)quinazolin-7-yl]methyl]-3-piperidyl]-N-methyl-carbamate

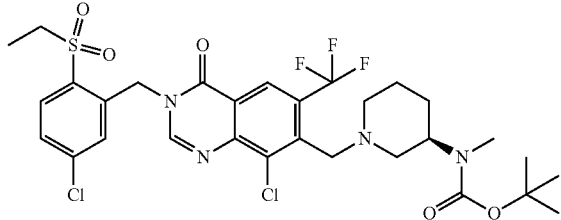 [SMILES: CCS(=O)(=O)c1ccc(Cl)cc1Cn1cnc2c(Cl)c(CN3CCC[C@@H](N(C)C(=O)OC(C)(C)C)C3)c(C(F)(F)F)cc2c1=O]

The title compound was synthesized from ethyl 2-amino-3-chloro-4-formyl-5-(trifluoromethyl)benzoate (Compound 111) under the same conditions as for Compounds k15, k16, k17, and k18. However, tert-butyl N-methyl-N-[(3R)-piperidin-3-yl]carbamate was used in place of tert-butyl N-methyl-N-[[(3S)-pyrrolidin-3-yl]methyl]carbamate as an amine, and chloroform was used in place of THF as a solvent under the conditions for Compound k15. In addition, DMF was used in place of dichloromethane as a solvent under the conditions for Compound k17.

Example 589

Compound K-14

8-Chloro-3-[(5-chloro-2-ethylsulfonylphenyl)methyl]-7-[[(3R)-3-(methylamino)piperidin-1-yl]methyl]-6-(trifluoromethyl)quinazolin-4-one

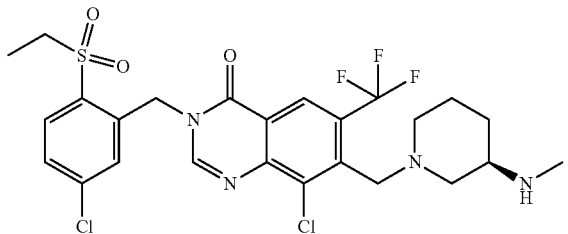 [SMILES: CCS(=O)(=O)c1ccc(Cl)cc1Cn1cnc2c(Cl)c(CN3CCC[C@@H](NC)C3)c(C(F)(F)F)cc2c1=O]

The title compound was synthesized from tert-butyl N-[(3R)-1-[[8-chloro-3-[(5-chloro-2-ethylsulfonyl-phenyl)methyl]-4-oxo-6-(trifluoromethyl)quinazolin-7-yl]methyl]-3-piperidyl]-N-methyl-carbamate (Compound k19) under the same conditions as for Compound A-2.

LCMS: m/z 591 [M+H]$^+$

HPLC retention time: 0.60 min (analysis condition D)

Example 590

Compound k20 tert-Butyl N-[(3R)-1-[[8-chloro-3-[(5-chloro-2-ethylsulfonyl-phenyl)methyl]-4-oxo-6-(trifluoromethyl)quinazolin-7-yl]methyl]-3-piperidyl]carbamate

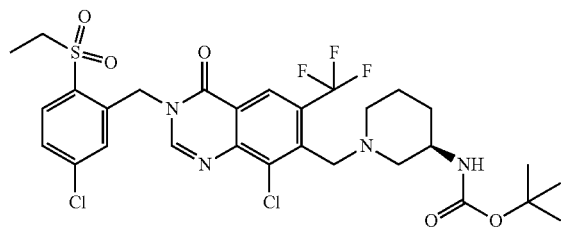 [SMILES: CCS(=O)(=O)c1ccc(Cl)cc1Cn1cnc2c(Cl)c(CN3CCC[C@@H](NC(=O)OC(C)(C)C)C3)c(C(F)(F)F)cc2c1=O]

The title compound was synthesized from ethyl 2-amino-3-chloro-4-formyl-5-(trifluoromethyl)benzoate (Compound 111) under the same conditions as for Compounds k15, k16, k17, and k18. However, tert-butyl N-[(3R)-piperidin-3-yl]carbamate was used in place of tert-butyl N-methyl-N-[[(3S)-pyrrolidin-3-yl]methyl]carbamate as an amine, and chloroform was used in place of THF as a solvent under the conditions for Compound k15. In addition, DMF was used in place of dichloromethane as a solvent under the conditions for Compound k17.

Example 591

Compound K-15

7-[[(3R)-3-Aminopiperidin-1-yl]methyl]-8-chloro-3-[(5-chloro-2-ethylsulfonylphenyl)methyl]-6-(trifluoromethyl)quinazolin-4-one

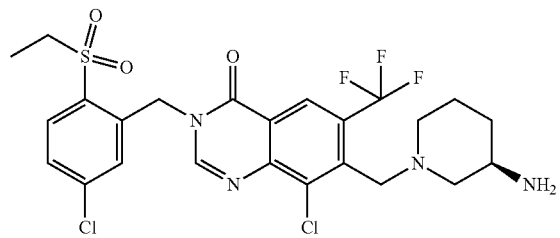 [SMILES: CCS(=O)(=O)c1ccc(Cl)cc1Cn1cnc2c(Cl)c(CN3CCC[C@@H](N)C3)c(C(F)(F)F)cc2c1=O]

The title compound was synthesized from tert-butyl N-[(3R)-1-[[8-chloro-3-[(5-chloro-2-ethylsulfonyl-phenyl)methyl]-4-oxo-6-(trifluoromethyl)quinazolin-7-yl]methyl]-3-piperidyl]carbamate (Compound k20) under the same conditions as for Compound A-2.

LCMS: m/z 577 [M+H]$^+$

HPLC retention time: 0.59 min (analysis condition D)

Example 592

Compound K-16

8-Chloro-3-[(5-chloro-2-ethylsulfonylphenyl)methyl]-7-[[(3R)-3-(dimethylamino)piperidin-1-yl]methyl]-6-(trifluoromethyl)quinazolin-4-one

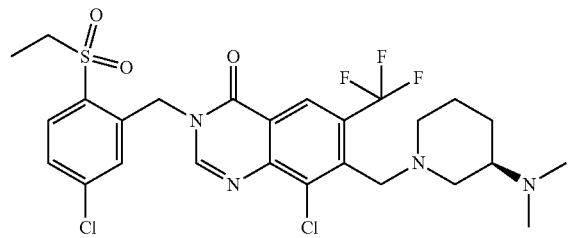 [SMILES: CCS(=O)(=O)c1ccc(Cl)cc1Cn1cnc2c(Cl)c(CN3CCC[C@@H](N(C)C)C3)c(C(F)(F)F)cc2c1=O]

The title compound was synthesized from 7-[[(3R)-3-aminopiperidin-1-yl]methyl]-8-chloro-3-[(5-chloro-2-ethylsulfonylphenyl)methyl]-6-(trifluoromethyl)quinazolin-4-one (Compound K-15) under the same conditions as for Compound G-2.

LCMS: m/z 605 [M+H]$^+$

HPLC retention time: 0.61 min (analysis condition D)

Example 593

Compound k21 tert-Butyl N-[2-[[(3S)-1-[[8-chloro-3-[(5-chloro-2-ethylsulfonylphenyl)methyl]-4-oxo-6-(trifluoromethyl)quinazolin-7-yl]methyl]piperidin-3-yl]amino]-2-oxoethyl]carbamate

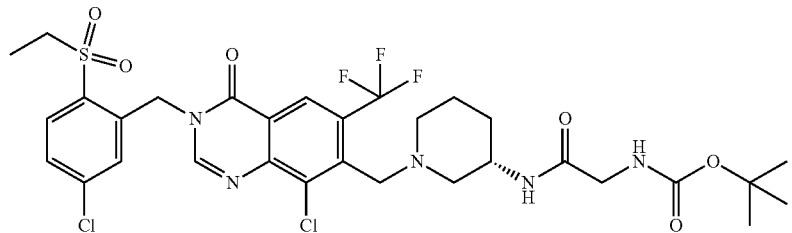 [SMILES: CCS(=O)(=O)c1ccc(Cl)cc1Cn1cnc2c(Cl)c(CN3CCC[C@H](NC(=O)CNC(=O)OC(C)(C)C)C3)c(C(F)(F)F)cc2c1=O]

The title compound was synthesized from 7-[[(3S)-3-aminopiperidin-1-yl]methyl]-8-chloro-3-[(5-chloro-2-ethylsulfonylphenyl)methyl]-6-(trifluoromethyl)quinazolin-4-one (Compound K-31) under the same conditions as for Compound e8. However, 2-[(2-methylpropan-2-yl)oxycarbonylamino]acetic acid was used in place of 2-amino-5-(trifluoromethyl)benzoic acid, HATU was used in place of HBTU as a condensing agent, and DMF was used in place of dichloromethane as a solvent.

Example 594

Compound K-17

2-Amino-N-[(3S)-1-[[8-chloro-3-[(5-chloro-2-ethylsulfonylphenyl)methyl]-4-oxo-6-(trifluoromethyl)quinazolin-7-yl]methyl]piperidin-3-yl]acetamide

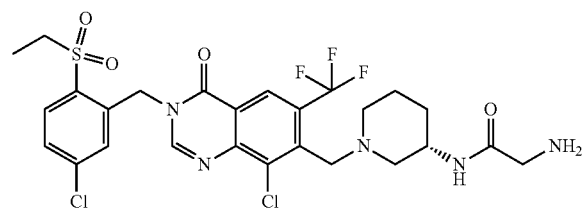 [SMILES: CCS(=O)(=O)c1ccc(Cl)cc1Cn1cnc2c(Cl)c(CN3CCC[C@H](NC(=O)CN)C3)c(C(F)(F)F)cc2c1=O]

The title compound was synthesized from tert-butyl N-[2-[[(3S)-1-[[8-chloro-3-[(5-chloro-2-ethylsulfonylphenyl)methyl]-4-oxo-6-(trifluoromethyl)quinazolin-7-yl]methyl]piperidin-3-yl]amino]-2-oxoethyl]carbamate (Compound k21) under the same conditions as for Compound A-2.

LCMS: m/z 634 [M+H]$^+$

HPLC retention time: 0.47 min (analysis condition D)

Example 595

Compound K-18

N-[(3S)-1-[[8-Chloro-3-[(5-chloro-2-ethylsulfonylphenyl)methyl]-4-oxo-6-(trifluoromethyl)quinazolin-7-yl]methyl]piperidin-3-yl]-2-(methylamino)acetamide The title compound was synthesized from 7-[[(3S)-3-aminopiperidin-1-yl]methyl]-8-chloro-3-[(5-chloro-2-ethylsulfonylphenyl)methyl]-6-(trifluoromethyl)quinazolin-4-one (Compound K-31) under the same conditions as for Compounds k21 and K-17. However, 2-[methyl-[(2-methylpropan-2-yl)oxycarbonyl]amino]acetic acid was used in place of 2-[(2-methylpropan-2-yl)oxycarbonylamino]acetic acid as a carboxylic acid under the conditions for Compound k21.

LCMS: m/z 648 [M+H]$^+$

HPLC retention time: 0.49 min (analysis condition D)

Example 596

Compound K-19

3-Amino-N-[(3S)-1-[[8-chloro-3-[(5-chloro-2-ethylsulfonylphenyl)methyl]-4-oxo-6-(trifluoromethyl)quinazolin-7-yl]methyl]piperidin-3-yl]propanamide

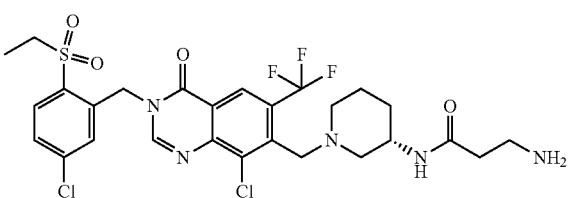 [SMILES: CCS(=O)(=O)c1ccc(Cl)cc1Cn1cnc2c(Cl)c(CN3CCC[C@H](NC(=O)CCN)C3)c(C(F)(F)F)cc2c1=O]

The title compound was synthesized from 7-[[(3S)-3-aminopiperidin-1-yl]methyl]-8-chloro-3-[(5-chloro-2-ethylsulfonylphenyl)methyl]-6-(trifluoromethyl)quinazolin-4-one (Compound K-31) under the same conditions as for Compounds k21 and K-17. However, 3-[(2-methylpropan-2-yl)oxycarbonylamino]propanoic acid was used in place of 2-[(2-methylpropan-2-yl)oxycarbonylamino]acetic acid as a carboxylic acid under the conditions for Compound k21.

LCMS: m/z 648 [M+H]+

HPLC retention time: 0.48 min (analysis condition D)

Example 597

Compound K-20

8-Chloro-3-[(5-chloro-2-ethylsulfonylphenyl)methyl]-7-[[(3S)-3-(2-hydroxyethylamino)piperidin-1-yl]methyl]-6-(trifluoromethyl)quinazolin-4-one

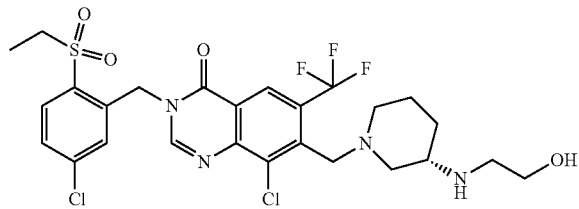 [SMILES: CCS(=O)(=O)c1ccc(Cl)cc1Cn1cnc2c(Cl)c(CN3CCC[C@H](NCCO)C3)c(C(F)(F)F)cc2c1=O]

2-Bromoethanol (174 mg, 1.40 mmol) and potassium carbonate (48.2 mg, 0.349 mmol) were added to a solution of 7-[[(3S)-3-aminopiperidin-1-yl]methyl]-8-chloro-3-[(5-chloro-2-ethylsulfonylphenyl)methyl]-6-(trifluoromethyl)quinazolin-4-one (Compound K-31, 80.6 mg, 0.140 mmol) in DMF (1.5 mL) at room temperature, and the mixture was stirred at 50° C. for six hours. After the reaction mixture was cooled to room temperature, water was added thereto and extraction was performed with ethyl acetate. The organic layer was washed with brine, and then dried over anhydrous sodium sulfate. After the drying agent was removed by filtration, concentration was performed under reduced pressure. The resulting residue was purified by silica gel column chromatography (methanol/dichloromethane) to give the title compound (30.9 mg, 36%) as a colorless foamy substance.

LCMS: m/z 621 [M+H]+

HPLC retention time: 0.59 min (analysis condition D)

Example 598

Compound k22

Ethyl 2-amino-3-chloro-4-[[(3S)-3-[ethyl-[(2-methylpropan-2-yl)oxycarbonyl]amino]piperidin-1-yl]methyl]-5-(trifluoromethyl)benzoate

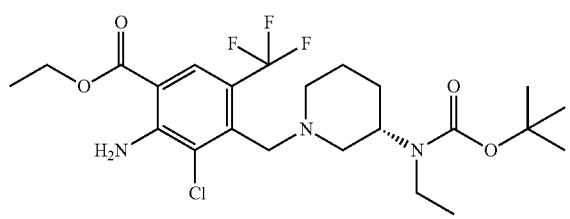 [SMILES: CCOC(=O)c1cc(C(F)(F)F)c(CN2CCC[C@H](N(CC)C(=O)OC(C)(C)C)C2)c(Cl)c1N]

The title compound was synthesized from ethyl 2-amino-3-chloro-4-formyl-5-(trifluoromethyl)benzoate (Compound 111) under the same conditions as for Compound i3. However, tert-butyl N-ethyl-N-[(3S)-piperidin-3-yl]carbamate was used in place of N-[(3S)-pyrrolidin-3-yl]acetamide as an amine and chloroform was used in place of THF as a solvent.

Example 599

Compound k23 tert-Butyl N-[(3S)-1-[[8-chloro-3-[(5-chloro-2-ethylsulfonylphenyl)methyl]-4-oxo-6-(trifluoromethyl)quinazolin-7-yl]methyl]piperidin-3-yl]-N-ethylcarbamate

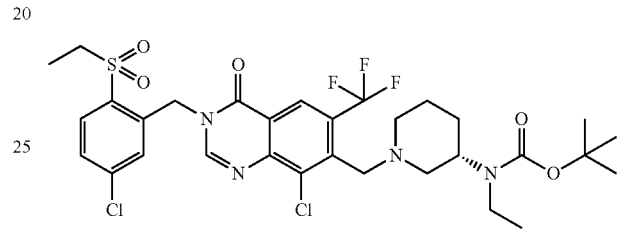

The title compound was synthesized from ethyl 2-amino-3-chloro-4-[[(3S)-3-[ethyl-[(2-methylpropan-2-yl)oxycarbonyl]amino]piperidin-1-yl]methyl]-5-(trifluoromethyl)benzoate (Compound k22) under the same conditions as for Compounds k2, k3, and k4. However, HATU was used in place of WSCDI as a condensing agent, and DMF was used in place of dichloromethane as a solvent under the conditions for Compound k3.

Example 600

Compound K-21

8-Chloro-3-[(5-chloro-2-ethylsulfonylphenyl)methyl]-7-[[(3S)-3-(ethylamino)piperidin-1-yl]methyl]-6-(trifluoromethyl)quinazolin-4-one

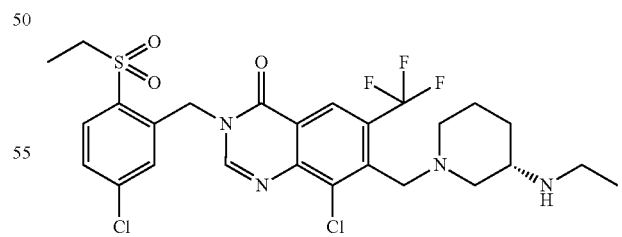

The title compound was synthesized from tert-butyl N-[(3S)-1-[[8-chloro-3-[(5-chloro-2-ethylsulfonylphenyl)methyl]-4-oxo-6-(trifluoromethyl)quinazolin-7-yl]methyl]piperidin-3-yl]-N-ethylcarbamate (Compound k23) under the same conditions as for Compound A-2.

LCMS: m/z 605 [M+H]+

HPLC retention time: 0.62 min (analysis condition D)

Example 601

Compound k24

Ethyl 4-[[(8aR)-3,4,6,7,8,8a-hexahydro-1H-pyrrolo[1,2-a]pyrazin-2-yl]methyl]-2-amino-3-chloro-5-(trifluoromethyl)benzoate

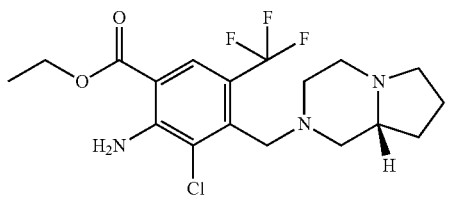 [SMILES: CCOC(=O)c1cc(C(F)(F)F)c(CN2CCN3CCC[C@@H]3C2)c(Cl)c1N]

The title compound was synthesized from ethyl 2-amino-3-chloro-4-formyl-5-(trifluoromethyl)benzoate (Compound 111) under the same conditions as for Compound i3. However, (8aR)-1,2,3,4,6,7,8,8a-octahydropyrrolo[1,2-a]pyrazine was used in place of N-[(3S)-pyrrolidin-3-yl]acetamide as an amine.

Example 602

Compound K-22

7-[[(8aR)-3,4,6,7,8,8a-Hexahydro-1H-pyrrolo[1,2-a]pyrazin-2-yl]methyl]-8-chloro-3-[(5-chloro-2-ethylsulfonylphenyl)methyl]-6-(trifluoromethyl)quinazolin-4-one

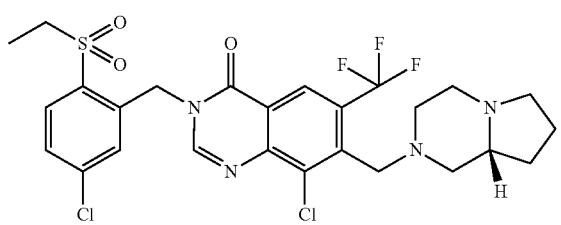 [SMILES: CCS(=O)(=O)c1ccc(Cl)cc1Cn1cnc2c(Cl)c(CN3CCN4CCC[C@@H]4C3)c(C(F)(F)F)cc2c1=O]

The title compound was synthesized from ethyl 4-[[(8aR)-3,4,6,7,8,8a-hexahydro-1H-pyrrolo[1,2-a]pyrazin-2-yl]methyl]-2-amino-3-chloro-5-(trifluoromethyl)benzoate (Compound k24) under the same conditions as for Compounds k2, k3, and k4.

LCMS: m/z 603 [M+H]$^+$

HPLC retention time: 0.58 min (analysis condition D)

Example 603

Compound k25

Ethyl 4-[[(8aS)-3,4,6,7,8,8a-hexahydro-1H-pyrrolo[1,2-a]pyrazin-2-yl]methyl]-2-amino-3-chloro-5-(trifluoromethyl)benzoate

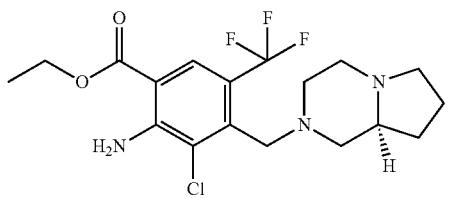 [SMILES: CCOC(=O)c1cc(C(F)(F)F)c(CN2CCN3CCC[C@H]3C2)c(Cl)c1N]

The title compound was synthesized from ethyl 2-amino-3-chloro-4-formyl-5-(trifluoromethyl)benzoate (Compound 111) under the same conditions as for Compound i3. However, (8aS)-1,2,3,4,6,7,8,8a-octahydropyrrolo[1,2-a]pyrazine was used in place of N-[(3S)-pyrrolidin-3-yl]acetamide as an amine.

Example 604

Compound K-23

7-[[(8aS)-3,4,6,7,8,8a-Hexahydro-1H-pyrrolo[1,2-a]pyrazin-2-yl]methyl]-8-chloro-3-[(5-chloro-2-ethylsulfonylphenyl methyl]-6-(trifluoromethyl)quinazolin-4-one

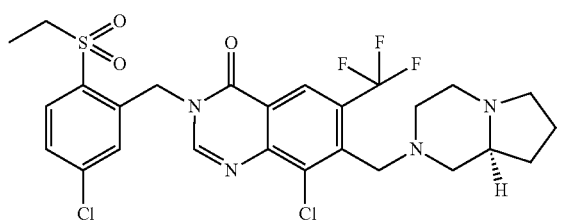 [SMILES: CCS(=O)(=O)c1ccc(Cl)cc1Cn1cnc2c(Cl)c(CN3CCN4CCC[C@H]4C3)c(C(F)(F)F)cc2c1=O]

The title compound was synthesized from ethyl 4-[[(8aS)-3,4,6,7,8,8a-hexahydro-1H-pyrrolo[1,2-a]pyrazin-2-yl]methyl]-2-amino-3-chloro-5-(trifluoromethyl)benzoate (Compound k25) under the same conditions as for Compounds k2, k3, and k4.

LCMS: m/z 603 [M+H]$^+$

HPLC retention time: 0.58 min (analysis condition D)

Example 605

Compound k26

Ethyl 2-amino-3-chloro-4-[[(3R)-3-[methyl-[(2-methylpropan-2-yl)oxycarbonyl]amino]pyrrolidin-1-yl]methyl]-5-(trifluoromethyl)benzoate

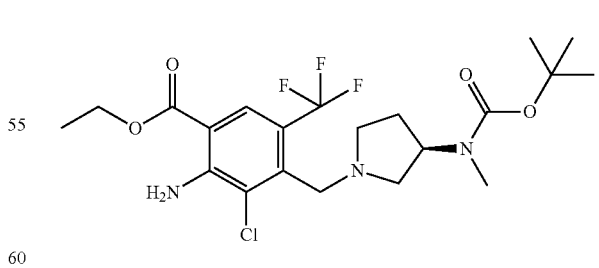

The title compound was synthesized from ethyl 2-amino-3-chloro-4-formyl-5-(trifluoromethyl)benzoate (Compound 111) under the same conditions as for Compound i3. However, tert-butyl N-methyl-N-[(3R)-pyrrolidin-3-yl]carbamate was used in place of N-[(3S)-pyrrolidin-3-yl]acetamide as an amine.

Example 606

Compound K-24

8-Chloro-3-[(5-chloro-2-ethylsulfonylphenyl)
methyl]-7-[[(3R)-3-(methylamino)pyrrolidin-1-yl]
methyl]-6-(trifluoromethyl)quinazolin-4-one

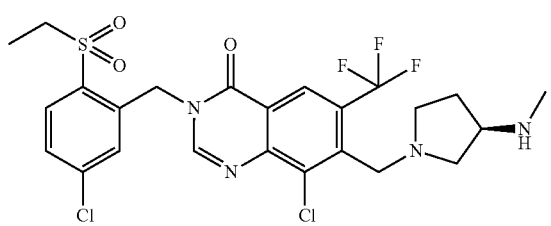 [SMILES: CCS(=O)(=O)c1ccc(Cl)cc1Cn1cnc2c(Cl)c(CN3CC[C@@H](NC)C3)c(C(F)(F)F)cc2c1=O]

The title compound was synthesized from ethyl 2-amino-3-chloro-4-[[(3R)-3-[methyl-[(2-methylpropan-2-yl)oxycarbonyl]amino]pyrrolidin-1-yl]methyl]-5-(trifluoromethyl)benzoate (Compound k26) under the same conditions as for Compounds k2, k3, k4, and K-1.

LCMS: m/z 577 [M+H]$^+$

HPLC retention time: 0.55 min (analysis condition D)

Example 607

Compound K-25

8-Chloro-3-[(5-chloro-2-ethylsulfonylphenyl)
methyl]-4-oxo-6-(trifluoromethyl)quinazoline-7-
carbaldehyde

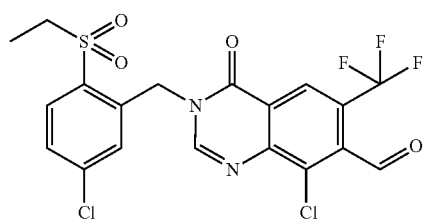 [SMILES: CCS(=O)(=O)c1ccc(Cl)cc1Cn1cnc2c(Cl)c(C=O)c(C(F)(F)F)cc2c1=O]

The title compound was synthesized from 2-amino-3-chloro-N-[(5-chloro-2-ethylsulfonylphenyl)methyl]-4-formyl-5-(trifluoromethyl)benzamide (Compound 113) under the same conditions as for Compound A-28.

LCMS: m/z 493 [M+H]$^+$

HPLC retention time: 0.87 min (analysis condition D)

Example 608

Compound k27 tert-Butyl N-[[(3R)-1-[[8-chloro-3-[(5-chloro-2-
methyl]-4-oxo-6-(trifluoromethyl)quinazolin-7-yl]
methyl]pyrrolidin-3-yl]methyl]carbamate

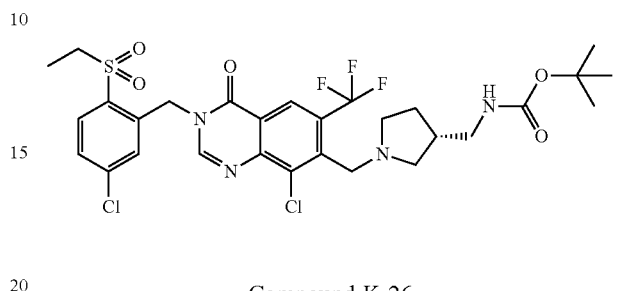

Compound K-26

8-Chloro-3-[(5-chloro-2-ethylsulfonylphenyl)
methyl]-7-(hydroxymethyl)-6-(trifluoromethyl)qui-
nazolin-4-one

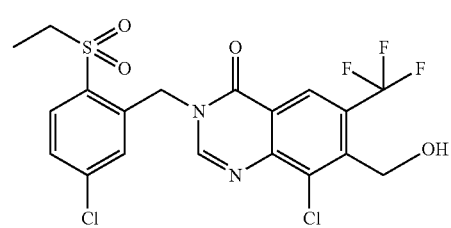 [SMILES: CCS(=O)(=O)c1ccc(Cl)cc1Cn1cnc2c(Cl)c(CO)c(C(F)(F)F)cc2c1=O]

LCMS: m/z 495 [M+H]$^+$

HPLC retention time: 0.75 min (analysis condition D)

Compounds k27 and K-26 were synthesized from 8-chloro-3-[(5-chloro-2-ethylsulfonylphenyl)methyl]-4-oxo-6-(trifluoromethyl)quinazoline-7-carbaldehyde (Compound K-25) under the same conditions as for Compound i3. However, tert-butyl N-[[(3S)-pyrrolidin-3-yl]methyl]carbamate was used in place of N-[(3S)-pyrrolidin-3-yl]acetamide as an amine.

Example 609

Compound K-27

7-[[(3R)-3-(Aminomethyl)pyrrolidin-1-yl]methyl]-8-
chloro-3-[(5-chloro-2-ethylsulfonylphenyl)methyl]-
6-(trifluoromethyl)quinazolin-4-one

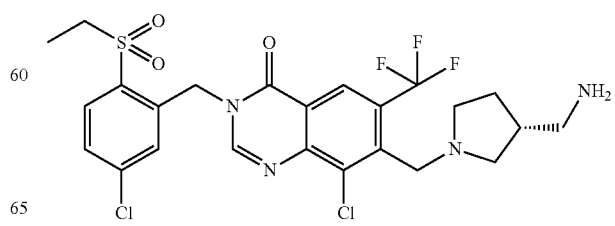

The title compound was synthesized from tert-butyl N-[[(3R)-1-[[8-chloro-3-[(5-chloro-2-ethylsulfonylphenyl)methyl]-4-oxo-6-(trifluoromethyl)quinazolin-7-yl]methyl]pyrrolidin-3-yl]methyl]carbamate (Compound k27) under the same conditions as for Compound 21.

LCMS: m/z 577 [M+H]+

HPLC retention time: 0.44 min (analysis condition D)

Example 610

Compound K-28

8-Chloro-3-[(5-chloro-2-ethylsulfonylphenyl)methyl]-7-[[(3R)-3-[(dimethylamino)methyl]pyrrolidin-1-yl]methyl]-6-(trifluoromethyl)quinazolin-4-one

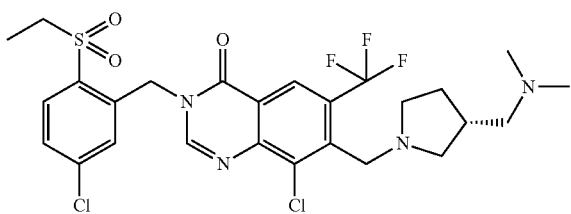 [SMILES: CCS(=O)(=O)c1ccc(Cl)cc1Cn1cnc2c(Cl)c(CN3CC[C@H](CN(C)C)C3)c(C(F)(F)F)cc2c1=O]

The title compound was synthesized from 7-[[(3R)-3-(aminomethyl)pyrrolidin-1-yl]methyl]-8-chloro-3-[(5-chloro-2-ethylsulfonylphenyl)methyl]-6-(trifluoromethyl)quinazolin-4-one (Compound K-27) under the same conditions as for Compound G-2.

LCMS: m/z 605 [M+H]+

HPLC retention time: 0.43 min (analysis condition D)

Example 611

Compound K-29

8-Chloro-3-[(5-chloro-2-ethylsulfonylphenyl)methyl]-7-[[(3R)-3-(2-oxopyrrolidin-1-yl)pyrrolidin-1-yl]methyl]-6-(trifluoromethyl)quinazolin-4-one

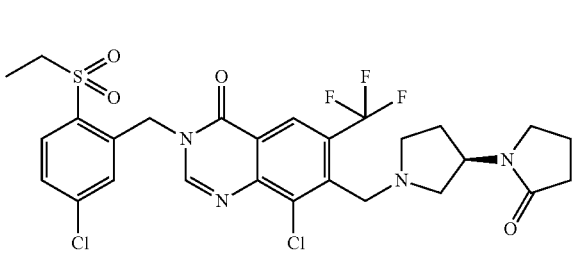 [SMILES: CCS(=O)(=O)c1ccc(Cl)cc1Cn1cnc2c(Cl)c(CN3CC[C@@H](N4CCCC4=O)C3)c(C(F)(F)F)cc2c1=O]

The title compound was synthesized from 8-chloro-3-[(5-chloro-2-ethylsulfonylphenyl)methyl]-4-oxo-6-(trifluoromethyl)quinazoline-7-carbaldehyde (Compound K-25) under the same conditions as for Compound i3. However, 1-[(3R)-pyrrolidin-3-yl]pyrrolidin-2-one was used in place of N-[(3S)-pyrrolidin-3-yl]acetamide as an amine.

LCMS: m/z 631 [M+H]+

HPLC retention time: 0.52 min (analysis condition F)

Example 612

Compound K-30

1-[[8-Chloro-3-[(5-chloro-2-ethylsulfonylphenyl)methyl]-4-oxo-6-(trifluoromethyl)quinazolin-7-yl]methyl]pyrrolidine-3-carboxamide

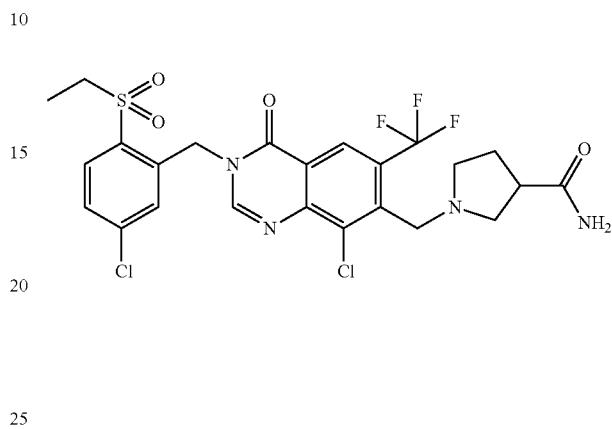

The title compound was synthesized from 8-chloro-3-[(5-chloro-2-ethylsulfonylphenyl)methyl]-4-oxo-6-(trifluoromethyl)quinazoline-7-carbaldehyde (Compound K-25) under the same conditions as for Compound i3. However, pyrrolidine-3-carboxamide was used in place of N-[(3S)-pyrrolidin-3-yl]acetamide as an amine.

LCMS: m/z 591 [M+H]+

HPLC retention time: 0.47 min (analysis condition F)

Example 613

Compound k28 tert-Butyl N-[(3S)-1-[[8-chloro-3-[(5-chloro-2-ethylsulfonylphenyl)methyl]-4-oxo-6-(trifluoromethyl)quinazolin-7-yl]methyl]piperidin-3-yl]carbamate

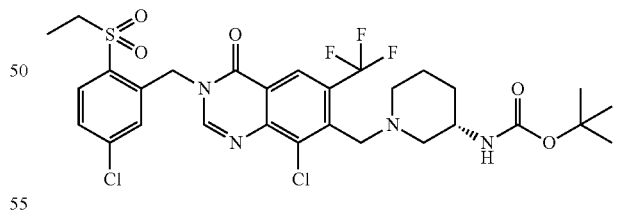

The title compound was synthesized from 8-chloro-3-[(5-chloro-2-ethylsulfonylphenyl)methyl]-4-oxo-6-(trifluoromethyl)quinazoline-7-carbaldehyde (Compound K-25) under the same conditions as for Compound i3. However, tert-butyl N-[(3S)-piperidin-3-yl]carbamate was used in place of N-[(3S)-pyrrolidin-3-yl]acetamide as an amine, and chloroform was used in place of THF as a solvent.

Example 614

Compound K-31

7-[[(3S)-3-Aminopiperidin-1-yl]methyl]-8-chloro-3-[(5-chloro-2-ethylsulfonylphenyl)methyl]-6-(trifluoromethyl)quinazolin-4-one

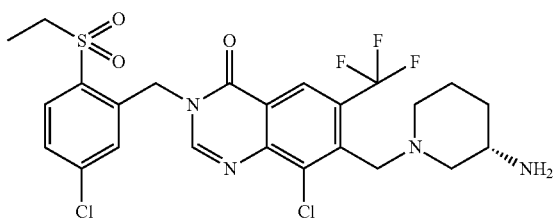 [SMILES: CCS(=O)(=O)c1ccc(Cl)cc1Cn1cnc2c(Cl)c(CN3CCC[C@H](N)C3)c(C(F)(F)F)cc2c1=O]

The title compound was synthesized from tert-butyl N-[(3S)-1-[[8-chloro-3-[(5-chloro-2-ethylsulfonylphenyl)methyl]-4-oxo-6-(trifluoromethyl)quinazolin-7-yl]methyl]piperidin-3-yl]carbamate (Compound k28) under the same conditions as for Compound A-2.

LCMS: m/z 577 [M+H]$^+$

HPLC retention time: 0.60 min (analysis condition D)

Example 615

Compound K-32

8-Chloro-3-[(5-chloro-2-ethylsulfonylphenyl)methyl]-7-[[(3S)-3-(dimethylamino)piperidin-1-yl]methyl]-6-(trifluoromethyl)quinazolin-4-one

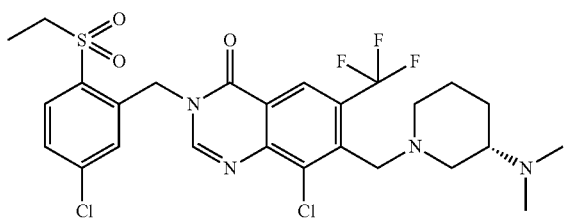 [SMILES: CCS(=O)(=O)c1ccc(Cl)cc1Cn1cnc2c(Cl)c(CN3CCC[C@H](N(C)C)C3)c(C(F)(F)F)cc2c1=O]

The title compound was synthesized from 7-[[(3S)-3-aminopiperidin-1-yl]methyl]-8-chloro-3-[(5-chloro-2-ethylsulfonylphenyl)methyl]-6-(trifluoromethyl)quinazolin-4-one (Compound K-31) under the same conditions as for Compound G-2.

LCMS: m/z 605 [M+H]$^+$

HPLC retention time: 0.61 min (analysis condition D)

Example 616

Compound K-33

8-Chloro-3-[(5-chloro-2-ethylsulfonylphenyl)methyl]-7-[[(3S)-3-(methylamino)piperidin-1-yl]methyl]-6-(trifluoromethyl)quinazolin-4-one

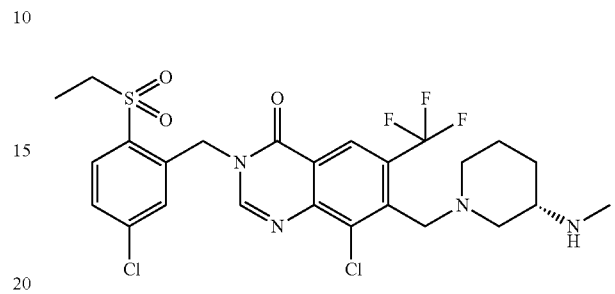

The title compound was synthesized from 8-chloro-3-[(5-chloro-2-ethylsulfonylphenyl)methyl]-4-oxo-6-(trifluoromethyl)quinazoline-7-carbaldehyde (Compound K-25) under the same conditions as for Compounds k28 and K-31. However, tert-butyl N-methyl-N-[(3S)-piperidin-3-yl]carbamate was used in place of tert-butyl N-[(3S)-piperidin-3-yl]carbamate as an amine under the conditions for k28.

LCMS: m/z 591 [M+H]$^+$

HPLC retention time: 0.60 min (analysis condition D)

Example 617

Compound K-34

[8-Chloro-3-[(5-chloro-2-ethylsulfonylphenyl)methyl]-4-oxo-6-(trifluoromethyl)quinazolin-7-yl]methyl methanesulfonate

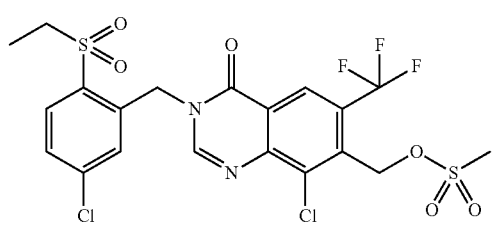 [SMILES: CCS(=O)(=O)c1ccc(Cl)cc1Cn1cnc2c(Cl)c(COS(C)(=O)=O)c(C(F)(F)F)cc2c1=O]

The title compound was synthesized from 8-chloro-3-[(5-chloro-2-ethylsulfonylphenyl)methyl]-7-(hydroxymethyl)-6-(trifluoromethyl)quinazolin-4-one (Compound K-26) under the same conditions as for Compound i10.

LCMS: m/z 573 [M+H]$^+$

HPLC retention time: 0.82 min (analysis condition F)

Example 618

Compound K-35

8-Chloro-3-[(5-chloro-2-ethylsulfonylphenyl)methyl]-7-[(3-oxopiperazin-1-yl)methyl]-6-(trifluoromethyl)quinazolin-4-one

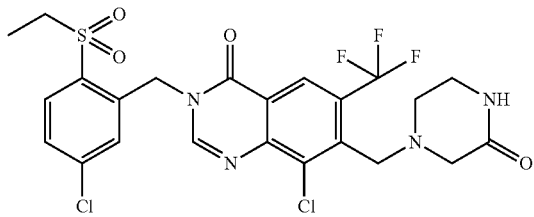 [SMILES: CCS(=O)(=O)c1ccc(Cl)cc1Cn1cnc2c(Cl)c(CN3CCNC(=O)C3)c(C(F)(F)F)cc2c1=O]

The title compound was synthesized from [8-chloro-3-[(5-chloro-2-ethylsulfonylphenyl)methyl]-4-oxo-6-(trifluoromethyl)quinazolin-7-yl]methyl methanesulfonate (Compound K-34) under the same conditions as for Compound j6. However, piperazin-2-one was used in place of tert-butyl N-[(3R)-pyrrolidin-3-yl]carbamate as an amine, and the reaction was performed without the addition of potassium carbonate.

LCMS: m/z 577 [M+H]$^+$

HPLC retention time: 0.71 min (analysis condition F)

Example 619

Compound K-36

(2S)-1-[[8-Chloro-3-[(5-chloro-2-ethylsulfonylphenyl)methyl]-4-oxo-6-(trifluoromethyl)quinazolin-7-yl]methyl]pyrrolidine-2-carboxamide

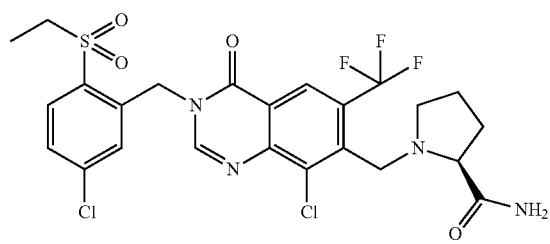 [SMILES: CCS(=O)(=O)c1ccc(Cl)cc1Cn1cnc2c(Cl)c(CN3CCC[C@H]3C(N)=O)c(C(F)(F)F)cc2c1=O]

The title compound was synthesized from [8-chloro-3-[(5-chloro-2-ethylsulfonylphenyl)methyl]-4-oxo-6-(trifluoromethyl)quinazolin-7-yl]methyl methanesulfonate (Compound K-34) under the same conditions as for Compound j6. However, (2S)-pyrrolidine-2-carboxamide was used in place of tert-butyl N-[(3R)-pyrrolidin-3-yl]carbamate as an amine, and the reaction was performed without the addition of potassium carbonate.

LCMS: m/z 591 [M+H]$^+$

HPLC retention time: 0.59 min (analysis condition F)

Example 620

Compound K-37

(2R)-1-[[8-Chloro-3-[(5-chloro-2-ethylsulfonylphenyl)methyl]-4-oxo-6-(trifluoromethyl)quinazolin-7-yl]methyl]pyrrolidine-2-carboxamide

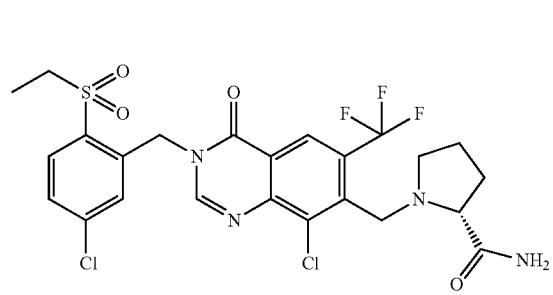 [SMILES: CCS(=O)(=O)c1ccc(Cl)cc1Cn1cnc2c(Cl)c(CN3CCC[C@@H]3C(N)=O)c(C(F)(F)F)cc2c1=O]

The title compound was synthesized from [8-chloro-3-[(5-chloro-2-ethylsulfonylphenyl)methyl]-4-oxo-6-(trifluoromethyl)quinazolin-7-yl]methyl methanesulfonate (Compound K-34) under the same conditions as for Compound j6. However, (2R)-pyrrolidine-2-carboxamide was used in place of tert-butyl N-[(3R)-pyrrolidin-3-yl]carbamate as an amine, and the reaction was performed without the addition of potassium carbonate.

LCMS: m/z 591 [M+H]$^+$

HPLC retention time: 0.59 min (analysis condition F)

Example 621

Compound K-38

(3S)-1-[[8-Chloro-3-[(5-chloro-2-ethylsulfonylphenyl)methyl]-4-oxo-6-(trifluoromethyl)quinazolin-7-yl]methyl]piperidine-3-carboxamide

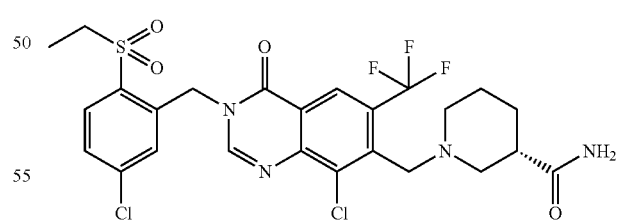

The title compound was synthesized from [8-chloro-3-[(5-chloro-2-ethylsulfonylphenyl)methyl]-4-oxo-6-(trifluoromethyl)quinazolin-7-yl]methyl methanesulfonate (Compound K-34) under the same conditions as for Compound j6. However, (3S)-piperidine-3-carboxamide was used in place of tert-butyl N-[(3R)-pyrrolidin-3-yl]carbamate as an amine.

LCMS: m/z 605 [M+H]$^+$

HPLC retention time: 0.50 min (analysis condition F)

Example 622

Compound K-39

(3R)-1-[[8-Chloro-3-[(5-chloro-2-ethylsulfonylphenyl)methyl]-4-oxo-6-(trifluoromethyl)quinazolin-7-yl]methyl]piperidine-3-carboxamide

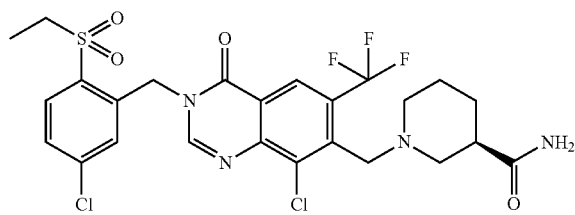 [SMILES: CCS(=O)(=O)c1ccc(Cl)cc1Cn1cnc2c(Cl)c(CN3CCC[C@@H](C(N)=O)C3)c(C(F)(F)F)cc2c1=O]

The title compound was synthesized from [8-chloro-3-[(5-chloro-2-ethylsulfonylphenyl)methyl]-4-oxo-6-(trifluoromethyl)quinazolin-7-yl]methyl methanesulfonate (Compound K-34) under the same conditions as for Compound j6. However, (3R)-piperidine-3-carboxamide was used in place of tert-butyl N-[(3R)-pyrrolidin-3-yl]carbamate as an amine.

LCMS: m/z 605 [M+H]$^+$

HPLC retention time: 0.49 min (analysis condition F)

Example 623

Compound k29

Ethyl 2-amino-4-chloro-3-fluoro-5-(trifluoromethyl)benzoate

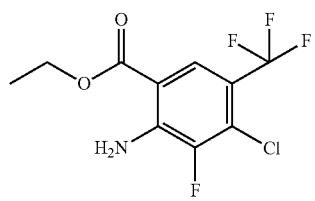 [SMILES: CCOC(=O)c1cc(C(F)(F)F)c(Cl)c(F)c1N]

N-Fluoro-N'-(chloromethyl)triethylenediamine bis(tetrafluoroborate) (1.98 g, 5.3 mmol) was added to a solution of ethyl 2-amino-4-chloro-5-(trifluoromethyl)benzoate (Compound 107, 652 mg, 2.4 mmol) in acetonitrile (13 ml), and the mixture was stirred at room temperature for 43 hours. The reaction mixture was concentrated under reduced pressure, and ethyl acetate was added to the resulting residue. This was washed with water and brine, and dried over anhydrous sodium sulfate. After the drying agent was removed by filtration, concentration was performed under reduced pressure. The resulting residue was purified by amino silica gel column chromatography (ethyl acetate/hexane) to give the title compound (186 mg, 27%) as a colorless solid.

LCMS: m/z 286 [M+H]$^+$

HPLC retention time: 0.97 min (analysis condition D)

Example 624

Compound k30 tert-Butyl 4-[[3-amino-4-ethoxycarbonyl-2-fluoro-6-(trifluoromethyl)phenyl]methyl]piperazine-1-carboxylate

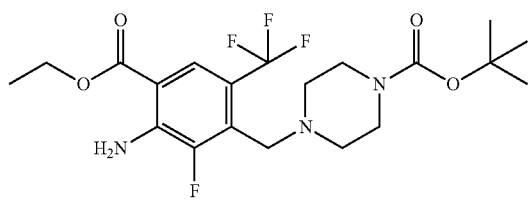 [SMILES: CCOC(=O)c1cc(C(F)(F)F)c(CN2CCN(C(=O)OC(C)(C)C)CC2)c(F)c1N]

The title compound was synthesized from ethyl 2-amino-4-chloro-3-fluoro-5-(trifluoromethyl)benzoate (Compound k29) under the same conditions as for Compound g1.

Example 625

Compound k31 tert-Butyl 4-[[3-[(5-chloro-2-ethylsulfonylphenyl)methyl]-8-fluoro-4-oxo-6-(trifluoromethyl)quinazolin-7-yl]methyl]piperazine-1-carboxylate

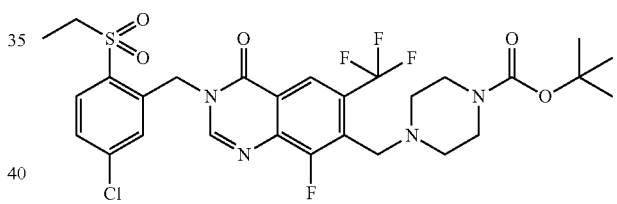

The title compound was synthesized from tert-butyl 4-[[3-amino-4-ethoxycarbonyl-2-fluoro-6-(trifluoromethyl)phenyl]methyl]piperazine-1-carboxylate (Compound k30) under the same conditions as for Compounds k2, k3, and k4.

Example 626

Compound K-40

3-[(5-Chloro-2-ethylsulfonylphenyl)methyl]-8-fluoro-7-(piperazin-1-ylmethyl)-6-(trifluoromethyl)quinazolin-4-one

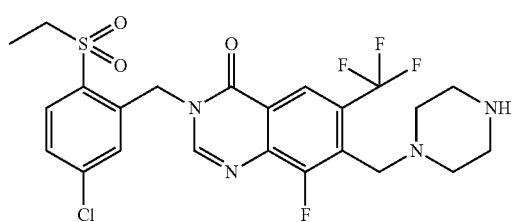 [SMILES: CCS(=O)(=O)c1ccc(Cl)cc1Cn1cnc2c(F)c(CN3CCNCC3)c(C(F)(F)F)cc2c1=O]

The title compound was synthesized from tert-butyl 4-[[3-[(5-chloro-2-ethylsulfonylphenyl)methyl]-8-fluoro-4-oxo-6-(trifluoromethyl)quinazolin-7-yl]methyl]piperazine-1-carboxylate (Compound k31) under the same conditions as for Compound A-2.

LCMS: m/z 547 [M+H]$^+$

HPLC retention time: 0.53 min (analysis condition D)

Example 627

Compound K-41

3-[(5-Chloro-2-ethylsulfonylphenyl)methyl]-8-fluoro-7-[(4-methylpiperazin-1-yl)methyl]-6-(trifluoromethyl)quinazolin-4-one

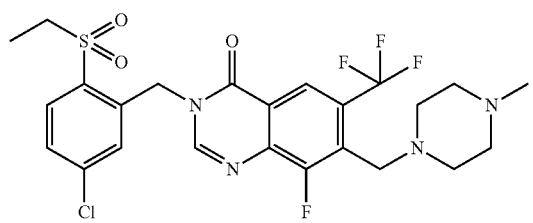 [SMILES: CCS(=O)(=O)c1ccc(Cl)cc1Cn1cnc2c(F)c(CN3CCN(C)CC3)c(C(F)(F)F)cc2c1=O]

The title compound was synthesized from 3-[(5-chloro-2-ethylsulfonylphenyl)methyl]-8-fluoro-7-(piperazin-1-ylmethyl)-6-(trifluoromethyl)quinazolin-4-one (Compound K-40) under the same conditions as for Compound G-2.

LCMS: m/z 561 [M+H]$^+$

HPLC retention time: 0.54 min (analysis condition D)

Example 628

Compound k32

Ethyl 2-amino-3-bromo-4-formyl-5-(trifluoromethyl)benzoate

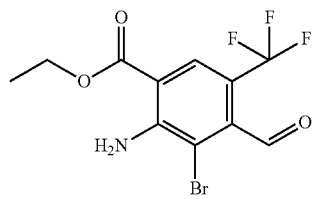 [SMILES: CCOC(=O)c1cc(C(F)(F)F)c(C=O)c(Br)c1N]

The title compound was synthesized from ethyl 2-amino-4-formyl-5-(trifluoromethyl)benzoate (Compound 110) under the same conditions as for Compound 111. However, NBS was used in place of NCS as a halogenating agent.

Example 629

Compound K-42

8-Bromo-3-[(5-chloro-2-ethylsulfonylphenyl)methyl]-7-(piperazin-1-ylmethyl)-6-(trifluoromethyl)quinazolin-4-one

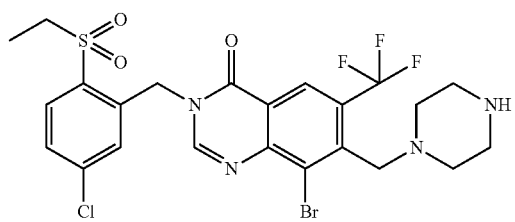 [SMILES: CCS(=O)(=O)c1ccc(Cl)cc1Cn1cnc2c(Br)c(CN3CCNCC3)c(C(F)(F)F)cc2c1=O]

The title compound was synthesized from ethyl 2-amino-3-bromo-4-formyl-5-(trifluoromethyl)benzoate (Compound k32) under the same conditions as for Compounds k15, k16, k17, k18, and K-10. However, tert-butyl piperazine-1-carboxylate was used in place of tert-butyl N-methyl-N-[[(3S)-pyrrolidin-3-yl]methyl]carbamate as an amine under the conditions for Compound k15, and toluene was used as a solvent, and p-toluenesulfonic acid monohydrate was added in place of formic acid as an acid under the conditions for Compound k18.

LCMS: m/z 607 [M+H]$^+$

HPLC retention time: 0.57 min (analysis condition D)

Example 630

Compound K-43

7-[[(3R)-3-Aminopyrrolidin-1-yl]methyl]-8-bromo-3-[(5-chloro-2-ethylsulfonylphenyl)methyl]-6-(trifluoromethyl)quinazolin-4-one

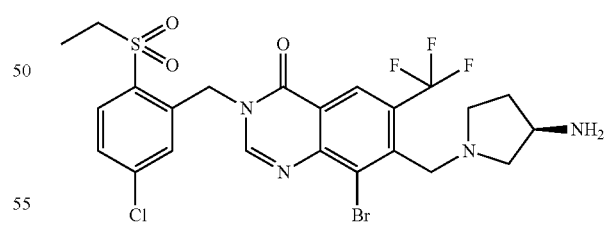

The title compound was synthesized from ethyl 2-amino-3-bromo-4-formyl-5-(trifluoromethyl)benzoate (Compound k32) under the same conditions as for Compounds k15, k16, k17, k18, and K-10. However, tert-butyl N-[(3R)-pyrrolidin-3-yl]carbamate was used in place of tert-butyl N-methyl-N-[[(3S)-pyrrolidin-3-yl]methyl]carbamate as an amine under the conditions for Compound k15.

LCMS: m/z 607 [M+H]$^+$

HPLC retention time: 0.55 min (analysis condition D)

Example 631

Compound k33

Ethyl 2-amino-3-bromo-4-[[(3S)-3-[methyl-[(2-methylpropan-2-yl)oxycarbonyl]amino]piperidin-1-yl]methyl]-5-(trifluoromethyl)benzoate

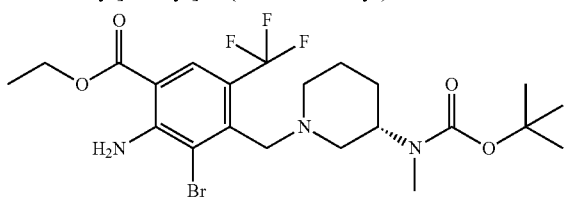

The title compound was synthesized from ethyl 2-amino-3-bromo-4-formyl-5-(trifluoromethyl)benzoate (Compound k32) under the same conditions as for Compound i3. However, tert-butyl N-methyl-N-[(3S)-piperidin-3-yl]carbamate was used in place of N-[(3S)-pyrrolidin-3-yl]acetamide as an amine. In addition, chloroform was used in place of THF as a solvent.

Example 632

Compound k34 tert-Butyl N-[(3S)-1-[[8-bromo-3-[(5-chloro-2-ethylsulfonylphenyl)methyl]-4-oxo-6-(trifluoromethyl)quinazolin-7-yl]methyl]piperidin-3-yl]-N-methylcarbamate

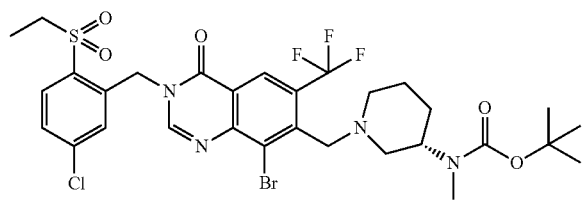 [SMILES: CCS(=O)(=O)c1ccc(Cl)cc1Cn1cnc2c(Br)c(CN3CCC[C@H](N(C)C(=O)OC(C)(C)C)C3)c(C(F)(F)F)cc2c1=O]

The title compound was synthesized from ethyl 2-amino-3-bromo-4-[[(3S)-3-[methyl-[(2-methylpropan-2-yl)oxycarbonyl]amino]piperidin-1-yl]methyl]-5-(trifluoromethyl)benzoate (Compound k33) under the same conditions as for Compounds k2, k3, and k4. However, HATU was used in place of WSCDI as a condensing agent, and DMF was used in place of dichloromethane as a solvent under the conditions for Compound k3.

Example 633

Compound K-44

8-Bromo-3-[(5-chloro-2-ethylsulfonylphenyl)methyl]-7-[[(3S)-3-(methylamino)piperidin-1-yl]methyl]-6-(trifluoromethyl)quinazolin-4-one

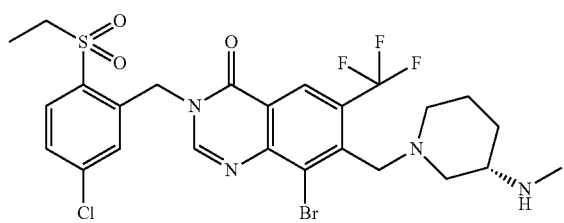 [SMILES: CCS(=O)(=O)c1ccc(Cl)cc1Cn1cnc2c(Br)c(CN3CCC[C@H](NC)C3)c(C(F)(F)F)cc2c1=O]

The title compound was synthesized from tert-butyl N-[(3S)-1-[[8-bromo-3-[(5-chloro-2-ethylsulfonylphenyl)methyl]-4-oxo-6-(trifluoromethyl)quinazolin-7-yl]methyl]piperidin-3-yl]-N-methylcarbamate (Compound k34) under the same conditions as for Compound 21.

LCMS: m/z 635 [M+H]$^+$
HPLC retention time: 0.59 min (analysis condition D)

Example 634

Compound K-45

3-[(5-Chloro-2-ethylsulfonylphenyl)methyl]-7-[[(3S)-3-(methylamino)piperidin-1-yl]methyl]-4-oxo-6-(trifluoromethyl)quinazoline-8-carbonitrile

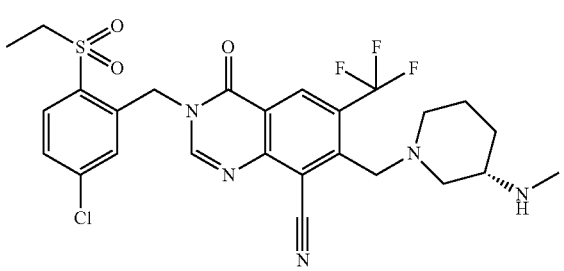 [SMILES: CCS(=O)(=O)c1ccc(Cl)cc1Cn1cnc2c(C#N)c(CN3CCC[C@H](NC)C3)c(C(F)(F)F)cc2c1=O]

Copper(I) cyanide (10.4 mg, 0.116 mmol) was added to a solution of 8-bromo-3-[(5-chloro-2-ethylsulfonylphenyl)methyl]-7-[[(3S)-3-(methylamino)piperidin-1-yl]methyl]-6-(trifluoromethyl)quinazolin-4-one (Compound K-44, 61.4 mg, 0.097 mmol) in DMF (1.0 ml) at room temperature, and it was irradiated with microwaves and stirred at 130 to 150° C. for 20 minutes. After the reaction mixture was cooled to room temperature, ethyl acetate was added thereto. This mixture was washed with a saturated aqueous sodium bicarbonate solution, water, and brine in this order and then the organic layer was dried over anhydrous sodium sulfate. After the drying agent was removed by filtration, concentration was performed under reduced pressure. The resulting residue was purified by preparative HPLC (water/acetonitrile, 0.05% TFA) and silica gel column chromatography (methanol/dichloromethane) to give the title compound (11.5 mg, 20%) as a colorless foamy substance.

LCMS: m/z 582 [M+H]$^+$
HPLC retention time: 0.57 min (analysis condition D)

Example 635

Compound k35 tert-Butyl N-[(3S)-1-[[3-[(5-chloro-2-ethylsulfonylphenyl)methyl]-8-methoxy-4-oxo-6-(trifluoromethyl)quinazolin-7-yl]methyl]piperidin-3-yl]-N-methylcarbamate

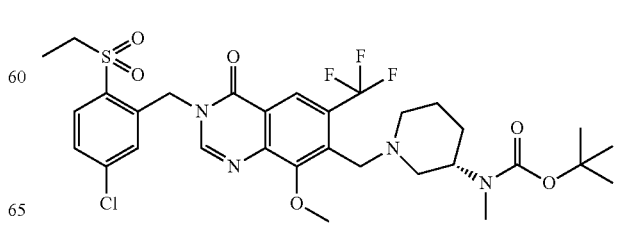

Sodium methoxide (11.0 mg, 0.203 mmol) and copper iodide (9.68 mg, 0.051 mmol) were added to a solution of tert-butyl N-[(3S)-1-[[8-bromo-3-[(5-chloro-2-ethylsulfonylphenyl)methyl]-4-oxo-6-(trifluoromethyl)quinazolin-7-yl]methyl]piperidin-3-yl]-N-methylcarbamate (Compound k34, 37.4 mg, 0.051 mmol) in MeOH (1.5 ml) at room temperature, and it was irradiated with microwaves and stirred at 110 to 130° C. for 30 minutes. After the reaction mixture was cooled to room temperature, ethyl acetate was added, and the organic layer was washed with water and brine and then dried over anhydrous sodium sulfate. After the drying agent was removed by filtration, concentration was performed under reduced pressure to give the title compound as a crude product (33.9 mg).

LCMS: m/z 687 [M+H]$^+$
HPLC retention time: 0.64 min (analysis condition D)

Example 636

Compound K-46

3-[(5-Chloro-2-ethylsulfonylphenyl)methyl]-8-methoxy-7-[[(3S)-3-(methylamino)piperidin-1-yl]methyl]-6-(trifluoromethyl)quinazolin-4-one

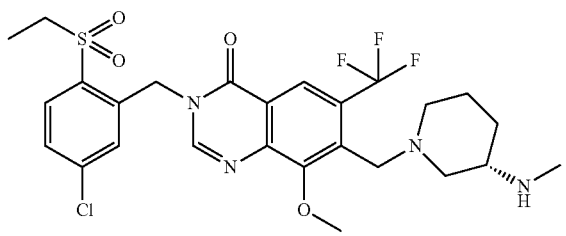 [SMILES: CCS(=O)(=O)c1ccc(Cl)cc1Cn1cnc2c(OC)c(CN3CCC[C@H](NC)C3)c(C(F)(F)F)cc2c1=O]

The title compound was synthesized from tert-butyl N-[(3S)-1-[[3-[(5-chloro-2-ethylsulfonylphenyl)methyl]-8-methoxy-4-oxo-6-(trifluoromethyl)quinazolin-7-yl]methyl]piperidin-3-yl]-N-methylcarbamate (Compound k35) under the same conditions as for Compound 21.

LCMS: m/z 587 [M+H]$^+$
HPLC retention time: 0.51 min (analysis condition D)

Example 637

Compound k36

Ethyl 2-amino-4-formyl-3-methyl-5-(trifluoromethyl)benzoate

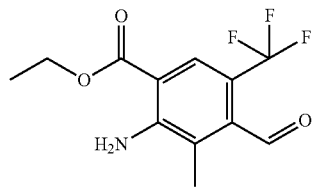 [SMILES: CCOC(=O)c1cc(C(F)(F)F)c(C=O)c(C)c1N]

The title compound was synthesized from ethyl 2-amino-3-bromo-4-formyl-5-(trifluoromethyl)benzoate (Compound k32) under the same conditions as for Compound 108. However, potassium methyltrifluoroborate was used in place of potassium vinyltrifluoroborate as an alkylating agent.

Example 638

Compound k37

Ethyl 2-amino-3-methyl-4-[[(3S)-3-[methyl-[(2-methylpropan-2-yl)oxycarbonyl]amino]piperidin-1-yl]methyl]-5-(trifluoromethyl)benzoate

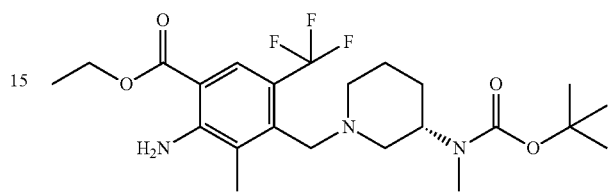

The title compound was synthesized from ethyl 2-amino-4-formyl-3-methyl-5-(trifluoromethyl)benzoate (Compound k36) under the same conditions as for Compound i3. However, tert-butyl N-methyl-N-[(3S)-piperidin-3-yl]carbamate was used in place of N-[(3S)-pyrrolidin-3-yl]acetamide as an amine, and chloroform was used in place of THF as a solvent.

Example 639

Compound K-47

3-[(5-Chloro-2-ethylsulfonylphenyl)methyl]-8-methyl-7-[[(3S)-3-(methylamino)piperidin-1-yl]methyl]-6-(trifluoromethyl)quinazolin-4-one

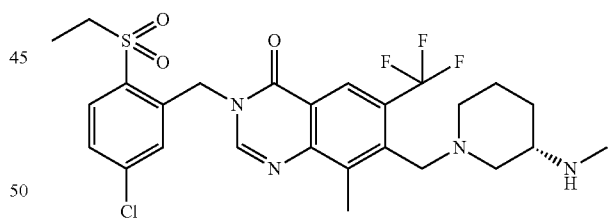

The title compound was synthesized from ethyl 2-amino-3-methyl-4-[[(3S)-3-[methyl-[(2-methylpropan-2-yl)oxycarbonyl]amino]piperidin-1-yl]methyl]-5-(trifluoromethyl)benzoate (Compound k37) under the same conditions as for Compounds k2, k3, k4, and K-1. However, HATU was used in place of WSCDI as a condensing agent, and DMF was used in place of dichloromethane as a solvent under the conditions for Compound k3.

LCMS: m/z 571 [M+H]$^+$
HPLC retention time: 0.59 min (analysis condition D)

Example 640

Compound k38

Ethyl 2-amino-3-ethenyl-4-formyl-5-(trifluoromethyl)benzoate

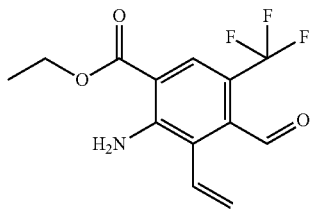 [SMILES: C=Cc1c(N)c(C(=O)OCC)cc(C(F)(F)F)c1C=O]

The title compound was synthesized from ethyl 2-amino-3-bromo-4-formyl-5-(trifluoromethyl)benzoate (Compound k32) under the same conditions as for Compound 108. However, DMF was used in place of toluene as a solvent.

Example 641

Compound k39

Ethyl 2-amino-3-ethenyl-4-[[(3S)-3-[methyl-[(2-methylpropan-2-yl)oxycarbonyl]amino]piperidin-1-yl]methyl]-5-(trifluoromethyl)benzoate

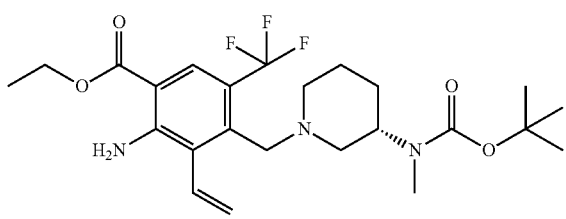 [SMILES: C=Cc1c(N)c(C(=O)OCC)cc(C(F)(F)F)c1CN1CCC[C@H](N(C)C(=O)OC(C)(C)C)C1]

The title compound was synthesized from ethyl 2-amino-3-ethenyl-4-formyl-5-(trifluoromethyl)benzoate (Compound k38) under the same conditions as for Compound i3. However, tert-butyl N-methyl-N-[(3S)-piperidin-3-yl]carbamate was used in place of N-[(3S)-pyrrolidin-3-yl]acetamide as an amine, and chloroform was used in place of a solvent and THF.

Example 642

Compound k40

Ethyl 2-amino-3-ethyl-4-[[(3S)-3-[methyl-[(2-methylpropan-2-yl)oxycarbonyl]amino]piperidin-1-yl]methyl]-5-(trifluoromethyl)benzoate

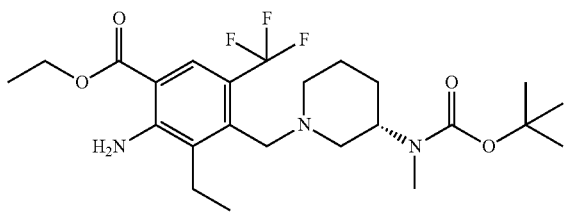 [SMILES: CCOC(=O)c1cc(C(F)(F)F)c(CN2CCC[C@H](N(C)C(=O)OC(C)(C)C)C2)c(CC)c1N]

The title compound was synthesized from ethyl 2-amino-3-ethenyl-4-[[(3S)-3-[methyl-[(2-methylpropan-2-yl)oxycarbonyl]amino]piperidin-1-yl]methyl]-5-(trifluoromethyl)benzoate (Compound k39) under the same conditions as for Compound A-63. However, ethyl acetate was used in place of a mixed solvent of methanol-ethyl acetate as a solvent.

Example 643

Compound K-48

3-[(5-Chloro-2-ethylsulfonylphenyl)methyl]-8-ethyl-7-[[(3S)-3-(methylamino)piperidin-1-yl]methyl]-6-(trifluoromethyl)quinazolin-4-one

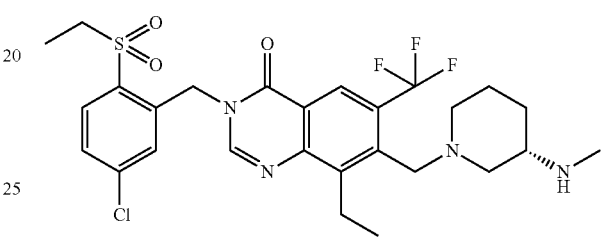

The title compound was synthesized from ethyl 2-amino-3-ethyl-4-[[(3S)-3-[methyl-[(2-methylpropan-2-yl)oxycarbonyl]amino]piperidin-1-yl]methyl]-5-(trifluoromethyl)benzoate (Compound k40) under the same conditions as for Compounds k2, k3, k4, and K-1. However, HATU was used in place of WSCDI as a condensing agent, and DMF was used in place of dichloromethane as a solvent under the conditions for Compound k3.

LCMS: m/z 585 [M+H]$^+$

HPLC retention time: 0.60 min (analysis condition D)

Example 644

Compound k41

Ethyl 2-amino-3-bromo-4-[[(3S)-3-[ethyl-[(2-methylpropan-2-yl)oxycarbonyl]amino]piperidin-1-yl]methyl]-5-(trifluoromethyl)benzoate

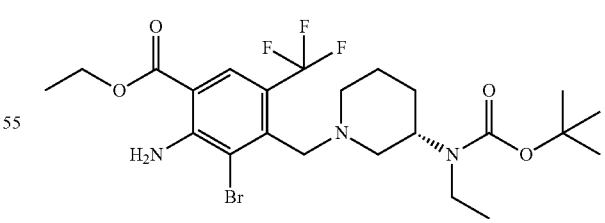

The title compound was synthesized from ethyl 2-amino-3-bromo-4-formyl-5-(trifluoromethyl)benzoate (Compound k32) under the same conditions as for Compound i3. However, tert-butyl N-ethyl-N-[(3S)-piperidin-3-yl]carbamate was used in place of N-[(3S)-pyrrolidin-3-yl]acetamide as an amine and chloroform was used in place of THF as a solvent.

Example 645

Compound k42 tert-Butyl N-[(3S)-1-[[8-bromo-3-[(5-chloro-2-ethyl-sulfonylphenyl)methyl]-4-oxo-6-(trifluoromethyl)quinazolin-7-yl]methyl]piperidin-3-yl]-N-ethylcarbamate

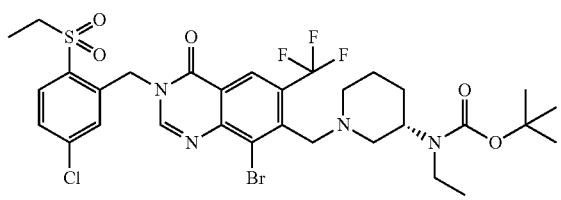

The title compound was synthesized from ethyl 2-amino-3-bromo-4-[[(3S)-3-[ethyl-[(2-methylpropan-2-yl)oxycarbonyl]amino]piperidin-1-yl]methyl]-5-(trifluoromethyl)benzoate (Compound k41) under the same conditions as for Compounds k2, k3, and k4. However, HATU was used in place of WSCDI as a condensing agent, and DMF was used in place of dichloromethane as a solvent under the conditions for Compound k3.

Example 646

Compound K-49

8-Bromo-3-[(5-chloro-2-ethylsulfonylphenyl)methyl]-7-[[(3S)-3-(ethylamino)piperidin-1-yl]methyl]-6-(trifluoromethyl)quinazolin-4-one

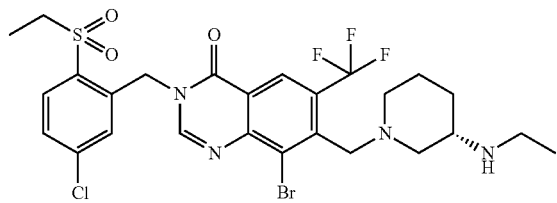 [SMILES: CCN[C@H]1CCCN(Cc2c(C(F)(F)F)cc3c(=O)n(Cc4cc(Cl)ccc4S(=O)(=O)CC)cnc3c2Br)C1]

The title compound was synthesized from tert-butyl N-[(3S)-1-[[8-bromo-3-[(5-chloro-2-ethylsulfonylphenyl)methyl]-4-oxo-6-(trifluoromethyl)quinazolin-7-yl]methyl]piperidin-3-yl]-N-ethylcarbamate (Compound k42) under the same conditions as for Compound A-2.

LCMS: m/z 649 [M+H]$^+$

HPLC retention time: 0.61 min (analysis condition D)

Example 647

Compound K-50

3-[(5-Chloro-2-ethylsulfonylphenyl)methyl]-7-[[(3S)-3-(ethylamino)piperidin-1-yl]methyl]-4-oxo-6-(trifluoromethyl)quinazoline-8-carbonitrile

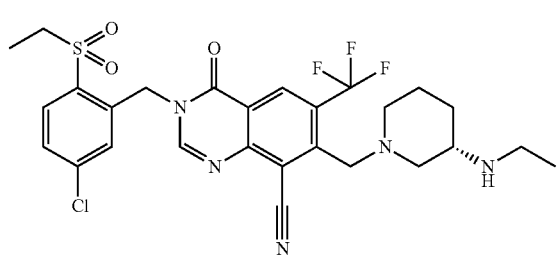 [SMILES: CCN[C@H]1CCCN(Cc2c(C(F)(F)F)cc3c(=O)n(Cc4cc(Cl)ccc4S(=O)(=O)CC)cnc3c2C#N)C1]

Sodium cyanide (6.87 mg, 0.140 mmol) and copper iodide (16.2 mg, 0.085 mmol) were added to a solution of 8-bromo-3-[(5-chloro-2-ethylsulfonylphenyl)methyl]-7-[[(3S)-3-(ethylamino)piperidin-1-yl]methyl]-6-(trifluoromethyl)quinazolin-4-one (Compound K-49, 53.3 mg, 0.082 mmol) in NMP (1.0 ml) at room temperature, and it was irradiated with microwaves and stirred at 140 to 160° C. for 30 minutes. After cooling to room temperature, the mixture was subjected to purification by preparative MPLC (water/acetonitrile, 0.1% FA) to give the title compound (35.1 mg, 72%) as a pale yellow foamy substance.

LCMS: m/z 596 [M+H]$^+$

HPLC retention time: 0.60 min (analysis condition D)

Example 648

Compound l1 tert-Butyl 4-[[4-ethoxycarbonyl-5-nitro-2-(trifluoromethoxy)phenyl]methyl]piperazine-1-carboxylate

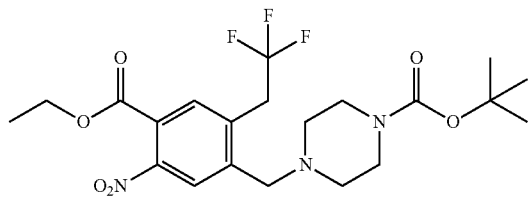 [SMILES: CCOC(=O)c1cc(CC(F)(F)F)c(CN2CCN(C(=O)OC(C)(C)C)CC2)cc1[N+](=O)[O-]]

The title compound was synthesized from ethyl 4-bromo-2-nitro-5-(trifluoromethoxy)benzoate (Compound 115) under the same conditions as for Compound g1.

Example 649

Compound l2 tert-Butyl 4-[[5-amino-4-ethoxycarbonyl-2-(trifluoromethoxy)phenyl]methyl]piperazine-1-carboxylate

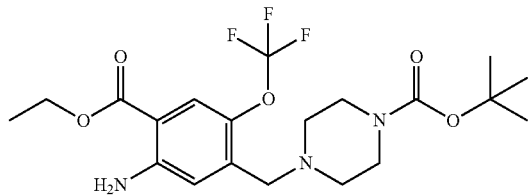

The title compound was synthesized from tert-butyl 4-[[4-ethoxycarbonyl-5-nitro-2-(trifluoromethoxy)phenyl]methyl]piperazine-1-carboxylate (Compound l1) under the same conditions as for Compound 39. However, a saturated aqueous ammonium chloride solution and iPrOH were used in place of a 37% aqueous hydrochloric acid solution and EtOH, and the reaction was performed at 80° C.

Example 650

Compound 13 tert-Butyl 4-[[3-amino-2-chloro-4-ethoxycarbonyl-6-(trifluoromethoxy)phenyl]methyl]piperazine-1-carboxylate

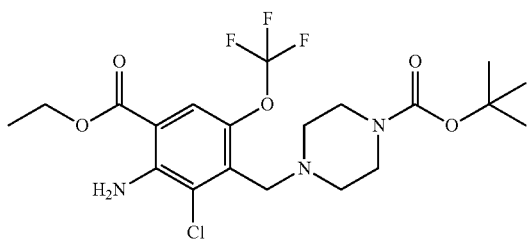 [SMILES: CCOC(=O)c1cc(OC(F)(F)F)c(CN2CCN(C(=O)OC(C)(C)C)CC2)c(Cl)c1N]

The title compound was synthesized from tert-butyl 4-[[5-amino-4-ethoxycarbonyl-2-(trifluoromethoxy)phenyl]methyl]piperazine-1-carboxylate (Compound 12) under the same conditions as for Compound 111.

Example 651

Compound 14

2-Amino-3-chloro-4-[[4-[(2-methylpropan-2-yl)oxycarbonyl]piperazin-1-yl]methyl]-5-(trifluoromethoxy)benzoic Acid

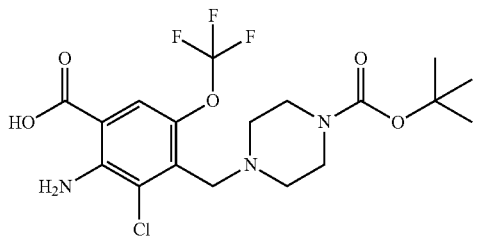 [SMILES: CC(C)(C)OC(=O)N1CCN(Cc2c(OC(F)(F)F)cc(C(=O)O)c(N)c2Cl)CC1]

The title compound was synthesized from tert-butyl 4-[[3-amino-2-chloro-4-ethoxycarbonyl-6-(trifluoromethoxy)phenyl]methyl]piperazine-1-carboxylate (Compound 13) under the same conditions as for Compound 85.

Example 652

Compound 15 tert-Butyl 4-[[3-amino-2-chloro-4-[(5-chloro-2-ethylsulfonylphenyl)methylcarbamoyl]-6-(trifluoromethoxy)phenyl]methyl]piperazine-1-carboxylate

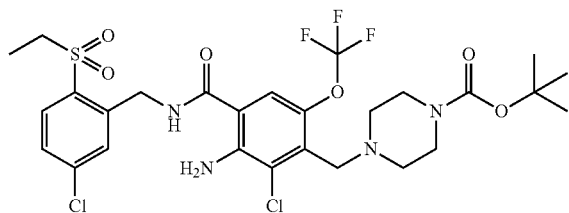 [SMILES: CCS(=O)(=O)c1ccc(Cl)cc1CNC(=O)c1cc(OC(F)(F)F)c(CN2CCN(C(=O)OC(C)(C)C)CC2)c(Cl)c1N]

The title compound was synthesized from (5-chloro-2-ethylsulfonylphenyl)methanamine hydrochloride (Compound 3) and 2-amino-3-chloro-4-[[4-[(2-methylpropan-2-yl)oxycarbonyl]piperazin-1-yl]methyl]-5-(trifluoromethoxy)benzoic acid (Compound 14) under the same conditions as for Compound e8. However, WSCDI was used in place of HBTU.

Example 653

Compound 16 tert-Butyl 4-[[8-chloro-3-[(5-chloro-2-ethylsulfonylphenyl)methyl]-4-oxo-6-(trifluoromethoxy)quinazolin-7-yl]methyl]piperazine-1-carboxylate

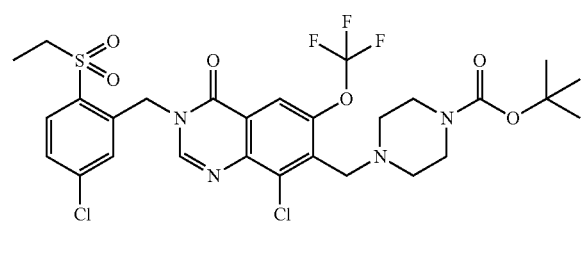 [SMILES: CCS(=O)(=O)c1ccc(Cl)cc1Cn1cnc2c(Cl)c(CN3CCN(C(=O)OC(C)(C)C)CC3)c(OC(F)(F)F)cc2c1=O]

The title compound was synthesized from tert-butyl (4-[[3-amino-2-chloro-4-[(5-chloro-2-ethylsulfonylphenyl)methylcarbamoyl]-6-(trifluoromethoxy)phenyl]methyl]piperazine-1-carboxylate (Compound 15) under the same conditions as for Compound A-28.

Example 654

Compound L-1

8-Chloro-3-[(5-chloro-2-ethylsulfonylphenyl)methyl]-7-(piperazin-1-ylmethyl)-6-(trifluoromethoxy)quinazolin-4-one

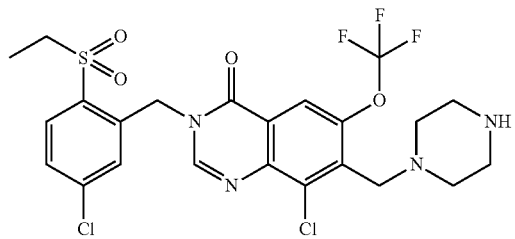 [SMILES: CCS(=O)(=O)c1ccc(Cl)cc1Cn1cnc2c(Cl)c(CN3CCNCC3)c(OC(F)(F)F)cc2c1=O]

The title compound was synthesized from tert-butyl 4-[[8-chloro-3-[(5-chloro-2-ethylsulfonylphenyl)methyl]-4-oxo-6-(trifluoromethoxy)quinazolin-7-yl]methyl]piperazine-1-carboxylate (Compound 16) under the same conditions as for Compound A-2.

LCMS: m/z 579 [M+H]$^+$

HPLC retention time: 0.54 min (analysis condition D)

Example 655

Compound L-2

8-Chloro-3-[(5-chloro-2-ethylsulfonylphenyl)methyl]-7-[(4-methylpiperazin-1-yl)methyl]-6-(trifluoromethoxy)quinazolin-4-one

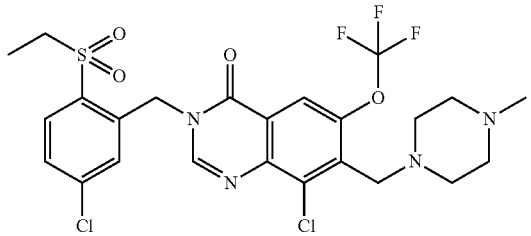 [SMILES: CCS(=O)(=O)c1ccc(Cl)cc1Cn1cnc2c(Cl)c(CN3CCN(C)CC3)c(OC(F)(F)F)cc2c1=O]

The title compound was synthesized from 8-chloro-3-[(5-chloro-2-ethylsulfonylphenyl)methyl]-7-(piperazin-1-ylmethyl)-6-(trifluoromethoxy)quinazolin-4-one (Compound L-1) under the same conditions as for Compound G-3. However, paraformaldehyde was used in place of acetone.

LCMS: m/z 593 [M+H]+

HPLC retention time: 0.56 min (analysis condition D)

Example 656

Compound L-3

8-Chloro-3-[(5-chloro-2-ethylsulfonylphenyl)methyl]-7-[[4-(oxan-4-yl)piperazin-1-yl]methyl]-6-(trifluoromethoxy)quinazolin-4-one

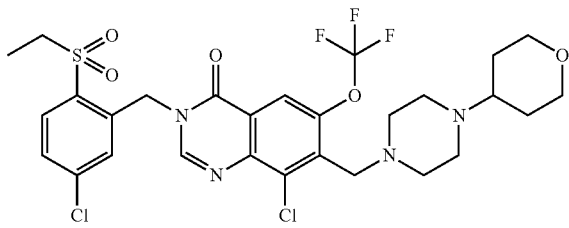 [SMILES: CCS(=O)(=O)c1ccc(Cl)cc1Cn1cnc2c(Cl)c(CN3CCN(C4CCOCC4)CC3)c(OC(F)(F)F)cc2c1=O]

The title compound was synthesized from 8-chloro-3-[(5-chloro-2-ethylsulfonylphenyl)methyl]-7-(piperazin-1-ylmethyl)-6-(trifluoromethoxy)quinazolin-4-one (Compound L-1) under the same conditions as for Compound G-3. However, tetrahydro-4H-pyran-4-one was used in place of acetone.

LCMS: m/z 663 [M+H]+

HPLC retention time: 0.57 min (analysis condition D)

Example 657

Compound 17

8-Chloro-3-[(5-chloro-2-ethylsulfonylphenyl)methyl]-7-(1,3-dioxolan-2-yl)-6-(trifluoromethoxy)quinazolin-4-one

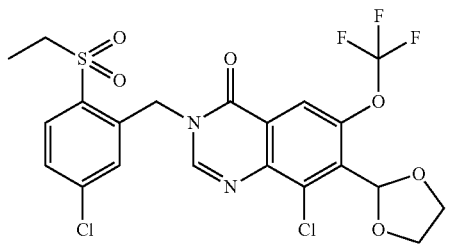 [SMILES: CCS(=O)(=O)c1ccc(Cl)cc1Cn1cnc2c(Cl)c(C3OCCO3)c(OC(F)(F)F)cc2c1=O]

The title compound was synthesized from 2-amino-3-chloro-N-[(5-chloro-2-ethylsulfonylphenyl)methyl]-4-(1,3-dioxolan-2-yl)-5-(trifluoromethoxy)benzamide (Compound 121) under the same conditions as for Compound A-28. However, PTSA was used in place of formic acid, and toluene was used as a solvent.

Example 658

Compound 18

8-Chloro-3-[(5-chloro-2-ethylsulfonylphenyl)methyl]-4-oxo-6-(trifluoromethoxy)quinazoline-7-carbaldehyde

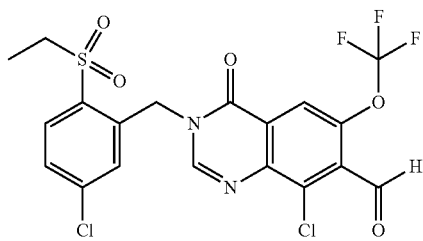 [SMILES: CCS(=O)(=O)c1ccc(Cl)cc1Cn1cnc2c(Cl)c(C=O)c(OC(F)(F)F)cc2c1=O]

Water (0.4 ml)/concentrated sulfuric acid (4 ml) was added to a solution of 8-chloro-3-[(5-chloro-2-ethylsulfonylphenyl)methyl]-7-(1,3-dioxolan-2-yl)-6-(trifluoromethoxy)quinazolin-4-one (Compound 17, 187 mg, 0.34 mmol) in NMP (4 ml), and the mixture was stirred at 80° C. for one hour and at 90° C. for additional six hours. After the reaction mixture was cooled to room temperature, water was added thereto and extraction was performed with ethyl acetate/hexane (2/1). The organic layer was dried over anhydrous sodium sulfate. After the drying agent was removed by filtration, concentration was performed under reduced pressure. The resulting residue was purified by silica gel chromatography (ethyl acetate/hexane) to give the title compound (146 mg, 85%) as a white solid.

LCMS: m/z 509 [M+H]+

HPLC retention time: 0.89 min (analysis condition D)

Example 659

Compound 19 tert-Butyl N-[(3R)-1-[[8-chloro-3-[(5-chloro-2-ethylsulfonylphenyl)methyl]-4-oxo-6-(trifluoromethoxy)quinazolin-7-yl]methyl]pyrrolidin-3-yl]carbamate

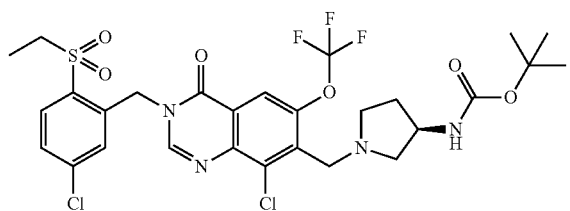 [SMILES: CCS(=O)(=O)c1ccc(Cl)cc1Cn1cnc2c(Cl)c(CN3CC[C@@H](NC(=O)OC(C)(C)C)C3)c(OC(F)(F)F)cc2c1=O]

The title compound was synthesized from 8-chloro-3-[(5-chloro-2-ethylsulfonylphenyl)methyl]-4-oxo-6-(trifluoromethoxy)quinazoline-7-carbaldehyde (Compound 18) under the same conditions as for Compound i3. However, tert-butyl N-[(3R)-pyrrolidin-3-yl]carbamate was used in place of N-[(3S)-pyrrolidin-3-yl]acetamide.

Example 660

Compound L-4

7-[[(3R)-3-Aminopyrrolidin-1-yl]methyl]-8-chloro-3-[(5-chloro-2-ethylsulfonylphenyl)methyl]-6-(trifluoromethoxy)quinazolin-4-one

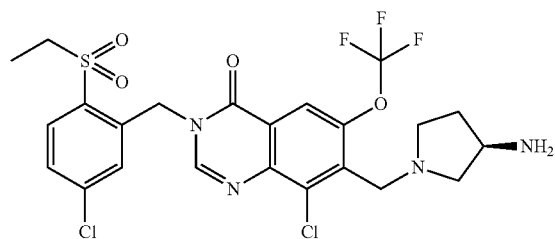 [SMILES: CCS(=O)(=O)c1ccc(Cl)cc1Cn1cnc2c(Cl)c(CN3CC[C@@H](N)C3)c(OC(F)(F)F)cc2c1=O]

The title compound was synthesized from tert-butyl N-[(3R)-1-[[8-chloro-3-[(5-chloro-2-ethylsulfonylphenyl)methyl]-4-oxo-6-(trifluoromethoxy)quinazolin-7-yl]methyl]pyrrolidin-3-yl]carbamate (Compound 19) under the same conditions as for Compound 21.

LCMS: m/z 579 [M+H]$^+$

HPLC retention time: 0.52 min (analysis condition D)

Example 661

Compound L-5

8-Chloro-3-[(5-chloro-2-ethylsulfonylphenyl)methyl]-7-[[(3R)-3-(methylamino)pyrrolidin-1-yl]methyl]-6-(trifluoromethoxy)quinazolin-4-one

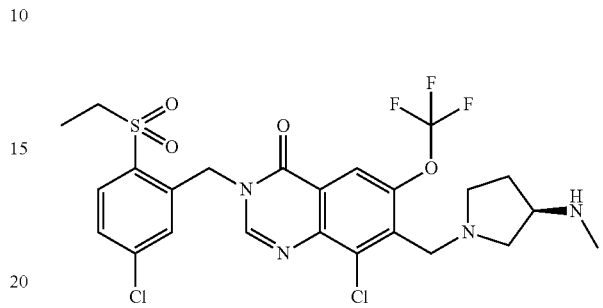

The title compound was synthesized from 8-chloro-3-[(5-chloro-2-ethylsulfonylphenyl)methyl]-4-oxo-6-(trifluoromethoxy)quinazoline-7-carbaldehyde (Compound 18) under the same conditions as for Compounds 19 and L-4. However, tert-butyl N-methyl-N-[(3R)-pyrrolidin-3-yl]carbamate was used in place of tert-butyl N-[(3R)-pyrrolidin-3-yl]carbamate under the conditions for Compound 19.

LCMS: m/z 593 [M+H]$^+$

HPLC retention time: 0.55 min (analysis condition D)

Example 662

Compound L-6

7-[[(3S)-3-(Aminomethyl)pyrrolidin-1-yl]methyl]-8-chloro-3-[(5-chloro-2-ethylsulfonylphenyl)methyl]-6-(trifluoromethoxy)quinazolin-4-one

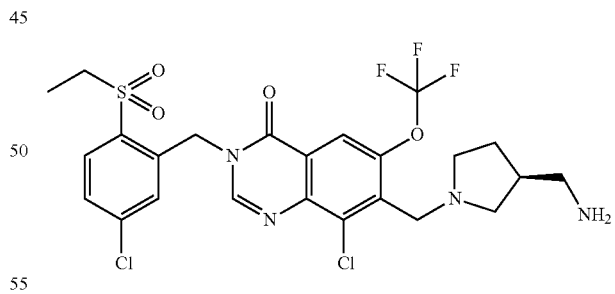

The title compound was synthesized from 8-chloro-3-[(5-chloro-2-ethylsulfonylphenyl)methyl]-4-oxo-6-(trifluoromethoxy)quinazoline-7-carbaldehyde (Compound 18) under the same conditions as for Compounds 19 and L-4. However, tert-butyl N-[[(3R)-pyrrolidin-3-yl]methyl]carbamate was used in place of tert-butyl N-[(3R)-pyrrolidin-3-yl]carbamate, and chloroform was used in place of THF as a solvent under the conditions for Compound 19.

LCMS: m/z 593 [M+H]$^+$

HPLC retention time: 0.46 min (analysis condition D)

Example 663

Compound L-7

8-Chloro-3-[(5-chloro-2-ethylsulfonylphenyl)methyl]-7-[[(3S)-3-(methylaminomethyl)pyrrolidin-1-yl]methyl]-6-(trifluoromethoxy)quinazolin-4-one

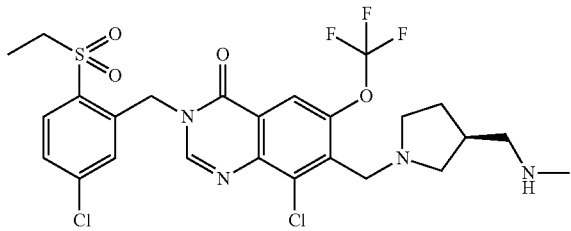 [SMILES: CCS(=O)(=O)c1ccc(Cl)cc1Cn1cnc2c(Cl)c(CN3CC[C@@H](CNC)C3)c(OC(F)(F)F)cc2c1=O]

The title compound was synthesized from 8-chloro-3-[(5-chloro-2-ethylsulfonylphenyl)methyl]-4-oxo-6-(trifluoromethoxy)quinazoline-7-carbaldehyde (Compound 18) under the same conditions as for Compounds 19 and L-4. However, tert-butyl N-methyl-N-[[(3R)-pyrrolidin-3-yl]methyl]carbamate was used in place of tert-butyl N-[(3R)-pyrrolidin-3-yl]carbamate, and chloroform was used in place of THF as a solvent under the conditions for Compound 19.

LCMS: m/z 607 [M+H]$^+$

HPLC retention time: 0.46 min (analysis condition D)

Example 664

Compound 110

Ethyl 2-amino-3-chloro-4-[[(3S)-3-[(2-methylpropan-2-yl)oxycarbonylamino]piperidin-1-yl]methyl]-5-(trifluoromethoxy)benzoate

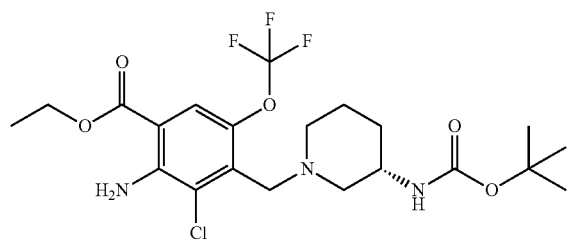 [SMILES: CCOC(=O)c1cc(OC(F)(F)F)c(CN2CCC[C@H](NC(=O)OC(C)(C)C)C2)c(Cl)c1N]

The title compound was synthesized from ethyl 2-amino-3-chloro-4-formyl-5-(trifluoromethoxy)benzoate (Compound 118) under the same conditions as for Compound i3. However, tert-butyl N-[(3S)-piperidin-3-yl]carbamate was used in place of N-[(3S)-pyrrolidin-3-yl]acetamide, and DCM was used in place of THF as a solvent.

Example 665

Compound 111

2-Amino-3-chloro-4-[[(3S)-3-[(2-methylpropan-2-yl)oxycarbonylamino]piperidin-1-yl]methyl]-5-(trifluoromethoxy)benzoic Acid

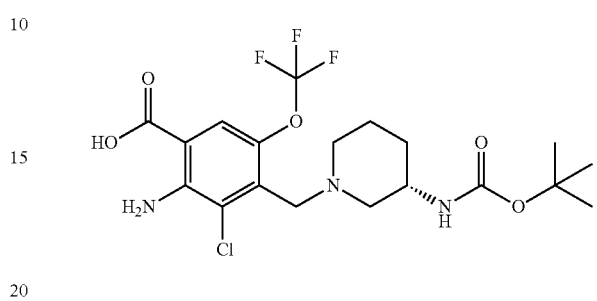

The title compound was synthesized from ethyl 2-amino-3-chloro-4-[[(3S)-3-[(2-methylpropan-2-yl)oxycarbonylamino]piperidin-1-yl]methyl]-5-(trifluoromethoxy)benzoate (Compound 110) under the same conditions as for Compound 85.

Example 666

Compound 112 tert-Butyl N-[(3S)-1-[[3-amino-2-chloro-4-[(5-chloro-2-ethylsulfonylphenyl)methylcarbamoyl]-6-(trifluoromethoxy)phenyl]methyl]piperidin-3-yl]carbamate

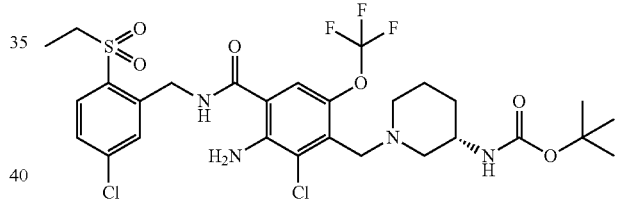

The title compound was synthesized from (5-chloro-2-ethylsulfonylphenyl)methanamine hydrochloride (Compound 3) and 2-amino-3-chloro-4-[[(3S)-3-[(2-methylpropan-2-yl)oxycarbonylamino]piperidin-1-yl]methyl]-5-(trifluoromethoxy)benzoic acid (Compound 111) under the same conditions as for Compound 113. However, DMF was used in place of DCM as a solvent.

Example 667

Compound 113 tert-Butyl N-[(3S)-1-[[8-chloro-3-[(5-chloro-2-ethylsulfonylphenyl)methyl]-4-oxo-6-(trifluoromethoxy)quinazolin-7-yl]methyl]piperidin-3-yl]carbamate

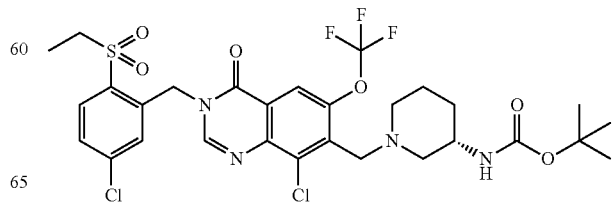

The title compound was synthesized from tert-butyl N-[(3S)-1-[[3-amino-2-chloro-4-[(5-chloro-2-ethylsulfonyl-phenyl)methylcarbamoyl]-6-(trifluoromethoxy)phenyl]methyl]piperidin-3-yl]carbamate (Compound 112) under the same conditions as for Compound A-28.

Example 668

Compound L-8

7-[[(3S)-3-Aminopiperidin-1-yl]methyl]-8-chloro-3-[(5-chloro-2-ethylsulfonylphenyl)methyl]-6-(trifluoromethoxy)quinazolin-4-one

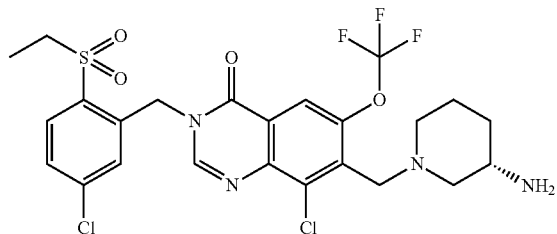 [SMILES: CCS(=O)(=O)c1ccc(Cl)cc1Cn1cnc2c(Cl)c(CN3CCC[C@H](N)C3)c(OC(F)(F)F)cc2c1=O]

The title compound was synthesized from tert-butyl N-[(3S)-1-[[8-chloro-3-[(5-chloro-2-ethylsulfonylphenyl)methyl]-4-oxo-6-(trifluoromethoxy)quinazolin-7-yl]methyl]piperidin-3-yl]carbamate (Compound 113) under the same conditions as for Compound A-2.

LCMS: m/z 593 [M+H]+

HPLC retention time: 0.57 min (analysis condition D)

Example 669

Compound L-9

8-Chloro-3-[(5-chloro-2-ethylsulfonylphenyl)methyl]-7-[[(3S)-3-(dimethylamino)piperidin-1-yl]methyl]-6-(trifluoromethoxy)quinazolin-4-one

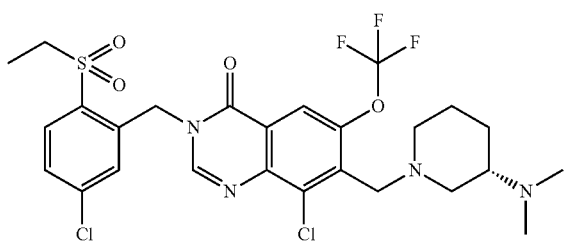 [SMILES: CCS(=O)(=O)c1ccc(Cl)cc1Cn1cnc2c(Cl)c(CN3CCC[C@H](N(C)C)C3)c(OC(F)(F)F)cc2c1=O]

The title compound was synthesized from 7-[[(3S)-3-aminopiperidin-1-yl]methyl]-8-chloro-3-[(5-chloro-2-ethylsulfonylphenyl)methyl]-6-(trifluoromethoxy)quinazolin-4-one (Compound L-8) under the same conditions as for Compound G-2.

LCMS: m/z 621 [M+H]+

HPLC retention time: 0.60 min (analysis condition D)

Example 670

Compound L-10

8-Chloro-3-[(5-chloro-2-ethylsulfonylphenyl)methyl]-7-[[(3S)-3-(methylamino)piperidin-1-yl]methyl]-6-(trifluoromethoxy)quinazolin-4-one

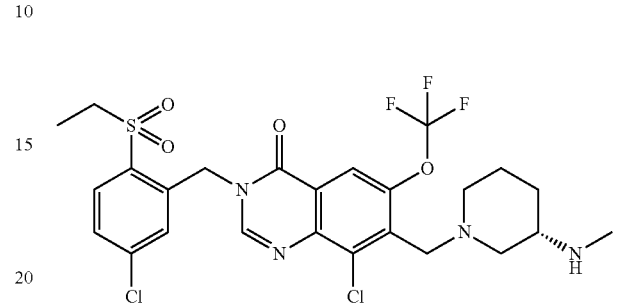

The title compound was synthesized from ethyl 2-amino-3-chloro-4-formyl-5-(trifluoromethoxy)benzoate (Compound 118) under the same conditions as for Compounds 110, 111, 112, 113, and L-8. However, tert-butyl N-methyl-N-[(3S)-piperidin-3-yl]carbamate was used in place of tert-butyl N-[(3S)-piperidin-3-yl]carbamate, and chloroform was used in place of DCM as a solvent under the conditions for 110. In addition, DCM was used in place of DMF as a solvent under the conditions for 112.

LCMS: m/z 607 [M+H]+

HPLC retention time: 0.60 min (analysis condition D)

Example 671

Compound 114

Ethyl 2-[bis[(2-methylpropan-2-yl)oxycarbonyl]amino]-3,5-dibromo-4-methylbenzoate

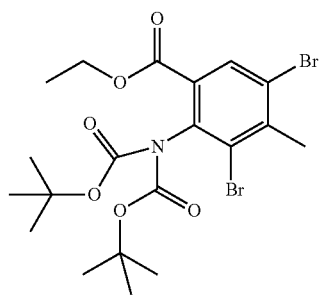 [SMILES: CCOC(=O)c1cc(Br)c(C)c(Br)c1N(C(=O)OC(C)(C)C)C(=O)OC(C)(C)C]

The title compound was synthesized from ethyl 2-amino-3,5-dibromo-4-methylbenzoate (Compound 132) under the same conditions as for Compound 104. However, acetonitrile was used in place of THF as a solvent.

Example 672

Compound 115

Ethyl 2-[bis[(2-methylpropan-2-yl)oxycarbonyl]amino]-3,5-dibromo-4-(bromomethyl)benzoate

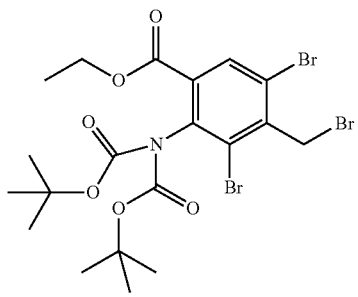 [SMILES: CCOC(=O)c1cc(Br)c(CBr)c(Br)c1N(C(=O)OC(C)(C)C)C(=O)OC(C)(C)C]

The title compound was synthesized from ethyl 2-[bis[(2-methylpropan-2-yl)oxycarbonyl]amino]-3,5-dibromo-4-methylbenzoate (Compound 114) under the same conditions as for Compound 15.

Example 673

Compound 116

Ethyl 2-amino-3,5-dibromo-4-(bromomethyl)benzoate

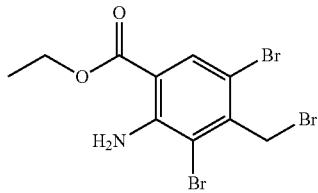 [SMILES: CCOC(=O)c1cc(Br)c(CBr)c(Br)c1N]

The title compound was synthesized from ethyl 2-[bis[(2-methylpropan-2-yl)oxycarbonyl]amino]-3,5-dibromo-4-(bromomethyl)benzoate (Compound 115) under the same conditions as for Compound A-2.

Example 674

Compound 117 tert-Butyl 4-[(3-amino-2,6-dibromo-4-ethoxycarbonylphenyl)methyl]piperazine-1-carboxylate

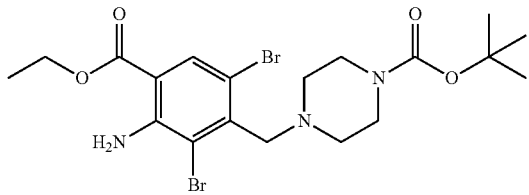 [SMILES: CCOC(=O)c1cc(Br)c(CN2CCN(C(=O)OC(C)(C)C)CC2)c(Br)c1N]

The title compound was synthesized from ethyl 2-amino-3,5-dibromo-4-(bromomethyl)benzoate (Compound 116) under the same conditions as for Compound 111. However, tert-butyl piperazine-1-carboxylate was used in place of tert-butyl N-[(3R)-pyrrolidin-3-yl]carbamate.

Example 675

Compound 118 tert-Butyl 4-[[6,8-dibromo-3-[(5-chloro-2-ethylsulfonylphenyl)methyl]-4-oxoquinazolin-7-yl]methyl]piperazine-1-carboxylate

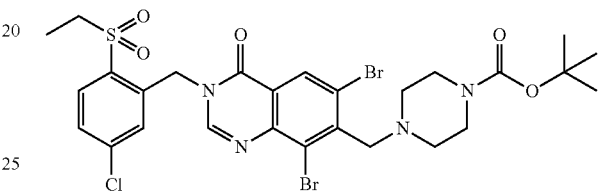

The title compound was synthesized from tert-butyl 4-[(3-amino-2,6-dibromo-4-ethoxycarbonylphenyl)methyl]piperazine-1-carboxylate (Compound 117) under the same conditions as for Compounds 111, 112, and 113. However, potassium hydroxide was used in place of sodium hydroxide under the conditions for Compound 111.

Example 676

Compound L-11

6,8-Dibromo-3-[(5-chloro-2-ethylsulfonylphenyl)methyl]-7-(piperazin-1-ylmethyl)quinazolin-4-one

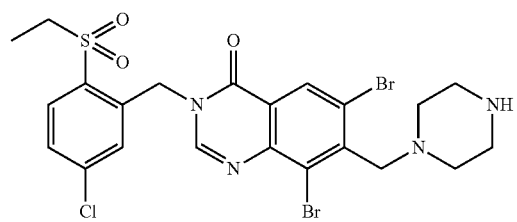 [SMILES: CCS(=O)(=O)c1ccc(Cl)cc1Cn1cnc2c(Br)c(CN3CCNCC3)c(Br)cc2c1=O]

The title compound was synthesized from tert-butyl 4-[[6,8-dibromo-3-[(5-chloro-2-ethylsulfonylphenyl)methyl]-4-oxoquinazolin-7-yl]methyl]piperazine-1-carboxylate (Compound 118) under the same conditions as for Compound 21.

LCMS: m/z 617 [M+H]$^+$

HPLC retention time: 0.53 min (analysis condition D)

Example 677

Compound L-12

6,8-Dibromo-3-[(5-chloro-2-ethylsulfonylphenyl)methyl]-7-[(4-propan-2-ylpiperazin-1-yl)methyl]quinazolin-4-one

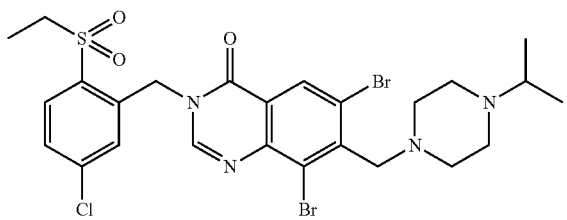 [SMILES: CCS(=O)(=O)c1ccc(Cl)cc1Cn1cnc2c(Br)c(CN3CCN(C(C)C)CC3)c(Br)cc2c1=O]

The title compound was synthesized from 6,8-dibromo-3-[(5-chloro-2-ethylsulfonylphenyl)methyl]-7-(piperazin-1-ylmethyl)quinazolin-4-one (Compound L-11) under the same conditions as for Compound G-3. However, 1,2-dichloroethane was used in place of THF, and the reaction was performed under microwave irradiation at 75° C.

LCMS: m/z 659 [M+H]$^+$

HPLC retention time: 0.56 min (analysis condition D)

Example 678

Compound L-13

6,8-Dibromo-3-[(5-chloro-2-ethylsulfonylphenyl)methyl]-7-[(4-cyclobutylpiperazin-1-yl)methyl]quinazolin-4-one

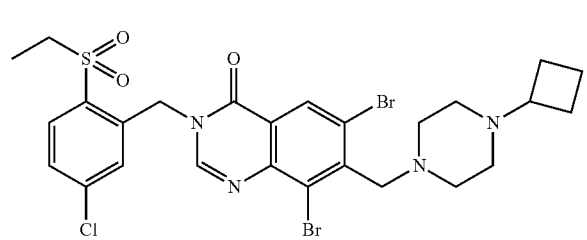 [SMILES: CCS(=O)(=O)c1ccc(Cl)cc1Cn1cnc2c(Br)c(CN3CCN(C4CCC4)CC3)c(Br)cc2c1=O]

The title compound was synthesized from 6,8-dibromo-3-[(5-chloro-2-ethylsulfonylphenyl)methyl]-7-(piperazin-1-ylmethyl)quinazolin-4-one (Compound L-11) under the same conditions as for Compound G-3. However, cyclobutanone was used in place of acetone, and 1,2-dichloroethane was used in place of THF as a solvent, and the reaction was performed under microwave irradiation at 80° C.

LCMS: m/z 671 [M+H]$^+$

HPLC retention time: 0.58 min (analysis condition D)

Example 679

Compound L-14

6,8-Dibromo-3-[(5-chloro-2-ethylsulfonylphenyl)methyl]-7-[(4-cyclohexylpiperazin-1-yl)methyl]quinazolin-4-one

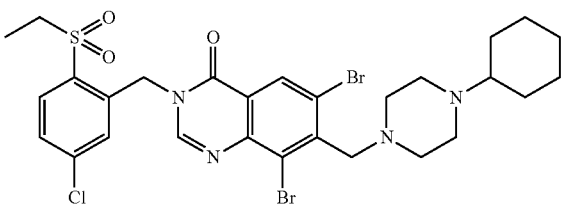 [SMILES: CCS(=O)(=O)c1ccc(Cl)cc1Cn1cnc2c(Br)c(CN3CCN(C4CCCCC4)CC3)c(Br)cc2c1=O]

The title compound was synthesized from 6,8-dibromo-3-[(5-chloro-2-ethylsulfonylphenyl)methyl]-7-(piperazin-1-ylmethyl)quinazolin-4-one (Compound L-11) under the same conditions as for Compound G-3. However, cyclohexanone was used in place of acetone, 1,4-dioxane was used in place of THF as a solvent, and the reaction was performed under microwave irradiation at 90° C.

LCMS: m/z 699 [M+H]$^+$

HPLC retention time: 0.62 min (analysis condition D)

Example 680

Amine 1

Potassium [[(3R)-3-[(2-methylpropan-2-yl)oxycarbonylamino]pyrrolidin-1-yl]methyl]trifluoroborate

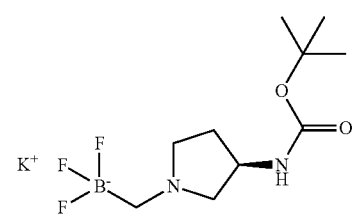 [SMILES: [K+] ; CC(C)(C)OC(=O)N[C@@H]1CCN(C[B-](F)(F)F)C1]

Potassium (bromomethyl)trifluoroborate (5.66 mg, 28.2 mmol) was added to a solution of (3R)-(+)-3-(tert-butoxycarbonylamino)pyrrolidine (5 g, 26.9 mmol) in THF (200 ml), and the mixture was refluxed for 13 hours. This was concentrated under reduced pressure. Acetone (300 ml) and potassium carbonate (3.71 g, 26.9 mmol) were added, and the mixture was stirred at room temperature and filtered through celite. The resulting solution was concentrated under reduced pressure to give the title compound as a crude product.

LCMS: m/z 267 [M−K]$^−$

Example 681

Amine 2

Potassium [(4-pyrrolidin-1-ylpiperidin-1-yl)methyl]trifluoroborate

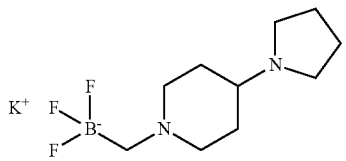 [SMILES: [K+] ; F[B-](F)(F)CN1CCC(N2CCCC2)CC1]

The title compound was synthesized from 4-pyrrolidin-1-ylpiperidine under the same conditions as for Amine 1.

LCMS: m/z 235 [M−K]−

Example 682

Amine 3

Potassium [(4-morpholin-4-ylpiperidin-1-yl)methyl]trifluoroborate

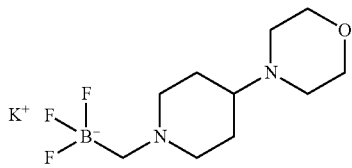 [SMILES: [K+] ; F[B-](F)(F)CN1CCC(N2CCOCC2)CC1]

The title compound was synthesized from 4-piperidin-4-ylmorpholine under the same conditions as for Amine 1.

Example 683

Amine 4

Potassium (4,4-difluoropiperidin-1-yl)methyltrifluoroborate

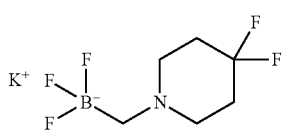

The title compound was synthesized from 4,4-difluoropiperidine under the same conditions as for Amine 1.

Example 684

Amine 5

Potassium [(3-piperidin-1-ylazetidin-1-yl)methyl]trifluoroborate

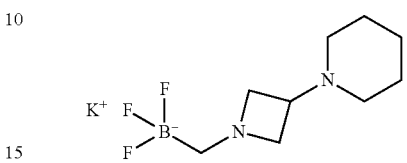

The title compound was synthesized from 1-(azetidin-3-yl)piperidine under the same conditions as for Amine 1. However, DMF was used in place of THF as a solvent.

Example 685

Amine 6 tert-Butyl N-methyl-N-[[(3S)-pyrrolidin-3-yl]methyl]carbamate

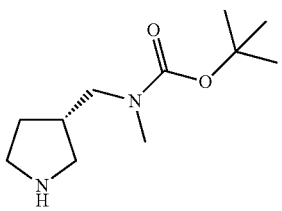

A solution of tert-butyl N-[[(3S)-pyrrolidin-3-yl]methyl]carbamate (1.00 g, 4.10 mmol) and triethylamine (2.28 ml, 16.4 mmol) in DCM (10 mL) was cooled to 0° C., after which a solution of benzyl chloroformate (0.760 ml, 5.32 mmol) in DCM (3.2 ml) was added dropwise over five minutes, and the mixture was stirred at 0° C. for 0.5 hours. Water was added to the reaction mixture, followed by extraction with ethyl acetate. The organic layer was washed with a saturated aqueous sodium bicarbonate solution, and then dried over anhydrous sodium sulfate. After the drying agent was removed by filtration, concentration was performed under reduced pressure. The resulting residue was purified by silica gel column chromatography (ethyl acetate/hexane) to yield benzyl (3R)-3-[[(2-methylpropan-2-yl)oxycarbonylamino]methyl]pyrrolidine-1-carboxylate (1.16 g, 85%) as a colorless oily substance.

LCMS: m/z 335 [M+H]+

HPLC retention time: 0.80 min (analysis condition D)

A solution of benzyl (3R)-3-[[(2-methylpropan-2-yl)oxycarbonylamino]methyl]pyrrolidine-1-carboxylate (1.16 g, 3.47 mmol) and methyl iodide (1.08 ml, 17.3 mmol) in DMF (7 ml) was cooled to 0° C., followed by addition of sodium hydride (>61% oil, 274 mg, 6.96 mmol), and it was stirred at room temperature for 2.5 hours. Water was added to the reaction mixture, followed by extraction with a mixed solvent of ethyl acetate and hexane. The organic layer was washed with brine, and then dried over anhydrous sodium sulfate. After the drying agent was removed by filtration, concentration was performed under reduced pressure. The resulting residue was purified by silica gel column chromatography (ethyl acetate/hexane) to yield benzyl (3R)-3-[[methyl-[(2-methylpropan-2-yl)oxycarbonyl]amino]methyl]pyrrolidine-1-carboxylate (1.16 g, 96%) as a colorless oily substance.

LCMS: m/z 349 [M+H]$^+$

HPLC retention time: 0.87 min (analysis condition D)

10% palladium on carbon (116 mg) was added to a solution of benzyl (3R)-3-[[methyl-[(2-methylpropan-2-yl)oxycarbonyl]amino]methyl]pyrrolidine-1-carboxylate (1.16 g, 3.33 mmol) in MeOH (11.6 ml) under argon atmosphere, and the mixture was stirred at room temperature for 14 hours under hydrogen atmosphere. The reaction mixture was filtered through celite, and the filtrate was then concentrated under reduced pressure to yield the title compound (733 mg, quant.) as a colorless oily substance.

$^1$H-NMR (400 MHz, CDCl$_3$) δ: 2.75-3.32 (5H, m), 2.87 (3H, s), 2.57-2.69 (1H, m), 2.32-2.46 (1H, m), 1.80-1.94 (1H, m), 1.35-1.55 (1H, m), 1.46 (9H, s).

Example 686

Amine 7 tert-Butyl N-methyl-N-[[(3R)-pyrrolidin-3-yl]methyl]carbamate

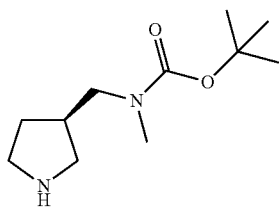

The title compound was synthesized from tert-butyl N-[[(3R)-pyrrolidin-3-yl]methyl]carbamate under the same conditions as for tert-butyl N-methyl-N-[[(3S)-pyrrolidin-3-yl]methyl]carbamate (Amine 6).

$^1$H-NMR (400 MHz, CDCl$_3$) δ: 2.79-3.31 (5H, m), 2.87 (3H, s), 2.59-2.69 (1H, m), 2.31-2.49 (1H, m), 1.79-1.95 (1H, m), 1.34-1.53 (1H, m), 1.46 (9H, s).

Example 687

Amine 8

1-[(3R)-Pyrrolidin-3-yl]pyrrolidin-2-one

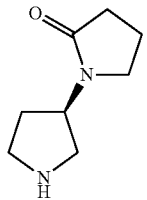 [SMILES: O=C1CCCN1[C@@H]1CCNC1]

1-[(3R)-pyrrolidin-3-yl]pyrrolidin-2-one was synthesized from (3R)-1-benzylpyrrolidin-3-amine according to the method described in a patent (WO2003051868).

Example 688

Amine 9 tert-Butyl N-ethyl-[(3S)-piperidin-3-yl]carbamate

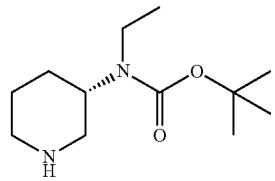 [SMILES: CCN(C(=O)OC(C)(C)C)[C@H]1CCCNC1]

The title compound was synthesized from tert-butyl N-[(3S)-piperidin-3-yl]carbamate under the same conditions as for tert-butyl N-methyl-N-[[(3S)-pyrrolidin-3-yl]methyl]carbamate (Amine 6). However, ethyl iodide was used in place of methyl iodide in the N-alkylation process.

$^1$H-NMR (400 MHz, CDCl$_3$, 60° C.) δ: 3.08-3.83 (5H, m), 2.87-2.98 (1H, m), 2.50-2.62 (1H, m), 1.59-1.93 (4H, m), 1.46 (9H, s), 1.10 (3H, t, J=7.04 Hz).

Example 689

Compound m1 tert-Butyl N-[(3S)-1-[[3-[(5-chloro-2-ethylsulfonylphenyl)methyl]-4-oxo-6-(trifluoromethyl)quinazolin-7-yl]methyl]-3-piperidyl]carbamate

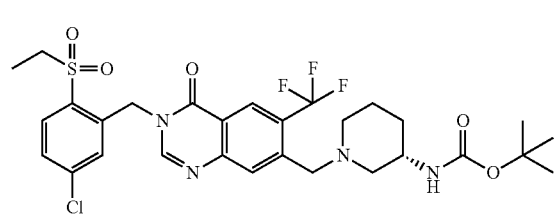 [SMILES: CCS(=O)(=O)c1ccc(Cl)cc1Cn1cnc2cc(CN3CCC[C@H](NC(=O)OC(C)(C)C)C3)c(C(F)(F)F)cc2c1=O]

The title compound was synthesized from [3-[(5-chloro-2-ethylsulfonylphenyl)methyl]-4-oxo-6-(trifluoromethyl)quinazolin-7-yl]methyl methanesulfonate (Compound i10) under the same conditions as for Compound j6. However, the reaction was performed without using potassium carbonate.

Example 690

Compound M-1

7-[[(3S)-3-Aminopiperidin-1-yl]methyl]-3-[(5-chloro-2-ethylsulfonylphenyl)methyl]-6-(trifluoromethyl)quinazolin-4-one

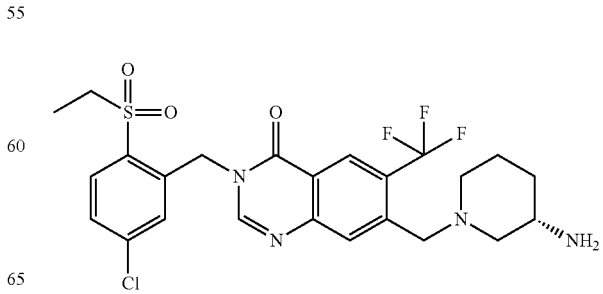

The title compound was synthesized from tert-butyl N-[(3S)-1-[[3-[(5-chloro-2-ethylsulfonyl-phenyl)methyl]-4-oxo-6-(trifluoromethyl)quinazolin-7-yl]methyl]-3-piperidyl]carbamate (Compound m1) under the same conditions as for Compound A-2.

LCMS: m/z 543 [M+H]+

HPLC retention time: 0.54 min (analysis condition: I)

Example 691

Compound M-2

N-[(3S)-1-[[3-[(5-Chloro-2-ethylsulfonylphenyl)methyl]-4-oxo-6-(trifluoromethyl)quinazolin-7-yl]methyl]piperidin-3-yl]acetamide

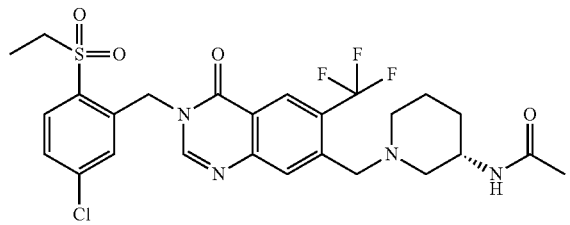 [SMILES: CCS(=O)(=O)c1ccc(Cl)cc1Cn1cnc2cc(CN3CCC[C@H](NC(C)=O)C3)c(C(F)(F)F)cc2c1=O]

The title compound was synthesized from 7-[[(3S)-3-aminopiperidin-1-yl]methyl]-3-[(5-chloro-2-ethylsulfonyl-phenyl)methyl]-6-(trifluoromethyl)quinazolin-4-one (Compound M-1) under the same conditions as for Compound I-19. However, the reaction was performed using triethylamine in place of pyridine.

LCMS: m/z 585 [M+H]+

HPLC retention time: 0.54 min (analysis condition: I)

Example 692

Compound m2 tert-Butyl N-[2-[[(3S)-1-[[8-chloro-3-[(5-chloro-2-ethylsulfonyl-phenyl)methyl]-4-oxo-6-(trifluoromethyl)quinazolin-7-yl]methyl]-3-piperidyl]amino]ethyl]carbamate

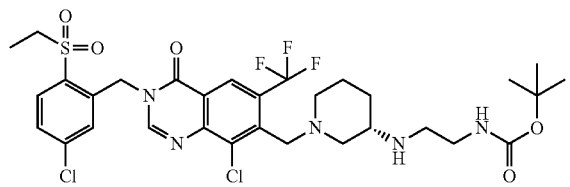 [SMILES: CCS(=O)(=O)c1ccc(Cl)cc1Cn1cnc2c(Cl)c(CN3CCC[C@H](NCCNC(=O)OC(C)(C)C)C3)c(C(F)(F)F)cc2c1=O]

Compound m3 tert-Butyl N-[2-[2-(tert-butoxycarbonylamino)ethyl-[(3S)-1-[[8-chloro-3-[(5-chloro-2-ethylsulfonyl-phenyl)methyl]-4-oxo-6-(trifluoromethyl)quinazolin-7-yl]methyl]-3-piperidyl]amino]ethyl]carbamate

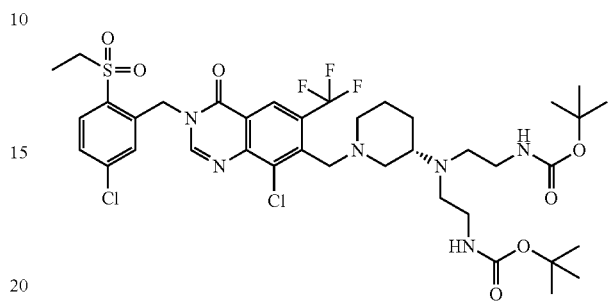

The title compounds (Compound m2 and m-3) were synthesized simultaneously from 7-[[(3S)-3-aminopiperidin-1-yl]methyl]-8-chloro-3-[(5-chloro-2-ethylsulfonylphenyl)methyl]-6-(trifluoromethyl)quinazolin-4-one (Compound K-31) under the same conditions as for Compound G-3. However, tert-butyl N-(2-oxoethyl)carbamate was used in place of acetone, chloroform was used in place of THF as a solvent, and the reaction was performed at 0° C.

Example 693

Compound M-3

7-[[(3S)-3-(2-Aminoethylamino)piperidin-1-yl]methyl]-8-chloro-3-[(5-chloro-2-ethylsulfonylphenyl)methyl]-6-(trifluoromethyl)quinazolin-4-one

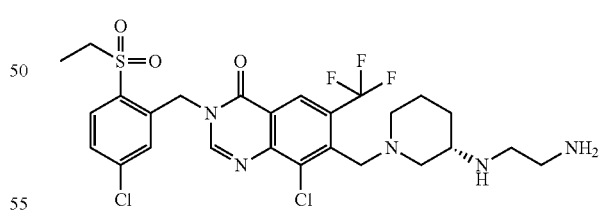

The title compound was synthesized from tert-butyl N-[2-[[(3S)-1-[[8-chloro-3-[(5-chloro-2-ethylsulfonyl-phenyl)methyl]-4-oxo-6-(trifluoromethyl)quinazolin-7-yl]methyl]-3-piperidyl]amino]ethyl]carbamate (Compound m2) under the same conditions as for Compound A-2.

LCMS: m/z 620 [M+H]+

HPLC retention time: 0.89 min (analysis condition: J)

Example 694

Compound M-4

7-[[(3S)-3-[Bis(2-aminoethyl)amino]piperidin-1-yl]methyl]-8-chloro-3-[(5-chloro-2-ethylsulfonylphenyl)methyl]-6-(trifluoromethyl)quinazolin-4-one

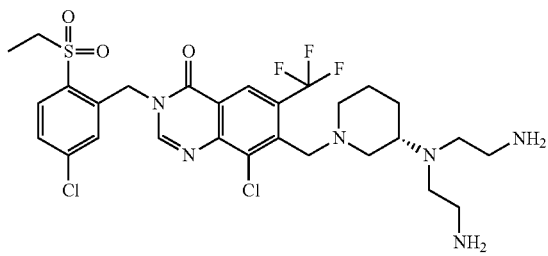 [SMILES: CCS(=O)(=O)c1ccc(Cl)cc1Cn1cnc2c(Cl)c(CN3CCC[C@H](N(CCN)CCN)C3)c(C(F)(F)F)cc2c1=O]

The title compound was synthesized from tert-butyl N-[2-[2-(tert-butoxycarbonylamino)ethyl-[(3S)-1-[[8-chloro-3-[(5-chloro-2-ethylsulfonyl-phenyl)methyl]-4-oxo-6-(trifluoromethyl)quinazolin-7-yl]methyl]-3-piperidyl]amino]ethyl]carbamate (Compound

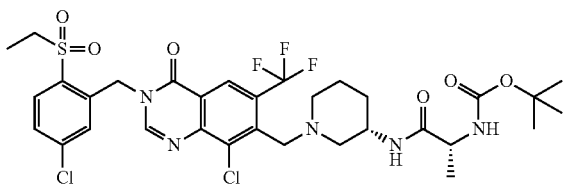 [SMILES: CCS(=O)(=O)c1ccc(Cl)cc1Cn1cnc2c(Cl)c(CN3CCC[C@H](NC(=O)[C@@H](C)NC(=O)OC(C)(C)C)C3)c(C(F)(F)F)cc2c1=O]

The title compound was synthesized from 7-[[(3S)-3-aminopiperidin-1-yl]methyl]-8-chloro-3-[(5-chloro-2-ethylsulfonylphenyl)methyl]-6-(trifluoromethyl)quinazolin-4-one (Compound K-31) under the same conditions as for Compound e8. However, (2R)-2-(tert-butoxycarbonylamino)propanoic acid was used in place of 2-amino-5-(trifluoromethyl)benzoic acid, HATU was used in place of HBTU as a condensing agent, and DMF was used in place of dichloromethane as a solvent.

Example 696

Compound M-5

(2R)-2-Amino-N-[(3S)-1-[[8-chloro-3-[(5-chloro-2-ethylsulfonylphenyl)methyl]-4-oxo-6-(trifluoromethyl)quinazolin-7-yl]methyl]piperidin-3-yl]propanamide

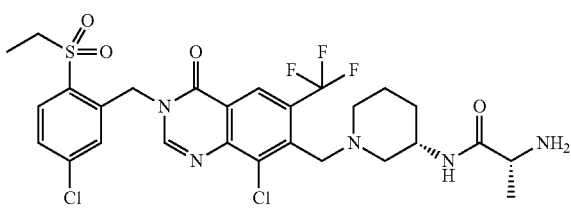 [SMILES: CCS(=O)(=O)c1ccc(Cl)cc1Cn1cnc2c(Cl)c(CN3CCC[C@H](NC(=O)[C@@H](C)N)C3)c(C(F)(F)F)cc2c1=O]

The title compound was synthesized from tert-butyl N-[(1R)-2-[[(3S)-1-[[8-chloro-3-[(5-chloro-2-ethylsulfonyl-phenyl)methyl]-4-oxo-6-(trifluoromethyl)quinazolin-7-yl]methyl]-3-piperidyl]amino]-1-methyl-2-oxo-ethyl]carbamate (Compound m4) under the same conditions as for Compound A-2.

LCMS: m/z 648 [M+H]$^+$
HPLC retention time: 0.83 min (analysis condition: J)

Example 697

Compound m5 tert-Butyl N-[(1S)-2-[[(3S)-1-[[8-chloro-3-[(5-chloro-2-ethylsulfonyl-phenyl)methyl]-4-oxo-6-(trifluoromethyl)quinazolin-7-yl]methyl]-3-piperidyl]amino]-1-methyl-2-oxo-ethyl]carbamate

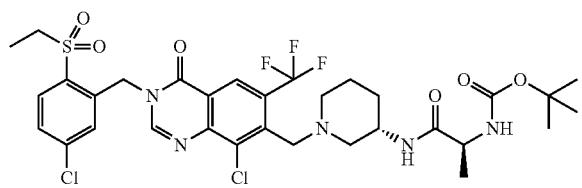 [SMILES: CCS(=O)(=O)c1ccc(Cl)cc1Cn1cnc2c(Cl)c(CN3CCC[C@H](NC(=O)[C@H](C)NC(=O)OC(C)(C)C)C3)c(C(F)(F)F)cc2c1=O]

The title compound was synthesized from 7-[[(3S)-3-aminopiperidin-1-yl]methyl]-8-chloro-3-[(5-chloro-2-ethylsulfonylphenyl)methyl]-6-(trifluoromethyl)quinazolin-4-one (Compound K-31) under the same conditions as for Compound e8. However, (2S)-2-(tert-butoxycarbonylamino)propanoic acid was used in place of 2-amino-5-(trifluoromethyl)benzoic acid, HATU was used in place of HBTU as a condensing agent, and DMF was used in place of dichloromethane as a solvent.

Example 698

Compound M-6

(2S)-2-Amino-N-[(3S)-1-[[8-chloro-3-[(5-chloro-2-ethylsulfonylphenyl)methyl]-4-oxo-6-(trifluoromethyl)quinazolin-7-yl]methyl]piperidin-3-yl]propanamide

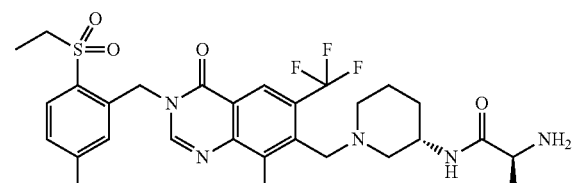

The title compound was synthesized from tert-butyl N-[(1S)-2-[[(3S)-1-[[8-chloro-3-[(5-chloro-2-ethylsulfonyl-phenyl)methyl]-4-oxo-6-(trifluoromethyl)quinazolin-7-yl]methyl]-3-piperidyl]amino]-1-methyl-2-oxo-ethyl]carbamate (Compound m5) under the same conditions as for Compound A-2.

LCMS: m/z 648 [M+H]$^+$
HPLC retention time: 0.83 min (analysis condition: J)

Example 699

Compound M-7

N-[(3R)-1-[[3-[(5-Chloro-2-ethylsulfonylphenyl methyl]-4-oxo-6-(trifluoromethyl)quinazolin-7-yl] methyl]pyrrolidin-3-yl]methanesulfonamide

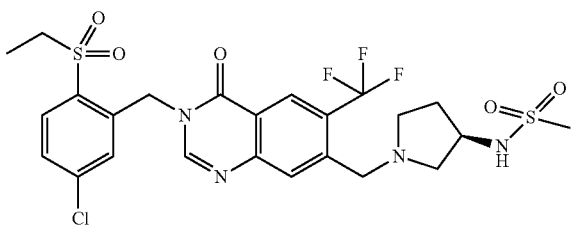 [SMILES: CCS(=O)(=O)c1ccc(Cl)cc1Cn1cnc2cc(CN3CC[C@@H](NS(C)(=O)=O)C3)c(C(F)(F)F)cc2c1=O]

The title compound was synthesized from 7-[[(3R)-3-aminopyrrolidin-1-yl]methyl]-3-[(5-chloro-2-ethylsulfonyl-phenyl)methyl]-6-(trifluoromethyl)quinazolin-4-one (Compound I-7) under the same conditions as for Compound i10.
LCMS: m/z 607 [M+H]$^+$
HPLC retention time: 0.53 min (analysis condition: I)

Example 700

Compound m6

Ethyl 2-amino-3-bromo-4-[[(3R)-3-(tert-butoxycarbonylamino)pyrrolidin-1-yl]methyl]-5-(trifluoromethyl)benzoate

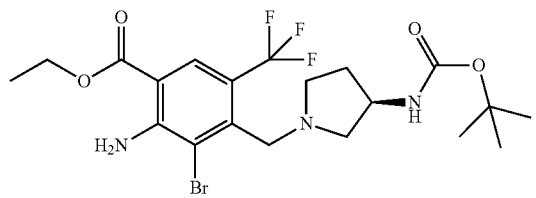 [SMILES: CCOC(=O)c1cc(C(F)(F)F)c(CN2CC[C@@H](NC(=O)OC(C)(C)C)C2)c(Br)c1N]

The title compound was synthesized from ethyl 2-amino-3-bromo-4-formyl-5-(trifluoromethyl)benzoate (Compound k32) under the same conditions as for Compound i3. However, tert-butyl N-[(3R)-pyrrolidin-3-yl]carbamate was used in place of N-[(3S)-pyrrolidin-3-yl]acetamide as an amine.

Example 701

Compound m7

Ethyl 2-amino-4-[[(3R)-3-(tert-butoxycarbonylamino)pyrrolidin-1-yl]methyl]-3-cyano-5-(trifluoromethyl)benzoate

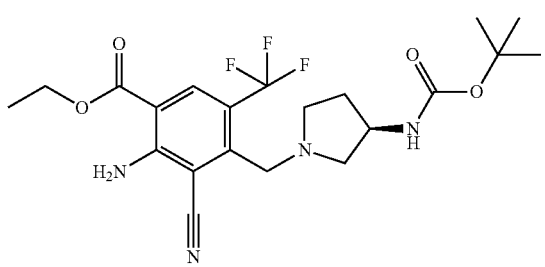 [SMILES: CCOC(=O)c1cc(C(F)(F)F)c(CN2CC[C@@H](NC(=O)OC(C)(C)C)C2)c(C#N)c1N]

The title compound was synthesized from ethyl 2-amino-3-bromo-4-[[(3R)-3-(tert-butoxycarbonylamino)pyrrolidin-1-yl]methyl]-5-(trifluoromethyl)benzoate (Compound m6) under the same conditions as for Compound K-50. However, DMF was used in place of NMP as a solvent.

Example 702

Compound m8

2-Amino-4-[[(3R)-3-(tert-butoxycarbonylamino)pyrrolidin-1-yl]methyl]-3-cyano-5-(trifluoromethyl)benzoic Acid

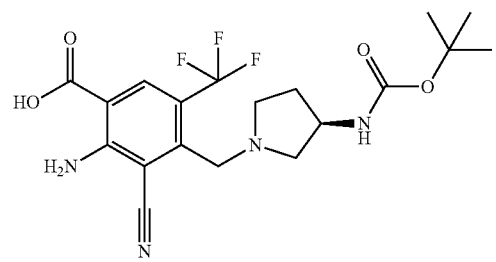 [SMILES: CC(C)(C)OC(=O)N[C@@H]1CCN(Cc2c(C(F)(F)F)cc(C(=O)O)c(N)c2C#N)C1]

The title compound was synthesized from ethyl 2-amino-4-[[(3R)-3-(tert-butoxycarbonylamino)pyrrolidin-1-yl]methyl]-3-cyano-5-(trifluoromethyl)benzoate (Compound m7) under the same conditions as for Compound 85.

Example 703

Compound m9 tert-Butyl N-[(3R)-1-[[3-amino-4-[(5-chloro-2-ethylsulfonyl-phenyl)methylcarbamoyl]-2-cyano-6-(trifluoromethyl)phenyl]methyl]pyrrolidin-3-yl]carbamate

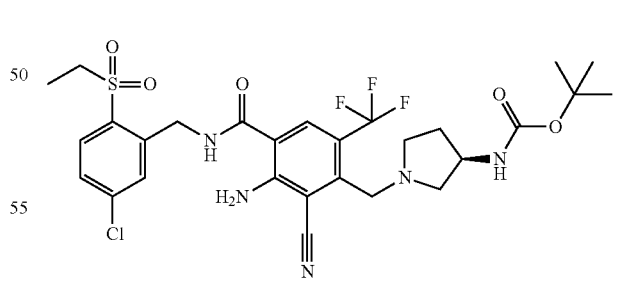

The title compound was synthesized from 2-amino-4-[[(3R)-3-(tert-butoxycarbonylamino)pyrrolidin-1-yl]methyl]-3-cyano-5-(trifluoromethyl)benzoic acid (Compound m8) under the same conditions as for Compound e8. However, HATU was used in place of HBTU as a condensing agent, and DMF was used in place of dichloromethane as a solvent.

Example 704

Compound m10 tert-Butyl N-[(3R)-1-[[3-[(5-chloro-2-ethylsulfonyl-phenyl)methyl]-8-cyano-4-oxo-6-(trifluoromethyl)quinazolin-7-yl]methyl]pyrrolidin-3-yl]carbamate

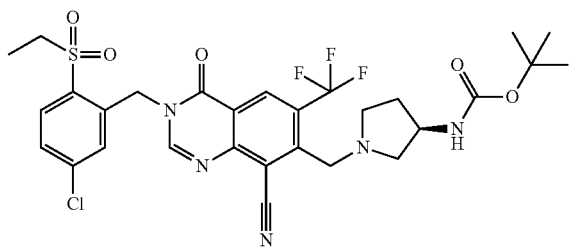 [SMILES: CCS(=O)(=O)c1ccc(Cl)cc1Cn1cnc2c(C#N)c(CN3CC[C@@H](NC(=O)OC(C)(C)C)C3)c(C(F)(F)F)cc2c1=O]

The title compound was synthesized from tert-butyl N-[(3R)-1-[[3-amino-4-[(5-chloro-2-ethylsulfonyl-phenyl)methylcarbamoyl]-2-cyano-6-(trifluoromethyl)phenyl]methyl]pyrrolidin-3-yl]carbamate (Compound m9) under the same conditions as for Compound 95. However, the heating was performed at 140° C., DMF dimethylacetal was used in place of formamide acetate, and DMF was used in place of ethanol as a solvent.

Example 705

Compound M-8

7-[[(3R)-3-Aminopyrrolidin-1-yl]methyl]-3-[(5-chloro-2-ethylsulfonylphenyl)methyl]-4-oxo-6-(trifluoromethyl)quinazoline-8-carbonitrile

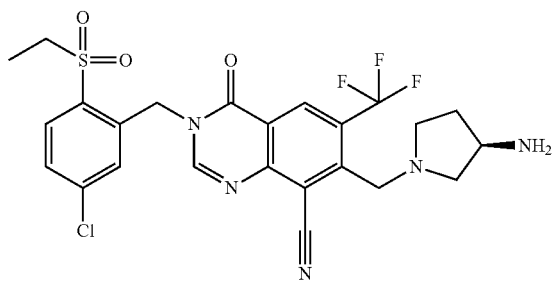 [SMILES: CCS(=O)(=O)c1ccc(Cl)cc1Cn1cnc2c(C#N)c(CN3CC[C@@H](N)C3)c(C(F)(F)F)cc2c1=O]

The title compound was synthesized from tert-butyl N-[(3R)-1-[[3-[(5-chloro-2-ethylsulfonyl-phenyl)methyl]-8-cyano-4-oxo-6-(trifluoromethyl)quinazolin-7-yl]methyl]pyrrolidin-3-yl]carbamate (Compound m10) under the same conditions as for Compound A-2.

LCMS: m/z 554 [M+H]$^+$
HPLC retention time: 0.56 min (analysis condition: I)

Example 706

Compound M-9

N-[(3R)-1-[[3-[(5-Chloro-2-ethylsulfonylphenyl)methyl]-8-cyano-4-oxo-6-(trifluoromethyl)quinazolin-7-yl]methyl]pyrrolidin-3-yl]methanesulfonamide

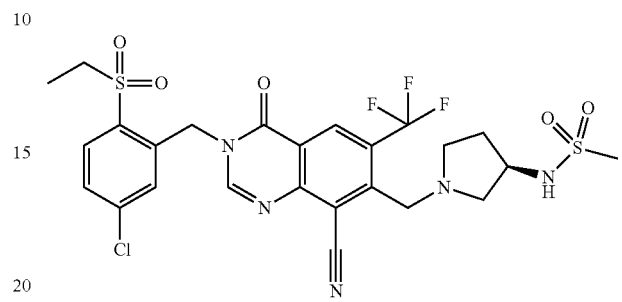

The title compound was synthesized from 7-[[(3R)-3-aminopyrrolidin-1-yl]methyl]-3-[(5-chloro-2-ethylsulfonyl-phenyl)methyl]-4-oxo-6-(trifluoromethyl)quinazoline-8-carbonitrile (Compound M-8) under the same conditions as for Compound i10.

LCMS: m/z 632 [M+H]$^+$
HPLC retention time: 0.77 min (analysis condition: I)

Example 707

Compound M-10

N-[(3R)-1-[[3-[(5-Chloro-2-ethylsulfonylphenyl)methyl]-8-cyano-4-oxo-6-(trifluoromethyl)quinazolin-7-yl]methyl]pyrrolidin-3-yl]acetamide

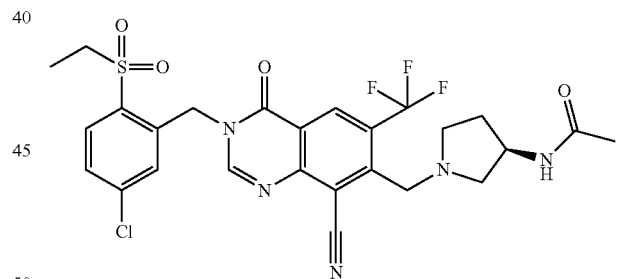

The title compound was synthesized from 7-[[(3R)-3-aminopyrrolidin-1-yl]methyl]-3-[(5-chloro-2-ethylsulfonyl-phenyl)methyl]-4-oxo-6-(trifluoromethyl)quinazoline-8-carbonitrile (Compound M-8) under the same conditions as for Compound I-19. However, triethylamine was used in place of pyridine.

LCMS: m/z 596 [M+H]$^+$
HPLC retention time: 0.63 min (analysis condition: I)

Pharmacological Study

1. Measurement of DDR1 Enzyme Inhibitory Activity

The DDR1 enzyme inhibitory activity was determined with human DDR1 enzyme prepared using the baculovirus expression system, based on the inhibitory activity of phosphorylation of a biotinylated peptide (HTDDGYMPM-SPGVA) by the enzyme. The phosphorylated biotinylated peptide was detected using time-resolved fluorescence, with an anti-phosphorylated tyrosine antibody conjugated with europium cryptate and streptavidin conjugated with XL665 which is a derivative of allophycocyanin. The 50% inhibitory concentration ($IC_{50}$) was calculated from the inhibition rate relative to the test substance-free control.

2. Measurement of DDR1 Binding Activity

DDR1 binding activity was measured using the LanthaScreen (Registered trademark) Eu Kinase Binding Assay (manufactured by Life Technologies Corporation). The test compound and the Alexa Fluor® 647-labeled Kinase Tracer 178 (manufactured by Life Technologies Corporation) were added to a mixture of DDR1 and the LanthaScreen (Registered trademark) Eu-anti-GST antibody. After one-hour reaction at room temperature, the fluorescence resonance energy transfer was measured. The 50% inhibitory concentration (IC50) was calculated from the inhibition rate relative to the test compound-free control.

3. Path-Hunter DDR1 Functional Assay

The human osteosarcoma cell line U2OS (manufactured by DiscoveRX Corporation) overexpressing DDR1 and SHC1 was suspended in a medium (MEM Eagle Medium manufactured by Life Technologies Corporation) supplemented with 10% fetal bovine serum and antibiotics (500 μg/mL geneticin (G418) manufactured by Life Technologies Corporation and 250 μg/mL hygromycin) to prepare a cell suspension at a concentration of 10000 cells/100 μL. This cell suspension was added to a 96-well plate, and the plate was incubated at 37° C. in a 5% carbon dioxide incubator for one hour. The medium was then removed after the cells were confirmed to have adhered to the plate. The test compound was serially diluted with dimethyl sulfoxide, and added to 50 μL of the Cell Planting 16 Reagent (manufactured by DiscoveRX Corporation); and then the mixture was dispensed into the 96-well plate. After one-hour incubation at 37° C. in the 5% carbon dioxide incubator, 50 μL of 100 μg/mL collagen for tissue culture (Collagen Type I-C manufactured by Nitta Gelatin Inc.) was dispensed, and the plate was incubated at 37° C. in the 5% carbon dioxide incubator for 24 hours. The incubated plate was returned to room temperature, and 25 μL of the prepared Path-Hunter Detection Kit (manufactured by DiscoveRX Corporation) was dispensed into the plate. The plate was protected from light, and incubated at room temperature for two hours. Measurement was performed at 1 sec/well on a fluorescence plate reader. The 50% inhibitory concentration (IC50) of the test compound was calculated from the value obtained when the test compound was added, relative to the test compound-free control.

The results are provided in Tables A1 to A12.

TABLE A1

| Example | Compound No. | DDR1 enzyme inhibition assay IC50 (uM) | DDR1 binding activity IC50 (uM) | Path Hunter DDR1 IC50 (uM) |
|---|---|---|---|---|
| 194 | A-33 | 0.085 | 0.045 | 1.79 |
| 200 | A-45 | 0.18 | 0.18 | 1.85 |
| 399 | H-1 | 0.12 | 0.030 | 0.40 |
| 400 | H-2 | 0.11 | 0.037 | 0.089 |
| 421 | H-21 | 0.11 | 0.14 | 0.19 |
| 562 | K-2 |  | 0.044 | 0.075 |
| 589 | K-14 |  | 0.022 | 0.46 |
| 591 | K-15 |  | 0.014 | 0.49 |
| 606 | K-24 |  | 0.027 | 2.29 |
| 614 | K-31 |  | 0.028 | 0.31 |
| 615 | K-32 |  | 0.031 | 0.72 |
| 616 | K-33 |  | 0.024 | 0.23 |

TABLE A2

| Example | Compound No. | DDR1 enzyme inhibition assay IC50 (uM) | DDR1 binding activity IC50 (uM) |
|---|---|---|---|
| 137 | A-1 | 0.17 | |
| 140 | A-2 | 0.04 | |
| 141 | A-3 | 0.11 | |
| 142 | A-4 | 1.35 | |
| 144 | A-5 | 0.88 | |
| 150 | A-6 | 0.07 | |
| 152 | A-7 | 0.80 | |
| 154 | A-8 | 0.55 | |
| 155 | A-9 | 0.18 | |
| 163 | A-10 | 0.12 | |
| 156 | A-11 | 0.40 | |
| 164 | A-12 | 0.20 | 0.012 |
| 173 | A-13 | 0.24 | |
| 157 | A-14 | 0.13 | |
| 165 | A-15 | 1.23 | |
| 158 | A-16 | 0.093 | |
| 166 | A-17 | 0.27 | |
| 171 | A-18 | 1.71 | |
| 159 | A-19 | 0.51 | |
| 167 | A-20 | 7.64 | |
| 160 | A-21 | 0.27 | |
| 168 | A-22 | 1.93 | |
| 161 | A-23 | 0.16 | |
| 169 | A-24 | 0.19 | |
| 162 | A-25 | | 0.042 |
| 170 | A-26 | | 0.026 |
| 175 | A-27 | 0.12 | 0.013 |
| 177 | A-28 | 0.088 | |
| 178 | A-29 | 0.34 | |
| 179 | A-30 | 0.10 | |
| 193 | A-31 | 0.38 | |
| 180 | A-32 | 0.29 | |
| 181 | A-34 | 0.068 | |

TABLE A3

| Example | Compound No. | DDR1 enzyme inhibition assay IC50 (uM) | DDR1 binding activity IC50 (uM) |
|---|---|---|---|
| 195 | A-35 | 0.095 | |
| 182 | A-36 | 0.25 | |
| 196 | A-37 | 0.43 | |
| 183 | A-38 | 0.48 | |
| 197 | A-39 | 1.75 | |
| 184 | A-40 | 0.35 | |
| 198 | A-41 | 1.95 | |
| 185 | A-42 | 3.10 | |
| 199 | A-43 | 0.60 | |
| 186 | A-44 | 0.29 | |
| 187 | A-46 | 0.42 | |
| 201 | A-47 | 0.25 | 0.018 |
| 188 | A-48 | 0.20 | |
| 202 | A-49 | 2.13 | |
| 189 | A-50 | 0.057 | |
| 203 | A-51 | 0.11 | |
| 190 | A-52 | 0.20 | |
| 204 | A-53 | 0.18 | |
| 191 | A-54 | 0.33 | |
| 205 | A-55 | 0.24 | |
| 192 | A-56 | 0.099 | |
| 206 | A-57 | 0.12 | |
| 207 | A-58 | 4.05 | |
| 208 | A-59 | 0.48 | |
| 209 | A-60 | 0.22 | |
| 210 | A-61 | 0.29 | |
| 211 | A-62 | 0.11 | |
| 212 | A-63 | 0.20 | |
| 213 | A-64 | 0.20 | |
| 214 | A-65 | 3.11 | |

TABLE A3-continued

| Example | Compound No. | DDR1 enzyme inhibition assay IC50 (uM) | DDR1 binding activity IC50 (uM) |
|---|---|---|---|
| 216 | A-66 | 0.052 | |
| 218 | B-1 | 0.25 | |
| 222 | B-2 | 0.16 | |

TABLE A4

| Example | Compound No. | DDR1 enzyme inhibition assay IC50 (uM) | DDR1 binding activity IC50 (uM) |
|---|---|---|---|
| 224 | B-3 | 0.14 | |
| 227 | B-4 | 0.11 | |
| 229 | B-5 | 0.14 | 0.077 |
| 231 | B-6 | 0.22 | 0.031 |
| 233 | B-7 | 0.36 | 0.039 |
| 235 | B-8 | | 0.089 |
| 237 | B-9 | 0.29 | 0.33 |
| 238 | B-10 | 0.25 | 0.047 |
| 239 | B-11 | 0.20 | 0.032 |
| 241 | B-12 | 0.15 | |
| 244 | B-13 | 0.74 | |
| 246 | B-14 | 0.29 | |
| 248 | B-15 | 0.86 | |
| 249 | B-16 | 1.47 | |
| 250 | B-17 | 0.41 | |
| 251 | B-18 | | 0.016 |
| 252 | B-19 | 0.33 | |
| 253 | B-20 | 0.14 | 0.043 |
| 254 | B-21 | 0.29 | 0.052 |
| 255 | B-22 | 0.34 | 0.051 |
| 256 | B-23 | | 0.091 |
| 257 | B-24 | 0.14 | 0.019 |
| 259 | C-1 | 0.11 | |
| 260 | C-2 | 0.16 | |
| 263 | C-3 | 0.12 | 0.051 |
| 264 | C-4 | 0.13 | 0.044 |
| 266 | C-5 | 0.13 | |
| 267 | C-6 | 0.25 | |
| 269 | C-7 | 0.75 | |
| 270 | C-8 | 6.40 | |
| 271 | C-9 | 0.099 | |
| 272 | C-10 | 0.11 | 1.80 |
| 273 | C-11 | 0.11 | |

TABLE A5

| Example | Compound No. | DDR1 enzyme inhibition assay IC50 (uM) | DDR1 binding activity IC50 (uM) |
|---|---|---|---|
| 274 | C-12 | 0.094 | 0.051 |
| 275 | C-13 | 0.11 | |
| 276 | C-14 | 0.10 | 0.44 |
| 278 | C-15 | 0.21 | |
| 279 | C-16 | 0.27 | |
| 282 | C-17 | 0.23 | |
| 283 | C-18 | 0.43 | |
| 284 | C-19 | 0.34 | |
| 285 | C-20 | 0.15 | |
| 286 | C-21 | 0.60 | |
| 287 | C-22 | 0.30 | |
| 288 | C-23 | 0.40 | |
| 289 | C-24 | 0.28 | |
| 290 | C-25 | 0.18 | |
| 291 | C-26 | 0.15 | |
| 292 | C-27 | 0.20 | |
| 293 | C-28 | 0.29 | |
| 294 | C-29 | 0.16 | |
| 295 | C-30 | 0.15 | |
| 296 | C-31 | 0.33 | |
| 297 | C-32 | 1.97 | |

TABLE A5-continued

| Example | Compound No. | DDR1 enzyme inhibition assay IC50 (uM) | DDR1 binding activity IC50 (uM) |
|---|---|---|---|
| 298 | C-33 | | 3.82 |
| 299 | C-34 | 0.17 | |
| 300 | C-35 | 0.21 | |
| 301 | C-36 | 0.28 | |
| 302 | C-37 | 0.24 | |
| 303 | C-38 | 0.28 | |
| 304 | C-39 | 0.14 | |
| 305 | C-40 | 0.19 | |
| 306 | C-41 | 0.11 | |
| 307 | C-42 | 0.45 | |
| 308 | C-43 | 0.33 | |
| 310 | D-1 | 2.36 | |

TABLE A6

| Example | Compound No. | DDR1 enzyme inhibition assay IC50 (uM) | DDR1 binding activity IC50 (uM) |
|---|---|---|---|
| 311 | D-2 | 0.41 | |
| 312 | D-3 | 0.43 | |
| 314 | D-4 | 0.58 | |
| 315 | D-5 | 0.13 | |
| 316 | D-6 | 0.093 | |
| 317 | D-7 | 0.16 | 2.50 |
| 319 | E-1 | 0.64 | |
| 348 | E-2 | 0.60 | |
| 321 | E-3 | 0.48 | |
| 349 | E-4 | 0.26 | |
| 322 | E-5 | 0.95 | |
| 350 | E-6 | 1.10 | |
| 323 | E-7 | 0.79 | |
| 351 | E-8 | 0.20 | |
| 325 | E-9 | 0.59 | |
| 352 | E-10 | 0.11 | 0.052 |
| 326 | E-11 | 0.54 | |
| 353 | E-12 | 0.39 | |
| 354 | E-13 | 0.14 | 0.023 |
| 355 | E-14 | 0.12 | |
| 330 | E-15 | 0.45 | |
| 356 | E-16 | 0.18 | 1.20 |
| 332 | E-17 | 0.15 | |
| 333 | E-18 | | 0.11 |
| 357 | E-19 | | 0.088 |
| 335 | E-20 | | 3.04 |
| 336 | E-21 | | 0.16 |
| 337 | E-22 | | 1.90 |
| 338 | E-23 | | 0.45 |
| 339 | E-24 | | 9.13 |
| 358 | E-25 | | 3.48 |
| 359 | E-26 | | 42.84 |
| 341 | E-27 | | 0.67 |

TABLE A7

| Example | Compound No. | DDR1 enzyme inhibition assay IC50 (uM) | DDR1 binding activity IC50 (uM) |
|---|---|---|---|
| 342 | E-28 | 0.63 | |
| 343 | E-29 | 0.37 | 2.13 |
| 360 | E-30 | 0.37 | 1.42 |
| 345 | E-31 | | 3.39 |
| 361 | E-32 | | 2.64 |
| 347 | E-33 | | 1.11 |
| 362 | F-1 | 0.20 | 0.11 |
| 363 | F-2 | 0.17 | 0.19 |
| 364 | F-3 | 0.49 | |
| 365 | F-4 | 0.26 | 0.025 |
| 366 | F-5 | 0.21 | 0.020 |
| 367 | F-6 | 0.49 | |

TABLE A7-continued

| Example | Compound No. | DDR1 enzyme inhibition assay IC50 (uM) | DDR1 binding activity IC50 (uM) |
|---|---|---|---|
| 368 | F-7 | 2.08 | |
| 369 | F-8 | 0.42 | 1.47 |
| 370 | F-9 | 0.81 | |
| 371 | F-10 | 1.34 | |
| 372 | F-11 | | 3.90 |
| 377 | G-1 | | 0.038 |
| 378 | G-2 | | 0.045 |
| 379 | G-3 | | 0.056 |
| 380 | G-4 | | 0.090 |
| 386 | G-5 | | 0.033 |
| 387 | G-6 | | 0.086 |
| 390 | G-7 | 0.16 | 0.59 |
| 391 | G-8 | 0.68 | |
| 396 | G-9 | | 0.25 |
| 401 | H-3 | 0.12 | 0.049 |
| 402 | H-4 | 0.12 | 0.061 |
| 403 | H-5 | | 0.72 |
| 404 | H-6 | | 0.066 |
| 405 | H-7 | | 0.083 |
| 406 | H-8 | | 0.098 |
| 407 | H-9 | | 0.16 |

TABLE A8

| Example | Compound No. | DDR1 enzyme inhibition assay IC50 (uM) | DDR1 binding activity IC50 (uM) |
|---|---|---|---|
| 408 | H-10 | | 0.15 |
| 409 | H-11 | | 0.060 |
| 410 | H-12 | | 0.11 |
| 411 | H-13 | | 0.090 |
| 413 | H-14 | | 0.16 |
| 415 | H-15 | | 1.03 |
| 416 | H-16 | | 0.15 |
| 417 | H-17 | | 0.19 |
| 418 | H-18 | | 0.22 |
| 419 | H-19 | | 0.86 |
| 420 | H-20 | | 0.36 |
| 422 | H-22 | | 0.29 |
| 423 | H-23 | | 0.60 |
| 435 | H-24 | 0.047 | |
| 436 | H-25 | | 0.69 |
| 437 | H-26 | | 0.92 |
| 438 | H-27 | | 0.43 |
| 439 | H-28 | | 1.89 |
| 424 | H-29 | | 0.15 |
| 425 | H-30 | | 0.055 |
| 426 | H-31 | | 0.13 |
| 427 | H-32 | | 0.084 |
| 428 | H-33 | | 0.076 |
| 429 | H-34 | | 0.041 |
| 430 | H-35 | | 0.10 |
| 431 | H-36 | | 0.18 |
| 432 | H-37 | | 0.026 |
| 433 | H-38 | | 0.063 |
| 440 | H-39 | | 0.037 |
| 441 | H-40 | | 0.15 |
| 444 | H-41 | 0.25 | |
| 450 | H-42 | | 0.082 |
| 451 | H-43 | | 0.060 |

TABLE A9

| Example | Compound No. | DDR1 enzyme inhibition assay IC50 (uM) | DDR1 binding activity IC50 (uM) |
|---|---|---|---|
| 452 | H-44 | | 0.076 |
| 453 | H-45 | | 0.10 |
| 454 | H-46 | | 0.57 |

TABLE A9-continued

| Example | Compound No. | DDR1 enzyme inhibition assay IC50 (uM) | DDR1 binding activity IC50 (uM) |
|---|---|---|---|
| 457 | H-47 | | 0.12 |
| 458 | H-48 | | 0.096 |
| 459 | H-49 | | 0.11 |
| 460 | H-50 | | 0.17 |
| 463 | I-1 | 0.16 | 0.036 |
| 464 | I-2 | 0.089 | 0.032 |
| 465 | I-3 | | 0.050 |
| 466 | I-4 | | 0.059 |
| 470 | I-5 | | 0.15 |
| 471 | I-6 | | 0.061 |
| 478 | I-7 | | 0.023 |
| 479 | I-8 | | 0.018 |
| 482 | I-9 | | 0.46 |
| 486 | I-10 | 0.096 | 0.083 |
| 487 | I-11 | | 0.048 |
| 488 | I-12 | | 0.096 |
| 489 | I-13 | | 0.11 |
| 491 | I-14 | | 0.23 |
| 496 | I-15 | | 0.25 |
| 502 | I-16 | | 0.76 |
| 508 | I-17 | | 0.32 |
| 509 | I-18 | | 0.24 |
| 510 | I-19 | | 0.93 |
| 515 | I-20 | | 1.54 |
| 516 | I-21 | | 3.78 |
| 517 | I-22 | | 6.72 |
| 518 | I-23 | | 11.03 |
| 520 | I-24 | | 0.083 |
| 526 | I-25 | 0.13 | 0.10 |
| 527 | I-26 | | 0.043 |
| 531 | I-27 | 0.096 | 0.028 |

TABLE A10

| Example | Compound No. | DDR1 enzyme inhibition assay IC50 (uM) | DDR1 binding activity IC50 (uM) |
|---|---|---|---|
| 537 | J-1 | 0.16 | 0.13 |
| 538 | J-2 | 0.16 | 0.11 |
| 539 | J-3 | 0.22 | 0.22 |
| 540 | J-4 | | 15.79 |
| 541 | J-5 | | 3.59 |
| 542 | J-6 | | 9.24 |
| 549 | J-7 | 0.17 | |
| 550 | J-8 | 0.14 | |
| 551 | J-9 | 0.12 | |
| 555 | J-10 | | 0.34 |
| 556 | J-11 | | 0.12 |
| 561 | K-1 | | 0.050 |
| 563 | K-3 | | 0.033 |
| 567 | K-4 | | 0.23 |
| 572 | K-5 | | 0.024 |
| 573 | K-6 | | 0.034 |
| 574 | K-7 | | 0.072 |
| 575 | K-8 | | 0.051 |
| 579 | K-9 | | 0.34 |
| 584 | K-10 | | 0.049 |
| 585 | K-11 | | 0.011 |
| 586 | K-12 | | 0.027 |
| 587 | K-13 | | 0.034 |
| 592 | K-16 | | 0.014 |
| 594 | K-17 | | 0.062 |
| 595 | K-18 | | 0.070 |
| 596 | K-19 | | 0.071 |
| 597 | K-20 | | 0.064 |
| 600 | K-21 | | 0.047 |
| 602 | K-22 | | 0.042 |
| 604 | K-23 | | 0.041 |
| 607 | K-25 | | 0.21 |
| 608 | K-26 | | 0.24 |

TABLE A11

| Example | Compound No. | DDR1 enzyme inhibition assay IC50 (uM) | DDR1 binding activity IC50 (uM) |
|---|---|---|---|
| 609 | K-27 | | 0.014 |
| 610 | K-28 | | 0.023 |
| 611 | K-29 | | 0.11 |
| 612 | K-30 | | 0.024 |
| 617 | K-34 | | 0.11 |
| 618 | K-35 | | 0.13 |
| 619 | K-36 | | 0.038 |
| 620 | K-37 | | 0.016 |
| 621 | K-38 | | 0.046 |
| 622 | K-39 | | 0.11 |
| 626 | K-40 | | 0.11 |
| 627 | K-41 | | 0.043 |
| 629 | K-42 | | 0.039 |
| 630 | K-43 | | 0.020 |
| 633 | K-44 | | 0.079 |
| 634 | K-45 | | 0.054 |
| 636 | K-46 | | 0.041 |
| 639 | K-47 | | 0.031 |
| 643 | K-48 | | 0.028 |
| 646 | K-49 | | 0.055 |
| 647 | K-50 | | 0.062 |
| 654 | L-1 | | 0.067 |
| 655 | L-2 | | 0.085 |
| 656 | L-3 | | 0.46 |
| 660 | L-4 | | 0.026 |
| 661 | L-5 | | 0.033 |
| 662 | L-6 | | 0.029 |
| 663 | L-7 | | 0.027 |
| 668 | L-8 | | 0.077 |
| 669 | L-9 | | 0.10 |
| 670 | L-10 | | 0.041 |
| 676 | L-11 | 0.090 | |
| 677 | L-12 | 0.20 | |
| 678 | L-13 | | 0.15 |
| 679 | L-14 | | 0.94 |

TABLE A12

| Example | Compound No. | DDR1 enzyme inhibition assay IC50 (uM) | DDR1 binding activity IC50 (uM) |
|---|---|---|---|
| 690 | M-1 | | 0.013 |
| 691 | M-2 | | 0.85 |
| 693 | M-3 | | 0.020 |
| 694 | M-4 | | 0.022 |
| 696 | M-5 | | 0.063 |
| 698 | M-6 | | 0.028 |
| 699 | M-7 | | 0.057 |
| 705 | M-8 | | 0.021 |
| 706 | M-9 | | 0.031 |
| 707 | M-10 | | 0.10 |

4. Measurement of Antitumor Effect

The antitumor effect was measured for representative examples of the compounds of the present invention.

The antitumor effect was measured using cancer-bearing mice in which the human endometrial cancer cell line MFE-280 (manufactured by DSMZ) was subcutaneously transplanted to the flank of BALB/c nude mice (manufactured by Charles River Laboratories Japan, Inc.).

About $1\times10^7$ MFE-280 cells were subcutaneously transplanted to the flank of the purchased nude mice after a one-week quarantine period. The tumor size was measured with calipers, and the tumor volume was calculated (tumor volume=length×breadth$^2$/2 (mm$^3$)). The mice were subjected to the experiment when the tumor volume was about 200 mm$^3$.

The test compound was suspended in the administration solution, and 0.4 mL of the suspension was orally administered once daily. The antitumor effect was calculated as inhibition of tumor growth by comparing the tumor growth between the drug-treated group and the administration solution-administered control group on the 11th day after the start of administration.

Tumor volume growth inhibition (TGI)=(1−tumor volume growth in drug-treated group/tumor volume growth in control group)×100(%)

The results are shown in Table B 1 and FIG. 1.

TABLE B1

| | Antitumor effect | |
|---|---|---|
| Compound No. | Dose (mg/kg) | TGI after 11 days (%) |
| A-45 | 200 | 72 |

5. Measurement of Inhibition of DDR1 Phosphorylation in Tumors

Inhibition of DDR1 by the test compound in MFE-280 tumors was measured using Western blotting.

Two hours after the final administration, tumors were homogenized and solubilized, subjected to SDS-PAGE, and then transferred to a PVDF membrane. After blocking, the membrane was treated with an anti-phosphorylated Y796-DDR1 antibody (manufactured by Sigma-Aldrich Co. LLC.), an anti-DDR1 antibody (manufactured by Santa Cruz Biotechnology, Inc.), and an anti-actin antibody (manufactured by Santa Cruz Biotechnology, Inc.). After the primary antibodies were washed off, the membrane was treated with an HRP-labeled secondary antibody. After the secondary antibody was washed off, signals were detected by a chemiluminescence method using ECL Plus or ECL (manufactured by GE Healthcare).

Figure 2:
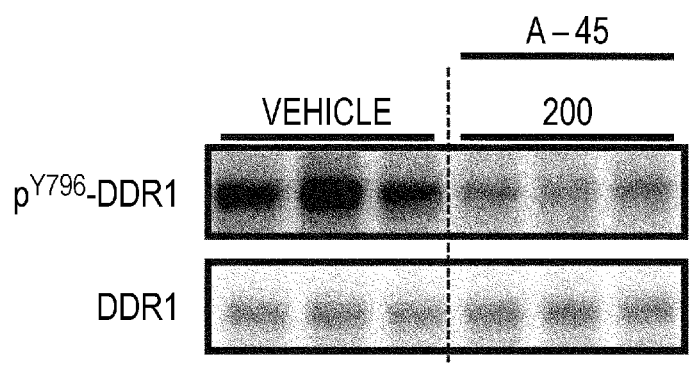
FIG. 2 shows a DDR1 phosphorylation inhibitory effect of Compound A-45 in tumors.

The results are shown in FIG. 2.

From these results, it was observed that the compounds of the present invention have a high DDR1 inhibitory activity and a high antitumor effect.

INDUSTRIAL APPLICABILITY

The present invention provides compounds having a DDR1 inhibitory effect. The present invention also provides pharmaceutical agents for prevention and/or treatment of cancer, prevention and/or treatment of cancer invasion and metastasis, and prevention and/or treatment of fibrosis and inflammation.

The invention claimed is:

1. A compound represented by general formula (I) below or a pharmaceutically acceptable salt thereof:

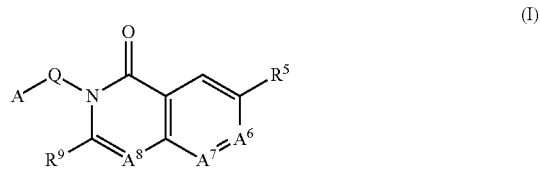

wherein
A represents formula (1) or (2) below:

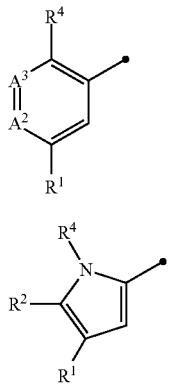

(1)

(2)

Q represents $CH_2$ or NH;
$R^1$ in formula (1) represents a $C_{1-6}$ alkyl group, $C_{1-6}$ alkoxy group, $C_{2-6}$ alkenyl group, $C_{2-6}$ alkynyl group, halogen atom, cyano group, nitro group or amino group, wherein the $C_{1-6}$ alkyl group, $C_{2-6}$ alkenyl group, $C_{2-6}$ alkynyl group, and $C_{1-6}$ alkoxy group may be substituted with 1 to 5 halogen atoms;
$R^1$ in formula (2) represents a hydrogen atom, $C_{1-6}$ alkyl group, $C_{1-6}$ alkoxy group, $C_{2-6}$ alkenyl group, $C_{2-6}$ alkynyl group, halogen atom, cyano group, nitro group or amino group, wherein the $C_{1-6}$ alkyl group, $C_{2-6}$ alkenyl group, $C_{2-6}$ alkynyl group, and $C_{1-6}$ alkoxy group may be substituted with 1 to 5 halogen atoms;
$A^2$ represents $CR^2$ or N;
$R^2$ represents a hydrogen atom, $C_{1-3}$ alkyl group, $C_{1-3}$ alkoxy group, or halogen atom;
$A^3$ represents $CR^3$ or N, wherein $A^2$ and $A^3$ are not both N;
$R^3$ represents a hydrogen atom, $C_{1-3}$ alkyl group, $C_{1-3}$ alkoxy group, or halogen atom;
$R^4$ represents a $C_{3-6}$ alkyl group, $C_{3-8}$ cycloalkyl group, ($C_{3-8}$ cycloalkyl)methyl group, $C_{1-6}$ alkylsulfonyl group, $C_{1-6}$ alkylsulfanyl group, $C_{1-6}$ alkylsulfinyl group, $C_{6-10}$ arylsulfonyl group, $C_{6-10}$ arylsulfinyl group, $C_{3-8}$ cycloalkylsulfonyl group, $C_{6-10}$ arylsulfinyl group, $C_{3-8}$ cycloalkylsulfanyl group or $C_{3-8}$ cycloalkylsulfinyl group, wherein the $C_{3-6}$ alkyl group, $C_{3-8}$ cycloalkyl group, ($C_{3-8}$ cycloalkyl)methyl group, $C_{1-6}$ alkylsulfonyl group, $C_{1-6}$ alkylsulfanyl group, $C_{1-6}$ alkylsulfinyl group, $C_{6-10}$ arylsulfonyl group, $C_{6-10}$ arylsulfanyl group, $C_{6-10}$ arylsulfinyl group, $C_{3-8}$ cycloalkylsulfonyl group, $C_{3-8}$ cycloalkylsulfanyl group, and $C_{3-8}$ cycloalkylsulfinyl group may be substituted with 1 to 5 halogen atoms;
$R^5$ represents a hydrogen atom, halogen atom, $C_{1-6}$ alkyl group, $C_{1-6}$ alkoxy group, $C_{2-6}$ alkenyl group, $C_{2-6}$ alkynyl group, nitro group, amino group, cyano group, $C_{1-6}$ alkylsulfonyl group, $C_{1-6}$ alkylsulfanyl group or $C_{1-6}$ alkylsulfinyl group, wherein the $C_{1-6}$ alkyl group, $C_{2-6}$ alkenyl group, $C_{2-6}$ alkynyl group, and $C_{1-6}$ alkoxy group may be substituted with 1 to 5 halogen atoms;
$A^6$ represents $CR^6$;
$R^6$ represents a hydrogen atom, $C_{1-6}$ alkyl group, $C_{1-6}$ alkoxy group, $C_{3-8}$ cycloalkyl group, $C_{2-6}$ alkenyl group, halogen atom, formyl group, [1,3]dioxolane, or a group represented by formula (i) below, wherein the $C_{1-6}$ alkyl group, $C_{1-6}$ alkoxy group, $C_{3-8}$ cycloalkyl group or $C_{2-6}$ alkenyl group may be substituted with 1 to 5 amino, hydroxyl, and/or $OSO_2CH_3$ groups, ●-X—Y—Z (i)

wherein in formula (i),
X represents —$(CH_2)_n$—, —$(CH_2)_nNH(CH_2)_l$—, or —$(CH_2)_nO(CH_2)_l$—;
Y represents a $C_{3-8}$ cycloalkyl group, 4- to 10-membered aromatic ring, 3- to 12-membered heterocycle, or 4- to 10-membered aromatic heterocycle, wherein the $C_{3-8}$ cycloalkyl group, 4- to 10-membered aromatic ring, 3- to 12-membered heterocycle, and 4- to 10-membered aromatic heterocycle may be substituted with 1 to 5 halogen atoms, oxo groups and/or $C_{1-3}$ alkyl groups;
Z represents a hydrogen atom, a $C_{1-6}$ alkyl group, a $C_{2-6}$ alkenyl group, a $C_{2-6}$ alkynyl group, a $C_{3-8}$ cycloalkyl group, —$(CH_2)_mNRaRb$, —$NHCO(CH_2)_mRc$, —$(CH_2)_mNHCORc$, —$NH(CH_2)_mCORc$, —$(CH_2)_mN(CH_3)CORc$, —$(CH_2)_mORd$, —$(CH_2)_mCORe$, —$(CH_2)_mCOORe$, —$(CH_2)_mNHSO_2Rf$, —$(CH_2)_mSO_2Rf$, —$(CH_2)_mCONRgRh$, a 4- to 10-membered aromatic ring, 4- to 10-membered aromatic heterocycle, or a 3- to 12-membered heterocycle, wherein the $C_{1-6}$ alkyl group may be substituted with 1 to 5 halogen atoms, hydroxyl groups, $C_{3-8}$ cycloalkyl groups, 4- to 10-membered aromatic rings, 4- to 10-membered aromatic heterocycles, 3- to 12-membered heterocycles, and/or cyano groups; and the 3- to 12-membered heterocycle and 4- to 10-membered aromatic heterocycle may be substituted with 1 to 5 halogen atoms, $C_{1-3}$ alkyl groups and/or oxo groups;
n represents 0, 1, 2, or 3;
l represents 0, 1, 2, or 3;
m represents 0, 1, 2, or 3;
Ra and Rb are identical or different, each representing a hydrogen atom, $C_{1-6}$ alkyl group, $C_{2-6}$ alkenyl group, $C_{2-6}$ alkynyl group, 3- to 12-membered heterocycle, 4- to 10-membered aromatic heterocycle, or —$SO_2CH_3$, wherein the $C_{1-6}$ alkyl group may be substituted with 1 to 5 halogen atoms, amino groups, mono-$C_{1-6}$ alkylamino groups, di-$C_{1-6}$ alkylamino groups, hydroxyl groups, and/or cyano groups;
Rc represents a $C_{1-6}$ alkyl group, $C_{2-6}$ alkenyl group, $C_{2-6}$ alkynyl group, $C_{1-6}$ alkoxy group, $C_{3-8}$ cycloalkyl group, amino group, mono-$C_{1-6}$ alkylamino group, di-$C_{1-6}$ alkylamino group or 3- to 12-membered heterocycle, wherein the $C_{1-6}$ alkyl group may be substituted with 1 to 3 amino groups, mono-$C_{1-6}$ alkylamino groups, di-$C_{1-6}$ alkylamino groups, and/or 3- to 12-membered heterocycles;
Rd represents a hydrogen atom, $C_{1-6}$ alkyl group, $C_{2-6}$ alkenyl group or $C_{2-6}$ alkynyl group, wherein the $C_{1-6}$ alkyl group, $C_{2-6}$ alkenyl group, and $C_{2-6}$ alkynyl group may be substituted with 1 to 5 $C_{1-6}$ alkoxy groups and/or amino groups;
Re represents a hydrogen atom or $C_{1-6}$ alkyl group, wherein the $C_{1-6}$ alkyl group may be substituted with an amino group;
Rf represents a $C_{1-6}$ alkyl group, an amino group, a mono-$C_{1-6}$ alkylamino group, or a di-$C_{1-6}$ alkylamino group, wherein the $C_{1-6}$ alkyl group, mono-$C_{1-6}$ alkylamino group, and di-$C_{1-6}$ alkylamino group may be substituted with 1 to 5 halogen atoms;
Rg and Rh are identical or different, each representing a hydrogen atom, $C_{1-6}$ alkyl group, or 3- to 12-membered heterocycle, wherein the $C_{1-6}$ alkyl group may be substituted with 1 to 3 amino groups, mono-$C_{1-6}$ alkylamino groups, and/or di-$C_{1-6}$ alkylamino groups;

$A^7$ represents $CR^7$; and $R^7$ represents a hydrogen atom, halogen atom, $C_{1-6}$ alkyl group, $C_{2-6}$ alkenyl group, $C_{1-6}$ alkoxy group, or a cyano group;

$A^8$ represents N; and $R^9$ represents a hydrogen atom or amino group.

2. The compound or pharmaceutically acceptable salt thereof according to claim 1, wherein A is formula (3) below:

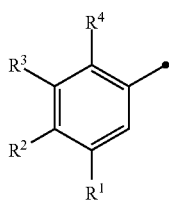

(3)

3. The compound or pharmaceutically acceptable salt thereof according to claim 1, wherein $R^4$ is a $C_{1-6}$ alkylsulfonyl group or $C_{1-6}$ alkylsulfanyl group.

4. The compound or pharmaceutically acceptable salt thereof according to claim 1, wherein $R^5$ represents a halogen atom, $C_{1-3}$ alkyl group, or $C_{1-3}$ alkoxy group, wherein the $C_{1-3}$ alkyl group or $C_{1-3}$ alkoxy group may be substituted with 1 to 5 halogen atoms.

5. The compound or pharmaceutically acceptable salt thereof according to claim 1, wherein $R^6$ represents a hydrogen atom or a group represented by formula (i) below:

(i)

wherein X represents $CH_2$ or $(CH_2)_2NH(CH_2)_2$;

Y represents piperazine, pyrrolidine, piperidine, morpholine, homomorpholine, 3,3-dimethylpiperazine, (R) or (S)-hexahydro-pyrrolo[1,2-a]pyrazine, 3-oxopiperazine, azetidine or 2-oxo-imidazolidine;

Z represents a hydrogen atom, a $C_{1-3}$ alkyl group, a $C_{4-6}$ cycloalkyl group, —$(CH_2)_m$Rc, —NHCO$(CH_2)_m$Rc, —$(CH_2)_m$NHCORc, —NH$(CH_2)_m$CORc, —$(CH_2)_m$N(CH_3)$CORc, ORd, —CORe, —COORe, —NHSO$_2$Rf, —SO$_2$Rf, —$(CH_2)_m$CONRgRh, or azetidine, piperazine, pyrrolidine, piperidine, tetrahydropyran, tetrahydrothiopyran, morpholine, or oxetane, wherein the azetidine, piperazine, pyrrolidine, piperidine, tetrahydropyran, tetrahydrothiopyran, morpholine, or oxetane may be substituted with 1 to 5 halogen atoms, $C_{1-3}$ alkyl groups, and/or oxo groups;

m represents 0 or 1;

Ra and Rb are identical or different, each representing a hydrogen atom, a $C_{1-3}$ alkyl group, —$SO_2CH_3$, prop-2-ynyl, or oxetane, wherein the $C_{1-3}$ alkyl group may be substituted with 1 to 5 halogen atoms or amino groups;

Rc represents a $C_{1-3}$ alkyl group, a $C_{1-4}$ alkoxy group, a $C_{4-6}$ cycloalkyl group, or an amino group, wherein the $C_{1-3}$ alkyl group may be substituted with 1 to 2 amino, mono-$C_{1-2}$ alkylamino, and/or di-$C_{1-2}$ alkylamino groups;

Rd represents a hydrogen atom, $C_{1-2}$ alkyl group, or $C_{2-3}$ alkenyl group, wherein the $C_{1-2}$ alkyl group may be substituted with 1 to 2 $C_{1-2}$ alkoxy groups;

Re represents a hydrogen atom or $C_{1-4}$ alkyl group, wherein the $C_{1-4}$ alkyl group may be substituted with an amino group;

Rf represents a $C_{1-3}$ alkyl group, an amino group, a mono-$C_{1-3}$ alkylamino group, or a di-$C_{1-3}$ alkylamino group; and Rg and Rh are identical or different, each representing a hydrogen atom or $C_{1-3}$ alkyl group.

6. The compound or pharmaceutically acceptable salt thereof according to claim 1, wherein $R^7$ represents a hydrogen atom or a halogen atom.

7. The compound or pharmaceutically acceptable salt thereof according to claim 1, wherein $R^9$ represents a hydrogen atom.

8. A pharmaceutical comprising the compound or pharmaceutically acceptable salt thereof according to claim 1 as an active ingredient.

9. A method for treating endometrial cancer, comprising administering a pharmaceutically effective amount of a composition comprising the compound or pharmaceutically acceptable salt thereof according to claim 1 to a patient in need thereof.

10. A method for treating fibrosis and/or inflammation, comprising administering a pharmaceutically effective amount of a composition comprising the compound or pharmaceutically acceptable salt thereof according to claim 1 to a patient in need thereof.

\* \* \* \* \*